US012760364B2

(12) United States Patent
Mcgovern et al.

(10) Patent No.: US 12,760,364 B2
(45) Date of Patent: Oct. 13, 2026

(54) METHODS AND SYSTEMS FOR CHARACTERIZING SEVERE CROHN'S DISEASE

(71) Applicant: CEDARS-SINAI MEDICAL CENTER, Los Angeles, CA (US)

(72) Inventors: Dermot P. Mcgovern, Los Angeles, CA (US); Dalin Li, Walnut, CA (US); Phillip Gu, Los Angeles, CA (US); Shishir Dube, Los Angeles, CA (US); Talin Haritunians, Los Angeles, CA (US); Marzieh Akhlaghpour, Rolling Hills Estates, CA (US)

(73) Assignee: CEDARS-SINAI MEDICAL CENTER, Los Angeles, CA (US)

( * ) Notice: Subject to any disclaimer, the term of this patent is extended or adjusted under 35 U.S.C. 154(b) by 1168 days.

(21) Appl. No.: 17/050,067

(22) PCT Filed: Apr. 24, 2019

(86) PCT No.: PCT/US2019/028902
§ 371 (c)(1),
(2) Date: Oct. 23, 2020

(87) PCT Pub. No.: WO2019/209942
PCT Pub. Date: Oct. 31, 2019

(65) Prior Publication Data

US 2021/0079473 A1 Mar. 18, 2021

Related U.S. Application Data

(60) Provisional application No. 62/662,009, filed on Apr. 24, 2018.

(51) Int. Cl.
*C12Q 1/6883* (2018.01)

(52) U.S. Cl.
CPC ...... *C12Q 1/6883* (2013.01); *C12Q 2600/112* (2013.01); *C12Q 2600/156* (2013.01)

(58) Field of Classification Search
CPC ............ C12Q 1/6883; C12Q 2600/112; C12Q 2600/156; G01N 2800/065
See application file for complete search history.

(56) References Cited

U.S. PATENT DOCUMENTS

| | | | | |
|---|---|---|---|---|
| 8,766,034 B2 | 7/2014 | Shih et al. | | |
| 10,322,174 B2 | 6/2019 | Bilsborough et al. | | |
| 10,633,449 B2 | 4/2020 | Shih et al. | | |
| 10,689,439 B2 * | 6/2020 | Watkins | ................. | C07K 16/24 |
| 11,440,954 B2 * | 9/2022 | Watkins | ................. | C07K 16/24 |
| 11,549,146 B2 | 1/2023 | Mcgovern et al. | | |
| 2011/0319284 A1 | 12/2011 | Wehkamp et al. | | |
| 2013/0137713 A1 | 5/2013 | Forbes et al. | | |
| 2015/0376707 A1 | 12/2015 | Targan et al. | | |
| 2016/0053007 A1 | 2/2016 | Siegel et al. | | |
| 2016/0096885 A1 | 4/2016 | Shih et al. | | |
| 2017/0166967 A1 | 6/2017 | Rotter et al. | | |
| 2018/0230543 A1 | 8/2018 | McGovern | | |
| 2018/0305459 A1 * | 10/2018 | McGovern | ......... | G01N 33/6854 |
| 2019/0203295 A1 | 7/2019 | Rotter et al. | | |
| 2019/0300957 A1 | 10/2019 | Gonsky et al. | | |
| 2020/0149110 A1 | 5/2020 | Targan et al. | | |
| 2023/0366028 A1 | 11/2023 | McGovern et al. | | |
| 2024/0034799 A1 | 2/2024 | Gonsky et al. | | |

FOREIGN PATENT DOCUMENTS

| | | | | |
|---|---|---|---|---|
| WO | WO-2005078138 A1 | 8/2005 | | |
| WO | WO-2010014905 A2 | 2/2010 | | |
| WO | WO-2010118210 A1 | 10/2010 | | |
| WO | WO-2010120814 A1 | 10/2010 | | |
| WO | WO-2011153501 A2 | 12/2011 | | |
| WO | WO 2015073580 A1 | 5/2015 | | |
| WO | WO-2017161342 A1 * | 9/2017 | ................ | A61P 1/00 |
| WO | WO-2017201461 A1 | 11/2017 | | |

OTHER PUBLICATIONS

MacCallum et al., 1996, J. Mol. Biol. 262: 732-745 (Year: 1996).*
Vajdos et al., 2002, J. Mol. Biol. 320: 415-428 (Year: 2002).*
Paul, Fundamental Immunology, 2003, 5th Edition, Raven Press, New York, Chapter 3, pp. 109-114 (Year: 2003).*
Casset et al., 2003, Biochemical and Biophysical Research Communications 307:198-205 (Year: 2003).*
Török et al., Pharmacogenomics (2008) 9(7), 881-893 (Year: 2008).*
Cleynen et al., Gut 2013; 62:1556-1565 (Year: 2013).*
Sela-Culang et al., 2013, Frontiers in Immunology 4(302): 1-13 (Year: 2013).*
Bank et al., The Pharmacogenomics Journal (2014) 14, 526-534 (Year: 2014).*
Mayo Clinic, Crohn's disease—Diagnosis and treatment—mayoclinic.org/diseases-conditions/crohns-disease/diagnosis-treatment/drc-20353309; date accessed: Feb. 20, 2024) (Year: 2024).*
Lazar et al. Transforming Growth Factor alpha: Mutation of Aspartic Acid 47 and Leucine 48 Results in Different Biological Activities. Mol. Cell. Biol., 8:1247-1252, 1988 (Year: 1988).*
Burgess et al. Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue. J. Cell Biol. 111:2129-2138, 1990 (Year: 1990).*
Warzocha et al., Leukemia and Lymphoma (1997) vol. 24. pp. 267-281 (Year: 1997).*

(Continued)

*Primary Examiner* — Vanessa L. Ford
*Assistant Examiner* — Danaya L Middleton
(74) *Attorney, Agent, or Firm* — JONES DAY

(57) ABSTRACT

The present disclosure describes methods, devices and systems of diagnosing, prognosing, and treating subjects with moderate to severe forms of Crohn's disease (CD) that is characterized by stricturing and internal penetrating disease phenotypes. Also described are methods and kits for characterizing a subtype of CD, and identifying a subject as being suitable for a therapy to treat the CD.

16 Claims, No Drawings

Specification includes a Sequence Listing.

(56) References Cited

OTHER PUBLICATIONS

Greenspan et al. 1999 Defining epitopes: It's not as easy as it seems; Nature Biotechnology, 17:936-937 (Year: 1999).*
Bork. Powers and Pitfalls in Sequence Analysis: The 70% Hurdle. Genome Research, 2000, 10:398-400 (Year: 2000).*
Skolnick et al., Trends Biotechnol. Jan. 2000;18(1):34-9 (Year: 2000).*
Silverberg, Genetic Studies in Inflammatory Bowel Disease, 2002, Institute of Medical Science, University of Toronto (Year: 2002).*
Aagaard et al., Advanced Drug Delivery Reviews 59 (2007) 75-86 (Year: 2007).*
Guido et al., Curr Med Chem. 2008;15(1):37-46 (Year: 2008).*
Verbeeten, Genetic and Serological Markers Associated With Pouchitis and a Crohn's Disease-Like Phenotype After Pelvic Pouch Surgery for Ulcerative Colitis, 2009, Institute of Medical Science, University of Toronto (Year: 2009).*
Cotterill, Inflammatory Bowel Disease Genetics, 2011, School of Medicine Faculty of Medical and Human Sciences University of Manchester (Year: 2011).*
McKeague et al., J Nucleic Acids. 2012;2012:748913. Epub Oct. 24, 2012 (Year: 2012).*
Clark et al., J. Med. Chem., 2014, 57 (12), pp. 5023-5038 (Year: 2014).*
Khan, The Genetic Susceptibility of South Asians to Inflammatory Bowel Disease, 2014, School of Medicine Faculty of Medical and Human Sciences (Year: 2014).*
Miosge, Proc Natl Acad Sci U S A. Sep. 15, 2015;112(37):E5189-98 (Year: 2015).*
Kulmanov et al., Bioinformatics, 34(4), 2018, 660-668 (Year: 2018).*
Drobez et al., Genetic Testing and Molecular Biomarkers, vol. 22, No. 3, 2018, pp. 143-151 (Year: 2018).*
Barber et al, Genetic markers predict primary non-response and durable response to anti-TNF biologic therapies in Crohn's disease, 2020, Division of Gastroenterology, Massachusetts General Hospital and Harvard Medical School (Year: 2020).*
Brown et al, J Immunol. May 1996;156(9):3285-9 (Year: 1996).*
Yamakazi et al, Human Molecular Genetics, 2005, vol. 14, No. 22: 3499-3506 (Year: 2005).*
Chatzikyriakidou et al.: Evidence of ERBBB3 gene association with rheumatoid arthritis predisposition. International Journal of Rheumatic Disease. pp. 146-149 (2014).
Craig et al.: Hematopoietic stem cell transplantation for severe Crohn's disease. Bone Marrow Transplanation. 32:S57-S59 (2003).
Prometheus Biosciences, Inc. Form S-1 Registration Statement as filed with the Securities and Exchange Commission on Feb. 19, 2021 (246 pages).
Rioux et al., Genome-wide association study identifies five novel susceptibility loci for Crohn disease and implicates autophagy in disease pathogenesis. Nature Genetics 39(5):596-604 (2007).
Chang et al.: Intestinal Stricture in Crohn's Disease; Intest Res.; 13(1): 19-26 (2015).
Cleynen et al.: Inherited determinants of Crohn's disease and ulcerative colitis phenotypes; Lancet;387(10014):156-167. Doi:10.1016/S0140-6736(15)00465-1 (2016).
Drobez et al.: DNA polymorphisms predict time to progression from uncomplicated to complicated Crohn's disease. European Journal of Gastroenterology & Hepatology; 30(4):447-455 (2018).
Gu et al.: Serological, genetic and clinical associations with increased health-care resource utilization in inflammatory bowel disease. Journal of digestive Disease; 19(1):15-23 (2017).
International Application No. PCT/US2019/028902 International Search Report and Written Opinion dated Sep. 30, 2019.
International Application No. PCT/US2019/028902 Invitation To Pay Additional Fees And, Where Applicable, Protest Fee dated Jul. 25, 2019.
Iskandar et al.: Biomarkers in Inflammatory Bowel Disease: Current Practices and Recent Advances; Transl Res; 159(4): 313-325 (2012).
Jostins et al.: Host-microbe interactions have shaped the genetic architecture of inflammatory bowel disease; Nature 491, 119-124 (2012).
Landers et al.: Selected loss of tolerance evidenced by Crohn's disease-associated immune responses to auto- and microbial antigens; Gastroenterology; 123:689-699 (2002).
O'Shea et al.: The JAK-STAT Pathway: Impact on Human Disease and Therapeutic Intervention. Annu Rev Med. 66:311-328 (2015).
Liu et al.: Association analyses identify 38 susceptibility loci for inflammatory bowel disease and highlight shared genetic risk across populations. Nat Genet. 47(9):979-986 (2015).
Marsal et al.: Management of Non-response and Loss of Response to Anti-tumor Necrosis Factor Therapy in Inflammatory Bowel Disease. Front Med (Lausanne). 9:897936 (2022).
Liu, Bin. et al. Leukemia Inhibitory Factor Promotes Tumor Growth and Metastasis in Human Osteosarcoma via Activating STAT3. APMIS 123:837-846 (2015).
Paul, William E. et al. Chapter 8:Fundamental Immunology. 3rd Edition Raven Press New York:292-295 (1993).
Saxon, Andrew. et al. A Distinct Subset of Antineutrophil Cytoplasmic Antibodies is Associated With Inflammatory Bowel Disease. The Journal of Allergy and Clinical Immunology 86(2):202-210 (1990).
Singh, Shailesh K, and Venkatesh Naini. Dosage forms: Non-Parenteral. Encyclopedia of Pharmaceutical Technology, 2nd Edition 1:754-757 (2002).
Song et al.: Direct detection of bacterial genomic DNA at sub-femtomolar concentrations using single molecule arrays. Anal Chern. 85(3):1932-1939 (2013).
Yang et al., 2014, "TNFSF15 is an independent predictor for the development of Crohn's disease-related complications in Koreans," J. Crohns Colitis, 8(10):1315-1326.

* cited by examiner

METHODS AND SYSTEMS FOR CHARACTERIZING SEVERE CROHN'S DISEASE

CROSS-REFERENCE

This application is a National Stage Entry of International Application No. PCT/US2019/028902 filed Apr. 24, 2019, which claims the benefit of U.S. Provisional Application Ser. No. 62/662,009 filed Apr. 24, 2018, and incorporated herein by reference in its entirety.

STATEMENT REGARDING FEDERALLY-SPONSORED RESEARCH OR DEVELOPMENT

This invention was made with government support under Grant No. U01 DK062413 and P01 DK046763 awarded by National Institutes of Health. The government has certain rights in the invention.

SEQUENCE LISTING

The instant application contains a Sequence Listing which has been submitted electronically in ASCII format and is hereby incorporated by reference in its entirety. Said ASCII copy created Apr. 22, 2019, is named 52388-736_601_SL.txt and is 364,884 bytes in size.

BACKGROUND

Inflammatory bowel disease (IBD) has two common forms, Crohn's disease (CD) and ulcerative colitis (UC), which are chronic, relapsing inflammatory disorders of the gastrointestinal tract. Genetic factors play an important role in IBD pathogenesis, and CD and UC are thought to be related disorders that share some genetic susceptibility loci but differ at others.

The high clinical heterogeneity and genetic complexity of CD and UC suggest that the underlying biological pathways driving disease differ in subgroups of patients. Significant efficacious responses to IBD therapies are difficult to achieve due to disease heterogeneity. Thus, the development of early and targeted therapeutics requires subgroup stratification and prognostic biomarker identification, particularly in predicting an overall mild, compared to severe, disease course.

There is a number of aggravating subclinical phenotypes of IBD that are present in certain sub-populations of CD and UC patients. One such condition is intestinal stricturing disease, which can result from long term intestinal inflammation or intestinal fibrosis that leads to the formation of scar tissue in the intestinal wall (fibrostenosis) or swelling. Both outcomes can cause narrowing, or obstruction, and are known as either fibrotic or inflammatory strictures. Severe strictures can lead to blockage of the intestine, leading to abdominal pain, bloating, nausea and the inability to pass stool. Another example is penetrating disease, which is the formation of fistula or extraluminal abscesses of the intestine.

Stricturing and penetrating CD results in significant morbidity. Intestinal strictures represent a common complication of CD; nearly 40% of CD patients develop clinically apparent strictures. Subclinical phenotypes like stricturing and penetrating disease are thought to be driven by a combination of clinical, serologic, and genetic factors. Due to the clinical, serologic and genetic heterogeneity of stricturing and penetrating disease, and IBD generally, conventional treatments such as immunomodulatory (e.g., anti-TNF therapies) are efficacious in only some of the patient population. A significant portion of the population experiences non-response to the conventional treatment or loss-of-response after a successful induction of the treatment. Surgery, in the form of structureplasty (reshaping of the intestine) or resection (removal of the intestine), is the only treatment option for patients that do not respond to first line therapies. Surgical treatments for IBD are invasive, causing post-operative risks for an estimated third of patients undergoing surgery, such as anastomotic leak, infection, and bleeding.

Thus, there is a need for methods and systems that identify subjects at risk for developing severe forms of CD in order to prescribe personalized treatment strategies that obviate a need for surgery and improve patient outcomes. Targeted therapeutic strategies alternative to general immunomodulatory approaches are needed to better address the underlying disease pathology unique to severe forms of CD characterized by subclinical phenotypes such as stricturing and penetrating disease.

SUMMARY

Aspects disclosed herein provide methods and systems for characterizing severe forms of Crohn's disease (CD) in a subject, as well as identifying a risk that a subject will develop the severe forms of CD. Targeted therapeutic approaches are also described herein, that may be suitable for subjects determined to be at risk of developing severe forms of CD. The methods and systems disclosed herein involve characterizing and identifying a risk of developing severe forms of CD based on a presence of certain genotypes, serological markers, or other biomarkers that are associated with subclinical phenotypes of severe forms of CD (e.g., stricturing and penetrating disease). The genotypes and biomarkers disclosed herein are further associated with disease location, which in some cases, can be used to target therapeutic strategies to the predominantly affected area. Exemplary therapeutic agents useful for this purpose are those that target pathways such as Prolactin signaling, autophagy, and Janus Kinase (JAK)/(Signal Transducer and Activator of Transcription (STAT) pathway.

Non-limiting practical applications of the associations between the genotypes, serological markers and other biomarkers described herein and incidences of clinical and subclinical phenotypes in certain populations of subjects are provided herein. For example, the genotypes and biomarkers of the present disclosure can be used to predict a risk that a subject will develop CD. The genotypes and biomarkers are also useful to predict whether a patient diagnosed with CD will develop a severe form of the disease, such as a subclinical phenotype thereof (e.g., stricturing/penetrating disease), and in some cases, also predict where in the intestine the subclinical phenotype will present. In addition, or alternatively, the genotypes and biomarkers disclosed herein are associated with an variation in an expression of certain genes or gene expression products involved in the pathogenesis and pathology of CD, which in some cases, means the genotypes and biomarkers can be used to identify a patient who may be suitable for treatment with therapy targeting that gene or gene expression product (e.g., a patient carrying a genotype associated with an increase in the gene expression product may be suitable for a treatment with an inhibitor of that gene expression product). In some cases, a subject is administered a therapeutic agent, provided the genotype disclosed herein is detected in a sample obtained from the subject. A further example of practical applications disclosed herein include laboratory-based methods of detecting the instant genotypes and biomarkers. Exemplary methodologies of detecting the genotype include genotyping devices and sequencing. Exemplary methodologies of detecting biomarkers (e.g., serological markers) include enzyme-linked immunosorbent assays (ELISA).

Aspects disclosed provide methods of treating a severe form of Crohn's disease (CD) in a subject, the method comprising administering to the subject a therapeutically effective amount of a therapeutic agent, provided the a genotype comprising at least one polymorphism associated with at least one of stricturing disease and internal penetrating disease that is characteristic of severe CD as indicated by a P value of at most $1.0E^{-5}$ is detected in a sample obtained from the subject. In some embodiments, the at least one polymorphism is associated with stricturing disease and is selected from the group consisting of rs7416358G, rs1070444A, rs11749180A, 12-54819630-G-INSERTION, rs12496281G, rs11171747C, rs116714418A, rs111455641G, rs9480689G, rs6879067A, rs11128532A, rs177665C, rs10775375A, rs6801634A, rs6962616A, rs7220814G, rs4325270T, rs768755T, rs17758350A, rs9480689G, rs525850A, rs4325270T, rs6962616A, rs10265554G, rs634641G, rs1493871G, rs12669698G, rs4332037A, rs17697480G, rs9480689G, rs6074737A, rs904910G, rs12972487A, rs445417A, rs63562C, rs7416358G, rs177665C, rs1070444A, rs10912583A, rs12914919G, rs2854725C, rs9480689G, rs71472147A, rs72939578A, rs658795A, rs17758350A, rs144260901A, rs10801129C, rs1702870A, rs10912583A, rs2452822C, rs7774349A, rs4705272G, rs117946479A, rs936126A, rs634641G, rs2314737G, rs3002685G, rs634641G, rs10134119T, rs3808240C, rs1890843G, and rs11829981A. In some embodiments, the at least one polymorphism is associated with internal penetrating disease and is selected from the group consisting of rs12496281G, rs2383184G, rs144260901A, rs6801634A, rs2383184G, and rs2954756G. In some embodiments, the at least one polymorphism is located at nucleoposition 26 or 31 within any one of SEQ ID NOS: 1-82. In some embodiments, the genotype is detected by a process comprising: (a) contacting the sample obtained from the subject with a nucleic acid sequence comprising a detectable moiety, the nucleic acid sequence capable of hybridizing to at least 20 contiguous nucleobases between nucleobase 16 and nucleobase 46 of at least one of SEQ ID NOS: 13-82; and (b) detecting binding between the nucleic acid sequence and the at least 20 contiguous nucleobases between nucleobase 16 and nucleobase 46 of at least one of SEQ ID NOS: 13-82. In some embodiments, the genotype is detected by sequencing genetic information contained in the sample obtained from the subject. In some embodiments, the methods further comprise determining whether the subject has or will develop at least one of a non-response and a loss-of-response to a standard treatment. In some embodiments, the standard treatment is selected from the group consisting of glucocorticosteriods, anti-TNF therapy, anti-a4-b7 therapy (vedolizumab), anti-IL12p40 therapy (ustekinumab), Thalidomide, and Cytoxin. In some embodiments, the therapeutic agent is a modulator of a gene or gene expression product expressed from the gene, the gene selected from group consisting of X—C Motif Chemokine Ligand 1 (XCL1), Dermatopontin (DPT), TNF Superfamily Member 4 (TNFSF4), C-Type Lectin Like 1 (CLECL1), CD69 Molecule (CD69), Fins Related Tyrosine Kinase 1 (FLT1), Mitogen-Activated Protein Kinase Kinase Kinase Kinase 4 (MAP4K4), Prostaglandin E Receptor 4 (PTGER4), interleukin 18 receptor 1 (IL18R1). 6-Phosphofructo-2-Kinase/Fructose-2,6-Biphosphatase 3 (PFKFB3), Interleukin 18 Receptor Accessory Protein (IL18RAP), Adenylate Cyclase 7 (ADCY7), B Lymphoid Tyrosine Kinase (BLK), G Protein-Coupled Receptor 65 (GPR65), Sprouty Related EVH1 Domain Containing 2 (SPRED2), Src Kinase Associated Phosphoprotein 2 (SKAP2), CD30 ligand (CD30L), Receptor Interacting Serine/Threonine Kinase 2 (RIPK2), and TNF Ligand Superfamily Member 15 (TL1A), an a combination thereof. In some embodiments, the modulator of the gene or gene expression product is selected from the group consisting of an antibody or antigen-binding fragment thereof, a small molecule, or a peptide. In some embodiments, the modulator of the gene or gene expression product is an agonist or a partial agonist. In some embodiments, the modulator of the gene or gene expression product is an antagonist or a partial antagonist. In some embodiments, the modulator of the gene or gene expression product is an allosteric modulator.

Aspects disclosed herein provide methods of characterizing an inflammatory bowel disease in a subject, the method comprising: (a) assaying genetic material in a sample obtained from a subject with an inflammatory bowel disease to detect a presence or an absence of a genotype comprising at least one polymorphism associated with at least one of stricturing disease and internal penetrating disease that is characteristic of severe CD as indicated by a P value of at most $1.0E^{-5}$; and (b) characterizing the inflammatory disease as a Crohn's disease (CD) provided the presence of the genotype is detected in step (a). In some embodiments, the at least one polymorphism is selected from the group consisting of rs2726797, rs7108993, rs79665096, rs7604404, rs73085878, rs78727269, rs2736352, rs4924935, rs11227112, rs2285043, rs6989059, rs3807552, rs111455641, rs9480689, rs7416358, rs6879067, rs11128532, rs177665, rs11171747, rs10775375, rs6801634, rs1070444, rs116714418, rs6962616, rs7220814, rs4325270, rs768755, rs17758350, rs9480689, rs525850, rs4325270, rs11749180, rs6962616, rs116714418, rs10265554, rs634641, rs1493871, rs12669698, rs4332037, rs17697480, rs9480689, rs6074737, rs904910, rs12972487, rs445417, rs635624, rs7416358, 12-54819630-G-INSERTION, rs177665, rs1070444, rs10912583, rs12914919, rs2854725, rs948068, rs71472147, rs72939578, rs658795, rs17758350, rs144260901, rs10801129, rs1702870, rs10912583, rs2452822, rs7774349, rs4705272, rs117946479, rs936126, rs634641, rs2314737, rs3002685, rs634641, rs12496281, rs10134119, rs3808240, rs1890843, rs11829981, rs12496281, rs2383184, rs144260901, rs6801634, rs2383184, and rs2954756. In some embodiments, the genotype is detected by a process comprising: (a) contacting the sample obtained from the subject with a nucleic acid sequence comprising a detectable moiety, the nucleic acid sequence capable of hybridizing to at least 20 contiguous nucleobases between nucleobase 16 and nucleobase 46 of at least one of SEQ ID NOS: 1-82; and (b) detecting binding between the nucleic acid sequence and the at least 20 contiguous nucleobases between nucleobase 16 and nucleobase 46 of at least one of SEQ ID NOS: 1-82. In some embodiments, the genotype is detected by sequencing genetic information contained in the sample obtained from the subject. In some embodiments, the further comprising characterizing the CD as a severe form of CD, the severe form of CD comprising stricturing disease or stricturing and internal penetrating disease, provided that the genotype detected in step (a) comprises at least one polymorphism selected from the group consisting of rs7416358G, rs1070444A, rs11749180A, 12-54819630-G-INSERTION, rs12496281G, rs11171747C, rs116714418A, rs111455641G, rs9480689G, rs6879067A, rs11128532A, rs177665C, rs10775375A, rs6801634A, rs6962616A, rs7220814G, rs4325270T, rs768755T, rs17758350A, rs9480689G, rs525850A, rs4325270T, rs6962616A, rs10265554G, rs634641G, rs1493871G, rs12669698G, rs4332037A, rs17697480G, rs9480689G, rs6074737A, rs904910G, rs12972487A, rs445417A, rs63562C, rs7416358G, rs177665C, rs1070444A, rs10912583A, rs12914919G, rs2854725C, rs9480689G, rs71472147A, rs72939578A, rs658795A, rs17758350A, rs144260901A, rs10801129C, rs1702870A, rs10912583A, rs2452822C, rs7774349A, rs4705272G, rs117946479A, rs936126A, rs634641G, rs2314737G, rs3002685G, rs634641G, rs10134119T, rs3808240C, rs1890843G, and rs11829981A. In some embodiments, methods further comprise characterizing the CD as a severe form of CD, the severe form of CD comprising internal penetrating disease, provided that the genotype detected in step (a) comprises at least one polymorphism selected from the group consisting of rs12496281G, rs2383184G, rs144260901A, rs6801634A, rs2383184G, and rs2954756G. In some embodiments, methods further comprise characterizing the severe form of CD by a disease location of the stricturing disease in the subject, the disease location selected from the group consisting of an ileum, an ilealcolonic region, and a colon. In some embodiments, methods further comprise characterizing the severe form of CD by a disease location of the internal penetrating disease in the subject, the disease location selected from the group consisting of an ileum, an ilealcolonic region, and a colon. In some embodiments, methods further comprise characterizing the CD as refractory. In some embodiments, the therapeutic agent is a modulator of a gene or gene expression product expressed from the gene, the gene selected from group consisting of X—C Motif Chemokine Ligand 1 (XCL1), Dermatopontin (DPT), TNF Superfamily Member 4 (TNFSF4), C-Type Lectin Like 1 (CLECL1), CD69 Molecule (CD69), Fins Related Tyrosine Kinase 1 (FLT1), Mitogen-Activated Protein Kinase Kinase Kinase Kinase 4 (MAP4K4), Prostaglandin E Receptor 4 (PTGER4), interleukin 18 receptor 1 (IL18R1). 6-Phosphofructo- 2-Kinase/Fructose-2,6-Biphosphatase 3 (PFKFB3), Interleukin 18 Receptor Accessory Protein (IL18RAP), Adenylate Cyclase 7 (ADCY7), B Lymphoid Tyrosine Kinase (BLK), G Protein-Coupled Receptor 65 (GPR65), Sprouty Related EVH1 Domain Containing 2 (SPRED2), Src Kinase Associated Phosphoprotein 2 (SKAP2), CD30 ligand (CD30L), Receptor Interacting Serine/Threonine Kinase 2 (RIPK2), and TNF Ligand Superfamily Member 15 (TL1A), and a combination thereof. In some embodiments, the modulator of the gene or gene expression product is selected from the group consisting of an antibody or antigen-binding fragment thereof, a small molecule, or a peptide. In some embodiments, the modulator of the gene or gene expression product is an agonist or a partial agonist. In some embodiments, the modulator of the gene or gene expression product is an antagonist or a partial antagonist. In some embodiments, the modulator of the gene or gene expression product is an allosteric modulator.

Aspects disclosed herein provide kits comprising: (a) at least one nucleic acid sequence comprising a detectable moiety, the at least one nucleic acid sequence comprising at least 20 contiguous nucleobases between nucleobase 16 and nucleobase 46 of at least one of SEQ ID NOS: 13-82, or a reverse complement thereof; and (b) at least one primer pair comprising a forward primer and a reverse primer, the forward primer comprising any one of SEQ ID NOS: 392-624 or a reverse complement thereof, the reverse primer comprising any one of SEQ ID NOS: 625-857 or a reverse complement thereof.

Aspects disclosed here provide methods of treating a severe form of Crohn's disease using the kit of the present disclosure, the method comprising: (a) introducing the at least one nucleic acid sequence and the at least one primer pair from the kit of the present disclosure to a sample obtained from a subject; (b) amplifying at least a portion of a target nucleic acid sequence contained in the sample, the target nucleic acid sequence provided in at least one of SEQ ID NOS: 1-82, to produce a detectable target nucleic acid sequence; (c) detecting a presence or an absence of the detectable target nucleic acid sequence; and (d) administering to the subject a therapeutically effective amount of a therapeutic agent, provided the a target nucleic acid sequence is detected in (c). In some embodiments, the methods further comprise determining whether the subject has or will develop at least one of a non-response and a loss-of-response to a standard treatment. In some embodiments, the standard treatment is selected from the group consisting of glucocorticosteriods, anti-TNF therapy, anti-a4-b7 therapy (vedolizumab), anti-IL12p40 therapy (ustekinumab), Thalidomide, and Cytoxin. In some embodiments, the therapeutic agent is a modulator of a gene or gene expression product expressed from the gene, the gene selected from group consisting of X—C Motif Chemokine Ligand 1 (XCL1), Dermatopontin (DPT), TNF Superfamily Member 4 (TNFSF4), C-Type Lectin Like 1 (CLECL1), CD69 Molecule (CD69), Fins Related Tyrosine Kinase 1 (FLT1), Mitogen-Activated Protein Kinase Kinase Kinase Kinase 4 (MAP4K4), Prostaglandin E Receptor 4 (PTGER4), interleukin 18 receptor 1 (IL18R1). 6-Phosphofructo-2-Kinase/Fructose-2,6-Biphosphatase 3 (PFKFB3), Interleukin 18 Receptor Accessory Protein (IL18RAP), Adenylate Cyclase 7 (ADCY7), B Lymphoid Tyrosine Kinase (BLK), G Protein-Coupled Receptor 65 (GPR65), Sprouty Related EVH1 Domain Containing 2 (SPRED2), Src Kinase Associated Phosphoprotein 2 (SKAP2), CD30 ligand (CD30L), Receptor Interacting Serine/Threonine Kinase 2 (RIPK2), and TNF Ligand Superfamily Member 15 (TL1A), an a combination thereof. In some embodiments, the modulator of the gene or gene expression product is selected from the group consisting of an antibody or antigen-binding fragment thereof, a small molecule, or a peptide. In some embodiments, the modulator of the gene or gene expression product is an agonist or a partial agonist. In some embodiments, the modulator of the gene or gene expression product is an antagonist or a partial antagonist. In some embodiments, the modulator of the gene or gene expression product is an allosteric modulator.

Aspects disclosed herein provide methods of characterizing an inflammatory bowel disease as Crohn's disease using the kit of the present disclosure, the method comprising: (a) introducing the at least one nucleic acid sequence and the at least one primer pair from the kit of the present disclosure to a sample obtained from a subject; (b) amplifying at least a portion of a target nucleic acid sequence contained in the sample, the target nucleic acid sequence provided in at least one of SEQ ID NOS: 1-82, to produce a detectable target nucleic acid sequence; (c) detecting a presence or an absence of the detectable target nucleic acid sequence; and (d) characterizing the inflammatory disease as Crohn's disease (CD) provided the presence of the detectable target nucleic acid sequence is detected in step (c). In some embodiments, methods further comprise characterizing the severe form of CD by a disease location of the stricturing disease in the subject, the disease location selected from the group consisting of an ileum, an ilealcolonic region, and a colon. In some embodiments, methods further comprise characterizing the severe form of CD by a disease location of the internal penetrating disease in the subject, the disease location selected from the group consisting of an ileum, an ilealcolonic region, and a colon. In some embodiments, methods further comprise characterizing the CD as refractory. In some embodiments, the therapeutic agent is a modulator of a gene or gene expression product expressed from the gene, the gene selected from group consisting of X—C Motif Chemokine Ligand 1 (XCL1), Dermatopontin (DPT), TNF Superfamily Member 4 (TNFSF4), C-Type Lectin Like 1 (CLECL1), CD69 Molecule (CD69), Fins Related Tyrosine Kinase 1 (FLT1), Mitogen-Activated Protein Kinase Kinase Kinase Kinase 4 (MAP4K4), Prostaglandin E Receptor 4 (PTGER4), interleukin 18 receptor 1 (IL18R1). 6-Phosphofructo-2-Kinase/Fructose-2,6-Biphosphatase 3 (PFKFB3), Interleukin 18 Receptor Accessory Protein (IL18RAP), Adenylate Cyclase 7 (ADCY7), B Lymphoid Tyrosine Kinase (BLK), G Protein-Coupled Receptor 65 (GPR65), Sprouty Related EVH1 Domain Containing 2 (SPRED2), Src Kinase Associated Phosphoprotein 2 (SKAP2), CD30 ligand (CD30L), Receptor Interacting Serine/Threonine Kinase 2 (RIPK2), and TNF Ligand Superfamily Member 15 (TL1A), an a combination thereof. In some embodiments, the modulator of the gene or gene expression product is selected from the group consisting of an antibody or antigen-binding fragment thereof, a small molecule, or a peptide. In some embodiments, the modulator of the gene or gene expression product is an agonist or a partial agonist. In some embodiments, the modulator of the gene or gene expression product is an antagonist or a partial antagonist. In some embodiments, the modulator of the gene or gene expression product is an allosteric modulator.

Aspects disclosed provide methods of treating a severe form of Crohn's disease (CD) in a subject, the method comprising: (a) obtaining a sample from a subject; (b) contacting the sample with an assay adapted to detect a genotype in the sample; and (c) administering to the subject a therapeutically effective amount of a therapeutic agent, provided the a genotype is detected in the sample obtained from the subject, the genotype comprising at least one polymorphism associated with at least one of stricturing disease and internal penetrating disease that is characteristic of severe CD as indicated by a P value of at most $1.0E^{-5}$. In some embodiments, the assay is a genotyping device. In some embodiments, the genotyping device is a sequencer. In some embodiments, the genotyping device is quantitative polymerase chain reaction (qPCR). In some embodiments, the at least one polymorphism is associated with stricturing disease and is selected from the group consisting of rs7416358G, rs1070444A, rs11749180A, 12-54819630-G-INSERTION, rs12496281G, rs11171747C, rs116714418A, rs111455641G, rs9480689G, rs6879067A, rs11128532A, rs177665C, rs10775375A, rs6801634A, rs6962616A, rs7220814G, rs4325270T, rs768755T, rs17758350A, rs9480689G, rs525850A, rs4325270T, rs6962616A, rs10265554G, rs634641G, rs1493871G, rs12669698G, rs4332037A, rs17697480G, rs9480689G, rs6074737A, rs904910G, rs12972487A, rs445417A, rs63562C, rs7416358G, rs177665C, rs1070444A, rs10912583A, rs12914919G, rs2854725C, rs9480689G, rs71472147A, rs72939578A, rs658795A, rs17758350A, rs144260901A, rs10801129C, rs1702870A, rs10912583A, rs2452822C, rs7774349A, rs4705272G, rs117946479A, rs936126A, rs634641G, rs2314737G, rs3002685G, rs634641G, rs10134119T, rs3808240C, rs1890843G, and rs11829981A. In some embodiments, the genotype device is a microarray. In some embodiments, the at least one polymorphism is associated with internal penetrating disease and is selected from the group consisting of rs12496281G, rs2383184G, rs144260901A, rs6801634A, rs2383184G, and rs2954756G. In some embodiments, the at least one polymorphism is located at nucleoposition 26 or 31 within any one of SEQ ID NOS: 1-82. In some embodiments, the genotype is detected by a process comprising: (a) contacting the sample obtained from the subject with a nucleic acid sequence comprising a detectable moiety, the nucleic acid sequence capable of hybridizing to at least 20 contiguous nucleobases between nucleobase 16 and nucleobase 46 of at least one of SEQ ID NOS: 13-82; and (b) detecting binding between the nucleic acid sequence and the at least 20 contiguous nucleobases between nucleobase 16 and nucleobase 46 of at least one of SEQ ID NOS: 13-82. In some embodiments, the genotype is detected by sequencing genetic information contained in the sample obtained from the subject. In some embodiments, the methods further comprise determining whether the subject has or will develop at least one of a non-response and a loss-of-response to a standard treatment. In some embodiments, the standard treatment is selected from the group consisting of glucocorticosteriods, anti-TNF therapy, anti-a4-b7 therapy (vedolizumab), anti-IL 12p40 therapy (ustekinumab), Thalidomide, and Cytoxin. In some embodiments, the therapeutic agent is a modulator of a gene or gene expression product expressed from the gene, the gene selected from group consisting of X—C Motif Chemokine Ligand 1 (XCL1), Dermatopontin (DPT), TNF Superfamily Member 4 (TNFSF4), C-Type Lectin Like 1 (CLECL1), CD69 Molecule (CD69), Fins Related Tyrosine Kinase 1 (FLT1), Mitogen-Activated Protein Kinase Kinase Kinase Kinase 4 (MAP4K4), Prostaglandin E Receptor 4 (PTGER4), interleukin 18 receptor 1 (IL18R1). 6-Phosphofructo-2-Kinase/Fructose-2,6-Biphosphatase 3 (PFKFB3), Interleukin 18 Receptor Accessory Protein (IL18RAP), Adenylate Cyclase 7 (ADCY7), B Lymphoid Tyrosine Kinase (BLK), G Protein-Coupled Receptor 65 (GPR65), Sprouty Related EVH1 Domain Containing 2 (SPRED2), Src Kinase Associated Phosphoprotein 2 (SKAP2), CD30 ligand (CD30L), Receptor Interacting Serine/Threonine Kinase 2 (RIPK2), and TNF Ligand Superfamily Member 15 (TL1A), an a combination thereof. In some embodiments, the modulator of the gene or gene expression product is selected from the group consisting of an antibody or antigen-binding fragment thereof, a small molecule, or a peptide. In some embodiments, the modulator of the gene or gene expression product is an agonist or a partial agonist. In some embodiments, the modulator of the gene or gene expression product is an antagonist or a partial antagonist. In some embodiments, the modulator of the gene or gene expression product is an allosteric modulator.

Aspects disclosed provide methods of treating a severe form of Crohn's disease (CD) in a subject, the method comprising: (a) contacting a sample obtained from a subject with an assay adapted to detect a genotype in the sample; and (b) administering to the subject a therapeutically effective amount of a therapeutic agent, provided the a genotype is detected in the sample obtained from the subject, the genotype comprising at least one polymorphism associated with at least one of stricturing disease and internal penetrating disease that is characteristic of severe CD as indicated by a P value of at most $1.0E^{-5}$. In some embodiments, the assay is a genotyping device. In some embodiments, the genotyping device is a sequencer. In some embodiments, the genotyping device is quantitative polymerase chain reaction (qPCR). In some embodiments, the genotype device is a microarray. In some embodiments, the at least one polymorphism is associated with stricturing disease and is selected from the group consisting of rs7416358G, rs1070444A, rs11749180A, 12-54819630-G-INSERTION, rs12496281G, rs11171747C, rs116714418A, rs111455641G, rs9480689G, rs6879067A, rs11128532A, rs177665C, rs10775375A, rs6801634A, rs6962616A, rs7220814G, rs4325270T, rs768755T, rs17758350A, rs9480689G, rs525850A, rs4325270T, rs6962616A, rs10265554G, rs634641G, rs1493871G, rs12669698G, rs4332037A, rs17697480G, rs9480689G, rs6074737A, rs904910G, rs12972487A, rs445417A, rs63562C, rs7416358G, rs177665C, rs1070444A, rs10912583A, rs12914919G, rs2854725C, rs9480689G, rs71472147A, rs72939578A, rs658795A, rs17758350A, rs144260901A, rs10801129C, rs1702870A, rs10912583A, rs2452822C, rs7774349A, rs4705272G, rs117946479A, rs936126A, rs634641G, rs2314737G, rs3002685G, rs634641G, rs10134119T, rs3808240C, rs1890843G, and rs11829981A. In some embodiments, the at least one polymorphism is associated with internal penetrating disease and is selected from the group consisting of rs12496281G, rs2383184G, rs144260901A, rs6801634A, rs2383184G, and rs2954756G. In some embodiments, the at least one polymorphism is located at nucleoposition 26 or 31 within any one of SEQ ID NOS: 1-82. In some embodiments, the genotype is detected by a process comprising: (a) contacting the sample obtained from the subject with a nucleic acid sequence comprising a detectable moiety, the nucleic acid sequence capable of hybridizing to at least 20 contiguous nucleobases between nucleobase 16 and nucleobase 46 of at least one of SEQ ID NOS: 13-82; and (b) detecting binding between the nucleic acid sequence and the at least 20 contiguous nucleobases between nucleobase 16 and nucleobase 46 of at least one of SEQ ID NOS: 13-82. In some embodiments, the genotype is detected by sequencing genetic information contained in the sample obtained from the subject. In some embodiments, the methods further comprise determining whether the subject has or will develop at least one of a non-response and a loss-of-response to a standard treatment. In some embodiments, the standard treatment is selected from the group consisting of glucocorticosteriods, anti-TNF therapy, anti-a4-b7 therapy (vedolizumab), anti-IL12p40 therapy (ustekinumab), Thalidomide, and Cytoxin. In some embodiments, the therapeutic agent is a modulator of a gene or gene expression product expressed from the gene, the gene selected from group consisting of X—C Motif Chemokine Ligand 1 (XCL1), Dermatopontin (DPT), TNF Superfamily Member 4 (TNFSF4), C-Type Lectin Like 1 (CLECL1), CD69 Molecule (CD69), Fins Related Tyrosine Kinase 1 (FLT1), Mitogen-Activated Protein Kinase Kinase Kinase Kinase 4 (MAP4K4), Prostaglandin E Receptor 4 (PTGER4), interleukin 18 receptor 1 (IL18R1). 6-Phosphofructo-2-Kinase/Fructose-2,6-Biphosphatase 3 (PFKFB3), Interleukin 18 Receptor Accessory Protein (IL18RAP), Adenylate Cyclase 7 (ADCY7), B Lymphoid Tyrosine Kinase (BLK), G Protein-Coupled Receptor 65 (GPR65), Sprouty Related EVH1 Domain Containing 2 (SPRED2), Src Kinase Associated Phosphoprotein 2 (SKAP2), CD30 ligand (CD30L), Receptor Interacting Serine/Threonine Kinase 2 (RIPK2), and TNF Ligand Superfamily Member 15 (TL1A), an a combination thereof. In some embodiments, the modulator of the gene or gene expression product is selected from the group consisting of an antibody or antigen-binding fragment thereof, a small molecule, or a peptide. In some embodiments, the modulator of the gene or gene expression product is an agonist or a partial agonist. In some embodiments, the modulator of the gene or gene expression product is an antagonist or a partial antagonist. In some embodiments, the modulator of the gene or gene expression product is an allosteric modulator.

Aspects disclosed provide methods of treating a severe form of Crohn's disease (CD) in a subject, the method comprising: (a) obtaining a sample from a subject; (b) contacting the sample with an assay adapted to detect a genotype in the sample; and (c) administering to the subject a therapeutically effective amount of a therapeutic agent, provided the a genotype is detected in the sample obtained from the subject, the genotype comprising at least one polymorphism selected from the group consisting of rs7416358G, rs1070444A, rs11749180A, 12-54819630-G-INSERTION, rs12496281G, rs11171747C, rs116714418A, rs111455641G, rs9480689G, rs6879067A, rs11128532A, rs177665C, rs10775375A, rs6801634A, rs6962616A, rs7220814G, rs4325270T, rs768755T, rs17758350A, rs9480689G, rs525850A, rs4325270T, rs6962616A, rs10265554G, rs634641G, rs1493871G, rs12669698G, rs4332037A, rs17697480G, rs9480689G, rs6074737A, rs904910G, rs12972487A, rs445417A, rs63562C, rs7416358G, rs177665C, rs1070444A, rs10912583A, rs12914919G, rs2854725C, rs9480689G, rs71472147A, rs72939578A, rs658795A, rs17758350A, rs144260901A, rs10801129C, rs1702870A, rs10912583A, rs2452822C, rs7774349A, rs4705272G, rs117946479A, rs936126A, rs634641G, rs2314737G, rs3002685G, rs634641G, rs10134119T, rs3808240C, rs1890843G, and rs11829981A, and a combination thereof. In some embodiments, the assay is a genotyping device. In some embodiments, the genotyping device is a sequencer. In some embodiments, the genotyping device is quantitative polymerase chain reaction (qPCR). In some embodiments, the genotype device is a microarray. In some embodiments, the at least one polymorphism is associated with stricturing disease and is selected from the group consisting of rs7416358G, rs1070444A, rs11749180A, 12-54819630-G-INSERTION, rs12496281G, rs11171747C, rs116714418A, rs111455641G, rs9480689G, rs6879067A, rs11128532A, rs177665C, rs10775375A, rs6801634A, rs6962616A, rs7220814G, rs4325270T, rs768755T, rs17758350A, rs9480689G, rs525850A, rs4325270T, rs6962616A, rs10265554G, rs634641G, rs1493871G, rs12669698G, rs4332037A, rs17697480G, rs9480689G, rs6074737A, rs904910G, rs12972487A, rs445417A, rs63562C, rs7416358G, rs177665C, rs1070444A, rs10912583A, rs12914919G, rs2854725C, rs9480689G, rs71472147A, rs72939578A, rs658795A, rs17758350A, rs144260901A, rs10801129C, rs1702870A, rs10912583A, rs2452822C, rs7774349A, rs4705272G, rs117946479A, rs936126A, rs634641G, rs2314737G, rs3002685G, rs634641G, rs10134119T, rs3808240C, rs1890843G, and rs11829981A. In some embodiments, the at least one polymorphism is associated with stricturing disease and is selected from the group consisting of rs7416358G, rs1070444A, rs11749180A, 12-54819630-G-INSERTION, rs12496281G, rs11171747C, rs116714418A, rs111455641G, rs9480689G, rs6879067A, rs11128532A, rs177665C, rs10775375A, rs6801634A, rs6962616A, rs7220814G, rs4325270T, rs768755T, rs17758350A, rs9480689G, rs525850A, rs4325270T, rs6962616A, rs10265554G, rs634641G, rs1493871G, rs12669698G, rs4332037A, rs17697480G, rs9480689G, rs6074737A, rs904910G, rs12972487A, rs445417A, rs63562C, rs7416358G, rs177665C, rs1070444A, rs10912583A, rs12914919G, rs2854725C, rs9480689G, rs71472147A, rs72939578A, rs658795A, rs17758350A, rs144260901A, rs10801129C, rs1702870A, rs10912583A, rs2452822C, rs7774349A, rs4705272G, rs117946479A, rs936126A, rs634641G, rs2314737G, rs3002685G, rs634641G, rs10134119T, rs3808240C, rs1890843G, and rs11829981A. In some embodiments, the genotype device is a microarray. In some embodiments, the at least one polymorphism is associated with internal penetrating disease and is selected from the group consisting of rs12496281G, rs2383184G, rs144260901A, rs6801634A, rs2383184G, and rs2954756G. In some embodiments, the at least one polymorphism is located at nucleoposition 26 or 31 within any one of SEQ ID NOS: 1-82. In some embodiments, the genotype is detected by a process comprising: (a) contacting the sample obtained from the subject with a nucleic acid sequence comprising a detectable moiety, the nucleic acid sequence capable of hybridizing to at least 20 contiguous nucleobases between nucleobase 16 and nucleobase 46 of at least one of SEQ ID NOS: 13-82; and (b) detecting binding between the nucleic acid sequence and the at least 20 contiguous nucleobases between nucleobase 16 and nucleobase 46 of at least one of SEQ ID NOS: 13-82. In some embodiments, the genotype is detected by sequencing genetic information contained in the sample obtained from the subject. In some embodiments, the methods further comprise determining whether the subject has or will develop at least one of a non-response and a loss-of-response to a standard treatment. In some embodiments, the standard treatment is selected from the group consisting of glucocorticosteriods, anti-TNF therapy, anti-a4-b7 therapy (vedolizumab), anti-IL12p40 therapy (ustekinumab), Thalidomide, and Cytoxin. In some embodiments, the therapeutic agent is a modulator of a gene or gene expression product expressed from the gene, the gene selected from group consisting of X—C Motif Chemokine Ligand 1 (XCL1), Dermatopontin (DPT), TNF Superfamily Member 4 (TNFSF4), C-Type Lectin Like 1 (CLECL1), CD69 Molecule (CD69), Fins Related Tyrosine Kinase 1 (FLT1), Mitogen-Activated Protein Kinase Kinase Kinase Kinase 4 (MAP4K4), Prostaglandin E Receptor 4 (PTGER4), interleukin 18 receptor 1 (IL18R1). 6-Phosphofructo-2-Kinase/Fructose-2,6-Biphosphatase 3 (PFKFB3), Interleukin 18 Receptor Accessory Protein (IL18RAP), Adenylate Cyclase 7 (ADCY7), B Lymphoid Tyrosine Kinase (BLK), G Protein-Coupled Receptor 65 (GPR65), Sprouty Related EVH1 Domain Containing 2 (SPRED2), Src Kinase Associated Phosphoprotein 2 (SKAP2), CD30 ligand (CD30L), Receptor Interacting Serine/Threonine Kinase 2 (RIPK2), and TNF Ligand Superfamily Member 15 (TL1A), an a combination thereof. In some embodiments, the modulator of the gene or gene expression product is selected from the group consisting of an antibody or antigen-binding fragment thereof, a small molecule, or a peptide. In some embodiments, the modulator of the gene or gene expression product is an agonist or a partial agonist. In some embodiments, the modulator of the gene or gene expression product is an antagonist or a partial antagonist. In some embodiments, the modulator of the gene or gene expression product is an allosteric modulator.

Aspects disclosed provide methods of treating a severe form of Crohn's disease (CD) in a subject, the method comprising: (a) contacting a sample obtained from a subject with an assay adapted to detect a genotype in the sample; and (b) administering to the subject a therapeutically effective amount of a therapeutic agent, provided the a genotype is detected in the sample obtained from the subject, the genotype comprising at least one polymorphism selected from the group consisting of rs7416358G, rs1070444A, rs11749180A, 12-54819630-G-INSERTION, rs12496281G, rs11171747C, rs116714418A, rs111455641G, rs9480689G, rs6879067A, rs11128532A, rs177665C, rs10775375A, rs6801634A, rs6962616A, rs7220814G, rs4325270T, rs768755T, rs17758350A, rs9480689G, rs525850A, rs4325270T, rs6962616A, rs10265554G, rs634641G, rs1493871G, rs12669698G, rs4332037A, rs17697480G, rs9480689G, rs6074737A, rs904910G, rs12972487A, rs445417A, rs63562C, rs7416358G, rs177665C, rs1070444A, rs10912583A, rs12914919G, rs2854725C, rs9480689G, rs71472147A, rs72939578A, rs658795A, rs17758350A, rs144260901A, rs10801129C, rs1702870A, rs10912583A, rs2452822C, rs7774349A, rs4705272G, rs117946479A, rs936126A, rs634641G, rs2314737G, rs3002685G, rs634641G, rs10134119T, rs3808240C, rs1890843G, and rs11829981A, and a combination thereof. In some embodiments, the assay is a genotyping device. In some embodiments, the genotyping device is a sequencer. In some embodiments, the genotyping device is quantitative polymerase chain reaction (qPCR). In some embodiments, the genotype device is a microarray. In some embodiments, the at least one polymorphism is associated with stricturing disease and is selected from the group consisting of rs7416358G, rs1070444A, rs11749180A, 12-54819630-G-INSERTION, rs12496281G, rs11171747C, rs116714418A, rs111455641G, rs9480689G, rs6879067A, rs11128532A, rs177665C, rs10775375A, rs6801634A, rs6962616A, rs7220814G, rs4325270T, rs768755T, rs17758350A, rs9480689G, rs525850A, rs4325270T, rs6962616A, rs10265554G, rs634641G, rs1493871G, rs12669698G, rs4332037A, rs17697480G, rs9480689G, rs6074737A, rs904910G, rs12972487A, rs445417A, rs63562C, rs7416358G, rs177665C, rs1070444A, rs10912583A, rs12914919G, rs2854725C, rs9480689G, rs71472147A, rs72939578A, rs658795A, rs17758350A, rs144260901A, rs10801129C, rs1702870A, rs10912583A, rs2452822C, rs7774349A, rs4705272G, rs117946479A, rs936126A, rs634641G, rs2314737G, rs3002685G, rs634641G, rs10134119T, rs3808240C, rs1890843G, and rs11829981A. In some embodiments, the at least one polymorphism is associated with internal penetrating disease and is selected from the group consisting of rs12496281G, rs2383184G, rs144260901A, rs6801634A, rs2383184G, and rs2954756G. In some embodiments, the at least one polymorphism is located at nucleoposition 26 or 31 within any one of SEQ ID NOS: 1-82. In some embodiments, the genotype is detected by a process comprising: (a) contacting the sample obtained from the subject with a nucleic acid sequence comprising a detectable moiety, the nucleic acid sequence capable of hybridizing to at least 20 contiguous nucleobases between nucleobase 16 and nucleobase 46 of at least one of SEQ ID NOS: 13-82; and (b) detecting binding between the nucleic acid sequence and the at least 20 contiguous nucleobases between nucleobase 16 and nucleobase 46 of at least one of SEQ ID NOS: 13-82. In some embodiments, the genotype is detected by sequencing genetic information contained in the sample obtained from the subject. In some embodiments, the methods further comprise determining whether the subject has or will develop at least one of a non-response and a loss-of-response to a standard treatment. In some embodiments, the standard treatment is selected from the group consisting of glucocorticosteriods, anti-TNF therapy, anti-a4-b7 therapy (vedolizumab), anti-IL12p40 therapy (ustekinumab), Thalidomide, and Cytoxin. In some embodiments, the therapeutic agent is a modulator of a gene or gene expression product expressed from the gene, the gene selected from group consisting of X—C Motif Chemokine Ligand 1 (XCL1), Dermatopontin (DPT), TNF Superfamily Member 4 (TNFSF4), C-Type Lectin Like 1 (CLECL1), CD69 Molecule (CD69), Fins Related Tyrosine Kinase 1 (FLT1), Mitogen-Activated Protein Kinase Kinase Kinase Kinase 4 (MAP4K4), Prostaglandin E Receptor 4 (PTGER4), interleukin 18 receptor 1 (IL18R1). 6-Phosphofructo-2-Kinase/Fructose-2,6-Biphosphatase 3 (PFKFB3), Interleukin 18 Receptor Accessory Protein (IL18RAP), Adenylate Cyclase 7 (ADCY7), B Lymphoid Tyrosine Kinase (BLK), G Protein-Coupled Receptor 65 (GPR65), Sprouty Related EVH1 Domain Containing 2 (SPRED2), Src Kinase Associated Phosphoprotein 2 (SKAP2), CD30 ligand (CD30L), Receptor Interacting Serine/Threonine Kinase 2 (RIPK2), and TNF Ligand Superfamily Member 15 (TL1A), an a combination thereof. In some embodiments, the modulator of the gene or gene expression product is selected from the group consisting of an antibody or antigen-binding fragment thereof, a small molecule, or a peptide. In some embodiments, the modulator of the gene or gene expression product is an agonist or a partial agonist. In some embodiments, the modulator of the gene or gene expression product is an antagonist or a partial antagonist. In some embodiments, the modulator of the gene or gene expression product is an allosteric modulator.

DETAILED DESCRIPTION

The present disclosure provides methods and systems for characterizing severe forms of CD that involve at least one stricturing, penetrating, and stricturing and penetrating disease phenotypes. Multiple case-control univariate analyses were performed comparing these subclinical phenotypes of CD that revealed genotypes and serological markers useful for characterizing severe forms of CD. The genotypes and serologies described can be detected in genetic material in a sample obtained from a subject. The genotypes and serologies detected in a sample obtained from a subject can be used to identify a risk that the subject may develop a severe form of CD, and in some cases, to pinpoint where in the subject the severe CD may manifest. The subjects identified to be at risk for developing severe forms of CD using the methods described herein are prescribed or administered a targeted therapeutic therapy (e.g., targeting Prolactin signaling, autophagy, and JAK/STAT pathways).

Subject

The subject disclosed herein can be a mammal, such as for example a mouse, rat, guinea pig, rabbit, non-human primate, or farm animal. In some instances, the subject is human. In some instances, the subject is a patient who is diagnosed with the disease or condition disclosed herein. In some instances, the subject is not diagnosed with the disease or condition. In some instances, the subject is suffering from a symptom related to a disease or condition disclosed herein (e.g., abdominal pain, cramping, diarrhea, rectal bleeding, fever, weight loss, fatigue, loss of appetite, dehydration, and malnutrition, anemia, or ulcers).

In some embodiments, the subject is susceptible to, or is inflicted with, thiopurine toxicity, or a disease caused by thiopurine toxicity (such as pancreatitis or leukopenia). The subject may experience, or is suspected of experiencing, non-response or loss-of-response to a standard treatment (e.g., anti-TNF alpha therapy, anti-a4-b7 therapy (vedolizumab), anti-IL12p40 therapy (ustekinumab), Thalidomide, or Cytoxin).

Disease or Condition

The disease or condition disclosed herein is an inflammatory bowel disease, such as Crohn's disease (CD) or ulcerative colitis (UC). A subject may suffer from fibrosis, fibrostenosis, or a fibrotic disease, either isolated or in combination with an inflammatory disease. In some cases, the CD is severe CD. The severe CD may result from inflammation that has led to the formation of scar tissue in the intestinal wall (fibrostenosis) and/or swelling. In some cases, the severe CD is characterized by the presence of fibrotic and/or inflammatory strictures. The strictures may be determined by computed tomography enterography (CTE), and magnetic resonance imaging enterography (MRE). The disease or condition may be characterized as refractory, which in some cases, means the disease is resistant to a standard treatment (e.g., anti-TNF therapy). Non-limiting examples of standard treatment include glucocorticosteriods, anti-TNF therapy, anti-a4-b7 therapy (vedolizumab), anti-IL12p40 therapy (ustekinumab), Thalidomide, and Cytoxin.

Genotypes

Disclosed herein, in some embodiments are genotypes that are detected in a sample obtained from a subject by analyzing the genetic material in the sample. In some instances, the subject may be human. In some embodiments, the genetic material is obtained from a subject having a disease or condition disclosed herein. In some cases, the genetic material is obtained from blood, serum, plasma, sweat, hair, tears, urine, and other techniques known by one of skill in the art. In some cases, the genetic material is obtained for a biopsy, e.g., from the intestinal track of the subject.

The genotypes of the present disclosure comprise genetic material that is deoxyribonucleic acid (DNA). In some instances, the genotype comprises a denatured DNA molecule or fragment thereof. In some instances, the genotype comprises DNA selected from: genomic DNA, viral DNA, mitochondrial DNA, plasmid DNA, amplified DNA, circular DNA, circulating DNA, cell-free DNA, or exosomal DNA. In some instances, the DNA is single-stranded DNA (ssDNA), double-stranded DNA, denaturing double-stranded DNA, synthetic DNA, and combinations thereof. The circular DNA may be cleaved or fragmented.

The genotypes disclosed herein comprise at least one polymorphisms at a gene or genetic locus described herein. In some instances, the gene or genetic locus is selected from the group consisting of Microtubule Associated Protein Tau (MAPT), Ankyrin 3 (ANK3), Somatostatin Receptor 3 (SSTR3), N(Alpha)-Acetyltransferase 80, NatH Catalytic Subunit (NAT6), Serine/Threonine Kinase 33 (STK33), Importin 5 (IMP5), Teneurin Transmembrane Protein 3 (ODZ3), RNA Polymerase III Subunit A (POLS), Integrin Subunit Alpha 6 (ITGA6), Fatty Acyl-CoA Reductase 1 (MLSTD2), Prokineticin 2 (PROK2), RING1 And YY1 Binding Protein (RYBP), Thyroid Stimulating Hormone Receptor (TSHR), RAS Guanyl Releasing Protein 3 (RASGRP3), Pyruvate Dehydrogenase El Beta Subunit (PDHB), Potassium Channel Tetramerization Domain Containing 6 (KCNQ1DN), Cyclin Dependent Kinase Inhibitor 1C (CDKN1C), CUB And Sushi Multiple Domains 1 (CSMD1), Nudix Hydrolase 12 (NUDT12), XK Related 6 (XKR6), Solute Carrier Family 2 Member 13 (SLC2A13), Beta-1,4-N-Acetyl-Galactosaminyltransferase 1

(B4GALNT1), OS9, Endoplasmic Reticulum Lectin (OS9), CTD Small Phosphatase 2 (CTDSP2), ATP23 Metallopeptidase And ATP Synthase Assembly Factor Homolog (XRCC6BP1), N-Acetylated Alpha-Linked Acidic Dipeptidase Like 1 (NAALADL1), Cell Division Cycle Associated 5 (CDCA5), Epidermal Growth Factor (EGF), Methionine Sulfoxide Reductase A (MSRA), Phosphoribosyl Pyrophosphate Synthetase Associated Protein 2 (PRPSAP2), Cytochrome P450 Family 2 Subfamily R Member 1 (CYP2R1), Calcitonin Related Polypeptide Alpha (CALCA), Dopa Decarboxylase (DDC), Calcium Voltage-Gated Channel Auxiliary Subunit Alpha2delta 2 (CACNA2D2), Proline Rich 20B (FLJ40296), Pvt1 Oncogene (PVT1), Zinc Finger Protein 184 (ZNF184), Tyrosine Kinase Non Receptor 1 (TNK1), Metaxin 1 (MTX1), TNF Alpha Induced Protein 3 (TNFAIP3), PERP, TP53 Apoptosis Effector (PERP), Stromal Antigen 3-Like 4 (Pseudogene) (STAG3L4), AUTS2, Activator Of Transcription And Developmental Regulator (AUTS2), Phosphatidylinositol Transfer Protein Beta (PITPNB), Ribosomal Protein L37 (RPL37), Caspase Recruitment Domain Family Member 6 (CARD6), Tetratricopeptide Repeat Domain 33 (TTC33), SPARC (Osteonectin), Cwcv And Kazal Like Domains Proteoglycan 3 (SPOCK3), Annexin A10 (ANXA10), Apolipoprotein B (APOB), BicC Family RNA Binding Protein 1 (BICC1), Nuclear Receptor Coactivator 2 (NCOA2), Programmed Cell Death 11 (PDCD11), Reticulon 4 Interacting Protein 1 (RTN4IP1), Engulfment And Cell Motility 1 (ELMO1), RNA Binding Motif Protein 6 (RBM6), Xylosyltransferase 1 (XYLT1), Neuropilin 2 (NRP2), Myeloma Overexpressed (MYEOV), Cyclin D1(CCND1), Olfactory Receptor Family 51 Subfamily G Member 1 (Gene/Pseudogene) (OR51G1), Olfactory Receptor Family 51 Subfamily A Member 4 (OR51A4), Potassium Voltage-Gated Channel Subfamily H Member 7 (KCNH7), Cell Adhesion Associated, Oncogene Regulated (CDON), RNA Pseudouridine Synthase D4 (RPUSD4), Interferon Epsilon (IFNE1), Methylthioadenosine Phosphorylase (MTAP), Elongator Acetyltransferase Complex Subunit 3 (ELP3), ZFP1 Zinc Finger Protein (ZFP1), Chymotrypsinogen B2 (CTRB2), Tektin 3 (TEKT3), CMT1A Duplicated Region Transcript 4 (CDRT4), SET Domain And Mariner Transposase Fusion Gene (SETMAR), TNF Superfamily Member 4 (TNFSF4), Ribosomal Protein S26 (RPS26), Erb-B2 Receptor Tyrosine Kinase 3 (ERBB3), Ryanodine Receptor 3 (RYR3), Solute Carrier Family 16 Member 10 (SLC16A10), Achaete-Scute Family BHLH Transcription Factor 2 (ASCL2), ATPase Phospholipid Transporting 8A1 (ATP8A1), Regulator Of G Protein Signaling 21 (RGS21), Regulator Of G Protein Signaling 1 (RGS1), Late Cornified Envelope 3E (LCE3E), Late Cornified Envelope 3D (LCE3D), Sulfite Oxidase (SUOX), IKAROS Family Zinc Finger 4 (IKZF4), Ribosomal Protein S26 (RPS26), Extended Synaptotagmin 1 (FAM62A), Myosin Light Chain 6B (MYL6B), SWI/SNF Related, Matrix Associated, Actin Dependent Regulator Of Chromatin Subfamily C Member 2 (SMARCC2), UDP-GlcNAc:BetaGal Beta-1,3-N-Acetylglucosaminyltransferase Like 1 (B3GNTL1), Interleukin 22 Receptor Subunit Alpha 2 (IL22RA2), PR/SET Domain 16 (PRDM16), Cutaneous T Cell Lymphoma-Associated Antigen 1 (CTAGE1), RB Binding Protein 8, Endonuclease (RBBP8), EH Domain Containing 3 (EHD3), Xanthine Dehydrogenase (XDH), BARX Homeobox 2 (BARX2), Methylcrotonoyl-CoA Carboxylase 1 (MCCC1), Solute Carrier Family 38 Member 3 (SLC38A3), G Protein Subunit Alpha 12 (GNAI2), Syntrophin Gamma 1 (SNTG1), Human Immunodeficiency Virus Type I Enhancer Binding Protein 2 (HIVEP2), Androgen Induced 1 (AIG1), BTB Domain Containing 3 (BTBD3), Serine Palmitoyltransferase Long Chain Base Subunit 3 (SPTLC3), RAB3 GTPase Activating Protein Catalytic Subunit 1 (RAB3GAP1), Zinc Finger RANBP2-Type Containing 3 (ZRANB3), Mitogen-Activated Protein Kinase Kinase Kinase 19 (YSK4), RAB3 GTPase Activating Protein Catalytic Subunit 1 (RAB3GAP1), Discoidin Domain Receptor Tyrosine Kinase 2 (DDR2), Fibronectin Leucine Rich Transmembrane Protein 3 (FLRT3), MACRO Domain Containing 2 (MACROD2), Spen Family Transcriptional Repressor (SPEN), Pituitary Tumor-Transforming 1 (PTTG1), ATPase Phospholipid Transporting 10B (Putative) (ATP10B), Solute Carrier Family 6 Member 11 (SLC6A11), X—C Motif Chemokine Ligand 1 (XCL1), Dermatopontin (DPT), Dishevelled Associated Activator Of Morphogenesis 1 (DAAM1), Dimethylarginine Dimethylaminohydrolase 1 (DDAH1), FYVE, RhoGEF And PH Domain Containing 5 (FGD5), Cyclin Dependent Kinase 14 (PFTK1), Splicing Factor 3b Subunit 3 (SF3B3), Inositol 1,4,5-Trisphosphate Receptor Type 2 (ITPR2), Hedgehog Acyltransferase (HHAT), Solute Carrier Family 14 Member 2 (SLC14A2), C-Type Lectin Like 1 (CLECL1), CD69 Molecule (CD69), Mitotic Arrest Deficient 1 Like 1 (MAD1L1), SH3 Domain Containing 19 (SH3D19), BR Serine/Threonine Kinase 1 (BRSK1), R-Spondin 2 (RSPO2), Eukaryotic Translation Initiation Factor 3 Subunit E (EIF3E), Adrenoceptor Beta 2 (ADRB2), SH3 Domain And Tetratricopeptide Repeats 2 (SH3TC2), Heparan Sulfate 6-O-Sulfotransferase 1 (HS6ST1), DNA Methyltransferase 3 Alpha (DNMT3A), Neurotrophic Receptor Tyrosine Kinase 1 (NTRK1), Platelet Endothelial Aggregation Receptor 1 (PEAR1), TEK Receptor Tyrosine Kinase (TEK), Extended Synaptotagmin 1 (FAM62A), Myosin Light Chain 6B (MYL6B), Zinc Finger CCCH-Type Containing 10 (ZC3H1O), Extended Synaptotagmin 1 (FAM62A), Nucleic Acid Binding Protein 2 (OBFC2B), Heparan Sulfate-Glucosamine 3-Sulfotransferase 3A1 (HS3ST3A1), CMT1A Duplicated Region Transcript 15 Pseudogene 1 (CDRT15P) Thyroid Stimulating Hormone Receptor (TSHR), General Transcription Factor IIA Subunit 1 (GTF2A1), Fins Related Tyrosine Kinase 1 (FLT1), Ring Finger Protein 5 Pseudogene 1 (RNF5P1), and Marker Of Proliferation Ki-67 (MKI67). The genotypes disclosed herein are, in some cases, a haplotype. In some instances, the genotype comprises a particular polymorphism, a polymorphism in linkage disequilibrium (LD) therewith, or a combination thereof. In some cases, LD is defined by an $r^2$ of at least or about 0.70, 0.75, 0.80, 0.85, 0.90, or 0.1. The genotypes disclosed herein can comprise at least or about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more polymorphisms.

The polymorphisms described herein can be a single nucleotide polymorphism, such as a single nucleotide polymorphism (SNP). In some instances, the polymorphism is an insertion or a deletion of at least one nucleobase (e.g., an indel). In some instances, the genotype may comprise a copy number variation (CNV), which is a variation in a number of a nucleic acid sequence between individuals in a given population. In some instances, the CNV comprises at least or about two, three, four, five, six, seven, eight, nine, ten, twenty, thirty, forty or fifty nucleic acid molecules. In some instances, the genotype is heterozygous. In some instances, the genotype is homozygous.

The genotypes presented herein, in some cases, are associated with a presence of a serological marker. A serological marker is a type of biomarker, such as an autoantigen, that represent a serological response to microbial antigens in the body of a subject. Non-limiting examples of serological markers include anti-neutrophil cytoplasmic antibody (ANCA), anti-*Saccharomyces cerevisiae* antibody (ASCA), anti-flagellin (CBirl) antibody, and *E. coli* outer membrane porin protein C (OmpC). The serological markers disclosed herein are useful for patient selection for treatment either alone, or in combination with the genotypes disclosed herein. The serological markers disclosed herein are also useful for the diagnosis, prognosis, prevention, treatment, and/or monitoring of the disease or conditions disclosed herein either alone, or in combination with the genotypes disclosed herein.

Genotype Embodiments

Disclosed herein, in some embodiments, are the following genotypes:

1. A genotype comprising at least one polymorphism at a gene or genetic locus. 2. The genotype of embodiment 1, wherein the gene or genetic locus is selected from the group consisting of MAPT, ANK3, C1QTNF6, SSTR3, NAT6, WBSCR16, LOC653375, STK33, IMP5, LOC728191, ODZ3, POLS, ITGA6, MLSTD2, LOC729147, PROK2, RYBP, C14orf145, TSHR, RASGRP3, PDHB, KCTD6, KCNQ1DN, CDKN1C, CSMD1, C5orf30, NUDT12, XKR6, LOC157740, SLC2A13, B4GALNT1, OS9, LOC100130776, CTDSP2, XRCC6BP1, NAALADL1, CDCA5, EGF, MSRA, LOC100132391, PRPSAP2, CYP2R1, CALCA, LOC100129427, DDC, LOC100129060, CACNA2D2, LOC100128485, FLJ40296, LOC100130336, LOC100131830, PVT1, LOC728724, ZNF184, LOC100131289, TNK1, MTX1, TNFAIP3, PERP, STAG3L4, AUTS2, PITPNB, RPL37, CARD6, TTC33. SPOCK3, ANXA10, APOB, LOC728640, BICC1, C6orf58, C6orf190, NCOA2, LOC100130862, PDCD11, C6orf199, FLJ42177, RTN4IP1, LOC64694, ELMO1, RBM6, XYLT1, LOC728222, NRP2, FLJ20309, MYEOV, CCND1, OR51G1, OR51A4, KCNH7, LOC259308, LOC100128556, CDON, RPUSD4, IFNE1, MTAP, ELP3, ZFP1, CTRB2, TEKT3, CDRT4, SETMAR, TNFSF4, LOC730070, RPS26, ERBB3, RYR3, SLC16A10, TH, ASCL2, ATP8A1, LOC389207, RGS21, RGS1, LCE3E, LCE3D, SUOX, IKZF4, FAM62A, MYL6B, SMARCC2, B3GNTL1, IL22RA2, PRDM16, CTAGE1, RBBP8, EHD3, XDH, BARX2, MCCC1, SLC38A3, GNAI2, SNTG1, HIVEP2, AIG1, BTBD3, SPTLC3, RAB3GAP1, ZRANB3, YSK4, DDR2, FLRT3, MACROD2, SPEN, PTTG1, ATP10B, SLC6A11, XCL1, DPT, LOC440181, DAAM1, DDAH1, FGD5, PFTK1, SF3B3, C16orf77, ITPR2, C12orf11, LOC100129235, HHAT, LOC100131669, SLC14A2, CLECL1, CD69, MAD1L1, LOC729979, LOC730018, SH3D19, BRSK1, RSPO2, EIF3E, ADRB2, SH3TC2, HS6ST1, LOC100130768, DNMT3A, NTRK1, PEAR1, TEK, FAM62A, ZC3H10, OBFC2B, LOC100129289, HS3ST3A1, CDRT15P, GTF2A1, FLT, LOC727894. LOC728544, FLJ43582, RNF5P1, MK167, and LOC728327.
3. The genotype embodiments 1-2, wherein the polymorphism is selected from Table 1.
4. The genotype of embodiments 1-3, wherein the genotype comprises at least 2, 3, 4, 5, 6, 7, 8, 9, 10, 11, 12, 13, 14, 15, 16, 17, 18, 19, 20, 21, 22, 23, 24, 25, 26, 27, 28, 29, or 30 polymorphisms selected from Table 1.
5. The genotype of embodiments 1-4, wherein the polymorphism is in linkage disequilibrium (LD) with a polymorphism in Table 1.
6. The genotype of embodiment 5, wherein LD is defined by (i) a D' value of at least about 0.70, or (ii) a D' value of 0 and an $r^2$ value of at least about 0.70.
7. The genotype of embodiment 5, wherein LD is defined by (i) a D' value of at least about 0.80, or (ii) a D' value of 0 and an $r^2$ value of at least about 0.80.
8. The genotype of embodiment 5, wherein LD is defined by (i) a D' value of at least about 0.90, or (ii) a D' value of 0 and an $r^2$ value of at least about 0.90.
9. The genotype of embodiment 5, wherein LD is defined by (i) a D' value of at least about 0.95, or (ii) a D' value of 0 and an $r^2$ value of at least about 0.95.
10. The genotype of embodiments 5-9, wherein the polymorphism is associated with Crohn's disease (CD) as indicated by a P value of at most $1.0\times10^{-4}$.
11. The genotype of embodiment 10, wherein the polymorphism is associated with CD as indicated by a P value of at most $1.0\times10^{-5}$.
12. The genotype of embodiments 10-11, wherein the polymorphism is associated with stricturing disease as indicated by a P value of at most $1.0\times10^{-5}$.
13. The genotype of embodiments 10-12, wherein the polymorphism is associated with penetrating disease as indicated by a P value of at most $1.0\times10^{-5}$.
14. The genotype of embodiments 1-13, wherein the genotype is heterozygous.
15. The genotype of embodiments, 1-13, wherein the genotype is homozygous.
16. The genotype of the previous embodiments, wherein the polymorphism is selected from the group consisting of rs2726797, rs7108993, rs79665096, rs7604404, rs73085878, rs78727269, rs2736352, rs4924935, rs11227112, rs2285043, rs6989059, rs3807552, rs111455641, rs9480689, rs7416358, rs6879067, rs11128532, rs177665, rs11171747, rs10775375, rs6801634, rs1070444, rs116714418, rs6962616, rs7220814, rs4325270, rs768755, rs17758350, rs9480689, rs525850, rs4325270, rs11749180, rs6962616, rs116714418, rs10265554, rs634641, rs1493871, rs12669698, rs4332037, rs17697480, rs9480689, rs6074737, rs904910, rs12972487, rs445417, rs635624, rs7416358, 12-54819630-G-INSERTION, rs177665, rs1070444, rs10912583, rs12914919, rs2854725, rs948068, rs71472147, rs72939578, rs658795, rs17758350, rs144260901, rs10801129, rs1702870, rs10912583, rs2452822, rs7774349, rs4705272, rs117946479, rs936126, rs634641, rs2314737, rs3002685, rs634641, rs12496281, rs10134119, rs3808240, rs1890843, rs11829981, rs12496281, rs2383184, rs144260901, rs6801634, rs2383184, rs2954756, and a polymorphism in LD therewith.
17. The genotype of the previous embodiments, wherein the polymorphism is selected from the group consisting of rs2726797, rs7108993, rs79665096, rs7604404, and any combination thereof.
18. The genotype of the previous embodiments, wherein the polymorphism is selected from the group consisting rs73085878, rs78727269, rs2736352, rs4924935, rs11227112, rs2285043, rs6989059, rs3807552, and any combination thereof.
19. The genotype of the previous embodiments, wherein the polymorphism is selected from the group consisting rs111455641, rs9480689, and any combination thereof.

20. The genotype of the previous embodiments, wherein the polymorphism is selected from the group consisting rs7416358, rs6879067, rs11128532, and any combination thereof.
21. The genotype of the previous embodiments, wherein the polymorphism is selected from the group consisting rs177665, rs11171747, and any combination thereof.
22. The genotype of the previous embodiments, wherein the polymorphism is rs10775375.
23. The genotype of the previous embodiments, wherein the polymorphism is rs6801634.
24. The genotype of the previous embodiments, wherein the polymorphism is selected from the group consisting rs1070444, rs116714418, rs6962616, rs7220814, rs4325270, rs768755, and any combination thereof.
25. The genotype of the previous embodiments, wherein the polymorphism is selected from the group consisting rs17758350, rs9480689, rs525850, rs4325270, and any combination thereof.
26. The genotype of the previous embodiments, wherein the polymorphism is selected from the group consisting rs11749180, rs6962616, rs116714418, rs10265554, rs634641, rs1493871, rs12669698, and any combination thereof.
27. The genotype of the previous embodiments, wherein the polymorphism is rs4332037.
28. The genotype of the previous embodiments, wherein the polymorphism is selected from the group consisting rs17697480, rs9480689, and any combination thereof.
29. The genotype of the previous embodiments, wherein the polymorphism is selected from the group consisting rs6074737, rs904910, rs12972487, rs445417, and any combination thereof.
30. The genotype of the previous embodiments, wherein the polymorphism is selected from the group consisting rs635624, rs7416358, and any combination thereof.
31. The genotype of the previous embodiments, wherein the polymorphism is selected from the group consisting 12-54819630-G-INSERTION, rs177665, and any combination thereof.
32. The genotype of the previous embodiments, wherein the polymorphism is selected from the group consisting rs1070444, rs10912583, rs12914919, rs2854725, and any combination thereof.
33. The genotype of the previous embodiments, wherein the polymorphism is selected from the group consisting rs948068, rs71472147, rs72939578, rs658795, rs17758350, rs144260901, and any combination thereof.
34. The genotype of the previous embodiments, wherein the polymorphism is selected from the group consisting rs10801129, rs1702870, rs10912583, rs2452822, rs7774349, and any combination thereof.
35. The genotype of the previous embodiments, wherein the polymorphism is selected from the group consisting rs4705272, rs117946479, and any combination thereof.
36. The genotype of the previous embodiments, wherein the polymorphism is rs936126.
37. The genotype of the previous embodiments, wherein the polymorphism is rs634641.
38. The genotype of the previous embodiments, wherein the polymorphism is selected from the group consisting rs2314737, rs3002685, rs634641, and any combination thereof.
39. The genotype of the previous embodiments, wherein the polymorphism is selected from the group consisting rs12496281, rs10134119, rs3808240, and any combination thereof.
40. The genotype of the previous embodiments, wherein the polymorphism is selected from the group consisting rs1890843, rs11829981, and any combination thereof.
41. The genotype of the previous embodiments, wherein the polymorphism is rs12496281.
42. The genotype of the previous embodiments, wherein the polymorphism is selected from the group consisting rs2383184, rs144260901, and any combination thereof.
43. The genotype of the previous embodiments, wherein the polymorphism is selected from the group consisting rs6801634, rs2383184, rs2954756, and any combination thereof.
44. The genotype of embodiment 16-43, wherein the polymorphism at rs2726797 comprises a C allele at nucleoposition 26 within SEQ ID NO: 1.
45. The genotype of embodiment 16-43, wherein the polymorphism at rs7108993 comprises a C allele at nucleoposition 26 within SEQ ID NO: 2.
46. The genotype of embodiment 16-43, wherein the polymorphism at rs79665096 comprises an A allele at nucleoposition 26 within SEQ ID NO: 3.
47. The genotype of embodiment 16-43, wherein the polymorphism at rs7604404 comprises an A allele at nucleoposition 26 within SEQ ID NO: 4.
48. The genotype of embodiment 16-43, wherein the polymorphism at rs73085878 comprises an A allele at nucleoposition 26 within SEQ ID NO: 5.
49. The genotype of embodiment 16-43, wherein the polymorphism at rs78727269 comprises an A allele at nucleoposition 26 within SEQ ID NO: 6.
50. The genotype of embodiment 16-43, wherein the polymorphism at rs2736352 comprises an A allele at nucleoposition 26 within SEQ ID NO: 7.
51. The genotype of embodiment 16-43, wherein the polymorphism at rs4924935 comprises a G allele at nucleoposition 26 within SEQ ID NO: 8.
52. The genotype of embodiment 16-43, wherein the polymorphism at rs11227112 comprises a G allele at nucleoposition 26 within SEQ ID NO: 9.
53. The genotype of embodiment 16-43, wherein the polymorphism at rs2285043 comprises an A allele at nucleoposition 26 within SEQ ID NO: 10.
54. The genotype of embodiment 16-43, wherein the polymorphism at rs6989059 comprises an A allele at nucleoposition 26 within SEQ ID NO: 11.
55. The genotype of embodiment 16-43, wherein the polymorphism at rs3807552 comprises an A allele at nucleoposition 26 within SEQ ID NO: 12.
56. The genotype of embodiment 16-43, wherein the polymorphism at rs111455641 comprises a G allele at nucleoposition 26 within SEQ ID NO: 13.
57. The genotype of embodiment 16-43, wherein the polymorphism at rs9480689 comprises a G allele at nucleoposition 26 within SEQ ID NO: 14.
58. The genotype of embodiment 16-43, wherein the polymorphism at rs7416358 comprises a G allele at nucleoposition 26 within SEQ ID NO: 15.
59. The genotype of embodiment 16-43, wherein the polymorphism at rs6879067 comprises an A allele at nucleoposition 26 within SEQ ID NO: 16.
60. The genotype of embodiment 16-43, wherein the polymorphism at rs11128532 comprises an A allele at nucleoposition 26 within SEQ ID NO: 17.

61. The genotype of embodiment 16-43, wherein the polymorphism at rs177665 comprises a C allele at nucleoposition 26 within SEQ ID NO: 18.
62. The genotype of embodiment 16-43, wherein the polymorphism at rs11171747 comprises a C allele at nucleoposition 26 within SEQ ID NO: 19.
63. The genotype of embodiment 16-43, wherein the polymorphism at rs10775375 comprises an A allele at nucleoposition 26 within SEQ ID NO: 20.
64. The genotype of embodiment 16-43, wherein the polymorphism at rs6801634 comprises an A allele at nucleoposition 26 within SEQ ID NO: 21.
65. The genotype of embodiment 16-43, wherein the polymorphism at rs1070444 comprises an A allele at nucleoposition 26 within SEQ ID NO: 22.
66. The genotype of embodiment 16-43, wherein the polymorphism at rs116714418 comprises an A allele at nucleoposition 26 within SEQ ID NO: 23.
67. The genotype of embodiment 16-43, wherein the polymorphism at rs6962616 comprises an A allele at nucleoposition 26 within SEQ ID NO: 24.
68. The genotype of embodiment 16-43, wherein the polymorphism at rs7220814 comprises a G allele at nucleoposition 26 within SEQ ID NO: 25.
69. The genotype of embodiment 16-43, wherein the polymorphism at rs4325270 comprises a T allele at nucleoposition 26 within SEQ ID NO: 26.
70. The genotype of embodiment 16-43, wherein the polymorphism at rs768755 comprises a T allele at nucleoposition 26 within SEQ ID NO: 27.
71. The genotype of embodiment 16-43, wherein the polymorphism at rs17758350 comprises an A allele at nucleoposition 31 within SEQ ID NO: 28.
72. The genotype of embodiment 16-43, wherein the polymorphism at rs9480689 comprises a G allele at nucleoposition 26 within SEQ ID NO: 29.
73. The genotype of embodiment 16-43, wherein the polymorphism at rs525850 comprises an A allele at nucleoposition 26 within SEQ ID NO: 30.
74. The genotype of embodiment 3116-43, wherein the polymorphism at rs4325270 comprises a T allele at nucleoposition 26 within SEQ ID NO: 31.
75. The genotype of embodiment 16-43, wherein the polymorphism at rs11749180 comprises an A allele at nucleoposition 26 within SEQ ID NO: 32.
76. The genotype of embodiment 16-43, wherein the polymorphism at rs6962616 comprises an A allele at nucleoposition 26 within SEQ ID NO: 33.
77. The genotype of embodiment 16-43, wherein the polymorphism at rs116714418 comprises an A allele at nucleoposition 26 within SEQ ID NO: 34.
78. The genotype of embodiment 16-43, wherein the polymorphism at rs10265554 comprises a G allele at nucleoposition 26 within SEQ ID NO: 35.
79. The genotype of embodiment 16-43, wherein the polymorphism at rs634641 comprises a G allele at nucleoposition 26 within SEQ ID NO: 36.
80. The genotype of embodiment 16-43, wherein the polymorphism at rs1493871 comprises a G allele at nucleoposition 26 within SEQ ID NO: 37.
81. The genotype of embodiment 16-43 wherein the polymorphism at rs12669698 comprises a G allele at nucleoposition 26 within SEQ ID NO: 38.
82. The genotype of embodiment 16-43, wherein the polymorphism at rs4332037 comprises an A allele at nucleoposition 26 within SEQ ID NO: 39.
83. The genotype of embodiment 16-43, wherein the polymorphism at rs17697480 comprises a G allele at nucleoposition 26 within SEQ ID NO: 40.
84. The genotype of embodiment 16-43, wherein the polymorphism at rs9480689 comprises a G allele at nucleoposition 26 within SEQ ID NO: 41.
85. The genotype of embodiment 16-43, wherein the polymorphism at rs6074737 comprises an A allele at nucleoposition 26 within SEQ ID NO: 42.
86. The genotype of embodiment 16-43, wherein the polymorphism at rs904910 comprises a G allele at nucleoposition 26 within SEQ ID NO: 43.
87. The genotype of embodiment 16-43, wherein the polymorphism at rs12972487 comprises an A allele at nucleoposition 26 within SEQ ID NO: 44.
88. The genotype of embodiment 16-43, wherein the polymorphism at rs445417 comprises an A allele at nucleoposition 26 within SEQ ID NO: 45.
89. The genotype of embodiment 16-43, wherein the polymorphism at rs635624 comprises a C allele at nucleoposition 26 within SEQ ID NO: 46.
90. The genotype of embodiment 16-43, wherein the polymorphism at rs7416358 comprises a G allele at nucleoposition 26 within SEQ ID NO: 47.
91. The genotype of embodiment 16-43, wherein the polymorphism at 12-54819630-G-INSERTION comprises an insertion of a G at nucleoposition 26 within SEQ ID NO: 48.
92. The genotype of embodiment 16-43, wherein the polymorphism at rs177665 comprises a C allele at nucleoposition 26 within SEQ ID NO: 49.
93. The genotype of embodiment 16-43, wherein the polymorphism at rs1070444 comprises an A allele at nucleoposition 26 within SEQ ID NO: 50.
94. The genotype of embodiment 16-43, wherein the polymorphism at rs10912583 comprises an A allele at nucleoposition 26 within SEQ ID NO: 51.
95. The genotype of embodiment 3116-43, wherein the polymorphism at rs12914919 comprises a G allele at nucleoposition 26 within SEQ ID NO: 52.
96. The genotype of embodiment 16-43, wherein the polymorphism at rs2854725 comprises a C allele at nucleoposition 26 within SEQ ID NO: 53.
97. The genotype of embodiment 16-43, wherein the polymorphism at rs9480689 comprises a G allele at nucleoposition 26 within SEQ ID NO: 54.
98. The genotype of embodiment 16-43, wherein the polymorphism at rs71472147 comprises an A allele at nucleoposition 26 within SEQ ID NO: 55.
99. The genotype of embodiment 16-43, wherein the polymorphism at rs72939578 comprises an A allele at nucleoposition 31 within SEQ ID NO: 56.
100. The genotype of embodiment 16-43, wherein the polymorphism at rs658795 comprises an A allele at nucleoposition 26 within SEQ ID NO: 57.
101. The genotype of embodiment 16-43, wherein the polymorphism at rs17758350 comprises an A allele at nucleoposition 31 within SEQ ID NO: 58.
102. The genotype of embodiment 16-43, wherein the polymorphism at rs144260901 comprises an A allele at nucleoposition 31 within SEQ ID NO: 59.
103. The genotype of embodiment 16-43, wherein the polymorphism at rs10801129 comprises a C allele at nucleoposition 26 within SEQ ID NO: 60.
104. The genotype of embodiment 16-43, wherein the polymorphism at rs1702870 comprises an A allele at nucleoposition 26 within SEQ ID NO: 61.

105. The genotype of embodiment 16-43, wherein the polymorphism at rs10912583 comprises an A allele at nucleoposition 26 within SEQ ID NO: 62.
106. The genotype of embodiment 16-43, wherein the polymorphism at rs2452822 comprises a C allele at nucleoposition 31 within SEQ ID NO: 63.
107. The genotype of embodiment 16-43, wherein the polymorphism at rs7774349 comprises an A allele at nucleoposition 26 within SEQ ID NO: 64.
108. The genotype of embodiment 16-43, wherein the polymorphism at rs4705272 comprises a G allele at nucleoposition 26 within SEQ ID NO: 65.
109. The genotype of embodiment 16-43, wherein the polymorphism at rs117946479 comprises an A allele at nucleoposition 31 within SEQ ID NO: 66.
110. The genotype of embodiment 16-43, wherein the polymorphism at rs936126 comprises an A allele at nucleoposition 26 within SEQ ID NO: 67.
111. The genotype of embodiment 16-43, wherein the polymorphism at rs634641 comprises a G allele at nucleoposition 26 within SEQ ID NO: 68.
112. The genotype of embodiment 16-43, wherein the polymorphism at rs2314737 comprises a G allele at nucleoposition 26 within SEQ ID NO: 69.
113. The genotype of embodiment 16-43, wherein the polymorphism at rs3002685 comprises a G allele at nucleoposition 26 within SEQ ID NO: 70.
114. The genotype of embodiment 16-43, wherein the polymorphism at rs634641 comprises a G allele at nucleoposition 26 within SEQ ID NO: 71.
115. The genotype of embodiment 16-43, wherein the polymorphism at rs12496281 comprises a G allele at nucleoposition 26 within SEQ ID NO: 72.
116. The genotype of embodiment 16-43, wherein the polymorphism at rs10134119 comprises a T allele at nucleoposition 26 within SEQ ID NO: 73.
117. The genotype of embodiment 16-43, wherein the polymorphism at rs3808240 comprises a C allele at nucleoposition 26 within SEQ ID NO: 74.
118. The genotype of embodiment 16-43, wherein the polymorphism at rs1890843 comprises a G allele at nucleoposition 26 within SEQ ID NO: 75.
119. The genotype of embodiment 16-43, wherein the polymorphism at rs11829981 comprises an A allele at nucleoposition 26 within SEQ ID NO: 76.
120. The genotype of embodiment 16-43, wherein the polymorphism at rs12496281 comprises a G allele at nucleoposition 26 within SEQ ID NO: 77.
121. The genotype of embodiment 16-43, wherein the polymorphism at rs2383184 comprises a G allele at nucleoposition 26 within SEQ ID NO: 78.
122. The genotype of embodiment 16-43, wherein the polymorphism at rs144260901 comprises an A allele at nucleoposition 31 within SEQ ID NO: 79.
123. The genotype of embodiment 16-43, wherein the polymorphism at rs6801634 comprises an A allele at nucleoposition 26 within SEQ ID NO: 80.
124. The genotype of embodiment 16-43, wherein the polymorphism at rs2383184 comprises a G allele at nucleoposition 26 within SEQ ID NO: 81.
125. The genotype of embodiment 16-43, wherein the polymorphism at rs2954756 comprises a G allele at nucleoposition 26 within SEQ ID NO: 82.

Aspects disclosed herein provide genotypes that are associated with, and therefore, indicative of, a subject having or being susceptible (e.g., at risk of) to developing a particular disease or condition, or a subclinical phenotype thereof. Table 1 provides polymorphisms significantly associated with non-stricturing and non-penetrating diseases (B1), stricturing (B2a), stricturing and internal penetrating (B2b), and isolated internal penetrating (B3). In some cases, associations between the polymorphism and the disease location in the ileal region of the intestine (L1), colon (L2), and colonic region of the intestine are also provided in Table 1. "CH" as used herein refers to the human chromosome on which the polymorphism is located. "BP" as used herein refers to the base pair location of the polymorphism on the human chromosome provided. "Al" as used herein refers to the minor allele of the polymorphism. "OR" as used herein refers to the odds ratio. An odds ratio provides a quantification of a strength of an association between the polymorphism and the subclinical phenotype within the studied population using a logistic regression. If OR<1, the minor allele correlates to a reduced risk of a patient exhibiting the listed phenotype. If OR>1 the minor allele correlates to an increased risk of a patient exhibiting the listed phenotype. "MAF" as used herein refers to the minor allele frequency in the studied population.

TABLE 1

Polymorphisms Associated with Subclinical Phenotypes of Severe CD

| Location | rs_id | SNP | CHR | BP | A1 | OR | P | MAF | Gene/ Locus | ss to rs Orientation/ Strand | 5' SEQ ID NO | 3' SEQ ID NO |
|---|---|---|---|---|---|---|---|---|---|---|---|---|
| B1 vs Ctrl | | | | | | | | | | | | |
| all | rs7108993 | rs7108993 | 11 | 8447193 | C | 0.771 | <1.0E−5 | 0.4187 | STK33 | fwd/T | 400 | 633 |
| all | rs7604404 | rs7604404 | 2 | 173308318 | A | 1.407 | <1.0E−5 | 0.1433 | ITGA6 | fwd/T | 413 | 646 |
| all | rs9880789 | rs9880789 | 3 | 71987258 | G | 1.418 | <1.0E−5 | 0.1027 | PROK2 \| RYBP | fwd/B | 421 | 654 |
| all | rs2726797 | rs2726797 | 4 | 183230887 | C | 0.7326 | <1.0E−5 | 0.2522 | LOC728191 \| ODZ3 | rev/B | 450 | 683 |
| all | rs79665096 | imm_10_61734528 | 10 | 62064522 | A | 0.2747 | <1.0E−5 | 0.01858 | ANK3 | rev/ | 485 | 718 |
| all | rs2675534 | rs2675534 | 4 | 183239761 | A | 0.703 | <1.0E−5 | 0.2059 | LOC728191 \| ODZ3 | rev/T | 503 | 736 |
| all | rs10769905 | rs10769905 | 11 | 8441716 | G | 0.774 | <1.0E−5 | 0.4172 | STK33 | fwd/B | 504 | 737 |
| all | rs2675537 | rs2675537 | 4 | 183237891 | C | 0.7388 | <1.0E−5 | 0.2091 | LOC728191 \| ODZ3 | rev/ | 505 | 738 |

TABLE 1-continued

Polymorphisms Associated with Subclinical Phenotypes of Severe CD

| Location | rs_id | SNP | CHR | BP | A1 | OR | P | MAF | Gene/Locus | ss to rs Orientation/Strand | 5' SEQ ID NO | 3' SEQ ID NO |
|---|---|---|---|---|---|---|---|---|---|---|---|---|
| all | rs7069191 | imm_10_62066379 | 10 | 62396373 | A | 0.7453 | <1.0E−5 | 0.204 | LOC729184 | fwd/B | 506 | 739 |
| all | rs17690703 | rs17690703 | 17 | 43925297 | A | 0.7606 | <1.0E−5 | 0.2497 | IMP5 \| MAPT | fwd/B | 507 | 740 |
| all | rs64547 | imm_22_35922450 | 22 | 37592504 | A | 1.255 | <1.0E−5 | 0.4321 | C1QTNF6 \| SSTR3 | fwd/B | 508 | 741 |
| all | rs920644 | imm_10_62111562 | 10 | 62441556 | A | 0.7555 | <1.0E−5 | 0.2023 | LOC729184 | fwd/B | 509 | 742 |
| all | rs2285043 | imm_3_50311059 | 3 | 50336055 | A | 6.318 | <1.0E−5 | 0.04332 | NAT6 \| | fwd/B | 510 | 743 |
| all | rs7926320 | rs7926320 | 11 | 13782568 | A | 1.253 | <1.0E−5 | 0.4115 | MLSTD2 \| LOC729147 | fwd/T | 511 | 744 |
| all | rs274700 | rs274700 | 5 | 6728995 | G | 0.6888 | <1.0E−5 | 0.1335 | POLS | rev/T | 512 | 745 |
| all | rs76090253 | chr17: 41358797 | 17 | 44002969 | C | 0.7648 | <1.0E−5 | 0.2176 | LOC100130148 \| MAPT | fwd/T | 513 | 746 |
| all | rs4731019 | imm_7_74118166 | 7 | 74480230 | G | 0.7964 | <1.0E−5 | 0.4533 | WBSCR16 | rev/B | 514 | 747 |
| all | rs4731019 | imm_7_74604123 | 7 | 74766187 | G | 0.7964 | <1.0E−5 | 0.4533 | LOC653375 | rev/B | 515 | 748 |
| all | rs7596259 | rs7596259 | 2 | 173305731 | A | 1.386 | <1.0E−5 | 0.1423 | ITGA6 | fwd/B | 516 | 749 |
| | | | | | B1 vs Ctrl L1 | | | | | | | |
| L1 | rs78727269 | imm_2_33520650 | 2 | 33667146 | A | 2.62 | <1.0E−5 | 0.05436 | RASGRP3 | fwd/B | 401 | 634 |
| L1 | rs73085878 | imm_3_58418103 | 3 | 58443063 | A | 3.751 | <1.0E−5 | 0.02285 | PDHB \| KCTD6 | fwd/T | 451 | 684 |
| L1 | rs13439849 | rs13439849 | 8 | 4049489 | C | 2.155 | <1.0E−5 | 0.08199 | CSMD1 | fwd/ | 517 | 750 |
| L1 | rs76339876 | 1kg_14_80498007 | 14 | 81428254 | C | 2.399 | <1.0E−5 | 0.0556 | TSHR | fwd/ | 518 | 751 |
| L1 | rs12786533 | rs12786533 | 11 | 2896313 | A | 2.449 | <1.0E−5 | 0.0874 | KCNQ1DN \| CDKN1C | fwd/T | 519 | 752 |
| L1 | rs45535733 | 1kg_14_80329007 | 14 | 81259254 | T | 2.334 | <1.0E−5 | 0.05809 | C14orf145 | fwd/ | 520 | 753 |
| L2 | rs77065481 | imm_12_56403034 | 12 | 58116767 | G | 3.093 | <1.0E−5 | 0.0206 | OS9 \| LOC100130776 | fwd/B | 422 | 655 |
| L2 | rs12507356 | rs12507356 | 4 | 110923328 | A | 4.702 | <1.0E−5 | 0.03315 | EGF | fwd/T | 423 | 656 |
| L2 | rs2736352 | 1kg_8_11133963 | 8 | 11096553 | A | 0.6064 | <1.0E−5 | 0.3746 | XKR6 \| LOC157740 | fwd/T | 452 | 685 |
| L2 | rs4924935 | rs4924935 | 17 | 18753870 | G | 1.536 | <1.0E−5 | 0.2966 | LOC100132391 \| PRPSAP2 | fwd/B | 472 | 705 |
| L2 | rs11227112 | rs11227112 | 11 | 64836816 | G | 2.354 | <1.0E−5 | 0.03531 | NAALADL1 \| CDCA5 | fwd/B | 486 | 719 |
| L2 | rs11564222 | imm_12_38645596 | 12 | 40359329 | G | 11.59 | <1.0E−5 | 0.01296 | SLC2A13 | fwd/T | 521 | 754 |
| L2 | rs77505508 | imm_12_56356895 | 12 | 58070628 | A | 3.073 | <1.0E−5 | 0.02087 | B4GALNT1 \| OS9 | fwd/ | 522 | 755 |
| L2 | rs11774569 | 1kg_8_11133464 | 8 | 11096054 | G | 0.6078 | <1.0E−5 | 0.3452 | XKR6 \| LOC157740 | fwd/B | 523 | 756 |
| L2 | rs117135945 | imm_12_56544697 | 12 | 58258430 | G | 2.594 | <1.0E−5 | 0.02797 | CTDSP2 \| XRCC6BP1 | fwd/ | 524 | 757 |
| L2 | rs116402229 | 1kg_5_102724875 | 5 | 102696976 | A | 3.644 | <1.0E−5 | 0.0102 | C5orf30 \| NUDT12 | fwd/T | 525 | 758 |
| L2 | rs13273009 | rs13273009 | 8 | 10234303 | G | 1.585 | <1.0E−5 | 0.2457 | MSRA | fwd/B | 526 | 759 |
| L2 | rs59536295 | seq-rs59536295 | 11 | 14956391 | A | 2.953 | <1.0E−5 | 0.0451 | CYP2R1 \| CALCA | fwd/B | 527 | 760 |
| | | | | | B1 vs Ctrl L3 | | | | | | | |
| L3 | rs6989059 | rs6989059 | 8 | 130118208 | A | 1.494 | <1.0E−5 | 0.1314 | PVT1 \| LOC728724 | fwd/T | 402 | 635 |
| L3 | rs2285043 | imm_3_50311059 | 3 | 50336055 | A | 9.215 | <1.0E−5 | 0.04332 | NAT6 \| | fwd/B | 453 | 686 |
| L3 | rs3807552 | 1kg_7_50578236 | 7 | 50610742 | A | 1.437 | <1.0E−5 | 0.2188 | LOC100129427 \| DDC | rev/T | 487 | 720 |
| L3 | rs12490809 | imm_3_50389408 | 3 | 50414404 | A | 6.634 | <1.0E−5 | 0.0385 | CACNA2D2 | fwd/B | 528 | 761 |
| L3 | rs4731019 | imm_7_74118166 | 7 | 74480230 | G | 0.7499 | <1.0E−5 | 0.4533 | WBSCR16 | rev/B | 529 | 762 |
| L3 | rs4731019 | imm_7_74604123 | 7 | 74766187 | G | 0.7499 | <1.0E−5 | 0.4533 | LOC653375 | rev/B | 530 | 763 |
| L3 | rs3774736 | imm_3_50165114 | 3 | 50190110 | A | 5.041 | <1.0E−5 | 0.04005 | LOC100129060 | fwd/T | 531 | 764 |
| L3 | rs4831929 | rs4831929 | 12 | 76340526 | A | 1.381 | <1.0E−5 | 0.229 | LOC100130336 \| LOC100131830 | rev/B | 532 | 765 |
| L3 | NA | rs2262121 | 9 | 78909677 | C | 0.1058 | <1.0E−5 | 0.4478 | NA | rev/B | 533 | 766 |
| L3 | rs1832696 | rs1832696 | 13 | 55107650 | G | 1.31 | <1.0E−5 | 0.4574 | LOC100128485 \| FLJ40296 | fwd/B | 534 | 767 |
| L3 | rs7926320 | rs7926320 | 11 | 13782568 | A | 1.317 | <1.0E−5 | 0.4115 | MLSTD2 \| LOC729147 | fwd/T | 535 | 768 |
| L3 | rs9468159 | rs9468159 | 6 | 27522374 | A | 1.565 | <1.0E−5 | 0.08056 | ZNF184 \| LOC100131289 | fwd/T | 536 | 769 |
| | | | | | B2a + B2b vs B1 | | | | | | | |
| all | rs111455641 | rs6741481 | 2 | 135874622 | G | 0.6735 | <1.0E−5 | 0.1756 | RAB3GAP1 | fwd/ | 454 | 687 |
| all | rs4954221 | rs4954221 | 2 | 135909462 | A | 0.6756 | <1.0E−5 | 0.1746 | RAB3GAP1 | fwd/T | 537 | 770 |
| all | rs57829242 | chr2: 135700642 | 2 | 135984172 | G | 0.6758 | <1.0E−5 | 0.202 | ZRANB3 | fwd/T | 538 | 771 |
| all | rs17293519 | rs17293519 | 2 | 135803766 | G | 0.6825 | <1.0E−5 | 0.1763 | YSK4 \| RAB3GAP1 | fwd/T | 539 | 772 |

TABLE 1-continued

Polymorphisms Associated with Subclinical Phenotypes of Severe CD

| Location | rs_id | SNP | CHR | BP | A1 | OR | P | MAF | Gene/ Locus | ss to rs Orientation/ Strand | 5' SEQ ID NO | 3' SEQ ID NO |
|---|---|---|---|---|---|---|---|---|---|---|---|---|
| all | NA | rs6999925 | 8 | 80786648 | A | 6.283 | <1.0E−5 | 0.3797 | NA | fwd/T | 540 | 773 |
| all | NA | rs17456596 | 8 | 80783998 | G | 7.926 | <1.0E−5 | 0.4425 | NA | fwd/T | 541 | 774 |
| all | rs7568525 | rs7568525 | 2 | 135849613 | A | 0.6459 | <1.0E−5 | 0.1554 | RAB3GAP1 | fwd/T | 542 | 775 |
| all | rs61087958 | chr2: 135590508 | 2 | 135874038 | A | 0.6815 | <1.0E−5 | 0.1743 | RAB3GAP1 | fwd/B | 543 | 776 |
| B2a + B2b vs B1 L1 | | | | | | | | | | | | |
| L1 | rs9480689 | rs9480689 | 6 | 107024432 | G | 2.915 | <1.0E−5 | 0.1226 | RTN4IP1 | fwd/T | 455 | 688 |
| B2a + B2b vs B1 L2 | | | | | | | | | | | | |
| L2 | rs2684866 | rs2684866 | 1 | 162726281 | A | 3.44 | <1.0E−5 | 0.2454 | DDR2 | fwd/T | 544 | 777 |
| L2 | rs6074737 | rs6074737 | 20 | 14420556 | A | 2.893 | <1.0E−5 | 0.4654 | FLRT3 \| MACROD2 | fwd/T | 545 | 778 |
| L2 | rs904910 | rs904910 | 1 | 16200163 | G | 2.925 | <1.0E−5 | 0.3161 | SPEN | fwd/T | 546 | 779 |
| L3 | rs7416358 | rs7416358 | 1 | 168653857 | G | 0.6526 | <1.0E−5 | 0.328 | XCL1 \| DPT | fwd/B | 392 | 625 |
| L3 | rs6879067 | 1kg_5_159872373 | 5 | 159939795 | A | 1.725 | <1.0E−5 | 0.1964 | PTTG1 \| ATP 10B | fwd/ | 473 | 706 |
| L3 | rs11128532 | rs11128532 | 3 | 10977277 | A | 1.487 | <1.0E−5 | 0.3482 | SLC6A11 | fwd/B | 488 | 721 |
| B2a + B2b vs B3 | | | | | | | | | | | | |
| all | rs11171747 | imm_12_54804675 | 12 | 56518408 | C | 0.5949 | <1.0E−5 | 0.3825 | ZC3H10 \| FAM62A | fwd/B | 403 | 636 |
| all | rs177665 | rs177665 | 7 | 90102196 | C | 0.5855 | <1.0E−5 | 0.4917 | LOC100129289 | rev/ | 456 | 689 |
| all | 12-54819630-G-INSERTION | 12-54819630-G-INSERTION | 12 | 56533363 | I | 0.5963 | <1.0E−5 | 0.3705 | FAM62A | fwd/ | 547 | 780 |
| all | rs112668709 | imm_12_54907064 | 12 | 56620797 | A | 0.5735 | <1.0E−5 | 0.4204 | OBFC2B | fwd/B | 548 | 781 |
| B2a + B2b vs B3 L1 | | | | | | | | | | | | |
| L1 | rs10775375 | rs10775375 | 17 | 13544722 | A | 0.2593 | <1.0E−5 | 0.2867 | HS3ST3A1 \| CDRT15P | fwd/T | 457 | 690 |
| B2a + B2b vs B3 L3 | | | | | | | | | | | | |
| L3 | rs6801634 | rs6801634 | 3 | 4354697 | A | 0.4949 | <1.0E−5 | 0.141 | SETMAR | fwd/T | 458 | 691 |
| L3 | rs7143837 | rs7143837 | 14 | 81640722 | T | 0.4588 | <1.0E−5 | 0.1032 | TSHR \| GTF2A1 | fwd/ | 549 | 782 |
| B2a + B2b vs Ctrl | | | | | | | | | | | | |
| all | rs1070444 | rs1070444 | 5 | 40839644 | A | 1.502 | <1.0E−5 | 0.1343 | RPL37 \| CARD6 | rev/B | 393 | 626 |
| all | rs116714418 | rs1062731 | 22 | 28248840 | A | 0.707 | <1.0E−5 | 0.223 | PITPNB | fwd/B | 404 | 637 |
| all | rs4325270 | rs4325270 | 10 | 60515468 | T | 0.7802 | <1.0E−5 | 0.4591 | LOC728640 \| BICC1 | fwd/ | 416 | 649 |
| all | rs768755 | imm_6_138303642 | 6 | 138261949 | T | 0.7769 | <1.0E−5 | 0.4307 | TNFAIP3 \| PERP | fwd/ | 419 | 652 |
| all | rs11749180 | rs11749180 | 5 | 40745746 | A | 1.458 | <1.0E−5 | 0.14 | TTC33 | fwd/T | 424 | 657 |
| all | rs6962616 | rs6962616 | 7 | 68060815 | A | 0.5406 | <1.0E−5 | 0.08535 | STAG3L4 \| AUTS2 | fwd/B | 489 | 722 |
| all | rs7220814 | 17_7231419 | 17 | 7290695 | G | 1.556 | <1.0E−5 | 0.06822 | TNK1 | fwd/T | 495 | 728 |
| all | rs10265554 | rs10265554 | 7 | 68051712 | G | 0.6152 | <1.0E−5 | 0.09114 | STAG3L4 \| AUTS2 | fwd/T | 550 | 783 |
| all | rs199862238 | imm_1_153447856 | 1 | 155181232 | A | 2.516 | <1.0E−5 | 0.01493 | MTX1 | fwd/ | 551 | 784 |
| all | rs1579609 | imm_6_138299141 | 6 | 138257448 | G | 0.7814 | <1.0E−5 | 0.4073 | TNFAIP3 \| PERP | fwd/B | 552 | 785 |
| all | rs9402929 | imm_6_138302337 | 6 | 138260644 | G | 0.7827 | <1.0E−5 | 0.4074 | TNFAIP3 \| PERP | fwd/B | 553 | 786 |
| all | rs2854725 | rs2854725 | 2 | 21237786 | C | 1.385 | <1.0E−5 | 0.1089 | APOB | rev/B | 554 | 787 |
| all | rs1579610 | imm_6_138299199 | 6 | 138257506 | C | 0.7846 | <1.0E−5 | 0.4077 | TNFAIP3 \| PERP | fwd/T | 555 | 788 |
| all | rs12645719 | rs126457 | 4 | 168576098 | A | 1.265 | <1.0E−5 | 0.3568 | SPOCK3 \| ANXA10 | fwd/B | 556 | 789 |
| B2a + B2b vs Ctrl L1 | | | | | | | | | | | | |
| L1 | rs525850 | imm_61_28020485 | 6 | 127978792 | A | 1.639 | <1.0E−5 | 0.4759 | C6orf58 \| C6orf190 | fwd/B | 409 | 642 |
| L1 | rs4325270 | rs4325270 | 10 | 60515468 | T | 0.6173 | <1.0E−5 | 0.4591 | LOC728640 \| BICC1 | fwd/ | 414 | 647 |
| L1 | rs658795 | imm_6_128029073 | 6 | 127987380 | A | 1.631 | <1.0E−5 | 0.4631 | C6orf58 \| C6orf190 | rev/B | 425 | 658 |
| L1 | rs476148 | imm_6_128029246 | 6 | 127987553 | A | 1.607 | <1.0E−5 | 0.487 | C6orf58 \| C6orf190 | rev/B | 426 | 659 |
| L1 | rs570462 | imm_6_128027316 | 6 | 127985623 | G | 1.607 | <1.0E−5 | 0.4871 | C6orf58 \| C6orf190 | rev/T | 427 | 660 |

TABLE 1-continued

Polymorphisms Associated with Subclinical Phenotypes of Severe CD

| Loca-tion | rs_id | SNP | CHR | BP | A1 | OR | P | MAF | Gene/ Locus | ss to rs Orien-tation/ Strand | 5' SEQ ID NO | 3' SEQ ID NO |
|---|---|---|---|---|---|---|---|---|---|---|---|---|
| L1 | rs568675 | imm_6_128027478 | 6 | 127985785 | G | 1.607 | <1.0E−5 | 0.4871 | C6orf58 \| C6orf190 | rev/B | 428 | 661 |
| L1 | rs474188 | imm_6_128029476 | 6 | 127987783 | C | 1.607 | <1.0E−5 | 0.487 | C6orf58 \| C6orf190 | rev/ | 429 | 662 |
| L1 | rs17758350 | rs17758350 | 8 | 71411688 | A | 1.976 | <1.0E−5 | 0.09848 | NCOA2 \| LOC100130862 | fwd/ | 459 | 692 |
| L1 | rs9480689 | rs9480689 | 6 | 107024432 | G | 1.941 | <1.0E−5 | 0.1226 | RTN4IP1 | fwd/T | 474 | 707 |
| L1 | rs4917389 | rs4917389 | 10 | 105194476 | A | 0.4625 | <1.0E−5 | 0.1473 | PDCD11 | fwd/B | 557 | 790 |
| L1 | rs6568591 | rs6568591 | 6 | 109992884 | G | 1.574 | <1.0E−5 | 0.2874 | C6orf199 | fwd/B | 558 | 791 |
| L1 | rs6925886 | rs6925886 | 6 | 109878515 | A | 1.572 | <1.0E−5 | 0.2877 | FLJ42177 \| C6orf199 | fwd/T | 559 | 792 |
| B2a + B2b vs Ctrl L3 | | | | | | | | | | | | |
| L3 | rs11749180 | rs11749180 | 5 | 40745746 | A | 1.563 | <1.0E−5 | 0.14 | TTC33 | fwd/T | 394 | 627 |
| L3 | rs116714418 | rs1062731 | 22 | 28248840 | A | 0.6567 | <1.0E−5 | 0.223 | PITPNB | fwd/B | 410 | 643 |
| L3 | rs634641 | rs634641 | 11 | 69386588 | G | 3.284 | <1.0E−5 | 0.0385 | MYEOV \| CCND1 | fwd/ | 417 | 650 |
| L3 | rs12669698 | 1kg_7_37404494 | 7 | 37437969 | G | 1.495 | <1.0E−5 | 0.1407 | LOC646942 \| ELMO1 | fwd/B | 420 | 653 |
| L3 | rs1070444 | rs1070444 | 5 | 40839644 | A | 1.556 | <1.0E−5 | 0.1343 | RPL37 \| CARD6 | rev/B | 430 | 663 |
| L3 | rs66863235 | imm_3_49968323 | 3 | 49993319 | G | 0.7162 | <1.0E−5 | 0.4611 | RBM6 | fwd/ | 431 | 664 |
| L3 | rs2080566 | rs2080566 | 2 | 206806379 | A | 1.32 | <1.0E−5 | 0.332 | NRP2 \| FLJ20309 | fwd/B | 432 | 665 |
| L3 | rs768755 | imm_6_138303642 | 6 | 13826149 | T | 0.7561 | <1.0E−5 | 0.4307 | TNFAIP3 \| PERP | fwd/ | 433 | 666 |
| L3 | rs6962616 | rs6962616 | 7 | 68060815 | A | 0.4465 | <1.0E−5 | 0.08535 | STAG3L4 \| AUTS2 | fwd/B | 475 | 708 |
| L3 | rs10265554 | rs10265554 | 7 | 68051712 | G | 0.5317 | <1.0E−5 | 0.09114 | STAG3L4 \| AUTS2 | fwd/T | 496 | 729 |
| L3 | rs1493871 | rs1493871 | 16 | 17882019 | G | 1.521 | <1.0E−5 | 0.1169 | XYLT1 \| LOC728222 | rev/T | 501 | 734 |
| L3 | rs840709 | rs840709 | 11 | 4951958 | G | 1.36 | <1.0E−5 | 0.2803 | OR51G1 \| OR51A4 | fwd/B | 560 | 793 |
| B2a vs B1 | | | | | | | | | | | | |
| all | rs11052804 | imm_12_9786609 | 12 | 9895342 | A | 1.951 | <1.0E−5 | 0.04818 | CLECL1 \| CD69 | fwd/B | 434 | 667 |
| all | rs4332037 | rs4332037 | 7 | 1950809 | A | 0.6438 | <1.0E−5 | 0.1849 | MAD1L1 | fwd/B | 460 | 693 |
| all | rs79665096 | imm_10_61734528 | 10 | 62064522 | A | 3.977 | <1.0E−5 | 0.01858 | ANK3 | rev/ | 561 | 794 |
| B2a vs B1 L1 | | | | | | | | | | | | |
| L1 | rs17697480 | rs17697480 | 16 | 87101424 | G | 3.563 | <1.0E−5 | 0.1392 | LOC729979 \| LOC730018 | fwd/ | 461 | 694 |
| L1 | rs9480689 | rs9480689 | 6 | 107024432 | G | 3.295 | <1.0E−5 | 0.1226 | RTN4IP1 | fwd/T | 476 | 709 |
| B2a vs B1 L2 | | | | | | | | | | | | |
| L2 | rs3736502 | imm_4_152284647 | 4 | 152065197 | A | 10.59 | <1.0E−5 | 0.03985 | SH3D19 | fwd/B | 435 | 668 |
| L2 | rs6074737 | rs6074737 | 20 | 14420556 | A | 3.745 | <1.0E−5 | 0.4654 | FLRT3 \| MACROD2 | fwd/T | 462 | 695 |
| L2 | rs904910 | rs904910 | 1 | 16200163 | G | 3.6 | <1.0E−5 | 0.3161 | SPEN | fwd/T | 477 | 710 |
| L2 | rs12972487 | seq-rs12972487 | 19 | 55817537 | A | 4.896 | <1.0E−5 | 0.0998 | BRSK1 | fwd/B | 490 | 723 |
| L2 | rs445417 | rs445417 | 20 | 14433643 | A | 3.556 | <1.0E−5 | 0.4828 | FLRT3 \| MACROD2 | fwd/T | 497 | 730 |
| L2 | rs12973169 | seq-rs12973169 | 19 | 55817676 | A | 4.186 | <1.0E−5 | 0.1002 | BRSK1 | fwd/T | 562 | 795 |
| B2a vs B1 L3 | | | | | | | | | | | | |
| L3 | rs7416358 | rs7416358 | 1 | 168653857 | G | 0.6406 | <1.0E−5 | 0.328 | XCL1 \| DPT | fwd/B | 405 | 638 |
| L3 | rs635624 | rs635624 | 8 | 109197799 | C | 1.525 | <1.0E−5 | 0.4876 | RSPO2 \| EIF3E | rev/ | 463 | 696 |
| L3 | rs684093 | rs684093 | 8 | 109199355 | G | 1.556 | <1.0E−5 | 0.4779 | RSPO2 \| EIF3E | rev/ | 563 | 796 |
| L3 | rs6879067 | 1kg_5_159872373 | 5 | 159939795 | A | 1.743 | <1.0E−5 | 0.1964 | PTTG1 \| ATP10B | fwd/ | 564 | 797 |
| B2a vs B3 | | | | | | | | | | | | |
| all | 12-54819630-G-INSERTION | 12-54819630-G-INSERTION | 12 | 56533363 | I | 0.5306 | <1.0E−5 | 0.3705 | FAM62A | fwd/ | 395 | 628 |
| all | rs7987649 | rs7987649 | 13 | 28894415 | G | 1.754 | <1.0E−5 | 0.3199 | FLT1 | fwd/T | 436 | 669 |
| all | rs177665 | rs177665 | 7 | 90102196 | C | 0.5591 | <1.0E−5 | 0.4917 | LOC100129289 | rev/ | 478 | 711 |
| all | rs11171747 | imm_12_54804675 | 12 | 56518408 | C | 0.5458 | <1.0E−5 | 0.3825 | ZC3H10 \| FAM62A | fwd/B | 565 | 798 |

TABLE 1-continued

| Polymorphisms Associated with Subclinical Phenotypes of Severe CD | | | | | | | | | | | | |
|---|---|---|---|---|---|---|---|---|---|---|---|---|
| Location | rs_id | SNP | CHR | BP | A1 | OR | P | MAF | Gene/ Locus | ss to rs Orientation/ Strand | 5' SEQ ID NO | 3' SEQ ID NO |
| all | rs112668709 | imm_12_54907064 | 12 | 56620797 | A | 0.5224 | <1.0E−5 | 0.4204 | OBFC2B | fwd/B | 566 | 799 |
| all | rs7960225 | imm_12_54851078 | 12 | 56564811 | A | 0.5863 | <1.0E−5 | 0.3565 | SMARCC2 | fwd/T | 567 | 800 |
| B2a vs B3 L1 | | | | | | | | | | | | |
| L1 | rs10775375 | rs10775375 | 17 | 13544722 | A | 0.2558 | <1.0E−5 | 0.2867 | HS3ST3A1 \| CDRT15P | fwd/T | 568 | 801 |
| B2a vs B3 L3 | | | | | | | | | | | | |
| L3 | rs7096293 | rs7096293 | 10 | 4241547 | C | 0.5439 | <1.0E−5 | 0.3764 | LOC727894 \| LOC728544 | fwd/T | 569 | 802 |
| B2a vs Ctrl | | | | | | | | | | | | |
| all | rs1070444 | rs1070444 | 5 | 40839644 | A | 1.536 | <1.0E−5 | 0.1343 | RPL37 \| CARD6 | rev/B | 396 | 629 |
| all | rs10912583 | imm_1_171547622 | 1 | 173280999 | A | 0.7262 | <1.0E−5 | 0.3939 | TNFSF4 \| LOC730070 | fwd/B | 406 | 639 |
| all | rs1179180 | rs11749180 | 5 | 40745746 | A | 1.488 | <1.0E−5 | 0.14 | TTC33 | fwd/T | 437 | 670 |
| all | rs12914919 | rs12914919 | 15 | 33693686 | G | 1.852 | <1.0E−5 | 0.0649 | RYR3 | fwd/B | 491 | 724 |
| all | rs2854725 | rs2854725 | 2 | 21237786 | C | 1.478 | <1.0E−5 | 0.1089 | APOB | rev/B | 498 | 731 |
| all | rs772926 | imm_12_54726515 | 12 | 56440248 | A | 4.071 | <1.0E−5 | 0.01006 | RPS26 \| ERBB3 | fwd/B | 570 | 803 |
| B2a vs Ctrl L1 | | | | | | | | | | | | |
| L1 | rs658795 | imm_6_128029073 | 6 | 127987380 | A | 1.746 | <1.0E−5 | 0.4631 | C6orf58 \| C6orf190 | rev/B | 415 | 648 |
| L1 | rs9480689 | rs9480689 | 6 | 107024432 | G | 2.228 | <1.0E−5 | 0.1226 | RTN4IP1 | fwd/T | 464 | 697 |
| L1 | rs71472147 | imm_11_2175557 | 11 | 2218981 | A | 2.046 | <1.0E−5 | 0.1223 | TH \| ASCL2 | fwd/ | 479 | 712 |
| L1 | rs72939578 | 1kg_6_111633302 | 6 | 111526609 | A | 4.254 | <1.0E−5 | 0.01356 | SLC16A10 | fwd/B | 492 | 725 |
| L1 | rs17758350 | rs17758350 | 8 | 71411688 | A | 2.016 | <1.0E−5 | 0.09848 | NCOA2 \| LOC100130862 | fwd/ | 500 | 733 |
| L1 | rs144260901 | imm_9_34751635 | 9 | 34761635 | A | 5.049 | <1.0E−5 | 0.01902 | LOC259308 \| LOC100128556 | fwd/ | 502 | 735 |
| L1 | rs525850 | imm_6_128020485 | 6 | 127978792 | A | 1.75 | <1.0E−5 | 0.4759 | C6orf58 \| C6orf190 | fwd/B | 571 | 804 |
| L1 | rs4945759 | rs4945759 | 6 | 107043751 | A | 1.896 | <1.0E−5 | 0.1432 | RTN4IP1 | fwd/T | 572 | 805 |
| L1 | rs476148 | imm_6_128029246 | 6 | 127987553 | A | 1.735 | <1.0E−5 | 0.487 | C6orf58 \| C6orf190 | rev/B | 573 | 806 |
| L1 | rs570462 | imm_6_128027316 | 6 | 127985623 | G | 1.735 | <1.0E−5 | 0.4871 | C6orf58 \| C6orf190 | rev/T | 574 | 807 |
| L1 | rs568675 | imm_6_128027478 | 6 | 127985785 | G | 1.735 | <1.0E−5 | 0.4871 | C6orf58 \| C6orf190 | rev/B | 575 | 808 |
| L1 | rs474188 | imm_6_128029476 | 6 | 127987783 | C | 1.734 | <1.0E−5 | 0.487 | C6orf58 \| C6orf190 | rev/ | 576 | 809 |
| L1 | rs7112535 | imm_11_2175558 | 11 | 2218982 | A | 1.974 | <1.0E−5 | 0.1198 | TH \| ASCL2 | fwd/T | 577 | 810 |
| L1 | rs17594783 | rs17594783 | 4 | 42845691 | G | 2.306 | <1.0E−5 | 0.04582 | ATP8A1 \| LOC389207 | fwd/T | 578 | 811 |
| B2a vs Ctrl L2 | | | | | | | | | | | | |
| L2 | rs10801129 | imm_1_190788214 | 1 | 192521591 | C | 3.292 | <1.0E−5 | 0.2577 | RGS21 \| RGS1 | fwd/B | 465 | 698 |
| L2 | rs6684404 | imm_1_190797238 | 1 | 192530615 | G | 3.769 | <1.0E−5 | 0.2728 | RGS21 \| RGS1 | fwd/T | 579 | 812 |
| L3 | rs10912583 | imm_1_171547622 | 1 | 173280999 | A | 0.6823 | <1.0E−5 | 0.3939 | TNFSF4 \| LOC730070 | fwd/B | 411 | 644 |
| B2a vs Ctrl L3 | | | | | | | | | | | | |
| L3 | rs7774349 | rs7774349 | 6 | 137475858 | A | 0.6782 | <1.0E−5 | 0.4594 | IL22RA2 | fwd/B | 418 | 651 |
| L3 | rs1702870 | imm_12_54743443 | 12 | 56457176 | A | 4.873 | <1.0E−5 | 0.0101 | RPS26 \| ERBB3 | rev/T | 480 | 713 |
| L3 | rs2452822 | imm_12_54714611 | 12 | 56428344 | C | 5.317 | <1.0E−5 | 0.01389 | IKZF4 | fwd/ | 499 | 732 |
| L3 | rs772926 | imm_12_54726515 | 12 | 56440248 | A | 4.833 | <1.0E−5 | 0.01006 | RPS26 \| ERBB3 | fwd/B | 580 | 813 |
| L3 | rs1581007 | imm_12_54747402 | 12 | 56461135 | C | 5.317 | <1.0E−5 | 0.01324 | RPS26 \| ERBB3 | rev/ | 581 | 814 |
| L3 | rs12126248 | imm_1_171549389 | 1 | 17328276 | G | 0.6628 | <1.0E−5 | 0.2734 | TNFSF4 \| LOC730070 | fwd/B | 582 | 815 |
| L3 | rs7224733 | rs7224733 | 17 | 81004770 | G | 0.632 | <1.0E−5 | 0.2238 | B3GNTL1 | fwd/T | 583 | 816 |
| L3 | rs202138565 | 12-54741792-CTC-DELETION | 12 | 56455525 | I | 5.801 | <1.0E−5 | 0.01346 | RPS26 \| ERBB3 | fwd/ | 584 | 817 |
| L3 | rs808896 | imm_12_54691421 | 12 | 56405154 | G | 4.849 | <1.0E−5 | 0.01387 | SUOX \| IKZF4 | fwd/B | 585 | 818 |

TABLE 1-continued

Polymorphisms Associated with Subclinical Phenotypes of Severe CD

| Location | rs_id | SNP | CHR | BP | A1 | OR | P | MAF | Gene/ Locus | ss to rs Orientation/ Strand | 5' SEQ ID NO | 3' SEQ ID NO |
|---|---|---|---|---|---|---|---|---|---|---|---|---|
| L3 | rs1689516 | imm_12_54695787 | 12 | 56409520 | G | 4.849 | <1.0E-5 | 0.01373 | SUOX \| IKZF4 | fwd/T | 586 | 819 |
| L3 | rs1619653 | imm_12_54712844 | 12 | 56426577 | A | 4.849 | <1.0E-5 | 0.0135 | IKZF4 | rev/T | 587 | 820 |
| L3 | rs705706 | imm_12_54722739 | 12 | 56436472 | A | 4.849 | <1.0E-5 | 0.0135 | RPS26 | fwd/B | 588 | 821 |
| L3 | rs772925 | imm_12_54726336 | 12 | 56440069 | A | 4.849 | <1.0E-5 | 0.01359 | RPS26 \| ERBB3 | fwd/B | 589 | 822 |
| L3 | rs1689507 | imm_12_54726968 | 12 | 56440701 | G | 4.849 | <1.0E-5 | 0.01345 | RPS26 \| ERBB3 | rev/T | 590 | 823 |
| L3 | rs1702875 | imm_12_54752220 | 12 | 56465953 | C | 4.849 | <1.0E-5 | 0.01359 | RPS26 \| ERBB3 | rev/B | 591 | 824 |
| L3 | rs7301099 | imm_12_54829965 | 12 | 56543698 | C | 4.825 | <1.0E-5 | 0.01251 | FAM62A \| MYL6B | fwd/B | 592 | 825 |
| L3 | rs773647 | imm_12_54855905 | 12 | 56569638 | G | 4.825 | <1.0E-5 | 0.01246 | SMARCC2 | fwd/ | 593 | 826 |
| L3 | rs72700983 | imm_1_150808526 | 1 | 152541902 | G | 0.6875 | <1.0E-5 | 0.3449 | LCE3E \| LCE3D | fwd/T | 594 | 827 |
| B2b vs B1 | | | | | | | | | | | | |
| all | rs17946479 | 1kg_7_37389853 | 7 | 37423328 | A | 4.244 | <1.0E-5 | 0.01427 | LOC646942 \| ELMO1 | fwd/ | 407 | 640 |
| all | rs4705272 | rs4705272 | 5 | 148237855 | G | 0.5885 | <1.0E-5 | 0.2281 | ADRB2 \| SH3TC2 | fwd/ | 466 | 699 |
| B2b vs B1 L1 | | | | | | | | | | | | |
| L1 | rs936126 | rs936126 | 2 | 129124335 | A | 2.636 | <1.0E-5 | 0.4916 | HS6ST1 \| LOC100130768 | fwd/T | 467 | 700 |
| B2b vs B1 L3 | | | | | | | | | | | | |
| L3 | rs6722613 | 1kg_2_25392861 | 2 | 25539357 | G | 1.603 | <1.0E-5 | 0.4271 | DNMT3A | fwd/T | 438 | 671 |
| L3 | rs2644621 | rs2644621 | 1 | 156861243 | A | 5.772 | <1.0E-5 | 0.1243 | NTRK1 \| PEAR1 | fwd/T | 439 | 672 |
| L3 | rs666478 | rs666478 | 9 | 27173180 | G | 1.579 | <1.0E-5 | 0.461 | TEK | rev/B | 440 | 673 |
| B2b vs B3 | | | | | | | | | | | | |
| all | rs4733883 | rs4733883 | 8 | 38437040 | A | 0.5541 | <1.0E-5 | 0.3315 | FLJ43582 \| RNF5P1 | fwd/T | 595 | 828 |
| B2b vs B3 L3 | | | | | | | | | | | | |
| L3 | rs7143837 | rs7143837 | 14 | 81640722 | T | 0.3454 | <1.0E-5 | 0.1032 | TSHR \| GTF2A1 | fwd/ | 596 | 829 |
| L3 | rs12249558 | rs12249558 | 10 | 130446595 | G | 3.297 | <1.0E-5 | 0.1248 | MKI67 \| LOC728327 | fwd/T | 597 | 830 |
| B2b vs Ctrl | | | | | | | | | | | | |
| all | rs634641 | rs634641 | 11 | 69386588 | G | 4.081 | <1.0E-5 | 0.0385 | MYEOV \| CCND1 | fwd/ | 397 | 630 |
| all | rs12669698 | 1kg_7_37404494 | 7 | 37437969 | G | 1.633 | <1.0E-5 | 0.1407 | LOC646942 \| ELMO1 | fwd/B | 441 | 674 |
| all | rs8097844 | rs8097844 | 18 | 20186986 | G | 1.44 | <1.0E-5 | 0.3225 | CTAGE1 \| RBBP8 | fwd/B | 442 | 675 |
| all | rs8085592 | rs8085592 | 18 | 20187420 | A | 1.439 | <1.0E-5 | 0.3227 | CTAGE1 \| RBBP8 | fwd/B | 443 | 676 |
| all | rs4309500 | rs4309500 | 18 | 20171748 | A | 1.437 | <1.0E-5 | 0.3156 | CTAGE1 \| RBBP8 | fwd/ | 444 | 677 |
| all | rs3002685 | rs3002685 | 1 | 3177480 | G | 1.523 | <1.0E-5 | 0.2097 | PRDM16 | fwd/T | 598 | 831 |
| all | rs6962616 | rs6962616 | 7 | 68060815 | A | 0.3783 | <1.0E-5 | 0.08535 | STAG3L4 \| AUTS2 | fwd/B | 599 | 832 |
| all | rs7130717 | rs7130717 | 11 | 129313340 | G | 1.563 | <1.0E-5 | 0.4695 | BARX2 | fwd/ | 600 | 833 |
| all | rs646103 | rs646103 | 2 | 31496984 | A | 0.6071 | <1.0E-5 | 0.1908 | EHD3 \| XDH | rev/T | 601 | 834 |
| B2b vs Ctrl L1 | | | | | | | | | | | | |
| L1 | rs2314737 | rs2314737 | 3 | 182783344 | G | 2.475 | <1.0E-5 | 0.3036 | MCCC1 | rev/B | 493 | 726 |
| B2b vs Ctrl L3 | | | | | | | | | | | | |
| L3 | rs634641 | rs634641 | 11 | 69386588 | G | 4.862 | <1.0E-5 | 0.0385 | MYEOV \| CCND1 | fwd/ | 408 | 641 |
| L3 | rs116714418 | rs1062731 | 22 | 28248840 | A | 0.5511 | <1.0E-5 | 0.223 | PITPNB | fwd/B | 445 | 678 |
| L3 | rs3002685 | rs3002685 | 1 | 3177480 | G | 1.718 | <1.0E-5 | 0.2097 | PRDM16 | fwd/T | 468 | 701 |
| L3 | rs2455099 | rs2455099 | 1 | 3181415 | A | 1.733 | <1.0E-5 | 0.1794 | PRDM16 | rev/T | 602 | 835 |
| L3 | rs8097844 | rs8097844 | 18 | 20186986 | G | 1.546 | <1.0E-5 | 0.3225 | CTAGE1 \| RBBP8 | fwd/B | 603 | 836 |
| L3 | rs8085592 | rs8085592 | 18 | 20187420 | A | 1.545 | <1.0E-5 | 0.3227 | CTAGE1 \| RBBP8 | fwd/B | 604 | 837 |

TABLE 1-continued

| Polymorphisms Associated with Subclinical Phenotypes of Severe CD | | | | | | | | | | | | |
|---|---|---|---|---|---|---|---|---|---|---|---|---|
| Loca-tion | rs_id | SNP | CHR | BP | A1 | OR | P | MAF | Gene/ Locus | ss to rs Orien-tation/ Strand | 5' SEQ ID NO | 3' SEQ ID NO |
| L3 | rs200145 | rs200145 | 6 | 143343770 | G | 0.5111 | <1.0E−5 | 0.1847 | HIVEP2 ǀ AIG1 | fwd/B | 605 | 838 |
| L3 | rs16915033 | rs16915033 | 8 | 51462627 | G | 1.823 | <1.0E−5 | 0.1003 | SNTG1 | fwd/T | 606 | 839 |
| L3 | rs41305602 | imm_3_50239710 | 3 | 50264706 | T | 3.453 | <1.0E−5 | 0.01202 | SLC38A3 ǀ GNAI2 | fwd/ | 607 | 840 |
| L3 | rs4309500 | rs4309500 | 18 | 20171748 | A | 1.525 | <1.0E−5 | 0.3156 | CTAGE1 ǀ RBBP8 | fwd/ | 608 | 841 |
| L3 | rs7233496 | rs7233496 | 18 | 20185643 | A | 1.517 | <1.0E−5 | 0.3197 | CTAGE1 ǀ RBBP8 | fwd/B | 609 | 842 |
| L3 | rs35929393 | 1kg_6_111635077 | 6 | 111528384 | A | 2.69 | <1.0E−5 | 0.02056 | SLC16A10 | fwd/ | 610 | 843 |
| L3 | rs398869 | rs398869 | 20 | 12893710 | G | 1.928 | <1.0E−5 | 0.06728 | BTBD3 ǀ SPTLC3 | rev/T | 611 | 844 |
| B3 vs B1 | | | | | | | | | | | | |
| all | rs12496281 | rs12496281 | 3 | 14973320 | G | 2.544 | <1.0E−5 | 0.07225 | FGD5 | fwd/T | 398 | 631 |
| all | rs3808240 | rs3808240 | 7 | 90468989 | C | 2.283 | <1.0E−5 | 0.08872 | PFTK1 | fwd/T | 412 | 645 |
| all | rs1352071 | imm_2_163065624 | 2 | 163357378 | G | 1.988 | <1.0E−5 | 0.1247 | KCNH 7 | rev/B | 446 | 679 |
| all | rs10134119 | rs10134119 | 14 | 59460239 | T | 1.66 | <1.0E−5 | 0.3622 | LOC440181 ǀ DAAM1 | fwd/ | 481 | 714 |
| all | rs6499323 | rs6499323 | 16 | 70624483 | G | 1.65 | <1.0E−5 | 0.262 | SF3B3 ǀ C16orf77 | fwd/T | 612 | 845 |
| all | rs11161618 | rs11161618 | 1 | 85915402 | A | 0.5485 | <1.0E−5 | 0.4417 | DDAH1 | fwd/B | 613 | 846 |
| B3 v B1 L2 | | | | | | | | | | | | |
| L2 | rs1890843 | rs1890843 | 1 | 210836847 | G | 7.977 | <1.0E−5 | 0.07966 | LOC100129235 ǀ HHAT | fwd/B | 469 | 702 |
| L2 | rs11829981 | rs11829981 | 12 | 27032213 | A | 16.23 | <1.0E−5 | 0.03272 | ITPR2 ǀ C12orf11 | fwd/T | 482 | 715 |
| L2 | rs7312159 | rs7312159 | 12 | 27027742 | A | 16.23 | <1.0E−5 | 0.03271 | ITPR2 ǀ C12orf11 | fwd/B | 614 | 847 |
| B3 vs B1 L3 | | | | | | | | | | | | |
| L3 | rs12496281 | rs12496281 | 3 | 14973320 | G | 3.021 | <1.0E−5 | 0.07225 | FGD5 | fwd/T | 399 | 632 |
| L3 | rs3808240 | rs3808240 | 7 | 90468989 | C | 2.67 | <1.0E−5 | 0.08872 | PFTK1 | fwd/T | 447 | 680 |
| L3 | rs11161618 | rs11161618 | 1 | 85915402 | A | 0.4755 | <1.0E−5 | 0.4417 | DDAH1 | fwd/B | 615 | 848 |
| L3 | rs28408641 | 1kg_18_41136921 | 18 | 42882923 | A | 0.4042 | <1.0E−5 | 0.1641 | LOC100131669 ǀ SLC14A2 | fwd/T | 616 | 849 |
| L3 | rs12455102 | 1kg_18_41137957 | 18 | 42883959 | C | 0.4042 | <1.0E−5 | 0.1644 | LOC100131669 ǀ SLC14A2 | fwd/T | 617 | 850 |
| L3 | rs6801634 | rs6801634 | 3 | 4354697 | A | 1.96 | <1.0E−5 | 0.141 | SETMAR | fwd/T | 618 | 851 |
| B3 vs Ctrl | | | | | | | | | | | | |
| all | rs1352071 | imm_2_163065624 | 2 | 163357378 | G | 1.832 | <1.0E−5 | 0.1247 | KCNH7 | rev/B | 448 | 681 |
| all | rs2383184 | rs2383184 | 9 | 21763566 | G | 2.397 | <1.0E−5 | 0.06435 | IFNE1 ǀ MTAP | rev/B | 470 | 703 |
| all | rs144260901 | imm_9_34751635 | 9 | 34761635 | A | 4.215 | <1.0E−5 | 0.01902 | LOC259308 ǀ LOC100128556 | fwd/ | 483 | 716 |
| all | rs7037277 | rs7037277 | 9 | 21772064 | G | 2.229 | <1.0E−5 | 0.06627 | IFNE1 ǀ MTAP | fwd/T | 619 | 852 |
| all | rs12419184 | rs12419184 | 11 | 126056308 | A | 1.803 | <1.0E−5 | 0.1124 | CDON ǀ RPUSD4 | fwd/B | 620 | 853 |
| all | rs351758 | rs351758 | 8 | 28029018 | A | 0.6242 | <1.0E−5 | 0.4949 | ELP3 | rev/B | 621 | 854 |
| B3 vs Ctrl L3 | | | | | | | | | | | | |
| L3 | rs1352071 | imm_2_163065624 | 2 | 163357378 | G | 1.988 | <1.0E−5 | 0.1247 | KCNH7 | rev/B | 449 | 682 |
| L3 | rs6801634 | rs6801634 | 3 | 4354697 | A | 1.989 | <1.0E−5 | 0.141 | SETMAR | fwd/T | 471 | 704 |
| L3 | rs2383184 | rs2383184 | 9 | 21763566 | G | 2.623 | <1.0E−5 | 0.06435 | IFNE1 ǀ MTAP | rev/B | 484 | 717 |
| L3 | rs2954756 | rs2954756 | 17 | 15339283 | G | 2.071 | <1.0E−5 | 0.134 | TEKT3 ǀ CDRT4 | fwd/B | 494 | 727 |
| L3 | rs12419184 | rs12419184 | 11 | 126056308 | A | 1.975 | <1.0E−5 | 0.1124 | CDON ǀ RPUSD4 | fwd/B | 622 | 855 |
| L3 | rs7037277 | rs7037277 | 9 | 21772064 | G | 2.441 | <1.0E−5 | 0.06627 | IFNE1 ǀ MTAP | fwd/T | 623 | 856 |
| L3 | rs74950346 | imm_16_73786858 | 16 | 75229357 | A | 2.25 | <1.0E−5 | 0.05648 | ZFP1 ǀ CTRB2 | fwd/ | 624 | 857 |

Methods

Methods of Detection

Methods disclosed herein for detecting a genotype in a sample from a subject comprise analyzing the genetic material in the sample to detect at least one of a presence, an absence, and a quantity of a nucleic acid sequence encompassing the genotype of interest. In some cases, the nucleic acid sequence comprises DNA. In some instances, the nucleic acid sequence comprises a denatured DNA molecule or fragment thereof. In some instances, the nucleic acid sequence comprises DNA selected from: genomic DNA, viral DNA, mitochondrial DNA, plasmid DNA, amplified DNA, circular DNA, circulating DNA, cell-free DNA, or exosomal DNA. In some instances, the DNA is single-stranded DNA (ssDNA), double-stranded DNA, denaturing double-stranded DNA, synthetic DNA, and combinations thereof. The circular DNA may be cleaved or fragmented. In some instances, the nucleic acid sequence comprises RNA. In some instances, the nucleic acid sequence comprises fragmented RNA. In some instances, the nucleic acid sequence comprises partially degraded RNA. In some instances, the nucleic acid sequence comprises a microRNA or portion thereof. In some instances, the nucleic acid sequence comprises an RNA molecule or a fragmented RNA molecule (RNA fragments) selected from: a microRNA (miRNA), a pre-miRNA, a pri-miRNA, a mRNA, a pre-mRNA, a viral RNA, a viroid RNA, a virusoid RNA, circular RNA (circRNA), a ribosomal RNA (rRNA), a transfer RNA (tRNA), a pre-tRNA, a long non-coding RNA (lncRNA), a small nuclear RNA (snRNA), a circulating RNA, a cell-free RNA, an exosomal RNA, a vector-expressed RNA, an RNA transcript, a synthetic RNA, and combinations thereof.

Nucleic acid-based detection techniques that may be useful for the methods herein include quantitative polymerase chain reaction (qPCR), gel electrophoresis, immunochemistry, in situ hybridization such as fluorescent in situ hybridization (FISH), cytochemistry, and next generation sequencing. In some embodiments, the methods involve TaqMan™ qPCR (real-time PCR assay), which involves a nucleic acid amplification reaction with a specific primer pair, and hybridization of the amplified nucleic acids with a hydrolysable probe specific to a target nucleic acid.

In some instances, the methods involve hybridization and/or amplification assays that include, but are not limited to, Southern or Northern analyses, polymerase chain reaction analyses, and probe arrays. Non-limiting amplification reactions include, but are not limited to, qPCR, self-sustained sequence replication, transcriptional amplification system, Q-Beta Replicase, rolling circle replication, or any other nucleic acid amplification known in the art. As discussed, reference to qPCR herein includes use of TaqMan™ (real-time PCR assay) methods. An additional exemplary hybridization assay includes the use of nucleic acid probes conjugated or otherwise immobilized on a bead, multi-well plate, or other substrate, wherein the nucleic acid probes are configured to hybridize with a target nucleic acid sequence of a genotype provided herein. A non-limiting method is one employed in Anal Chem. 2013 Feb. 5; 85(3):1932-9.

In some embodiments, detecting the presence or absence of a genotype comprises sequencing genetic material from the subject. Sequencing can be performed with any appropriate sequencing technology, including but not limited to single-molecule real-time (SMRT) sequencing, Polony sequencing, sequencing by ligation, reversible terminator sequencing, proton detection sequencing, ion semiconductor sequencing, nanopore sequencing, electronic sequencing, pyrosequencing, Maxam-Gilbert sequencing, chain termination (e.g., Sanger) sequencing, +S sequencing, or sequencing by synthesis. Sequencing methods also include next-generation sequencing, e.g., modern sequencing technologies such as Illumina® (Illumina, Inc.) sequencing (e.g., Solexa), Roche 454 sequencing, Ion torrent sequencing, and SOLiD sequencing. In some cases, next-generation sequencing involves high-throughput sequencing methods. Additional sequencing methods available to one of skill in the art may also be employed.

In some instances, a number of nucleotides that are sequenced are at least 5, 10, 15, 20, 25, 30, 35, 40, 45, 50, 100, 150, 200, 300, 400, 500, 2000, 4000, 6000, 8000, 10000, 20000, 50000, 100000, or more than 100000 nucleotides. In some instances, the number of nucleotides sequenced is in a range of about 1 to about 100000 nucleotides, about 1 to about 10000 nucleotides, about 1 to about 1000 nucleotides, about 1 to about 500 nucleotides, about 1 to about 300 nucleotides, about 1 to about 200 nucleotides, about 1 to about 100 nucleotides, about 5 to about 100000 nucleotides, about 5 to about 10000 nucleotides, about 5 to about 1000 nucleotides, about 5 to about 500 nucleotides, about 5 to about 300 nucleotides, about 5 to about 200 nucleotides, about 5 to about 100 nucleotides, about 10 to about 100000 nucleotides, about 10 to about 10000 nucleotides, about 10 to about 1000 nucleotides, about 10 to about 500 nucleotides, about 10 to about 300 nucleotides, about 10 to about 200 nucleotides, about 10 to about 100 nucleotides, about 20 to about 100000 nucleotides, about 20 to about 10000 nucleotides, about 20 to about 1000 nucleotides, about 20 to about 500 nucleotides, about 20 to about 300 nucleotides, about 20 to about 200 nucleotides, about 20 to about 100 nucleotides, about 30 to about 100000 nucleotides, about 30 to about 10000 nucleotides, about 30 to about 1000 nucleotides, about 30 to about 500 nucleotides, about 30 to about 300 nucleotides, about 30 to about 200 nucleotides, about 30 to about 100 nucleotides, about 50 to about 100000 nucleotides, about 50 to about 10000 nucleotides, about 50 to about 1000 nucleotides, about 50 to about 500 nucleotides, about 50 to about 300 nucleotides, about 50 to about 200 nucleotides, or about 50 to about 100 nucleotides.

Exemplary probes comprise a nucleic acid sequence of at least 10 contiguous nucleic acids provided in any one of SEQ ID NOS: 1-82, including nucleoposition 26 or 31 within any one of SEQ ID NOS: 1-82, or a reverse complement thereof. In some instances, the probes comprises a nucleic acid at nucleoposition 26 that is, or is a complement to, the allele provided in Table 1 corresponding to the polymorphism being detected. In some embodiments, the exemplary probes comprise at least a portion of a nucleic acid sequence flanking the 3' end of the risk allele, and at least a portion of a nucleic acid sequence flanking the 5' end of the risk allele, such as those provided in Table 1.

Examples of molecules that are utilized as probes include, but are not limited to, RNA and DNA. In some embodiments, the term "probe" with regards to nucleic acids, refers to any molecule that is capable of selectively binding to a specifically intended target nucleic acid sequence. In some instances, probes are specifically designed to be labeled, for example, with a radioactive label, a fluorescent label, an enzyme, a chemiluminescent tag, a colorimetric tag, or other labels or tags that are known in the art. In some instances, the fluorescent label comprises a fluorophore. In some instances, the fluorophore is an aromatic or heteroaromatic compound. In some instances, the fluorophore is a pyrene, anthracene, naphthalene, acridine, stilbene, benzoxaazole, indole, benzindole, oxazole, thiazole, benzothiazole, canine, carbocyanine, salicylate, anthranilate, xanthenes dye, coumarin. Exemplary xanthene dyes include, e.g., fluorescein and rhodamine dyes. Fluorescein and rhodamine dyes include, but are not limited to 6-carboxyfluorescein (FAM), 2'7'-dimethoxy-4'5'-dichloro-6-carboxyfluorescein (JOE), tetrachlorofluorescein (TET), 6-carboxyrhodamine (R6G), N,N,N; N'-tetramethyl-6-carboxyrhodamine (TAMRA), 6-carboxy-X-rhodamine (ROX). Suitable fluorescent probes also include the naphthylamine dyes that have an amino group in the alpha or beta position. For example, naphthylamino compounds include 1-dimethylaminonaphthyl-5-sulfonate, 1-anilino-8-naphthalene sulfonate and 2-p-toluidinyl-6-naphthalene sulfonate, 5-(2'-aminoethyl) aminonaphthalene-1-sulfonic acid (EDANS). Exemplary coumarins include, e.g., 3-phenyl-7-isocyanatocoumarin; acridines, such as 9-isothiocyanatoacridine and acridine orange; N-(p-(2-benzoxazolyl)phenyl) maleimide; cyanines, such as, e.g., indodicarbocyanine 3 (Cy3), indodicarbocyanine 5 (Cy5), indodicarbocyanine 5.5 (Cy5.5), 3-(-carboxy-pentyl)-3'-ethyl-5,5'-dimethyloxacarbocyanine (CyA); 1H, 5H, 11H, 15H-Xantheno[2,3, 4-ij: 5,6, 7-i'j']diquinolizin-18-ium, 9-[2 (or 4)-[[[6-[2,5-dioxo-1-pyrrolidinyl)oxy]-6-oxohexyl]amino]sulfonyl]-4 (or 2)-sulfophenyl]-2,3, 6,7, 12,13, 16,17-octahydro-inner salt (TR or Texas Red); or BODIPY™ dyes. In some cases, the probe comprises FAM as the dye label.

In some instances, primers and/or probes described herein for detecting a target nucleic acid are used in an amplification reaction. In some instances, the amplification reaction is qPCR. An exemplary qPCR is a method employing a TaqMan™ (real-time PCR assay) assay.

In some instances, qPCR comprises using an intercalating dye. Examples of intercalating dyes include SYBR green I, SYBR green II, SYBR gold, ethidium bromide, methylene blue, Pyronin Y, DAPI, acridine orange, Blue View or phycoerythrin. In some instances, the intercalating dye is SYBR.

In some instances, a number of amplification cycles for detecting a target nucleic acid in an amplification assay is about 5 to about 30 cycles. In some instances, the number of amplification cycles for detecting a target nucleic acid is at least about 5 cycles. In some instances, the number of amplification cycles for detecting a target nucleic acid is at most about 30 cycles. In some instances, the number of amplification cycles for detecting a target nucleic acid is about 5 to about 10, about 5 to about 15, about 5 to about 20, about 5 to about 25, about 5 to about 30, about 10 to about 15, about 10 to about 20, about 10 to about 25, about 10 to about 30, about 15 to about 20, about 15 to about 25, about 15 to about 30, about 20 to about 25, about 20 to about 30, or about 25 to about 30 cycles.

In one aspect, the methods provided herein for determining the presence, absence, and/or quantity of a nucleic acid sequence from a particular genotype comprise an amplification reaction such as qPCR. In an exemplary method, genetic material is obtained from a sample of a subject, e.g., a sample of blood or serum. In certain embodiments where nucleic acids are extracted, the nucleic acids are extracted using any technique that does not interfere with subsequent analysis. In certain embodiments, this technique uses alcohol precipitation using ethanol, methanol or isopropyl alcohol. In certain embodiments, this technique uses phenol, chloroform, or any combination thereof. In certain embodiments, this technique uses cesium chloride. In certain embodiments, this technique uses sodium, potassium or ammonium acetate or any other salt commonly used to precipitate DNA. In certain embodiments, this technique utilizes a column or resin based nucleic acid purification scheme such as those commonly sold commercially, one non-limiting example would be the GenElute™ (RNA/DNA purification kit) Bacterial Genomic DNA Kit available from Sigma Aldrich® (Sigma-Aldrich Corporation). In certain embodiments, after extraction the nucleic acid is stored in water, Tris buffer, or Tris-EDTA buffer before subsequent analysis. In an exemplary embodiment, the nucleic acid material is extracted in water. In some cases, extraction does not comprise nucleic acid purification.

In the exemplary qPCR assay, the nucleic acid sample is combined with primers and probes specific for a target nucleic acid that may or may not be present in the sample, and a DNA polymerase. An amplification reaction is performed with a thermal cycler that heats and cools the sample for nucleic acid amplification, and illuminates the sample at a specific wavelength to excite a fluorophore on the probe and detect the emitted fluorescence. For TaqMan™ (real-time PCR assay) methods, the probe may be a hydrolysable probe comprising a fluorophore and quencher that is hydrolyzed by DNA polymerase when hybridized to a target nucleic acid. In some cases, the presence of a target nucleic acid is determined when the number of amplification cycles to reach a threshold value is less than 30, 29, 28, 27, 26, 25, 24, 23, 22, 21, or 20 cycles.

The target nucleic acid sequence can comprise at least 10 contiguous nucleic acids comprising a polymorphism selected from the group consisting of rs2726797, rs7108993, rs79665096, rs7604404, rs73085878, rs78727269, rs2736352, rs4924935, rs11227112, rs2285043, rs6989059, rs3807552, rs111455641, rs9480689, rs7416358, rs6879067, rs11128532, rs177665, rs11171747, rs10775375, rs6801634, rs1070444, rs116714418, rs6962616, rs7220814, rs4325270, rs768755, rs17758350, rs9480689, rs525850, rs4325270, rs11749180, rs6962616, rs116714418, rs10265554, rs634641, rs1493871, rs12669698, rs4332037, rs17697480, rs9480689, rs6074737, rs904910, rs12972487, rs445417, rs635624, rs7416358, 12-54819630-G-INSERTION, rs177665, rs1070444, rs10912583, rs12914919, rs2854725, rs948068, rs71472147, rs72939578, rs658795, rs17758350, rs144260901, rs10801129, rs1702870, rs10912583, rs2452822, rs7774349, rs4705272, rs117946479, rs936126, rs634641, rs2314737, rs3002685, rs634641, rs12496281, rs10134119, rs3808240, rs1890843, rs11829981, rs12496281, rs2383184, rs144260901, rs6801634, rs2383184, rs2954756, provided in any one of SEQ ID NOS: 1-82. The primers and probes in the assay may include any combination of the primers and probes described herein. As such, a multiplex assay may be performed where combination of polymorphisms is detectable in the assay, the combination comprising at least one polymorphism at a nucleoposition 26 within any one of SEQ ID NOS: 1-82. In some instances, an exemplary probe to detect the polymorphism has a nucleic acid sequence provided in SEQ ID NO: 1, or its reverse complement. In some instances, provided is a probe comprises at least 70%, 80%, 85%, 90%, 91%, 92%, 93%, 94%, 95%, 96%, 97%, 98% or 99% sequence identity to any one of SEQ ID NOS: 1-82, or its reverse complement. In some instances, forward and reverse primers are used to amplify the target nucleic acid sequence. Forward and reverse primers may comprise a nucleic acid sequence flanking the allele ("N") in any one of SEQ ID NOS: 1-82, or a reverse complement thereof. Forward and reverse primers may comprise a nucleic acid sequence flanking the allele ("N") that is 70%, 80%, 85%, 90%, 91%, 92%, 93%, 94%, 95%, 96%, 97%, 98% or 99% sequence identity to any one of SEQ ID NOS: 1-82, or a reverse complement thereof.

To practice the methods and systems provided herein, genetic material may be extracted from a sample obtained from a subject, e.g., a sample of blood or serum. In certain embodiments where nucleic acids are extracted, the nucleic acids are extracted using any technique that does not interfere with subsequent analysis. In certain embodiments, this technique uses alcohol precipitation using ethanol, methanol or isopropyl alcohol. In certain embodiments, this technique uses phenol, chloroform, or any combination thereof. In certain embodiments, this technique uses cesium chloride. In certain embodiments, this technique uses sodium, potassium or ammonium acetate or any other salt commonly used to precipitate DNA. In certain embodiments, this technique utilizes a column or resin based nucleic acid purification scheme such as those commonly sold commercially, one non-limiting example would be the GenElute™ (RNA/DNA purification kit) Bacterial Genomic DNA Kit available from Sigma Aldrich® (Sigma-Aldrich Corporation). In certain embodiments, after extraction the nucleic acid is stored in water, Tris buffer, or Tris-EDTA buffer before subsequent analysis. In an exemplary embodiment, the nucleic acid material is extracted in water. In some cases, extraction does not comprise nucleic acid purification. In certain embodiments, RNA may be extracted from cells using RNA extraction techniques including, for example, using acid phenol/guanidine isothiocyanate extraction (RNAzol B; Biogenesis), RNeasy® (RNA extraction kit) RNA preparation kits (Qiagen) or PAXgene (PreAnalytix, Switzerland).

In some embodiments, methods of detecting a presence, absence, or level of a target protein (e.g., biomarker) in the sample obtained from the subject involve detecting protein activity or expression. A target protein may be detected by use of an antibody-based assay, where an antibody specific to the target protein is utilized. In some embodiments, antibody-based detection methods utilize an antibody that binds to any region of target protein. An exemplary method of analysis comprises performing an enzyme-linked immunosorbent assay (ELISA). The ELISA assay may be a sandwich ELISA or a direct ELISA. Another exemplary method of analysis comprises a single molecule array, e.g., Simoa® (single molecule array immunoassay). Other exemplary methods of detection include immunohistochemistry and lateral flow assay. Additional exemplary methods for detecting target protein include, but are not limited to, gel electrophoresis, capillary electrophoresis, high performance liquid chromatography (HPLC), thin layer chromatography (TLC), hyperdiffusion chromatography, and the like, or various immunological methods such as fluid or gel precipitation reactions, immunodiffusion (single or double), immunoelectrophoresis, radioimmunoassay (RIA), immunofluorescent assays, and Western blotting. In some embodiments, antibodies, or antibody fragments, are used in methods such as Western blots or immunofluorescence techniques to detect the expressed proteins. The antibody or protein can be immobilized on a solid support for Western blots and immunofluorescence techniques. Suitable solid phase supports or carriers include any support capable of binding an antigen or an antibody. Exemplary supports or carriers include glass, polystyrene, polypropylene, polyethylene, dextran, nylon, amylases, natural and modified celluloses, polyacrylamides, gabbros, and magnetite.

In some cases, a target protein may be detected by detecting binding between the target protein and a binding partner of the target protein. In some cases, the target protein comprises a protein expressed from a gene selected from the group consisting MAPT, ANK3, C1QTNF6, SSTR3, NAT6, WBSCR16, LOC653375, STK33, IMP5, LOC728191, ODZ3, POLS, ITGA6, MLSTD2, LOC729147, PROK2, RYBP, C14orf45, TSHR, RASGRP3, PDHB, KCTD6, KCNQ1DN, CDKN1C, CSMD1, C5orf30, NUDT12, XKR6, LOC157740, SLC2A13, B4GALNT1, OS9, LOC100130776, CTDSP2, XRCC6BP1, NAALADL1, CDCA5, EGF, MSRA, LOC100132391, PRPSAP2, CYP2R1, CALCA, LOC100129427, DDC, LOC100129060, CACNA2D2, LOC100128485, FLJ40296, LOC100130336, LOC100131830, PVT1, LOC728724, ZNF184, LOC100131289, TNK1, MTX1, TNFAIP3, PERP, STAG3L4, AUTS2, PITPNB, RPL37, CARD6, TTC33. SPOCK3, ANXA10, APOB, LOC728640, BICC1, C6orf58, C6orf190, NCOA2, LOC100130862, PDCD11, C6orf199, FLJ42177, RTN4IP1, LOC64694, ELMO1, RBM6, XYLT1, LOC728222, NRP2, FLJ20309, MYEOV, CCND1, OR51G1, OR51A4, KCNH7, LOC259308, LOC100128556, CDON, RPUSD4, IFNE1, MTAP, ELP3, ZFP1, CTRB2, TEKT3, CDRT4, SETMAR, TNFSF4, LOC730070, RPS26, ERBB3, RYR3, SLC16A10, TH, ASCL2, ATP8A1, LOC389207, RGS21, RGS1, LCE3E, LCE3D, SUOX, IKZF4, FAM62A, MYL6B, SMARCC2, B3GNTL1, IL22RA2, PRDM16, CTAGE1, RBBP8, EHD3, XDH, BARX2, MCCC1, SLC38A3, GNAI2, SNTG1, HIVEP2, AIG1, BTBD3, SPTLC3, RAB3GAP1, ZRANB3, YSK4, DDR2, FLRT3, MACROD2, SPEN, PTTG1, ATP10B, SLC6A11, XCL1, DPT, LOC440181, DAAM1, DDAH1, FGD5, PFTK1, SF3B3, C16orf77, ITPR2, C12orf11, LOC100129235, HHAT, LOC100131669, SLC14A2, CLECL1, CD69, MAD1L1, LOC729979, LOC730018, SH3D19, BRSK1, RSPO2, EIF3E, ADRB2, SH3TC2, HS6ST1, LOC100130768, DNMT3A, NTRK1, PEAR1, TEK, FAM62A, ZC3H10, OBFC2B, LOC100129289, HS3ST3A1, CDRT15P, GTF2A1, FLT, LOC727894. LOC728544, FLJ43582, RNF5P1, MKI67, and LOC728327. Exemplary methods of analysis of protein-protein binding comprise performing an assay in vivo or in vitro, or ex vivo. In some instances, the method of analysis comprises an assay such as a co-immunoprecipitation (co-IP), pull-down, crosslinking protein interaction analysis, labeled transfer protein interaction analysis, or Far-western blot analysis, FRET based assay, including, for example FRET-FLIM, a yeast two-hybrid assay, BiFC, or split luciferase assay.

Disclosed herein are methods of detecting a presence or a level of one or more serological markers in a sample obtained from a subject. In some embodiments, the one or more serological markers comprises anti-*Saccharomyces cerevisiae* antibody (ASCA), an anti-neutrophil cytoplasmic antibody (ANCA), antibody against *E. coli* outer membrane porin protein C (anti-OmpC), anti-chitin antibody, pANCA antibody, anti-I2 antibody, and anti-Cbir1 flagellin antibody. In some embodiments, the antibodies comprises immunoglobulin A (IgA), immunoglobulin G (IgG), immunoglobulin E (IgE), or immunoglobulin M (IgM), immunoglobulin D (IgD), or a combination thereof. Any suitable method for detecting a target protein or biomarker disclosed herein may be used to detect a presence, absence, or level of a serological marker. In some embodiments, the presence or the level of the one or more serological markers is detected using an enzyme-linked immunosorbent assay (ELISA), a single molecule array (Simoa®), immunohistochemistry, internal transcribed spacer (ITS) sequencing, or any combination thereof. In some embodiments, the ELISA is a fixed leukocyte ELISA. In some embodiments, the ELISA is a fixed neutrophil ELISA. A fixed leukocyte or neutrophil ELISA may be useful for the detection of certain serological markers, such as those described in Saxon et al., A distinct subset of antineutrophil cytoplasmic antibodies is associated with inflammatory bowel disease, J. Allergy Clin. Immuno. 86:2; 202-210 (August 1990). In some embodiments, ELISA units (EU) are used to measure positivity of a presence or level of a serological marker (e.g., seropositivity), which reflects a percentage of a standard or reference value. In some embodiments, the standard comprises pooled sera obtained from well-characterized patient population (e.g., diagnosed with the same disease or condition the subject has, or is suspected of having) reported as being seropositive for the serological marker of interest. In some embodiments, the control or reference value comprises 10, 20, 30, 40, 50, 60, 70, 80, 90, or 100 EU. In some instances, a quartile sum scores are calculated using, for example, the methods reported in Landers C J, Cohavy O, Misra R. et al., Selected loss of tolerance evidenced by Crohn's disease-associated immune responses to auto- and microbial antigens. Gastroenterology (2002)123:689-699.

Methods of Treatment

Disclosed herein are methods of treating a disease or condition, or a symptom of the disease or condition, in a subject, comprising administrating of therapeutic effective amount of one or more therapeutic agents to the subject. In some embodiments, the one or more therapeutic agents is administered to the subject alone (e.g., standalone therapy). In some embodiments, the one or more therapeutic agents is administered in combination with an additional agent. In some embodiments, the therapeutic agent is a first-line therapy for the disease or condition. In some embodiments, the therapeutic agent is a second-line, third-line, or fourth-line therapy, for the disease or condition.

Therapeutic Agent

Disclosed herein, in some embodiments, are therapeutic agents useful for the treatment of a disease or condition, or symptom of the disease or condition, disclosed herein. In some embodiments, the therapeutic agent comprises a modulator of a gene or gene expression product disclosed herein (such as, for e.g., genes containing, or associated with, a genotype disclosed herein). Non-limiting examples of genes affected by, or associated with, a presence of a genotype disclosed herein includes X—C Motif Chemokine Ligand 1 (XCL1), Dermatopontin (DPT), TNF Superfamily Member 4 (TNFSF4), C-Type Lectin Like 1 (CLECL1), CD69 Molecule (CD69), and Fins Related Tyrosine Kinase 1 (FLT1). In some embodiments, the therapeutic agent comprises at least one a modulator of Mitogen-Activated Protein Kinase Kinase Kinase Kinase 4 (MAP4K4), Prostaglandin E Receptor 4 (PTGER4), interleukin 18 receptor 1 (IL18R1). 6-Phosphofructo-2-Kinase/Fructose-2,6-Biphosphatase 3 (PFKFB3), Interleukin 18 Receptor Accessory Protein (IL18RAP), Adenylate Cyclase 7 (ADCY7), B Lymphoid Tyrosine Kinase (BLK), G Protein-Coupled Receptor 65 (GPR65), Sprouty Related EVH1 Domain Containing 2 (SPRED2), Src Kinase Associated Phosphoprotein 2 (SKAP2), CD30 ligand (CD30L), Receptor Interacting Serine/Threonine Kinase 2 (RIPK2), and TNF Ligand Superfamily Member 15 (TL1A).

XCL1/DPT Modulators

Chemokine Ligand 1 (XCL1) (HGNC: 10645 Entrez Gene: 6375 Ensembl: ENSG00000143184 OMIM: 600250 UniProtKB: P479920) is an antimicrobial gene that encodes a member of the chemokine superfamily. XCL1 is thought to be specifically chemotactic for T cells. Dermatopontin (DPT) (HGNC: 3011 Entrez Gene: 1805 Ensembl: ENSG00000143196 OMIM: 125597 UniProtKB: Q07507) is an extracellular matrix protein that is thought to be involved in antimicrobial response, by modifying the behavior of TGF-beta through interaction with decorin.

In some embodiments, the therapeutic agent comprises a modulator, agonist, and/or antagonist of at least one of XCL1 oand DPT. In some embodiments, the therapeutic agent is effective to modify expression and/or activity of XCL1 or DPT. Therapeutic agents that modify expression and/or activity of XCL1 or DPT may also be referred to herein as XCL1 or DPT-targeting agents. Alternatively or additionally, compositions, kits and methods disclosed herein may comprise and/or utilize a therapeutic agent or use thereof, wherein the therapeutic agent modifies expression and/or activity of a protein that functions upstream or downstream of a pathway that involves XCL1 or DPT. In some embodiments, the modulator of XCL1 or DPT is effective to increase or activate the activity or expression of XCL1 or DPT in the subject (e.g., agonist or partial agonist). In some embodiments, the modulator of XCL1 or DPT is effective to decrease or reduce the activity or expression of XCL1 or DPT (e.g., antagonist or partial antagonist).

In some embodiments, the XCL1 or DPT modulator is an antibody, an antigen binding fragment, a RNA interfering agent (RNAi), a small interfering RNA (siRNA), a short hairpin RNA (shRNA), a microRNA (miRNA), an antisense oligonucleotide, a peptide, a peptidomimetic, a small molecule, or an aptamer.

In some instances, the therapeutic agent is an antagonist of XCL1 or DPT. In some instances, the antagonist acts as an inverse agonist. In some instances, the therapeutic agent is an allosteric modulator of XCL1 or DPT. In some instances, the therapeutic agent is an agonist of XCL1 or DPT.

In some instances, the subject has a genotype that is associated with, or causes, an increased expression of XCL1 or DPT. In some instances, the subject has a genotype that is associated with, or causes increased activity of XCL1 or DPT. In some instances, the genotype is associated with, or causes and increase expression of XCL1 or DPT. In some instances, the genotype is associated with, or causes an increase activity of XCL1 or DPT. In these instances, it may be suitable to use an XCL1 or DPT antagonist to bring XCL1 or DPT activity back to a normal level, e.g., that of a person without the IBD of the subject.

In some instances, the subject has a genotype that is associated with, or causes decreased expression of XCL1 or DPT. In some instances, the subject has a genotype is associated with, or causes, decreased activity of XCL1 or DPT. In some instances, the genotype is associated with, or causes, a decrease in expression of XCL1 or DPT. In some instances, the genotype is associated with, or causes, decreased activity of XCL1 or DPT. In these instances, it may be suitable to use an XCL1 or DPT agonist to bring XCL1 or DPT activity back to a normal level, e.g., that of a person without the IBD of the subject.

In some instances, the therapeutic agent is a small molecule drug. By way of non-limiting example, a small molecule drug may be a chemical compound. In some instances, the therapeutic agent is a large molecule drug. Large molecule drugs generally comprise a peptide or nucleic acid. By way of non-limiting example, the large molecule drug may comprise an antibody or antigen binding antibody fragment. In some instances, the therapeutic agent comprises a small molecule and a large molecule. By way of non-limiting example, the therapeutic agent may comprise an antibody-drug conjugate.

In some instances, the therapeutic agent is a small molecule that binds XCL1 or DPT. In some instances, the small molecule that binds XCL1 or DPT is an XCL1 or DPT agonist. In some instances, the small molecule that binds XCL1 or DPT is an XCL1 or DPT partial agonist. In some instances, the small molecule that binds XCL1 or DPT is an XCL1 or DPT antagonist. In some instances, the small molecule that binds XCL1 or DPT is an XCL1 or DPT partial agonist.

In some embodiments, the modulator of XCL1 comprises an XCL1 polypeptide. In some embodiments, the XCL1 polypeptide comprises a human XCL1 (huXCL1), or a homolog thereof. In some instances the polypeptide is an antagonist, agonist or modulator (e.g., allosteric modulator, orthosteric modulator) of XCL1 or DPT. In some embodiments, the XCL1 polypeptide comprises a recombinant XCL1 polypeptide. In some embodiments, the recombinant huXCL1 protein comprises SEQ ID NO: 858, which is the amino acid sequence of human XCL1 (NCBI Reference Sequence No. NP_002986). In some embodiments, the XCL1 polypeptide comprises a recombinant XCL1 polypeptide. In some embodiments, the huXCL1 comprises an amino acid sequence about 99%, 98%, 97%, 96%, 95%, 94%, 93%, 92%, 91%, or 90% homologous to SEQ ID NO: 858. In some embodiments, the recombinant huXCL1 precursor protein comprises SEQ ID NO: 859, which is the amino acid sequence of human DPT (NCBI Reference Sequence No. NP_001928). In some embodiments, the huXCL1 or DPT comprises an amino acid sequence about 99%, 98%, 97%, 96%, 95%, 94%, 93%, 92%, 91%, or 90% homologous to SEQ ID NO: 859.

In some instances, the XCL1 or DPT polypeptide is truncated. In some instances, the truncation is an N-terminal deletion. In other instances, the truncation is a C-terminal deletion. In additional instances, the truncation comprises both N-terminal and C-terminal deletions. For example, the truncation can be a deletion of at least or about 1, 2, 3, 4, 5, 6, 7, 8, 9, 10, 11, 12, 13, 14, 15, 20, or more residues from either the N-terminus or the C-terminus, or both termini. In some cases, the XCL1 or DPT polypeptide comprises an N-terminal deletion of at least or about 1, 2, 3, 4, 5, 6, 7, 8, 9, 10, 11, 12, 13, 14, 15, 20, or more residues. In some cases, the XCL1 or DPT polypeptide comprises an N-terminal deletion of at least or about 1, 2, 3, 4, 5, 6, 7, 8, 9, or 10 residues.

In some embodiments, the XCL1 or DPT polypeptide has an enhanced plasma half-life. In some instances, the plasma half-life comprises at least 30 minutes, 45 minutes, 60 minutes, 75 minutes, or 90 minutes, 2 hours, 3 hours, 4 hours, 5 hours, 6 hours, 7 hours, 8 hours, 9 hours, 10 hours, 11 hours, 12 hours, 18 hours, 24 hours, 36 hours, 48 hours, 3 days, 4 days, 5 days, 6 days, 7 days, 10 days, 12 days, 14 days, 21 days, 28 days, 30 days, or longer than the plasma half-life of the wild-type XCL1 or DPT protein.

In some embodiments, the XCL1 or DPT polypeptide is a conjugate. In some embodiments, the XCL1 or DPT conjugate comprises an XCL1 or DPT polypeptide comprising at least one amino acid and a conjugating moiety bound to the at least one 1 amino acid. In some embodiments, the at least one amino acid is located proximal to the N-terminus (e.g., proximal to the N-terminal residue). For example, the at least one amino acid is located optionally within the first 10, 20, 30, 40, or 50 residues from the N-terminus. In some cases, the at least one amino acid is located at the N-terminus (i.e., the at least one amino acid is the N-terminal residue of the XCL1 or DPT polypeptide). In other embodiments, the at least one amino acid is located proximal to the C-terminus (e.g., proximal to the C-terminal residue). For example, the at least one amino acid is located optionally within the first 10, 20, 30, 40, or 50 residues from the C-terminus. In some cases, the at least one amino acid is located at the C-terminus (i.e., the at least one amino acid is the C-terminal residue of the XCL1 or DPT polypeptide). In some instances, the XCL1 or DPT conjugate has an enhanced plasma half-life, such as the half-lives described herein. In some embodiments, the XCL1 or DPT conjugate is functionally active (e.g., retains activity). In some embodiments, the XCL1 or DPT conjugate is not functionally active (e.g., devoid of activity). In some embodiments, the conjugating moiety comprises a polymer comprising Polyethylene glycol (PEG).

In some embodiments, the XCL1 or DPT polypeptide is fused with a second polypeptide. In some embodiments, the second polypeptide comprises a polypeptide with a long plasma half-life relative to the plasma half-life of the XCL1 or DPT polypeptide. In some embodiments, the second polypeptide comprises an antibody or antibody fragment. In some embodiments, the antibody or antibody fragment comprises an IgG1, IgG2, IgG4, IgG3, or IgE. In some embodiments, the IgG is an Fc. In some embodiments, the IgG Fc is human. In some instances, the long plasma half-life polypeptide comprises HSA, transferrin, IgA monomer, Retinol-binding protein, Factor H, Factor XIII, C-reactive protein, Factor IX, Fibrinogen, IFN-alpha, Pentameric IgM, IL-2, or Thyroglobulin.

TNFSF4 Modulators

TNF Superfamily Member 4 (TNFSF4) (HGNC: 11892 Entrez Gene: 7124 Ensembl: ENSG00000232810 OMIM: 191160 UniProtKB: P01375) encodes a multifunctional proinflammatory cytokine that belongs to the tumor necrosis factor (TNF) superfamily (TNFL4). TNFSF4 is secreted by macrophages, and is involved in regulation of cell proliferation, differentiation, apoptosis, and lipid metabolism.

In some embodiments, the therapeutic agent comprises a modulator, agonist, and/or antagonist of at least one of TNFL4 or the gene encoding TNFL4 (TNFSF4). In some embodiments, the therapeutic agent is effective to modify expression and/or activity of TNFL4. Therapeutic agents that modify expression and/or activity of TNFL4 may also be referred to herein as TNFL4-targeting agents. Alternatively or additionally, compositions, kits and methods disclosed herein may comprise and/or utilize a therapeutic agent or use thereof, wherein the therapeutic agent modifies expression and/or activity of a protein that functions upstream or downstream of a pathway that involves TNFL4 or the gene encoding TNFL4 (TNFSF4). In some embodiments, the modulator of TNFL4 is effective to increase or activate the activity or expression of TNFL4 in the subject (e.g., agonist or partial agonist). In some embodiments, the modulator of TNFL4 is effective to decrease or reduce the activity or expression of TNFL4 (e.g., antagonist or partial antagonist).

In some embodiments, the TNFL4 modulator is an antibody, an antigen binding fragment, a RNA interfering agent (RNAi), a small interfering RNA (siRNA), a short hairpin RNA (shRNA), a microRNA (miRNA), an antisense oligonucleotide, a peptide, a peptidomimetic, a small molecule, or an aptamer.

In some instances, the therapeutic agent is an antagonist of TNFL4. In some instances, the antagonist acts as an inverse agonist. In some instances, the therapeutic agent is an allosteric modulator of TNFL4. In some instances, the therapeutic agent is an agonist of TNFL4.

In some instances, the subject has a genotype that is associated with, or causes, an increased expression of TNFL4. In some instances, the subject has a genotype that is associated with, or causes increased activity of TNFL4. In some instances, the genotype is associated with, or causes and increase expression of TNFL4. In some instances, the genotype is associated with, or causes an increase activity of TNFL4. In these instances, it may be suitable to use a TNFL4 antagonist to bring TNFL4 activity back to a normal level, e.g., that of a person without the IBD of the subject.

In some instances, the subject has a genotype that is associated with, or causes decreased expression of TNFL4. In some instances, the subject has a genotype is associated with, or causes, decreased activity of TNFL4. In some instances, the genotype is associated with, or causes, a decrease in expression of TNFL4. In some instances, the genotype is associated with, or causes, decreased activity of TNFL4. In these instances, it may be suitable to use a TNFL4 agonist to bring TNFL4 activity back to a normal level, e.g., that of a person without the IBD of the subject.

In some instances, the therapeutic agent is a small molecule drug. By way of non-limiting example, a small molecule drug may be a chemical compound. In some instances, the therapeutic agent is a large molecule drug. Large molecule drugs generally comprise a peptide or nucleic acid. By way of non-limiting example, the large molecule drug may comprise an antibody or antigen binding antibody fragment. In some instances, the therapeutic agent comprises a small molecule and a large molecule. By way of non-limiting example, the therapeutic agent may comprise an antibody-drug conjugate. In some instances, the antibody or antigen-binding fragment is a neutralizing antibody or antigen-binding fragment. In some instances, the antibody is a monoclonal antibody. A non-limiting example of a neutralizing monoclonal antibody against TNFL4 includes oxelumab.

In some instances, the therapeutic agent is a small molecule that binds TNFL4. In some instances, the small molecule that binds TNFL4 is a TNFL4 agonist. In some instances, the small molecule that binds TNFL4 is a TNFL4 partial agonist. In some instances, the small molecule that binds TNFL4 is a TNFL4 antagonist. In some instances, the small molecule that binds TNFL4 is a TNFL4 partial agonist.

In some embodiments, the modulator of TNFL4 comprises a TNFL4 polypeptide. In some embodiments, the TNFL4 polypeptide comprises a human TNFL4 (huTNFSF4), or a homolog thereof. In some instances the polypeptide is an antagonist, agonist or modulator (e.g., allosteric modulator, orthosteric modulator) of TNFL4. In some embodiments, the TNFL4 polypeptide comprises a recombinant TNFL4 polypeptide. In some embodiments, the recombinant huTNFL4 protein comprises SEQ ID NO: 860, which is the amino acid sequence of human TNFL4 (NCBI Reference Sequence No. NP_003317). In some embodiments, the TNFL4 polypeptide comprises a recombinant TNFL4 polypeptide. In some embodiments, the huTNFL4 comprises an amino acid sequence about 99%, 98%, 97%, 96%, 95%, 94%, 93%, 92%, 91%, or 90% homologous to SEQ ID NO: 860. In some embodiments, the recombinant huTNFSF4 precursor protein comprises SEQ ID NO: 861, which is the amino acid sequence of human TNFL4 (NCBI Reference Sequence No. NP_001284491). In some embodiments, the huTNFL4 comprises an amino acid sequence about 99%, 98%, 97%, 96%, 95%, 94%, 93%, 92%, 91%, or 90% homologous to SEQ ID NO: 861.

In some instances, the TNFL4 polypeptide is truncated. In some instances, the truncation is an N-terminal deletion. In other instances, the truncation is a C-terminal deletion. In additional instances, the truncation comprises both N-terminal and C-terminal deletions. For example, the truncation can be a deletion of at least or about 1, 2, 3, 4, 5, 6, 7, 8, 9, 10, 11, 12, 13, 14, 15, 20, or more residues from either the N-terminus or the C-terminus, or both termini. In some cases, the TNFL4 polypeptide comprises an N-terminal deletion of at least or about 1, 2, 3, 4, 5, 6, 7, 8, 9, 10, 11, 12, 13, 14, 15, 20, or more residues. In some cases, the TNFL4 polypeptide comprises an N-terminal deletion of at least or about 1, 2, 3, 4, 5, 6, 7, 8, 9, or 10 residues.

In some embodiments, the TNFL4 polypeptide has an enhanced plasma half-life. In some instances, the plasma half-life comprises at least 30 minutes, 45 minutes, 60 minutes, 75 minutes, or 90 minutes, 2 hours, 3 hours, 4 hours, 5 hours, 6 hours, 7 hours, 8 hours, 9 hours, 10 hours, 11 hours, 12 hours, 18 hours, 24 hours, 36 hours, 48 hours, 3 days, 4 days, 5 days, 6 days, 7 days, 10 days, 12 days, 14 days, 21 days, 28 days, 30 days, or longer than the plasma half-life of the wild-type TNFL4 protein.

In some embodiments, the TNFL4 polypeptide is a conjugate. In some embodiments, the TNFL4 conjugate comprises an TNFL4 polypeptide comprising at least one amino acid and a conjugating moiety bound to the at least one 1 amino acid. In some embodiments, the at least one amino acid is located proximal to the N-terminus (e.g., proximal to the N-terminal residue). For example, the at least one amino acid is located optionally within the first 10, 20, 30, 40, or 50 residues from the N-terminus. In some cases, the at least one amino acid is located at the N-terminus (i.e., the at least one amino acid is the N-terminal residue of the TNFL4 polypeptide). In other embodiments, the at least one amino acid is located proximal to the C-terminus (e.g., proximal to the C-terminal residue). For example, the at least one amino acid is located optionally within the first 10, 20, 30, 40, or 50 residues from the C-terminus. In some cases, the at least one amino acid is located at the C-terminus (i.e., the at least one amino acid is the C-terminal residue of the TNFL4 polypeptide). In some instances, the TNFL4 conjugate has an enhanced plasma half-life, such as the half-lives described herein. In some embodiments, the TNFL4 conjugate is functionally active (e.g., retains activity). In some embodiments, the TNFL4 conjugate is not functionally active (e.g., devoid of activity). In some embodiments, the conjugating moiety comprises a polymer comprising Polyethylene glycol (PEG).

In some embodiments, the TNFL4 polypeptide is fused with a second polypeptide. In some embodiments, the second polypeptide comprises a polypeptide with a long plasma half-life relative to the plasma half-life of the TNFL4 polypeptide. In some embodiments, the second polypeptide comprises an antibody or antibody fragment. In some embodiments, the antibody or antibody fragment comprises an IgG1, IgG2, IgG4, IgG3, or IgE. In some embodiments, the IgG is an Fc. In some embodiments, the IgG Fc is human. In some instances, the long plasma half-life polypeptide comprises HSA, transferrin, IgA monomer, Retinol-binding protein, Factor H, Factor XIII, C-reactive protein, Factor IX, Fibrinogen, IFN-alpha, Pentameric IgM, IL-2, or Thyroglobulin.

CLECL1/CD69 Modulators

C-Type Lectin Like 1 (CLECL1) (HGNC: 24462 Entrez Gene: 160365 Ensembl: ENSG00000184293 OMIM:

607467 UniProtKB: Q8IZS7) encodes a type II transmembrane, C-type lectin-like protein that is highly expressed in B cells. CLECL1 may act as a T-cell costimulatory molecule that enhances interleukin-4 (IL-4) production, and maybe involved in the regulation of the immune response. CD69 Molecule (CD69) (HGNC: 1694 Entrez Gene: 969 Ensembl: ENSG00000110848 OMIM: 107273 UniProtKB: Q07108) encodes a member of the calcium dependent lectin superfamily of type II transmembrane receptors. Expression of the encoded protein is induced upon activation of T lymphocytes, and may play a role in proliferation.

In some embodiments, the therapeutic agent comprises a modulator, agonist, and/or antagonist of at least one of CLECL1 or CD69. In some embodiments, the therapeutic agent is effective to modify expression and/or activity of CLECL1 or CD69. Therapeutic agents that modify expression and/or activity of CLECL1 or CD69 may also be referred to herein as CLECL1 or CD69-targeting agents. Alternatively or additionally, compositions, kits and methods disclosed herein may comprise and/or utilize a therapeutic agent or use thereof, wherein the therapeutic agent modifies expression and/or activity of a protein that functions upstream or downstream of a pathway that involves CLECL1 or CD69 or the gene encoding CLECL1 or CD69. In some embodiments, the modulator of CLECL1 or CD69 is effective to increase or activate the activity or expression of CLECL1 or CD69 in the subject (e.g., agonist or partial agonist). In some embodiments, the modulator of CLECL1 or CD69 is effective to decrease or reduce the activity or expression of CLECL1 or CD69 (e.g., antagonist or partial antagonist).

In some embodiments, the CLECL1 or CD69 modulator is an antibody, an antigen binding fragment, a RNA interfering agent (RNAi), a small interfering RNA (siRNA), a short hairpin RNA (shRNA), a microRNA (miRNA), an antisense oligonucleotide, a peptide, a peptidomimetic, a small molecule, or an aptamer.

In some instances, the therapeutic agent is an antagonist of CLECL1 or CD69. In some instances, the antagonist acts as an inverse agonist. In some instances, the therapeutic agent is an allosteric modulator of CLECL1 or CD69. In some instances, the therapeutic agent is an agonist of CLECL1 or CD69.

In some instances, the subject has a genotype that is associated with, or causes, an increased expression of CLECL1 or CD69. In some instances, the subject has a genotype that is associated with, or causes increased activity of CLECL1 or CD69. In some instances, the genotype is associated with, or causes and increase expression of CLECL1 or CD69. In some instances, the genotype is associated with, or causes an increase activity of CLECL1 or CD69. In these instances, it may be suitable to use a CLECL1 or CD69 antagonist to bring CLECL1 or CD69 activity back to a normal level, e.g., that of a person without the IBD of the subject.

In some instances, the subject has a genotype that is associated with, or causes decreased expression of CLECL1 or CD69. In some instances, the subject has a genotype is associated with, or causes, decreased activity of CLECL1 or CD69. In some instances, the genotype is associated with, or causes, a decrease in expression of CLECL1 or CD69. In some instances, the genotype is associated with, or causes, decreased activity of CLECL1 or CD69. In these instances, it may be suitable to use a CLECL1 or CD69 agonist to bring CLECL1 or CD69 activity back to a normal level, e.g., that of a person without the IBD of the subject.

In some instances, the therapeutic agent is a small molecule drug. By way of non-limiting example, a small molecule drug may be a chemical compound. In some instances, the therapeutic agent is a large molecule drug. Large molecule drugs generally comprise a peptide or nucleic acid. By way of non-limiting example, the large molecule drug may comprise an antibody or antigen binding antibody fragment. In some instances, the therapeutic agent comprises a small molecule and a large molecule. By way of non-limiting example, the therapeutic agent may comprise an antibody-drug conjugate.

In some instances, the therapeutic agent is a small molecule that binds CLECL1 or CD69. In some instances, the small molecule that binds CLECL1 or CD69 is a CLECL1 or CD69 agonist. In some instances, the small molecule that binds CLECL1 or CD69 is a CLECL1 or CD69 partial agonist. In some instances, the small molecule that binds CLECL1 or CD69 is a CLECL1 or CD69 antagonist. In some instances, the small molecule that binds CLECL1 or CD69 is a CLECL1 or CD69 partial agonist.

In some embodiments, the modulator of CLECL1 or CD69 comprises a CLECL1 polypeptide. In some embodiments, the CLECL1 polypeptide comprises a human CLECL1 (huCLECL1), or a homolog thereof. In some instances the polypeptide is an antagonist, agonist or modulator (e.g., allosteric modulator, orthosteric modulator) of CLECL1. In some embodiments, the CLECL1 polypeptide comprises a recombinant CLECL1 polypeptide. In some embodiments, the recombinant huCLECL1 protein comprises SEQ ID NO: 862, which is the amino acid sequence of human CLECL1 or CD69 (NCBI Reference Sequence No. NP_001240677). In some embodiments, the CLECL1 polypeptide comprises a recombinant CLECL1 polypeptide. In some embodiments, the huCLECL1 comprises an amino acid sequence about 99%, 98%, 97%, 96%, 95%, 94%, 93%, 92%, 91%, or 90% homologous to SEQ ID NO: 862. In some embodiments, the recombinant huCLECL1 protein comprises SEQ ID NO: 863, which is the amino acid sequence of human CLECL1 (NCBI Reference Sequence No. NP_001240679). In some embodiments, the huCLECL1 comprises an amino acid sequence about 99%, 98%, 97%, 96%, 95%, 94%, 93%, 92%, 91%, or 90% homologous to SEQ ID NO: 863. In some embodiments, the recombinant huCLECL1 protein comprises SEQ ID NO: 864, which is the amino acid sequence of human CLECL. In some embodiments, the huCLECL1 comprises an amino acid sequence about 99%, 98%, 97%, 96%, 95%, 94%, 93%, 92%, 91%, or 90% homologous to SEQ ID NO: 864. In some embodiments, the recombinant huCLECL1 protein comprises SEQ ID NO: 865, which is the amino acid sequence of human CLECL1 (NCBI Reference Sequence No. NP_001254630). In some embodiments, the huCLECL1 comprises an amino acid sequence about 99%, 98%, 97%, 96%, 95%, 94%, 93%, 92%, 91%, or 90% homologous to SEQ ID NO: 865. In some embodiments, the agonist of CLECL1 or CD69 comprises a CD69 polypeptide. In some embodiments, the recombinant huCD69 protein comprises SEQ ID NO: 866, which is the amino acid sequence of human CD69 (NCBI Reference Sequence No. NP_001772). In some embodiments, the huCD69 comprises an amino acid sequence about 99%, 98%, 97%, 96%, 95%, 94%, 93%, 92%, 91%, or 90% homologous to SEQ ID NO: 866.

In some instances, the CLECL1 or CD69 polypeptide is truncated. In some instances, the truncation is an N-terminal deletion. In other instances, the truncation is a C-terminal deletion. In additional instances, the truncation comprises both N-terminal and C-terminal deletions. For example, the truncation can be a deletion of at least or about 1, 2, 3, 4, 5, 6, 7, 8, 9, 10, 11, 12, 13, 14, 15, 20, or more residues from either the N-terminus or the C-terminus, or both termini. In some cases, the CLECL1 or CD69 polypeptide comprises an N-terminal deletion of at least or about 1, 2, 3, 4, 5, 6, 7, 8, 9, 10, 11, 12, 13, 14, 15, 20, or more residues. In some cases, the CLECL1 or CD69 polypeptide comprises an N-terminal deletion of at least or about 1, 2, 3, 4, 5, 6, 7, 8, 9, or 10 residues.

In some embodiments, the CLECL1 or CD69 polypeptide has an enhanced plasma half-life. In some instances, the plasma half-life comprises at least 30 minutes, 45 minutes, 60 minutes, 75 minutes, or 90 minutes, 2 hours, 3 hours, 4 hours, 5 hours, 6 hours, 7 hours, 8 hours, 9 hours, 10 hours, 11 hours, 12 hours, 18 hours, 24 hours, 36 hours, 48 hours, 3 days, 4 days, 5 days, 6 days, 7 days, 10 days, 12 days, 14 days, 21 days, 28 days, 30 days, or longer than the plasma half-life of the wild-type CLECL1 or CD69 protein.

In some embodiments, the CLECL1 or CD69 polypeptide is a conjugate. In some embodiments, the CLECL1 or CD69 conjugate comprises an CLECL1 or CD69 polypeptide comprising at least one amino acid and a conjugating moiety bound to the at least one 1 amino acid. In some embodiments, the at least one amino acid is located proximal to the N-terminus (e.g., proximal to the N-terminal residue). For example, the at least one amino acid is located optionally within the first 10, 20, 30, 40, or 50 residues from the N-terminus. In some cases, the at least one amino acid is located at the N-terminus (i.e., the at least one amino acid is the N-terminal residue of the CLECL1 or CD69 polypeptide). In other embodiments, the at least one amino acid is located proximal to the C-terminus (e.g., proximal to the C-terminal residue). For example, the at least one amino acid is located optionally within the first 10, 20, 30, 40, or 50 residues from the C-terminus. In some cases, the at least one amino acid is located at the C-terminus (i.e., the at least one amino acid is the C-terminal residue of the CLECL1 or CD69 polypeptide). In some instances, the CLECL1 or CD69 conjugate has an enhanced plasma half-life, such as the half-lives described herein. In some embodiments, the CLECL1 or CD69 conjugate is functionally active (e.g., retains activity). In some embodiments, the CLECL1 or CD69 conjugate is not functionally active (e.g., devoid of activity). In some embodiments, the conjugating moiety comprises a polymer comprising Polyethylene glycol (PEG).

In some embodiments, the CLECL1 or CD69 polypeptide is fused with a second polypeptide. In some embodiments, the second polypeptide comprises a polypeptide with a long plasma half-life relative to the plasma half-life of the CLECL1 or CD69 polypeptide. In some embodiments, the second polypeptide comprises an antibody or antibody fragment. In some embodiments, the antibody or antibody fragment comprises an IgG1, IgG2, IgG4, IgG3, or IgE. In some embodiments, the IgG is an Fc. In some embodiments, the IgG Fc is human. In some instances, the long plasma half-life polypeptide comprises HSA, transferrin, IgA monomer, Retinol-binding protein, Factor H, Factor XIII, C-reactive protein, Factor IX, Fibrinogen, IFN-alpha, Pentameric IgM, IL-2, or Thyroglobulin.

VEGFR1 Modulators

Fins Related Tyrosine Kinase 1 (FLT1) (HGNC: 3763 Entrez Gene: 2321 Ensembl: ENSG00000102755 OMIM: 165070 UniProtKB: P17948) encodes a member of the vascular endothelial growth factor receptor (VEGFR) family called vascular endothelial growth factor receptor 1 (VEGFR1). In some embodiments, the therapeutic agent comprises a modulator, agonist, and/or antagonist of at least one of VEGFR1. In some embodiments, the modulator of VEGFR is an antagonist of VEGFR. Non-limiting example of antagonist of VEGFR1 include ABT-869, Axitinib, IMC-1C11, Lenvatinib, N-(4-chlorophenyl)-2-[(pyridin-4-ylmethyl)amino]benzamide, Nintedanib, OSI-930, Pazopanib, Regorafenib, Sorafenib, Sunitinib, TG100801, Vatalanib, Motesanib, and Vandetanib.

In some embodiments, the therapeutic agent is effective to modify expression and/or activity of VEGFR1. Therapeutic agents that modify expression and/or activity of VEGFR1 may also be referred to herein as VEGFR1-targeting agents. Alternatively or additionally, compositions, kits and methods disclosed herein may comprise and/or utilize a therapeutic agent or use thereof, wherein the therapeutic agent modifies expression and/or activity of a protein that functions upstream or downstream of a pathway that involves VEGFR1 or the gene encoding VEGFR1 (FLT1). In some embodiments, the modulator of VEGFR1 is effective to increase or activate the activity or expression of VEGFR1 in the subject (e.g., agonist or partial agonist). In some embodiments, the modulator of VEGFR1 is effective to decrease or reduce the activity or expression of VEGFR1 (e.g., antagonist or partial antagonist). In some instances, the therapeutic agent is an allosteric modulator of VEGFR1.

In some embodiments, the VEGFR1 modulator is an antibody, an antigen binding fragment, a RNA interfering agent (RNAi), a small interfering RNA (siRNA), a short hairpin RNA (shRNA), a microRNA (miRNA), an antisense oligonucleotide, a peptide, a peptidomimetic, a small molecule, or an aptamer.

In some instances, the subject has a genotype that is associated with, or causes, an increased expression of VEGFR1. In some instances, the subject has a genotype that is associated with, or causes increased activity of VEGFR1. In some instances, the genotype is associated with, or causes and increase expression of VEGFR1. In some instances, the genotype is associated with, or causes an increase activity of VEGFR1. In these instances, it may be suitable to use a VEGFR1 antagonist to bring VEGFR1 activity back to a normal level, e.g., that of a person without the IBD of the subject.

In some instances, the subject has a genotype that is associated with, or causes decreased expression of VEGFR1. In some instances, the subject has a genotype is associated with, or causes, decreased activity of VEGFR1. In some instances, the genotype is associated with, or causes, a decrease in expression of VEGFR1. In some instances, the genotype is associated with, or causes, decreased activity of VEGFR1. In these instances, it may be suitable to use a VEGFR1 agonist to bring VEGFR1 activity back to a normal level, e.g., that of a person without the IBD of the subject.

In some instances, the therapeutic agent is a small molecule drug. By way of non-limiting example, a small molecule drug may be a chemical compound. In some instances, the therapeutic agent is a large molecule drug. Large molecule drugs generally comprise a peptide or nucleic acid. By way of non-limiting example, the large molecule drug may comprise an antibody or antigen binding antibody fragment. In some instances, the therapeutic agent comprises a small molecule and a large molecule. By way of non-limiting example, the therapeutic agent may comprise an antibody-drug conjugate.

In some instances, the therapeutic agent is a small molecule that binds VEGFR1. In some instances, the small molecule that binds VEGFR1 is a VEGFR1 agonist. In some instances, the small molecule that binds VEGFR1 is a VEGFR1 partial agonist. In some instances, the small molecule that binds VEGFR1 is a VEGFR1 antagonist. In some instances, the small molecule that binds VEGFR1 is a VEGFR1 partial agonist.

In some embodiments, the therapeutic agent comprises a VEGFR1 polypeptide. In some embodiments, the VEGFR1 polypeptide comprises a human VEGFR1 (huVEGFR1), or a homolog thereof. In some instances the polypeptide is an antagonist, agonist or modulator (e.g., allosteric modulator, orthosteric modulator) of VEGFR1. In some embodiments, the VEGFR1 polypeptide comprises a recombinant VEGFR1 polypeptide. In some embodiments, the recombinant huVEGFR1 protein comprises SEQ ID NO: 867), which is the amino acid sequence of human VEGFR1 (NCBI Reference Sequence No. NP_002010). In some embodiments, the VEGFR1 polypeptide comprises a recombinant VEGFR1 polypeptide. In some embodiments, the huVEGFR1 comprises an amino acid sequence about 99%, 98%, 97%, 96%, 95%, 94%, 93%, 92%, 91%, or 90% homologous to SEQ ID NO: 867.

In some embodiments, the recombinant huVEGFR1 protein comprises SEQ ID NO: 868, which is the amino acid sequence of human VEGFR1 (NCBI Reference Sequence No. NP_001153392). In some embodiments, the huVEGFR1 comprises an amino acid sequence about 99%, 98%, 97%, 96%, 95%, 94%, 93%, 92%, 91%, or 90% homologous to SEQ ID NO: 868.

In some embodiments, the recombinant huVEGFR1 protein comprises SEQ ID NO: 869, which is the amino acid sequence of human VEGFR1 (NCBI Reference Sequence No. NP_001153502). In some embodiments, the huVEGFR1 comprises an amino acid sequence about 99%, 98%, 97%, 96%, 95%, 94%, 93%, 92%, 91%, or 90% homologous to SEQ ID NO: 869.

In some embodiments, the recombinant huVEGFR1 protein comprises SEQ ID NO: 870, which is the amino acid sequence of human VEGFR1 (NCBI Reference Sequence No. NP_001153503). In some embodiments, the huVEGFR1 comprises an amino acid sequence about 99%, 98%, 97%, 96%, 95%, 94%, 93%, 92%, 91%, or 90% homologous to SEQ ID NO: 870.

In some instances, the VEGFR1 polypeptide is truncated. In some instances, the truncation is an N-terminal deletion. In other instances, the truncation is a C-terminal deletion. In additional instances, the truncation comprises both N-terminal and C-terminal deletions. For example, the truncation can be a deletion of at least or about 1, 2, 3, 4, 5, 6, 7, 8, 9, 10, 11, 12, 13, 14, 15, 20, or more residues from either the N-terminus or the C-terminus, or both termini. In some cases, the VEGFR1 polypeptide comprises an N-terminal deletion of at least or about 1, 2, 3, 4, 5, 6, 7, 8, 9, 10, 11, 12, 13, 14, 15, 20, or more residues. In some cases, the VEGFR1 polypeptide comprises an N-terminal deletion of at least or about 1, 2, 3, 4, 5, 6, 7, 8, 9, or 10 residues.

In some embodiments, the VEGFR1 polypeptide has an enhanced plasma half-life. In some instances, the plasma half-life comprises at least 30 minutes, 45 minutes, 60 minutes, 75 minutes, or 90 minutes, 2 hours, 3 hours, 4 hours, 5 hours, 6 hours, 7 hours, 8 hours, 9 hours, 10 hours, 11 hours, 12 hours, 18 hours, 24 hours, 36 hours, 48 hours, 3 days, 4 days, 5 days, 6 days, 7 days, 10 days, 12 days, 14 days, 21 days, 28 days, 30 days, or longer than the plasma half-life of the wild-type VEGFR1 protein.

In some embodiments, the VEGFR1 polypeptide is a conjugate. In some embodiments, the VEGFR1 conjugate comprises an VEGFR1 polypeptide comprising at least one amino acid and a conjugating moiety bound to the at least one 1 amino acid. In some embodiments, the at least one amino acid is located proximal to the N-terminus (e.g., proximal to the N-terminal residue). For example, the at least one amino acid is located optionally within the first 10, 20, 30, 40, or 50 residues from the N-terminus. In some cases, the at least one amino acid is located at the N-terminus (i.e., the at least one amino acid is the N-terminal residue of the VEGFR1 polypeptide). In other embodiments, the at least one amino acid is located proximal to the C-terminus (e.g., proximal to the C-terminal residue). For example, the at least one amino acid is located optionally within the first 10, 20, 30, 40, or 50 residues from the C-terminus. In some cases, the at least one amino acid is located at the C-terminus (i.e., the at least one amino acid is the C-terminal residue of the VEGFR1 polypeptide). In some instances, the VEGFR1 conjugate has an enhanced plasma half-life, such as the half-lives described herein. In some embodiments, the VEGFR1 conjugate is functionally active (e.g., retains activity). In some embodiments, the VEGFR1 conjugate is not functionally active (e.g., devoid of activity). In some embodiments, the conjugating moiety comprises a polymer comprising Polyethylene glycol (PEG).

In some embodiments, the VEGFR1 polypeptide is fused with a second polypeptide. In some embodiments, the second polypeptide comprises a polypeptide with a long plasma half-life relative to the plasma half-life of the VEGFR1 polypeptide. In some embodiments, the second polypeptide comprises an antibody or antibody fragment. In some embodiments, the antibody or antibody fragment comprises an IgG1, IgG2, IgG4, IgG3, or IgE. In some embodiments, the IgG is an Fc. In some embodiments, the IgG Fc is human. In some instances, the long plasma half-life polypeptide comprises HSA, transferrin, IgA monomer, Retinol-binding protein, Factor H, Factor XIII, C-reactive protein, Factor IX, Fibrinogen, IFN-alpha, Pentameric IgM, IL-2, or Thyroglobulin.

TEK Modulators

TEK Receptor Tyrosine Kinase (TEK) (HGNC: 11724 Entrez Gene: 7010 Ensembl: ENSG00000120156 OMIM: 600221 UniProtKB: Q02763) encodes a receptor that belongs to the protein tyrosine kinase Tie2 family, Angiopoietin-1 receptor (TIE2). In some embodiments, the therapeutic agent comprises a modulator, agonist, and/or antagonist of at least one of TIE2. In some embodiments, the therapeutic agent is effective to modify expression and/or activity of TIE2. Therapeutic agents that modify expression and/or activity of TIE2 may also be referred to herein as TIE2-targeting agents. Alternatively or additionally, compositions, kits and methods disclosed herein may comprise and/or utilize a therapeutic agent or use thereof, wherein the therapeutic agent modifies expression and/or activity of a protein that functions upstream or downstream of a pathway that involves TIE2 or the gene encoding TIE2 (TEK). In some embodiments, the modulator of TIE2 is effective to increase or activate the activity or expression of TIE2 in the subject (e.g., agonist or partial agonist). In some embodiments, the modulator of TIE2 is effective to decrease or reduce the activity or expression of TIE2 (e.g., antagonist or partial antagonist). In some instances, the therapeutic agent is an allosteric modulator of TIE2.

In some embodiments, the TIE2 modulator is an antibody, an antigen binding fragment, a RNA interfering agent (RNAi), a small interfering RNA (siRNA), a short hairpin RNA (shRNA), a microRNA (miRNA), an antisense oligonucleotide, a peptide, a peptidomimetic, a small molecule, or an aptamer.

In some instances, the subject has a genotype that is associated with, or causes, an increased expression of TIE2. In some instances, the subject has a genotype that is associated with, or causes increased activity of TIE2. In some instances, the genotype is associated with, or causes and increase expression of TIE2. In some instances, the genotype is associated with, or causes an increase activity of TIE2. In these instances, it may be suitable to use a TIE2 antagonist to bring TIE2 activity back to a normal level, e.g., that of a person without the IBD of the subject.

In some instances, the subject has a genotype that is associated with, or causes decreased expression of TIE2. In some instances, the subject has a genotype is associated with, or causes, decreased activity of TIE2. In some instances, the genotype is associated with, or causes, a decrease in expression of TIE2. In some instances, the genotype is associated with, or causes, decreased activity of TIE2. In these instances, it may be suitable to use a TIE2 agonist to bring TIE2 activity back to a normal level, e.g., that of a person without the IBD of the subject.

In some instances, the therapeutic agent is a small molecule drug. By way of non-limiting example, a small molecule drug may be a chemical compound. In some instances, the therapeutic agent is a large molecule drug. Large molecule drugs generally comprise a peptide or nucleic acid. By way of non-limiting example, the large molecule drug may comprise an antibody or antigen binding antibody fragment. In some instances, the therapeutic agent comprises a small molecule and a large molecule. By way of non-limiting example, the therapeutic agent may comprise an antibody-drug conjugate.

In some instances, the therapeutic agent is a small molecule that binds TIE2. In some instances, the small molecule that binds TIE2 is a TIE2 agonist. In some instances, the small molecule that binds TIE2 is a TIE2 partial agonist. In some instances, the small molecule that binds TIE2 is a TIE2 antagonist. In some instances, the small molecule that binds TIE2 is a TIE2 partial agonist.

In some embodiments, the therapeutic agent comprises a TIE2 polypeptide. In some embodiments, the TIE2 polypeptide comprises a human TIE2 (huTIE2), or a homolog thereof. In some instances the polypeptide is an antagonist, agonist or modulator (e.g., allosteric modulator, orthosteric modulator) of TIE2.

In some embodiments, the TIE2 polypeptide comprises a recombinant TIE2 polypeptide. In some embodiments, the recombinant huTIE2 protein comprises SEQ ID NO: 871, which is the amino acid sequence of human TIE2 (NCBI Reference Sequence No. NP_000450). In some embodiments, the huTIE2 comprises an amino acid sequence about 99%, 98%, 97%, 96%, 95%, 94%, 93%, 92%, 91%, or 90% homologous to SEQ ID NO: 871.

In some embodiments, the recombinant huTIE2 protein comprises SEQ ID NO: 872, which is the amino acid sequence of human TIE2 (NCBI Reference Sequence No. NP_005251619). In some embodiments, the huTIE2 comprises an amino acid sequence about 99%, 98%, 97%, 96%, 95%, 94%, 93%, 92%, 91%, or 90% homologous to SEQ ID NO: 872.

In some embodiments, the recombinant huTIE2 protein comprises SEQ ID NO: 873, which is the amino acid sequence of human TIE2 (NCBI Reference Sequence No. NP_01277007). In some embodiments, the huTIE2 comprises an amino acid sequence about 99%, 98%, 97%, 96%, 95%, 94%, 93%, 92%, 91%, or 90% homologous to SEQ ID NO: 873.

In some instances, the TIE2 polypeptide is truncated. In some instances, the truncation is an N-terminal deletion. In other instances, the truncation is a C-terminal deletion. In additional instances, the truncation comprises both N-terminal and C-terminal deletions. For example, the truncation can be a deletion of at least or about 1, 2, 3, 4, 5, 6, 7, 8, 9, 10, 11, 12, 13, 14, 15, 20, or more residues from either the N-terminus or the C-terminus, or both termini. In some cases, the TIE2 polypeptide comprises an N-terminal deletion of at least or about 1, 2, 3, 4, 5, 6, 7, 8, 9, 10, 11, 12, 13, 14, 15, 20, or more residues. In some cases, the TIE2 polypeptide comprises an N-terminal deletion of at least or about 1, 2, 3, 4, 5, 6, 7, 8, 9, or 10 residues.

In some embodiments, the TIE2 polypeptide has an enhanced plasma half-life. In some instances, the plasma half-life comprises at least 30 minutes, 45 minutes, 60 minutes, 75 minutes, or 90 minutes, 2 hours, 3 hours, 4 hours, 5 hours, 6 hours, 7 hours, 8 hours, 9 hours, 10 hours, 11 hours, 12 hours, 18 hours, 24 hours, 36 hours, 48 hours, 3 days, 4 days, 5 days, 6 days, 7 days, 10 days, 12 days, 14 days, 21 days, 28 days, 30 days, or longer than the plasma half-life of the wild-type TIE2 protein.

In some embodiments, the TIE2 polypeptide is a conjugate. In some embodiments, the TIE2 conjugate comprises an TIE2 polypeptide comprising at least one amino acid and a conjugating moiety bound to the at least one 1 amino acid. In some embodiments, the at least one amino acid is located proximal to the N-terminus (e.g., proximal to the N-terminal residue). For example, the at least one amino acid is located optionally within the first 10, 20, 30, 40, or 50 residues from the N-terminus. In some cases, the at least one amino acid is located at the N-terminus (i.e., the at least one amino acid is the N-terminal residue of the TIE2 polypeptide). In other embodiments, the at least one amino acid is located proximal to the C-terminus (e.g., proximal to the C-terminal residue). For example, the at least one amino acid is located optionally within the first 10, 20, 30, 40, or 50 residues from the C-terminus. In some cases, the at least one amino acid is located at the C-terminus (i.e., the at least one amino acid is the C-terminal residue of the TIE2 polypeptide). In some instances, the TIE2 conjugate has an enhanced plasma half-life, such as the half-lives described herein. In some embodiments, the TIE2 conjugate is functionally active (e.g., retains activity). In some embodiments, the TIE2 conjugate is not functionally active (e.g., devoid of activity). In some embodiments, the conjugating moiety comprises a polymer comprising Polyethylene glycol (PEG).

In some embodiments, the TIE2 polypeptide is fused with a second polypeptide. In some embodiments, the second polypeptide comprises a polypeptide with a long plasma half-life relative to the plasma half-life of the TIE2 polypeptide. In some embodiments, the second polypeptide comprises an antibody or antibody fragment. In some embodiments, the antibody or antibody fragment comprises an IgG1, IgG2, IgG4, IgG3, or IgE. In some embodiments, the IgG is an Fc. In some embodiments, the IgG Fc is human. In some instances, the long plasma half-life polypeptide comprises HSA, transferrin, IgA monomer, Retinol-binding protein, Factor H, Factor XIII, C-reactive protein, Factor IX, Fibrinogen, IFN-alpha, Pentameric IgM, IL-2, or Thyroglobulin.

KCNH7 Modulators

Potassium Voltage-Gated Channel Subfamily H Member 7 (KCNH7) (HGNC: 18863 Entrez Gene: 90134 Ensembl: ENSG00000184611 OMIM: 608169 UniProtKB: Q9NS40) encodes a member of the potassium channel, voltage-gated, subfamily H (KCNH7). In some embodiments, the therapeutic agent comprises a modulator, agonist, and/or antagonist of at least one of KCNH7. A non-limiting example of a modulator of KCNH7 is Dalfampridine. In some embodiments, the therapeutic agent is effective to modify expression and/or activity of KCNH7. Therapeutic agents that modify expression and/or activity of KCNH7 may also be referred to herein as KCNH7-targeting agents. Alternatively or additionally, compositions, kits and methods disclosed herein may comprise and/or utilize a therapeutic agent or use thereof, wherein the therapeutic agent modifies expression and/or activity of a protein that functions upstream or downstream of a pathway that involves KCNH7 or the gene encoding KCNH7. In some embodiments, the modulator of KCNH7 is effective to increase or activate the activity or expression of KCNH7 in the subject (e.g., agonist or partial agonist). In some embodiments, the modulator of KCNH7 is effective to decrease or reduce the activity or expression of KCNH7 (e.g., antagonist or partial antagonist). In some instances, the therapeutic agent is an allosteric modulator of KCNH7.

In some embodiments, the KCNH7 modulator is an antibody, an antigen binding fragment, a RNA interfering agent (RNAi), a small interfering RNA (siRNA), a short hairpin RNA (shRNA), a microRNA (miRNA), an antisense oligonucleotide, a peptide, a peptidomimetic, a small molecule, or an aptamer.

In some instances, the subject has a genotype that is associated with, or causes, an increased expression of KCNH7. In some instances, the subject has a genotype that is associated with, or causes increased activity of KCNH7. In some instances, the genotype is associated with, or causes and increase expression of KCNH7. In some instances, the genotype is associated with, or causes an increase activity of KCNH7. In these instances, it may be suitable to use a KCNH7 antagonist to bring KCNH7 activity back to a normal level, e.g., that of a person without the IBD of the subject.

In some instances, the subject has a genotype that is associated with, or causes decreased expression of KCNH7. In some instances, the subject has a genotype is associated with, or causes, decreased activity of KCNH7. In some instances, the genotype is associated with, or causes, a decrease in expression of KCNH7. In some instances, the genotype is associated with, or causes, decreased activity of KCNH7. In these instances, it may be suitable to use a KCNH7 agonist to bring KCNH7 activity back to a normal level, e.g., that of a person without the IBD of the subject.

In some instances, the therapeutic agent is a small molecule drug. By way of non-limiting example, a small molecule drug may be a chemical compound. In some instances, the therapeutic agent is a large molecule drug. Large molecule drugs generally comprise a peptide or nucleic acid. By way of non-limiting example, the large molecule drug may comprise an antibody or antigen binding antibody fragment. In some instances, the therapeutic agent comprises a small molecule and a large molecule. By way of non-limiting example, the therapeutic agent may comprise an antibody-drug conjugate.

In some instances, the therapeutic agent is a small molecule that binds KCNH7. In some instances, the small molecule that binds KCNH7 is a KCNH7 agonist. In some instances, the small molecule that binds KCNH7 is a KCNH7 partial agonist. In some instances, the small molecule that binds KCNH7 is a KCNH7 antagonist. In some instances, the small molecule that binds KCNH7 is a KCNH7 partial agonist.

In some embodiments, the therapeutic agent comprises a KCNH7 polypeptide. In some embodiments, the KCNH7 polypeptide comprises a human KCNH7 (huKCNH7), or a homolog thereof. In some instances the polypeptide is an antagonist, agonist or modulator (e.g., allosteric modulator, orthosteric modulator) of KCNH7. In some embodiments, the KCNH7 polypeptide comprises a recombinant KCNH7 polypeptide. In some embodiments, the recombinant huKCNH7 protein comprises SEQ ID NO: 874, which is the amino acid sequence of human KCNH7 (NCBI Reference Sequence No. NP_150375). In some embodiments, the KCNH7 polypeptide comprises a recombinant KCNH7 polypeptide. In some embodiments, the huKCNH7 comprises an amino acid sequence about 99%, 98%, 97%, 96%, 95%, 94%, 93%, 92%, 91%, or 90% homologous to SEQ ID NO: 874.

In some embodiments, the recombinant huKCNH7 protein comprises SEQ ID NO: 875, which is the amino acid sequence of human KCNH7 (NCBI Reference Sequence No. NP_775185). In some embodiments, the huKCNH7 comprises an amino acid sequence about 99%, 98%, 97%, 96%, 95%, 94%, 93%, 92%, 91%, or 90% homologous to SEQ ID NO: 875.

In some instances, the KCNH7 polypeptide is truncated. In some instances, the truncation is an N-terminal deletion. In other instances, the truncation is a C-terminal deletion. In additional instances, the truncation comprises both N-terminal and C-terminal deletions. For example, the truncation can be a deletion of at least or about 1, 2, 3, 4, 5, 6, 7, 8, 9, 10, 11, 12, 13, 14, 15, 20, or more residues from either the N-terminus or the C-terminus, or both termini. In some cases, the KCNH7 polypeptide comprises an N-terminal deletion of at least or about 1, 2, 3, 4, 5, 6, 7, 8, 9, 10, 11, 12, 13, 14, 15, 20, or more residues. In some cases, the KCNH7 polypeptide comprises an N-terminal deletion of at least or about 1, 2, 3, 4, 5, 6, 7, 8, 9, or 10 residues.

In some embodiments, the KCNH7 polypeptide has an enhanced plasma half-life. In some instances, the plasma half-life comprises at least 30 minutes, 45 minutes, 60 minutes, 75 minutes, or 90 minutes, 2 hours, 3 hours, 4 hours, 5 hours, 6 hours, 7 hours, 8 hours, 9 hours, 10 hours, 11 hours, 12 hours, 18 hours, 24 hours, 36 hours, 48 hours, 3 days, 4 days, 5 days, 6 days, 7 days, 10 days, 12 days, 14 days, 21 days, 28 days, 30 days, or longer than the plasma half-life of the wild-type KCNH7 protein.

In some embodiments, the KCNH7 polypeptide is a conjugate. In some embodiments, the KCNH7 conjugate comprises an KCNH7 polypeptide comprising at least one amino acid and a conjugating moiety bound to the at least one 1 amino acid. In some embodiments, the at least one amino acid is located proximal to the N-terminus (e.g., proximal to the N-terminal residue). For example, the at least one amino acid is located optionally within the first 10, 20, 30, 40, or 50 residues from the N-terminus. In some cases, the at least one amino acid is located at the N-terminus (i.e., the at least one amino acid is the N-terminal residue of the KCNH7 polypeptide). In other embodiments, the at least one amino acid is located proximal to the C-terminus (e.g., proximal to the C-terminal residue). For example, the at least one amino acid is located optionally within the first 10, 20, 30, 40, or 50 residues from the C-terminus. In some cases, the at least one amino acid is located at the C-terminus (i.e., the at least one amino acid is the C-terminal residue of the KCNH7 polypeptide). In some instances, the KCNH7 conjugate has an enhanced plasma half-life, such as the half-lives described herein. In some embodiments, the KCNH7 conjugate is functionally active (e.g., retains activity). In some embodiments, the KCNH7 conjugate is not functionally active (e.g., devoid of activity). In some embodiments, the conjugating moiety comprises a polymer comprising Polyethylene glycol (PEG).

In some embodiments, the KCNH7 polypeptide is fused with a second polypeptide. In some embodiments, the second polypeptide comprises a polypeptide with a long plasma half-life relative to the plasma half-life of the KCNH7 polypeptide. In some embodiments, the second polypeptide comprises an antibody or antibody fragment. In some embodiments, the antibody or antibody fragment comprises an IgG1, IgG2, IgG4, IgG3, or IgE. In some embodiments, the IgG is an Fc. In some embodiments, the IgG Fc is human. In some instances, the long plasma half-life polypeptide comprises HSA, transferrin, IgA monomer, Retinol-binding protein, Factor H, Factor XIII, C-reactive protein, Factor IX, Fibrinogen, IFN-alpha, Pentameric IgM, IL-2, or Thyroglobulin.

CD30L Modulators

In some embodiments, the therapeutic agent is a modulator of CD30 ligand (CD30L). In some embodiments, the modulator of CD30L is an agonist or an antagonist of CD30L. In some instances, the antagonist of CD30L is an inhibitor of CD30L. In some embodiments, an inhibitor of CD30L specifically binds directly or indirectly to CD30L, CD30, or a molecule that interferes directly or indirectly with binding between CD30L and CD30. In some embodiments, as used herein, an inhibitor of CD30L comprises an agent that modulates at least one functional activity of CD30L, such as binding to CD30. Non-limiting examples of inhibitors of CD30L include agents that specifically bind to CD30L, including a polypeptide such as an anti-CD30L antibody or antigen binding fragment thereof, and a nucleic acid, e.g., an antisense construct, siRNA, and ribozyme. An antisense construct includes an expression plasmid that when transcribed in the cell produces RNA complementary to a portion of mRNA encoding CD30L, and an oligonucleotide that inhibits protein expression by hybridizing with the CD30L mRNA. In some embodiments the inhibitor of CD30L comprises a non-polypeptide or non-nucleic acid portion as an active agent that binds to and inhibits CD30L activity.

In some embodiments, an inhibitor of CD30L is a polypeptide that binds to CD30L and/or CD30. In some cases, the polypeptide is a CD30 polypeptide or a portion thereof, wherein the portion retains the ability to bind to CD30L. A portion of a CD30 polypeptide includes at least about 10, 15, 20, 25, 30, 35, 40, 45, or 50 amino acids that have at least about 85%, 90%, or 95% identity to human CD30 having SEQ ID NO: 94, or SEQ ID NO: 95, or a sequence of any CD30 protein-coding isoform (for e.g., P28908). For example, an inhibitor of CD30L comprises a CD30 polypeptide that comprises all or part of the extracellular region of human CD30. In some embodiments, the CD30 polypeptide comprises amino acids 19-390 of SEQ ID NO: 18 or a binding fragment thereof, having at least about 85%, 90%, or 95% sequence identity to CD30. In some embodiments, the CD30 polypeptide is a homologue of mammalian CD30, e.g., the CD30 polypeptide inhibitor of CD30L is a viral CD30 polypeptide or fragment thereof. As a non-limiting example, the viral CD30 polypeptide comprises viral CD30 from a poxvirus, such as ectromelia virus or cowpox virus.

In a non-limiting example, the inhibitor is an anti-CD30L antibody or an anti-CD30 antibody. As used herein, an antibody includes an antigen-binding fragment of a full length antibody, e.g., a Fab or scFv. In some embodiments, the antibody binds to the extracellular domain of CD30L. In some embodiments, an anti-CD30L antibody comprises a heavy chain comprising three complementarity-determining regions: HCDR1, HCDR2, and HCDR3; and a light chain comprising three complementarity-determining regions: LCDR1, LCDR2, and LCDR3. In some embodiments, the anti-CD30L antibody comprises a HCDR1 comprising SEQ ID NO: 100, a HCDR2 comprising SEQ ID NO: 101, a HCDR3 comprising SEQ ID NO: 102, a LCDR1 comprising SEQ ID NO: 103, a LCDR2 comprising SEQ ID NO: 104, and a LCDR3 comprising SEQ ID NO: 105.

In some embodiments, the anti-CD30L antibody comprises a HCDR1 comprising SEQ ID NO: 106, a HCDR2 comprising SEQ ID NO: 107, a HCDR3 comprising SEQ ID NO: 108, a LCDR1 comprising SEQ ID NO: 109, a LCDR2 comprising SEQ ID NO: 110, and a LCDR3 comprising SEQ ID NO: 111.

In some embodiments, the anti-CD30L antibody comprises a HCDR1 comprising SEQ ID NO: 112, a HCDR2 comprising SEQ ID NO: 113, a HCDR3 comprising SEQ ID NO: 114, a LCDR1 comprising SEQ ID NO: 115, a LCDR2 comprising SEQ ID NO: 116, and a LCDR3 comprising SEQ ID NO: 117.

In some embodiments, the anti-CD30L antibody comprises a HCDR1 comprising SEQ ID NO: 118, a HCDR2 comprising SEQ ID NO: 119, a HCDR3 comprising SEQ ID NO: 120, a LCDR1 comprising SEQ ID NO: 121, a LCDR2 comprising SEQ ID NO: 122, and a LCDR3 comprising SEQ ID NO: 123.

In some embodiments, the anti-CD30L antibody comprises a HCDR1 comprising SEQ ID NO: 124, a HCDR2 comprising SEQ ID NO: 125, a HCDR3 comprising SEQ ID NO: 126, a LCDR1 comprising SEQ ID NO: 127, a LCDR2 comprising SEQ ID NO: 128, and a LCDR3 comprising SEQ ID NO: 129.

In some embodiments, the anti-CD30L antibody comprises a HCDR1 comprising SEQ ID NO: 130, a HCDR2 comprising SEQ ID NO: 131, a HCDR3 comprising SEQ ID NO: 132, a LCDR1 comprising SEQ ID NO: 133, a LCDR2 comprising SEQ ID NO: 134, and a LCDR3 comprising SEQ ID NO: 135.

In some cases, the anti-CD30L antibody comprises a heavy chain (HC) variable domain comprising SEQ ID NO: 136 and a light chain (LC) variable domain comprising SEQ ID NO: 137. In some cases, the anti-CD30L antibody comprises a heavy chain (HC) variable domain comprising SEQ ID NO: 138 and a light chain (LC) variable domain comprising SEQ ID NO: 139. In some cases, the anti-CD30L antibody comprises a heavy chain (HC) variable domain comprising SEQ ID NO: 140 and a light chain (LC) variable domain comprising SEQ ID NO: 141. In some cases, the anti-CD30L antibody comprises a heavy chain (HC) variable domain comprising SEQ ID NO: 142 and a light chain (LC) variable domain comprising SEQ ID NO: 143. In some cases, the anti-CD30L antibody comprises a heavy chain (HC) variable domain comprising SEQ ID NO: 144 and a light chain (LC) variable domain comprising SEQ ID NO: 145. In some cases, the anti-CD30L antibody comprises a heavy chain (HC) variable domain comprising SEQ ID NO: 146 and a light chain (LC) variable domain comprising SEQ ID NO: 154. In some cases, the anti-CD30L antibody comprises a heavy chain (HC) variable domain comprising SEQ ID NO: 147 and a light chain (LC) variable domain comprising SEQ ID NO: 154. In some cases, the anti-CD30L antibody comprises a heavy chain (HC) variable domain comprising SEQ ID NO: 148 and a light chain (LC) variable domain comprising SEQ ID NO: 154. In some cases, the anti-CD30L antibody comprises a heavy chain (HC) variable domain comprising SEQ ID NO: 149 and a light chain (LC) variable domain comprising SEQ ID NO: 154. In some cases, the anti-CD30L antibody comprises a heavy chain (HC) variable domain comprising SEQ ID NO: 150 and a light chain (LC) variable domain comprising SEQ ID NO: 154. In some cases, the anti-CD30L antibody comprises a heavy chain (HC) variable domain comprising SEQ ID NO: 151 and a light chain (LC) variable domain comprising SEQ ID NO: 154. In some cases, the anti-CD30L antibody comprises a heavy chain (HC) variable domain comprising SEQ ID NO: 152 and a light chain (LC) variable domain comprising SEQ ID NO: 154. In some cases, the anti-CD30L antibody comprises a heavy chain (HC) variable domain comprising SEQ ID NO: 153 and a light chain (LC) variable domain comprising SEQ ID NO: 154.

In some embodiments, the anti-CD30 antibody comprises a heavy chain variable region comprising SEQ ID NO: 96 and a light chain variable region comprising SEQ ID NO: 97. Non-limiting examples of anti-CD30 antibodies include MDX-60, Ber-H2, SGN-30 (cAC10), Ki-4.dgA, HRS-3/A9, AFM13, and H22xKi-4.

In some embodiments, the anti-CD30 antibody comprises an antibody drug conjugate. As a non-limiting example, the antibody drug conjugate is brentuximab, an anti-CD30 antibody conjugated to monomethyl auristatin E.

RIPK2 Modulators

Disclosed herein, in some embodiments, are therapeutic agents useful for the treatment of a disease or condition, or symptom of the disease or condition, disclosed herein. Disclosed herein, in some embodiments, are modulators of RIPK2 activity or expression that are useful for the treatment of an inflammatory, fibrotic, and/or fibrostenotic disease or condition. In some embodiments, the inflammatory disease comprises inflammatory bowel disease (IBD), Crohn's disease (CD), and/or ulcerative colitis (UC). In some embodiments, a modulator of RIPK2 activity or expression comprises an antagonist or a partial antagonist of RIPK2. In some embodiments, the RIPK2 antagonist or partial antagonist comprises an antibody or antigen-binding fragment, or a small molecule.

In some embodiments, the RIPK2 antagonist or partial antagonist comprises a type I RIPK2 inhibitor effective to bind to the ATP binding pocket of an active conformation of the RIPK2 kinase domain. In some embodiments, the RIPK2 antagonist or partial antagonist comprises a type I½ RIPK2 inhibitor effective to bind to the ATP binding pocket of an inactive conformation of the RIPK2 kinase domain without displacing the RIPK2 kinase activation segment. In some embodiments, the RIPK2 antagonist or partial antagonist comprises a type II RIPK2 inhibitor effective to displace a RIPK2 kinase activation segment. In some embodiments, the RIPK2 antagonist or partial antagonist comprises a type III RIPK2 inhibitor effective to bind an allosteric site of RIPK2 located in the cleft between the small and large lobes adjacent to the ATP binding pocket. In some embodiments, the RIPK2 antagonist or partial antagonist comprises a type IV RIPK2 inhibitor effective to bind an allosteric site of RIPK2 located outside of the cleft and the phospho acceptor region. In some embodiments, the RIPK2 antagonist or partial antagonist comprises a type V RIPK2 inhibitor effective to span two regions of the RIPK2 kinase domain. In some embodiments, the RIPK2 antagonist or partial antagonist comprises a type VI RIPK2 inhibitor effective to form a covalent adduct with RIPK2. In some embodiments, the RIPK2 antagonist or partial antagonist comprises a RIPK2 inhibitor effective to inhibit RIPK2 ubiquitination. In some embodiments, the RIPK2 antagonist or partial antagonist comprises a RIPK2 inhibitor effective to inhibit RIPK2 autophosphorylation. In some embodiments, the RIPK2 antagonist or partial antagonist comprises a RIPK2 inhibitor effective to block NOD-dependent tumor necrosis factor production without affecting lipopolysaccharide-dependent pathways. In some embodiments, the RIPK2 antagonist or partial antagonist comprises ponatinib, sorafenib, regorafenib, gefitinib, or erlotinib. In some embodiments, the RIPK2 antagonist or partial antagonist comprises GSK2983559, GSK583, Inhibitor 7, Biaryl Urea, CSR35, CSLP37, CSLP43, RIPK2 inhibitor 1, CS6, PP2, WEHI-345, SB203580, OD36, OD38, RIPK2-IN-8, RIPK2-IN-1, or RIPK2-IN-2, or any combination thereof.

Disclosed herein, in some embodiments, are antagonists or partial antagonists of RIPK2 having a structure of Formula (I) or a pharmaceutically acceptable salt or isotopic variant thereof:

Formula (I)

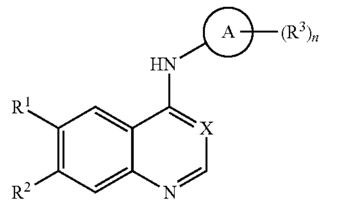

wherein

Ring A is $C_{3-8}$cycloalkyl, $C_{2-9}$heterocycloalkyl, $C_{2-9}$heteroaryl, or 6- to 10-membered aryl;

X is N or $CR^4$;

$R^1$ and $R^2$ are independently —H, halogen, —OH, —$OR^5$, —CN, —$N(R^6)_2$, —$NR^6C(O)R^5$, —$C(O)OR^5$, —$C(O)N(R^6)_2$, $C_{1-6}$alkyl, $C_{2-6}$alkenyl, $C_{2-6}$alkynyl, $C_{3-8}$cycloalkyl, —$C_{1-6}$alkyl-OH, —$C_{1-6}$alkyl-$OR^5$, —$C_{1-6}$alkyl-$N(R^6)_2$, —O—$C_{1-6}$alkyl, —O—$C_{1-6}$alkyl-OH, —O—$C_{1-6}$alkyl-$OR^5$, —O—$C_{1-6}$alkyl-$N(R^6)_2$, or —$S(=O)_2R$;

each $R^3$ is independently —H, halogen, —$NO_2$, —CN, —OH, —OR, —$SR^5$, —$N(R^6)_2$, —S(O)R, —$S(=O)_2R^5$, —$NR^6S(=O)_2R^5$, —$S(=O)_2N(R^6)_2$, —$C(O)R^5$, —$C(O)OR^5$, —$OC(O)R^5$, —$C(O)N(R^6)_2$, —$OC(O)N(R^6)_2$, —$NR^6C(O)N(R^6)_2$, —$NR^6C(O)R^5$, —$NR^6C(O)OR^5$, $C_{1-6}$alkyl, $C_{2-6}$alkenyl, $C_{2-6}$alkynyl, $C_{1-6}$haloalkyl, $C_{1-6}$heteroalkyl, —O—$C_{1-6}$alkyl, $C_{3-8}$cycloalkyl, $C_{2-9}$heterocycloalkyl, $C_{2-9}$heteroaryl, 6- to 10-membered aryl, or —O-phenyl, wherein each alkyl, haloalkyl, heteroalkyl, cycloalkyl, heterocycloalkyl, aryl, and heteroaryl is optionally substituted with one or more $R^7$;

$R^4$ is —H, halogen, $C_{1-6}$alkyl, $C_{2-6}$alkenyl, $C_{2-6}$alkynyl, $C_{1-6}$haloalkyl, $C_{3-8}$cycloalkyl, —$C_{1-6}$alkyl-$C_{3-8}$cycloalkyl, phenyl, —$C_{1-6}$alkyl-phenyl, $C_{2-9}$heterocycloalkyl, —$C_{1-6}$alkyl-$C_{2-9}$heterocycloalkyl, $C_{2-9}$heteroaryl, or —$C_{1-6}$alkyl-$C_{2-9}$heteroaryl, wherein the alkyl, haloalkyl, cycloalkyl, phenyl, heteroaryl, and heterocycloalkyl are optionally substituted;

each $R^5$ is independently —H, $C_{1-6}$alkyl, $C_{2-6}$alkenyl, $C_{2-6}$alkynyl, $C_{1-6}$haloalkyl, $C_{3-8}$cycloalkyl, —$C_{1-6}$alkyl-$C_{3-8}$cycloalkyl, phenyl, —$C_{1-6}$alkyl-phenyl, $C_{2-9}$heterocycloalkyl, —$C_{1-6}$alkyl-$C_{2-9}$heterocycloalkyl, $C_{2-9}$heteroaryl, or —$C_{1-6}$alkyl-$C_{2-9}$heteroaryl;

each $R^6$ is independently —H, $C_{1-6}$alkyl, $C_{2-6}$alkenyl, $C_{2-6}$alkynyl, $C_{1-6}$haloalkyl, $C_{3-8}$cycloalkyl, —$C_{1-6}$alkyl-$C_{3-8}$cycloalkyl, phenyl, —$C_{1-6}$alkyl-phenyl, or $C_{2-9}$heteroaryl; or two $R^6$ substituents are taken together with the nitrogen atom to which they are attached to form a 5- or 6-membered heterocycle; and $R^7$ is —H, halogen, $C_{1-6}$alkyl, $C_{2-6}$alkenyl, $C_{2-6}$alkynyl, $C_{1-6}$haloalkyl, $C_{3-8}$cycloalkyl, —$C_{1-6}$alkyl-$C_{3-8}$cycloalkyl, phenyl, —$C_{1-6}$alkyl-phenyl, $C_{2-9}$heterocycloalkyl, —$C_{1-6}$alkyl-$C_{2-9}$heterocycloalkyl, $C_{2-9}$heteroaryl, or —$C_{1-6}$alkyl-$C_{2-9}$heteroaryl; and n is 0, 1, 2, 3, 4, or 5.

In some embodiments of a compound of Formula (I), Ring A is $C_{3-8}$cycloalkyl, $C_{2-9}$-heterocycloalkyl, $C_{2-9}$heteroaryl, or 6- to 10-membered aryl. In some embodiments of a compound of Formula (I), Ring A is $C_{3-7}$heteroaryl or 6-membered aryl. In some embodiments of a compound of Formula (I), Ring A is pyrrazolyl. In some embodiments of a compound of Formula (I), Ring A is $C_7$heteroaryl. In some embodiments of a compound of Formula (I), Ring A is phenyl.

In some embodiments, for a compound of Formula (I), X is N or $CR^4$. In some embodiments, for a compound of Formula (I), X is N or CH. In some embodiments, for a compound of Formula (I), X is N. In some embodiments, for a compound of Formula (I), X is CH.

In some embodiments, for a compound of Formula (I), $R^1$ is —H, halogen, —OH, —CN, —$N(R^6)_2$, —$NR^6C(O)R^5$, —$C(O)OR^5$, —$C(O)N(R^6)_2$, $C_{1-6}$alkyl, $C_{2-6}$alkenyl, $C_{2-6}$alkynyl, $C_{3-8}$cycloalkyl, —$C_{1-6}$ alkyl-OH, —$C_{1-6}$alkyl-$OR^5$, —$C_{1-6}$alkyl-$N(R^6)_2$, —O—$C_{1-6}$alkyl, —O—$C_{1-6}$alkyl-OH, —O—$C_{1-6}$alkyl-$OR^5$, —O—$C_{1-6}$alkyl-$N(R^6)_2$, or —$S(=O)_2R^5$. In some embodiments, for a compound of Formula (I), $R^1$ is $C_{1-6}$alkyl, $C_{2-6}$alkenyl, —$C_{1-6}$alkyl-OH, —$C_{1-6}$alkyl-$OR^5$, —$C_{1-6}$alkyl-$N(R^6)_2$, —O—$C_{1-6}$alkyl, —O—$C_{1-6}$alkyl-OH, —O—$C_{1-6}$alkyl-$OR^5$, —O—$C_{1-6}$alkyl-$N(R^6)_2$, or —$S(=O)_2R^5$. In some embodiments, for a compound of Formula (I), $R^1$ is —O—$C_{1-6}$alkyl, —O—$C_{1-6}$alkyl-$OR^5$, —O—$C_{1-6}$alkyl-$N(R^6)_2$, or —$S(=O)_2R^5$. In some embodiments, for a compound of Formula (I), $R^1$ is —O—$C_{1-6}$alkyl. In some embodiments, for a compound of Formula (I), $R^1$ is —$OCH_3$. In some embodiments, for a compound of Formula (I), $R^1$ is —O—$C_{1-6}$alkyl-$OR^5$. In some embodiments, for a compound of Formula (I), $R^1$ is —$OCH_2CH_2OCH_3$. In some embodiments, for a compound of Formula (I), $R^1$ is —O—$C_{1-6}$alkyl-$N(R^6)_2$. In some embodiments, for a compound of Formula (I), $R^1$ is —O $CH_2CH_2CH_2$ morpholine. In some embodiments, for a compound of Formula (I), $R^1$ is —$S(=O)_2R^5$. In some embodiments, for a compound of Formula (I), $R^1$ is —$S(=O)_2$tert-butyl.

In some embodiments, for a compound of Formula (I), $R^2$ is —H, halogen, —OH, —CN, —$N(R^6)_2$, —$NR^6C(O)R^5$, —$C(O)OR^5$, —$C(O)N(R^6)_2$, $C_{1-6}$alkyl, $C_{2-6}$alkenyl, $C_{2-6}$alkynyl, $C_{3-8}$cycloalkyl, —$C_{1-6}$ alkyl-OH, —$C_{1-6}$alkyl-$OR^5$, —$C_{1-6}$alkyl-$N(R^6)_2$, —O—$C_{1-6}$alkyl, —O—$C_{1-6}$alkyl-OH, —O—$C_{1-6}$alkyl-$OR^5$, —O—$C_{1-6}$alkyl-$N(R^6)_2$, or —$S(=O)_2R^5$. In some embodiments, for a compound of Formula (I), $R^2$ is —H, —O—$C_{1-6}$alkyl, —O—$C_{1-6}$alkyl-$OR^5$, or —O—$C_{1-6}$alkyl-OH. In some embodiments, for a compound of Formula (I), $R^2$ is —H. In some embodiments, for a compound of Formula (I), $R^2$ is —O—$C_{1-6}$alkyl. In some embodiments, for a compound of Formula (I), $R^2$ is —$OCH_3$. In some embodiments, for a compound of Formula (I), $R^2$ is —O—$C_{1-6}$alkyl-$OR^5$. In some embodiments, for a compound of Formula (I), $R^2$ is —$OCH_2CH_2OCH_3$. In some embodiments, for a compound of Formula (I), $R^2$ is —O—$C_{1-6}$alkyl-OH. In some embodiments, for a compound of Formula (I), $R^2$ is —$OCH_2CH_2OH$.

In some embodiments, for a compound of Formula (I), R3 is —H, halogen, —$NO_2$, —CN, —OH, —$OR^5$, —$SR^5$, —$N(R^6)_2$, —$S(O)R^5$, —$S(=O)_2R^5$, —$NR^6S(=O)_2R^5$, —$S(=O)_2N(R^6)_2$, —$C(O)R^5$, —$C(O)OR^5$, —$OC(O)R^5$, —$C(O)N(R^6)_2$, —$OC(O)N(R^6)_2$, —$NR^6C(O)N(R^6)_2$, —$NR^6C(O)R^5$, —$NR^6C(O)OR^5$, $C_{1-6}$alkyl, $C_{2-6}$alkenyl, $C_{2-6}$alkynyl, $C_{1-6}$haloalkyl, $C_{1-6}$heteroalkyl, —O—$C_{1-6}$alkyl, $C_{3-8}$cycloalkyl, $C_{2-9}$heterocycloalkyl, $C_{2-9}$heteroaryl, 6- to 10-membered aryl, or —O-phenyl, wherein each alkyl, haloalkyl, heteroalkyl, cycloalkyl, heterocycloalkyl, aryl, and heteroaryl is optionally substituted with one or more $R^7$. In some embodiments, for a compound of Formula (I), $R^3$ is —H, halogen, $C_{1-6}$alkyl, $C_{2-6}$alkynyl, or —O-phenyl. In some embodiments, for a compound of Formula (I), $R^3$ is —H. In some embodiments, for a compound of Formula (I), $R^3$ is —Cl. In some embodiments, for a compound of Formula (I), $R^3$ is —F. In some embodiments, for a compound of Formula (I), $R^3$ is —$CH_3$. In some embodiments, for a compound of Formula (I), $R^3$ is —CCH. In some embodiments, for a compound of Formula (I), $R^3$ is —O-phenyl.

In some embodiments, for a compound of Formula (I), n is 0, 1, 2, or 3. In some embodiments, for a compound of Formula (I), n is 1, 2, or 3. In some embodiments, for a compound of Formula (I), n is 1 or 2. In some embodiments, for a compound of Formula (I), n is 0. In some embodiments, for a compound of Formula (I), n is 1. In some embodiments, for a compound of Formula (I), n is 2. In some embodiments, for a compound of Formula (I), n is 3.

Disclosed herein, in some embodiments, are antagonists or partial antagonists of RIPK2 having a structure of Formula (Ia) or a pharmaceutically acceptable salt or isotopic variant thereof:

Formula (Ia)

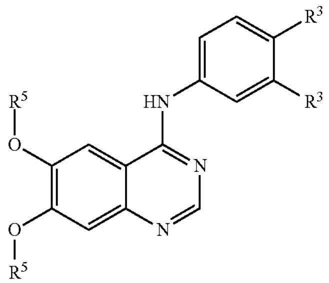

wherein;

each $R^3$ is independently —H, halogen, —C≡CH, or —O-aryl; and each $R^5$ is independently $C_{1-6}$ alkyl, —$C_{1-6}$alkyl-O—$C_{1-6}$alkyl, or —$C_{1-6}$alkyl-heterocycloalkyl.

Disclosed herein, in some embodiments, are antagonists or partial antagonists of RIPK2 having a structure of Formula (Ia) or a pharmaceutically acceptable salt or isotopic variant thereof:

Formula (Ia)

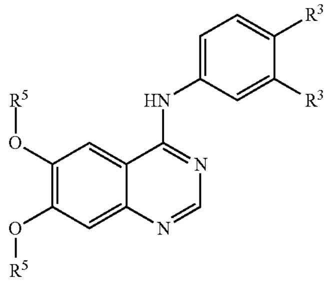

wherein;

each $R^3$ is independently —H, —Cl, —F, —C≡CH, or —O-phenyl; and each $R^5$ is independently —$CH_3$, —$CH_2CH_2OCH_3$, or —$CH_2CH_2CH_2$morpholine.

Disclosed herein, in some embodiments, are antagonists or partial antagonists of RIPK2 having a structure of Formula (Ib) or a pharmaceutically acceptable salt or isotopic variant thereof:

Formula (Ib)

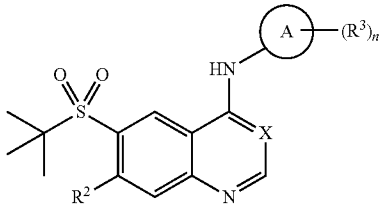

wherein;

Ring A is $C_{3-7}$heteroaryl;

X is N or CH;

$R^2$ is —H, —$OC_{1-6}$alkyl, or —O—$C_{1-6}$alkyl-OH;

each $R^3$ is independently —H, —$C_{1-6}$alkyl, or halogen; and n is 0, 1, or 2.

Disclosed herein, in some embodiments, are antagonists or partial antagonists of RIPK2 having a structure of Formula (Ib) or a pharmaceutically acceptable salt or isotopic variant thereof:

Formula (Ib)

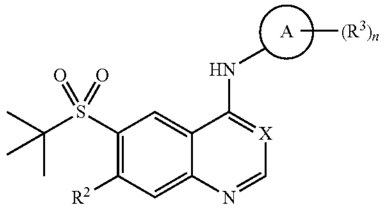

wherein;

Ring A is $C_{3-7}$heteroaryl;

X is N or CH;

$R^2$ is —H, —$OCH_3$, or —$OCH_2CH_2OH$;

each $R^3$ is independently —H, —$CH_3$, or —F; and n is 0, 1, or 2.

In some embodiments a compound of Formula (I) or a pharmaceutically acceptable salt or isotopic variant thereof has the structure of:

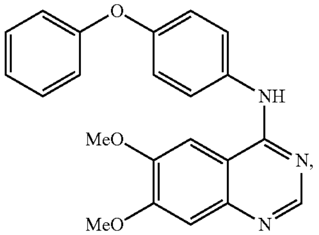

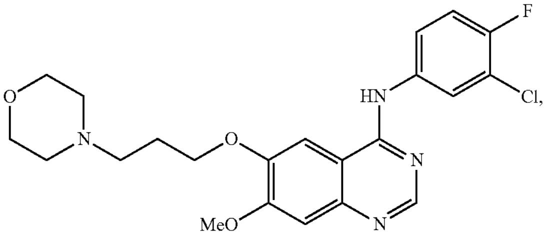

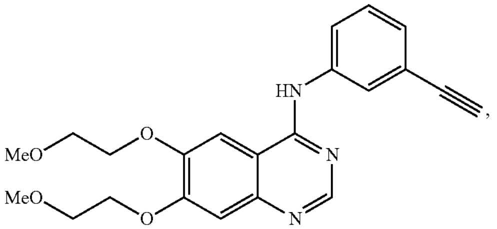

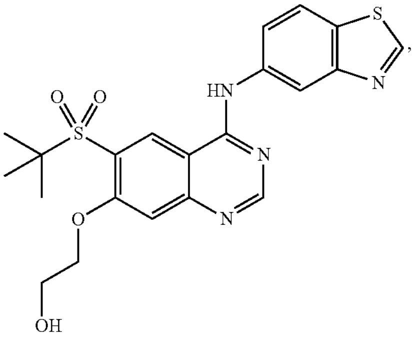

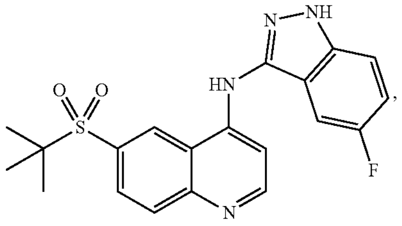

or

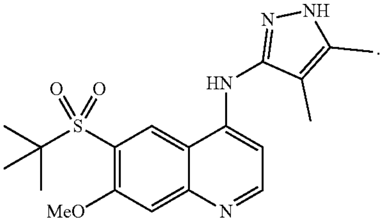

Disclosed herein, in some embodiments, are antagonists or partial antagonists of RIPK2 having a structure of Formula (II) or a pharmaceutically acceptable salt or isotopic variant thereof:

Formula (II)

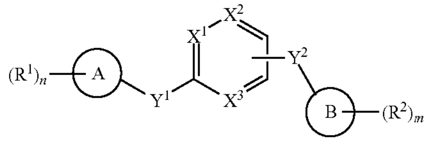

wherein

Rings A and B are independently $C_{3-8}$cycloalkyl, $C_{2-9}$heterocycloalkyl, $C_{2-9}$heteroaryl, or 6- to 10-membered aryl;

$X^1$, $X^2$, and $X^3$ are independently N or $CR^4$;

$Y^1$ and $Y^2$ are independently a bond, —O—, —S—, —$C(R^5)_2$, —$NR^6$—, —$NR^6C(O)$—, —$C(O)NR^6$—, or —$NR^6C(O)NR^6$—;

each $R^1$ and $R^2$ is independently —H, halogen, —$NO_2$, —CN, —OH, —$OR^5$, —$SR^5$, —$N(R^6)_2$, —S(O)R, —$S(=O)_2R^5$, —$NR^6S(=O)_2R^5$, —$S(=O)_2N(R^6)_2$, —$SCH_2C(O)OR^5$, —$C(O)R^5$, —$C(O)OR^5$, — $OC(O)R^5$, —$C(O)N(R^6)_2$, —$OC(O)N(R^6)_2$, —$NR^6C(O)N(R^6)_2$, —$NR^6C(O)R^5$, —$NR^6C(O)OR^5$, $C_{1-6}$alkyl, $C_{2-6}$alkenyl, $C_{2-6}$alkynyl, $C_{1-6}$haloalkyl, $C_{1-6}$heteroalkyl, —O—$C_{1-6}$alkyl, $C_{3-8}$cycloalkyl, $C_{2-9}$heterocycloalkyl, $C_{2-9}$heteroaryl, 6- to 10-membered aryl, or —O-phenyl, wherein each alkyl, haloalkyl, heteroalkyl, cycloalkyl, heterocycloalkyl, aryl, and heteroaryl is optionally substituted with one or more $R^7$;

each $R^4$ is independently —H, halogen, —$N(R^6)_2$, —$NO_2$, $C_{1-6}$alkyl, $C_{2-6}$alkenyl, $C_{2-6}$alkynyl, $C_{1-6}$ haloalkyl, $C_{3-8}$cycloalkyl, —$C_{1-6}$alkyl-$C_{3-8}$cycloalkyl, phenyl, —$C_{1-6}$alkyl-phenyl, $C_{2-9}$heterocycloalkyl, —$C_{1-6}$alkyl-$C_{2-9}$heterocycloalkyl, $C_{2-9}$heteroaryl, or —$C_{1-6}$alkyl-$C_{2-9}$heteroaryl, wherein the alkyl, haloalkyl, cycloalkyl, phenyl, heteroaryl, and heterocycloalkyl are optionally substituted;

each $R^5$ is independently —H, $C_{1-6}$alkyl, $C_{2-6}$alkenyl, $C_{2-6}$alkynyl, $C_{1-6}$haloalkyl, $C_{3-8}$cycloalkyl, —$C_{1-6}$alkyl-$C_{3-8}$cycloalkyl, phenyl, —$C_{1-6}$alkyl-phenyl, $C_{2-9}$heterocycloalkyl, —$C_{1-6}$alkyl-$C_{2-9}$heterocycloalkyl, $C_{2-9}$heteroaryl, or —$C_{1-6}$alkyl-$C_{2-9}$heteroaryl;

each $R^6$ is independently —H, $C_{1-6}$alkyl, $C_{2-6}$alkenyl, $C_{2-6}$alkynyl, $C_{1-6}$haloalkyl, $C_{3-8}$cycloalkyl, —$C_{1-6}$alkyl-$C_{3-8}$cycloalkyl, phenyl, —$C_{1-6}$alkyl-phenyl, or $C_{2-9}$heteroaryl; or two $R^6$ are taken together with the nitrogen atom to which they are attached to form a 5- or 6-membered heterocycle; and $R^7$ is —H, halogen, $C_{1-6}$alkyl, $C_{2-6}$alkenyl, $C_{2-6}$alkynyl, $C_{1-6}$haloalkyl, $C_{3-8}$cycloalkyl, —$C_{1-6}$alkyl-$C_{3-8}$cycloalkyl, phenyl, —$C_{1-6}$alkyl-phenyl, $C_{2-9}$heterocycloalkyl, —$C_{1-6}$alkyl-$C_{2-9}$heterocycloalkyl, $C_{2-9}$heteroaryl, or —$C_{1-6}$alkyl-$C_{2-9}$heteroaryl; and m and n are each independently 0, 1, 2, 3, 4, or 5.

In some embodiments, for a compound of Formula (II), Rings A and B are independently $C_{3-8}$cycloalkyl, $C_{2-9}$heterocycloalkyl, $C_{2-9}$heteroaryl, or 6- to 10-membered aryl. In some embodiments, for a compound of Formula (II), Rings A and B are independently $C_{2-9}$heteroaryl or 6- to 10-membered aryl. In some embodiments, for a compound of Formula (II), Ring A is phenyl. In some embodiments, for a compound of Formula (II), Ring A is pyridyl. In some embodiments, for a compound of Formula (II), Ring A is furanyl. In some embodiments, for a compound of Formula (II), Ring B is phenyl. In some embodiments, for a compound of Formula (II), Ring B is pyrrazolyl. In some embodiments, for a compound of Formula (II), Ring B is pyridyl. In some embodiments, for a compound of Formula (II), Ring B is isoxazolyl. In some embodiments, for a compound of Formula (II), Ring A is phenyl and Ring B is pyrrazolyl. In some embodiments, for a compound of Formula (II), Ring A is phenyl and Ring B is phenyl. In some embodiments, for a compound of Formula (II), Ring A is phenyl and Ring B is pyridyl. In some embodiments, for a compound of Formula (II), Ring A is pyridyl and Ring B is phenyl. In some embodiments, for a compound of Formula (II), Ring A is pyridyl and Ring B is isoxazolyl. In some embodiments, for a compound of Formula (II), Ring A is isoxazoylyl and Ring B is pyridyl. In some embodiments, for a compound of Formula (II), Ring A is furanyl and Ring B is phenyl.

In some embodiments, for a compound of Formula (II), $X^1$, $X^2$, and $X^3$ are independently N or $CR^4$. In some embodiments, for a compound of Formula (II), $X^1$ is CH. In some embodiments, for a compound of Formula (II), $X^1$ is CF. In some embodiments, for a compound of Formula (II), $X^1$ is $CCH_3$. In some embodiments, for a compound of Formula (II), $X^1$ is $CNH_2$. In some embodiments, for a compound of Formula (II), $X^1$ is N. In some embodiments, for a compound of Formula (II), $X^2$ is CH. In some embodiments, for a compound of Formula (II), $X^2$ is CF. In some embodiments, for a compound of Formula (II), $X^2$ is N. In some embodiments, for a compound of Formula (II), $X^2$ is C—N-methylpyrazine. In some embodiments, for a compound of Formula (II), $X^3$ is CH. In some embodiments, for a compound of Formula (II), $X^3$ is N. In some embodiments, for a compound of Formula (II), $X^1$ is CF and $X^2$ and $X^3$ are CH. In some embodiments, for a compound of Formula (II), $X^2$ is CF and $X^1$ and $X^3$ are CH. In some embodiments, for a compound of Formula (II), $X^1$, $X^2$, and $X^3$ are CH. In some embodiments, for a compound of Formula (II), $X^1$ is $CCH_3$ and $X^2$ and $X^3$ are CH. In some embodiments, for a compound of Formula (II), $X^1$ is $CNH_2$, $X^2$ is N, and $X^3$ is CH. In some embodiments, for a compound of Formula (II), $X^2$ is C—N-methylpyrazine and $X^1$ and $X^3$ are N.

In some embodiments, for a compound of Formula (II), $Y^1$ and $Y^2$ are independently a bond, —O—, —S—, —$C(R^5)_2$, —$NR^6$—, —$NR^6C(O)$—, —$C(O)NR^6$—, or —$NR^6C(O)NR^6$—. In some embodiments, for a compound of Formula (II), $Y^1$ is —$NR^6C(O)$—. In some embodiments, for a compound of Formula (II), $Y^1$ is —O—. In some embodiments, for a compound of Formula (II), $Y^1$ is —$NR^6C(O)NR^6$—. In some embodiments, for a compound of Formula (II), $Y^1$ is a bond. In some embodiments, for a compound of Formula (II), $Y^1$ is —$NR^6$—. In some embodiments, for a compound of Formula (II), $Y^2$ is —$NR^6C(O)$—. In some embodiments, for a compound of Formula (II), $Y^2$ is —O—. In some embodiments, for a compound of Formula (II), $Y^2$ is —$NR^6C(O)NR^6$—. In some embodiments, for a compound of Formula (II), $Y^2$ is a bond. In some embodiments, for a compound of Formula (II), $Y^1$ is —S—. In some embodiments, for a compound of Formula (II), $Y^1$ and $Y^2$ are —NHC(O)—. In some embodiments, for a compound of Formula (II), $Y^1$ is —O— and $Y^2$ is —NHC(O)NH—. In some embodiments, for a compound of Formula (II), $Y^1$ is —NHC(O)NH— and $Y^2$ is —O—. In some embodiments, for a compound of Formula (II), $Y^1$ and $Y^2$ are bonds. In some embodiments, for a compound of Formula (II), $Y^1$ is —NH— and $Y^2$ is —S—.

In some embodiments, for a compound of Formula (II), $R^1$ is —H, halogen, —$NO_2$, —CN, —OH, —$OR^5$, —$SR^5$, —$N(R^6)_2$, —$S(O)R^5$, —$S(=O)_2R^5$, —$NR^6S(=O)_2R^5$, —$S(=O)_2N(R^6)_2$, —$C(O)R^5$, —$C(O)OR^5$, —$OC(O)R^5$, —C(O)N($R^6$)$_2$, —OC(O)N($R^6$)$_2$, —NR$^6$C(O)N($R^6$)$_2$, —NR$^6$C(O)R$^5$, —NR$^6$C(O)OR$^5$, $C_{1-6}$alkyl, $C_{2-6}$alkenyl, $C_{2-6}$alkynyl, $C_{1-6}$haloalkyl, $C_{1-6}$heteroalkyl, —O—$C_{1-6}$alkyl, $C_{3-8}$cycloalkyl, $C_{2-9}$heterocycloalkyl, $C_{2-9}$heteroaryl, 6- to 10-membered aryl, or —O-phenyl, wherein each alkyl, haloalkyl, heteroalkyl, cycloalkyl, heterocycloalkyl, aryl, and heteroaryl is optionally substituted with one or more $R^7$. In some embodiments, for a compound of Formula (II), $R^1$ is —Cl. In some embodiments, for a compound of Formula (II), $R^1$ is —F. In some embodiments, for a compound of Formula (II), $R^1$ is —C(O)NHCH$_3$. In some embodiments, for a compound of Formula (II), $R^1$ is 2-methylpyrrazolyl. In some embodiments, for a compound of Formula (II), $R^1$ is N-methylimidazolyl. In some embodiments, for a compound of Formula (II), $R^1$ is tert-butyl. In some embodiments, for a compound of Formula (II), $R^1$ is —NHC(O)cyclopropyl. In some embodiments, for a compound of Formula (II), $R^1$ is —SCH$_2$C(O)OH. In some embodiments, for a compound of Formula (II), $R^1$ is —OCH$_3$. In some embodiments, for a compound of Formula (II), $R^1$ is —NHS(=O)$_2$CH$_2$CH$_2$CH$_3$.

In some embodiments, for a compound of Formula (II), $R^2$ is —H, halogen, —NO$_2$, —CN, —OH, —OR$^5$, —SR$^5$, —N($R^6$)$_2$, —S(O)R$^5$, —S(=O)$_2$R$^5$, —NR$^6$S(=O)$_2$R$^5$, —S(=O)$_2$N($R^6$)$_2$, —C(O)R$^5$, —C(O)OR$^5$, —OC(O)R$^5$, —C(O)N($R^6$)$_2$, —OC(O)N($R^6$)$_2$, —NR$^6$C(O)N($R^6$)$_2$, —NR$^6$C(O)R$^5$, —NR$^6$C(O)OR$^5$, $C_{1-6}$alkyl, $C_{2-6}$alkenyl, $C_{2-6}$alkynyl, $C_{1-6}$haloalkyl, $C_{1-6}$heteroalkyl, —O—$C_{1-6}$alkyl, $C_{3-8}$cycloalkyl, $C_{2-9}$heterocycloalkyl, $C_{2-6}$heteroaryl, 6- to 10-membered aryl, or —O-phenyl, wherein each alkyl, haloalkyl, heteroalkyl, cycloalkyl, heterocycloalkyl, aryl, and heteroaryl is optionally substituted with one or more $R^7$. In some embodiments, for a compound of Formula (II), $R^2$ is —Cl. In some embodiments, for a compound of Formula (II), $R^2$ is —F. In some embodiments, for a compound of Formula (II), $R^2$ is —C(O)NHCH$_3$. In some embodiments, for a compound of Formula (II), $R^1$ is 2-methylpyrrazolyl. In some embodiments, for a compound of Formula (II), $R^1$ is N-methylimidazolyl. In some embodiments, for a compound of Formula (II), $R^2$ is —CH$_2$-(2-iso-propylimidazole). In some embodiments, for a compound of Formula (II), $R^2$ is tert-butyl. In some embodiments, for a compound of Formula (II), $R^2$ is —CH$_3$. In some embodiments, for a compound of Formula (II), $R^2$ is —C(O)NHCH$_3$. In some embodiments, for a compound of Formula (II), $R^2$ is pyrazinyl.

In some embodiments, for a compound of Formula (II), m is 1 or 2. In some embodiments, for a compound of Formula (II), m is 1. In some embodiments, for a compound of Formula (II), m is 2. In some embodiments, for a compound of Formula (II), n is 1 or 2. In some embodiments, for a compound of Formula (II), n is 1. In some embodiments, for a compound of Formula (II), n is 2.

Disclosed herein, in some embodiments, are antagonists or partial antagonists of RIPK2 having a structure of Formula (IIa) or a pharmaceutically acceptable salt or isotopic variant thereof:

Formula (IIa)

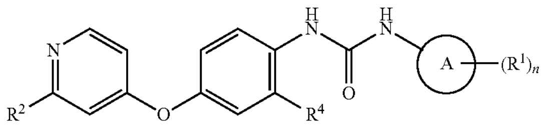

wherein

Ring A is phenyl or isoxazolyl;

each $R^1$ is independently $C_{1-6}$alkyl, halogen, —$C_{1-6}$fluoroalkyl, or —S—$C_{1-6}$alkyl-C(O)OH;

$R^2$ is —H or —C(O)NHCH$_3$;

$R^4$ is —H or halogen; and m is 1 or 2.

Disclosed herein, in some embodiments, are antagonists or partial antagonists of RIPK2 having a structure of Formula (IIa) or a pharmaceutically acceptable salt or isotopic variant thereof:

Formula (IIa)

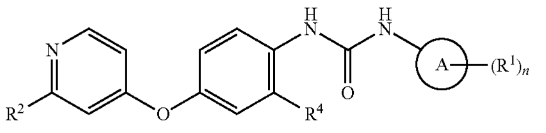

wherein

Ring A is phenyl or isoxazolyl;

each $R^1$ is independently tert-butyl, —Cl, —F, —CF$_3$, or —SCH$_2$C(O)OH;

$R^2$ is —H or —C(O)NHCH$_3$;

$R^4$ is —H or halogen; and m is 1 or 2.

Disclosed herein, in some embodiments, are antagonists or partial antagonists of RIPK2 having a structure of Formula (IIb) or a pharmaceutically acceptable salt or isotopic variant thereof:

Formula (IIb)

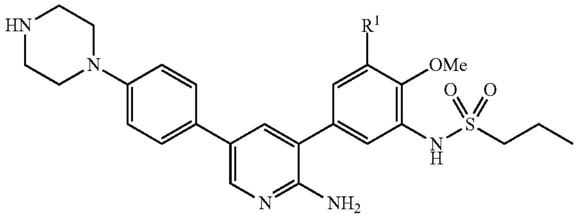

wherein $R^1$ is halogen or —OR$^5$.

In some embodiments a compound of Formula (II) or a pharmaceutically acceptable salt or isotopic variant thereof has the structure of:

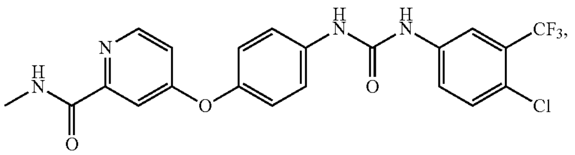

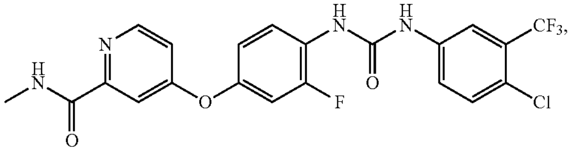

-continued

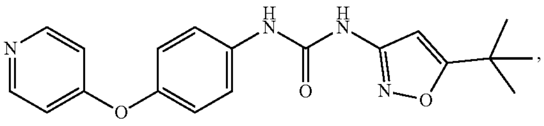

,

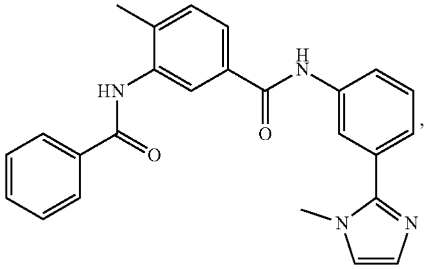

,

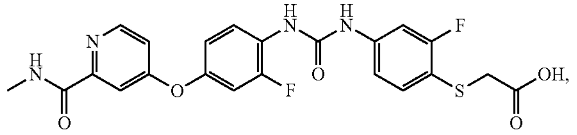

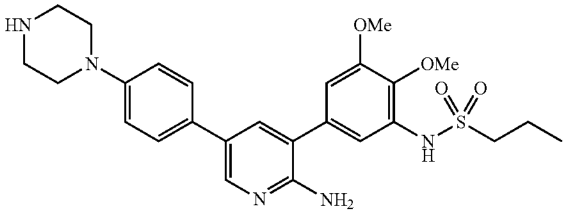

,

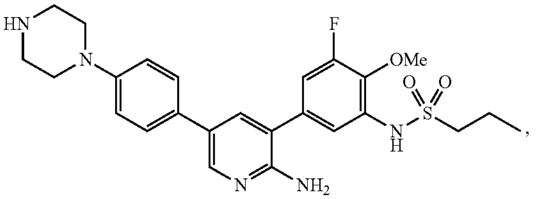

, or

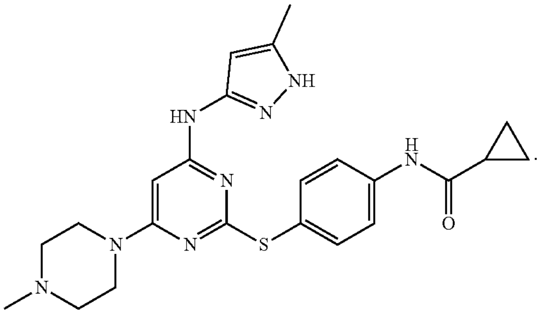

.

Disclosed herein, in some embodiments, are antagonists or partial antagonists of RIPK2 having a structure of Formula (III) or a pharmaceutically acceptable salt or isotopic variant thereof:

Formula (III)

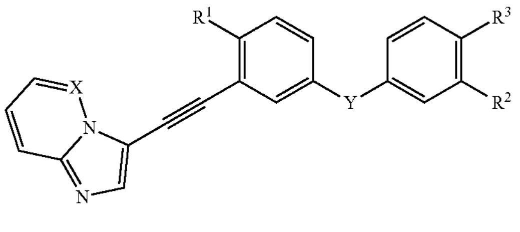

wherein

X is N or $CR^4$;

Y is a bond, —O—, —S—, —$C(R^5)_2$, —$NR^6$—, —$NR^6C(O)$—, —$C(O)NR^6$—, or —$NR^6C(O)NR^6$—;

$R^1$ is —H, halogen, —OH, —CN, —$N(R^6)_2$, —$NR^6C(O)R^5$, —$C(O)OR^5$, —$C(O)N(R^6)_2$, $C_{1-6}$alkyl, $C_{2-6}$alkenyl, $C_{2-6}$alkynyl, $C_{3-8}$cycloalkyl, —$C_{1-6}$alkyl-OH, —$C_{1-6}$alkyl-$OR^5$, —$C_{1-6}$alkyl-$N(R^6)_2$, —O—$C_{1-6}$alkyl, —O—$C_{1-6}$alkyl-OH, —O—$C_{1-6}$alkyl-$OR^5$, —O—$C_{1-6}$alkyl-$N(R^6)_2$, or —$S(=O)_2R^5$;

$R^2$ and $R^3$ are independently —H, halogen, —$NO_2$, —CN, —OH, —$OR^5$, —$SR^5$, —$N(R^6)_2$, —S(O)R, —$S(=O)_2R^5$, —$NR^6S(=O)_2R^5$, —$S(=O)_2N(R^6)_2$, —$C(O)R^5$, —$C(O)OR^5$, —$OC(O)R^5$, —$C(O)N(R^6)_2$, —$OC(O)N(R^6)_2$, —$NR^6C(O)N(R^6)_2$, —$NR^6C(O)R^5$, —$NR^6C(O)OR^5$, $C_{1-6}$alkyl, $C_{2-6}$alkenyl, $C_{2-6}$alkynyl, $C_{1-6}$haloalkyl, $C_{1-6}$heteroalkyl, —O—$C_{1-6}$alkyl, $C_{3-8}$cycloalkyl, $C_{2-9}$heterocycloalkyl, $C_{2-9}$heteroaryl, 6- to 10-membered aryl, or —O-phenyl, wherein each alkyl, haloalkyl, heteroalkyl, cycloalkyl, heterocycloalkyl, aryl, and heteroaryl is optionally substituted with one or more $R^7$; or $R^2$ and $R^3$ are taken together with the atoms to which they are attached to form an optionally substituted $C_{3-8}$cycloalkyl; and $R^4$ is hydrogen, halogen, —$N(R^6)_2$, —$NO_2$, $C_{1-6}$alkyl, $C_{2-6}$alkenyl, $C_{2-6}$alkynyl, $C_{1-6}$haloalkyl, $C_{3-8}$cycloalkyl, —$C_{1-6}$alkyl-$C_{3-8}$cycloalkyl, phenyl, —$C_{1-6}$alkyl-phenyl, $C_{2-9}$heterocycloalkyl, —$C_{1-6}$alkyl-$C_{2-9}$heterocycloalkyl, $C_{2-9}$heteroaryl, or —$C_{1-6}$alkyl-$C_{2-9}$heteroaryl, wherein the alkyl, haloalkyl, cycloalkyl, phenyl, heteroaryl, and heterocycloalkyl are optionally substituted;

$R^5$ is —H, $C_{1-6}$alkyl, $C_{2-6}$alkenyl, $C_{2-6}$alkynyl, $C_{1-6}$haloalkyl, $C_{3-8}$cycloalkyl, —$C_{1-6}$alkyl-$C_{3-8}$cycloalkyl, phenyl, —$C_{1-6}$alkyl-phenyl, $C_{2-9}$heterocycloalkyl, —$C_{1-6}$alkyl-$C_{2-9}$heterocycloalkyl, $C_{2-9}$heteroaryl, or —$C_{1-6}$alkyl-$C_{2-9}$heteroaryl;

each $R^6$ is independently —H, $C_{1-6}$alkyl, $C_{2-6}$alkenyl, $C_{2-6}$alkynyl, $C_{1-6}$haloalkyl, $C_{3-8}$cycloalkyl, —$C_{1-6}$alkyl-$C_{3-8}$cycloalkyl, phenyl, —$C_{1-6}$alkyl-phenyl, or $C_{2-9}$heteroaryl; or two $R^6$ substituents are taken together with the nitrogen atom to which they are attached to form a 5- or 6-membered heterocycle; and $R^7$ is —H, halogen, $C_{1-6}$alkyl, $C_{2-6}$alkenyl, $C_{2-6}$alkynyl, $C_{1-6}$haloalkyl, $C_{3-8}$cycloalkyl, —$C_{1-6}$alkyl-$C_{3-8}$cycloalkyl, phenyl, —$C_{1-6}$alkyl-phenyl, $C_{2-9}$heterocycloalkyl, —$C_{1-6}$alkyl-$C_{2-9}$heterocycloalkyl, $C_{2-9}$heteroaryl, or —$C_{1-6}$alkyl-$C_{2-9}$heteroaryl.

In some embodiments, for a compound of Formula (III), X is N or $CR^4$. In some embodiments, for a compound of Formula (III), X is N and CH. In some embodiments, for a compound of Formula (III), X is N. In some embodiments, for a compound of Formula (III), X is CH.

In some embodiments, for a compound of Formula (III), Y is a bond, —O—, —S—, —$C(R^5)_2$, —$NR^6$—, —$NR^6C(O)$—, —$C(O)NR^6$—, or —$NR^6C(O)NR^6$—. In some embodiments, for a compound of Formula (III), Y is —$NR^6C(O)$— or —$C(O)NR^6$—. In some embodiments, for a compound of Formula (III), Y is —NHC(O)—. In some embodiments, for a compound of Formula (III), Y is —C(O)NH—.

In some embodiments, for a compound of Formula (III), $R^1$ is —H, halogen, —OH, —CN, —$N(R^6)_2$, —$NR^6C(O)R^5$, —$C(O)OR^5$, —$C(O)N(R^6)_2$, $C_{1-6}$alkyl, $C_{2-6}$alkenyl, $C_{2-6}$alkynyl, $C_{3-8}$cycloalkyl, —$C_{1-6}$ alkyl-OH, —$C_{1-6}$alkyl-$OR^5$, —$C_{1-6}$alkyl-$N(R^6)_2$, —O—$C_{1-6}$alkyl, —O—$C_{1-6}$alkyl-OH, —O—$C_{1-6}$alkyl-$OR^5$, —O—$C_{1-6}$ alkyl-$N(R^6)_2$, or —$S(=O)_2R^5$. In some embodiments, for a compound of Formula (III), $R^1$ is —H, halogen, —OH, —CN, —$N(R^6)_2$, $C_{1-6}$alkyl, $C_{2-6}$alkynyl, or $C_{3-8}$cycloalkyl. In some embodiments, for a compound of Formula (III), $R^1$ is $C_{1-6}$alkyl. In some embodiments, for a compound of Formula (III), $R^1$ is —$CH_3$. In some embodiments, for a compound of Formula (III), $R^1$ is tert-butyl.

In some embodiments, for a compound of Formula (III), $R^2$ is —H, halogen, —$NO_2$, —CN, —OH, —$OR^5$, —$SR^5$, —$N(R^6)_2$, —$S(O)R^5$, —$S(=O)_2R^5$, —$NR^6S(=O)_2R^5$, —$S(=O)_2N(R^6)_2$, —$C(O)R^5$, —$C(O)OR^5$, —$OC(O)R^5$, —$C(O)N(R^6)_2$, —$OC(O)N(R^6)_2$, —$NR^6C(O)N(R^6)_2$, —$NR^6C(O)R^5$, —$NR^6C(O)OR^5$, $C_{1-6}$alkyl, $C_{2-6}$alkenyl, $C_{2-6}$alkynyl, $C_{1-6}$haloalkyl, $C_{1-6}$heteroalkyl, —O—$C_{1-6}$alkyl, $C_{3-8}$cycloalkyl, $C_{2-9}$heterocycloalkyl, $C_{2-9}$heteroaryl, 6- to 10-membered aryl, or —O-phenyl, wherein each alkyl, haloalkyl, heteroalkyl, cycloalkyl, heterocycloalkyl, aryl, and heteroaryl is optionally substituted with one or more $R^7$, or $R^2$ and $R^3$ are taken together with the atoms to which they are attached to form an optionally substituted $C_{3-8}$cycloalkyl. In some embodiments, for a compound of Formula (III), $R^2$ is —H, halogen, —$NO_2$, —CN, —OH, —OR, $C_{1-6}$alkyl, $C_{1-6}$haloalkyl, $C_{1-6}$heteroalkyl, $C_{3-8}$cycloalkyl, $C_{2-9}$heterocycloalkyl, $C_{2-9}$heteroaryl, or 6- to 10-membered aryl, or $R^2$ and $R^3$ are taken together with the atoms to which they are attached to form an optionally substituted $C_{3-8}$cycloalkyl. In some embodiments, for a compound of Formula (III), $R^2$ is $C_{1-6}$alkyl, $C_{1-6}$haloalkyl, or $C_{3-8}$cycloalkyl, or R2 and R3 are taken together with the atoms to which they are attached to form an optionally substituted $C_{3-8}$cycloalkyl. In some embodiments, for a compound of Formula (III), $R^2$ is —$CH_3$, —$CF_3$, or cyclopropyl, or $R^2$ and R3 are taken together with the atoms to which they are attached to form an optionally substituted $C_{3-8}$cycloalkyl. In some embodiments, for a compound of Formula (III), $R^2$ is —$CH_3$, —$CF_3$, or cyclopropyl. In some embodiments, for a compound of Formula (III), $R^2$ is —$CH_3$. In some embodiments, for a compound of Formula (III), $R^2$ is —$CF_3$. In some embodiments, for a compound of Formula (III), $R^2$ is cyclopropyl. In some embodiments, for a compound of Formula (III), $R^2$ and $R^3$ are taken together with the atoms to which they are attached to form a $C_5$ cycloalkyl. In some embodiments, for a compound of Formula (III), $R^2$ and $R^3$ are taken together with the atoms to which they are attached to form a Cs cycloalkyl substituted with an N-methylpiperazine.

In some embodiments, for a compound of Formula (III), $R^3$ is —H, halogen, —$NO_2$, —CN, —OH, —$OR^5$, —$SR^5$, —$N(R^6)_2$, —$S(O)R^5$, —$S(=O)_2R^5$, —$NR^6S(=O)_2R^5$, —$S(=O)_2N(R^6)_2$, —$C(O)R^5$, —C(O)ORS, —$OC(O)R^5$, —$C(O)N(R^6)_2$, —$OC(O)N(R^6)_2$, —$NR^6C(O)N(R^6)_2$, —$NR^6C(O)R^5$, —$NR^6$C(O)ORS, $C_{1-6}$alkyl, $C_{2-6}$alkenyl, $C_{2-6}$alkynyl, $C_{1-6}$haloalkyl, $C_{1-6}$heteroalkyl, —O—$C_{1-6}$alkyl, $C_{3-8}$cycloalkyl, $C_{2-9}$heterocycloalkyl, $C_{2-9}$heteroaryl, 6- to 10-membered aryl, or —O-phenyl, wherein each alkyl, haloalkyl, heteroalkyl, cycloalkyl, heterocycloalkyl, aryl, and heteroaryl is optionally substituted with one or more $R^7$, or $R^2$ and $R^3$ are taken together with the atoms to which they are attached to form an optionally substituted $C_{3-8}$cycloalkyl. In some embodiments, for a compound of Formula (III), $R^3$ is —H, halogen, —CN, —$OR^5$, —$N(R^6)_2$, —$S(=O)_2R^5$, —$C(O)R^5$, —C(O)ORS, —$NR^6C(O)N(R^6)_2$, —$NR^6C(O)R^5$, —$NR^6C(O)OR^5$, $C_{1-6}$alkyl, $C_{1-6}$heteroalkyl, $C_{2-9}$heterocycloalkyl, or $C_{2-9}$heteroaryl, wherein each alkyl, heteroalkyl, heterocycloalkyl, and heteroaryl is optionally substituted with one or more $R^7$, or $R^2$ and $R^3$ are taken together with the atoms to which they are attached to form an optionally substituted $C_{3-8}$cycloalkyl. In some embodiments, for a compound of Formula (III), $R^3$ is $C_{1-6}$alkyl substituted with $C_{2-9}$heterocycloalkyl. In some embodiments, for a compound of Formula (III), $R^3$ is $CH_2$—N—methylpiperazine. In some embodiments, for a compound of Formula (III), $R^2$ and $R^3$ are taken together with the atoms to which they are attached to form a $C_5$ cycloalkyl. In some embodiments, for a compound of Formula (III), $R^2$ and $R^3$ are taken together with the atoms to which they are attached to form a $C_5$ cycloalkyl substituted with an N-methylpiperazine.

Disclosed herein, in some embodiments, are antagonists or partial antagonists of RIPK2 having a structure of Formula (III) or a pharmaceutically acceptable salt or isotopic variant thereof:

Formula (III)

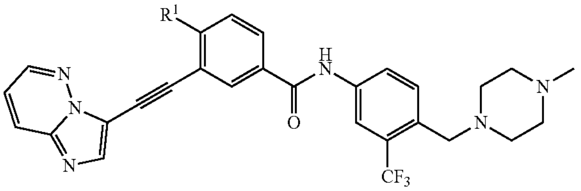

wherein $R^1$ is $C_{1-6}$alkyl.

In some embodiments a compound of Formula (III) or a pharmaceutically acceptable salt or isotopic variant thereof has the structure of

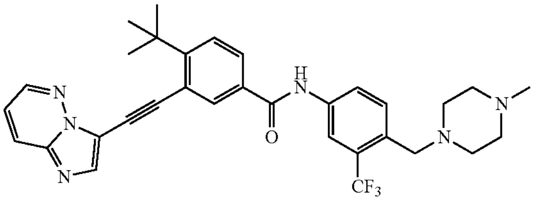

or

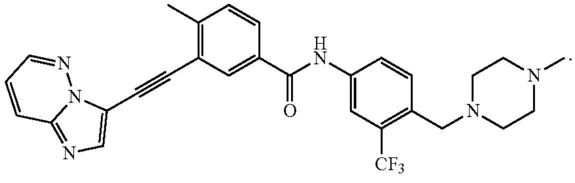

Disclosed herein, in some embodiments, are antagonists or partial antagonists of RIPK2 having a structure of Formula (IV) or a pharmaceutically acceptable salt or isotopic variant thereof:

Formula (IV)

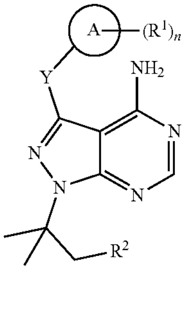

wherein

Ring A is $C_{3-8}$cycloalkyl, $C_{2-9}$heterocycloalkyl, $C_{2-9}$heteroaryl, or 6- to 10-membered aryl;

Y is a bond, —O—, —S—, —$C(R^5)_2$—, —$NR^6$—, —$NR^6C(O)$—, —$C(O)NR^6$—, or —$NR^6C(O)NR^6$—;

$R^1$ is —H, halogen, —OH, —CN, —$N(R^6)_2$, —$NR^6C(O)R^5$, —$C(O)OR^5$, —$C(O)N(R^6)_2$, $C_{1-6}$alkyl, $C_{2-6}$alkenyl, $C_{2-6}$alkynyl, $C_{3-8}$cycloalkyl, —$C_{1-6}$alkyl-OH, —$C_{1-6}$alkyl-$OR^5$, —$C_{1-6}$alkyl-$N(R^6)_2$, —O—$C_{1-6}$alkyl, —O—$C_{1-6}$alkyl-OH, —O—$C_{1-6}$alkyl-$OR^5$, —O—$C_{1-6}$alkyl-$N(R^6)_2$, or —$S(=O)_2R^5$;

$R^2$ is —H, halogen, —$NO_2$, —CN, —OH, —$OR^5$, —$SR^5$, —$N(R^6)_2$, —$S(O)R^5$, —$S(=O)_2R^5$, —$NR^6S(=O)_2R^5$, —$S(=O)_2N(R^6)_2$, —$C(O)R^5$, —$C(O)OR^5$, —$OC(O)R^5$, —$C(O)N(R^6)_2$, —$OC(O)N(R^6)_2$, —$NR^6C(O)N(R^6)_2$, —$NR^6C(O)R^5$, —$NR^6C(O)OR^5$, $C_{1-6}$alkyl, $C_{2-6}$alkenyl, $C_{2-6}$alkynyl, $C_{1-6}$haloalkyl, $C_{1-6}$heteroalkyl, —O—$C_{1-6}$alkyl, $C_{3-8}$cycloalkyl, $C_{2-9}$heterocycloalkyl, $C_{2-9}$heteroaryl, 6- to 10-membered aryl, or —O-phenyl, wherein each alkyl, haloalkyl, heteroalkyl, cycloalkyl, heterocycloalkyl, aryl, and heteroaryl is optionally substituted with one or more $R^7$;

$R^5$ is —H, $C_{1-6}$alkyl, $C_{2-6}$alkenyl, $C_{2-6}$alkynyl, $C_{1-6}$haloalkyl, $C_{3-8}$cycloalkyl, —$C_{1-6}$alkyl-$C_{3-8}$cycloalkyl, phenyl, —$C_{1-6}$alkyl-phenyl, $C_{2-9}$heterocycloalkyl, —$C_{1-6}$alkyl-$C_{2-9}$heterocycloalkyl, $C_{2-9}$heteroaryl, or —$C_{1-6}$alkyl-$C_{2-9}$heteroaryl;

each $R^6$ is independently —H, $C_{1-6}$alkyl, $C_{2-6}$alkenyl, $C_{2-6}$alkynyl, $C_{1-6}$haloalkyl, $C_{3-8}$cycloalkyl, —$C_{1-6}$alkyl-$C_{3-8}$cycloalkyl, phenyl, —$C_{1-6}$alkyl-phenyl, or $C_{2-9}$heteroaryl; or two $R^6$ substituents are taken together with the nitrogen atom to which they are attached to form a 5- or 6-membered heterocycle;

$R^7$ is —H, halogen, $C_{1-6}$alkyl, $C_{2-6}$alkenyl, $C_{2-6}$alkynyl, $C_{1-6}$haloalkyl, $C_{3-8}$cycloalkyl, —$C_{1-6}$alkyl-$C_{3-8}$cycloalkyl, phenyl, —$C_{1-6}$alkyl-phenyl, $C_{2-9}$heterocycloalkyl, —$C_{1-6}$alkyl-$C_{2-9}$heterocycloalkyl, $C_{2-9}$heteroaryl, or —$C_{1-6}$alkyl-$C_{2-9}$heteroaryl; and n is 0, 1, 2, 3, 4, or 5.

In some embodiments, for a compound of Formula (IV), Ring A is $C_{3-8}$cycloalkyl, $C_{2-9}$heterocycloalkyl, $C_{2-9}$heteroaryl, or 6- to 10-membered aryl. In some embodiments, for a compound of Formula (IV), Ring A is 6- to 10-membered aryl. In some embodiments, for a compound of Formula (IV), Ring A is phenyl. In some embodiments, for a compound of Formula (IV), Ring A is naphthyl.

In some embodiments, for a compound of Formula (IV), Y is a bond, —O—, —S—, —$C(R^5)_2$—, —$NR^6$—, —$NR^6C(O)$—, —$C(O)NR^6$—, or —$NR^6C(O)NR^6$—. In some embodiments, for a compound of Formula (IV), Y is a bond or —$C(R^5)_2$—. In some embodiments, for a compound of Formula (IV), Y is a bond. In some embodiments, for a compound of Formula (IV), Y is —$CH_2$—.

In some embodiments, for a compound of Formula (IV), $R^1$ is —H, halogen, —OH, —CN, —$N(R^6)_2$, —$NR^6C(O)R^5$, —$C(O)OR^5$, —$C(O)N(R^6)_2$, $C_{1-6}$alkyl, $C_{2-6}$alkenyl, $C_{2-6}$alkynyl, $C_{3-8}$cycloalkyl, —$C_{1-6}$ alkyl-OH, —$C_{1-6}$alkyl-$OR^5$, —$C_{1-6}$alkyl-$N(R^6)_2$, —O—$C_{1-6}$alkyl, —O—$C_{1-6}$alkyl-OH, —O—$C_{1-6}$alkyl-$OR^5$, —O—$C_{1-6}$alkyl-$N(R^6)_2$, or —$S(=O)_2R^5$. In some embodiments, for a compound of Formula (IV), $R^1$ is —H, halogen, or $C_{1-6}$alkyl. In some embodiments, for a compound of Formula (IV), $R^1$ is —H, —Cl, or $CH_3$. In some embodiments, for a compound of Formula (IV), $R^1$ is —H. In some embodiments, for a compound of Formula (IV), $R^1$ is —Cl. In some embodiments, for a compound of Formula (IV), $R^1$ is —$CH_3$.

In some embodiments, for a compound of Formula (IV), $R^2$ is —H, halogen, —$NO_2$, —CN, —OH, —$OR^5$, —$SR^5$, —$N(R^6)_2$, —$S(O)R^5$, —$S(=O)_2R^5$, —$NR^6S(=O)_2R^5$, —$S(=O)_2N(R^6)_2$, —$C(O)R^5$, —$C(O)OR^5$, —$OC(O)R^5$, —$C(O)N(R^6)_2$, —$OC(O)N(R^6)_2$, —$NR^6C(O)N(R^6)_2$, —$NR^6C(O)R^5$, —$NR^6C(O)OR^5$, $C_{1-6}$alkyl, $C_{2-6}$alkenyl, $C_{2-6}$alkynyl, $C_{1-6}$haloalkyl, $C_{1-6}$heteroalkyl, —O—$C_{1-6}$alkyl, $C_{3-8}$cycloalkyl, $C_{2-9}$heterocycloalkyl, $C_{2-9}$heteroaryl, 6- to 10-membered aryl, or —O-phenyl, wherein each alkyl, haloalkyl, heteroalkyl, cycloalkyl, heterocycloalkyl, aryl, and heteroaryl is optionally substituted with one or more $R^7$. In some embodiments, for a compound of Formula (IV), $R^2$ is —H or —$NR^6C(O)R^5$. In some embodiments, for a compound of Formula (IV), $R^2$ is —H or —$NR^6C(O)C_{2-9}$heteroaryl. In some embodiments, for a compound of Formula (IV), $R^2$ is —H. In some embodiments, for a compound of Formula (IV), $R^2$ is —NHC(O)pyridyl.

In some embodiments, for a compound of Formula (IV), n is 1, 2, or 3. In some embodiments, for a compound of Formula (IV), n is 1 or 2. In some embodiments, for a compound of Formula (IV), n is 1. In some embodiments, for a compound of Formula (IV), n is 2. In some embodiments, for a compound of Formula (IV), n is 3.

Disclosed herein, in some embodiments, are antagonists or partial antagonists of RIPK2 having a structure of Formula (IVa) or a pharmaceutically acceptable salt or isotopic variant thereof:

Formula (IVa)

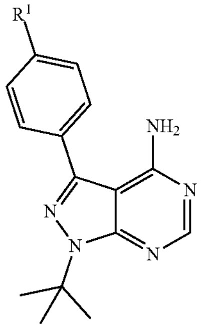

wherein $R^1$ is halogen or $C_{1-6}$alkyl.

Disclosed herein, in some embodiments, are antagonists or partial antagonists of RIPK2 having a structure of Formula (IVb) or a pharmaceutically acceptable salt or isotopic variant thereof:

Formula (IVb)

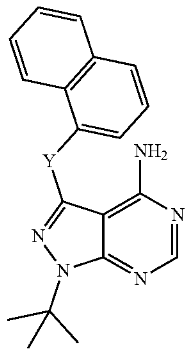

wherein Y is a bond or —$C_{1-3}$alkyl-.

Disclosed herein, in some embodiments, are antagonists or partial antagonists of RIPK2 having a structure of Formula (IVb) or a pharmaceutically acceptable salt or isotopic variant thereof:

Formula (IVb)

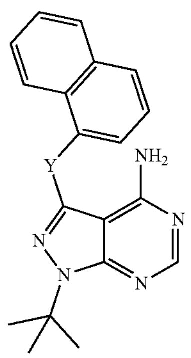

wherein

Y is a bond or $—CH_2—$.

In some embodiments a compound of Formula (IV) or a pharmaceutically acceptable salt

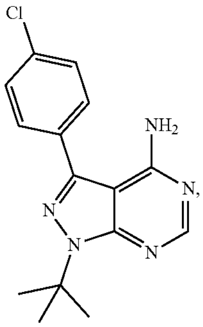

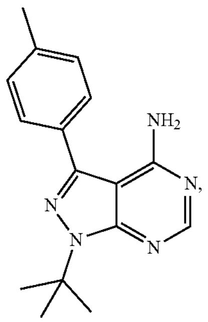

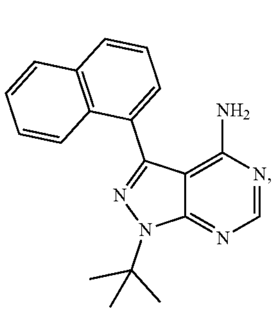

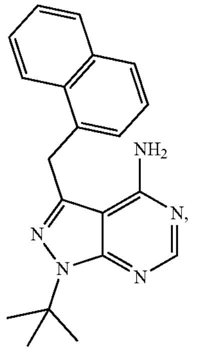

or

-continued

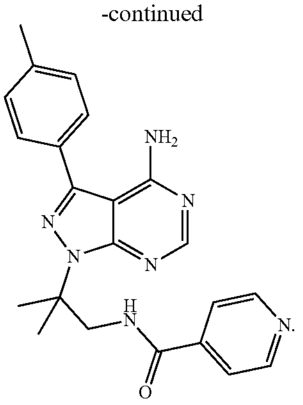

Disclosed herein, in some embodiments, are antagonists or partial antagonists of RIPK2 having a structure of Formula (V) or a pharmaceutically acceptable salt or isotopic variant thereof:

Formula (V)

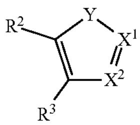

wherein $X^1$ and $X^2$ are independently N or $CR^4$;

Y is S, O, or $NR^1$;

$R^1$ is —H, $—S(=O)_2R^5$, $—S(=O)_2N(R^6)_2$, $—C(O)R^5$, $—C(O)OR^5$, $—C(O)N(R^6)_2$, $C_{1-6}$alkyl, $C_{2-6}$alkenyl, $C_{2-6}$alkynyl, $C_{1-6}$haloalkyl, $C_{1-6}$heteroalkyl, $C_{3-8}$cycloalkyl, $C_{2-9}$heterocycloalkyl, $C_{2-9}$heteroaryl, or 6- to 10-membered aryl, wherein each alkyl, haloalkyl, heteroalkyl, cycloalkyl, heterocycloalkyl, aryl, and heteroaryl is optionally substituted with one or more $R^7$;

$R^2$ is —H, halogen, $—NO_2$, —CN, —OH, $—OR^5$, $—SR^5$, $—N(R^6)_2$, —S(O)R, $—S(=O)_2R^5$, $—NR^6S(=O)_2R^5$, $—S(=O)_2N(R^6)_2$, $—C(O)R^5$, $—C(O)OR^5$, —OC(O)R, $—C(O)N(R^6)_2$, $—OC(O)N(R^6)_2$, $—NR^6C(O)N(R^6)_2$, $—NR^6C(O)R^5$, $—NRC(O)OR^5$, $C_{1-6}$alkyl, $C_{2-6}$alkenyl, $C_{2-6}$alkynyl, $C_{1-6}$ haloalkyl, $C_{1-6}$heteroalkyl, $—O—C_{1-6}$alkyl, $C_{3-8}$cycloalkyl, $C_{2-9}$heterocycloalkyl, $C_{2-9}$heteroaryl, 6- to 10-membered aryl, or —O-phenyl, wherein each alkyl, haloalkyl, heteroalkyl, cycloalkyl, heterocycloalkyl, aryl, and heteroaryl is optionally substituted with one or more $R^7$; or $R^1$ and $R^2$ are taken together with the atoms to which they are attached to form an optionally substituted $C_{3-8}$heterocycloalkyl; and $R^3$ and $R^4$ are independently —H, halogen, $—NO_2$, —CN, —OH, —OR, $—SR^5$, $—N(R^6)_2$, —S(O)R, $—S(=O)_2R^5$, $—NR^6S(=O)_2R^5$, $—S(=O)_2N(R^6)_2$, $—C(O)R^5$, $—C(O)OR^5$, $—OC(O)R^5$, $—C(O)N(R^6)_2$, $—OC(O)N(R^6)_2$, $—NR^6C(O)N(R^6)_2$, $—NR^6C(O)R^5$, $—NR^6C(O)OR^5$, $C_{1-6}$alkyl, $C_{2-6}$alkenyl, $C_{2-6}$alkynyl, $C_{1-6}$haloalkyl, $C_{1-6}$heteroalkyl, $—O—C_{1-6}$alkyl, $C_{3-8}$cycloalkyl, $C_{2-9}$heterocycloalkyl, $C_{2-9}$heteroaryl, 6- to 10-membered aryl, or —O-phenyl, wherein each alkyl, haloalkyl, heteroalkyl, cycloalkyl, heterocycloalkyl, aryl, and heteroaryl is optionally substituted with one or more $R^7$;

$R^5$ is —H, $C_{1-6}$alkyl, $C_{2-6}$alkenyl, $C_{2-6}$alkynyl, $C_{1-6}$haloalkyl, $C_{3-8}$cycloalkyl, —$C_{1-6}$alkyl-$C_{3-8}$cycloalkyl, phenyl, —$C_{1-6}$alkyl-phenyl, $C_{2-9}$heterocycloalkyl, —$C_{1-6}$alkyl-$C_{2-9}$heterocycloalkyl, $C_{2-9}$heteroaryl, or —$C_{1-6}$alkyl-$C_{2-9}$heteroaryl;

each $R^6$ is independently —H, $C_{1-6}$alkyl, $C_{2-6}$alkenyl, $C_{2-6}$alkynyl, $C_{1-6}$haloalkyl, $C_{3-8}$cycloalkyl, —$C_{1-6}$alkyl-$C_{3-8}$cycloalkyl, phenyl, —$C_{1-6}$alkyl-phenyl, or $C_{2-9}$heteroaryl; or two $R^6$ substituents are taken together with the nitrogen atom to which they are attached to form a 5- or 6-membered heterocycle; and $R^1$ is —H, halogen, —S(═O)$CH_3$, —$N(R^6)_2$, —C(O)N$(R^6)_2$, $C_{1-6}$alkyl, $C_{2-6}$alkenyl, $C_{2-6}$alkynyl, $C_{1-6}$ haloalkyl, $C_{1-6}$heteroalkyl, $C_{3-8}$cycloalkyl, —$C_{1-6}$alkyl-$C_{3-8}$cycloalkyl, phenyl, —$C_{1-6}$alkyl-phenyl, $C_{2-9}$heterocycloalkyl, —$C_{1-6}$alkyl-$C_{2-9}$heterocycloalkyl, $C_{2-9}$heteroaryl, or —$C_{1-6}$alkyl-$C_{2-9}$heteroaryl.

In some embodiments, for a compound of Formula (V), $X^1$ and $X^2$ are independently N or $CR^4$. In some embodiments, for a compound of Formula (V), $X^1$ is N. In some embodiments, for a compound of Formula (V), $X^1$ is $CR^4$. In some embodiments, for a compound of Formula (V), $X^2$ is N. In some embodiments, for a compound of Formula (V), $X^2$ is $CR^4$. In some embodiments, for a compound of Formula (V), $X^1$ is N and $X^2$ is $CR^4$. In some embodiments, for a compound of Formula (V), $X^1$ is $CR^4$ and $X^2$ is N.

In some embodiments, for a compound of Formula (V), Y is S, O, or $NR^1$. In some embodiments, for a compound of Formula (V), Y is S. In some embodiments, for a compound of Formula (V), Y is NH. In some embodiments, for a compound of Formula (V), Y is $NR^1$.

In some embodiments, for a compound of Formula (V), $R^1$ is —H, —S(═O)$_2R^5$, —S(═O)$_2N(R^6)_2$, —C(O)$R^5$, —C(O)O$R^5$, —C(O)N$(R^6)_2$, $C_{1-6}$alkyl, $C_{2-6}$alkenyl, $C_{2-6}$alkynyl, $C_{1-6}$haloalkyl, $C_{1-6}$heteroalkyl, $C_{3-8}$cycloalkyl, $C_{2-9}$heterocycloalkyl, $C_{2-9}$heteroaryl, or 6- to 10-membered aryl, wherein each alkyl, haloalkyl, heteroalkyl, cycloalkyl, heterocycloalkyl, aryl, and heteroaryl is optionally substituted with one or more $R^7$. In some embodiments, for a compound of Formula (V), $R^1$ is —H, $C_{1-6}$ alkyl, $C_{3-8}$cycloalkyl, $C_{2-9}$heterocycloalkyl, $C_{2-9}$heteroaryl, or 6- to 10-membered aryl, wherein each cycloalkyl, heterocycloalkyl, aryl, and heteroaryl is optionally substituted with one or more $R^7$. In some embodiments, for a compound of Formula (V), $R^1$ is aryl optionally substituted with one or more $R^7$. In some embodiments, for a compound of Formula (V), $R^1$ is 2,4-dichlorophenyl.

In some embodiments, for a compound of Formula (V), $R^2$ is —H, halogen, —$NO_2$, —CN, —OH, —O$R^5$, —S$R^5$, —$N(R^6)_2$, —S(O)$R^5$, —S(═O)$_2R^5$, —N$R^6$S(═O)$_2R^5$, —S(═O)$_2N(R^6)_2$, —C(O)$R^5$, —C(O)O$R^5$, —OC(O)$R^5$, —C(O)N$(R^6)_2$, —OC(O)N$(R^6)_2$, —N$R^6$C(O)N$(R^6)_2$, —N$R^6$C(O)$R^5$, —N$R^6$C(O)O$R^5$, $C_{1-6}$alkyl, $C_{2-6}$alkenyl, $C_{2-6}$alkynyl, $C_{1-6}$haloalkyl, $C_{1-6}$heteroalkyl, —O—$C_{1-6}$alkyl, $C_{3-8}$cycloalkyl, $C_{2-9}$heterocycloalkyl, $C_{2-9}$heteroaryl, 6- to 10-membered aryl, or —O-phenyl, wherein each alkyl, haloalkyl, heteroalkyl, cycloalkyl, heterocycloalkyl, aryl, and heteroaryl is optionally substituted with one or more $R^7$, or $R^1$ and $R^2$ are taken together with the atoms to which they are attached to form an optionally substituted $C_{3-8}$heterocycloalkyl. In some embodiments, for a compound of Formula (V), $R^2$ is —H, halogen, —S(═O)$_2R^5$, —N$R^6$S(═O)$_2R^5$, —S(═O)$_2N(R^6)_2$, —C(O)$R^5$, —C(O)O$R^5$, —C(O)N$(R^6)_2$, $C_{1-6}$ alkyl, $C_{2-6}$alkenyl, $C_{2-6}$alkynyl, $C_{3-8}$cycloalkyl, $C_{2-9}$heterocycloalkyl, $C_{2-9}$heteroaryl, 6- to 10-membered aryl, or —O-phenyl, wherein each alkyl, cycloalkyl, heterocycloalkyl, aryl, and heteroaryl is optionally substituted with one or more $R^7$, or $R^1$ and $R^2$ are taken together with the atoms to which they are attached to form an optionally substituted $C_{3-8}$heterocycloalkyl. In some embodiments, for a compound of Formula (V), $R^2$ is —C(O)N$(R^6)_2$ or 6-membered aryl optionally substituted with one or more $R^7$. In some embodiments, for a compound of Formula (V), $R^2$ is 4-fluorophenyl. In some embodiments, for a compound of Formula (V), $R^2$ is 4-chlorophenyl. In some embodiments, for a compound of Formula (V), $R^2$ is 2-methylpyridinyl. In some embodiments, for a compound of Formula (V), $R^2$ is —C(O)NH-(2-methyl-6-chlorophenyl). In some embodiments, for a compound of Formula (V), $R^1$ and $R^2$ are taken together with the atoms to which they are attached to form an optionally substituted $C_{3-8}$heterocycloalkyl. In some embodiments, for a compound of Formula (V), $R^1$ and $R^2$ are taken together with the atoms to which they are attached to form a $C_5$ heterocycloalkyl.

In some embodiments, for a compound of Formula (V), $R^3$ is —H, halogen, —$NO_2$, —CN, —OH, —O$R^5$, —S$R^5$, —$N(R^6)_2$, —S(O)$R^5$, —S(═O)$_2R^5$, —N$R^6$S(═O)$_2R^5$, —S(═O)$_2N(R^6)_2$, —C(O)$R^5$, —C(O)O$R^5$, —OC(O)$R^5$, —C(O)N$(R^6)_2$, —OC(O)N$(R^6)_2$, —N$R^6$C(O)N$(R^6)_2$, —N$R^6$C(O)$R^5$, —N$R^6$C(O)O$R^5$, $C_{1-6}$alkyl, $C_{2-6}$alkenyl, $C_{2-6}$alkynyl, $C_1$-6haloalkyl, $C_{1-6}$heteroalkyl, —O—$C_{1-6}$alkyl, $C_{3-8}$cycloalkyl, $C_{2-9}$heterocycloalkyl, $C_{2-9}$heteroaryl, 6- to 10-membered aryl, or —O-phenyl, wherein each alkyl, haloalkyl, heteroalkyl, cycloalkyl, heterocycloalkyl, aryl, and heteroaryl is optionally substituted with one or more $R^7$. In some embodiments, for a compound of Formula (V), $R^3$ is —H, $C_{1-6}$alkyl, $C_{2-6}$alkenyl, $C_{2-6}$alkynyl, $C_{1-6}$haloalkyl, $C_{1-6}$heteroalkyl, —O—$C_{1-6}$alkyl, $C_{3-8}$cycloalkyl, $C_{2-9}$heterocycloalkyl, $C_{2-9}$heteroaryl, 6- to 10-membered aryl, or —O-phenyl, wherein each alkyl, haloalkyl, heteroalkyl, cycloalkyl, heterocycloalkyl, aryl, and heteroaryl is optionally substituted with one or more $R^7$. In some embodiments, for a compound of Formula (V), $R^3$ is —H or $C_{2-9}$heteroaryl optionally substituted with one or more $R^7$. In some embodiments, for a compound of Formula (V), $R^3$ is H. In some embodiments, for a compound of Formula (V), $R^3$ is $C_{2-9}$heteroaryl optionally substituted with one or more $R^7$. In some embodiments, for a compound of Formula (V), $R^3$ is optionally substituted pyridinyl. In some embodiments, for a compound of Formula (V), $R^3$ is optionally substituted quinolinyl. In some embodiments, for a compound of Formula (V), $R^3$ is optionally substituted [1,2,4]triazolopyridinyl.

In some embodiments, for a compound of Formula (V), $R^4$ is —H, halogen, —$NO_2$, —CN, —OH, —O$R^5$, —S$R^5$, —$N(R^6)_2$, —S(O)$R^5$, —S(═O)$_2R^5$, —N$R^6$S(═O)$_2R^5$, —S(═O)$_2N(R^6)_2$, —C(O)$R^5$, —C(O)O$R^5$, —OC(O)$R^5$, —C(O)N$(R^6)_2$, —OC(O)N$(R^6)_2$, —N$R^6$C(O)N$(R^6)_2$, —N$R^6$C(O)$R^5$, —N$R^6$C(O)O$R^5$, $C_{1-6}$alkyl, $C_{2-6}$alkenyl, $C_{2-6}$alkynyl, $C_{1-6}$haloalkyl, $C_{1-6}$heteroalkyl, —O—$C_{1-6}$alkyl, $C_{3-8}$cycloalkyl, $C_{2-9}$heterocycloalkyl, $C_{2-9}$heteroaryl, 6- to 10-membered aryl, or —O-phenyl, wherein each alkyl, haloalkyl, heteroalkyl, cycloalkyl, heterocycloalkyl, aryl, and heteroaryl is optionally substituted with one or more $R^7$. In some embodiments, for a compound of Formula (V), $R^4$ is —H, —$N(R^6)_2$, —C(O)$R^5$, —C(O)O$R^5$, —OC(O)R, —C(O)N$(R^6)_2$, —OC(O)N$(R^6)_2$, $C_{1-6}$alkyl, $C_{2-6}$alkenyl, $C_{2-6}$alkynyl, $C_{1-6}$haloalkyl, $C_{1-6}$heteroalkyl, —O—$C_{1-6}$alkyl, $C_{3-8}$cycloalkyl, $C_{2-9}$heterocycloalkyl, $C_{2-9}$heteroaryl, 6- to 10-membered aryl, or —O-phenyl, wherein each alkyl, haloalkyl, heteroalkyl, cycloalkyl, heterocycloalkyl, aryl, and heteroaryl is optionally substituted with one or more $R^7$. In some embodiments, for a compound of Formula (V), $R^4$ is —$N(R^6)_2$, $C_{1-6}$alkyl, $C_{2-9}$heteroaryl, or 6- to 10-membered aryl, wherein each aryl and heteroaryl is optionally substituted with one or more $R^7$. In some embodiments, for a compound of Formula (V), $R^4$ is optionally substituted phenyl. In some embodiments, for a compound of Formula (V), $R^4$ is optionally substituted pyridyl. In some embodiments, for a compound of Formula (V), $R^4$ is —NHpyrimidine. In some embodiments, for a compound of Formula (V), $R^4$ is —$CH_2$phenyl. In some embodiments, for a compound of Formula (V), $R^4$ is $CH_2$NHphenyl.

In some embodiments a compound of Formula (V) or a pharmaceutically acceptable salt or isotopic variant thereof has the structure of:

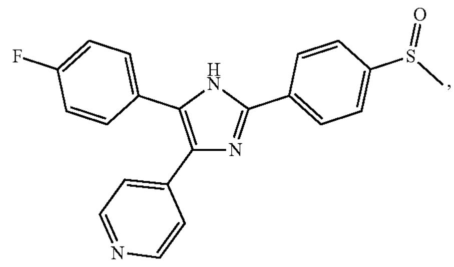

,

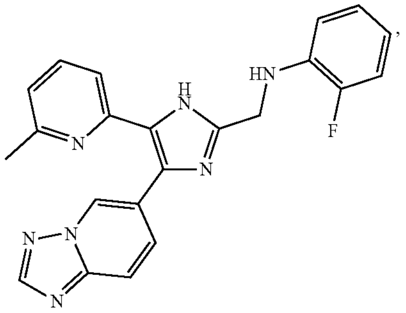

,

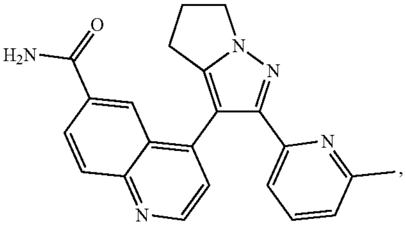

,

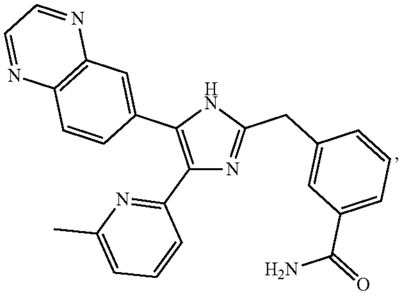

, or

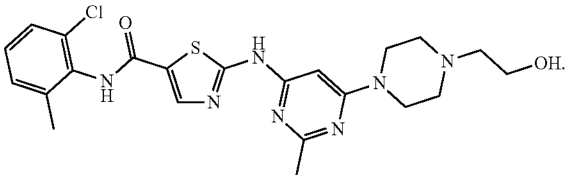

.

Disclosed herein, in some embodiments, are antagonists or partial antagonists of RIPK2 having a structure of Formula (VI) or a pharmaceutically acceptable salt or isotopic variant thereof:

Formula (VI)

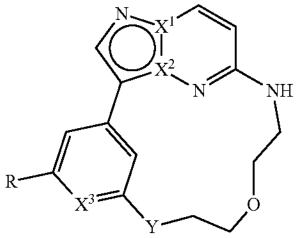

wherein $X^1$ and $X^2$ are independently N or C;

$X^3$ is N or $CR^4$;

Y is a bond, —O—, —S—, —$C(R^5)_2$, —$NR^6$—, —$NR^6C(O)$—, —$C(O)NR^6$—, or —$NR^6C(O)NR^6$—;

R is —H, halogen, —$NO_2$, —CN, —OH, —OR, —$SR^5$, —$N(R^6)_2$, —$S(O)R^5$, —$S(=O)_2R^5$, —$NR^6S(=O)_2R^5$, —$S(=O)_2N(R^6)_2$, —$C(O)R^5$, —$C(O)OR^5$, —OC(O)R, —$C(O)N(R^6)_2$, —$OC(O)N(R^6)_2$, —$NR^6C(O)N(R^6)_2$, —$NR^6C(O)R^5$, —$NR^6C(O)OR^5$, $C_{1-6}$alkyl, $C_{2-6}$alkenyl, $C_{2-6}$alkynyl, $C_{1-6}$ haloalkyl, $C_{1-6}$heteroalkyl, —O—$C_{1-6}$alkyl, $C_{3-8}$cycloalkyl, $C_{2-9}$heterocycloalkyl, $C_{2-9}$heteroaryl, 6- to 10-membered aryl, or —O-phenyl, wherein each alkyl, haloalkyl, heteroalkyl, cycloalkyl, heterocycloalkyl, aryl, and heteroaryl is optionally substituted with one or more $R^7$;

$R^4$ is —H, halogen, $C_{1-6}$alkyl, $C_{2-6}$alkenyl, $C_{2-6}$alkynyl, $C_{1-6}$haloalkyl, $C_{3-8}$cycloalkyl, —$C_{1-6}$alkyl-$C_{3-8}$cycloalkyl, phenyl, —$C_{1-6}$alkyl-phenyl, $C_{2-9}$heterocycloalkyl, —$C_{1-6}$alkyl-$C_{2-9}$heterocycloalkyl, $C_{2-9}$heteroaryl, or —$C_{1-6}$alkyl-$C_{2-9}$heteroaryl, wherein the alkyl, haloalkyl, cycloalkyl, phenyl, heteroaryl, and heterocycloalkyl are optionally substituted;

$R^5$ is —H, $C_{1-6}$alkyl, $C_{2-6}$alkenyl, $C_{2-6}$alkynyl, $C_{1-6}$haloalkyl, $C_{3-8}$cycloalkyl, —$C_{1-6}$alkyl-$C_{3-8}$cycloalkyl, phenyl, —$C_{1-6}$alkyl-phenyl, $C_{2-9}$heterocycloalkyl, —$C_{1-6}$alkyl-$C_{2-9}$heterocycloalkyl, $C_{2-9}$heteroaryl, or —$C_{1-6}$alkyl-$C_{2-9}$heteroaryl;

each $R^6$ is independently —H, $C_{1-6}$alkyl, $C_{2-6}$alkenyl, $C_{2-6}$alkynyl, $C_{1-6}$haloalkyl, $C_{3-8}$cycloalkyl, —$C_{1-6}$alkyl-$C_{3-8}$cycloalkyl, phenyl, —$C_{1-6}$alkyl-phenyl, or $C_{2-9}$heteroaryl; or two $R^6$ are taken together with the nitrogen atom to which they are attached to form a 5- or 6-membered heterocycle; and $R^7$ is —H, halogen, —$S(=O)CH_3$, —$N(R^6)_2$, —$C(O)N(R^6)_2$, $C_{1-6}$alkyl, $C_{2-6}$alkenyl, $C_{2-6}$alkynyl, $C_{1-6}$haloalkyl, $C_{1-6}$heteroalkyl, $C_{3-8}$cycloalkyl, —$C_{1-6}$alkyl-$C_{3-8}$cycloalkyl, phenyl, —$C_{1-6}$alkyl-phenyl, C2-9heterocycloalkyl, —$C_{1-6}$alkyl-$C_{2-9}$heterocycloalkyl, $C_{2-9}$heteroaryl, or —$C_{1-6}$alkyl-$C_{2-9}$heteroaryl.

In some embodiments, for a compound of Formula (VII), $X^1$ and $X^2$ are independently N or C. In some embodiments, for a compound of Formula (VII), $X^1$ is N. In some embodiments, for a compound of Formula (VII), $X^1$ is C. In some embodiments, for a compound of Formula (VII), $X^2$ is N. In some embodiments, for a compound of Formula (VII), $X^2$ is C. In some embodiments, for a compound of Formula (VII), $X^1$ is N and $X^2$ is C. In some embodiments, for a compound of Formula (VII), $X^1$ is C and $X^2$ is N.

In some embodiments, for a compound of Formula (VII), $X^3$ is N or $CR^4$. In some embodiments, for a compound of Formula (VII), $X^3$ is N or CH. In some embodiments, for a compound of Formula (VII), $X^3$ is N. In some embodiments, for a compound of Formula (VII), $X^3$ is CH.

In some embodiments, for a compound of Formula (VI), Y is a bond, —O—, —S—, —$C(R^5)_2$, —$NR^6$—, —$NR^6C$(O)—, —$C(O)NR^6$—, or —$NR^6C(O)NR^6$—. In some embodiments, for a compound of Formula (VI), Y is —O— or —$NR^6$—. In some embodiments, for a compound of Formula (VI), Y is —O— or —NH—. In some embodiments, for a compound of Formula (VI), Y is —O—. In some embodiments, for a compound of Formula (VI), Y is —NH—.

In some embodiments, for a compound of Formula (VI), R is —H, halogen, —$NO_2$, —CN, —OH, —$OR^5$, —$SR^5$, —$N(R^6)_2$, —$S(O)R^5$, —$S(=O)_2R^5$, —$NR^6S(=O)_2R^5$, —$S(=O)_2N(R^6)_2$, —$C(O)R^5$, —$C(O)OR^5$, —$OC(O)R^5$, —$C(O)N(R^6)_2$, —$OC(O)N(R^6)_2$, —$NR^6C(O)N(R^6)_2$, —$NR^6C(O)R^5$, —$NR^6C(O)OR^5$, $C_{1-6}$alkyl, $C_{2-6}$alkenyl, $C_{2-6}$alkynyl, $C_{1-6}$haloalkyl, $C_{1-6}$heteroalkyl, —O—$C_{1-6}$alkyl, $C_{3-8}$cycloalkyl, $C_{2-9}$heterocycloalkyl, $C_{2-9}$heteroaryl, 6- to 10-membered aryl, or —O-phenyl, wherein each alkyl, haloalkyl, heteroalkyl, cycloalkyl, heterocycloalkyl, aryl, and heteroaryl is optionally substituted with one or more $R^7$. In some embodiments, for a compound of Formula (VI), R is —H, halogen, —$S(=O)_2R^5$, —$NR^6S(=O)_2R^5$, —$S(=O)_2N(R^6)_2$, —$C(O)R^5$, —$C(O)OR^5$, —OC(O)R, —$C(O)N(R^6)_2$, —$OC(O)N(R^6)_2$, $C_{1-6}$alkyl, $C_{2-6}$alkenyl, $C_{1-6}$heteroalkyl, $C_{3-8}$cycloalkyl, $C_{2-9}$heterocycloalkyl, $C_{2-9}$heteroaryl, 6- to 10-membered aryl, or —O-phenyl, wherein each alkyl, heteroalkyl, cycloalkyl, heterocycloalkyl, aryl, and heteroaryl is optionally substituted with one or more $R^7$. In some embodiments, for a compound of Formula (VI), R is —H or halogen. In some embodiments, for a compound of Formula (VI), R is —H. In some embodiments, for a compound of Formula (VI), R is —Cl.

In some embodiments a compound of Formula (VI) or a pharmaceutically acceptable salt or isotopic variant thereof has the structure of:

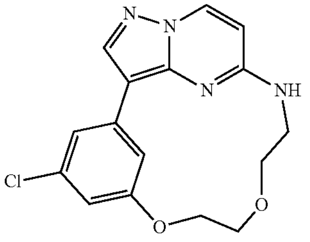

or

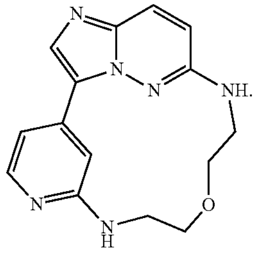

Disclosed herein, in some embodiments, are antagonists or partial antagonists of RIPK2 having a structure of Formula (VII) or a pharmaceutically acceptable salt or isotopic variant thereof:

Formula (VII)

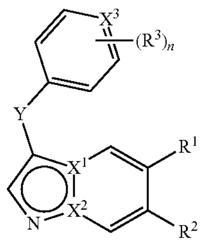

wherein $X^1$ and $X^2$ are independently N or C;

$X^3$ is N or $CR^4$;

Y is a bond, —O—, —S—, —$C(R^5)_2$, —$NR^6$—, —$NR^6C$(O)—, —$C(O)NR^6$—, or —$NR^6C(O)NR^6$—;

$R^1$ and $R^2$ are independently —H, halogen, —OH, —CN, —$N(R^6)_2$, —$NR^6C(O)R^5$, —$C(O)OR^5$, —$C(O)N(R^6)_2$, $C_{1-6}$alkyl, $C_{2-6}$alkenyl, $C_{2-6}$alkynyl, $C_{3-8}$cycloalkyl, —$C_{1-6}$alkyl-OH, —$C_{1-6}$alkyl-$OR^5$, —$C_{1-6}$alkyl-$N(R^6)_2$, —O—$C_{1-6}$alkyl, —O—$C_{1-6}$alkyl-OH, —O—$C_{1-6}$alkyl-$OR^5$, —O—$C_{1-6}$alkyl-$N(R^6)_2$, or —$S(=O)_2R^5$;

$R^3$ is —H, halogen, —$NO_2$, —CN, —OH, —$OR^5$, —$SR^5$, —$N(R^6)_2$, —S(O)R, —$S(=O)_2R^5$, —$NR^6S(=O)_2R^5$, —$S(=O)_2N(R^6)_2$, —$C(O)R^5$, —$C(O)OR^5$, —OC(O)R, —$C(O)N(R^6)_2$, —$OC(O)N(R^6)_2$, —$NR^6C(O)N(R^6)_2$, —$NR^6C(O)R^5$, —$NR^6C(O)OR^5$, $C_{1-6}$alkyl, $C_{2-6}$alkenyl, $C_{2-6}$alkynyl, $C_{1-6}$haloalkyl, $C_{1-6}$heteroalkyl, —O—$C_{1-6}$alkyl, $C_{3-8}$cycloalkyl, $C_{2-9}$heterocycloalkyl, $C_{2-9}$heteroaryl, 6- to 10-membered aryl, or —O-phenyl, wherein each alkyl, haloalkyl, heteroalkyl, cycloalkyl, heterocycloalkyl, aryl, and heteroaryl is optionally substituted with one or more $R^7$;

$R^4$ is —H, halogen, $C_{1-6}$alkyl, $C_{2-6}$alkenyl, $C_{2-6}$alkynyl, $C_{1-6}$haloalkyl, $C_{3-8}$cycloalkyl, —$C_{1-6}$alkyl-$C_{3-8}$cycloalkyl, phenyl, —$C_{1-6}$alkyl-phenyl, $C_{2-9}$heterocycloalkyl, —$C_{1-6}$alkyl-$C_{2-9}$heterocycloalkyl, $C_{2-9}$heteroaryl, or —$C_{1-6}$alkyl-$C_{2-9}$heteroaryl, wherein the alkyl, haloalkyl, cycloalkyl, phenyl, heteroaryl, and heterocycloalkyl are optionally substituted;

$R^5$ is —H, $C_{1-6}$alkyl, $C_{2-6}$alkenyl, $C_{2-6}$alkynyl, $C_{1-6}$haloalkyl, $C_{3-8}$cycloalkyl,—$C_{1-6}$alkyl-$C_{3-8}$cycloalkyl, phenyl, —$C_{1-6}$alkyl-phenyl, $C_{2-9}$heterocycloalkyl, —$C_{1-6}$alkyl-$C_{2-9}$heterocycloalkyl, $C_{2-9}$heteroaryl, or —$C_{1-6}$alkyl-$C_{2-9}$heteroaryl;

each $R^6$ is independently —H, $C_{1-6}$alkyl, $C_{2-6}$alkenyl, $C_{2-6}$alkynyl, $C_{1-6}$haloalkyl, $C_{3-8}$cycloalkyl, —$C_{1-6}$alkyl-$C_{3-8}$cycloalkyl, phenyl,—$C_{1-6}$alkyl-phenyl, or $C_{2-9}$heteroaryl; or two $R^6$ substituents are taken together with the nitrogen atom to which they are attached to form a 5- or 6-membered heterocycle;

$R^7$ is —H, halogen, —$S(=O)CH_3$, —$N(R^6)_2$, —$C(O)N(R^6)_2$, $C_{1-6}$alkyl, $C_{2-6}$alkenyl, $C_{2-6}$alkynyl, $C_{1-6}$ haloalkyl, $C_{1-6}$heteroalkyl, $C_{3-8}$cycloalkyl, —$C_{1-6}$alkyl-$C_{3-8}$cycloalkyl, phenyl, —$C_{1-6}$alkyl-phenyl, $C_{2-9}$heterocycloalkyl, —$C_{1-6}$alkyl-$C_{2-9}$heterocycloalkyl, $C_{2-9}$heteroaryl, or —$C_{1-6}$alkyl-$C_2$-heteroaryl; and n is 0, 1, 2, 3, 4, or 5.

In some embodiments, for a compound of Formula (VII), $X^1$ and $X^2$ are independently N or C. In some embodiments, for a compound of Formula (VII), $X^1$ is N. In some embodiments, for a compound of Formula (VII), $X^1$ is C. In some embodiments, for a compound of Formula (VII), $X^2$ is N. In some embodiments, for a compound of Formula (VII), $X^2$ is C. In some embodiments, for a compound of Formula (VII), $X^1$ is N and $X^2$ is C. In some embodiments, for a compound of Formula (VII), $X^1$ is C and $X^2$ is N.

In some embodiments, for a compound of Formula (VII), $X^3$ is N or $CR^4$. In some embodiments, for a compound of Formula (VII), $X^3$ is N or CH. In some embodiments, for a compound of Formula (VII), $X^3$ is N. In some embodiments, for a compound of Formula (VII), $X^3$ is CH.

In some embodiments, for a compound of Formula (VII), Y is a bond, —O—, —S—, —$C(R^5)_2$, —$NR^6$—, —$NR^6C$(O)—, —C(O)$NR^6$—, or —$NR^6C(O)NR^6$—. In some embodiments, for a compound of Formula (VII), Y is a bond, —$NR^6C(O)$—, or —C(O)$NR^6$—. In some embodiments, for a compound of Formula (VII), Y is a bond, —NHC(O)—, or —C(O)NH—. In some embodiments, for a compound of Formula (VII), Y is a bond. In some embodiments, for a compound of Formula (VII), Y is —NHC(O)—. In some embodiments, for a compound of Formula (VII), Y is —C(O)NH—.

In some embodiments, for a compound of Formula (VII), $R^1$ is —H, halogen, —OH, —CN, —$N(R^6)_2$, —$NR^6C(O)R^5$, —C(O)$OR^5$, —C(O)$N(R^6)_2$, $C_{1-6}$alkyl, $C_{2-6}$alkenyl, $C_{2-6}$alkynyl, $C_{3-8}$cycloalkyl, —$C_{1-6}$alkyl-OH, —$C_{1-6}$alkyl-$OR^5$, —$C_{1-6}$alkyl-$N(R^6)_2$, —O—$C_{1-6}$alkyl, —O—$C_{1-6}$alkyl-OH, —O—$C_{1-6}$alkyl-$OR^5$, —O—$C_{1-6}$alkyl-$N(R^6)_2$, or —$S(=O)_2R^5$. In some embodiments, for a compound of Formula (VII), $R^1$ is —H, halogen, —$N(R^6)_2$, —$NR^6C(O)R^5$, $C_{1-6}$alkyl, $C_{3-8}$cycloalkyl,—$C_{1-6}$alkyl-OH, —$C_{1-6}$alkyl-$OR^5$, —$C_{1-6}$alkyl-$N(R^6)_2$, —O—$C_{1-6}$alkyl-$N(R^6)_2$, or —$S(=O)_2R^5$. In some embodiments, for a compound of Formula (VII), $R^1$ is —H or —$S(=O)_2R^5$. In some embodiments, for a compound of Formula (VII), $R^1$ is —H. In some embodiments, for a compound of Formula (VII), $R^1$ is —$S(=O)_2$iso-propyl. In some embodiments, for a compound of Formula (VII), $R^1$ is —$S(=O)_2$tert-butyl.

In some embodiments, for a compound of Formula (VII), $R^2$ is —H, halogen, —OH, —CN, —$N(R^6)_2$, —$NR^6C(O)R^5$, —C(O)$OR^5$, —C(O)$N(R^6)_2$, $C_{1-6}$alkyl, $C_{2-6}$alkenyl, $C_{2-6}$alkynyl, $C_{3-8}$cycloalkyl, —$C_{1-6}$ alkyl-OH, —$C_{1-6}$alkyl-$OR^5$, —$C_{1-6}$alkyl-$N(R^6)_2$, —O—$C_{1-6}$alkyl, —O—$C_{1-6}$alkyl-OH, —O—$C_{1-6}$alkyl-$OR^5$, —O—$C_{1-6}$alkyl-$N(R^6)_2$, or —$S(=O)_2R^5$. In some embodiments, for a compound of Formula (VII), $R^2$ is —H, $C_{1-6}$alkyl, $C_{2-6}$alkenyl, $C_{2-6}$alkynyl, $C_{3-8}$cycloalkyl, —O—$C_{1-6}$alkyl, —O—$C_{1-6}$alkyl-OH, or —O—$C_{1-6}$alkyl-$OR^5$. In some embodiments, for a compound of Formula (VII), $R^2$ is —H or —O—$C_{1-6}$alkyl. In some embodiments, for a compound of Formula (VII), $R^2$ is —H. In some embodiments, for a compound of Formula (VII), $R^2$ is —$OCH_3$. In some embodiments, for a compound of Formula (VII), $R^2$ is —$OCH_2CH_3$.

In some embodiments, for a compound of Formula (VII), $R^3$ is —H, halogen, —$NO_2$, —CN, —OH, —$OR^5$, —$SR^5$, —$N(R^6)_2$, —S(O)$R^5$, —$S(=O)_2R^5$, —$NR^6S(=O)_2R^5$, —$S(=O)_2N(R^6)_2$, —C(O)$R^5$, —C(O)$OR^5$, —OC(O)$R^5$, —C(O)$N(R^6)_2$, —OC(O)$N(R^6)_2$, —$NR^6C(O)N(R^6)_2$, —$NR^6C(O)R^5$, —$NR^6C(O)OR^5$, $C_{1-6}$alkyl, $C_{2-6}$ alkenyl, $C_{2-6}$alkynyl, $C_{1-6}$haloalkyl, $C_{1-6}$heteroalkyl, —O—$C_{1-6}$alkyl, $C_{3-8}$cycloalkyl, $C_{2-9}$heterocycloalkyl, $C_{2-9}$heteroaryl, 6- to 10-membered aryl, or —O-phenyl, wherein each alkyl, haloalkyl, heteroalkyl, cycloalkyl, heterocycloalkyl, aryl, and heteroaryl is optionally substituted with one or more $R^7$. In some embodiments, for a compound of Formula (VII), $R^3$ is —H, halogen, —$N(R^6)_2$, —$S(=O)_2R^5$, —$NR^6S(=O)_2R^5$, —$S(=O)_2N(R^6)_2$, —$NR^6C(O)N(R^6)_2$, —$NR^6C(O)R^5$, —$NR^6C(O)OR^5$, $C_{1-6}$alkyl, $C_{1-6}$heteroalkyl, —O—$C_{1-6}$alkyl, $C_{3-8}$cycloalkyl, $C_{2-9}$heterocycloalkyl, $C_{2-9}$heteroaryl, or 6- to 10-membered aryl, wherein each alkyl, heteroalkyl, cycloalkyl, heterocycloalkyl, aryl, and heteroaryl is optionally substituted with one or more RI. In some embodiments, for a compound of Formula (VII), $R^3$ is —H, halogen, —$N(R^6)_2$, or $C_{1-6}$alkyl. In some embodiments, for a compound of Formula (VII), R3 is —H. In some embodiments, for a compound of Formula (VII), $R^3$ is —Cl. In some embodiments, for a compound of Formula (VII), $R^3$ is —F. In some embodiments, for a compound of Formula (VII), $R^3$ is —$CH_3$.

In some embodiments a compound of Formula (VII) or a pharmaceutically acceptable salt or isotopic variant thereof has the structure of:

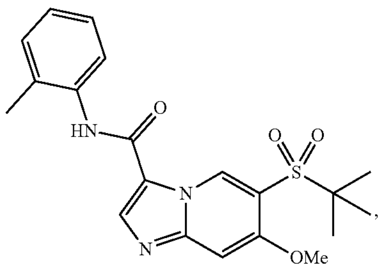

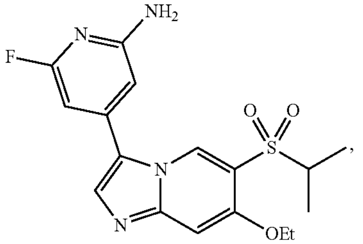

or

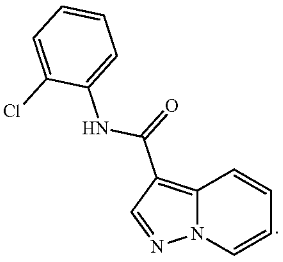

Disclosed herein, in some embodiments, are antagonists or partial antagonists of RIPK2 having a structure of Formula (VIII) or a pharmaceutically acceptable salt or isotopic variant thereof:

Formula (VIII)

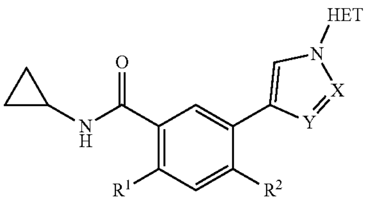

wherein:

HET is

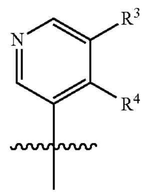

or

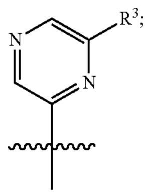

X is N and Y is CH; or

X is CH and Y is N;

$R^1$ is —H, or —F;

$R^2$ is $C_{1-3}$alkyl, —Cl, or —F;

$R^3$ and $R^4$ are each independently —H; —OR; —O—$C_{1-6}$alkyl-O—$C_{1-3}$alkyl; —O—$C_{3-6}$cycloalkyl; —C(O)$R^5$, $C_{1-6}$alkyl optionally substituted with one to three —OH, —F, $C_{3-8}$heterocycloalkyl optionally substituted with oxo, $C_{3-6}$cycloalkyl, —C(O)$OR^5$, —O—$C_{1-6}$alkyl, aryl, —N($R^5$)($R^6$), —CN, or —C(O)N($R^5$)($R^6$); $C_{3-6}$cycloalkyl optionally substituted with one to three —OH, one to three —F, $C_{1-6}$alkyl, —O—$C_{1-6}$alkyl, $C_{1-6}$alkyl-O$C_{1-6}$alkyl, $C_{1-6}$alkyl-OH, —$CF_3$, —CN, —O$C_{3-6}$ cycloalkyl, —C(O)OH, —C(O)$OR^5$, $C_{3-6}$cycloalkyl, 5-6 membered heteroaryl, $C_{3-6}$heterocycloalkyl, N($R^5$)($R^6$), or —C(O)N($R^5$)($R^6$); —C(O)$OR^5$; —C(O)N($R^5$)($R^6$); —S(═O)$_2$N($R^5$)($R^6$); —S(O)$_n$—$R^5$; a 4-10 membered monocyclic, bicyclic, or spirocyclic heterocyclyl group containing nitrogen, sulfur, or oxygen and optionally substituted with one to three —N($R^5$)($R^6$), halogen, —$C_{1-6}$alkyl, —O—$C_{1-6}$alkyl, or —$C_{1-6}$haloalkyl; aryl; —N($R^5$)($R^6$); or halogen;

$R^5$ and $R^6$ are each independently —H; —$C_{1-6}$alkyl-$C_{3-8}$heterocycloalkyl; a 4-6 membered heterocycloalkyl wherein the heterocycloalkyl ring is optionally substituted with one to three $C_{1-6}$alkyl, —O$C_{1-6}$alkyl, —$C_{1-6}$haloalkyl, $C_{1-6}$cycloalkyl, halogen, acyl, heterocycloalkyl, heterocycloalkyl-$C_{1-6}$alkyl, heterocycloalkyl-O—$C_{1-6}$alkyl, heterocycloalkyl-OH, heterocycloalkyl-C(O)$CH_3$, heterocycloalkyl-C(O)O$C_{1-3}$alkyl, —$C_{1-6}$alkyl-heterocycloalkyl, —$C_{1-6}$alkyl-heterocycloalkyl-$C_{1-6}$alkyl, —$C_{1-6}$alkyl-OH, —$C_{1-6}$alkyl-O—$C_{1-6}$alkyl, $C_{3-6}$cycloalkyl, —$C_{1-6}$alkyl-cycloalkyl, $C_{3-6}$cycloalkyl-$C_{1-6}$alkyl, $C_{3-6}$ cycloalkyl-O—$C_{1-6}$alkyl, or $C_{3-6}$cycloalkyl-O—$C_{1-6}$alkyl-OH; acyl; $C_{3-6}$cycloalkyl-C(O)—$C_{1-3}$alkyl; —C(O)—$C_{1-3}$alkyl-O—$CH_3$; —C(O)—$C_{1-3}$alkyl; —C(O)—$C_{3-6}$cycloalkyl; —C(O)—NH—$C_{1-3}$ alkyl; —C(O)—NH—$C_{1-3}$alkyl; —C(O)—NH—$C_{3-6}$cycloalkyl optionally monosubstituted or disubstituted with —$C_{1-3}$alkyl-OH, —C(O)—NH—$C_{3-6}$heterocyclyl, —C(O)-aryl, —C(O)— heteroaryl, or —S(O)$_n$—$C_{1-3}$alkyl; and $C_{1-6}$alkyl optionally substituted with —OH, O—$C_{1-3}$alkyl, $C_{3-6}$cycloalkyl, heterocyclyl, aryl, —NH—$C_{1-3}$alkyl, or —N—($C_{1-3}$alkyl)$_2$; or $R^5$ and $R^6$ together with the nitrogen atom to which they are attached form a 5-6 membered heterocyclic ring optionally substituted with methyl; and n is 0, 1, or 2.

In some embodiments, for a compound of Formula (VIII), HET is

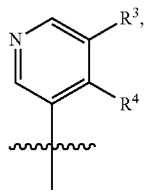

X is N, Y is CH, and n is 1 or 2. In some embodiments, for a compound of Formula (VIII), HET is

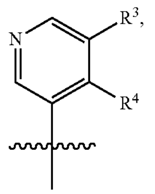

X is N, Y is CH, $R^2$ is —$CH_3$ or —Cl, $R^4$ is H, and n is 2. In some embodiments, for a compound of Formula (VIII), HET is

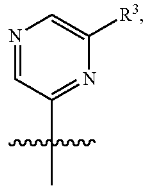

X is N, Y is CH, $R^2$ is —$CH_3$ or —Cl, and n is 2. In some embodiments, for a compound of Formula (VIII), HET is

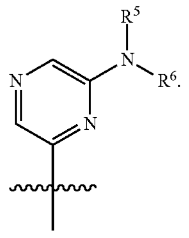

In some embodiments, for a compound of Formula (VIII), HET is

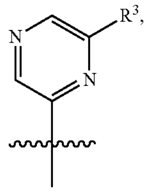

X is CH, Y is N, $R^2$ is —$CH_3$ or —Cl, and n is 2. In some embodiments, for a compound of Formula (VIII), HET is

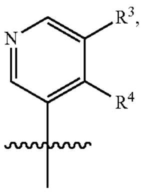
X is CH, Y is N, $R^2$ is $—CH_3$ or —Cl, $R^4$ is —H, and n is 2. In some embodiments, for a compound of Formula (VIII), HET is
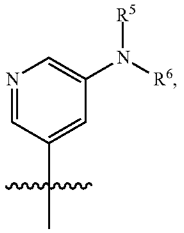
X is CH, Y is N, $R^2$ is $—CH_3$ or —Cl, $R^4$ is —H, and n is 2.
In some embodiments, for a compound of Formula (VIII), HET is
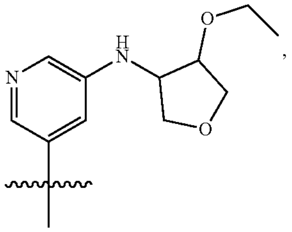
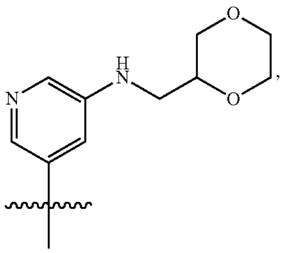
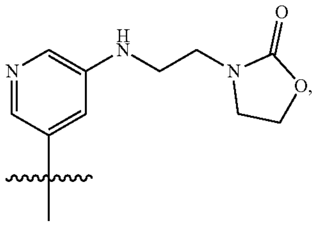
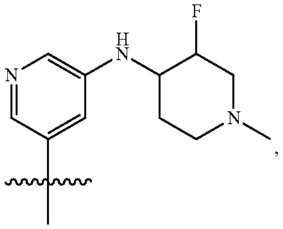
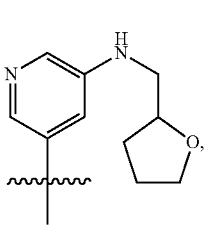
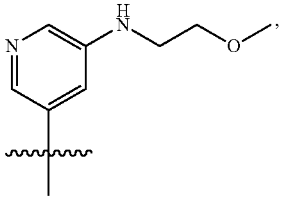
-continued
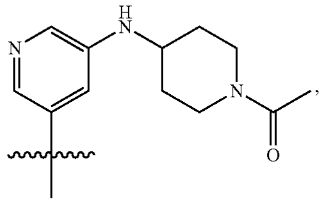
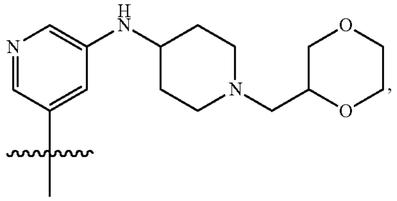
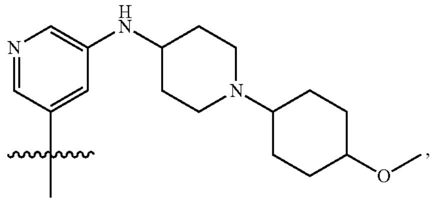
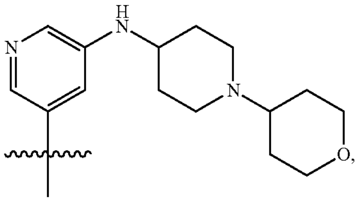
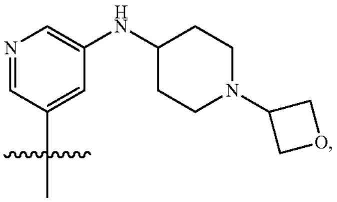
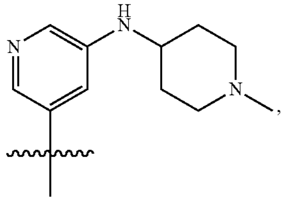
or
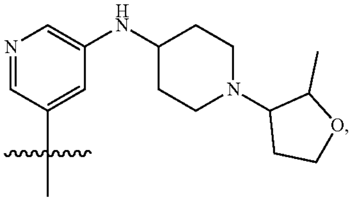
X is N, Y is CH, R is —F, and $R^2$ is $—CH_3$. In some embodiments, for a compound of Formula (VIII), HET is

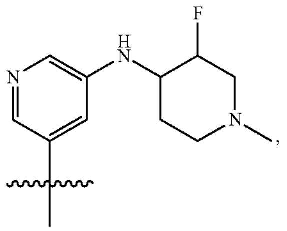
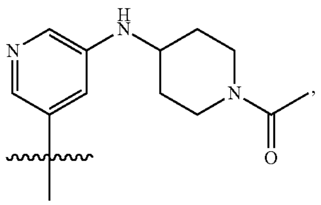
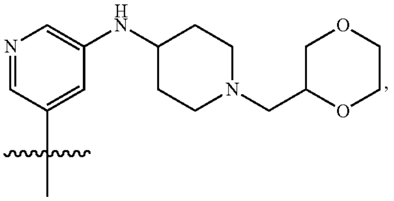
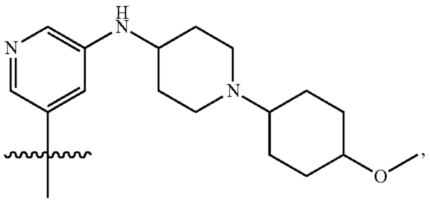
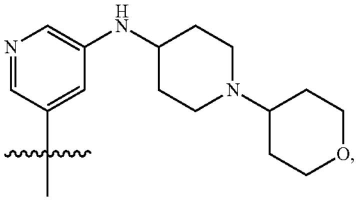
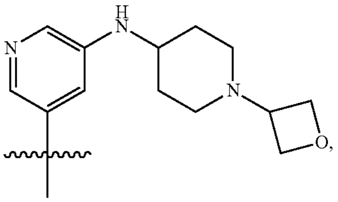
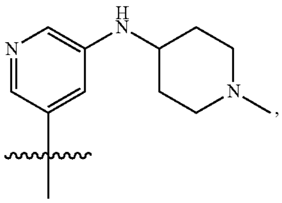
or
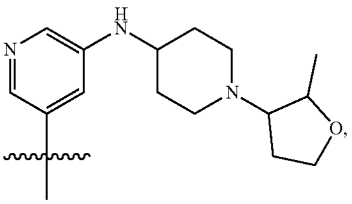
X is N, Y is CH, $R^1$ is —F, and $R^2$ is —$CH_3$. In some embodiments, for a compound of Formula (VIII), HET is
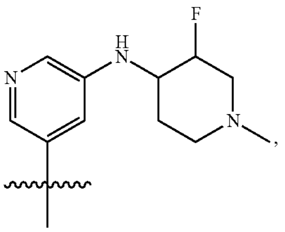
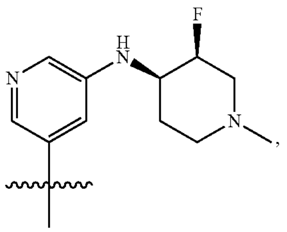
or
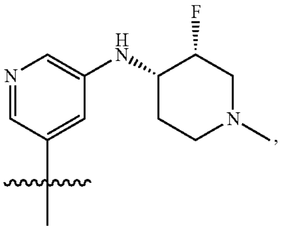
X is N, Y is CH, $R^1$ is —F, and $R^2$ is —$CH_3$.
In some embodiments, for a compound of Formula (VIII), HET is
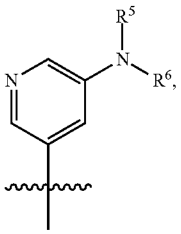
X is N, Y is CH, $R^2$ is —$CH_3$ or —Cl, $R^4$ is H, and n is 2. In some embodiments, for a compound of Formula (VIII), HET is
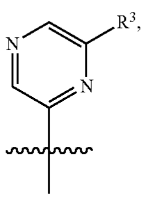
X is N, and Y is CH. In some embodiments, for a compound of Formula (VIII), HET is

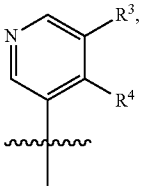
X is CH, and Y is N. In some embodiments, for a compound of Formula (VIII), HET is
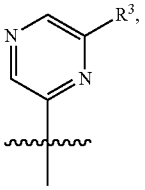
X is CH, and Y is N.
In some embodiments, for a compound of Formula (VIII), HET is
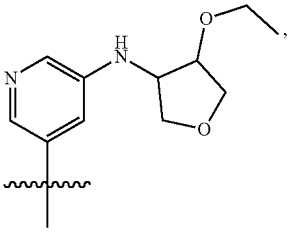
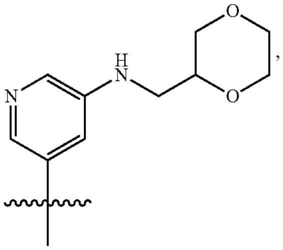
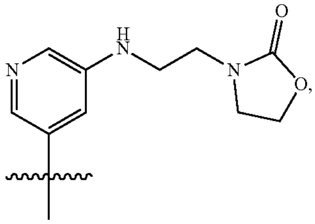
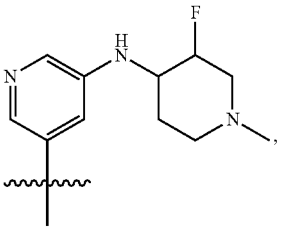
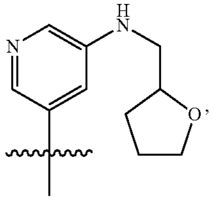
-continued
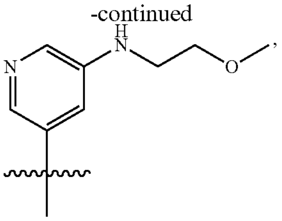
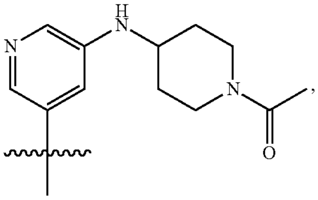
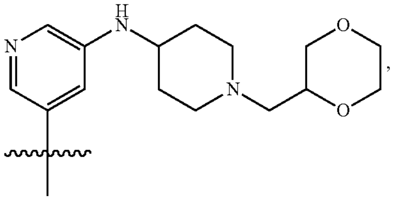
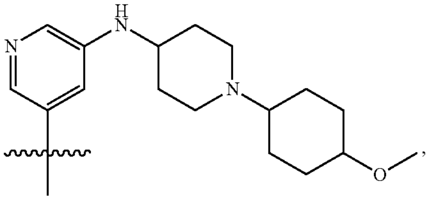
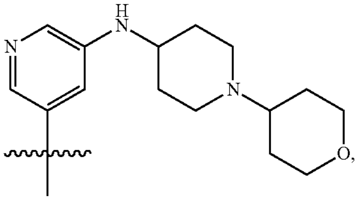
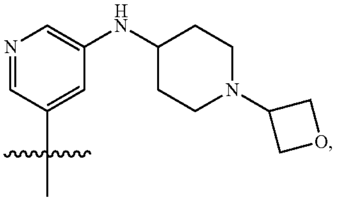
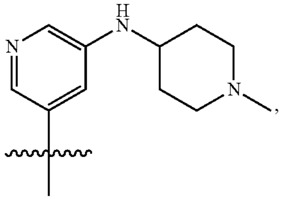
or
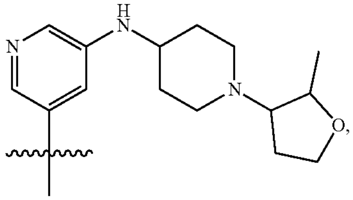
X is N, Y is CH, $R^2$ is —$CH_3$ or —Cl, $R^4$ is H, and n is 2.
In some embodiments, a compound of Formula (VIII), or a pharmaceutically acceptable salt or isotopic variant thereof, has the structure of

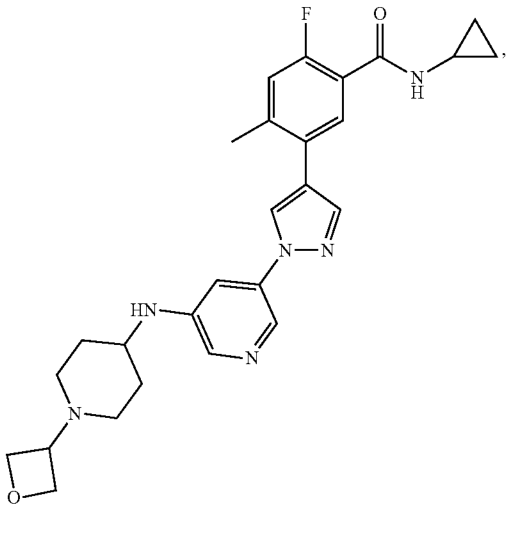
-continued
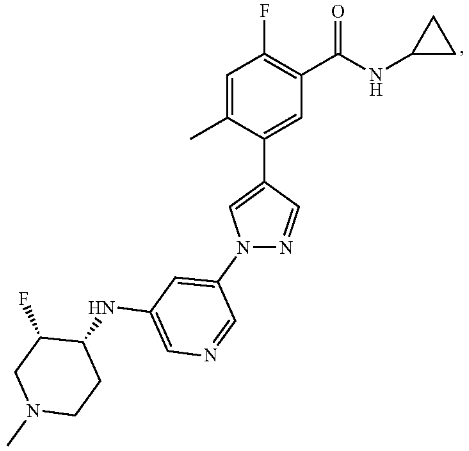
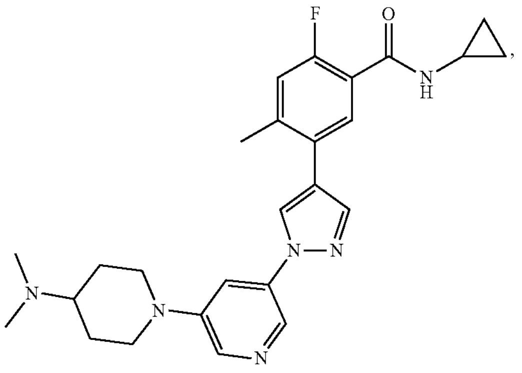
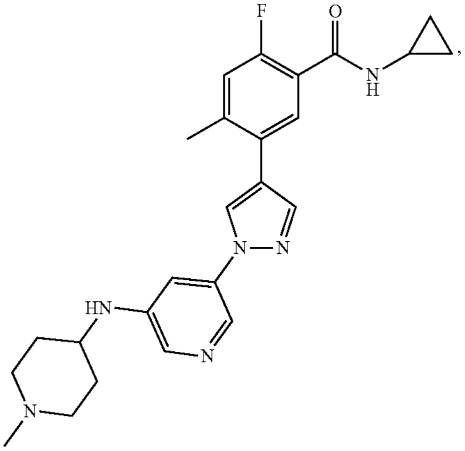
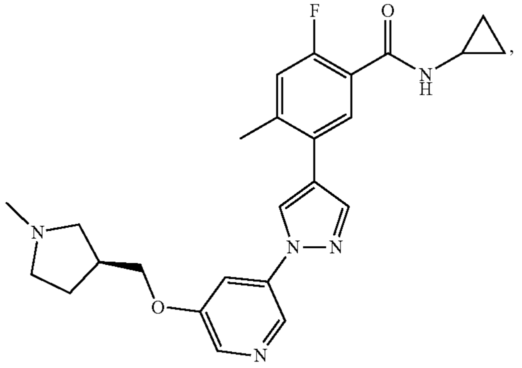
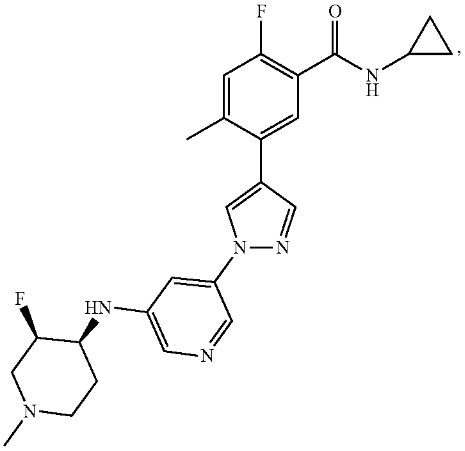
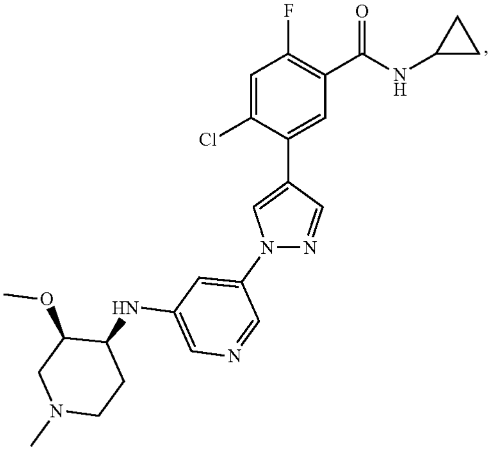

-continued

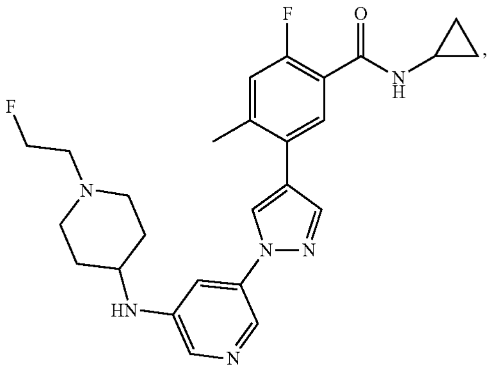

,

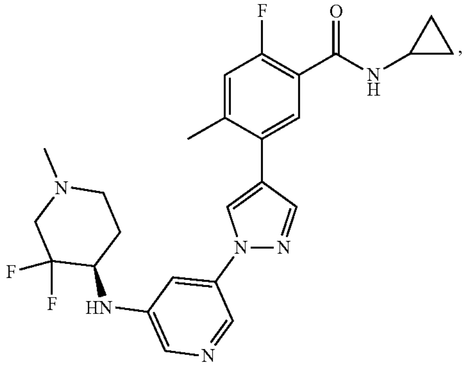

, or

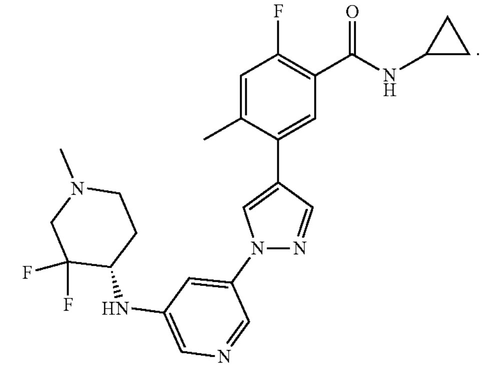

.

Disclosed herein, in some embodiments, are antagonists or partial antagonists of RIPK2 having a structure of Formula (IX), or a pharmaceutically acceptable salt or isotopic variant thereof:

Formula (IX)

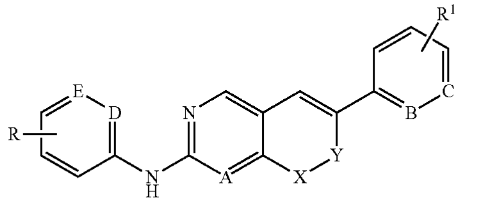

wherein

R is —H; or

R is

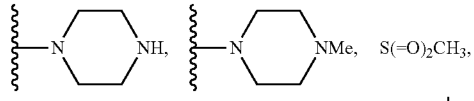

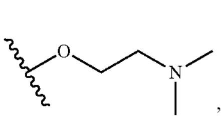

, or

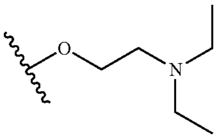

at one at one available ring position;

A and D are independently N or CH;

E is N, CH, or CR;

B and C are independently N, CH, or C—Cl;

$R^1$ is H; or $R^1$ is C—Cl, C—F, C—$OCH_3$, C—$C(CH_3)_3$, or C—OH at one available ring position; and X—Y are C═C or

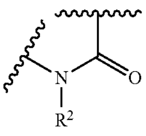

wherein $R^2$ is —H, $C_{1-6}$alkyl, $C_{1-6}$alkyl-OH, $C_{1-6}$alkyl-$OC_{1-6}$alkyl, or $C_{1-6}$alkyl-aryl.

In some embodiments, for a compound of Formula (IX), $R^2$ is methyl, ethyl, isobutyl, 2-hydroxyethyl, 2-methoxyethyl, benzyl, or phenethyl. In some embodiments, for a compound of Formula (IX), $R^2$ is methyl. In some embodiments, for a compound of Formula (IX), $R^2$ is ethyl. In some embodiments, for a compound of Formula (IX), $R^2$ is isobutyl. In some embodiments, for a compound of Formula (IX), $R^2$ is 2-hydroxyethyl. In some embodiments, for a compound of Formula (IX), $R^2$ is 2-methoxyethyl. In some embodiments, for a compound of Formula (IX), $R^2$ is benzyl. In some embodiments, for a compound of Formula (IX), $R^2$ is phenethyl.

In some embodiments, a compound of Formula (IX), or a pharmaceutically acceptable salt and isotopic variant thereof, has the structure of:

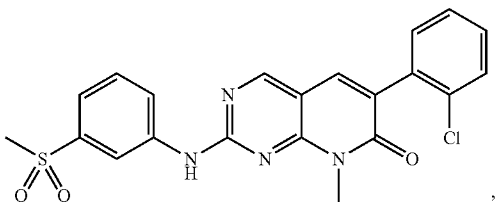

,

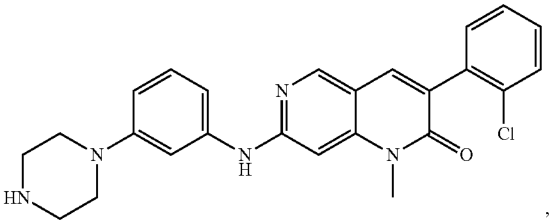

,

-continued

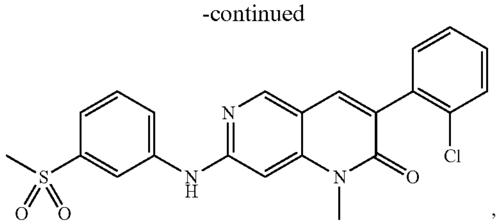

,

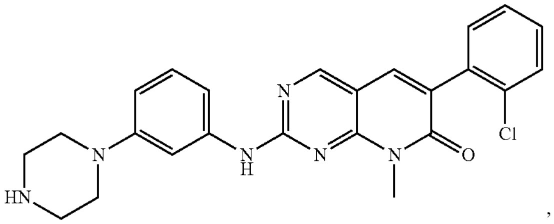

, or

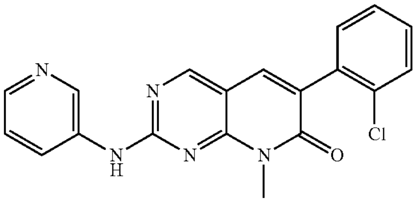

.

Disclosed herein, in some embodiments, are antagonists or partial antagonists of RIPK2 having a structure of Formula (IXa) or a pharmaceutically acceptable salt and isotopic variant thereof:

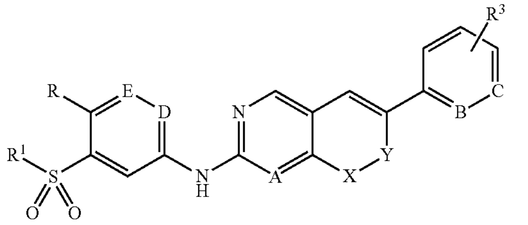

wherein

R is —H,

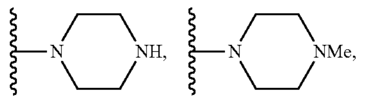

$S(=O)_2CH_3$,

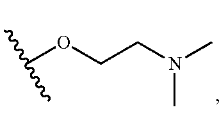

, or

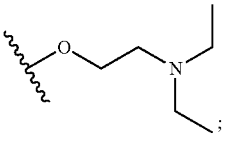

;

$R^1$ is $C_{1-6}$alkyl or 6- to 10-membered aryl;

A and D are independently N or CH;

E is N, CH, or CR;

B and C are independently N, CH, or C—Cl;

$R^3$ is H; or $R^3$ is C—Cl, C—F, C—$OCH_3$, C—$C(CH_3)_3$, or C—OH at one available ring position; and X—Y are C═C or

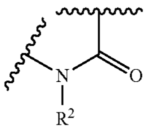

wherein $R^2$ is —H, $C_{1-6}$alkyl, $C_{1-6}$alkyl-OH, $C_{1-6}$alkyl-$OC_{1-6}$alkyl, or $C_{1-6}$alkyl-aryl.

In some embodiments, for a compound of Formula (IXa), $R^1$ is methyl, ethyl, or propyl. In some embodiments, for a compound of Formula (IXa), $R^1$ is methyl. In some embodiments, for a compound of Formula (IXa), $R^1$ is ethyl. In some embodiments, for a compound of Formula (IXa), $R^1$ is propyl.

In some embodiments, for a compound of Formula (IXa), $R^2$ is methyl, ethyl, isobutyl, 2-hydroxyethyl, 2-methoxyethyl, benzyl, or phenethyl. In some embodiments, for a compound of Formula (IXa), $R^2$ is methyl. In some embodiments, for a compound of Formula (IXa), $R^2$ is ethyl. In some embodiments, for a compound of Formula (IXa), $R^2$ is isobutyl. In some embodiments, for a compound of Formula (IXa), $R^2$ is 2-hydroxyethyl. In some embodiments, for a compound of Formula (IXa), $R^2$ is 2-methoxyethyl. In some embodiments, for a compound of Formula (IXa), $R^2$ is benzyl. In some embodiments, for a compound of Formula (IXa), $R^2$ is phenethyl.

Disclosed herein, in some embodiments, are antagonists or partial antagonists of RIPK2 having a structure of Formula (X), or a pharmaceutically acceptable salt or isotopic variant thereof:

Formula (X)

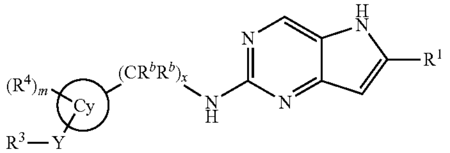

wherein

Cy is $C_{3-8}$cycloalkyl, $C_{2-9}$heterocycloalkyl, 6- to 10-membered aryl, or $C_{2-9}$heteroaryl;

Y is absent, —$CR^bR^b$—, —O—, —$NR^b$—, or —$S(O)_n$—;

$R^1$ is $C_{3-8}$cycloalkyl, $C_{2-9}$heterocycloalkyl, 6- to 10-membered aryl, or $C_{2-9}$heteroaryl, each of which is optionally substituted with one to three $R^a$;

$R^3$ is —H, $C_{2-9}$heterocycloalkyl, or $C_{2-9}$heteroaryl, wherein the heterocycloalkyl and heteroaryl are optionally substituted with one to three —F, —Cl, —Br, I, —CN, —$NO_2$, —OR, $C_{1-4}$alkyl, —$C_{1-3}$ alkyl-$OR^b$,—$C_{1-3}$alkyl-$NR^bR^b$, $C_{1-4}$haloalkyl, $C_{1-4}$haloalkoxy, $C_{3-8}$cycloalkyl, —$NR^bR^b$, —$C(O)NR^bR^b$, —$NR^bC(O)NR^bR^b$, —$S(O)_nNR^bR^b$, $C(O)OR^b$, —$OC(O)OR^b$, —$S(O)R^b$, —$NR^bS(O)_nR^b$, —$C(S)OR^b$, —$OC(S)R^b$, —$NR^bC(O)R^b$, —$C(S)NR^bR^b$, —$NR^bC(S)R^b$, —$NR^bC(O)OR^b$, —$OC(O)NR^bR^b$, —$NR^bC(S)OR^b$, —$OC(S)NR^bR^b$, —$NRC(S)NR^bR^b$, —$C(S)R^b$, or —$C(O)R^b$;

each $R^4$ is independently halogen, —CN, —$NR^bR^b$, —OR, $C_{1-4}$alkyl, —$C_{1-3}$alkyl-$OR^b$, —$C_{1-3}$alkyl-$NR^bR^b$, $C_{1-4}$haloalkyl, or $C_{1-4}$haloalkoxy;

each $R^a$ is independently —F, —Cl, —Br, I, —CN, $OR^b$, $C_{1-4}$alkyl, $C_{2-6}$alkenyl, $C_{2-6}$alkynyl, $C_{1-4}$ haloalkyl, $C_{1-4}$haloalkoxy,—$C_{1-3}$alkyl-$OR^b$, or —$C_{1-3}$alkyl-$NR^bR^b$;

each $R^b$ is independently —H or $C_{1-4}$alkyl;

x is 0, 1, 2, 3, or 4;

each m is independently 0, 1, 2, or 3; and each n is independently 0, 1, or 2.

Disclosed herein, in some embodiments, are antagonists or partial antagonists of RIPK2 having a structure of Formula (Xa) or a pharmaceutically acceptable salt or isotopic variant thereof:

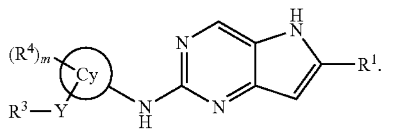

Disclosed herein, in some embodiments, are antagonists or partial antagonists of RIPK2 having a structure of Formula (Xb) or a pharmaceutically acceptable salt or isotopic variant thereof:

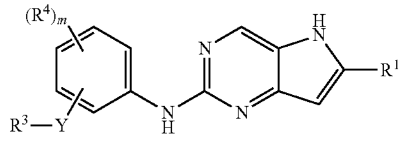

In some embodiments, for a compound of Formula (X), $R^1$ is optionally substituted phenyl, optionally substituted cyclopentyl, optionally substituted cyclohexyl, optionally substituted thienyl, optionally substituted pyridinyl, optionally substituted thiazolyl, optionally substituted pyrrolyl, optionally substituted imidazolyl, optionally substituted furanyl, optionally substituted oxazolyl, optionally substituted isoxazolyl, optionally substituted pyrazolyl, optionally substituted isothiazolyl, optionally substituted pyrmidinyl, optionally substituted pyrazinyl, optionally substituted pyridazinyl, optionally substituted oxadiazolyl, optionally substituted tetrahydropyranyl, optionally substituted triazolyl, or optionally substituted thiadiazolyl. In some embodiments, for a compound of Formula (X), $R^1$ is optionally substituted phenyl, optionally substituted cyclopentyl, optionally substituted thienyl, or optionally substituted tetrahydropyranyl. In some embodiments, for a compound of Formula (X), $R^1$ is optionally substituted phenyl. In some embodiments, for a compound of Formula (X), $R^1$ is optionally substituted cyclopentyl. In some embodiments, for a compound of Formula (X), $R^1$ is optionally substituted thienyl. In some embodiments, for a compound of Formula (X), $R^1$ is optionally substituted tetrahydropyranyl.

In some embodiments, for a compound of Formula (X), $R^3$ is optionally substituted monocyclic heterocycloalkyl or optionally substituted monocyclic heteroaryl. In some embodiments, for a compound of Formula (X), $R^3$ is optionally substituted monocyclic heterocycloalkyl. In some embodiments, for a compound of Formula (X), $R^3$ is optionally substituted monocyclic heterocycloaryl.

In some embodiments, for a compound of Formula (X), m is 0 to 3. In some embodiments, for a compound of Formula (X), m is 0. In some embodiments, for a compound of Formula (X), m is 1. In some embodiments, for a compound of Formula (X), m is 2. In some embodiments, for a compound of Formula (X), m is 3.

In some embodiments, for a compound of Formula (X), $R^3$ is optionally substituted azetidinyl, optionally substituted morpholinyl, optionally substituted piperazinyl, optionally substituted piperidinyl, optionally substituted tetrahydropyranyl, optionally substituted pyrrolidinyl, optionally substituted thiomorpholinyl, optionally substituted tetrahydrofuryanyl, optionally substituted homomorpholinyl, optionally substituted homopiperazinyl, optionally substituted thiomorpholine dioxide, or optionally substituted thienomorpholine oxide. In some embodiments, for a compound of Formula (X), $R^3$ is optionally substituted morpholinyl, optionally substituted piperazinyl, optionally substituted piperidinyl, or optionally substituted thiomorpholinyl. In some embodiments, for a compound of Formula (X), $R^3$ is optionally substituted morpholinyl. In some embodiments, for a compound of Formula (X), $R^3$ is optionally substituted piperazinyl. In some embodiments, for a compound of Formula (X), $R^3$ is optionally substituted piperidinyl. In some embodiments, for a compound of Formula (X), $R^3$ is optionally substituted thiomorpholinyl.

Disclosed herein, in some embodiments, are antagonists or partial antagonists of RIPK2 having a structure of Formula (Xc) or a pharmaceutically acceptable salt or isotopic variant thereof:

Formula (Xc)

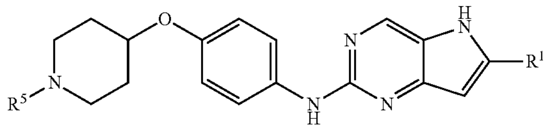

wherein $R^5$ is $C_{1-4}$alkyl or —$C_{1-3}$alkyl-$OR^b$.

Disclosed herein, in some embodiments, are antagonists or partial antagonists of RIPK2 having a structure of Formula (Xd) or a pharmaceutically acceptable salt or isotopic variant thereof:

Formula (Xd)

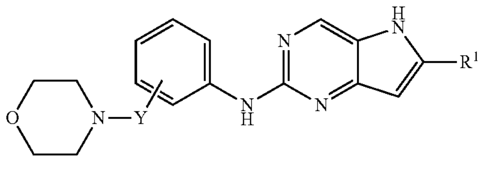

wherein:

Y is absent or —$CH_2$—; and

Y is attached to the meta or para position of the phenyl ring.

Disclosed herein, in some embodiments, are antagonists or partial antagonists of RIPK2 having a structure of Formula (Xe) or a pharmaceutically acceptable salt or isotopic variant thereof:

Formula (Xe)

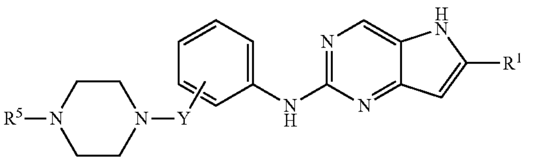

wherein $R^5$ is —H, $C_{1-4}$alkyl, or —$C_{1-3}$alkyl-$OR^b$;

Y is absent or —$CH_2$—; and

Y is attached to the meta or para position of the phenyl ring.

In some embodiments, for a compound of Formula (X), $R^1$ is

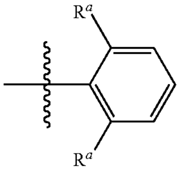

or

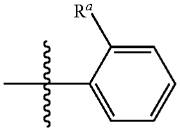

.

In some embodiments, for a compound of Formula (X), $R^1$ is

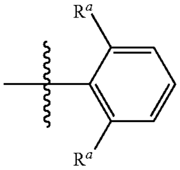

or

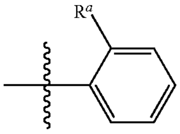

, wherein each $R^a$ is independently —F, —Cl, or —$CH_3$.

TL1A Modulators

In some embodiments, the therapeutic agent comprises a modulator of Tumor Necrosis Factor Ligand 1A (TL1A) (UniProtKB: O95150). In some embodiments, the modulator of TL1A is an antagonist of TL1A. In some embodiments the therapeutic agent comprises an inhibitor of TL1A expression or activity. In some cases, the inhibitor of TL1A expression or activity is effective to inhibit TL1A-DR3 binding. In some embodiments, the inhibitor of TL1A expression or activity comprises an allosteric modulator of TL1A. An allosteric modulator of TL1A may indirectly influence the effects TL1A on DR3, or TR6/DcR3 on TL1A or DR3. The inhibitor of TL1A expression or activity may be a direct inhibitor or indirect inhibitor. Non-limiting examples of an inhibitor of TL1A expression include RNA to protein TL1A translation inhibitors, antisense oligonucleotides targeting the TNFSF15 mRNA (such as miRNAs, or siRNA), epigenetic editing (such as targeting the DNA-binding domain of TNFSF15, or post-translational modifications of histone tails and/or DNA molecules). Non-limiting examples of an inhibitor of TL1A activity include antagonists to the TL1A receptors, (DR3 and TR6/DcR3), antagonists to TL1A antigen, and antagonists to gene expression products involved in TL1A mediated disease. Antagonists as disclosed herein, may include, but are not limited to, an anti-TL1A antibody, an anti-TL1A-binding antibody fragment, or a small molecule. The small molecule may be a small molecule that binds to TL1A or DR3. The anti-TL1A antibody may be monoclonal or polyclonal. The anti-TL1A antibody may be humanized or chimeric. The anti-TL1A antibody may be a fusion protein. The anti-TL1A antibody may be a blocking anti-TL1A antibody. A blocking antibody blocks binding between two proteins, e.g., a ligand and its receptor. Therefore, a TL1A blocking antibody includes an antibody that prevents binding of TL1A to DR3 or TR6/DcR3 receptors. In a non-limiting example, the TL1A blocking antibody binds to DR3. In another example, the TL1A blocking antibody binds to DcR3. In some cases, the TL1A antibody is an anti-TL1A antibody that specifically binds to TL1A.

The anti-TL1A antibody may comprise one or more of the antibody sequences of Table 2. The anti-DR3 antibody may comprise an amino acid sequence that is at least 85% identical to any one of SEQ ID NOS: 358-370 and an amino acid sequence that is at least 85% identical to any one of SEQ ID NOS: 371-375. The anti-DR3 antibody may comprise an amino acid sequence comprising the HCDR1, HCDR2, HCDR3 domains of any one of SEQ ID NOS: 358-370 and the LCDR1, LCDR2, and LCDR3 domains of any one of SEQ ID NOS: 371-375.

In some embodiments, an anti-TL1A antibody comprises a heavy chain comprising three complementarity-determining regions: HCDR1, HCDR2, and HCDR3; and a light chain comprising three complementarity-determining regions: LCDR1, LCDR2, and LCDR3. In some embodiments, the anti-TL1A antibody comprises a HCDR1 comprising SEQ ID NO: 209, a HCDR2 comprising SEQ ID NO: 210, a HCDR3 comprising SEQ ID NO: 211, a LCDR1 comprising SEQ ID NO: 212, a LCDR2 comprising SEQ ID NO: 213, and a LCDR3 comprising SEQ ID NO: 214. In some cases, the anti-TL1A antibody comprises a heavy chain (HC) variable domain comprising SEQ ID NO: 215 and a light chain (LC) variable domain comprising SEQ ID NO: 216.

In some embodiments, the anti-TL1A antibody comprises a HCDR1 comprising SEQ ID NO: 217, a HCDR2 comprising SEQ ID NO: 218, a HCDR3 comprising SEQ ID NO: 219, a LCDR1 comprising SEQ ID NO: 220, a LCDR2 comprising SEQ ID NO: 221, and a LCDR3 comprising SEQ ID NO: 222. In some cases, the anti-TL1A antibody comprises a heavy chain (HC) variable domain comprising SEQ ID NO: 223 and a light chain (LC) variable domain comprising SEQ ID NO: 224.

In some embodiments, the anti-TL1A antibody comprises a HCDR1 comprising SEQ ID NO: 225, a HCDR2 comprising SEQ ID NO: 226, a HCDR3 comprising SEQ ID NO: 227, a LCDR1 comprising SEQ ID NO: 228, a LCDR2 comprising SEQ ID NO: 229, and a LCDR3 comprising SEQ ID NO: 230. In some cases, the anti-TL1A antibody comprises a heavy chain (HC) variable domain comprising SEQ ID NO: 231 and a light chain (LC) variable domain comprising SEQ ID NO: 232.

In some embodiments, the anti-TL1A antibody comprises a HCDR1 comprising SEQ ID NO: 233, a HCDR2 comprising SEQ ID NO: 234, a HCDR3 comprising SEQ ID NO: 235, a LCDR1 comprising SEQ ID NO: 239, a LCDR2 comprising SEQ ID NO: 240, and a LCDR3 comprising SEQ ID NO: 241. In some cases, the anti-TL1A antibody comprises a HCDR1 comprising SEQ ID NO: 2000136, a HCDR2 comprising SEQ ID NO: 237, a HCDR3 comprising SEQ ID NO: 238, a LCDR1 comprising SEQ ID NO: 239, a LCDR2 comprising SEQ ID NO: 240, and a LCDR3 comprising SEQ ID NO: 241. In some cases, the anti-TL1A antibody comprises a heavy chain (HC) variable domain comprising SEQ ID NO: 242 and a light chain (LC) variable domain comprising SEQ ID NO: 243. In some cases, the anti-TL1A antibody comprises a heavy chain comprising SEQ ID NO: 244. In some cases, the anti-TL1A antibody comprises a light chain comprising SEQ ID NO: 245.

In some embodiments, the anti-TL1A antibody comprises a HCDR1 comprising SEQ ID NO: 246, a HCDR2 comprising SEQ ID NO: 247, a HCDR3 comprising SEQ ID NO: 248, a LCDR1 comprising SEQ ID NO: 249, a LCDR2 comprising SEQ ID NO: 250, and a LCDR3 comprising SEQ ID NO: 251. In some cases, the anti-TL1A antibody comprises a heavy chain (HC) variable domain comprising SEQ ID NO: 252 and a light chain (LC) variable domain comprising SEQ ID NO: 253.

In some embodiments, the anti-TL1A antibody comprises a HCDR1 comprising SEQ ID NO: 254, a HCDR2 comprising SEQ ID NO: 255, a HCDR3 comprising SEQ ID NO: 256, a LCDR1 comprising SEQ ID NO: 257, a LCDR2 comprising SEQ ID NO: 258, and a LCDR3 comprising SEQ ID NO: 259. In some cases, the anti-TL1A antibody comprises a heavy chain (HC) variable domain comprising SEQ ID NO: 260 and a light chain (LC) variable domain comprising SEQ ID NO: 261.

In some embodiments, the anti-TL1A antibody comprises a HCDR1 comprising SEQ ID NO: 262, a HCDR2 comprising SEQ ID NO: 264, a HCDR3 comprising SEQ ID NO: 265, a LCDR1 comprising SEQ ID NO: 267, a LCDR2 comprising SEQ ID NO: 269, and a LCDR3 comprising SEQ ID NO: 270. In some cases, the anti-TL1A antibody comprises a heavy chain (HC) variable domain comprising SEQ ID NO: 271 and a light chain (LC) variable domain comprising SEQ ID NO: 275. In some cases, the anti-TL1A antibody comprises a heavy chain (HC) variable domain comprising SEQ ID NO: 271 and a light chain (LC) variable domain comprising SEQ ID NO: 276. In some cases, the anti-TL1A antibody comprises a heavy chain (HC) variable domain comprising SEQ ID NO: 271 and a light chain (LC) variable domain comprising SEQ ID NO: 277. In some cases, the anti-TL1A antibody comprises a heavy chain (HC) variable domain comprising SEQ ID NO: 271 and a light chain (LC) variable domain comprising SEQ ID NO: 278.

In some embodiments, the anti-TL1A antibody comprises a HCDR1 comprising SEQ ID NO: 262, a HCDR2 comprising SEQ ID NO: 264, a HCDR3 comprising SEQ ID NO: 265, a LCDR1 comprising SEQ ID NO: 268, a LCDR2 comprising SEQ ID NO: 269, and a LCDR3 comprising SEQ ID NO: 270. In some cases, the anti-TL1A antibody comprises a heavy chain (HC) variable domain comprising SEQ ID NO: 271 and a light chain (LC) variable domain comprising SEQ ID NO: 279. In some cases, the anti-TL1A antibody comprises a heavy chain (HC) variable domain comprising SEQ ID NO: 271 and a light chain (LC) variable domain comprising SEQ ID NO: 280. In some cases, the anti-TL1A antibody comprises a heavy chain (HC) variable domain comprising SEQ ID NO: 271 and a light chain (LC) variable domain comprising SEQ ID NO: 281. In some cases, the anti-TL1A antibody comprises a heavy chain (HC) variable domain comprising SEQ ID NO: 271 and a light chain (LC) variable domain comprising SEQ ID NO: 282.

In some embodiments, the anti-TL1A antibody comprises a HCDR1 comprising SEQ ID NO: 262, a HCDR2 comprising SEQ ID NO: 264, a HCDR3 comprising SEQ ID NO: 265, a LCDR1 comprising SEQ ID NO: 267, a LCDR2 comprising SEQ ID NO: 269, and a LCDR3 comprising SEQ ID NO: 270. In some cases, the anti-TL1A antibody comprises a heavy chain (HC) variable domain comprising SEQ ID NO: 272 and a light chain (LC) variable domain comprising SEQ ID NO: 275. In some cases, the anti-TL1A antibody comprises a heavy chain (HC) variable domain comprising SEQ ID NO: 272 and a light chain (LC) variable domain comprising SEQ ID NO: 276. In some cases, the anti-TL1A antibody comprises a heavy chain (HC) variable domain comprising SEQ ID NO: 272 and a light chain (LC) variable domain comprising SEQ ID NO: 277. In some cases, the anti-TL1A antibody comprises a heavy chain (HC) variable domain comprising SEQ ID NO: 272 and a light chain (LC) variable domain comprising SEQ ID NO: 278.

In some embodiments, the anti-TL1A antibody comprises a HCDR1 comprising SEQ ID NO: 262, a HCDR2 comprising SEQ ID NO: 264, a HCDR3 comprising SEQ ID NO: 265, a LCDR1 comprising SEQ ID NO: 268, a LCDR2 comprising SEQ ID NO: 269, and a LCDR3 comprising SEQ ID NO: 270. In some cases, the anti-TL1A antibody comprises a heavy chain (HC) variable domain comprising SEQ ID NO: 272 and a light chain (LC) variable domain comprising SEQ ID NO: 279. In some cases, the anti-TL1A antibody comprises a heavy chain (HC) variable domain comprising SEQ ID NO: 272 and a light chain (LC) variable domain comprising SEQ ID NO: 280. In some cases, the anti-TL1A antibody comprises a heavy chain (HC) variable domain comprising SEQ ID NO: 272 and a light chain (LC) variable domain comprising SEQ ID NO: 281. In some cases, the anti-TL1A antibody comprises a heavy chain (HC) variable domain comprising SEQ ID NO: 272 and a light chain (LC) variable domain comprising SEQ ID NO: 282.

In some embodiments, the anti-TL1A antibody comprises a HCDR1 comprising SEQ ID NO: 263, a HCDR2 comprising SEQ ID NO: 264, a HCDR3 comprising SEQ ID NO: 266, a LCDR1 comprising SEQ ID NO: 267, a LCDR2 comprising SEQ ID NO: 269, and a LCDR3 comprising SEQ ID NO: 270. In some cases, the anti-TL1A antibody comprises a heavy chain (HC) variable domain comprising SEQ ID NO: 273 and a light chain (LC) variable domain comprising SEQ ID NO: 275. In some cases, the anti-TL1A antibody comprises a heavy chain (HC) variable domain comprising SEQ ID NO: 273 and a light chain (LC) variable domain comprising SEQ ID NO: 276. In some cases, the anti-TL1A antibody comprises a heavy chain (HC) variable domain comprising SEQ ID NO: 273 and a light chain (LC) variable domain comprising SEQ ID NO: 277. In some cases, the anti-TL1A antibody comprises a heavy chain (HC) variable domain comprising SEQ ID NO: 273 and a light chain (LC) variable domain comprising SEQ ID NO: 278. In some cases, the anti-TL1A antibody comprises a heavy chain (HC) variable domain comprising SEQ ID NO: 273 and a light chain (LC) variable domain comprising SEQ ID NO: 279. In some cases, the anti-TL1A antibody comprises a heavy chain (HC) variable domain comprising SEQ ID NO: 273 and a light chain (LC) variable domain comprising SEQ ID NO: 280. In some cases, the anti-TL1A antibody comprises a heavy chain (HC) variable domain comprising SEQ ID NO: 273 and a light chain (LC) variable domain comprising SEQ ID NO: 281. In some cases, the anti-TL1A antibody comprises a heavy chain (HC) variable domain comprising SEQ ID NO: 273 and a light chain (LC) variable domain comprising SEQ ID NO: 282.

In some embodiments, the anti-TL1A antibody comprises a HCDR1 comprising SEQ ID NO: 263, a HCDR2 comprising SEQ ID NO: 264, a HCDR3 comprising SEQ ID NO: 266, a LCDR1 comprising SEQ ID NO: 268, a LCDR2 comprising SEQ ID NO: 269, and a LCDR3 comprising SEQ ID NO: 270. In some cases, the anti-TL1A antibody comprises a heavy chain (HC) variable domain comprising SEQ ID NO: 274 and a light chain (LC) variable domain comprising SEQ ID NO: 279. In some cases, the anti-TL1A antibody comprises a heavy chain (HC) variable domain comprising SEQ ID NO: 274 and a light chain (LC) variable domain comprising SEQ ID NO: 280. In some cases, the anti-TL1A antibody comprises a heavy chain (HC) variable domain comprising SEQ ID NO: 274 and a light chain (LC) variable domain comprising SEQ ID NO: 281. In some cases, the anti-TL1A antibody comprises a heavy chain (HC) variable domain comprising SEQ ID NO: 274 and a light chain (LC) variable domain comprising SEQ ID NO: 282. In some cases, the anti-TL1A antibody comprises a heavy chain (HC) variable domain comprising SEQ ID NO: 274 and a light chain (LC) variable domain comprising SEQ ID NO: 275. In some cases, the anti-TL1A antibody comprises a heavy chain (HC) variable domain comprising SEQ ID NO: 274 and a light chain (LC) variable domain comprising SEQ ID NO: 276. In some cases, the anti-TL1A antibody comprises a heavy chain (HC) variable domain comprising SEQ ID NO: 274 and a light chain (LC) variable domain comprising SEQ ID NO: 277. In some cases, the anti-TL1A antibody comprises a heavy chain (HC) variable domain comprising SEQ ID NO: 274 and a light chain (LC) variable domain comprising SEQ ID NO: 278.

In some embodiments, the anti-TL1A antibody comprises a HCDR1 comprising SEQ ID NO: 283, a HCDR2 comprising SEQ ID NO: 284, a HCDR3 comprising SEQ ID NO: 285, a LCDR1 comprising SEQ ID NO: 286, a LCDR2 comprising SEQ ID NO: 287, and a LCDR3 comprising SEQ ID NO: 288. In some cases, the anti-TL1A antibody comprises a heavy chain (HC) variable domain comprising SEQ ID NO: 289 and a light chain (LC) variable domain comprising SEQ ID NO: 294. In some cases, the anti-TL1A antibody comprises a heavy chain (HC) variable domain comprising SEQ ID NO: 289 and a light chain (LC) variable domain comprising SEQ ID NO: 295. In some cases, the anti-TL1A antibody comprises a heavy chain (HC) variable domain comprising SEQ ID NO: 289 and a light chain (LC) variable domain comprising SEQ ID NO: 296. In some cases, the anti-TL1A antibody comprises a heavy chain (HC) variable domain comprising SEQ ID NO: 289 and a light chain (LC) variable domain comprising SEQ ID NO: 297. In some cases, the anti-TL1A antibody comprises a heavy chain (HC) variable domain comprising SEQ ID NO: 290 and a light chain (LC) variable domain comprising SEQ ID NO: 294. In some cases, the anti-TL1A antibody comprises a heavy chain (HC) variable domain comprising SEQ ID NO: 290 and a light chain (LC) variable domain comprising SEQ ID NO: 295. In some cases, the anti-TL1A antibody comprises a heavy chain (HC) variable domain comprising SEQ ID NO: 290 and a light chain (LC) variable domain comprising SEQ ID NO: 296. In some cases, the anti-TL1A antibody comprises a heavy chain (HC) variable domain comprising SEQ ID NO: 290 and a light chain (LC) variable domain comprising SEQ ID NO: 297. In some cases, the anti-TL1A antibody comprises a heavy chain (HC) variable domain comprising SEQ ID NO: 291 and a light chain (LC) variable domain comprising SEQ ID NO: 294. In some cases, the anti-TL1A antibody comprises a heavy chain (HC) variable domain comprising SEQ ID NO: 291 and a light chain (LC) variable domain comprising SEQ ID NO: 295. In some cases, the anti-TL1A antibody comprises a heavy chain (HC) variable domain comprising SEQ ID NO: 291 and a light chain (LC) variable domain comprising SEQ ID NO: 296. In some cases, the anti-TL1A antibody comprises a heavy chain (HC) variable domain comprising SEQ ID NO: 291 and a light chain (LC) variable domain comprising SEQ ID NO: 297. In some cases, the anti-TL1A antibody comprises a heavy chain (HC) variable domain comprising SEQ ID NO: 292 and a light chain (LC) variable domain comprising SEQ ID NO: 294. In some cases, the anti-TL1A antibody comprises a heavy chain (HC) variable domain comprising SEQ ID NO: 292 and a light chain (LC) variable domain comprising SEQ ID NO: 295. In some cases, the anti-TL1A antibody comprises a heavy chain (HC) variable domain comprising SEQ ID NO: 292 and a light chain (LC) variable domain comprising SEQ ID NO: 296. In some cases, the anti-TL1A antibody comprises a heavy chain (HC) variable domain comprising SEQ ID NO: 292 and a light chain (LC) variable domain comprising SEQ ID NO: 297. In some cases, the anti-TL1A antibody comprises a heavy chain (HC) variable domain comprising SEQ ID NO: 293 and a light chain (LC) variable domain comprising SEQ ID NO: 294. In some cases, the anti-TL1A antibody comprises a heavy chain (HC) variable domain comprising SEQ ID NO: 293 and a light chain (LC) variable domain comprising SEQ ID NO: 295. In some cases, the anti-TL1A antibody comprises a heavy chain (HC) variable domain comprising SEQ ID NO: 293 and a light chain (LC) variable domain comprising SEQ ID NO: 296. In some cases, the anti-TL1A antibody comprises a heavy chain (HC) variable domain comprising SEQ ID NO: 293 and a light chain (LC) variable domain comprising SEQ ID NO: 297.

In some embodiments, the anti-TL1A antibody comprises a HCDR1 comprising SEQ ID NO: 298, a HCDR2 comprising SEQ ID NO: 299, a HCDR3 comprising SEQ ID NO: 300, a LCDR1 comprising SEQ ID NO: 301, a LCDR2 comprising SEQ ID NO: 302, and a LCDR3 comprising SEQ ID NO: 303. In some cases, the anti-TL1A antibody comprises a heavy chain (HC) variable domain comprising SEQ ID NO: 304 and a light chain (LC) variable domain comprising SEQ ID NO: 305. In some cases, the anti-TL1A antibody comprises a heavy chain (HC) variable domain comprising SEQ ID NO: 306 and a light chain (LC) variable domain comprising SEQ ID NO: 307. In some cases, the anti-TL1A antibody comprises a heavy chain (HC) variable domain comprising SEQ ID NO: 308 and a light chain (LC) variable domain comprising SEQ ID NO: 309. In some cases, the anti-TL1A antibody comprises a heavy chain (HC) variable domain comprising SEQ ID NO: 310 and a light chain (LC) variable domain comprising SEQ ID NO: 311. In some cases, the anti-TL1A antibody comprises a heavy chain (HC) variable domain comprising SEQ ID NO: 312 and a light chain (LC) variable domain comprising SEQ ID NO: 313. In some cases, the anti-TL1A antibody comprises a heavy chain (HC) variable domain comprising SEQ ID NO: 314 and a light chain (LC) variable domain comprising SEQ ID NO: 315. In some cases, the anti-TL1A antibody comprises a heavy chain (HC) variable domain comprising SEQ ID NO: 316 and a light chain (LC) variable domain comprising SEQ ID NO: 317. In some cases, the anti-TL1A antibody comprises a heavy chain (HC) variable domain comprising SEQ ID NO: 318 and a light chain (LC) variable domain comprising SEQ ID NO: 319. In some cases, the anti-TL1A antibody comprises a heavy chain (HC) variable domain comprising SEQ ID NO: 320 and a light chain (LC) variable domain comprising SEQ ID NO: 321. In some cases, the anti-TL1A antibody comprises a heavy chain (HC) variable domain comprising SEQ ID NO: 322 and a light chain (LC) variable domain comprising SEQ ID NO: 323. In some cases, the anti-TL1A antibody comprises a heavy chain (HC) variable domain comprising SEQ ID NO: 324 and a light chain (LC) variable domain comprising SEQ ID NO: 325. In some cases, the anti-TL1A antibody comprises a heavy chain (HC) variable domain comprising SEQ ID NO: 326 and a light chain (LC) variable domain comprising SEQ ID NO: 327.

In some embodiments, the anti-TL1A antibody comprises a HCDR1 comprising SEQ ID NO: 328, a HCDR2 comprising SEQ ID NO: 329, a HCDR3 comprising SEQ ID NO: 330, a LCDR1 comprising SEQ ID NO: 331, a LCDR2 comprising SEQ ID NO: 332, and a LCDR3 comprising SEQ ID NO: 333. In some cases, the anti-TL1A antibody comprises a heavy chain (HC) variable domain comprising SEQ ID NO: 334 and a light chain (LC) variable domain comprising SEQ ID NO: 335.

In some embodiments, the anti-TL1A antibody comprises a HCDR1 comprising SEQ ID NO: 336, a HCDR2 comprising SEQ ID NO: 337, a HCDR3 comprising SEQ ID NO: 338, a LCDR1 comprising SEQ ID NO: 339, a LCDR2 comprising SEQ ID NO: 340, and a LCDR3 comprising SEQ ID NO: 341. In some cases, the anti-TL1A antibody comprises a heavy chain (HC) variable domain comprising SEQ ID NO: 342 and a light chain (LC) variable domain comprising SEQ ID NO: 343.

In some embodiments, the anti-TL1A antibody comprises a HCDR1 comprising SEQ ID NO: 346, a HCDR2 comprising SEQ ID NO: 347, a HCDR3 comprising SEQ ID NO: 348, a LCDR1 comprising SEQ ID NO: 349, a LCDR2 comprising SEQ ID NO: 350, and a LCDR3 comprising SEQ ID NO: 351. In some cases, the anti-TL1A antibody comprises a heavy chain (HC) variable domain comprising SEQ ID NO: 344 and a light chain (LC) variable domain comprising SEQ ID NO: 345. In some cases, the anti-TL1A antibody comprises a heavy chain (HC) variable domain comprising SEQ ID NO: 352 and a light chain (LC) variable domain comprising SEQ ID NO: 353. In some cases, the anti-TL1A antibody comprises a heavy chain (HC) variable domain comprising SEQ ID NO: 354 and a light chain (LC) variable domain comprising SEQ ID NO: 355. In some cases, the anti-TL1A antibody comprises a heavy chain (HC) variable domain comprising SEQ ID NO: 356 and a light chain (LC) variable domain comprising SEQ ID NO: 357.

In some embodiments, the anti-TL1A antibody comprises a HCDR1 comprising SEQ ID NO: 376, a HCDR2 comprising SEQ ID NO: 377, a HCDR3 comprising SEQ ID NO: 378, a LCDR1 comprising SEQ ID NO: 379, a LCDR2 comprising SEQ ID NO: 380, and a LCDR3 comprising SEQ ID NO: 381. In some cases, the anti-TL1A antibody comprises a heavy chain (HC) variable domain comprising SEQ ID NO: 382 and a light chain (LC) variable domain comprising SEQ ID NO: 383.

In some embodiments, the anti-TL1A antibody comprises a HCDR1 comprising SEQ ID NO: 384, a HCDR2 comprising SEQ ID NO: 385, a HCDR3 comprising SEQ ID NO: 386, a LCDR1 comprising SEQ ID NO: 387, a LCDR2 comprising SEQ ID NO: 388, and a LCDR3 comprising SEQ ID NO: 399. In some cases, the anti-TL1A antibody comprises a heavy chain (HC) variable domain comprising SEQ ID NO: 390 and a light chain (LC) variable domain comprising SEQ ID NO: 391.

In some embodiments, the anti-TL1A antibody comprises one or more of A101-A177 of Table 17. In some embodiments, the anti-TL1A antibody is A100. In some embodiments, the anti-TL1A antibody is A101. In some embodiments, the anti-TL1A antibody is A102. In some embodiments, the anti-TL1A antibody is A103. In some embodiments, the anti-TL1A antibody is A104. In some embodiments, the anti-TL1A antibody is A105. In some embodiments, the anti-TL1A antibody is A106. In some embodiments, the anti-TL1A antibody is A107. In some embodiments, the anti-TL1A antibody is A108. In some embodiments, the anti-TL1A antibody is A109. In some embodiments, the anti-TL1A antibody is Al 10. In some embodiments, the anti-TL1A antibody is A111. In some embodiments, the anti-TL1A antibody is A112. In some embodiments, the anti-TL1A antibody is A113. In some embodiments, the anti-TL1A antibody is A114. In some embodiments, the anti-TL1A antibody is A115. In some embodiments, the anti-TL1A antibody is A116. In some embodiments, the anti-TL1A antibody is Al 17. In some embodiments, the anti-TL1A antibody is A118. In some embodiments, the anti-TL1A antibody is A119. In some embodiments, the anti-TL1A antibody is A120. In some embodiments, the anti-TL1A antibody is A121. In some embodiments, the anti-TL1A antibody is A122. In some embodiments, the anti-TL1A antibody is A123. In some embodiments, the anti-TL1A antibody is A124. In some embodiments, the anti-TL1A antibody is A125. In some embodiments, the anti-TL1A antibody is A126. In some embodiments, the anti-TL1A antibody is A127. In some embodiments, the anti-TL1A antibody is A128. In some embodiments, the anti-TL1A antibody is A129. In some embodiments, the anti-TL1A antibody is A130. In some embodiments, the anti-TL1A antibody is A131. In some embodiments, the anti-TL1A antibody is A132. In some embodiments, the anti-TL1A antibody is A133. In some embodiments, the anti-TL1A antibody is A134. In some embodiments, the anti-TL1A antibody is A135. In some embodiments, the anti-TL1A antibody is A136. In some embodiments, the anti-TL1A antibody is A137. In some embodiments, the anti-TL1A antibody is A138. In some embodiments, the anti-TL1A antibody is A139. In some embodiments, the anti-TL1A antibody is A140. In some embodiments, the anti-TL1A antibody is A141. In some embodiments, the anti-TL1A antibody is A142. In some embodiments, the anti-TL1A antibody is A143. In some embodiments, the anti-TL1A antibody is A144. In some embodiments, the anti-TL1A antibody is A145. In some embodiments, the anti-TL1A antibody is A146. In some embodiments, the anti-TL1A antibody is A147. In some embodiments, the anti-TL1A antibody is A148. In some embodiments, the anti-TL1A antibody is A149. In some embodiments, the anti-TL1A antibody is A150. In some embodiments, the anti-TL1A antibody is A151. In some embodiments, the anti-TL1A antibody is A152. In some embodiments, the anti-TL1A antibody is A153. In some embodiments, the anti-TL1A antibody is A154. In some embodiments, the anti-TL1A antibody is A155. In some embodiments, the anti-TL1A antibody is A156. In some embodiments, the anti-TL1A antibody is A157. In some embodiments, the anti-TL1A antibody is A158. In some embodiments, the anti-TL1A antibody is A159. In some embodiments, the anti-TL1A antibody is A160. In some embodiments, the anti-TL1A antibody is A161. In some embodiments, the anti-TL1A antibody is A162. In some embodiments, the anti-TL1A antibody is A163. In some embodiments, the anti-TL1A antibody is A164. In some embodiments, the anti-TL1A antibody is A165. In some embodiments, the anti-TL1A antibody is A166. In some embodiments, the anti-TL1A antibody is A167. In some embodiments, the anti-TL1A antibody is A168. In some embodiments, the anti-TL1A antibody is A169. In some embodiments, the anti-TL1A antibody is A170. In some embodiments, the anti-TL1A antibody is A171. In some embodiments, the anti-TL1A antibody is A172. In some embodiments, the anti-TL1A antibody is A173. In some embodiments, the anti-TL1A antibody is A174. In some embodiments, the anti-TL1A antibody is A175. In some embodiments, the anti-TL1A antibody is A176. In some embodiments, the anti-TL1A antibody is A177.

In some embodiments, the anti-DR3 is A178. In some embodiments, the anti-DR3 is A179. In some embodiments, the anti-DR3 is A180. In some embodiments, the anti-DR3 is A181. In some embodiments, the anti-DR3 is A182. In some embodiments, the anti-DR3 is A183. In some embodiments, the anti-DR3 is A184. In some embodiments, the anti-DR3 is A185. In some embodiments, the anti-DR3 is A186. In some embodiments, the anti-DR3 is A187. In some embodiments, the anti-DR3 is A188. In some embodiments, the anti-DR3 is A189. In some embodiments, the anti-DR3 is A190. In some embodiments, the anti-DR3 is A191. In some embodiments, the anti-DR3 is A192. In some embodiments, the anti-DR3 is A193. In some embodiments, the anti-DR3 is A194. In some embodiments, the anti-DR3 is A195. In some embodiments, the anti-DR3 is A196. In some embodiments, the anti-DR3 is A197. In some embodiments, the anti-DR3 is A198. In some embodiments, the anti-DR3 is A199. In some embodiments, the anti-DR3 is A200. In some embodiments, the anti-DR3 is A201. In some embodiments, the anti-DR3 is A202. In some embodiments, the anti-DR3 is A203. In some embodiments, the anti-DR3 is A204. In some embodiments, the anti-DR3 is A205. In some embodiments, the anti-DR3 is A206. In some embodiments, the anti-DR3 is A207. In some embodiments, the anti-DR3 is A208. In some embodiments, the anti-DR3 is A209. In some embodiments, the anti-DR3 is A210. In some embodiments, the anti-DR3 is A211. In some embodiments, the anti-DR3 is A212. In some embodiments, the anti-DR3 is A213. In some embodiments, the anti-DR3 is A214. In some embodiments, the anti-DR3 is A215. In some embodiments, the anti-DR3 is A216. In some embodiments, the anti-DR3 is A217. In some embodiments, the anti-DR3 is A218. In some embodiments, the anti-DR3 is A219. In some embodiments, the anti-DR3 is A220. In some embodiments, the anti-DR3 is A221. In some embodiments, the anti-DR3 is A222. In some embodiments, the anti-DR3 is A223. In some embodiments, the anti-DR3 is A224. In some embodiments, the anti-DR3 is A225. In some embodiments, the anti-DR3 is A226. In some embodiments, the anti-DR3 is A227. In some embodiments, the anti-DR3 is A228. In some embodiments, the anti-DR3 is A229. In some embodiments, the anti-DR3 is A230. In some embodiments, the anti-DR3 is A231. In some embodiments, the anti-DR3 is A232. In some embodiments, the anti-DR3 is A233. In some embodiments, the anti-DR3 is A234. In some embodiments, the anti-DR3 is A235. In some embodiments, the anti-DR3 is A236. In some embodiments, the anti-DR3 is A237. In some embodiments, the anti-DR3 is A238. In some embodiments, the anti-DR3 is A239. In some embodiments, the anti-DR3 is A240. In some embodiments, the anti-DR3 is A241. In some embodiments, the anti-DR3 is A242.

TABLE 2

Non-Limiting Examples of anti-TL1A and anti-DR3 Antibodies

| Antibody Name | HC Variable Domain (SEQ ID NO) | LC Variable Domain (SEQ ID NO) |
|---|---|---|
| A100 | 215 | 216 |
| A101 | 223 | 224 |
| A102 | 231 | 232 |
| A103 | 242 | 243 |
| A104 | 252 | 253 |
| A105 | 260 | 261 |
| A106 | 271 | 275 |
| A107 | 271 | 276 |
| A108 | 271 | 277 |
| A109 | 271 | 278 |
| A110 | 271 | 279 |
| A111 | 271 | 280 |
| A112 | 271 | 281 |
| A113 | 271 | 282 |
| A114 | 272 | 275 |
| A115 | 272 | 276 |
| A116 | 272 | 277 |
| A117 | 272 | 278 |
| A118 | 272 | 279 |
| A119 | 272 | 280 |
| A120 | 272 | 281 |
| A121 | 272 | 282 |
| A122 | 273 | 275 |
| A123 | 273 | 276 |
| A124 | 273 | 277 |

Modulators of Certain Pathways

In some embodiments, the therapeutic agent is capable of modulating an expression of a gene, or an activity or an expression of a gene expression product expressed from the gene involved in a pathway implicated in the pathology or pathogenesis of a disease or condition disclosed herein. In some instances, the pathway comprises the Janus Kinase (JAK)./Signal Transducer and Transcription Activator (STAT) pathway. Non-limiting genes involved in the JAK/STAT pathway include Interferon Regulatory Factor 1 (IRF1), Klotho Beta (KLB), Mitogen-Activated Protein Kinase Kinase 1 (MAP2K1), Nuclear Receptor Subfamily 3 Group C Member 1 (NR3C1), Protein Kinase C Beta (PRKCB), Protein Kinase C Epsilon (PRKCE), Protein Kinase C Gamma (PRKCG), Protein Kinase C Eta (PRKCH), Protein Kinase C Theta (PRKCQ), Prolactin Receptor (PRLR), Protein Tyrosine Phosphatase, Non-Receptor Type 11 (PTPN11), Signal Transducer And Activator Of Transcription 1 (STAT1), Signal Transducer And Activator Of Transcription 5A (STAT5A), and Signal Transducer And Activator Of Transcription 5B (STAT5B).

In some instances, the pathway comprises the genes or gene expression products expressed from gens involved in autophagy pathways. Non-limiting examples of genes involved in autophagy include Autophagy Related 10 (ATG10), Autophagy Related 16 Like 1 (ATG16L1), Autophagy Related 4A Cysteine Peptidase (ATG4A), Autophagy Related 4C Cysteine Peptidase (ATG4C), Cathepsin H (CTSH), Sequestosome 1 (SQSTM1), Unc-51 Like Autophagy Activating Kinase 1 (ULK1), and WD Repeat And FYVE Domain Containing 3 (WDFY3).

Further provided are therapeutic agents capable of modulating an expression of a gene, or an activity or an expression of a gene expression product expressed from the gene that is involved implicated in inflammatory bowel disease (IBD) pathogenesis. In some embodiments, the gene is selected from the group consisting of Mitogen-Activated Protein Kinase Kinase Kinase Kinase 4 (MAP4K4), Prostaglandin E Receptor 4 (PTGER4), Interleukin 18 Receptor 1 (IL18R1), Interleukin 18 Receptor Accessory Protein (IL18RAP), Adenylate Cyclase 7 (ADCY7), B Lymphoid Tyrosine Kinase (BLK), G Protein-Coupled Receptor 65 (GPR65), Sprouty Related EVH1 Domain Containing 2 (SPRED2), and Src Kinase Associated Phosphoprotein 2 (SKAP2). The amino acid sequence for IL18R1 is provided in SEQ ID NOS: 83-84. The amino acid sequence for IL18RAP is provided in SEQ ID NOS: 85-89. The amino acid sequence for GPR65 is provided in SEQ ID NO: 90. The amino acid sequence for SPRED2 is provided in SEQ ID NO: 91. The amino acid sequence for SKAP2 is provided in SEQ ID NOS: 92-93.

Non-limiting examples of MAP4K4 modulators include GNE-220 and PF-6260933. Non-limiting examples of PTGER4 modulators include grapiprant (CJ-023,423), ONO-AE3-208, GW627368X, AH23848, ONO-AE2-227, ONO-AE1-734, AGN205203, rivenprost (ONO-4819), CJ-023,423, and BGC20-1531. Exemplary modulators of PFKFB3 include, but are not limited to 3-(3-pyridinyl)-1-(4-pyridinyl)-2-propen-1-one (3PO), 1-(4-pyridinyl)-3-(2-quinolinyl)-2-propen-1-one (PFK15), 5-triazolo-2-arylpyridazinone,125 1-(3-pyridinyl)-3-(2-quinolinyl)-2-propen-1-one (PQP), 126 5, 6, 7, 8-tetrahydroxy-2-(4-hydroxyphenyl) chrome-4-one (N4A), and 7, 8-dihydroxy-3-(4-hydroxyphenyl) chromen-4-one (YN1). Non-limiting modulators of ADCY7 include forskolin and colforsin daropate. Non-limiting examples of GPR65 modulators include BTB09089 (3-[(2,4-dichlorophenyl)methylsulfanyl]-1,6-dimethylpyridazino[4,5-e][1,3,4]thiadiazin-5-one), and ZINC62678696.

The therapeutic agent targeting the above genes or gene expression products may be an antibody or antigen binding fragment thereof. The therapeutic agent may be a small molecule. The therapeutic agent may be a peptide or a protein. The therapeutic agent may be an agonist, or partial agonist. The therapeutic agent may be an allosteric modulator, such as a positive allosteric modulator (PAM). The therapeutic agent may be an antagonist, or partial antagonist. The therapeutic agent may be an inverse agonist. The therapeutic agent may be a negative allosteric modulator (NAM).

In some embodiments, the therapeutic agent comprises an agonist of Janus Kinase 1 (JAK1). Non-limiting examples of JAK1 inhibitors include Ruxolitinib (INCB018424), S-Ruxolitinib (INCB018424), Baricitinib (LY3009104, INCB028050), Filgotinib (GLPG0634), Momelotinib (CYT387), Cerdulatinib (PRT062070, PRT2070), LY2784544, NVP-BSK805, 2HCl, Tofacitinib (CP-690550, Tasocitinib), XL019, Pacritinib (SB1518), or ZM 39923 HCl.

Dosages and Routes of Administration

In general, methods disclosed herein comprise administering a therapeutic agent by oral administration. However, in some instances, methods comprise administering a therapeutic agent by intraperitoneal injection. In some instances, methods comprise administering a therapeutic agent in the form of an anal suppository. In some instances, methods comprise administering a therapeutic agent by intravenous ("i.v.") administration. It is conceivable that one may also administer therapeutic agents disclosed herein by other routes, such as subcutaneous injection, intramuscular injection, intradermal injection, transdermal injection percutaneous administration, intranasal administration, intralymphatic injection, rectal administration intragastric administration, or any other suitable parenteral administration. In some embodiments, routes for local delivery closer to site of injury or inflammation are preferred over systemic routes. Routes, dosage, time points, and duration of administrating therapeutics may be adjusted. In some embodiments, administration of therapeutics is prior to, or after, onset of either, or both, acute and chronic symptoms of the disease or condition.

An effective dose and dosage of therapeutics to prevent or treat the disease or condition disclosed herein is defined by an observed beneficial response related to the disease or condition, or symptom of the disease or condition. Beneficial response comprises preventing, alleviating, arresting, or curing the disease or condition, or symptom of the disease or condition (e.g., reduced instances of diarrhea, rectal bleeding, weight loss, and size or number of intestinal lesions or strictures, reduced fibrosis or fibrogenesis, reduced fibrostenosis, reduced inflammation). In some embodiments, the beneficial response may be measured by detecting a measurable improvement in the presence, level, or activity, of biomarkers, transcriptomic risk profile, or intestinal microbiome in the subject. An "improvement," as used herein refers to shift in the presence, level, or activity towards a presence, level, or activity, observed in normal individuals (e.g. individuals who do not suffer from the disease or condition). In instances wherein the therapeutic agent is not therapeutically effective or is not providing a sufficient alleviation of the disease or condition, or symptom of the disease or condition, then the dosage amount and/or route of administration may be changed, or an additional agent may be administered to the subject, along with the therapeutic agent. In some embodiments, as a patient is started on a regimen of a therapeutic agent, the patient is also weaned off (e.g., step-wise decrease in dose) a second treatment regimen.

Suitable dose and dosage administrated to a subject is determined by factors including, but no limited to, the particular therapeutic agent, disease condition and its severity, the identity (e.g., weight, sex, age) of the subject in need of treatment, and can be determined according to the particular circumstances surrounding the case, including, e.g., the specific agent being administered, the route of administration, the condition being treated, and the subject or host being treated. In general, however, doses employed for adult human treatment are typically in the range of 0.01 mg-5000 mg per day. In one aspect, doses employed for adult human treatment are from about 1 mg to about 1000 mg per day. In one embodiment, the desired dose is conveniently presented in a single dose or in divided doses administered simultaneously (or over a short period of time) or at appropriate intervals, for example as two, three, four or more sub-doses per day. Non-limiting examples of effective dosages of for oral delivery of a therapeutic agent include between about 0.1 mg/kg and about 100 mg/kg of body weight per day, and preferably between about 0.5 mg/kg and about 50 mg/kg of body weight per day. In other instances, the oral delivery dosage of effective amount is about 1 mg/kg and about 10 mg/kg of body weight per day of active material. Non-limiting examples of effective dosages for intravenous administration of the therapeutic agent include at a rate between about 0.01 to 100 pmol/kg body weight/min. In some embodiments, the daily dosage or the amount of active in the dosage form are lower or higher than the ranges indicated herein, based on a number of variables in regard to an individual treatment regime. In various embodiments, the daily and unit dosages are altered depending on a number of variables including, but not limited to, the activity of the therapeutic agent used, the disease or condition to be treated, the mode of administration, the requirements of the individual subject, the severity of the disease or condition being treated, and the judgment of the practitioner.

In some embodiments, the administration of the therapeutic agent is hourly, once every 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours 22 hours, 23 hours, 1 day, 2 days, 3 days, 4 days, 5 days, 6 days, 7 days, 8 days, 9 days, 10 days, 11 days, 12 days, 13 days, 14 days, 15 days, 1 month, 2 months, 3 months, 4 months, 5 months, 6 months, 7 months, 8 months, 9 months, 10 months, 11 months, 1 year, 2 years, 3 years, 4 years, or 5 years, or 10 years. The effective dosage ranges may be adjusted based on subject's response to the treatment. Some routes of administration will require higher concentrations of effective amount of therapeutics than other routes.

In certain embodiments wherein the patient's condition does not improve, upon the doctor's discretion the administration of therapeutic agent is administered chronically, that is, for an extended period of time, including throughout the duration of the patient's life in order to ameliorate or otherwise control or limit the symptoms of the patient's disease or condition. In certain embodiments wherein a patient's status does improve, the dose of therapeutic agent being administered may be temporarily reduced or temporarily suspended for a certain length of time (i.e., a "drug holiday"). In specific embodiments, the length of the drug holiday is between 2 days and 1 year, including by way of example only, 2 days, 3 days, 4 days, 5 days, 6 days, 7 days, 10 days, 12 days, 15 days, 20 days, 28 days, or more than 28 days. The dose reduction during a drug holiday is, by way of example only, by 10%-100%, including by way of example only 10%, 15%, 20%, 25%, 30%, 35%, 40%, 45%, 50%, 55%, 60%, 65%, 70%, 75%, 80%, 85%, 90%, 95%, and 100%. In certain embodiments, the dose of drug being administered may be temporarily reduced or temporarily suspended for a certain length of time (i.e., a "drug diversion"). In specific embodiments, the length of the drug diversion is between 2 days and 1 year, including by way of example only, 2 days, 3 days, 4 days, 5 days, 6 days, 7 days, 10 days, 12 days, 15 days, 20 days, 28 days, or more than 28 days. The dose reduction during a drug diversion is, by way of example only, by 10%-100%, including by way of example only 10%, 15%, 20%, 25%, 30%, 35%, 40%, 45%, 50%, 55%, 60%, 65%, 70%, 75%, 80%, 85%, 90%, 95%, and 100%. After a suitable length of time, the normal dosing schedule is optionally reinstated.

In some embodiments, once improvement of the patient's conditions has occurred, a maintenance dose is administered if necessary. Subsequently, in specific embodiments, the dosage or the frequency of administration, or both, is reduced, as a function of the symptoms, to a level at which the improved disease, disorder or condition is retained. In certain embodiments, however, the patient requires intermittent treatment on a long-term basis upon any recurrence of symptoms.

Toxicity and therapeutic efficacy of such therapeutic regimens are determined by standard pharmaceutical procedures in cell cultures or experimental animals, including, but not limited to, the determination of the LD50 and the ED50. The dose ratio between the toxic and therapeutic effects is the therapeutic index and it is expressed as the ratio between LD50 and ED50. In certain embodiments, the data obtained from cell culture assays and animal studies are used in formulating the therapeutically effective daily dosage range and/or the therapeutically effective unit dosage amount for use in mammals, including humans. In some embodiments, the daily dosage amount of the therapeutic agent described herein lies within a range of circulating concentrations that include the ED50 with minimal toxicity. In certain embodiments, the daily dosage range and/or the unit dosage amount varies within this range depending upon the dosage form employed and the route of administration utilized.

Additional Therapeutic Agent

A therapeutic agent may be used alone or in combination with an additional therapeutic agent. In some cases, an "additional therapeutic agent" as used herein is administered alone. The therapeutic agents may be administered together or sequentially. The combination therapies may be administered within the same day, or may be administered one or more days, weeks, months, or years apart. In some cases, a therapeutic agent provided herein is administered if the subject is determined to be non-responsive to a first line of therapy, e.g., such as TNF inhibitor. Such determination may be made by treatment with the first line therapy and monitoring of disease state and/or diagnostic determination that the subject would be non-responsive to the first line therapy.

In some embodiments, the additional therapeutic agent comprises an anti-TNF therapy, e.g., an anti-TNFα therapy. In some embodiments, the additional therapeutic agent comprises a second-line treatment to an anti-TNF therapy. In some embodiments, the additional therapeutic agent comprises an immunosuppressant, or a class of drugs that suppress, or reduce, the strength of the immune system. In some embodiments, the immunosuppressant is an antibody. Non-limiting examples of immunosuppressant therapeutic agents include STELARA® (ustekinumab) azathioprine (AZA), 6-mercaptopurine (6-MP), methotrexate, cyclosporin A. (CsA).

In some embodiments, the additional therapeutic agent comprises a selective anti-inflammatory drug, or a class of drugs that specifically target pro-inflammatory molecules in the body. In some embodiments, the anti-inflammatory drug comprises an antibody. In some embodiments, the anti-inflammatory drug comprises a small molecule. Non-limiting examples of anti-inflammatory drugs include ENTYVIO (vedolizumab), corticosteroids, aminosalicylates, mesalamine, balsalazide (Colazal) and olsalazine (Dipentum).

In some embodiments, the additional therapeutic agent comprises a stem cell therapy. The stem cell therapy may be embryonic or somatic stem cells. The stem cells may be isolated from a donor (allogeneic) or isolated from the subject (autologous). The stem cells may be expanded adipose-derived stem cells (eASCs), hematopoietic stem cells (HSCs), mesenchymal stem (stromal) cells (MSCs), or induced pluripotent stem cells (iPSCs) derived from the cells of the subject. In some embodiments, the therapeutic agent comprises Cx601/Alofisel® (darvadstrocel).

In some embodiments, the additional therapeutic agent comprises a small molecule. The small molecule may be used to treat inflammatory diseases or conditions, or fibrostenonic or fibrotic disease. Non-limiting examples of small molecules include Otezla® (apremilast), alicaforsen, or ozanimod (RPC-1063).

The additional therapeutic agent may comprise an antimycotic agent. In some instances, the antimycotic agent comprises an active agent that inhibits growth of a fungus. In some instances, the antimycotic agent comprises an active agent that kills a fungus. In some embodiments, the antimycotic agent comprises polyene, an azole, an echinocandin, an flucytosine, an allylamine, a tolnaftate, or griseofulvin, or a combination thereof. In other embodiments, the azole comprises triazole, imidazole, clotrimazole, ketoconazole, itraconazole, terconazole, oxiconazole, miconazole, econazole, tioconazole, voriconazole, fluconazole, isavuconazole, itraconazole, pramiconazole, ravuconazole, or posaconazole. In some other embodiments, the polyene comprises amphotericin B, nystatin, or natamycin. In yet other embodiments, the echinocandin comprises caspofungin, anidulafungin, or micafungin. In various other embodiments, the allylamine comprises naftifine or terbinafine.

Pharmaceutical Composition

A pharmaceutical composition, as used herein, refers to a mixture of a therapeutic agent, with other chemical components (i.e. pharmaceutically acceptable inactive ingredients), such as carriers, excipients, binders, filling agents, suspending agents, flavoring agents, sweetening agents, disintegrating agents, dispersing agents, surfactants, lubricants, colorants, diluents, solubilizers, moistening agents, plasticizers, stabilizers, penetration enhancers, wetting agents, antifoaming agents, antioxidants, preservatives, or one or more combination thereof. Optionally, the compositions include two or more therapeutic agent (e.g., one or more therapeutic agents and one or more additional agents) as discussed herein. In practicing the methods of treatment or use provided herein, therapeutically effective amounts of therapeutic agents described herein are administered in a pharmaceutical composition to a mammal having a disease, disorder, or condition to be treated, e.g., an inflammatory disease, fibrostenotic disease, and/or fibrotic disease. In some embodiments, the mammal is a human. A therapeutically effective amount can vary widely depending on the severity of the disease, the age and relative health of the subject, the potency of the therapeutic agent used and other factors. The therapeutic agents can be used singly or in combination with one or more therapeutic agents as components of mixtures.

The pharmaceutical formulations described herein are administered to a subject by appropriate administration routes, including but not limited to, intravenous, intraarterial, oral, parenteral, buccal, topical, transdermal, rectal, intramuscular, subcutaneous, intraosseous, transmucosal, inhalation, or intraperitoneal administration routes. The pharmaceutical formulations described herein include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

Pharmaceutical compositions including a therapeutic agent are manufactured in a conventional manner, such as, by way of example only, by means of conventional mixing, dissolving, granulating, dragee-making, levigating, emulsifying, encapsulating, entrapping or compression processes.

The pharmaceutical compositions may include at least a therapeutic agent as an active ingredient in free-acid or free-base form, or in a pharmaceutically acceptable salt form. In addition, the methods and pharmaceutical compositions described herein include the use of N-oxides (if appropriate), crystalline forms, amorphous phases, as well as active metabolites of these compounds having the same type of activity. In some embodiments, therapeutic agents exist in unsolvated form or in solvated forms with pharmaceutically acceptable solvents such as water, ethanol, and the like. The solvated forms of the therapeutic agents are also considered to be disclosed herein.

In some embodiments, a therapeutic agent exists as a tautomer. All tautomers are included within the scope of the agents presented herein. As such, it is to be understood that a therapeutic agent or a salt thereof may exhibit the phenomenon of tautomerism whereby two chemical compounds that are capable of facile interconversion by exchanging a hydrogen atom between two atoms, to either of which it forms a covalent bond. Since the tautomeric compounds exist in mobile equilibrium with each other they may be regarded as different isomeric forms of the same compound.

In some embodiments, a therapeutic agent exists as an enantiomer, diastereomer, or other stereoisomeric form. The agents disclosed herein include all enantiomeric, diastereomeric, and epimeric forms as well as mixtures thereof.

In some embodiments, therapeutic agents described herein may be prepared as prodrugs. A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. An example, without limitation, of a prodrug would be a therapeutic agent described herein, which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid group where the peptide is metabolized to reveal the active moiety. In certain embodiments, upon in vivo administration, a prodrug is chemically converted to the biologically, pharmaceutically or therapeutically active form of the therapeutic agent. In certain embodiments, a prodrug is enzymatically metabolized by one or more steps or processes to the biologically, pharmaceutically or therapeutically active form of the therapeutic agent.

Prodrug forms of the therapeutic agents, wherein the prodrug is metabolized in vivo to produce an agent as set forth herein are included within the scope of the claims. Prodrug forms of the herein described therapeutic agents, wherein the prodrug is metabolized in vivo to produce an agent as set forth herein are included within the scope of the claims. In some cases, some of the therapeutic agents described herein may be a prodrug for another derivative or active compound. In some embodiments described herein, hydrazones are metabolized in vivo to produce a therapeutic agent.

In certain embodiments, compositions provided herein include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

In some embodiments, formulations described herein benefit from antioxidants, metal chelating agents, thiol containing compounds and other general stabilizing agents. Examples of such stabilizing agents, include, but are not limited to: (a) about 0.5% to about 2% w/v glycerol, (b) about 0.10% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (1) pentosan polysulfate and other heparinoids, (m) divalent cations such as magnesium and zinc; or (n) combinations thereof.

The pharmaceutical compositions described herein are formulated into any suitable dosage form, including but not limited to, aqueous oral dispersions, liquids, gels, syrups, elixirs, slurries, suspensions, solid oral dosage forms, aerosols, controlled release formulations, fast melt formulations, effervescent formulations, lyophilized formulations, tablets, powders, pills, dragees, capsules, delayed release formulations, extended release formulations, pulsatile release formulations, multiparticulate formulations, and mixed immediate release and controlled release formulations. In one aspect, a therapeutic agent as discussed herein, e.g., therapeutic agent is formulated into a pharmaceutical composition suitable for intramuscular, subcutaneous, or intravenous injection. In one aspect, formulations suitable for intramuscular, subcutaneous, or intravenous injection include physiologically acceptable sterile aqueous or non-aqueous solutions, dispersions, suspensions or emulsions, and sterile powders for reconstitution into sterile injectable solutions or dispersions. Examples of suitable aqueous and non-aqueous carriers, diluents, solvents, or vehicles include water, ethanol, polyols (propyleneglycol, polyethylene-glycol, glycerol, cremophor and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants. In some embodiments, formulations suitable for subcutaneous injection also contain additives such as preserving, wetting, emulsifying, and dispensing agents. Prevention of the growth of microorganisms can be ensured by various antibacterial and antifungal agents, such as parabens, chlorobutanol, phenol, sorbic acid, and the like. In some cases it is desirable to include isotonic agents, such as sugars, sodium chloride, and the like. Prolonged absorption of the injectable pharmaceutical form can be brought about by the use of agents delaying absorption, such as aluminum monostearate and gelatin.

For intravenous injections or drips or infusions, a therapeutic agent described herein is formulated in aqueous solutions, preferably in physiologically compatible buffers such as Hank's solution, Ringer's solution, or physiological saline buffer. For transmucosal administration, penetrants appropriate to the barrier to be permeated are used in the formulation. Such penetrants are generally known in the art. For other parenteral injections, appropriate formulations include aqueous or nonaqueous solutions, preferably with physiologically compatible buffers or excipients. Such excipients are known.

Parenteral injections may involve bolus injection or continuous infusion. Formulations for injection may be presented in unit dosage form, e.g., in ampoules or in multi dose containers, with an added preservative. The pharmaceutical composition described herein may be in a form suitable for parenteral injection as a sterile suspensions, solutions or emulsions in oily or aqueous vehicles, and may contain formulatory agents such as suspending, stabilizing and/or dispersing agents. In one aspect, the active ingredient is in powder form for constitution with a suitable vehicle, e.g., sterile pyrogen-free water, before use.

For administration by inhalation, a therapeutic agent is formulated for use as an aerosol, a mist or a powder. Pharmaceutical compositions described herein are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Capsules and cartridges of, such as, by way of example only, gelatin for use in an inhaler or insufflator may be formulated containing a powder mix of the therapeutic agent described herein and a suitable powder base such as lactose or starch.

Representative intranasal formulations are described in, for example, U.S. Pat. Nos. 4,476,116, 5,116,817 and 6,391,452. Formulations that include a therapeutic agent are prepared as solutions in saline, employing benzyl alcohol or other suitable preservatives, fluorocarbons, and/or other solubilizing or dispersing agents known in the art. See, for example, Ansel, H. C. et al., Pharmaceutical Dosage Forms and Drug Delivery Systems, Sixth Ed. (1995). Preferably these compositions and formulations are prepared with suitable nontoxic pharmaceutically acceptable ingredients. These ingredients are known to those skilled in the preparation of nasal dosage forms and some of these can be found in REMINGTON: THE SCIENCE AND PRACTICE OF PHARMACY, 21st edition, 2005. The choice of suitable carriers is dependent upon the exact nature of the nasal dosage form desired, e.g., solutions, suspensions, ointments, or gels. Nasal dosage forms generally contain large amounts of water in addition to the active ingredient. Minor amounts of other ingredients such as pH adjusters, emulsifiers or dispersing agents, preservatives, surfactants, gelling agents, or buffering and other stabilizing and solubilizing agents are optionally present. Preferably, the nasal dosage form should be isotonic with nasal secretions.

Pharmaceutical preparations for oral use are obtained by mixing one or more solid excipient with one or more of the therapeutic agents described herein, optionally grinding the resulting mixture, and processing the mixture of granules, after adding suitable auxiliaries, if desired, to obtain tablets or dragee cores. Suitable excipients include, for example, fillers such as sugars, including lactose, sucrose, mannitol, or sorbitol; cellulose preparations such as, for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. If desired, disintegrating agents are added, such as the cross linked croscarmellose sodium, polyvinylpyrrolidone, agar, or alginic acid or a salt thereof such as sodium alginate. In some embodiments, dyestuffs or pigments are added to the tablets or dragee coatings for identification or to characterize different combinations of active therapeutic agent doses.

In some embodiments, pharmaceutical formulations of a therapeutic agent are in the form of a capsules, including push fit capsules made of gelatin, as well as soft, sealed capsules made of gelatin and a plasticizer, such as glycerol or sorbitol. The push fit capsules contain the active ingredients in admixture with filler such as lactose, binders such as starches, and/or lubricants such as talc or magnesium stearate and, optionally, stabilizers. In soft capsules, the active therapeutic agent is dissolved or suspended in suitable liquids, such as fatty oils, liquid paraffin, or liquid polyethylene glycols. In some embodiments, stabilizers are added. A capsule may be prepared, for example, by placing the bulk blend of the formulation of the therapeutic agent inside of a capsule. In some embodiments, the formulations (non-aqueous suspensions and solutions) are placed in a soft gelatin capsule. In other embodiments, the formulations are placed in standard gelatin capsules or non-gelatin capsules such as capsules comprising HPMC. In other embodiments, the formulation is placed in a sprinkle capsule, wherein the capsule is swallowed whole or the capsule is opened and the contents sprinkled on food prior to eating.

All formulations for oral administration are in dosages suitable for such administration. In one aspect, solid oral dosage forms are prepared by mixing a therapeutic agent with one or more of the following: antioxidants, flavoring agents, and carrier materials such as binders, suspending agents, disintegration agents, filling agents, surfactants, solubilizers, stabilizers, lubricants, wetting agents, and diluents. In some embodiments, the solid dosage forms disclosed herein are in the form of a tablet, (including a suspension tablet, a fast-melt tablet, a bite-disintegration tablet, a rapid-disintegration tablet, an effervescent tablet, or a caplet), a pill, a powder, a capsule, solid dispersion, solid solution, bioerodible dosage form, controlled release formulations, pulsatile release dosage forms, multiparticulate dosage forms, beads, pellets, granules. In other embodiments, the pharmaceutical formulation is in the form of a powder. Compressed tablets are solid dosage forms prepared by compacting the bulk blend of the formulations described above. In various embodiments, tablets will include one or more flavoring agents. In other embodiments, the tablets will include a film surrounding the final compressed tablet. In some embodiments, the film coating can provide a delayed release of a therapeutic agent from the formulation. In other embodiments, the film coating aids in patient compliance (e.g., Opadry® (coatings or sugar coating)). Film coatings including Opadry® (coatings or sugar coating) typically range from about 1% to about 3% of the tablet weight. In some embodiments, solid dosage forms, e.g., tablets, effervescent tablets, and capsules, are prepared by mixing particles of a therapeutic agent with one or more pharmaceutical excipients to form a bulk blend composition. The bulk blend is readily subdivided into equally effective unit dosage forms, such as tablets, pills, and capsules. In some embodiments, the individual unit dosages include film coatings. These formulations are manufactured by conventional formulation techniques.

In another aspect, dosage forms include microencapsulated formulations. In some embodiments, one or more other compatible materials are present in the microencapsulation material. Exemplary materials include, but are not limited to, pH modifiers, erosion facilitators, anti-foaming agents, antioxidants, flavoring agents, and carrier materials such as binders, suspending agents, disintegration agents, filling agents, surfactants, solubilizers, stabilizers, lubricants, wetting agents, and diluents. Exemplary useful microencapsulation materials include, but are not limited to, hydroxypropyl cellulose ethers (HPC) such as Klucel® (hydroxypropyl cellulose) or Nisso HPC, low-substituted hydroxypropyl cellulose ethers (L-HPC), hydroxypropyl methyl cellulose ethers (HPMC) such as Seppifilm-LC, Pharmacoat® (hydroxypropyl methylcellulose), Metolose® (cellulose ether) SR, Methocel®-E, Opadry® (coatings or sugar coating) YS, PrimaFlo, Benecel MP824, and Benecel MP843, methylcellulose polymers such as Methocel®-A, hydroxypropylmethylcellulose acetate stearate Aqoat (HF-LS, HF-LG, HF-MS) and Metolose® (cellulose ether), Ethylcelluloses (EC) and mixtures thereof such as E461 (cellulose ethers), Ethocel® (cellulose ether), Aqualon®-EC (ether-based ethyl cellulose), Surelease® (aqueous ethylcellulose dispersion), Polyvinyl alcohol (PVA) such as Opadry® (coatings or sugar coating) AMB, hydroxyethylcelluloses such as Natrosol® (hydroxyethyl cellulose), carboxymethylcelluloses and salts of carboxymethylcelluloses (CMC) such as Aqualon®-CMC (ether-based ethyl cellulose), polyvinyl alcohol and polyethylene glycol co-polymers such as Kollicoat IR® (polyethylene glycol-polyvinyl alcohol graft copolymer), monoglycerides (Myverol), triglycerides (KLX), polyethylene glycols, modified food starch, acrylic polymers and mixtures of acrylic polymers with cellulose ethers such as Eudragit® (polymethacrylate-based copolymers) (e.g., Eudragit® EPO, Eudragit® L30D-55, Eudragit® FS 30D Eudragit® L100-55, Eudragit® L100, Eudragit® S100, Eudragit® RD100, Eudragit® E100, Eudragit® L12.5, Eudragit® S12.5, Eudragit® NE30D, and Eudragit® NE 40D), cellulose acetate phthalate, sepifilms such as mixtures of HPMC and stearic acid, cyclodextrins, and mixtures of these materials.

Liquid formulation dosage forms for oral administration are optionally aqueous suspensions selected from the group including, but not limited to, pharmaceutically acceptable aqueous oral dispersions, emulsions, solutions, elixirs, gels, and syrups. See, e.g., Singh et al., Encyclopedia of Pharmaceutical Technology, 2nd Ed., pp. 754-757 (2002). In addition to therapeutic agent the liquid dosage forms optionally include additives, such as: (a) disintegrating agents; (b) dispersing agents; (c) wetting agents; (d) at least one preservative, (e) viscosity enhancing agents, (f) at least one sweetening agent, and (g) at least one flavoring agent. In some embodiments, the aqueous dispersions further includes a crystal-forming inhibitor.

In some embodiments, the pharmaceutical formulations described herein are self-emulsifying drug delivery systems (SEDDS). Emulsions are dispersions of one immiscible phase in another, usually in the form of droplets. Generally, emulsions are created by vigorous mechanical dispersion. SEDDS, as opposed to emulsions or microemulsions, spontaneously form emulsions when added to an excess of water without any external mechanical dispersion or agitation. An advantage of SEDDS is that only gentle mixing is required to distribute the droplets throughout the solution. Additionally, water or the aqueous phase is optionally added just prior to administration, which ensures stability of an unstable or hydrophobic active ingredient. Thus, the SEDDS provides an effective delivery system for oral and parenteral delivery of hydrophobic active ingredients. In some embodiments, SEDDS provides improvements in the bioavailability of hydrophobic active ingredients. Methods of producing self-emulsifying dosage forms include, but are not limited to, for example, U.S. Pat. Nos. 5,858,401, 6,667,048, and 6,960,563.

Buccal formulations that include a therapeutic agent are administered using a variety of formulations known in the art. For example, such formulations include, but are not limited to, U.S. Pat. Nos. 4,229,447, 4,596,795, 4,755,386, and 5,739,136. In addition, the buccal dosage forms described herein can further include a bioerodible (hydrolysable) polymeric carrier that also serves to adhere the dosage form to the buccal mucosa. For buccal or sublingual administration, the compositions may take the form of tablets, lozenges, or gels formulated in a conventional manner.

For intravenous injections, a therapeutic agent is optionally formulated in aqueous solutions, preferably in physiologically compatible buffers such as Hank's solution, Ringer's solution, or physiological saline buffer. For transmucosal administration, penetrants appropriate to the barrier to be permeated are used in the formulation. For other parenteral injections, appropriate formulations include aqueous or nonaqueous solutions, preferably with physiologically compatible buffers or excipients.

Parenteral injections optionally involve bolus injection or continuous infusion. Formulations for injection are optionally presented in unit dosage form, e.g., in ampoules or in multi dose containers, with an added preservative. In some embodiments, a pharmaceutical composition described herein is in a form suitable for parenteral injection as a sterile suspensions, solutions or emulsions in oily or aqueous vehicles, and contain formulatory agents such as suspending, stabilizing and/or dispersing agents. Pharmaceutical formulations for parenteral administration include aqueous solutions of an agent that modulates the activity of a carotid body in water soluble form. Additionally, suspensions of an agent that modulates the activity of a carotid body are optionally prepared as appropriate, e.g., oily injection suspensions.

Conventional formulation techniques include, e.g., one or a combination of methods: (1) dry mixing, (2) direct compression, (3) milling, (4) dry or non-aqueous granulation, (5) wet granulation, or (6) fusion. Other methods include, e.g., spray drying, pan coating, melt granulation, granulation, fluidized bed spray drying or coating (e.g., wurster coating), tangential coating, top spraying, tableting, extruding and the like.

Suitable carriers for use in the solid dosage forms described herein include, but are not limited to, acacia, gelatin, colloidal silicon dioxide, calcium glycerophosphate, calcium lactate, maltodextrin, glycerine, magnesium silicate, sodium caseinate, soy lecithin, sodium chloride, tricalcium phosphate, dipotassium phosphate, sodium stearoyl lactylate, carrageenan, monoglyceride, diglyceride, pregelatinized starch, hydroxypropylmethylcellulose, hydroxypropylmethylcellulose acetate stearate, sucrose, microcrystalline cellulose, lactose, mannitol and the like.

Suitable filling agents for use in the solid dosage forms described herein include, but are not limited to, lactose, calcium carbonate, calcium phosphate, dibasic calcium phosphate, calcium sulfate, microcrystalline cellulose, cellulose powder, dextrose, dextrates, dextran, starches, pregelatinized starch, hydroxypropylmethycellulose (HPMC), hydroxypropylmethycellulose phthalate, hydroxypropylmethylcellulose acetate stearate (HPMCAS), sucrose, xylitol, lactitol, mannitol, sorbitol, sodium chloride, polyethylene glycol, and the like.

Suitable disintegrants for use in the solid dosage forms described herein include, but are not limited to, natural starch such as corn starch or potato starch, a pregelatinized starch, or sodium starch glycolate, a cellulose such as methylcrystalline cellulose, methylcellulose, microcrystalline cellulose, croscarmellose, or a cross-linked cellulose, such as cross-linked sodium carboxymethylcellulose, cross-linked carboxymethylcellulose, or cross-linked croscarmellose, a cross-linked starch such as sodium starch glycolate, a cross-linked polymer such as crospovidone, a cross-linked polyvinylpyrrolidone, alginate such as alginic acid or a salt of alginic acid such as sodium alginate, a gum such as agar, guar, locust bean, Karaya, pectin, or tragacanth, sodium starch glycolate, bentonite, sodium lauryl sulfate, sodium lauryl sulfate in combination starch, and the like.

Binders impart cohesiveness to solid oral dosage form formulations: for powder filled capsule formulation, they aid in plug formation that can be filled into soft or hard shell capsules and for tablet formulation, they ensure the tablet remaining intact after compression and help assure blend uniformity prior to a compression or fill step. Materials suitable for use as binders in the solid dosage forms described herein include, but are not limited to, carboxymethylcellulose, methylcellulose, hydroxypropylmethylcellulose, hydroxypropylmethylcellulose acetate stearate, hydroxyethylcellulose, hydroxypropylcellulose, ethylcellulose, and microcrystalline cellulose, microcrystalline dextrose, amylose, magnesium aluminum silicate, polysaccharide acids, bentonites, gelatin, polyvinylpyrrolidone/vinyl acetate copolymer, crospovidone, povidone, starch, pregelatinized starch, tragacanth, dextrin, a sugar, such as sucrose, glucose, dextrose, molasses, mannitol, sorbitol, xylitol, lactose, a natural or synthetic gum such as acacia, tragacanth, ghatti gum, mucilage of isapol husks, starch, polyvinylpyrrolidone, larch arabogalactan, polyethylene glycol, waxes, sodium alginate, and the like.

In general, binder levels of 20-70% are used in powder-filled gelatin capsule formulations. Binder usage level in tablet formulations varies whether direct compression, wet granulation, roller compaction, or usage of other excipients such as fillers which itself can act as moderate binder. Binder levels of up to 70% in tablet formulations is common.

Suitable lubricants or glidants for use in the solid dosage forms described herein include, but are not limited to, stearic acid, calcium hydroxide, talc, corn starch, sodium stearyl fumerate, alkali-metal and alkaline earth metal salts, such as aluminum, calcium, magnesium, zinc, stearic acid, sodium stearates, magnesium stearate, zinc stearate, waxes, Stearowet®, boric acid, sodium benzoate, sodium acetate, sodium chloride, leucine, a polyethylene glycol or a methoxypolyethylene glycol such as Carbowax™ (polyethylene glycol), PEG 4000, PEG 5000, PEG 6000, propylene glycol, sodium oleate, glyceryl behenate, glyceryl palmitostearate, glyceryl benzoate, magnesium or sodium lauryl sulfate, and the like.

Suitable diluents for use in the solid dosage forms described herein include, but are not limited to, sugars (including lactose, sucrose, and dextrose), polysaccharides (including dextrates and maltodextrin), polyols (including mannitol, xylitol, and sorbitol), cyclodextrins and the like.

Suitable wetting agents for use in the solid dosage forms described herein include, for example, oleic acid, glyceryl monostearate, sorbitan monooleate, sorbitan monolaurate, triethanolamine oleate, polyoxyethylene sorbitan monooleate, polyoxyethylene sorbitan monolaurate, quaternary ammonium compounds (e.g., Polyquat 10® (polyquaternium-10)), sodium oleate, sodium lauryl sulfate, magnesium stearate, sodium docusate, triacetin, vitamin E TPGS and the like.

Suitable surfactants for use in the solid dosage forms described herein include, for example, sodium lauryl sulfate, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF Enzymes, LLC), and the like.

Suitable suspending agents for use in the solid dosage forms described here include, but are not limited to, polyvinylpyrrolidone, e.g., polyvinylpyrrolidone K12, polyvinylpyrrolidone K17, polyvinylpyrrolidone K25, or polyvinylpyrrolidone K30, polyethylene glycol, e.g., the polyethylene glycol can have a molecular weight of about 300 to about 6000, or about 3350 to about 4000, or about 7000 to about 5400, vinyl pyrrolidone/vinyl acetate copolymer (S630), sodium carboxymethylcellulose, methylcellulose, hydroxy-propylmethylcellulose, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like.

Suitable antioxidants for use in the solid dosage forms described herein include, for example, e.g., butylated hydroxytoluene (BHT), sodium ascorbate, and tocopherol.

It should be appreciated that there is considerable overlap between additives used in the solid dosage forms described herein. Thus, the above-listed additives should be taken as merely exemplary, and not limiting, of the types of additives that can be included in solid dosage forms of the pharmaceutical compositions described herein. The amounts of such additives can be readily determined by one skilled in the art, according to the particular properties desired.

In various embodiments, the particles of a therapeutic agents and one or more excipients are dry blended and compressed into a mass, such as a tablet, having a hardness sufficient to provide a pharmaceutical composition that substantially disintegrates within less than about 30 minutes, less than about 35 minutes, less than about 40 minutes, less than about 45 minutes, less than about 50 minutes, less than about 55 minutes, or less than about 60 minutes, after oral administration, thereby releasing the formulation into the gastrointestinal fluid.

In other embodiments, a powder including a therapeutic agent is formulated to include one or more pharmaceutical excipients and flavors. Such a powder is prepared, for example, by mixing the therapeutic agent and optional pharmaceutical excipients to form a bulk blend composition. Additional embodiments also include a suspending agent and/or a wetting agent. This bulk blend is uniformly subdivided into unit dosage packaging or multi-dosage packaging units.

In still other embodiments, effervescent powders are also prepared. Effervescent salts have been used to disperse medicines in water for oral administration.

In some embodiments, the pharmaceutical dosage forms are formulated to provide a controlled release of a therapeutic agent. Controlled release refers to the release of the therapeutic agent from a dosage form in which it is incorporated according to a desired profile over an extended period of time. Controlled release profiles include, for example, sustained release, prolonged release, pulsatile release, and delayed release profiles. In contrast to immediate release compositions, controlled release compositions allow delivery of an agent to a subject over an extended period of time according to a predetermined profile. Such release rates can provide therapeutically effective levels of agent for an extended period of time and thereby provide a longer period of pharmacologic response while minimizing side effects as compared to conventional rapid release dosage forms. Such longer periods of response provide for many inherent benefits that are not achieved with the corresponding short acting, immediate release preparations.

In some embodiments, the solid dosage forms described herein are formulated as enteric coated delayed release oral dosage forms, i.e., as an oral dosage form of a pharmaceutical composition as described herein which utilizes an enteric coating to affect release in the small intestine or large intestine. In one aspect, the enteric coated dosage form is a compressed or molded or extruded tablet/mold (coated or uncoated) containing granules, powder, pellets, beads or particles of the active ingredient and/or other composition components, which are themselves coated or uncoated. In one aspect, the enteric coated oral dosage form is in the form of a capsule containing pellets, beads or granules, which include a therapeutic agent that are coated or uncoated.

Any coatings should be applied to a sufficient thickness such that the entire coating does not dissolve in the gastrointestinal fluids at pH below about 5, but does dissolve at pH about 5 and above. Coatings are typically selected from any of the following: Shellac—this coating dissolves in media of pH>7; Acrylic polymers—examples of suitable acrylic polymers include methacrylic acid copolymers and ammonium methacrylate copolymers. The Eudragit® (polymethacrylate-based copolymers) series E, L, S, RL, RS and NE (Rohm Pharma) are available as solubilized in organic solvent, aqueous dispersion, or dry powders. The Eudragit® (polymethacrylate-based copolymers) series RL, NE, and RS are insoluble in the gastrointestinal tract but are permeable and are used primarily for colonic targeting. The Eudragit® (polymethacrylate-based copolymers) series E dissolve in the stomach. The Eudragit® (polymethacrylate-based copolymers) series L, L-30D and S are insoluble in stomach and dissolve in the intestine; Poly Vinyl Acetate Phthalate (PVAP)—PVAP dissolves in pH >5, and it is much less permeable to water vapor and gastric fluids. Conventional coating techniques such as spray or pan coating are employed to apply coatings. The coating thickness must be sufficient to ensure that the oral dosage form remains intact until the desired site of topical delivery in the intestinal tract is reached.

In other embodiments, the formulations described herein are delivered using a pulsatile dosage form. A pulsatile dosage form is capable of providing one or more immediate release pulses at predetermined time points after a controlled lag time or at specific sites. Exemplary pulsatile dosage forms and methods of their manufacture are disclosed in U.S. Pat. Nos. 5,011,692, 5,017,381, 5,229,135, 5,840,329 and 5,837,284. In one embodiment, the pulsatile dosage form includes at least two groups of particles, (i.e. multiparticulate) each containing the formulation described herein. The first group of particles provides a substantially immediate dose of a therapeutic agent upon ingestion by a mammal. The first group of particles can be either uncoated or include a coating and/or sealant. In one aspect, the second group of particles comprises coated particles. The coating on the second group of particles provides a delay of from about 2 hours to about 7 hours following ingestion before release of the second dose. Suitable coatings for pharmaceutical compositions are described herein or known in the art.

In some embodiments, pharmaceutical formulations are provided that include particles of a therapeutic agent and at least one dispersing agent or suspending agent for oral administration to a subject. The formulations may be a powder and/or granules for suspension, and upon admixture with water, a substantially uniform suspension is obtained.

In some embodiments, particles formulated for controlled release are incorporated in a gel or a patch or a wound dressing.

In one aspect, liquid formulation dosage forms for oral administration and/or for topical administration as a wash are in the form of aqueous suspensions selected from the group including, but not limited to, pharmaceutically acceptable aqueous oral dispersions, emulsions, solutions, elixirs, gels, and syrups. See, e.g., Singh et al., Encyclopedia of Pharmaceutical Technology, 2nd Ed., pp. 754-757 (2002). In addition to the particles of a therapeutic agent, the liquid dosage forms include additives, such as: (a) disintegrating agents; (b) dispersing agents; (c) wetting agents; (d) at least one preservative, (e) viscosity enhancing agents, (f) at least one sweetening agent, and (g) at least one flavoring agent. In some embodiments, the aqueous dispersions can further include a crystalline inhibitor.

In some embodiments, the liquid formulations also include inert diluents commonly used in the art, such as water or other solvents, solubilizing agents, and emulsifiers. Exemplary emulsifiers are ethyl alcohol, isopropyl alcohol, ethyl carbonate, ethyl acetate, benzyl alcohol, benzyl benzoate, propyleneglycol, 1,3-butyleneglycol, dimethylformamide, sodium lauryl sulfate, sodium doccusate, cholesterol, cholesterol esters, taurocholic acid, phosphotidylcholine, oils, such as cottonseed oil, groundnut oil, corn germ oil, olive oil, castor oil, and sesame oil, glycerol, tetrahydrofurfuryl alcohol, polyethylene glycols, fatty acid esters of sorbitan, or mixtures of these substances, and the like.

Furthermore, pharmaceutical compositions optionally include one or more pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

Additionally, pharmaceutical compositions optionally include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

Other pharmaceutical compositions optionally include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

In one embodiment, the aqueous suspensions and dispersions described herein remain in a homogenous state, as defined in The USP Pharmacists' Pharmacopeia (2005 edition, chapter 905), for at least 4 hours. In one embodiment, an aqueous suspension is re-suspended into a homogenous suspension by physical agitation lasting less than 1 minute. In still another embodiment, no agitation is necessary to maintain a homogeneous aqueous dispersion.

Examples of disintegrating agents for use in the aqueous suspensions and dispersions include, but are not limited to, a starch, e.g., a natural starch such as corn starch or potato starch, a pregelatinized starch, or sodium starch glycolate; a cellulose such as methylcrystalline cellulose, methylcellulose, croscarmellose, or a cross-linked cellulose, such as cross-linked sodium carboxymethylcellulose, cross-linked carboxymethylcellulose, or cross-linked croscarmellose; a cross-linked starch such as sodium starch glycolate; a cross-linked polymer such as crospovidone; a cross-linked polyvinylpyrrolidone; alginate such as alginic acid or a salt of alginic acid such as sodium alginate; a gum such as agar, guar, locust bean, Karaya, pectin, or tragacanth; sodium starch glycolate; bentonite; a natural sponge; a surfactant; a resin such as a cation-exchange resin; citrus pulp; sodium lauryl sulfate; sodium lauryl sulfate in combination starch; and the like.

In some embodiments, the dispersing agents suitable for the aqueous suspensions and dispersions described herein include, for example, hydrophilic polymers, electrolytes, Tween® 60 or 80 (viscous liquid), PEG, polyvinylpyrrolidone, and the carbohydrate-based dispersing agents such as, for example, hydroxypropylcellulose and hydroxypropyl cellulose ethers, hydroxypropyl methylcellulose and hydroxypropyl methylcellulose ethers, carboxymethylcellulose sodium, methylcellulose, hydroxyethylcellulose, hydroxypropylmethyl-cellulose phthalate, hydroxypropylmethyl-cellulose acetate stearate, noncrystalline cellulose, magnesium aluminum silicate, triethanolamine, polyvinyl alcohol (PVA), polyvinylpyrrolidone/vinyl acetate copolymer, 4-(1,1,3,3-tetramethylbutyl)-phenol polymer with ethylene oxide and formaldehyde (also known as tyloxapol), poloxamers; and poloxamines. In other embodiments, the dispersing agent is selected from a group not comprising one of the following agents: hydrophilic polymers; electrolytes; Tween® 60 or 80 (viscous liquid); PEG; polyvinylpyrrolidone (PVP); hydroxypropylcellulose and hydroxypropyl cellulose ethers; hydroxypropyl methylcellulose and hydroxypropyl methylcellulose ethers; carboxymethylcellulose sodium; methylcellulose; hydroxyethylcellulose; hydroxypropylmethyl-cellulose phthalate; hydroxypropylmethyl-cellulose acetate stearate; non-crystalline cellulose; magnesium aluminum silicate; triethanolamine; polyvinyl alcohol (PVA); 4-(1,1,3,3-tetramethylbutyl)-phenol polymer with ethylene oxide and formaldehyde; poloxamers; or poloxamines.

Wetting agents suitable for the aqueous suspensions and dispersions described herein include, but are not limited to, cetyl alcohol, glycerol monostearate, polyoxyethylene sorbitan fatty acid esters (e.g., the commercially available Tweens® (viscous liquid) such as e.g., Tween 20® and Tween 80®, and polyethylene glycols, oleic acid, glyceryl monostearate, sorbitan monooleate, sorbitan monolaurate, triethanolamine oleate, polyoxyethylene sorbitan monooleate, polyoxyethylene sorbitan monolaurate, sodium oleate, sodium lauryl sulfate, sodium docusate, triacetin, vitamin E TPGS, sodium taurocholate, simethicone, phosphotidylcholine and the like.

Suitable preservatives for the aqueous suspensions or dispersions described herein include, for example, potassium sorbate, parabens (e.g., methylparaben and propylparaben), benzoic acid and its salts, other esters of parahydroxybenzoic acid such as butylparaben, alcohols such as ethyl alcohol or benzyl alcohol, phenolic compounds such as phenol, or quaternary compounds such as benzalkonium chloride. Preservatives, as used herein, are incorporated into the dosage form at a concentration sufficient to inhibit microbial growth.

Suitable viscosity enhancing agents for the aqueous suspensions or dispersions described herein include, but are not limited to, methyl cellulose, xanthan gum, carboxymethyl cellulose, hydroxypropyl cellulose, hydroxypropylmethyl cellulose, Plasdon® S-630 (copovidone), carbomer, polyvinyl alcohol, alginates, acacia, chitosans and combinations thereof. The concentration of the viscosity enhancing agent will depend upon the agent selected and the viscosity desired.

Examples of sweetening agents suitable for the aqueous suspensions or dispersions described herein include, for example, acacia syrup, acesulfame K, alitame, aspartame, chocolate, cinnamon, citrus, cocoa, cyclamate, dextrose, fructose, ginger, glycyrrhetinate, *glycyrrhiza* (licorice) syrup, monoammonium glyrrhizinate (MagnaSweet®), malitol, mannitol, menthol, neohesperidine DC, neotame, Prosweet® Powder (flavor masking systems), saccharin, sorbitol, *stevia*, sucralose, sucrose, sodium saccharin, saccharin, aspartame, acesulfame potassium, mannitol, sucralose, tagatose, thaumatin, vanilla, xylitol, or any combination thereof.

In some embodiments, a therapeutic agent is prepared as transdermal dosage form. In some embodiments, the transdermal formulations described herein include at least three components: (1) a therapeutic agent; (2) a penetration enhancer; and (3) an optional aqueous adjuvant. In some embodiments the transdermal formulations include additional components such as, but not limited to, gelling agents, creams and ointment bases, and the like. In some embodiments, the transdermal formulation is presented as a patch or a wound dressing. In some embodiments, the transdermal formulation further include a woven or non-woven backing material to enhance absorption and prevent the removal of the transdermal formulation from the skin. In other embodiments, the transdermal formulations described herein can maintain a saturated or supersaturated state to promote diffusion into the skin.

In one aspect, formulations suitable for transdermal administration of a therapeutic agent described herein employ transdermal delivery devices and transdermal delivery patches and can be lipophilic emulsions or buffered, aqueous solutions, dissolved and/or dispersed in a polymer or an adhesive. In one aspect, such patches are constructed for continuous, pulsatile, or on demand delivery of pharmaceutical agents. Still further, transdermal delivery of the therapeutic agents described herein can be accomplished by means of iontophoretic patches and the like. In one aspect, transdermal patches provide controlled delivery of a therapeutic agent. In one aspect, transdermal devices are in the form of a bandage comprising a backing member, a reservoir containing the therapeutic agent optionally with carriers, optionally a rate controlling barrier to deliver the therapeutic agent to the skin of the host at a controlled and predetermined rate over a prolonged period of time, and means to secure the device to the skin.

In further embodiments, topical formulations include gel formulations (e.g., gel patches which adhere to the skin). In some of such embodiments, a gel composition includes any polymer that forms a gel upon contact with the body (e.g., gel formulations comprising hyaluronic acid, pluronic polymers, poly(lactic-co-glycolic acid (PLGA)-based polymers or the like). In some forms of the compositions, the formulation comprises a low-melting wax such as, but not limited to, a mixture of fatty acid glycerides, optionally in combination with cocoa butter which is first melted. Optionally, the formulations further comprise a moisturizing agent.

In certain embodiments, delivery systems for pharmaceutical therapeutic agents may be employed, such as, for example, liposomes and emulsions. In certain embodiments, compositions provided herein can also include an mucoadhesive polymer, selected from among, for example, carboxymethylcellulose, carbomer (acrylic acid polymer), poly (methylmethacrylate), polyacrylamide, polycarbophil, acrylic acid/butyl acrylate copolymer, sodium alginate and dextran.

In some embodiments, a therapeutic agent described herein may be administered topically and can be formulated into a variety of topically administrable compositions, such as solutions, suspensions, lotions, gels, pastes, medicated sticks, balms, creams or ointments. Such pharmaceutical therapeutic agents can contain solubilizers, stabilizers, tonicity enhancing agents, buffers and preservatives.

Numbered Embodiments

Disclosed herein, in some embodiments, are the following:

1. A method of identifying a risk of developing a disease or condition in a subject, the method comprising:
   a. providing a sample obtained from a subject;
   b. analyzing the sample to detect a presence or the absence of a genotype in the sample; and
   c. identifying a risk of developing a disease or condition in the subject, provided the presence of the genotype is detected in the sample obtained from the subject.
2. The method of embodiment 1, wherein the disease or condition is selected from the group consisting of Crohn's disease (CD), ulcerative colitis (UC), and inflammatory bowel disease (IBD).
3. The method of embodiment 2, wherein, the CD is a severe form of CD characterized by a subclinical phenotype selected from the group consisting of stricturing disease, internal penetrating disease, and stricturing and internal penetrating disease.
4. The method of embodiments 1-3, wherein the subject is human.
5. The method of embodiment 1, further comprising:
   a. treating or preventing the disease or condition in the subject comprising administering to the subject a therapeutically effective amount of a therapeutic agent.
6. The method of embodiment 5, further comprising treating or preventing the disease or condition in the subject comprising administering to the subject a therapeutically effective amount of an additional therapeutic agent.
7. The method of embodiment 5, further comprising prescribing to the subject a therapeutically effective amount of at least one of a therapeutic agent and an additional therapeutic agent.
8. The method of embodiments 5-7, wherein the therapeutic agent is a modulator of a gene or gene expression product expressed from the gene involved in prolactin signaling.
9. The method of embodiment 8, wherein the gene is selected from the group consisting of Interferon Regulatory Factor 1 (IRF1), Klotho Beta (KLB), Mitogen-Activated Protein Kinase Kinase 1 (MAP2K1), Nuclear Receptor Subfamily 3 Group C Member 1 (NR3C1), Protein Kinase C Beta (PRKCB), Protein Kinase C Epsilon (PRKCE), Protein Kinase C Gamma (PRKCG), Protein Kinase C Eta (PRKCH), Protein Kinase C Theta (PRKCQ), Prolactin Receptor (PRLR), Protein Tyrosine Phosphatase, Non-Receptor Type 11 (PTPN11), Signal Transducer And Activator Of Transcription 1 (STAT1), Signal Transducer And Activator Of Transcription 5A (STAT5A), and Signal Transducer And Activator Of Transcription 5B (STAT5B).
10. The method of embodiments 5-7, wherein the therapeutic agent is a modulator of a gene or gene expression product expressed from the gene involved in autophagy.
11. The method of embodiment 10, wherein the gene is selected from the group consisting of Autophagy Related 10 (ATG10), Autophagy Related 16 Like 1 (ATG16L1), Autophagy Related 4A Cysteine Peptidase (ATG4A), Autophagy Related 4C Cysteine Peptidase (ATG4C), Cathepsin H (CTSH), Sequestosome 1

(SQSTM1), Unc-51 Like Autophagy Activating Kinase 1 (ULK1), and WD Repeat And FYVE Domain Containing 3 (WDFY3).

12. The method of embodiments 5-7, wherein the therapeutic agent is a modulator of Janus Kinase 1 (JAK1).
13. The method of embodiments 5-7, wherein the therapeutic agent is a modulator of Tumor Necrosis Factor Ligand 1A (TL1A).
14. The method of embodiments 1-13, wherein the genotype comprises a polymorphism provided in Table 1, or a polymorphism in linkage disequilibrium (LD) therewith.
15. The method of embodiment 14, wherein LD is defined by an $r^2$ value of at least about 0.70, 0.75, 0.80, 0.85, 0.90, 0.95, 0.96, 0.97, 0.98, 0.99, or 1.0.
16. The method of embodiment 15, wherein the LD is defined by $r^2$ value of between 0.85-0.90, 0.90-0.95, and 0.95-1.0.
17. The method of embodiments 14-16, wherein genotype comprises at least 2, 3, 4, 5, 6, 7, 8, 9, 10, 11, 12, 13, 14, 15, 16, 17, 18, 19, 20, 21, 22, 23, 24, 25, 26, 27, 28, 29, 30, or more polymorphisms provided in Table 1.
18. The method of embodiments 1-17, wherein analyzing the sample to detect the presence or the absence of a genotype in the sample of step (b) comprises:
    a. contacting a nucleic acid sequence that is capable of hybridizing to the genotype to the sample; and
    b. detecting binding between the nucleic acid sequence and the genotype.
19. The method of embodiment 18, wherein the nucleic acid comprises a detectable moiety.
20. The method of embodiments 1-19, wherein analyzing the sample to detect the presence or the absence of a genotype in the sample of step (b) comprises sequencing genetic information in the sample obtained from the subject.
21. The method of embodiments 1-20, further comprising:
    a. analyzing the sample to detect a presence of a serological marker in the sample; and
    b. identifying the risk of developing the disease or condition in the subject, provided the presence of the serological marker is detected in the sample obtained from the subject.
22. The method of embodiment 21, wherein analyzing the sample to detect a presence of the serological marker in the sample of step (a) comprises:
    a. contacting an antibody or antigen-binding fragment that is capable of binding to at least part of the serological marker or antigen thereof to the sample; and
    b. detecting binding between the antibody or antigen-binding fragment and the serological marker or antigen thereof.
23. The method of embodiment 22, wherein analyzing the sample to detect a presence of the serological marker in the sample of step (a) comprises using an enzyme-linked immunosorbent assay (ELISA).
24. The method of embodiments 21-23, wherein the serological marker is selected from the group consisting of anti-*Saccharomyces cerevisiae* antibody (ASCA), an anti-neutrophil cytoplasmic antibody (ANCA), anti-*Escherichia coli* outer membrane porin protein C (anti-OmpC) antibody, anti-I2 antibody, and anti-Cbir1 flagellin antibody.
25. A method of characterizing a subtype of a disease or condition, the method comprising:
    a. analyzing a sample obtained from a subject with a disease or a condition to detect a presence or an absence of a genotype in the sample; and
    b. characterizing the disease or the condition as a severe form of the disease or the condition, provided the presence of the genotype is detected in the sample obtained from the subject.
26. The method of embodiment 25, wherein the disease or condition is selected from the group consisting of Crohn's disease (CD), ulcerative colitis (UC), and inflammatory bowel disease (IBD).
27. The method of embodiment 25-26, wherein subtype is selected from the group consisting of stricturing disease, internal penetrating disease, and stricturing and internal penetrating disease.
28. The method of embodiments 25-27, wherein the subject is human.
29. The method of embodiment 25, further comprising treating the disease or condition in the subject comprising administering to the subject a therapeutically effective amount of a therapeutic agent.
30. The method of embodiment 25, further comprising treating the disease or condition in the subject comprising administering to the subject a therapeutically effective amount of an additional therapeutic agent.
31. The method of embodiment 25, further comprising prescribing to the subject a therapeutically effective amount of at least one of a therapeutic agent and an additional therapeutic agent.
32. The method of embodiment 29-31, wherein the therapeutic agent is a modulator of a gene or gene expression product expressed from the gene involved in prolactin signaling.
33. The method of embodiment 32, wherein the gene is selected from the group consisting of Interferon Regulatory Factor 1 (IRF1), Klotho Beta (KLB), Mitogen-Activated Protein Kinase Kinase 1 (MAP2K1), Nuclear Receptor Subfamily 3 Group C Member 1 (NR3C1), Protein Kinase C Beta (PRKCB), Protein Kinase C Epsilon (PRKCE), Protein Kinase C Gamma (PRKCG), Protein Kinase C Eta (PRKCH), Protein Kinase C Theta (PRKCQ), Prolactin Receptor (PRLR), Protein Tyrosine Phosphatase, Non-Receptor Type 11 (PTPN11), Signal Transducer And Activator Of Transcription 1 (STAT1), Signal Transducer And Activator Of Transcription 5A (STAT5A), and Signal Transducer And Activator Of Transcription 5B (STAT5B).
34. The method of embodiments 29-31, wherein the therapeutic agent is a modulator of a gene or gene expression product expressed from the gene involved in autophagy.
35. The method of embodiment 34, wherein the gene is selected from the group consisting of Autophagy Related 10 (ATG10), Autophagy Related 16 Like 1 (ATG16L1), Autophagy Related 4A Cysteine Peptidase (ATG4A), Autophagy Related 4C Cysteine Peptidase (ATG4C), Cathepsin H (CTSH), Sequestosome 1 (SQSTM1), Unc-51 Like Autophagy Activating Kinase 1 (ULK1), and WD Repeat And FYVE Domain Containing 3 (WDFY3).
36. The method of embodiments 29-31, wherein the therapeutic agent is a modulator of Janus Kinase 1 (JAK1).
37. The method of embodiments 29-31, wherein the therapeutic agent is a modulator of Tumor Necrosis Factor Ligand 1A (TL1A).

38. The method of embodiments 25-37, wherein the genotype comprises a polymorphism provided in Table 1, or a polymorphism in linkage disequilibrium (LD) therewith.
39. The method of embodiments 38, wherein LD is defined by an $r^2$ value of at least about 0.70, 0.75, 0.80, 0.85, 0.90, 0.95, 0.96, 0.97, 0.98, 0.99, or 1.0.
40. The method of embodiment 38, wherein the LD is defined by $r^2$ value of between 0.85-0.90, 0.90-0.95, and 0.95-1.0.
41. The method of embodiments 25-40, wherein genotype comprises at least 2, 3, 4, 5, 6, 7, 8, 9, 10, 11, 12, 13, 14, 15, 16, 17, 18, 19, 20, 21, 22, 23, 24, 25, 26, 27, 28, 29, 30, or more polymorphisms provided in Table 1.
42. The method of embodiments 25-41, wherein analyzing the sample to detect the presence or the absence of a genotype in the sample of step (b) comprises:
    a. contacting a nucleic acid sequence that is capable of hybridizing to the genotype to the sample; and
    b. detecting binding between the nucleic acid sequence and the genotype.
43. The method of embodiment 42, wherein the nucleic acid comprises a detectable moiety.
44. The method of embodiments 45-43, wherein analyzing the sample to detect the presence or the absence of a genotype in the sample of step (b) comprises sequencing genetic information in the sample obtained from the subject.
45. The method of embodiments 25-44, further comprising:
    a. analyzing the sample to detect a presence of a serological marker in the sample; and
    b. identifying the risk of developing the disease or condition in the subject, provided the presence of the serological marker is detected in the sample obtained from the subject.
46. The method of embodiment 45, wherein analyzing the sample to detect a presence of the serological marker in the sample of step (a) comprises:
    a. contacting an antibody or antigen-binding fragment that is capable of binding to at least part of the serological marker or antigen thereof to the sample; and
    b. detecting binding between the antibody or antigen-binding fragment and the serological marker or antigen thereof.
47. The method of embodiment 46, wherein analyzing the sample to detect a presence of the serological marker in the sample of step (a) comprises using an enzyme-linked immunosorbent assay (ELISA).
48. The method of embodiments 45-47, wherein the serological marker is selected from the group consisting of anti-*Saccharomyces cerevisiae* antibody (ASCA), an anti-neutrophil cytoplasmic antibody (ANCA), anti-*Escherichia coli* outer membrane porin protein C (anti-OmpC) antibody, anti-I2 antibody, and anti-Cbir1 flagellin antibody.
49. The method of embodiment 38-48, wherein the polymorphism is selected from the group consisting of rs2726797, rs7108993, rs79665096, rs7604404, rs73085878, rs78727269, rs2736352, rs4924935, rs11227112, rs2285043, rs6989059, rs3807552, rs111455641, rs9480689, rs7416358, rs6879067, rs11128532, rs177665, rs11171747, rs10775375, rs6801634, rs1070444, rs116714418, rs6962616, rs7220814, rs4325270, rs768755, rs17758350, rs9480689, rs525850, rs4325270, rs11749180, rs6962616, rs116714418, rs10265554, rs634641, rs1493871, rs12669698, rs4332037, rs17697480, rs9480689, rs6074737, rs904910, rs12972487, rs445417, rs635624, rs7416358, 12-54819630-G-INSERTION, rs177665, rs1070444, rs10912583, rs12914919, rs2854725, rs948068, rs71472147, rs72939578, rs658795, rs17758350, rs144260901, rs10801129, rs1702870, rs10912583, rs2452822, rs7774349, rs4705272, rs117946479, rs936126, rs634641, rs2314737, rs3002685, rs634641, rs12496281, rs10134119, rs3808240, rs1890843, rs11829981, rs12496281, rs2383184, rs144260901, rs6801634, rs2383184, rs2954756, and a polymorphism in LD therewith.
50. The method of the previous embodiments, wherein the polymorphism is selected from the group consisting of rs2726797, rs7108993, rs79665096, rs7604404, and any combination thereof.
51. The method of the previous embodiments, wherein the polymorphism is selected from the group consisting rs73085878, rs78727269, rs2736352, rs4924935, rs11227112, rs2285043, rs6989059, rs3807552, and any combination thereof.
52. The method of the previous embodiments, wherein the polymorphism is selected from the group consisting rs111455641, rs9480689, and any combination thereof.
53. The method of the previous embodiments, wherein the polymorphism is selected from the group consisting rs7416358, rs6879067, rs11128532, and any combination thereof.
54. The method of the previous embodiments, wherein the polymorphism is selected from the group consisting rs177665, rs11171747, and any combination thereof.
55. The method of the previous embodiments, wherein the polymorphism is rs10775375.
56. The method of the previous embodiments, wherein the polymorphism is rs6801634.
57. The method of the previous embodiments, wherein the polymorphism is selected from the group consisting rs1070444, rs116714418, rs6962616, rs7220814, rs4325270, rs768755, and any combination thereof.
58. The method of the previous embodiments, wherein the polymorphism is selected from the group consisting rs17758350, rs9480689, rs525850, rs4325270, and any combination thereof.
59. The method of the previous embodiments, wherein the polymorphism is selected from the group consisting rs11749180, rs6962616, rs116714418, rs10265554, rs634641, rs1493871, rs12669698, and any combination thereof.
60. The method of the previous embodiments, wherein the polymorphism is rs4332037.
61. The method of the previous embodiments, wherein the polymorphism is selected from the group consisting rs17697480, rs9480689, and any combination thereof.
62. The method of the previous embodiments, wherein the polymorphism is selected from the group consisting rs6074737, rs904910, rs12972487, rs445417, and any combination thereof.
63. The method of the previous embodiments, wherein the polymorphism is selected from the group consisting rs635624, rs7416358, and any combination thereof.
64. The method of the previous embodiments, wherein the polymorphism is selected from the group consisting 12-54819630-G-INSERTION, rs177665, and any combination thereof.

65. The method of the previous embodiments, wherein the polymorphism is selected from the group consisting rs1070444, rs10912583, rs12914919, rs2854725, and any combination thereof.
66. The method of the previous embodiments, wherein the polymorphism is selected from the group consisting rs948068, rs71472147, rs72939578, rs658795, rs17758350, rs144260901, and any combination thereof.
67. The method of the previous embodiments, wherein the polymorphism is selected from the group consisting rs10801129, rs1702870, rs10912583, rs2452822, rs7774349, and any combination thereof.
68. The method of the previous embodiments, wherein the polymorphism is selected from the group consisting rs4705272, rs117946479, and any combination thereof.
69. The method of embodiment 49-68, wherein the polymorphism at rs2726797 comprises a C allele at nucleoposition 26 within SEQ ID NO: 1.
70. The method of embodiment 49-68, wherein the polymorphism at rs7108993 comprises a C allele at nucleoposition 26 within SEQ ID NO: 2.
71. The method of embodiment 49-68, wherein the polymorphism at rs79665096 comprises an A allele at nucleoposition 26 within SEQ ID NO: 3.
72. The method of embodiment 49-68, wherein the polymorphism at rs7604404 comprises an A allele at nucleoposition 26 within SEQ ID NO: 4.
73. The method of embodiment 49-68, wherein the polymorphism at rs73085878 comprises an A allele at nucleoposition 26 within SEQ ID NO: 5.
74. The method of embodiment 49-68, wherein the polymorphism at rs78727269 comprises an A allele at nucleoposition 26 within SEQ ID NO: 6.
75. The method of embodiment 49-68, wherein the polymorphism at rs2736352 comprises an A allele at nucleoposition 26 within SEQ ID NO: 7.
76. The method of embodiment 49-68, wherein the polymorphism at rs4924935 comprises a G allele at nucleoposition 26 within SEQ ID NO: 8.
77. The method of embodiment 49-68, wherein the polymorphism at rs11227112 comprises a G allele at nucleoposition 26 within SEQ ID NO: 9.
78. The method of embodiment 49-68, wherein the polymorphism at rs2285043 comprises an A allele at nucleoposition 26 within SEQ ID NO: 10.
79. The method of embodiment 49-68, wherein the polymorphism at rs6989059 comprises an A allele at nucleoposition 26 within SEQ ID NO: 11.
80. The method of embodiment 49-68, wherein the polymorphism at rs3807552 comprises an A allele at nucleoposition 26 within SEQ ID NO: 12.
81. The method of embodiment 49-68, wherein the polymorphism at rs111455641 comprises a G allele at nucleoposition 26 within SEQ ID NO: 13.
82. The method of embodiment 49-68, wherein the polymorphism at rs9480689 comprises a G allele at nucleoposition 26 within SEQ ID NO: 14.
83. The method of embodiment 49-68, wherein the polymorphism at rs7416358 comprises a G allele at nucleoposition 26 within SEQ ID NO: 15.
84. The method of embodiment 49-68, wherein the polymorphism at rs6879067 comprises an A allele at nucleoposition 26 within SEQ ID NO: 16.
85. The method of embodiment 49-68, wherein the polymorphism at rs11128532 comprises an A allele at nucleoposition 26 within SEQ ID NO: 17.
86. The method of embodiment 49-68, wherein the polymorphism at rs177665 comprises a C allele at nucleoposition 26 within SEQ ID NO: 18.
87. The method of embodiment 49-68, wherein the polymorphism at rs11171747 comprises a C allele at nucleoposition 26 within SEQ ID NO: 19.
88. The method of embodiment 49-68, wherein the polymorphism at rs10775375 comprises an A allele at nucleoposition 26 within SEQ ID NO: 20.
89. The method of embodiment 49-68, wherein the polymorphism at rs6801634 comprises an A allele at nucleoposition 26 within SEQ ID NO: 21.
90. The method of embodiment 49-68, wherein the polymorphism at rs1070444 comprises an A allele at nucleoposition 26 within SEQ ID NO: 22.
91. The method of embodiment 49-68, wherein the polymorphism at rs116714418 comprises an A allele at nucleoposition 26 within SEQ ID NO: 23.
92. The method of embodiment 49-68, wherein the polymorphism at rs6962616 comprises an A allele at nucleoposition 26 within SEQ ID NO: 24.
93. The method of embodiment 49-68, wherein the polymorphism at rs7220814 comprises a G allele at nucleoposition 26 within SEQ ID NO: 25.
94. The method of embodiment 49-68, wherein the polymorphism at rs4325270 comprises a T allele at nucleoposition 26 within SEQ ID NO: 26.
95. The method of embodiment 49-68, wherein the polymorphism at rs768755 comprises a T allele at nucleoposition 26 within SEQ ID NO: 27.
96. The method of embodiment 49-68, wherein the polymorphism at rs17758350 comprises an A allele at nucleoposition 31 within SEQ ID NO: 28.
97. The method of embodiment 49-68, wherein the polymorphism at rs9480689 comprises a G allele at nucleoposition 26 within SEQ ID NO: 29.
98. The method of embodiment 49-68, wherein the polymorphism at rs525850 comprises an A allele at nucleoposition 26 within SEQ ID NO: 30.
99. The method of embodiment 49-68, wherein the polymorphism at rs4325270 comprises a T allele at nucleoposition 26 within SEQ ID NO: 31.
100. The method of embodiment 49-68, wherein the polymorphism at rs11749180 comprises an A allele at nucleoposition 26 within SEQ ID NO: 32.
101. The method of embodiment 49-68, wherein the polymorphism at rs6962616 comprises an A allele at nucleoposition 26 within SEQ ID NO: 33.
102. The method of embodiment 49-68, wherein the polymorphism at rs116714418 comprises an A allele at nucleoposition 26 within SEQ ID NO: 34.
103. The method of embodiment 49-68, wherein the polymorphism at rs10265554 comprises a G allele at nucleoposition 26 within SEQ ID NO: 35.
104. The method of embodiment 49-68, wherein the polymorphism at rs634641 comprises a G allele at nucleoposition 26 within SEQ ID NO: 36.
105. The method of embodiment 49-68, wherein the polymorphism at rs1493871 comprises a G allele at nucleoposition 26 within SEQ ID NO: 37.
106. The method of embodiment 49-68, wherein the polymorphism at rs12669698 comprises a G allele at nucleoposition 26 within SEQ ID NO: 38.
107. The method of embodiment 49-68, wherein the polymorphism at rs4332037 comprises an A allele at nucleoposition 26 within SEQ ID NO: 39.

108. The method of embodiment 49-68, wherein the polymorphism at rs17697480 comprises a G allele at nucleoposition 26 within SEQ ID NO: 40.
109. The method of embodiment 49-68, wherein the polymorphism at rs9480689 comprises a G allele at nucleoposition 26 within SEQ ID NO: 41.
110. The method of embodiment 49-68, wherein the polymorphism at rs6074737 comprises an A allele at nucleoposition 26 within SEQ ID NO: 42.
111. The method of embodiment 49-68, wherein the polymorphism at rs904910 comprises a G allele at nucleoposition 26 within SEQ ID NO: 43.
112. The method of embodiment 49-68, wherein the polymorphism at rs12972487 comprises an A allele at nucleoposition 26 within SEQ ID NO: 44.
113. The method of embodiment 49-68, wherein the polymorphism at rs445417 comprises an A allele at nucleoposition 26 within SEQ ID NO: 45.
114. The method of embodiment 49-68, wherein the polymorphism at rs635624 comprises a C allele at nucleoposition 26 within SEQ ID NO: 46.
115. The method of embodiment 49-68, wherein the polymorphism at rs7416358 comprises a G allele at nucleoposition 26 within SEQ ID NO: 47.
116. The method of embodiment 49-68, wherein the polymorphism at 12-54819630-G-INSERTION comprises an insertion of a G at nucleoposition 26 within SEQ ID NO: 48.
117. The method of embodiment 49-68, wherein the polymorphism at rs177665 comprises a C allele at nucleoposition 26 within SEQ ID NO: 49.
118. The method of embodiment 49-68, wherein the polymorphism at rs1070444 comprises an A allele at nucleoposition 26 within SEQ ID NO: 50.
119. The method of embodiment 49-68, wherein the polymorphism at rs10912583 comprises an A allele at nucleoposition 26 within SEQ ID NO: 51.
120. The method of embodiment 49-68, wherein the polymorphism at rs12914919 comprises a G allele at nucleoposition 26 within SEQ ID NO: 52.
121. The method of embodiment 49-68, wherein the polymorphism at rs2854725 comprises a C allele at nucleoposition 26 within SEQ ID NO: 53.
122. The method of embodiment 49-68, wherein the polymorphism at rs9480689 comprises a G allele at nucleoposition 26 within SEQ ID NO: 54.
123. The method of embodiment 49-68, wherein the polymorphism at rs71472147 comprises an A allele at nucleoposition 26 within SEQ ID NO: 55.
124. The method of embodiment 49-68, wherein the polymorphism at rs72939578 comprises an A allele at nucleoposition 31 within SEQ ID NO: 56.
125. The method of embodiment 49-68, wherein the polymorphism at rs658795 comprises an A allele at nucleoposition 26 within SEQ ID NO: 57.
126. The method of embodiment 49-68, wherein the polymorphism at rs17758350 comprises an A allele at nucleoposition 31 within SEQ ID NO: 58.
127. The method of embodiment 49-68, wherein the polymorphism at rs144260901 comprises an A allele at nucleoposition 31 within SEQ ID NO: 59.
128. The method of embodiment 49-68, wherein the polymorphism at rs110801129 comprises a C allele at nucleoposition 26 within SEQ ID NO: 60.
129. The method of embodiment 49-68, wherein the polymorphism at rs1702870 comprises an A allele at nucleoposition 26 within SEQ ID NO: 61.
130. The method of embodiment 49-68, wherein the polymorphism at rs10912583 comprises an A allele at nucleoposition 26 within SEQ ID NO: 62.
131. The method of embodiment 49-68, wherein the polymorphism at rs2452822 comprises a C allele at nucleoposition 31 within SEQ ID NO: 63.
132. The method of embodiment 49-68, wherein the polymorphism at rs7774349 comprises an A allele at nucleoposition 26 within SEQ ID NO: 64.
133. The method of embodiment 49-68, wherein the polymorphism at rs4705272 comprises a G allele at nucleoposition 26 within SEQ ID NO: 65.
134. The method of embodiment 49-68, wherein the polymorphism at rs117946479 comprises an A allele at nucleoposition 31 within SEQ ID NO: 66.
135. The method of embodiment 49-68, wherein the polymorphism at rs936126 comprises an A allele at nucleoposition 26 within SEQ ID NO: 67.
136. The method of embodiment 49-68, wherein the polymorphism at rs634641 comprises a G allele at nucleoposition 26 within SEQ ID NO: 68.
137. The method of embodiment 49-68, wherein the polymorphism at rs2314737 comprises a G allele at nucleoposition 26 within SEQ ID NO: 69.
138. The method of embodiment 49-68, wherein the polymorphism at rs3002685 comprises a G allele at nucleoposition 26 within SEQ ID NO: 70.
139. The method of embodiment 49-68, wherein the polymorphism at rs634641 comprises a G allele at nucleoposition 26 within SEQ ID NO: 71.
140. The method of embodiment 49-68, wherein the polymorphism at rs12496281 comprises a G allele at nucleoposition 26 within SEQ ID NO: 72.
141. The method of embodiment 49-68, wherein the polymorphism at rs10134119 comprises a T allele at nucleoposition 26 within SEQ ID NO: 73.
142. The method of embodiment 49-68, wherein the polymorphism at rs3808240 comprises a C allele at nucleoposition 26 within SEQ ID NO: 74.
143. The method of embodiment 49-68, wherein the polymorphism at rs1890843 comprises a G allele at nucleoposition 26 within SEQ ID NO: 75.
144. The method of embodiment 49-68, wherein the polymorphism at rs11829981 comprises an A allele at nucleoposition 26 within SEQ ID NO: 76.
145. The method of embodiment 49-68, wherein the polymorphism at rs12496281 comprises a G allele at nucleoposition 26 within SEQ ID NO: 77.
146. The method of embodiment 49-68, wherein the polymorphism at rs2383184 comprises a G allele at nucleoposition 26 within SEQ ID NO: 78.
147. The method of embodiment 49-68, wherein the polymorphism at rs144260901 comprises an A allele at nucleoposition 31 within SEQ ID NO: 79.
148. The method of embodiment 49-68, wherein the polymorphism at rs6801634 comprises an A allele at nucleoposition 26 within SEQ ID NO: 80.
149. The method of embodiment 49-68, wherein the polymorphism at rs2383184 comprises a G allele at nucleoposition 26 within SEQ ID NO: 81.
150. The method of embodiment 49-68, wherein the polymorphism at rs2954756 comprises a G allele at nucleoposition 26 within SEQ ID NO: 82.
151. The method of any previous embodiment, wherein the therapeutic agent is a modulator of a gene or gene expression product expressed from the gene, the gene selected from group consisting of X—C Motif Chemokine Ligand 1 (XCL1), Dermatopontin (DPT), TNF Superfamily Member 4 (TNFSF4), C-Type Lectin Like 1 (CLECL1), CD69 Molecule (CD69), Fins Related Tyrosine Kinase 1 (FLT1), Mitogen-Activated Protein Kinase Kinase Kinase Kinase 4 (MAP4K4), Prostaglandin E Receptor 4 (PTGER4), interleukin 18 receptor 1 (IL18R1). 6-Phosphofructo-2-Kinase/Fructose-2, 6-Biphosphatase 3 (PFKFB3), Interleukin 18 Receptor Accessory Protein (IL18RAP), Adenylate Cyclase 7 (ADCY7), B Lymphoid Tyrosine Kinase (BLK), G Protein-Coupled Receptor 65 (GPR65), Sprouty Related EVH1 Domain Containing 2 (SPRED2), Src Kinase Associated Phosphoprotein 2 (SKAP2), CD30 ligand (CD30L), Receptor Interacting Serine/Threonine Kinase 2 (RIPK2), and TNF Ligand Superfamily Member 15 (TL1A), an a combination thereof.

152. The method of any previous embodiment, wherein the modulator of the gene or gene expression product is selected from the group consisting of an antibody or antigen-binding fragment thereof, a small molecule, or a peptide.

153. The method of any previous embodiment, wherein the modulator of the gene or gene expression product is an agonist or a partial agonist.

154. The method of any previous embodiment, wherein the modulator of the gene or gene expression product is an antagonist or a partial antagonist. In some embodiments, the modulator of the gene or gene expression product is an allosteric modulator.

Kits and Compositions

Compositions

Disclosed herein, in some embodiments, are compositions useful for the detection of a genotype or biomarker in a sample obtained from a subject according to the methods described herein. Aspects disclosed herein provide compositions comprises a polynucleotide sequence comprising at least 10 but less than 50 contiguous nucleotides of any one of SEQ ID NOS: 1-82, or reverse complements thereof, wherein the contiguous polynucleotide sequence comprises a detectable molecule. In some embodiments, the polynucleotide sequence comprises the nucleobase at position 26 or 31 in any one of SEQ ID NOS: 1-82. In various embodiments, the detectable molecule comprises a fluorophore. In other embodiments, the polynucleotide sequences further comprise a quencher.

Also disclosed herein are compositions comprising an antibody or antigen-binding fragment that specifically binds to a serological marker described herein, or antigen thereof, wherein the antibody or antigen-binding fragment comprises a detectable molecule. In various embodiments, the antibody comprises a monoclonal antibody, a chimeric antibody, a CDR-grafted antibody, a Fab, a Fab', a F(ab')2, a Fv, a disulfide linked Fv, a scFv, a single domain antibody, a diabody, a multispecific antibody, a dual specific antibody, an anti-idiotypic antibody, or a bispecific antibody. In some embodiments, the antibody or antigen-binding fragment comprises an IgG antibody, an IgM antibody, and/or an IgE antibody. In some embodiments, the detectable molecule comprises a fluorophore. In some embodiments, the antibody or antigen-binding fragment is conjugated to a paramagnetic particle (e.g., bead).

Kits

Disclosed herein, in some embodiments, are kits useful for to detect the genotypes and/or biomarkers disclosed herein. In some embodiments, the kits disclosed herein may be used to diagnose and/or treat a disease or condition in a subject; or select a patient for treatment and/or monitor a treatment disclosed herein. In some embodiments, the kit comprises the compositions described herein, which can be used to perform the methods described herein. Kits comprise an assemblage of materials or components, including at least one of the compositions. Thus, in some embodiments the kit contains a composition including of the pharmaceutical composition, for the treatment of IBD. In other embodiments, the kits contains all of the components necessary and/or sufficient to perform an assay for detecting and measuring IBD markers, including all controls, directions for performing assays, and any necessary software for analysis and presentation of results.

In some instances, the kits described herein comprise components for detecting the presence, absence, and/or quantity of a target nucleic acid and/or protein described herein. In some embodiments, the kit further comprises components for detecting the presence, absence, and/or quantity of a serological marker described herein. In some embodiments, the kit comprises the compositions (e.g., primers, probes, antibodies) described herein. The disclosure provides kits suitable for assays such as enzyme-linked immunosorbent assay (ELISA), single-molecular array (Simoa®), PCR, and qPCR. The exact nature of the components configured in the kit depends on its intended purpose.

In some embodiments, the kits described herein are configured for the purpose of treating and/or characterizing a disease or condition (e.g., Crohn's disease), or subclinical phenotype thereof (e.g., stricturing, penetrating, or stricturing and penetrating disease phenotypes) in a subject. In some embodiments, the kit is configured particularly for the purpose of treating mammalian subjects. In some embodiments, the kit is configured particularly for the purpose of treating human subjects. In further embodiments, the kit is configured for veterinary applications, treating subjects such as, but not limited to, farm animals, domestic animals, and laboratory animals. In some embodiments, the kit is configured to select a subject for a therapeutic agent, such as those disclosed herein. In some embodiments, the kit is configured to select a subject for treatment with a therapeutic agent disclosed herein.

Instructions for use may be included in the kit. Optionally, the kit also contains other useful components, such as, diluents, buffers, pharmaceutically acceptable carriers, syringes, catheters, applicators, pipetting or measuring tools, bandaging materials or other useful paraphernalia. The materials or components assembled in the kit can be provided to the practitioner stored in any convenient and suitable ways that preserve their operability and utility. For example the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as compositions and the like. The packaging material is constructed by well-known methods, preferably to provide a sterile, contaminant-free environment. The packaging materials employed in the kit are those customarily utilized in gene expression assays and in the administration of treatments. As used herein, the term "package" refers to a suitable solid matrix or material such as glass, plastic, paper, foil, and the like, capable of holding the individual kit components. Thus, for example, a package can be a glass vial or prefilled syringes used to contain suitable quantities of the pharmaceutical composition. The packaging material has an external label which indicates the contents and/or purpose of the kit and its components.

Systems

Disclosed herein, in some embodiments, is a system for detecting a particular genotype described herein in a subject. The system is configured to implement the methods described in this disclosure, including, but not limited to, detecting the presence of a particular CD subtype to determine whether the subject is suitable for treatment with a particular therapy.

In some embodiments, disclosed herein is a system for detecting at least one polymorphism provided in Table 1 in a subject, comprising: (a) a computer processing device, optionally connected to a computer network; and (b) a software module executed by the computer processing device to analyze a target nucleic acid sequence of a at least one polymorphism provided in Table 1 in a sample from a subject. In some instances, the system comprises a central processing unit (CPU), memory (e.g., random access memory, flash memory), electronic storage unit, computer program, communication interface to communicate with one or more other systems, and any combination thereof. In some instances, the system is coupled to a computer network, for example, the Internet, intranet, and/or extranet that is in communication with the Internet, a telecommunication, or data network. In some embodiments, the system comprises a storage unit to store data and information regarding any aspect of the methods described in this disclosure. Various aspects of the system are a product or article or manufacture.

One feature of a computer program includes a sequence of instructions, executable in the digital processing device's CPU, written to perform a specified task. In some embodiments, computer readable instructions are implemented as program modules, such as functions, features, Application Programming Interfaces (APIs), data structures, and the like, that perform particular tasks or implement particular abstract data types. In light of the disclosure provided herein, those of skill in the art will recognize that a computer program may be written in various versions of various languages.

The functionality of the computer readable instructions are combined or distributed as desired in various environments. In some instances, a computer program comprises one sequence of instructions or a plurality of sequences of instructions. A computer program may be provided from one location. A computer program may be provided from a plurality of locations. In some embodiment, a computer program includes one or more software modules. In some embodiments, a computer program includes, in part or in whole, one or more web applications, one or more mobile applications, one or more standalone applications, one or more web browser plug-ins, extensions, add-ins, or add-ons, or combinations thereof.

Web Application

In some embodiments, a computer program includes a web application. In light of the disclosure provided herein, those of skill in the art will recognize that a web application may utilize one or more software frameworks and one or more database systems. A web application, for example, is created upon a software framework such as Microsoft®.NET (Microsoft Corporation) or Ruby on Rails (RoR). A web application, in some instances, utilizes one or more database systems including, by way of non-limiting examples, relational, non-relational, feature oriented, associative, and XML database systems. Suitable relational database systems include, by way of non-limiting examples, Microsoft®SQL Server (Microsoft Corporation), mySQL™, and Oracle®. Those of skill in the art will also recognize that a web application may be written in one or more versions of one or more languages. In some embodiments, a web application is written in one or more markup languages, presentation definition languages, client-side scripting languages, server-side coding languages, database query languages, or combinations thereof. In some embodiments, a web application is written to some extent in a markup language such as Hypertext Markup Language (HTML), Extensible Hypertext Markup Language (XHTML), or eXtensible Markup Language (XML). In some embodiments, a web application is written to some extent in a presentation definition language such as Cascading Style Sheets (CSS). In some embodiments, a web application is written to some extent in a client-side scripting language such as Asynchronous Javascript and XML (AJAX), Flash® Actionscript (Adobe Flash), Javascript, or Silverlight® (Microsoft Silverlight). In some embodiments, a web application is written to some extent in a server-side coding language such as Active Server Pages (ASP), ColdFusion® (Adobe ColdFusion), Perl, Java™ (Java programming language), JavaServer Pages (JSP), Hypertext Preprocessor (PHP), Python™ (Python programming language), Ruby, Tcl, Smalltalk, WebDNA® (scripting language application), or Groovy. In some embodiments, a web application is written to some extent in a database query language such as Structured Query Language (SQL). A web application may integrate enterprise server products such as IBM® Lotus Domino® (International Business Machines Corporation collaborative software platform). A web application may include a media player element. A media player element may utilize one or more of many suitable multimedia technologies including, by way of non-limiting examples, Adobe® Flash® (Adobe Flash), HTML 5, Apple® QuickTime® (Apple Inc. QuickTime multimedia player), Microsoft® Silverlight® (Microsoft Silverlight), Java™ (Java programming language), and Unity® (Unity Technologies).

Mobile Application

In some instances, a computer program includes a mobile application provided to a mobile digital processing device. The mobile application may be provided to a mobile digital processing device at the time it is manufactured. The mobile application may be provided to a mobile digital processing device via the computer network described herein.

A mobile application is created by techniques known to those of skill in the art using hardware, languages, and development environments known to the art. Those of skill in the art will recognize that mobile applications may be written in several languages. Suitable programming languages include, by way of non-limiting examples, C, C++, C#, Featureive-C, Java™ (Java programming language), Javascript, Pascal, Feature Pascal, Python™ (Python programming language), Ruby, VB.NET, WML, and XHTML/HTML with or without CSS, or combinations thereof.

Suitable mobile application development environments are available from several sources. Commercially available development environments include, by way of non-limiting examples, AirplaySDK, alcheMo, Appcelerator® (Axway Inc. open source development platform), Celsius, Bedrock, Flash Lite, .NET Compact Framework, Rhomobile, and WorkLight Mobile Platform. Other development environments may be available without cost including, by way of non-limiting examples, Lazarus, MobiFlex, MoSync, and Phonegap. Also, mobile device manufacturers distribute software developer kits including, by way of non-limiting examples, iPhone and iPad (iOS) SDK, Android™ SDK (Android mobile operating system), BlackBerry® SDK (BlackBerry Limited), BREW SDK, Palm® OS SDK (Palm official software development kits), Symbian SDK, webOS® (LG webOS) SDK, and Windows® Mobile SDK (Microsoft Windows operating system).

Those of skill in the art will recognize that several commercial forums are available for distribution of mobile applications including, by way of non-limiting examples, Apple® App Store (Apple Inc.), Android™ Market (Android mobile), BlackBerry® App World (BlackBerry Limited), App Store for Palm devices, App Catalog for webOS® (LG webOS), Windows® Marketplace for Mobile (Microsoft Windows), Ovi Store for Nokia® devices (Nokia Corporation), Samsung® Apps (Samsung Electronics Co., Ltd.), and Nintendo® DSi Shop (Nintendo Co., Ltd.).

Standalone Application

In some embodiments, a computer program includes a standalone application, which is a program that may be run as an independent computer process, not an add-on to an existing process, e.g., not a plug-in. Those of skill in the art will recognize that standalone applications are sometimes compiled. In some instances, a compiler is a computer program(s) that transforms source code written in a programming language into binary feature code such as assembly language or machine code. Suitable compiled programming languages include, by way of non-limiting examples, C, C++, Featureive-C, COBOL, Delphi, Eiffel, Java™ (Java programming language), Lisp, Python™ (Python programming language), Visual Basic, and VB .NET, or combinations thereof. Compilation may be often performed, at least in part, to create an executable program. In some instances, a computer program includes one or more executable complied applications.

Web Browser Plug-In

A computer program, in some aspects, includes a web browser plug-in. In computing, a plug-in, in some instances, is one or more software components that add specific functionality to a larger software application. Makers of software applications may support plug-ins to enable third-party developers to create abilities which extend an application, to support easily adding new features, and to reduce the size of an application. When supported, plug-ins enable customizing the functionality of a software application. For example, plug-ins are commonly used in web browsers to play video, generate interactivity, scan for viruses, and display particular file types. Those of skill in the art will be familiar with several web browser plug-ins including, Adobe® Flash® Player (Adobe Flash Player), Microsoft® Silverlight® (Microsoft Silverlight), and Apple® QuickTime®. (Apple Inc. QuickTime multimedia player) The toolbar may comprise one or more web browser extensions, add-ins, or add-ons. The toolbar may comprise one or more explorer bars, tool bands, or desk bands.

In view of the disclosure provided herein, those of skill in the art will recognize that several plug-in frameworks are available that enable development of plug-ins in various programming languages, including, by way of non-limiting examples, C++, Delphi, Java™ (Java programming language), PHP, Python™ (Python programming language), and VB .NET, or combinations thereof.

In some embodiments, Web browsers (also called Internet browsers) are software applications, designed for use with network-connected digital processing devices, for retrieving, presenting, and traversing information resources on the World Wide Web. Suitable web browsers include, by way of non-limiting examples, Microsoft® Internet Explorer® (Microsoft Internet Browser), Mozilla® Firefox® (Mozilla Firefox Browsers), Google® Chrome (Google LLC), Apple® (Apple Inc.), Safari® (Safari application program), Opera Software® Opera® (Opera Browser), and KDE Konqueror. The web browser, in some instances, is a mobile web browser. Mobile web browsers (also called mircrobrowsers, mini-browsers, and wireless browsers) may be designed for use on mobile digital processing devices including, by way of non-limiting examples, handheld computers, tablet computers, netbook computers, subnotebook computers, smartphones, music players, personal digital assistants (PDAs), and handheld video game systems. Suitable mobile web browsers include, by way of non-limiting examples, Google® Android® browser (Google LLC Android mobile web browser), RIM BlackBerry® Browser (BlackBerry Limited), Apple® Safari® (Apple Inc. Safari application program), Palm® Blazer (Palm, Inc.), Palm® WebOS® Browser (Palm, Inc. (LG webOS), Mozilla® Firefox® for mobile (Mozilla Firefox Browsers), Microsoft® Internet Explorer® (Microsoft Internet Browser) Mobile, Amazon® Kindle® Basic Web (Amazon.com, Inc. Kindle E-readers), Nokia® Browser (Nokia Corporation), Opera Software® Opera® Mobile (Opera Browser), and Sony® PSP™ browser (Sony Group Corporation PlayStation® Portable).

Software Modules

The medium, method, and system disclosed herein comprise one or more softwares, servers, and database modules, or use of the same. In view of the disclosure provided herein, software modules may be created by techniques known to those of skill in the art using machines, software, and languages known to the art. The software modules disclosed herein may be implemented in a multitude of ways. In some embodiments, a software module comprises a file, a section of code, a programming feature, a programming structure, or combinations thereof. A software module may comprise a plurality of files, a plurality of sections of code, a plurality of programming features, a plurality of programming structures, or combinations thereof. By way of non-limiting examples, the one or more software modules comprise a web application, a mobile application, and/or a standalone application. Software modules may be in one computer program or application. Software modules may be in more than one computer program or application. Software modules may be hosted on one machine. Software modules may be hosted on more than one machine. Software modules may be hosted on cloud computing platforms. Software modules may be hosted on one or more machines in one location. Software modules may be hosted on one or more machines in more than one location.

Databases

The medium, method, and system disclosed herein comprise one or more databases, or use of the same. In view of the disclosure provided herein, those of skill in the art will recognize that many databases are suitable for storage and retrieval of geologic profile, operator activities, division of interest, and/or contact information of royalty owners. Suitable databases include, by way of non-limiting examples, relational databases, non-relational databases, feature oriented databases, feature databases, entity-relationship model databases, associative databases, and XML databases. In some embodiments, a database is internet-based. In some embodiments, a database is web-based. In some embodiments, a database is cloud computing-based. A database may be based on one or more local computer storage devices.

Data Transmission

The subject matter described herein, including methods for detecting a particular CD subtype, are configured to be performed in one or more facilities at one or more locations. Facility locations are not limited by country and include any country or territory. In some instances, one or more steps are performed in a different country than another step of the method. In some instances, one or more steps for obtaining a sample are performed in a different country than one or more steps for detecting the presence or absence of a particular CD subtype from a sample. In some embodiments, one or more method steps involving a computer system are performed in a different country than another step of the methods provided herein. In some embodiments, data processing and analyses are performed in a different country or location than one or more steps of the methods described herein. In some embodiments, one or more articles, products, or data are transferred from one or more of the facilities to one or more different facilities for analysis or further analysis. An article includes, but is not limited to, one or more components obtained from a subject, e.g., processed cellular material. Processed cellular material includes, but is not limited to, cDNA reverse transcribed from RNA, amplified RNA, amplified cDNA, sequenced DNA, isolated and/or purified RNA, isolated and/or purified DNA, and isolated and/or purified polypeptide. Data includes, but is not limited to, information regarding the stratification of a subject, and any data produced by the methods disclosed herein. In some embodiments of the methods and systems described herein, the analysis is performed and a subsequent data transmission step will convey or transmit the results of the analysis.

In some embodiments, any step of any method described herein is performed by a software program or module on a computer. In additional or further embodiments, data from any step of any method described herein is transferred to and from facilities located within the same or different countries, including analysis performed in one facility in a particular location and the data shipped to another location or directly to an individual in the same or a different country. In additional or further embodiments, data from any step of any method described herein is transferred to and/or received from a facility located within the same or different countries, including analysis of a data input, such as genetic or processed cellular material, performed in one facility in a particular location and corresponding data transmitted to another location, or directly to an individual, such as data related to the diagnosis, prognosis, responsiveness to therapy, or the like, in the same or different location or country.

Business Methods Utilizing a Computer

The methods described herein may utilize one or more computers. The computer may be used for managing customer and sample information such as sample or customer tracking, database management, analyzing molecular profiling data, analyzing cytological data, storing data, billing, marketing, reporting results, storing results, or a combination thereof. The computer may include a monitor or other graphical interface for displaying data, results, billing information, marketing information (e.g. demographics), customer information, or sample information. The computer may also include means for data or information input. The computer may include a processing unit and fixed or removable media or a combination thereof. The computer may be accessed by a user in physical proximity to the computer, for example via a keyboard and/or mouse, or by a user that does not necessarily have access to the physical computer through a communication medium such as a modem, an internet connection, a telephone connection, or a wired or wireless communication signal carrier wave. In some cases, the computer may be connected to a server or other communication device for relaying information from a user to the computer or from the computer to a user. In some cases, the user may store data or information obtained from the computer through a communication medium on media, such as removable media. It is envisioned that data relating to the methods can be transmitted over such networks or connections for reception and/or review by a party. The receiving party can be but is not limited to an individual, a health care provider or a health care manager. In one embodiment, a computer-readable medium includes a medium suitable for transmission of a result of an analysis of a biological sample, such as exosome bio-signatures. The medium can include a result regarding an exosome bio-signature of a subject, wherein such a result is derived using the methods described herein.

The entity obtaining a report regarding a risk of developing a severe form of Crohn's disease may enter sample information into a database for the purpose of one or more of the following: inventory tracking, assay result tracking, order tracking, customer management, customer service, billing, and sales. Sample information may include, but is not limited to: customer name, unique customer identification, customer associated medical professional, indicated assay or assays, assay results, adequacy status, indicated adequacy tests, medical history of the individual, preliminary diagnosis, suspected diagnosis, sample history, insurance provider, medical provider, third party testing center or any information suitable for storage in a database. Sample history may include but is not limited to: age of the sample, type of sample, method of acquisition, method of storage, or method of transport.

The database may be accessible by a customer, medical professional, insurance provider, or other third party. Database access may take the form of electronic communication such as a computer or telephone. The database may be accessed through an intermediary such as a customer service representative, business representative, consultant, independent testing center, or medical professional. The availability or degree of database access or sample information, such as assay results, may change upon payment of a fee for products and services rendered or to be rendered. The degree of database access or sample information may be restricted to comply with generally accepted or legal requirements for patient or customer confidentiality.

Further Embodiments

Disclosed herein, in some embodiments, are the following:

1. A computer system for evaluating a sample from a subject, the system comprising:
   a. a central computing environment;
   b. an input device operatively connected to said central computing environment, wherein said input device is configured to receive a presence or absence of a genotype that correlates with a disease state in the sample;
   c. a trained algorithm executed by said central computing environment, wherein the trained algorithm is configured to use the presence or absence of the genotype to classify said sample as a disease or normal sample; and
   d. an output device operatively connected to said central computing environment, wherein said output device is configured to provide information on the classification to a user.
2. The computer system of embodiment 1, wherein the disease state comprises at least one of Crohn's disease (CD), ulcerative colitis (UC), and inflammatory bowel disease (IBD).

3. The computer system of embodiment 1 or embodiment 2, wherein the disease state is a severe form of CD characterized by a subclinical phenotype selected from the group consisting of stricturing disease, internal penetrating disease, and stricturing and internal penetrating disease.
4. The computer system of any previous embodiment, wherein the sample comprises whole blood, plasma, serum, or tissue.
5. The computer system of any previous embodiment, wherein the genotype comprises at least one polymorphism at a nucleoposition 26 or 31 within any one of SEQ ID NOS: 1-82, a polymorphism in linkage disequilibrium (LD) therewith, and any combination thereof.
6. The computer system of embodiment 5, where LD is defined by an $r^2$ value of at least 0.80, 0.85, 0.90, 0.95, or 1.0.
7. The computer system of any previous embodiment, wherein the genotype is associated with a risk that a subject has, or will develop, the disease state by a P value of at most about $1.0\times10^{-5}$.
8. The computer system of any previous embodiment, wherein said output device provides a report summarizing said information on said classification.
9. The computer system of any previous embodiment, wherein said report comprises a recommendation for treatment of said disease state.
10. The computer system of embodiment 13, wherein the treatment comprises administration of therapeutic agent.
11. The computer system of embodiment 14, wherein the therapeutic agent is a modulator of a gene or gene expression product expressed from the gene involved in prolactin signaling.
12. The computer system of embodiment 11, wherein the gene is selected from the group consisting of Interferon Regulatory Factor 1 (IRF1), Klotho Beta (KLB), Mitogen-Activated Protein Kinase Kinase 1 (MAP2K1), Nuclear Receptor Subfamily 3 Group C Member 1 (NR3C1), Protein Kinase C Beta (PRKCB), Protein Kinase C Epsilon (PRKCE), Protein Kinase C Gamma (PRKCG), Protein Kinase C Eta (PRKCH), Protein Kinase C Theta (PRKCQ), Prolactin Receptor (PRLR), Protein Tyrosine Phosphatase, Non-Receptor Type 11 (PTPN11), Signal Transducer And Activator Of Transcription 1 (STAT1), Signal Transducer And Activator Of Transcription 5A (STAT5A), and Signal Transducer And Activator Of Transcription 5B (STAT5B).
13. The method of embodiments 10, wherein the therapeutic agent is a modulator of a gene or gene expression product expressed from the gene involved in autophagy.
14. The method of embodiment 13, wherein the gene is selected from the group consisting of Autophagy Related 10 (ATG10), Autophagy Related 16 Like 1 (ATG16L1), Autophagy Related 4A Cysteine Peptidase (ATG4A), Autophagy Related 4C Cysteine Peptidase (ATG4C), Cathepsin H (CTSH), Sequestosome 1 (SQSTM1), Unc-51 Like Autophagy Activating Kinase 1 (ULK1), and WD Repeat And FYVE Domain Containing 3 (WDFY3).
15. The method of embodiment 10, wherein the therapeutic agent is a modulator of Janus Kinase 1 (JAK1).
16. The method of embodiment 10, wherein the therapeutic agent is a modulator of a gene or gene expression product expressed from the gene, the gene selected from group consisting of X—C Motif Chemokine Ligand 1 (XCL1), Dermatopontin (DPT), TNF Superfamily Member 4 (TNFSF4), C-Type Lectin Like 1 (CLECL1), CD69 Molecule (CD69), Fins Related Tyrosine Kinase 1 (FLT1), Mitogen-Activated Protein Kinase Kinase Kinase Kinase 4 (MAP4K4), Prostaglandin E Receptor 4 (PTGER4), interleukin 18 receptor 1 (IL18R1). 6-Phosphofructo-2-Kinase/Fructose-2, 6-Biphosphatase 3 (PFKFB3), Interleukin 18 Receptor Accessory Protein (IL18RAP), Adenylate Cyclase 7 (ADCY7), B Lymphoid Tyrosine Kinase (BLK), G Protein-Coupled Receptor 65 (GPR65), Sprouty Related EVH1 Domain Containing 2 (SPRED2), Src Kinase Associated Phosphoprotein 2 (SKAP2), CD30 ligand (CD30L), Receptor Interacting Serine/Threonine Kinase 2 (RIPK2), and TNF Ligand Superfamily Member 15 (TL1A), an a combination thereof.
17. The method of embodiment 1-16, further wherein the inputting device is further configured to receive a presence or absence of a serological marker that correlates with the disease state in the sample.
18. The method of embodiment 17, wherein the trained algorithm is further configured to use the presence or absence of the serological marker to classify said sample as the disease or normal sample; and
19. The method of embodiments 17-18, wherein the serological marker is selected from the group consisting of anti-*Saccharomyces cerevisiae* antibody (ASCA), an anti-neutrophil cytoplasmic antibody (ANCA), anti-*Escherichia coli* outer membrane porin protein C (anti-OmpC) antibody, anti-I2 antibody, and anti-Cbir1 flagellin antibody.
20. Use of a composition comprising one or more binding agents for generating a report that classifies a sample from as subject as disease or non-disease of a disease state, wherein the one or more binding agents specifically bind to a polymorphism at a nucleoposition 26 or 31within any one of SEQ ID NOS: 1-82, its compliment, a polymorphism in linkage disequilibrium (LD) therewith, and any combination thereof.
21. The use of embodiment 20, wherein generating the report further comprises:
  a. providing the sample from the subject;
  b. assaying the sample from the subject for detecting the presence of the one or more polymorphisms in one or more genes;
  c. generating the report based on the result of step (b); and
  d. determining whether said subject has or is likely to have the disease based on the results of step (b).
22. The use of embodiment 20 or 21, wherein the disease state is selected from the group consisting of inflammatory bowel disease (IBD), Crohn's disease (CD), and ulcerative colitis (UC).
23. The use of embodiment 22, wherein the CD is a severe form of CD characterized by a subclinical phenotype selected from the group consisting of stricturing disease, internal penetrating disease, and stricturing and internal penetrating disease.
24. The use of any of embodiments 20-23, wherein the sample comprises whole blood, plasma, serum, or tissue.
25. The use of embodiment 21-24, wherein assaying the sample from the subject for detecting the presence of the one or more polymorphisms of step (b) comprises:

a. contacting the sample with the one or more binding agents that specifically bind to the one or more polymorphisms; and
b. determining whether the sample specifically binds to said one or more binding agents, wherein binding of the sample to the one or more binding agents indicates the presence of the polymorphism in the subject.

26. The use of embodiment 20-24, wherein assaying the sample from the subject for detecting the presence of the one or more polymorphisms of step (b) comprises sequencing of the sample.

27. The use of embodiment 20-26, wherein the one or more binding agents specifically bind to a serological marker or antigen thereof.

28. The use of embodiments 27, wherein the serological marker is selected from the group consisting of anti-*Saccharomyces cerevisiae* antibody (ASCA), an anti-neutrophil cytoplasmic antibody (ANCA), anti-*Escherichia coli* outer membrane porin protein C (anti-OmpC) antibody, anti-I2 antibody, and anti-Cbir1 flagellin antibody.

29. The use of embodiments 27-28, wherein generating the report further comprises:
a. providing the sample from the subject;
b. assaying the sample from the subject for detecting the presence of the serological marker;
c. generating the report based on the result of step (b); and
d. determining whether said subject has or is likely to have the disease based on the results of step (b).

30. The use of embodiment 29, wherein assaying the sample from the subject for detecting the presence of the serological marker of step (b) comprises:
a. contacting the sample with the one or more binding agents that specifically bind to the serological marker; and
b. determining whether the sample specifically binds to said one or more binding agents, wherein binding of the sample to the one or more binding agents indicates the presence of the of the serological marker in the subject.

31. The use of embodiment 20, wherein the polymorphism is selected from the group consisting of rs2726797, rs7108993, rs79665096, rs7604404, rs73085878, rs78727269, rs2736352, rs4924935, rs11227112, rs2285043, rs6989059, rs3807552, rs111455641, rs9480689, rs7416358, rs6879067, rs11128532, rs177665, rs11171747, rs10775375, rs6801634, rs1070444, rs116714418, rs6962616, rs7220814, rs4325270, rs768755, rs17758350, rs9480689, rs525850, rs4325270, rs11749180, rs6962616, rs116714418, rs10265554, rs634641, rs1493871, rs12669698, rs4332037, rs17697480, rs9480689, rs6074737, rs904910, rs12972487, rs445417, rs635624, rs7416358, 12-54819630-G-INSERTION, rs177665, rs1070444, rs10912583, rs12914919, rs2854725, rs948068, rs71472147, rs72939578, rs658795, rs17758350, rs144260901, rs10801129, rs1702870, rs10912583, rs2452822, rs7774349, rs4705272, rs117946479, rs936126, rs634641, rs2314737, rs3002685, rs634641, rs12496281, rs10134119, rs3808240, rs1890843, rs11829981, rs12496281, rs2383184, rs144260901, rs6801634, rs2383184, rs2954756, and a polymorphism in LD therewith.

32. The use of the previous embodiments, wherein the polymorphism is selected from the group consisting of rs2726797, rs7108993, rs79665096, rs7604404, and any combination thereof.

33. The use of the previous embodiments, wherein the polymorphism is selected from the group consisting rs73085878, rs78727269, rs2736352, rs4924935, rs11227112, rs2285043, rs6989059, rs3807552, and any combination thereof.

34. The use of the previous embodiments, wherein the polymorphism is selected from the group consisting rs111455641, rs9480689, and any combination thereof.

35. The use of the previous embodiments, wherein the polymorphism is selected from the group consisting rs7416358, rs6879067, rs11128532, and any combination thereof.

36. The use of the previous embodiments, wherein the polymorphism is selected from the group consisting rs177665, rs11171747, and any combination thereof.

37. The use of the previous embodiments, wherein the polymorphism is rs10775375.

38. The use of the previous embodiments, wherein the polymorphism is rs6801634.

39. The use of the previous embodiments, wherein the polymorphism is selected from the group consisting rs1070444, rs116714418, rs6962616, rs7220814, rs4325270, rs768755, and any combination thereof.

40. The use of the previous embodiments, wherein the polymorphism is selected from the group consisting rs17758350, rs9480689, rs525850, rs4325270, and any combination thereof.

41. The use of the previous embodiments, wherein the polymorphism is selected from the group consisting rs11749180, rs6962616, rs116714418, rs10265554, rs634641, rs1493871, rs12669698, and any combination thereof.

42. The use of the previous embodiments, wherein the polymorphism is rs4332037.

43. The use of the previous embodiments, wherein the polymorphism is selected from the group consisting rs17697480, rs9480689, and any combination thereof.

44. The use of the previous embodiments, wherein the polymorphism is selected from the group consisting rs6074737, rs904910, rs12972487, rs445417, and any combination thereof.

45. The use of the previous embodiments, wherein the polymorphism is selected from the group consisting rs635624, rs7416358, and any combination thereof.

46. The use of the previous embodiments, wherein the polymorphism is selected from the group consisting 12-54819630-G-INSERTION, rs177665, and any combination thereof.

47. The use of the previous embodiments, wherein the polymorphism is selected from the group consisting rs1070444, rs10912583, rs12914919, rs2854725, and any combination thereof.

48. The use of the previous embodiments, wherein the polymorphism is selected from the group consisting rs948068, rs71472147, rs72939578, rs658795, rs17758350, rs144260901, and any combination thereof.

49. The use of the previous embodiments, wherein the polymorphism is selected from the group consisting rs10801129, rs1702870, rs10912583, rs2452822, rs7774349, and any combination thereof.

50. The use of the previous embodiments, wherein the polymorphism is selected from the group consisting rs4705272, rs117946479, and any combination thereof.
51. The use of the previous embodiments, wherein the polymorphism is rs936126.
52. The use of the previous embodiments, wherein the polymorphism is rs634641.
53. The use of the previous embodiments, wherein the polymorphism is selected from the group consisting rs2314737, rs3002685, rs634641, and any combination thereof.
54. The use of the previous embodiments, wherein the polymorphism is selected from the group consisting rs12496281, rs10134119, rs3808240, and any combination thereof.
55. The use of the previous embodiments, wherein the polymorphism is selected from the group consisting rs1890843, rs11829981, and any combination thereof.
56. The use of the previous embodiments, wherein the polymorphism is rs12496281.
57. The use of the previous embodiments, wherein the polymorphism is selected from the group consisting rs2383184, rs144260901, and any combination thereof.
58. The use of the previous embodiments, wherein the polymorphism is selected from the group consisting rs6801634, rs2383184, rs2954756, and any combination thereof.
59. The use of embodiment 31-58, wherein the polymorphism at rs2726797 comprises a C allele at nucleoposition 26 within SEQ ID NO: 1.
60. The use of embodiment 31-58, wherein the polymorphism at rs7108993 comprises a C allele at nucleoposition 26 within SEQ ID NO: 2.
61. The use of embodiment 31-58, wherein the polymorphism at rs79665096 comprises an A allele at nucleoposition 26 within SEQ ID NO: 3.
62. The use of embodiment 31-58, wherein the polymorphism at rs7604404 comprises an A allele at nucleoposition 26 within SEQ ID NO: 4.
63. The use of embodiment 31-58, wherein the polymorphism at rs73085878 comprises an A allele at nucleoposition 26 within SEQ ID NO: 5.
64. The use of embodiment 31-58, wherein the polymorphism at rs78727269 comprises an A allele at nucleoposition 26 within SEQ ID NO: 6.
65. The use of embodiment 31-58, wherein the polymorphism at rs2736352 comprises an A allele at nucleoposition 26 within SEQ ID NO: 7.
66. The use of embodiment 31-58, wherein the polymorphism at rs4924935 comprises a G allele at nucleoposition 26 within SEQ ID NO: 8.
67. The use of embodiment 31-58, wherein the polymorphism at rs11227112 comprises a G allele at nucleoposition 26 within SEQ ID NO: 9.
68. The use of embodiment 31-58, wherein the polymorphism at rs2285043 comprises an A allele at nucleoposition 26 within SEQ ID NO: 10.
69. The use of embodiment 31-58, wherein the polymorphism at rs6989059 comprises an A allele at nucleoposition 26 within SEQ ID NO: 11.
70. The use of embodiment 31-58, wherein the polymorphism at rs3807552 comprises an A allele at nucleoposition 26 within SEQ ID NO: 12.
71. The use of embodiment 31-58, wherein the polymorphism at rs111455641 comprises a G allele at nucleoposition 26 within SEQ ID NO: 13.
72. The use of embodiment 31-58, wherein the polymorphism at rs9480689 comprises a G allele at nucleoposition 26 within SEQ ID NO: 14.
73. The use of embodiment 31-58, wherein the polymorphism at rs7416358 comprises a G allele at nucleoposition 26 within SEQ ID NO: 15.
74. The use of embodiment 31-58, wherein the polymorphism at rs6879067 comprises an A allele at nucleoposition 26 within SEQ ID NO: 16.
75. The use of embodiment 31-58, wherein the polymorphism at rs11128532 comprises an A allele at nucleoposition 26 within SEQ ID NO: 17.
76. The use of embodiment 31-58, wherein the polymorphism at rs177665 comprises a C allele at nucleoposition 26 within SEQ ID NO: 18.
77. The use of embodiment 31-58, wherein the polymorphism at rs11171747 comprises a C allele at nucleoposition 26 within SEQ ID NO: 19.
78. The use of embodiment 31-58, wherein the polymorphism at rs10775375 comprises an A allele at nucleoposition 26 within SEQ ID NO: 20.
79. The use of embodiment 31-58, wherein the polymorphism at rs6801634 comprises an A allele at nucleoposition 26 within SEQ ID NO: 21.
80. The use of embodiment 31-58, wherein the polymorphism at rs1070444 comprises an A allele at nucleoposition 26 within SEQ ID NO: 22.
81. The use of embodiment 31-58, wherein the polymorphism at rs116714418 comprises an A allele at nucleoposition 26 within SEQ ID NO: 23.
82. The use of embodiment 31-58, wherein the polymorphism at rs6962616 comprises an A allele at nucleoposition 26 within SEQ ID NO: 24.
83. The use of embodiment 31-58, wherein the polymorphism at rs7220814 comprises a G allele at nucleoposition 26 within SEQ ID NO: 25.
84. The use of embodiment 31-58, wherein the polymorphism at rs4325270 comprises a T allele at nucleoposition 26 within SEQ ID NO: 26.
85. The use of embodiment 31-58, wherein the polymorphism at rs768755 comprises a T allele at nucleoposition 26 within SEQ ID NO: 27.
86. The use of embodiment 31-58, wherein the polymorphism at rs17758350 comprises an A allele at nucleoposition 31 within SEQ ID NO: 28.
87. The use of embodiment 31-58, wherein the polymorphism at rs9480689 comprises a G allele at nucleoposition 26 within SEQ ID NO: 29.
88. The use of embodiment 31-58, wherein the polymorphism at rs525850 comprises an A allele at nucleoposition 26 within SEQ ID NO: 30.
89. The use of embodiment 31-58, wherein the polymorphism at rs4325270 comprises a T allele at nucleoposition 26 within SEQ ID NO: 31.
90. The use of embodiment 31-58, wherein the polymorphism at rs11749180 comprises an A allele at nucleoposition 26 within SEQ ID NO: 32.
91. wherein the polymorphism at rs6962616 comprises an A allele at nucleoposition 26 within SEQ ID NO: 33.
92. The use of embodiment 31-58, wherein the polymorphism at rs116714418 comprises an A allele at nucleoposition 26 within SEQ ID NO: 34.
93. The use of embodiment 31-58, wherein the polymorphism at rs10265554 comprises a G allele at nucleoposition 26 within SEQ ID NO: 35.

94. The use of embodiment 31-58, wherein the polymorphism at rs634641 comprises a G allele at nucleoposition 26 within SEQ ID NO: 36.
95. The use of embodiment 31-58, wherein the polymorphism at rs1493871 comprises a G allele at nucleoposition 26 within SEQ ID NO: 37.
96. The use of embodiment 31-58, wherein the polymorphism at rs12669698 comprises a G allele at nucleoposition 26 within SEQ ID NO: 38.
97. The use of embodiment 31-58, wherein the polymorphism at rs4332037 comprises an A allele at nucleoposition 26 within SEQ ID NO: 39.
98. The use of embodiment 31-58, wherein the polymorphism at rs17697480 comprises a G allele at nucleoposition 26 within SEQ ID NO: 40.
99. The use of embodiment 31-58, wherein the polymorphism at rs9480689 comprises a G allele at nucleoposition 26 within SEQ ID NO: 41.
100. The use of embodiment 31-58, wherein the polymorphism at rs6074737 comprises an A allele at nucleoposition 26 within SEQ ID NO: 42.
101. The use of embodiment 31-58, wherein the polymorphism at rs904910 comprises a G allele at nucleoposition 26 within SEQ ID NO: 43.
102. The use of embodiment 31-58, wherein the polymorphism at rs12972487 comprises an A allele at nucleoposition 26 within SEQ ID NO: 44.
103. The use of embodiment 31-58, wherein the polymorphism at rs445417 comprises an A allele at nucleoposition 26 within SEQ ID NO: 45.
104. The use of embodiment 31-58, wherein the polymorphism at rs635624 comprises a C allele at nucleoposition 26 within SEQ ID NO: 46.
105. The use of embodiment 31-58, wherein the polymorphism at rs7416358 comprises a G allele at nucleoposition 26 within SEQ ID NO: 47.
106. The use of embodiment 31-58, wherein the polymorphism at 12-54819630-G-INSERTION comprises an insertion of a G at nucleoposition 26 within SEQ ID NO: 48.
107. The use of embodiment 31-58, wherein the polymorphism at rs177665 comprises a C allele at nucleoposition 26 within SEQ ID NO: 49.
108. The use of embodiment 31-58, wherein the polymorphism at rs1070444 comprises an A allele at nucleoposition 26 within SEQ ID NO: 50.
109. The use of embodiment 31-58, wherein the polymorphism at rs10912583 comprises an A allele at nucleoposition 26 within SEQ ID NO: 51.
110. The use of embodiment 31-58, wherein the polymorphism at rs12914919 comprises a G allele at nucleoposition 26 within SEQ ID NO: 52.
111. The use of embodiment 31-58, wherein the polymorphism at rs2854725 comprises a C allele at nucleoposition 26 within SEQ ID NO: 53.
112. The use of embodiment 31-58, wherein the polymorphism at rs9480689 comprises a G allele at nucleoposition 26 within SEQ ID NO: 54.
113. The use of embodiment 31-58, wherein the polymorphism at rs71472147 comprises an A allele at nucleoposition 26 within SEQ ID NO: 55.
114. The use of embodiment 31-58, wherein the polymorphism at rs72939578 comprises an A allele at nucleoposition 31 within SEQ ID NO: 56.
115. The use of embodiment 31-58, wherein the polymorphism at rs658795 comprises an A allele at nucleoposition 26 within SEQ ID NO: 57.
116. The use of embodiment 31-58, wherein the polymorphism at rs17758350 comprises an A allele at nucleoposition 31 within SEQ ID NO: 58.
117. The use of embodiment 31-58, wherein the polymorphism at rs144260901 comprises an A allele at nucleoposition 31 within SEQ ID NO: 59.
118. The use of embodiment 31-58, wherein the polymorphism at rs10801129 comprises a C allele at nucleoposition 26 within SEQ ID NO: 60.
119. The use of embodiment 31-58, wherein the polymorphism at rs1702870 comprises an A allele at nucleoposition 26 within SEQ ID NO: 61.
120. The use of embodiment 31-58, wherein the polymorphism at rs10912583 comprises an A allele at nucleoposition 26 within SEQ ID NO: 62.
121. The use of embodiment 31-58, wherein the polymorphism at rs2452822 comprises a C allele at nucleoposition 31 within SEQ ID NO: 63.
122. The use of embodiment 31-58, wherein the polymorphism at rs7774349 comprises an A allele at nucleoposition 26 within SEQ ID NO: 64.
123. The use of embodiment 31-58, wherein the polymorphism at rs4705272 comprises a G allele at nucleoposition 26 within SEQ ID NO: 65.
124. The use of embodiment 31-58, wherein the polymorphism at rs117946479 comprises an A allele at nucleoposition 31 within SEQ ID NO: 66.
125. The use of embodiment 31-58, wherein the polymorphism at rs936126 comprises an A allele at nucleoposition 26 within SEQ ID NO: 67.
126. The use of embodiment 31-58, wherein the polymorphism at rs634641 comprises a G allele at nucleoposition 26 within SEQ ID NO: 68.
127. The use of embodiment 31-58, wherein the polymorphism at rs2314737 comprises a G allele at nucleoposition 26 within SEQ ID NO: 69.
128. The use of embodiment 31-58, wherein the polymorphism at rs3002685 comprises a G allele at nucleoposition 26 within SEQ ID NO: 70.
129. The use of embodiment 31-58, wherein the polymorphism at rs634641 comprises a G allele at nucleoposition 26 within SEQ ID NO: 71.
130. The use of embodiment 31-58, wherein the polymorphism at rs12496281 comprises a G allele at nucleoposition 26 within SEQ ID NO: 72.
131. The use of embodiment 31-58, wherein the polymorphism at rs10134119 comprises a T allele at nucleoposition 26 within SEQ ID NO: 73.
132. The use of embodiment 31-58, wherein the polymorphism at rs3808240 comprises a C allele at nucleoposition 26 within SEQ ID NO: 74.
133. The use of embodiment 31-58, wherein the polymorphism at rs1890843 comprises a G allele at nucleoposition 26 within SEQ ID NO: 75.
134. The use of embodiment 31-58, wherein the polymorphism at rs11829981 comprises an A allele at nucleoposition 26 within SEQ ID NO: 76.
135. The use of embodiment 31-58, wherein the polymorphism at rs12496281 comprises a G allele at nucleoposition 26 within SEQ ID NO: 77.
136. The use of embodiment 31-58, wherein the polymorphism at rs2383184 comprises a G allele at nucleoposition 26 within SEQ ID NO: 78.
137. The use of embodiment 31-58, wherein the polymorphism at rs144260901 comprises an A allele at nucleoposition 31 within SEQ ID NO: 79.

138. The use of embodiment 31-58, wherein the polymorphism at rs6801634 comprises an A allele at nucleoposition 26 within SEQ ID NO: 80.
139. The use of embodiment 31-58, wherein the polymorphism at rs2383184 comprises a G allele at nucleoposition 26 within SEQ ID NO: 81.
140. The use of embodiment 31-58, wherein the polymorphism at rs2954756 comprises a G allele at nucleoposition 26 within SEQ ID NO: 82.

EXAMPLES

The following examples are not intended to limit the scope of the claims to the invention, but are rather intended to be exemplary of certain embodiments. Any variations in the exemplified methods which occur to the skilled artisan are intended to fall within the scope of the present invention.

Example 1. Genotypic, Clinical, and Serological Associations with Severe CD

Identification of Genotypes Associated with Severe CD

1919 Caucasian patients with Crohn's disease (CD) were recruited at Inflammatory Bowel Disease Centers. The patient cohorts recruited are described in Table 3. A modified Montreal classification was used: non-stricturing/non-penetrating (B1): stricturing (B2a), stricturing and penetrating (B2b), and isolated internal penetrating (B3). Disease location was defined by the Montreal classification: ileal (L1), colonic (L2), ileocolonic (L3). The diagnosis of each patient was based on standard endoscopic, histologic, and radiographic features.

TABLE 3

Demographic Data of Study Cohort

| | B1 (n = 928) | B2a (n = 522) | B2b (n = 336) | B3 (n = 203) |
|---|---|---|---|---|
| Average Age, years (SD) | 40.71 (17.88) | 47.54 (16.69) | 45.20 (15.14) | 42.89 (15.36) |
| Male (%) | 51.72 | 51.34 | 54.76 | 54.68 |
| Average Age of Diagnosis, years (SD) | 25.99 (16.07) | 26.50 (14.36) | 23.55 (11.58) | 23.82 (11.82) |
| Mean Disease Duration, years (SD) | 14.51 (9.72) | 21.01 (12.27) | 21.66 (12.52) | 19.04 (11.54) |
| Disease Location (%) | | | | |
| Ileal (L1) | 13.78 | 27.20 | 24.15 | 14.87 |
| Colonic (L2) | 25.69 | 7.60 | 2.79 | 11.28 |
| Ileocolonic (L3) | 60.53 | 65.20 | 73.07 | 73.85 |
| Family History of IBD (%) | 69.10 | 67.40 | 66.98 | 68.75 |
| Early Steroid Use, <1 year of diagnosis (%) | 30.00 | 47.58 | 45.35 | 33.81 |
| Perianal involvement (%) | 27.97 | 39.73 | 29.25 | 35.43 |

Blood samples were collected from patients at the time of enrollment. Blood samples were also collected from individuals without CD. Genotyping was performed at Cedars-Sinai Medical Center using Illumina® (Illumina, Inc.) ImmunoChip on all samples collected. Case-control univariate analyses comparing stricturing (B2a), stricturing and penetrating (B2b), and isolated internal penetrating (B3) to non-stricturing/non-penetrating B1 at various disease locations were performed. Markers/SNPs were excluded from analysis if: there were deviations in Hardy-Weinberg Equilibrium in controls with p<1.0E-5; genotyping rate <95%; missingness in SNPs >2% and minor allele frequency <1%. Related individuals (Pi-hat scores >0.25) were identified using identity-by-descent and excluded from analysis (PLINK). Admixture was used to generate ethnicity proportion estimations for all individuals. Only subjects identified by admixture as Caucasian (proportion <0.75) were included in the analysis. Table 1 provides polymorphisms significantly associated with subclinical phenotypes of severe CD.

Disease Location is Associated with Severe Crohn's Disease

Severe Crohn's disease (CD) is characterized by a need to undergo surgical treatment. In addition, patients with severe CD typically experience a faster progression to a first surgery, and in some cases, a second surgery. Such surgical treatments include, but are not limited to strictureplasty and small bowel resection or removal. Disease location is associated with CD patient outcomes. For example, CD patients with stricturing disease in the ileum, as compared to the colon, statistically have poorer outcomes (e.g., faster progression to surgery) and a poorer quality of life. The predictive power of the PRS to identify CD patients who are at risk of developing severe forms of CD inform treatment regimens for these individuals that may include earlier interventions that are aggressive to prevent the onset of stricturing or penetrating disease.

To determine whether disease location (e.g., ileum (L1), ileocolonic region (L2), colon(L3)) is associated with a greater risk of developing severe CD, three polygenic risk score (PRS) were calculated for the subjects in the study cohort (Table 3) for inflammatory bowel disease (IBD), ulcerative colitis (UC) and CD. The PRS scores were calculated using the methods in Cleynen I, Boucher G, Jostins L, et al. Inherited determinants of Crohn's disease and ulcerative colitis phenotypes: a genetic association study. Lancet. 2016; 387(10014):156-167, involving known IBD, CD, and UC loci weighted for effect sizes. A linear regression between the PRS score versus the number of stricture-related surgeries in the patient cohort and incidences of stricturing (B2a) and stricturing and penetrating (B2b), were performed. The PRS was calculated, and results are summarized in Table 4.

TABLE 4

| Linear Regression: Polygenic Risk Score v. Number of Stricture-Related Surgeries | | | | | | |
|---|---|---|---|---|---|---|
| | Ileal (L1) | | Colonic (L2) | | Ileocolonic (L3) | |
| Variable | Beta | P | Beta | P | Beta | P |
| IBD PRS | 0.07 | 0.21 | 0.30 | 0.05 | 0.06 | 0.24 |
| UC PRS | 0.06 | 0.32 | −0.32 | 0.04 | −0.04 | 0.45 |
| CD PRS | 0.08 | 0.20 | 0.34 | 0.03 | 0.10 | 0.05 |

The CD PRS was associated with stricturing (p=0.012, OR 1.20). The CD PRS was associated with need for stricture-related surgeries (p=0.0117, OR 1.28) in L3. The CD PRS was also associated with number of stricture-related surgeries in L2 (p=0.0264, beta (b): 0.34) and L3 (p=0.0475, b: 0.102) locations. In L2, UC PRS was protective of stricturing (p=0.0184, OR 0.662) and number of stricture-related surgeries (p=0.045, b: −0.318). These findings suggest that CD patients with a high CD PRS may benefit from an earlier and more aggressive treatment regiment, than CD patients with a high UC PRS.

Identifying Serological Markers Associated with Severe CD

The blood samples collected from the patient cohort from Table 3 were processed to isolate the blood plasma. Serological marker levels were measured using an enzyme-linked immunosorbent assay (ELISA) in the plasma using monoclonal antibodies specific to the serological marker or antigen thereof. Antibodies against *Saccharomyces cerevisiae* antibody, neutrophil cytoplasmic antibody (ANCA), antibodies against *E. coli* outer membrane porin protein C (anti-OmpC), antibodies against 12, and antibodies against Cbir1 flagellin antibody were used. Quartile sum scores (QSS) were calculated for the serologies using methods provided in Landers C J, Cohavy O, Misra R. et al., Selected loss of tolerance evidenced by Crohn's disease-associated immune responses to auto- and microbial antigens. Gastroenterology (2002)123689-699. A logistic regression analysis was performed to look at an association between stricturing disease (B2a)/stricturing and penetrating (B2b) and quartile sum score. The results are provided in Table 5.

Stricturing was associated with ASCA seropositivity in Li and L3 (p<0.001, OR 1.97-3.2). Stricturing was also associated with ASCA in L2 (p=0.002'7, OR 2.44). Higher QSS (p<0.01, OR 1.15-1.22) was associated with stricturing in all three locations. In L3, ANCA seropositivity was associated with Bi (p=2.76E-5, OR 0.52). ASCA seropositivity (p=1.5E-5, OR 2.47) and elevated QSS (p=1.6E-6, OR 1.19) were associated with B3 behavior in L3. In L2, stricturing was associated with perianal disease (p<0.006, OR 3.78). Without wishing to be bound my any particular theory, these findings suggest that certain serological markers can be used as predictors of severe forms of CD characterized by stricturing or penetrating disease phenotypes in various disease locations. For example, ASCA may be used to predict stricturing disease in the ileal region of the intestine, which is associated with poorer patient outcomes and quality of life. Such a patient may benefit from an earlier and more aggressive treatment strategy.

Logistic Regression Analysis: Stricturing Disease v. Multiple Variables

Multiple logistic regression analyses were performed, looking at the association between stricturing disease (B2a)/stricturing and penetrating (B2b) and multiple variables in Table 6. Family history of IBD did not have a statistically significant association with stricturing disease in any disease locations. Similarly, CD patients with high UC PRS have a lower probability of developing colonic stricturing and ileocolonic stricturing, as compared with ileal stricturing. In contrast, perianal involvement was associated with stricturing in colonic CD. The term "perianal involvement" refers to perianal disease, which is a disease that affects the tissue around of the anus or the rectum of a patient that has been diagnosed using standard endoscopic, histologic, and radiographic features. "PRS" means polygenic risk score. "OR" refers to the odds ratio. "CI" refers to the confidence interval.

TABLE 5

| Serology Association with Stricturing Disease by Disease Location | | | | | | |
|---|---|---|---|---|---|---|
| | Ileal (L1) | | Colonic (L2) | | Ileocolonic (L3) | |
| Variable | p | OR [95% CI] | p | OR [95% CI] | p | OR [95% CI] |
| ANCA Seropositivity | 0.6384 | 0.73 [0.36-1.58] | 0.3865 | 0.75 [4.23-1.30] | 0.0009 | 0.56 [0.41-0.77] |
| Anti-Cbir Seropositivity | 0.2808 | 1.47 [0.91-2.40] | 0.0688 | 1.84 [1.04-3.24] | 0.0037 | 1.53 [1.17-2.01] |
| Anti-I2 Seropositivity | 0.0207 | 2.97 [1.44-6.61] | 0.1755 | 1.65 [0.88-3.11] | 1.08E−06 | 2.34 [1.69-3.25] |
| Anti-Ompc Seropositivity | 0.0168 | 3.49 [1.64-8.62] | 0.1216 | 1.73 [0.937-3.17] | 0.0002 | 1.88 [1.38-2.58] |
| ASCA Seropositivity | 0.02071 | 2.005 [1.22-3.31] | 0.0128 | 2.44 [1.36-4.38] | 5.81E−13 | 2.89 [2.19-3.82] |
| Quartile Sum Score | 0.0007 | 1.17 [1.072-1.29] | 0.0025 | 1.15 [1.052-1.27] | 2.48E−16 | 1.22 [1.16-1.28] |

TABLE 6

| Summary of Clinical and Genetic Associations with Stricturing CD by Disease Location | | | | | | |
|---|---|---|---|---|---|---|
| | Ileal (L1) | | Colonic (L2) | | Ileocolonic (L3) | |
| Variable | p | OR [95% CI] | p | OR [95% CI] | p | OR [95% CI] |
| Early Steroid Use | 0.9900 | 7.6e7 [0-NA] | 0.9920 | 1.13e8 [0-NA] | 0.2983 | 1.79 [0.643-5.44] |
| Family History of IBD | 0.8328 | 0.90 [0.57-1.44] | 0.3865 | 0.74 [0.41-1.30] | 0.0833 | 1.33 [1.01-1.77] |
| Perianal Involvement | 0.9496 | 0.96 [0.48-2.05] | 0.0017 | 3.78 [1.86-7.85] | 0.2040 | 1.27 [0.91-1.80] |
| PRS for all IBD | 0.8749 | 0.97 [0.75-1.25] | 0.2245 | 1.23 [0.923-1.66] | 0.4343 | 1.06 [0.925-1.21] |
| PRS for Ulcerative colitis | 0.8328 | 0.94 [0.74-1.19] | 0.0184 | 0.662 [0.49-0.875] | 0.0058 | 0.82 [0.72-0.94] |
| PRS for Crohn's disease | 0.8328 | 0.954 [0.753-1.21] | 0.0688 | 1.38 [1.03-1.87] | 0.0176 | 1.20 [1.04-1.38] |

Example 2. Pathway Enrichment Analysis

To determine which molecular pathways play a role in severe CD, a pathway analysis tool (Ingenuity Pathway Analysis) was used on polymorphisms detected in Example 1 (P<0.05), positive for an association with stricturing (B2a), stricturing and penetrating (B2b), or isolated internal penetrating (B3), was performed. Enriched pathways included Prolactin Signaling (p=1.86E-3) and Autophagy (p=2.20E-3), which are both involved in CD and Janus Kinase 2 (JAK2)/Signal Transducer and Transcription Activator (STAT) activation. Table 7 provides the results from this study.

TABLE 7

| Pathway Enrichment Analysis | |
|---|---|
| Top Canonical Pathways | P Value |
| T Helper Cell Differentiation | 6.40E−05 |
| Th1 and Th2 Activation Pathway | 1.81E−03 |
| Prolactin Signaling | 1.86E−03 |
| Autophagy | 2.20E−03 |
| Protein Kinase A Signaling | 2.97E−03 |
| Crosstalk between Dendritic Cells and Natural Killer Cells | 3.18E−03 |
| GP6 Signaling Pathway | 3.99E−03 |
| Th1 Pathway | 4.70E−03 |
| Th2 Pathway | 4.82E−03 |
| Sonic Hedgehog Signaling | 5.59E−03 |

Genes involved in the enriched Prolactin Signaling include IRF1, KLB, MAP2K1, NR3C1, PRKCB, PRKCE, PRKCG, PRKCH, PRKCQ, PRLR, PTPN11, STAT1, STAT5A, and STAT5B. Genes involved in the enriched Autophagy include ATG10, ATG16L1, ATG4A, ATG4C, CTSH, SQSTM1, ULK1, WDFY3. Without being bound by any particular theory, these findings suggestion that a therapeutic strategy targeting the genes, or gene expression products expressed from these genes may be appropriate for patients selected using genotypes associated with B2a, B2b, and B3.

Example 3. Treating Severe Crohn's Disease

An inflammatory disease is treated in a subject, by first, determining a genotype comprising a polymorphism selected from Table 1, or selected from the group consisting of rs7416358G, rs1070444A, rs11749180A, 12-54819630-G-INSERTION, rs12496281G, rs11171747C, rs116714418A, rs111455641G, rs9480689G, rs6879067A, rs11128532A, rs177665C, rs10775375A, rs6801634A, rs6962616A, rs7220814G, rs4325270T, rs768755T, rs17758350A, rs9480689G, rs525850A, rs4325270T, rs6962616A, rs10265554G, rs634641G, rs1493871G, rs12669698G, rs4332037A, rs176974806G, rs9480689G, rs6074737A, rs904910G, rs12972487A, rs445417A, rs63562C, rs7416358G, rs177665C, rs1070444A, rs10912583A, rs12914919G, rs2854725C, rs9480689G, rs71472147A, rs72939578A, rs658795A, rs17758350A, rs144260901A, rs10801129C, rs1702870A, rs10912583A, rs2452822C, rs7774349A, rs4705272G, rs117946479A, rs936126A, rs634641G, rs2314737G, rs3002685G, rs634641G, rs10134119T, rs3808240C, rs1890843G, and rs11829981A. Optionally, the subject is, or is susceptible to be, non-responsive to certain therapies such as anti-TNF, steroids, or immunomodulators, such as those disclosed herein. A sample of whole blood is obtained from the subject. An assay is performed on the sample obtained from the subject to detect a presence or absence of the genotype by Illumina® (Illumina, Inc.) ImmunoArray or polymerase chain reaction (PCR) under standard hybridization conditions. In addition, or alternatively, a sample of intestinal tissue is obtained from the subject. In addition, or alternatively, a sample of blood plasma is obtained from the subject. An assay is performed on the sample obtained from the subject to detect a presence of a serological marker selected from the group consisting of ASCA, ANCA, anti-OmpC antibody, anti-I2 antibody, or anti-Cbir1 antibody by ELISA accordingly to manufacture instructions.

The subject is determined to have, or be at risk for developing, a severe form of Crohn's disease if the genotype and/or the serological marker is detected in the sample obtained from the subject. A therapeutically effective amount of an a therapeutic agent disclosed herein is administered to the subject, provided the subject is determined to have the genotype and/or serological marker.

Example 4. Phase 1A Clinical Trial

A phase 1 clinical trial is performed to evaluate the safety, tolerability, pharmacokinetics and pharmacodynamics of an therapeutic agent in subjects with Crohn's disease having a genotype comprising at least one polymorphism selected from the group consisting of rs7416358G, rs1070444A, rs11749180A, 12-54819630-G-INSERTION, rs12496281G, rs11171747C, rs116714418A, rs111455641G, rs9480689G, rs6879067A, rs11128532A, rs177665C, rs10775375A, rs6801634A, rs6962616A, rs7220814G, rs4325270T, rs768755T, rs17758350A, rs9480689G, rs525850A, rs4325270T, rs6962616A, rs10265554G, rs634641G, rs1493871G, rs12669698G, rs4332037A, rs17697480G, rs9480689G, rs6074737A, rs904910G, rs12972487A, rs445417A, rs63562C, rs7416358G, rs177665C, rs1070444A, rs10912583A, rs12914919G, rs2854725C, rs9480689G, rs71472147A, rs72939578A, rs658795A, rs17758350A, rs144260901A, rs10801129C, rs1702870A, rs10912583A, rs2452822C, rs7774349A, rs4705272G, rs117946479A, rs936126A, rs634641G, rs2314737G, rs3002685G, rs634641G, rs10134119T, rs3808240C, rs1890843G, and rs11829981A.

Single ascending dose (SAD) arms: Subjects in each group (subjects are grouped based on the presence or absence of the genotype) receive either a single dose of the antibody or a placebo. Exemplary doses are 1, 3, 10, 30, 100, 300, 600 and 800 mg of antibody. Safety monitoring and PK assessments are performed for a predetermined time. Based on evaluation of the PK data, and if the antibody is deemed to be well tolerated, dose escalation occurs, either within the same groups or a further group of healthy subjects. Dose escalation continues until the maximum dose has been attained unless predefined maximum exposure is reached or intolerable side effects become apparent.

Multiple ascending dose (MAD) arms: Subjects in each group (subjects are grouped based on the presence or absence of the genotype) receive multiple doses of the antibody or a placebo. The dose levels and dosing intervals are selected as those that are predicted to be safe from the SAD data. Dose levels and dosing frequency are chosen to achieve therapeutic drug levels within the systemic circulation that are maintained at steady state for several days to allow appropriate safety parameters to be monitored. Samples are collected and analyzed to determination PK profiles.

Inclusion Criteria: Subjects of non-childbearing potential between the ages of 18 and 55 years having obstructive Crohn's disease. Female subjects of non-childbearing potential must meet at least one of the following criteria: (1) achieved postmenopausal status, defined as: cessation of regular menses for at least 12 consecutive months with no alternative pathological or physiological cause; and have a serum follicle stimulating hormone (FSH) level within the laboratory's reference range for postmenopausal females; (2) have undergone a documented hysterectomy and/or bilateral oophorectomy; (3) have medically confirmed ovarian failure. All other female subjects (including females with tubal ligations and females that do not have a documented hysterectomy, bilateral oophorectomy and/or ovarian failure) will be considered to be of childbearing potential. Body Mass Index (BMI) of 17.5 to 30.5 kg/m2; and a total body weight >50 kg (110 lbs). Evidence of a personally signed and dated informed consent document indicating that the subject (or a legal representative) has been informed of all pertinent aspects of the study.

Two groups of subjects are selected: subjects having the genotype, and subjects lacking the genotype.

Exclusion Criteria: Evidence or history of clinically significant hematological, renal, endocrine, pulmonary, gastrointestinal, cardiovascular, hepatic, psychiatric, neurologic, or allergic disease (including drug allergies, but excluding untreated, asymptomatic, seasonal allergies at time of dosing) or than Crohn's disease. Subjects with a history of or current positive results for any of the following serological tests: Hepatitis B surface antigen (HBsAg), Hepatitis B core antibody (HBcAb), anti-Hepatitis C antibody (HCV Ab) or human immunodeficiency virus (HIV). Subjects with a history of allergic or anaphylactic reaction to a therapeutic drug. Treatment with an investigational drug within 30 days (or as determined by the local requirement, whichever is longer) or 5 half-lives or 180 days for biologics preceding the first dose of study medication. Pregnant females; breastfeeding females; and females of childbearing potential.

Primary Outcome Measures: Incidence of dose limiting or intolerability treatment related adverse events (AEs) [Time Frame: 12 weeks]. Incidence, severity and causal relationship of treatment emergent AEs (TEAEs) and withdrawals due to treatment emergent adverse events [Time Frame: 12 weeks]. Incidence and magnitude of abnormal laboratory findings [Time Frame: 12 weeks]. Abnormal and clinically relevant changes in vital signs, blood pressure (BP) and electrocardiogram (ECG) parameters [Time Frame: 12 weeks].

Secondary Outcome Measures:

Single Ascending Dose: Maximum Observed Plasma Concentration (Cmax) [Time Frame: 12 weeks]. Single Ascending Dose: Time to Reach Maximum Observed Plasma Concentration (Tmax) [Time Frame: 12 weeks]. Single Ascending Dose: Area under the plasma concentration-time profile from time zero to 14 days (AUC14 days) [Time Frame: 12 weeks]. Single Ascending Dose: Area under the plasma concentration-time profile from time zero extrapolated to infinite time (AUCinf) [Time Frame: 12 weeks]. Single Ascending Dose: Area under the plasma concentration-time profile from time zero to the time of last quantifiable concentration (AUClast) [Time Frame: 12 weeks]. Single Ascending Dose: Dose normalized maximum plasma concentration (Cmax[dn]) [Time Frame: 12 weeks]. Single Ascending Dose: Dose normalized area under the plasma concentration-time profile from time zero extrapolated to infinite time (AUCinf[dn]) [Time Frame: 12 weeks]. Single Ascending Dose: Dose normalized area under the plasma concentration-time profile from time zero to the time of last quantifiable concentration (AUClast[dn]) [Time Frame: 12 weeks]. Single Ascending Dose: Plasma Decay Half-Life (t½) [Time Frame: 12 weeks]. Plasma decay half-life is the time measured for the plasma concentration to decrease by one half Single Ascending Dose: Mean residence time (MRT) [Time Frame: 12 weeks]. Single Ascending Dose: Volume of Distribution at Steady State (Vss) [Time Frame: 6 weeks]. Volume of distribution is defined as the theoretical volume in which the total amount of drug would need to be uniformly distributed to produce the desired blood concentration of a drug. Steady state volume of distribution (Vss) is the apparent volume of distribution at steady-state. Single Ascending Dose: Systemic Clearance (CL) [Time Frame: 6]. CL is a quantitative measure of the rate at which a drug substance is removed from the body.

Multiple Ascending Dose First Dose: Maximum Observed Plasma Concentration (Cmax) [Time Frame: 12 weeks]. Multiple Ascending Dose First Dose: Time to Reach Maximum Observed Plasma Concentration (Tmax) [Time Frame: 12 weeks]. Multiple Ascending Dose First Dose: Area under the plasma concentration-time profile from time zero to time $\tau$, the dosing interval where $\tau$=2 weeks (AUC$\tau$) [Time Frame: 12 weeks]. Multiple Ascending Dose First Dose: Dose normalized maximum plasma concentration (Cmax[dn]) [Time Frame: 12 weeks]. Multiple Ascending Dose First Dose: Dose normalized Area under the plasma concentration-time profile from time zero to time $\tau$, the dosing interval where $\tau$=2 weeks (AUC$\tau$ [dn]) [Time Frame: 12 weeks]. Plasma Decay Half-Life (t½) [Time Frame: 12 weeks]. Plasma decay half-life is the time measured for the plasma concentration to decrease by one half Multiple Ascending Dose First Dose: Mean residence time (MRT) [Time Frame: 12 weeks]. Apparent Volume of Distribution (Vz/F) [Time Frame: 12 weeks]. Volume of distribution is defined as the theoretical volume in which the total amount of drug would need to be uniformly distributed to produce the desired plasma concentration of a drug. Apparent volume of distribution after oral dose (Vz/F) is influenced by the fraction absorbed. Multiple Ascending Dose First Dose: Volume of Distribution at Steady State (Vss) [Time Frame: 12 weeks]. Volume of distribution is defined as the theoretical volume in which the total amount of drug would need to be uniformly distributed to produce the desired blood concentration of a drug. Steady state volume of distribution (Vss) is the apparent volume of distribution at steady-state. Multiple Ascending Dose First Dose: Apparent Oral Clearance (CL/F) [Time Frame: 12 weeks]. Clearance of a drug is a measure of the rate at which a drug is metabolized or eliminated by normal biological processes. Clearance obtained after oral dose (apparent oral clearance) is influenced by the fraction of the dose absorbed. Clearance is estimated from population pharmacokinetic (PK) modeling. Drug clearance is a quantitative measure of the rate at which a drug substance is removed from the blood. Multiple Ascending Dose First Dose: Systemic Clearance (CL) [Time Frame: 12 weeks]. CL is a quantitative measure of the rate at which a drug substance is removed from the body.

Multiple Ascending Dose Multiple Dose: Maximum Observed Plasma Concentration (Cmax) [Time Frame: 12 weeks]. Multiple Ascending Dose Multiple Dose: Time to Reach Maximum Observed Plasma Concentration (Tmax) [Time Frame: 12 weeks]. Multiple Ascending Dose Multiple Dose: Area under the plasma concentration-time profile from time zero to time τ, the dosing interval where $\tau=^2$ weeks (AUCτ) [Time Frame: 12 weeks]. Multiple Ascending Dose Multiple Dose: Dose normalized maximum plasma concentration (Cmax[dn]) [Time Frame: 12 weeks]. Multiple Ascending Dose Multiple Dose: Dose normalized Area under the plasma concentration-time profile from time zero to time τ, the dosing interval where τ=2 weeks (AUCτ [dn]) [Time Frame: 12 weeks]. Multiple Ascending Dose Multiple Dose: Plasma Decay Half-Life (t½) [Time Frame: 12 weeks]. Plasma decay half-life is the time measured for the plasma concentration to decrease by one half. Multiple Ascending Dose Multiple Dose: Apparent Volume of Distribution (Vz/F) [Time Frame: 12 weeks]. Volume of distribution is defined as the theoretical volume in which the total amount of drug would need to be uniformly distributed to produce the desired plasma concentration of a drug. Apparent volume of distribution after oral dose (Vz/F) is influenced by the fraction absorbed. Multiple Ascending Dose Multiple Dose: Volume of Distribution at Steady State (Vss) [Time Frame: 12 weeks]. Volume of distribution is defined as the theoretical volume in which the total amount of drug would need to be uniformly distributed to produce the desired blood concentration of a drug. Steady state volume of distribution (Vss) is the apparent volume of distribution at steady-state.

Multiple Ascending Dose Multiple Dose: Apparent Oral Clearance (CL/F) [Time Frame: 12 weeks]. Clearance of a drug is a measure of the rate at which a drug is metabolized or eliminated by normal biological processes. Clearance obtained after oral dose (apparent oral clearance) is influenced by the fraction of the dose absorbed. Clearance was estimated from population pharmacokinetic (PK) modeling. Drug clearance is a quantitative measure of the rate at which a drug substance is removed from the blood. Multiple Ascending Dose Multiple Dose: Systemic Clearance (CL) [Time Frame: 12 weeks]. CL is a quantitative measure of the rate at which a drug substance is removed from the body. Multiple Ascending Dose Multiple Dose: Minimum Observed Plasma Trough Concentration (Cmin) [Time Frame: 12 weeks]. Multiple Ascending Dose Multiple Dose: Average concentration at steady state (Cav) [Time Frame: 12 weeks]. Multiple Ascending Dose Multiple Dose: Observed accumulation ratio (Rac) [Time Frame: 12 weeks]. Multiple Ascending Dose Multiple Dose: Peak to trough fluctuation (PTF) [Time Frame: 12 weeks]. Multiple Ascending Dose Additional Parameter: estimate of bioavailability (F) for subcutaneous administration at the corresponding intravenous dose [Time Frame: 12 weeks]. Immunogenicity for both Single Ascending Dose and Multiple Ascending Dose: Development of anti-drug antibodies (ADA) [Time Frame: 12 weeks].

Example 5: Phase 1B Clinical Trial

A phase 1b open label clinical trial is performed to evaluate efficacy of an therapeutic agent on CD patients having a genotype comprising at least one polymorphism selected from the group consisting of rs7416358G, rs1070444A, rs11749180A, 12-54819630-G-INSERTION, rs12496281G, rs11171747C, rs116714418A, rs111455641G, rs9480689G, rs6879067A, rs11128532A, rs177665C, rs10775375A, rs6801634A, rs6962616A, rs7220814G, rs4325270T, rs768755T, rs17758350A, rs9480689G, rs525850A, rs4325270T, rs6962616A, rs10265554G, rs634641G, rs1493871G, rs12669698G, rs4332037A, rs17697480G, rs9480689G, rs6074737A, rs904910G, rs12972487A, rs445417A, rs63562C, rs7416358G, rs177665C, rs1070444A, rs10912583A, rs12914919G, rs2854725C, rs9480689G, rs71472147A, rs72939578A, rs658795A, rs17758350A, rs144260901A, rs10801129C, rs1702870A, rs10912583A, rs2452822C, rs7774349A, rs4705272G, rs117946479A, rs936126A, rs634641G, rs2314737G, rs3002685G, rs634641G, rs10134119T, rs3808240C, rs1890843G, and rs11829981A. Arms: 10 patients positive for rs911605A are administered the antibody. 5-10 patients negative for the genotype are administered the antibody. Patients are monitored in real-time. Central ready of endoscopy and biopsy is employed, with readers blinded to point of time of treatment and endpoints.

Inclusion Criteria: Two groups of subjects are selected: subjects having the genotype, and subjects lacking the genotype.

Primary Outcome Measures: Simple Endoscopic Score for Crohn's Disease (SESCD), Crohn's Disease Activity Index (CDAI), and Patient Reported Outcome (PRO). If the genotype positive group shows 50% reduction from baseline, a Phase 2a clinical trial is performed.

Inclusion Criteria: PRO entry criteria: Abdominal pain score of 2 or more and/or stool frequency score of 4 or more. Primary outcome would be pain core of 0 or 1 and stool frequency score of 3 or less with no worsening from baseline. Endoscopy entry criteria: SESCD ileum only entry at score of 4 and 6 if colon is involved. Primary endoscopic outcome is 40-50% delta of mean SESCD.

Example 6: Phase 2A Clinical Trial

A phase 2a clinical trial is performed to evaluate efficacy of an therapeutic agent on CD patients having a genotype comprising at least one polymorphism selected from the group consisting of rs7416358G, rs1070444A, rs11749180A, 12-54819630-G-INSERTION, rs12496281G, rs11171747C, rs116714418A, rs111455641G, rs9480689G, rs6879067A, rs11128532A, rs177665C, rs10775375A, rs6801634A, rs6962616A, rs7220814G, rs4325270T, rs768755T, rs17758350A, rs9480689G, rs525850A, rs4325270T, rs6962616A, rs10265554G, rs634641G, rs1493871G, rs12669698G, rs4332037A, rs17697480G, rs9480689G, rs6074737A, rs904910G, rs12972487A, rs445417A, rs63562C, rs7416358G, rs177665C, rs1070444A, rs10912583A, rs12914919G, rs2854725C, rs9480689G, rs71472147A, rs72939578A, rs658795A, rs17758350A, rs144260901A, rs10801129C, rs1702870A, rs10912583A, rs2452822C, rs7774349A, rs4705272G, rs117946479A, rs936126A, rs634641G, rs2314737G, rs3002685G, rs634641G, rs10134119T, rs3808240C, rs1890843G, and rs11829981A.

Arms: 40 patients per arm (antibody and placebo arms) are treated with antibody or placebo for 12 weeks. An interim analysis is performed after 20 patients from each group are treated at the highest dose to look for a 40-50% delta between placebo and treated group in primary outcome (50% reduction from baseline in SESCD, CDAI, and PRO).

Primary Outcome Measures: Simple Endoscopic Score for Crohn's Disease (SESCD), Crohn's Disease Activity Index (CDAI), and Patient Reported Outcome (PRO).

Inclusion Criteria: PRO entry criteria: Abdominal pain score of 2 or more and/or stool frequency score of 4 or more. Primary outcome would be pain core of 0 or 1 and stool frequency score of 3 or less with no worsening from baseline. Endoscopy entry criteria: SESCD ileum only entry at score of 4 and 6 if colon is involved. Primary endoscopic outcome is 40-50% delta of mean SESCD.

While preferred embodiments have been shown and described herein, it will be obvious to those skilled in the art that such embodiments are provided by way of example only. Numerous variations, changes, and substitutions will occur to those skilled in the art without departing from the scope of this application. Various alternatives to the embodiments described herein may be employed in practicing the scope of this application.

While preferred embodiments of the present examples have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

The invention claimed is:

1. A method of treating Crohn's disease (CD) in a subject, the method comprising administering to the subject a therapeutically effective amount of an anti-tumor necrosis factor ligand 1A (anti-TL1A) antibody, wherein the subject has at least one polymorphism selected from the group consisting of rs112668709A, rs66863235G, rs570462G, rs568675G, rs476148A, rs474188C, rs1579609G, rs1579610C, rs9402929G, rs6722613G, rs11161618A, rs17456596G, rs177665C, rs2314737G, rs351758A, rs4325270T, rs445417A, rs525850A, rs6074737A, rs635624C, rs658795A, rs666478G, rs684093G, rs7130717G, rs7416358G, rs768755T, rs7774349A, and rs936126A, and wherein the subject has non-stricturing and non-penetrating CD, and wherein the anti-TL1A antibody comprises a heavy chain variable domain comprising the amino acid sequence of SEQ ID NO: 356 and a light chain variable domain comprising the amino acid sequence of SEQ ID NO: 357.

2. The method of claim 1, wherein the at least one polymorphism is selected from the group consisting of rs525850A, rs570462G, rs568675G, rs658795A, rs476148A, rs474188C, rs6722613G, rs17456596G, rs2314737G, rs445417A, rs635624C, rs666478G, rs684093G, rs7130717G, and rs936126A.

3. The method of claim 1, wherein the polymorphism is detected by a process comprising:

a) contacting a sample obtained from the subject with a nucleic acid sequence comprising a detectable moiety, wherein the nucleic acid sequence is capable of hybridizing to at least 20 contiguous nucleobases between nucleobase 16 and nucleobase 46 of at least one of SEQ ID NOS: 13-82; and b) detecting binding between the nucleic acid sequence and the at least 20 contiguous nucleobases between nucleobase 16 and nucleobase 46 of at least one of SEQ ID NOS: 13-82.

4. The method of claim 1, wherein the polymorphism is detected by sequencing genetic information contained in a sample obtained from the subject.

5. The method of claim 1, wherein the at least one polymorphism comprises at least two polymorphisms selected from the group consisting of rs112668709A, rs66863235G, rs570462G, rs568675G, rs476148A, rs474188C, rs1579609G, rs1579610C, rs9402929G, rs6722613G, rs11161618A, rs17456596G, rs177665C, rs2314737G, rs351758A, rs4325270T, rs445417A, rs525850A, rs6074737A, rs635624C, rs658795A, rs666478G, rs684093G, rs7130717G, rs7416358G, rs768755T, rs7774349A, and rs936126A.

6. The method of claim 5, wherein the at least one polymorphism comprises three or more polymorphisms selected from the group consisting of rs112668709A, rs66863235G, rs570462G, rs568675G, rs476148A, rs474188C, rs1579609G, rs1579610C, rs9402929G, rs6722613G, rs11161618A, rs17456596G, rs177665C, rs2314737G, rs351758A, rs4325270T, rs445417A, rs525850A, rs6074737A, rs635624C, rs658795A, rs666478G, rs684093G, rs7130717G, rs7416358G, rs768755T, rs7774349A, and rs936126A.

7. The method of claim 1, wherein the CD is located in the ileal region of the subject.

8. The method of claim 7, wherein the at least one polymorphism comprises one or more polymorphisms selected from the group consisting of rs936126A, rs570462G, rs568675G, rs658795A, rs476148A, and rs474188C.

9. The method of claim 1, wherein the CD is located in the ileocolonic region of the subject.

10. The method of claim 9, wherein the at least one polymorphism further comprises one or both of rs2314737G and rs445417A.

11. The method of claim 1, wherein the CD is located in the colonic region of the subject.

12. The method of claim 11, wherein the at least one polymorphism further comprises one or more of rs635624C, rs684093G, and rs6722613G.

13. The method of claim 1, wherein the subject has seropositivity for one or more of anti-flagellin, anti-I2, anti-*Escherichia coli* outer membrane porin C, and anti-*Saccharomyces cerevisiae*.

14. The method of claim 1, wherein the CD is CD with perianal involvement.

15. The method of claim 14, wherein the CD is located in the colonic region of the subject.

16. The method of claim 1, wherein the CD is located in the ileal region, ileocolonic region, or colonic region of the subject.

* * * * *

SEQUENCE LISTING

```
<160> NUMBER OF SEQ ID NOS: 875

<210> SEQ ID NO 1
<211> LENGTH: 51
<212> TYPE: DNA
<213> ORGANISM: Homo sapiens
<220> FEATURE:
<221> NAME/KEY: modified_base
<222> LOCATION: (26)..(26)
<223> OTHER INFORMATION: a, c, t, g, unknown or other

<400> SEQUENCE: 1

gcaatttcgt aacagaggta taatcncttg ctctcaaccg tatagactgg g            51


<210> SEQ ID NO 2
<211> LENGTH: 51
<212> TYPE: DNA
<213> ORGANISM: Homo sapiens
<220> FEATURE:
<221> NAME/KEY: modified_base
<222> LOCATION: (26)..(26)
<223> OTHER INFORMATION: a, c, t, g, unknown or other

<400> SEQUENCE: 2

tgtgtttcaa tatttccatg tctttntgct tcaaatatgc ttcttataaa t            51


<210> SEQ ID NO 3
<211> LENGTH: 51
<212> TYPE: DNA
<213> ORGANISM: Homo sapiens
<220> FEATURE:
<221> NAME/KEY: modified_base
<222> LOCATION: (26)..(26)
<223> OTHER INFORMATION: a, c, t, g, unknown or other

<400> SEQUENCE: 3

cactgtttga aaattgagag actgcncatc aaaatctaga gttccagtta c            51
```

<210> SEQ ID NO 4
<211> LENGTH: 51
<212> TYPE: DNA
<213> ORGANISM: Homo sapiens
<220> FEATURE:
<221> NAME/KEY: modified_base
<222> LOCATION: (26)..(26)
<223> OTHER INFORMATION: a, c, t, g, unknown or other

<400> SEQUENCE: 4
ggtttagtag agtcttttca acaatngagt ttccagcctt atgcccaagc t 51

<210> SEQ ID NO 5
<211> LENGTH: 51
<212> TYPE: DNA
<213> ORGANISM: Homo sapiens
<220> FEATURE:
<221> NAME/KEY: modified_base
<222> LOCATION: (26)..(26)
<223> OTHER INFORMATION: a, c, t, g, unknown or other

<400> SEQUENCE: 5
agcaggtaac ctagaaggtg aaattnaggt cagaaatttc aactggcttt g 51

<210> SEQ ID NO 6
<211> LENGTH: 51
<212> TYPE: DNA
<213> ORGANISM: Homo sapiens
<220> FEATURE:
<221> NAME/KEY: modified_base
<222> LOCATION: (26)..(26)
<223> OTHER INFORMATION: a, c, t, g, unknown or other

<400> SEQUENCE: 6
acaaaattat gtatatagtg tgaccncatt tgcttaaaaa atatatatgt a 51

<210> SEQ ID NO 7
<211> LENGTH: 51
<212> TYPE: DNA
<213> ORGANISM: Homo sapiens
<220> FEATURE:
<221> NAME/KEY: modified_base
<222> LOCATION: (26)..(26)
<223> OTHER INFORMATION: a, c, t, g, unknown or other

<400> SEQUENCE: 7
acagatgcac tacatctttg ctaccntagt agagaaaata tctcagatat g 51

<210> SEQ ID NO 8
<211> LENGTH: 51
<212> TYPE: DNA
<213> ORGANISM: Homo sapiens
<220> FEATURE:
<221> NAME/KEY: modified_base
<222> LOCATION: (26)..(26)
<223> OTHER INFORMATION: a, c, t, g, unknown or other

<400> SEQUENCE: 8
tggtggccct gttggcatta ctgggnagag cttgcctgag aataaaatca c 51

<210> SEQ ID NO 9
<211> LENGTH: 51
<212> TYPE: DNA
<213> ORGANISM: Homo sapiens
<220> FEATURE:
<221> NAME/KEY: modified_base
<222> LOCATION: (26)..(26)
<223> OTHER INFORMATION: a, c, t, g, unknown or other

<400> SEQUENCE: 9
actggccaag taaccacaga catggncctt cttcacactg agtccacctg c 51

<210> SEQ ID NO 10
<211> LENGTH: 51
<212> TYPE: DNA
<213> ORGANISM: Homo sapiens
<220> FEATURE:
<221> NAME/KEY: modified_base
<222> LOCATION: (26)..(26)
<223> OTHER INFORMATION: a, c, t, g, unknown or other

<400> SEQUENCE: 10
tttcccatct taaccaaggt cctgcngtcc ggcaggtcta tgctgggggt t 51

<210> SEQ ID NO 11
<211> LENGTH: 51
<212> TYPE: DNA
<213> ORGANISM: Homo sapiens
<220> FEATURE:
<221> NAME/KEY: modified_base
<222> LOCATION: (26)..(26)
<223> OTHER INFORMATION: a, c, t, g, unknown or other

<400> SEQUENCE: 11
gataactctt cttggctcaa tttcancatc tcactcatcc atctatccat t 51

<210> SEQ ID NO 12
<211> LENGTH: 51
<212> TYPE: DNA
<213> ORGANISM: Homo sapiens
<220> FEATURE:
<221> NAME/KEY: modified_base
<222> LOCATION: (26)..(26)
<223> OTHER INFORMATION: a, c, t, g, unknown or other

<400> SEQUENCE: 12
gctcataggc cttacaacca cagacntgct gggtcgcggc agtgatcaac c 51

<210> SEQ ID NO 13
<211> LENGTH: 61
<212> TYPE: DNA
<213> ORGANISM: Homo sapiens
<220> FEATURE:
<221> NAME/KEY: modified_base
<222> LOCATION: (31)..(31)
<223> OTHER INFORMATION: a, c, t, g, unknown or other

<400> SEQUENCE: 13
agataaatcc ctttgatatt aaaaaaaaaa ntaatgcatt tacgagatta ggaaattaga 60
g 61

<210> SEQ ID NO 14
<211> LENGTH: 51
<212> TYPE: DNA
<213> ORGANISM: Homo sapiens
<220> FEATURE:
<221> NAME/KEY: modified_base
<222> LOCATION: (26)..(26)
<223> OTHER INFORMATION: a, c, t, g, unknown or other

<400> SEQUENCE: 14
atggagcaaa atccagtggc aataangaac ttaaggttta gaatgtactt c 51

<210> SEQ ID NO 15

<211> LENGTH: 51
<212> TYPE: DNA
<213> ORGANISM: Homo sapiens
<220> FEATURE:
<221> NAME/KEY: modified_base
<222> LOCATION: (26)..(26)
<223> OTHER INFORMATION: a, c, t, g, unknown or other

<400> SEQUENCE: 15
tctagttggt catcttcgcc ccacancccc ggaagattct ctttgaatag t 51

<210> SEQ ID NO 16
<211> LENGTH: 51
<212> TYPE: DNA
<213> ORGANISM: Homo sapiens
<220> FEATURE:
<221> NAME/KEY: modified_base
<222> LOCATION: (26)..(26)
<223> OTHER INFORMATION: a, c, t, g, unknown or other

<400> SEQUENCE: 16
tttacttcat atttattttt gaatcngtcc actttttcct ttcacaatta c 51

<210> SEQ ID NO 17
<211> LENGTH: 51
<212> TYPE: DNA
<213> ORGANISM: Homo sapiens
<220> FEATURE:
<221> NAME/KEY: modified_base
<222> LOCATION: (26)..(26)
<223> OTHER INFORMATION: a, c, t, g, unknown or other

<400> SEQUENCE: 17
attctgacct gtcactgtgc caggcngtct acctgctgta tctcctgcca t 51

<210> SEQ ID NO 18
<211> LENGTH: 51
<212> TYPE: DNA
<213> ORGANISM: Homo sapiens
<220> FEATURE:
<221> NAME/KEY: modified_base
<222> LOCATION: (26)..(26)
<223> OTHER INFORMATION: a, c, t, g, unknown or other

<400> SEQUENCE: 18
cagcaggcag gtattaggag gattanagca ttgacactaa ggtttaaatg c 51

<210> SEQ ID NO 19
<211> LENGTH: 51
<212> TYPE: DNA
<213> ORGANISM: Homo sapiens
<220> FEATURE:
<221> NAME/KEY: modified_base
<222> LOCATION: (26)..(26)
<223> OTHER INFORMATION: a, c, t, g, unknown or other

<400> SEQUENCE: 19
atttatgtta gagaaatctc tgttcnctag tgataagccc aagggctatg t 51

<210> SEQ ID NO 20
<211> LENGTH: 51
<212> TYPE: DNA
<213> ORGANISM: Homo sapiens
<220> FEATURE:
<221> NAME/KEY: modified_base
<222> LOCATION: (26)..(26)
<223> OTHER INFORMATION: a, c, t, g, unknown or other

<400> SEQUENCE: 20
tatgtctgag gattttgaga tgtgcntata tgcaattatg tatgaatttt g 51

<210> SEQ ID NO 21
<211> LENGTH: 51
<212> TYPE: DNA
<213> ORGANISM: Homo sapiens
<220> FEATURE:
<221> NAME/KEY: modified_base
<222> LOCATION: (26)..(26)
<223> OTHER INFORMATION: a, c, t, g, unknown or other

<400> SEQUENCE: 21
ctccctggca cttgctcctg tctccnccat ggagagaact atgatgataa c 51

<210> SEQ ID NO 22
<211> LENGTH: 51
<212> TYPE: DNA
<213> ORGANISM: Homo sapiens
<220> FEATURE:
<221> NAME/KEY: modified_base
<222> LOCATION: (26)..(26)
<223> OTHER INFORMATION: a, c, t, g, unknown or other

<400> SEQUENCE: 22
tataaaatta ctgaatatcc cataantata tatgattata attggtcaaa g 51

<210> SEQ ID NO 23
<211> LENGTH: 51
<212> TYPE: DNA
<213> ORGANISM: Homo sapiens
<220> FEATURE:
<221> NAME/KEY: modified_base
<222> LOCATION: (26)..(26)
<223> OTHER INFORMATION: a, c, t, g, unknown or other

<400> SEQUENCE: 23
tgtttgtcta acaggagcct gaaaantgtc tagtatttat tataaatcag a 51

<210> SEQ ID NO 24
<211> LENGTH: 51
<212> TYPE: DNA
<213> ORGANISM: Homo sapiens
<220> FEATURE:
<221> NAME/KEY: modified_base
<222> LOCATION: (26)..(26)
<223> OTHER INFORMATION: a, c, t, g, unknown or other

<400> SEQUENCE: 24
tagctagaaa ttaacacatg cccggnacat agtagctgtt tgttcagtaa a 51

<210> SEQ ID NO 25
<211> LENGTH: 61
<212> TYPE: DNA
<213> ORGANISM: Homo sapiens
<220> FEATURE:
<221> NAME/KEY: modified_base
<222> LOCATION: (31)..(31)
<223> OTHER INFORMATION: a, c, t, g, unknown or other

<400> SEQUENCE: 25
tgtggaggat gaactggatc cctctccgac ngagacagaa agaaggcaaa tctttgggat 60
g 61

<210> SEQ ID NO 26
<211> LENGTH: 51
<212> TYPE: DNA

-continued

<213> ORGANISM: Homo sapiens
<220> FEATURE:
<221> NAME/KEY: modified_base
<222> LOCATION: (26)..(26)
<223> OTHER INFORMATION: a, c, t, g, unknown or other

<400> SEQUENCE: 26
tttatttttt ttttcttttt ggcctnagtt tcaatgacat tctggaagat g 51

<210> SEQ ID NO 27
<211> LENGTH: 51
<212> TYPE: DNA
<213> ORGANISM: Homo sapiens
<220> FEATURE:
<221> NAME/KEY: modified_base
<222> LOCATION: (26)..(26)
<223> OTHER INFORMATION: a, c, t, g, unknown or other

<400> SEQUENCE: 27
atgaagagag ttcagaaagc aagganatga caagtcctaa caagttgtta g 51

<210> SEQ ID NO 28
<211> LENGTH: 61
<212> TYPE: DNA
<213> ORGANISM: Homo sapiens
<220> FEATURE:
<221> NAME/KEY: modified_base
<222> LOCATION: (31)..(31)
<223> OTHER INFORMATION: a, c, t, g, unknown or other

<400> SEQUENCE: 28
tccccatatc ttttggttcc aagtgcctca ncctctctgt ctatgtagaa cggaaacttg 60
c 61

<210> SEQ ID NO 29
<211> LENGTH: 51
<212> TYPE: DNA
<213> ORGANISM: Homo sapiens
<220> FEATURE:
<221> NAME/KEY: modified_base
<222> LOCATION: (26)..(26)
<223> OTHER INFORMATION: a, c, t, g, unknown or other

<400> SEQUENCE: 29
atggagcaaa atccagtggc aataangaac ttaaggttta gaatgtactt c 51

<210> SEQ ID NO 30
<211> LENGTH: 51
<212> TYPE: DNA
<213> ORGANISM: Homo sapiens
<220> FEATURE:
<221> NAME/KEY: modified_base
<222> LOCATION: (26)..(26)
<223> OTHER INFORMATION: a, c, t, g, unknown or other

<400> SEQUENCE: 30
aaaagacatg ataaagtagt gatacngaaa caaaaattag ctgcttaaat c 51

<210> SEQ ID NO 31
<211> LENGTH: 51
<212> TYPE: DNA
<213> ORGANISM: Homo sapiens
<220> FEATURE:
<221> NAME/KEY: modified_base
<222> LOCATION: (26)..(26)
<223> OTHER INFORMATION: a, c, t, g, unknown or other

<400> SEQUENCE: 31
tttatttttt ttttcttttt ggcctnagtt tcaatgacat tctggaagat g 51

<210> SEQ ID NO 32
<211> LENGTH: 51
<212> TYPE: DNA
<213> ORGANISM: Homo sapiens
<220> FEATURE:
<221> NAME/KEY: modified_base
<222> LOCATION: (26)..(26)
<223> OTHER INFORMATION: a, c, t, g, unknown or other

<400> SEQUENCE: 32
gctcaagcaa tcttcctgcc tcggcntctc aaagcacaga aattacagac a 51

<210> SEQ ID NO 33
<211> LENGTH: 51
<212> TYPE: DNA
<213> ORGANISM: Homo sapiens
<220> FEATURE:
<221> NAME/KEY: modified_base
<222> LOCATION: (26)..(26)
<223> OTHER INFORMATION: a, c, t, g, unknown or other

<400> SEQUENCE: 33
tagctagaaa ttaacacatg cccggnacat agtagctgtt tgttcagtaa a 51

<210> SEQ ID NO 34
<211> LENGTH: 51
<212> TYPE: DNA
<213> ORGANISM: Homo sapiens
<220> FEATURE:
<221> NAME/KEY: modified_base
<222> LOCATION: (26)..(26)
<223> OTHER INFORMATION: a, c, t, g, unknown or other

<400> SEQUENCE: 34
tgtttgtcta acaggagcct gaaaantgtc tagtatttat tataaatcag a 51

<210> SEQ ID NO 35
<211> LENGTH: 51
<212> TYPE: DNA
<213> ORGANISM: Homo sapiens
<220> FEATURE:
<221> NAME/KEY: modified_base
<222> LOCATION: (26)..(26)
<223> OTHER INFORMATION: a, c, t, g, unknown or other

<400> SEQUENCE: 35
ggtggatgta gacattcact ccctcnaagt tttcctgtaa gttagctccc a 51

<210> SEQ ID NO 36
<211> LENGTH: 51
<212> TYPE: DNA
<213> ORGANISM: Homo sapiens
<220> FEATURE:
<221> NAME/KEY: modified_base
<222> LOCATION: (26)..(26)
<223> OTHER INFORMATION: a, c, t, g, unknown or other

<400> SEQUENCE: 36
ggagtggaaa taacttgatt ggggtntatg ttatatatca tataattcac t 51

<210> SEQ ID NO 37
<211> LENGTH: 51
<212> TYPE: DNA
<213> ORGANISM: Homo sapiens
<220> FEATURE:

<221> NAME/KEY: modified_base
<222> LOCATION: (26)..(26)
<223> OTHER INFORMATION: a, c, t, g, unknown or other

<400> SEQUENCE: 37
gcattgcact tcccttgttt tccacntagg atgtaatttc cagcaccact g 51

<210> SEQ ID NO 38
<211> LENGTH: 51
<212> TYPE: DNA
<213> ORGANISM: Homo sapiens
<220> FEATURE:
<221> NAME/KEY: modified_base
<222> LOCATION: (26)..(26)
<223> OTHER INFORMATION: a, c, t, g, unknown or other

<400> SEQUENCE: 38
aacaaaaacc caatctatat attcanggaa atgtaaacat tcaattaatc a 51

<210> SEQ ID NO 39
<211> LENGTH: 51
<212> TYPE: DNA
<213> ORGANISM: Homo sapiens
<220> FEATURE:
<221> NAME/KEY: modified_base
<222> LOCATION: (26)..(26)
<223> OTHER INFORMATION: a, c, t, g, unknown or other

<400> SEQUENCE: 39
tgagccagac aacttgagtt gccttnggcc ttcctggatt cagcactcaa c 51

<210> SEQ ID NO 40
<211> LENGTH: 51
<212> TYPE: DNA
<213> ORGANISM: Homo sapiens
<220> FEATURE:
<221> NAME/KEY: modified_base
<222> LOCATION: (26)..(26)
<223> OTHER INFORMATION: a, c, t, g, unknown or other

<400> SEQUENCE: 40
aggcatttcc cagagccttt tgctgnaatg ttctaaaatg cagcatcgac a 51

<210> SEQ ID NO 41
<211> LENGTH: 51
<212> TYPE: DNA
<213> ORGANISM: Homo sapiens
<220> FEATURE:
<221> NAME/KEY: modified_base
<222> LOCATION: (26)..(26)
<223> OTHER INFORMATION: a, c, t, g, unknown or other

<400> SEQUENCE: 41
atggagcaaa atccagtggc aataangaac ttaaggttta gaatgtactt c 51

<210> SEQ ID NO 42
<211> LENGTH: 51
<212> TYPE: DNA
<213> ORGANISM: Homo sapiens
<220> FEATURE:
<221> NAME/KEY: modified_base
<222> LOCATION: (26)..(26)
<223> OTHER INFORMATION: a, c, t, g, unknown or other

<400> SEQUENCE: 42
gtcatgggat ttttacagag ttaagnagta aaagaaagcc catgaaaatg a 51

<210> SEQ ID NO 43
<211> LENGTH: 51
<212> TYPE: DNA
<213> ORGANISM: Homo sapiens
<220> FEATURE:
<221> NAME/KEY: modified_base
<222> LOCATION: (26)..(26)
<223> OTHER INFORMATION: a, c, t, g, unknown or other

<400> SEQUENCE: 43
tggattctac aaacaatact ttaacntgga aatgtgtact tggatgaaga a 51

<210> SEQ ID NO 44
<211> LENGTH: 51
<212> TYPE: DNA
<213> ORGANISM: Homo sapiens
<220> FEATURE:
<221> NAME/KEY: modified_base
<222> LOCATION: (26)..(26)
<223> OTHER INFORMATION: a, c, t, g, unknown or other

<400> SEQUENCE: 44
tttccctcca gtggctcatg ggactngtag ttccttggcc agagctggtc g 51

<210> SEQ ID NO 45
<211> LENGTH: 51
<212> TYPE: DNA
<213> ORGANISM: Homo sapiens
<220> FEATURE:
<221> NAME/KEY: modified_base
<222> LOCATION: (26)..(26)
<223> OTHER INFORMATION: a, c, t, g, unknown or other

<400> SEQUENCE: 45
tatcatttct caactattga tttcanttac cttatctagg tccttaggac a 51

<210> SEQ ID NO 46
<211> LENGTH: 51
<212> TYPE: DNA
<213> ORGANISM: Homo sapiens
<220> FEATURE:
<221> NAME/KEY: modified_base
<222> LOCATION: (26)..(26)
<223> OTHER INFORMATION: a, c, t, g, unknown or other

<400> SEQUENCE: 46
aggcagacag agctcaggcg gtaacnctcc ctcatcctcc actcacctcc t 51

<210> SEQ ID NO 47
<211> LENGTH: 51
<212> TYPE: DNA
<213> ORGANISM: Homo sapiens
<220> FEATURE:
<221> NAME/KEY: modified_base
<222> LOCATION: (26)..(26)
<223> OTHER INFORMATION: a, c, t, g, unknown or other

<400> SEQUENCE: 47
tctagttggt catcttcgcc ccacancccc ggaagattct ctttgaatag t 51

<210> SEQ ID NO 48
<211> LENGTH: 51
<212> TYPE: DNA
<213> ORGANISM: Homo sapiens
<220> FEATURE:
<221> NAME/KEY: modified_base
<222> LOCATION: (26)..(26)
<223> OTHER INFORMATION: a, c, t, g, unknown or other

<400> SEQUENCE: 48
gtggtctcta ccaccctcca gcagangcag gttgctctgc gggttgtggg c 51

<210> SEQ ID NO 49
<211> LENGTH: 51
<212> TYPE: DNA
<213> ORGANISM: Homo sapiens
<220> FEATURE:
<221> NAME/KEY: modified_base
<222> LOCATION: (26)..(26)
<223> OTHER INFORMATION: a, c, t, g, unknown or other

<400> SEQUENCE: 49
cagcaggcag gtattaggag gattanagca ttgacactaa ggtttaaatg c 51

<210> SEQ ID NO 50
<211> LENGTH: 51
<212> TYPE: DNA
<213> ORGANISM: Homo sapiens
<220> FEATURE:
<221> NAME/KEY: modified_base
<222> LOCATION: (26)..(26)
<223> OTHER INFORMATION: a, c, t, g, unknown or other

<400> SEQUENCE: 50
tataaaatta ctgaatatcc cataantata tatgattata attggtcaaa g 51

<210> SEQ ID NO 51
<211> LENGTH: 51
<212> TYPE: DNA
<213> ORGANISM: Homo sapiens
<220> FEATURE:
<221> NAME/KEY: modified_base
<222> LOCATION: (26)..(26)
<223> OTHER INFORMATION: a, c, t, g, unknown or other

<400> SEQUENCE: 51
gatttggaga cgaggagcaa caaatnggta atggacacat cctctgatag c 51

<210> SEQ ID NO 52
<211> LENGTH: 51
<212> TYPE: DNA
<213> ORGANISM: Homo sapiens
<220> FEATURE:
<221> NAME/KEY: modified_base
<222> LOCATION: (26)..(26)
<223> OTHER INFORMATION: a, c, t, g, unknown or other

<400> SEQUENCE: 52
ttcagcacta ttcagcgcct atcacngcca gctgaaaact gtatagccat t 51

<210> SEQ ID NO 53
<211> LENGTH: 51
<212> TYPE: DNA
<213> ORGANISM: Homo sapiens
<220> FEATURE:
<221> NAME/KEY: modified_base
<222> LOCATION: (26)..(26)
<223> OTHER INFORMATION: a, c, t, g, unknown or other

<400> SEQUENCE: 53
attcagcttt gtgtaactgg gtaacnacac acttgtgaaa gttttttttt c 51

<210> SEQ ID NO 54
<211> LENGTH: 51
<212> TYPE: DNA
<213> ORGANISM: Homo sapiens
<220> FEATURE:
<221> NAME/KEY: modified_base
<222> LOCATION: (26)..(26)
<223> OTHER INFORMATION: a, c, t, g, unknown or other

<400> SEQUENCE: 54
atggagcaaa atccagtggc aataangaac ttaaggttta gaatgtactt c 51

<210> SEQ ID NO 55
<211> LENGTH: 61
<212> TYPE: DNA
<213> ORGANISM: Homo sapiens
<220> FEATURE:
<221> NAME/KEY: modified_base
<222> LOCATION: (31)..(31)
<223> OTHER INFORMATION: a, c, t, g, unknown or other

<400> SEQUENCE: 55
cccacagtcg agtgcagagg tctccgaagc nctcagtccc gcctacaatc tagccatggg 60
g 61

<210> SEQ ID NO 56
<211> LENGTH: 61
<212> TYPE: DNA
<213> ORGANISM: Homo sapiens
<220> FEATURE:
<221> NAME/KEY: modified_base
<222> LOCATION: (31)..(31)
<223> OTHER INFORMATION: a, c, t, g, unknown or other

<400> SEQUENCE: 56
gtgattgtca ggcattatgg aaaggtcaaa naaaatatgc tcactggcta tctatggccc 60
a 61

<210> SEQ ID NO 57
<211> LENGTH: 51
<212> TYPE: DNA
<213> ORGANISM: Homo sapiens
<220> FEATURE:
<221> NAME/KEY: modified_base
<222> LOCATION: (26)..(26)
<223> OTHER INFORMATION: a, c, t, g, unknown or other

<400> SEQUENCE: 57
tttacaattt tcaccaagga atcttngtaa gtatggtaac cttctattct g 51

<210> SEQ ID NO 58
<211> LENGTH: 61
<212> TYPE: DNA
<213> ORGANISM: Homo sapiens
<220> FEATURE:
<221> NAME/KEY: modified_base
<222> LOCATION: (31)..(31)
<223> OTHER INFORMATION: a, c, t, g, unknown or other

<400> SEQUENCE: 58
tccccatatc ttttggttcc aagtgcctca ncctctctgt ctatgtagaa cggaaacttg 60
c 61

<210> SEQ ID NO 59
<211> LENGTH: 61
<212> TYPE: DNA
<213> ORGANISM: Homo sapiens
<220> FEATURE:
<221> NAME/KEY: modified_base
<222> LOCATION: (31)..(31)

<223> OTHER INFORMATION: a, c, t, g, unknown or other

<400> SEQUENCE: 59
gttggttgct attagagact ggtggtcagg ntatggcatg gtagagagag agccctactc 60
a 61

<210> SEQ ID NO 60
<211> LENGTH: 51
<212> TYPE: DNA
<213> ORGANISM: Homo sapiens
<220> FEATURE:
<221> NAME/KEY: modified_base
<222> LOCATION: (26)..(26)
<223> OTHER INFORMATION: a, c, t, g, unknown or other

<400> SEQUENCE: 60
gaaaagatag cacatagtga attctnaata tatgtatctc ttattagatt t 51

<210> SEQ ID NO 61
<211> LENGTH: 51
<212> TYPE: DNA
<213> ORGANISM: Homo sapiens
<220> FEATURE:
<221> NAME/KEY: modified_base
<222> LOCATION: (26)..(26)
<223> OTHER INFORMATION: a, c, t, g, unknown or other

<400> SEQUENCE: 61
tcctgcattc tggattttgc tgatcntgtg gcatctttcc tctgtcctat g 51

<210> SEQ ID NO 62
<211> LENGTH: 51
<212> TYPE: DNA
<213> ORGANISM: Homo sapiens
<220> FEATURE:
<221> NAME/KEY: modified_base
<222> LOCATION: (26)..(26)
<223> OTHER INFORMATION: a, c, t, g, unknown or other

<400> SEQUENCE: 62
gatttggaga cgaggagcaa caaatnggta atggacacat cctctgatag c 51

<210> SEQ ID NO 63
<211> LENGTH: 61
<212> TYPE: DNA
<213> ORGANISM: Homo sapiens
<220> FEATURE:
<221> NAME/KEY: modified_base
<222> LOCATION: (31)..(31)
<223> OTHER INFORMATION: a, c, t, g, unknown or other

<400> SEQUENCE: 63
attctccaaa cccagccctg ctgagttcct nttctccaca ggcgaaaagc agatgcgctt 60
c 61

<210> SEQ ID NO 64
<211> LENGTH: 51
<212> TYPE: DNA
<213> ORGANISM: Homo sapiens
<220> FEATURE:
<221> NAME/KEY: modified_base
<222> LOCATION: (26)..(26)
<223> OTHER INFORMATION: a, c, t, g, unknown or other

<400> SEQUENCE: 64
gaaccctgac ttggataata cagatngcga gattggagca atgactaaag c 51

<210> SEQ ID NO 65
<211> LENGTH: 51
<212> TYPE: DNA
<213> ORGANISM: Homo sapiens
<220> FEATURE:
<221> NAME/KEY: modified_base
<222> LOCATION: (26)..(26)
<223> OTHER INFORMATION: a, c, t, g, unknown or other

<400> SEQUENCE: 65
gaaaggacct catcactctt cccatntaga tgccttgcta gtgaatcaga g 51

<210> SEQ ID NO 66
<211> LENGTH: 61
<212> TYPE: DNA
<213> ORGANISM: Homo sapiens
<220> FEATURE:
<221> NAME/KEY: modified_base
<222> LOCATION: (31)..(31)
<223> OTHER INFORMATION: a, c, t, g, unknown or other

<400> SEQUENCE: 66
catttccttt taatgtcgta actatgttac nggaaaagag tctaatcata gattatttta 60
g 61

<210> SEQ ID NO 67
<211> LENGTH: 51
<212> TYPE: DNA
<213> ORGANISM: Homo sapiens
<220> FEATURE:
<221> NAME/KEY: modified_base
<222> LOCATION: (26)..(26)
<223> OTHER INFORMATION: a, c, t, g, unknown or other

<400> SEQUENCE: 67
gatgagctga gctcttagaa gtaacngctg gcattcacac tctgtgctct a 51

<210> SEQ ID NO 68
<211> LENGTH: 51
<212> TYPE: DNA
<213> ORGANISM: Homo sapiens
<220> FEATURE:
<221> NAME/KEY: modified_base
<222> LOCATION: (26)..(26)
<223> OTHER INFORMATION: a, c, t, g, unknown or other

<400> SEQUENCE: 68
ggagtggaaa taacttgatt ggggtntatg ttatatatca tataattcac t 51

<210> SEQ ID NO 69
<211> LENGTH: 51
<212> TYPE: DNA
<213> ORGANISM: Homo sapiens
<220> FEATURE:
<221> NAME/KEY: modified_base
<222> LOCATION: (26)..(26)
<223> OTHER INFORMATION: a, c, t, g, unknown or other

<400> SEQUENCE: 69
taaggtgtgt aaggaaagtg aaatgngttt tttttgtttt gttttgtttt g 51

<210> SEQ ID NO 70
<211> LENGTH: 51
<212> TYPE: DNA
<213> ORGANISM: Homo sapiens
<220> FEATURE:

<221> NAME/KEY: modified_base
<222> LOCATION: (26)..(26)
<223> OTHER INFORMATION: a, c, t, g, unknown or other

<400> SEQUENCE: 70
aggaaagggc agacatcaag ggaccngaag accccagaag cttcagttct g 51

<210> SEQ ID NO 71
<211> LENGTH: 51
<212> TYPE: DNA
<213> ORGANISM: Homo sapiens
<220> FEATURE:
<221> NAME/KEY: modified_base
<222> LOCATION: (26)..(26)
<223> OTHER INFORMATION: a, c, t, g, unknown or other

<400> SEQUENCE: 71
ggagtggaaa taacttgatt ggggtntatg ttatatatca tataattcac t 51

<210> SEQ ID NO 72
<211> LENGTH: 51
<212> TYPE: DNA
<213> ORGANISM: Homo sapiens
<220> FEATURE:
<221> NAME/KEY: modified_base
<222> LOCATION: (26)..(26)
<223> OTHER INFORMATION: a, c, t, g, unknown or other

<400> SEQUENCE: 72
aagaatgagt atagaatatg tgatcngaag taactgcaaa actgagtcac t 51

<210> SEQ ID NO 73
<211> LENGTH: 51
<212> TYPE: DNA
<213> ORGANISM: Homo sapiens
<220> FEATURE:
<221> NAME/KEY: modified_base
<222> LOCATION: (26)..(26)
<223> OTHER INFORMATION: a, c, t, g, unknown or other

<400> SEQUENCE: 73
ttatttgtaa tcaacatgta gttggntctt gctttttatc aaatctgtca c 51

<210> SEQ ID NO 74
<211> LENGTH: 51
<212> TYPE: DNA
<213> ORGANISM: Homo sapiens
<220> FEATURE:
<221> NAME/KEY: modified_base
<222> LOCATION: (26)..(26)
<223> OTHER INFORMATION: a, c, t, g, unknown or other

<400> SEQUENCE: 74
tctggttatt tttcacactt cttccnaatg gtatcatagg atgctatgcc t 51

<210> SEQ ID NO 75
<211> LENGTH: 51
<212> TYPE: DNA
<213> ORGANISM: Homo sapiens
<220> FEATURE:
<221> NAME/KEY: modified_base
<222> LOCATION: (26)..(26)
<223> OTHER INFORMATION: a, c, t, g, unknown or other

<400> SEQUENCE: 75
ttagaccttg ggaaagctac ttctcngagc cttagtttcc gtatctacta a 51

<210> SEQ ID NO 76
<211> LENGTH: 51
<212> TYPE: DNA
<213> ORGANISM: Homo sapiens
<220> FEATURE:
<221> NAME/KEY: modified_base
<222> LOCATION: (26)..(26)
<223> OTHER INFORMATION: a, c, t, g, unknown or other

<400> SEQUENCE: 76
aagatgtcaa atattctcta cataangatt ttaattttaa aaataagact t 51

<210> SEQ ID NO 77
<211> LENGTH: 51
<212> TYPE: DNA
<213> ORGANISM: Homo sapiens
<220> FEATURE:
<221> NAME/KEY: modified_base
<222> LOCATION: (26)..(26)
<223> OTHER INFORMATION: a, c, t, g, unknown or other

<400> SEQUENCE: 77
aagaatgagt atagaatatg tgatcngaag taactgcaaa actgagtcac t 51

<210> SEQ ID NO 78
<211> LENGTH: 51
<212> TYPE: DNA
<213> ORGANISM: Homo sapiens
<220> FEATURE:
<221> NAME/KEY: modified_base
<222> LOCATION: (26)..(26)
<223> OTHER INFORMATION: a, c, t, g, unknown or other

<400> SEQUENCE: 78
ttttctaaga ggtatgcaca atttangtat tttatgtaat aataattgaa a 51

<210> SEQ ID NO 79
<211> LENGTH: 61
<212> TYPE: DNA
<213> ORGANISM: Homo sapiens
<220> FEATURE:
<221> NAME/KEY: modified_base
<222> LOCATION: (31)..(31)
<223> OTHER INFORMATION: a, c, t, g, unknown or other

<400> SEQUENCE: 79
gttggttgct attagagact ggtggtcagg ntatggcatg gtagagagag agccctactc 60
a 61

<210> SEQ ID NO 80
<211> LENGTH: 51
<212> TYPE: DNA
<213> ORGANISM: Homo sapiens
<220> FEATURE:
<221> NAME/KEY: modified_base
<222> LOCATION: (26)..(26)
<223> OTHER INFORMATION: a, c, t, g, unknown or other

<400> SEQUENCE: 80
ctccctggca cttgctcctg tctccnccat ggagagaact atgatgataa c 51

<210> SEQ ID NO 81
<211> LENGTH: 51
<212> TYPE: DNA
<213> ORGANISM: Homo sapiens
<220> FEATURE:
<221> NAME/KEY: modified_base
<222> LOCATION: (26)..(26)

<223> OTHER INFORMATION: a, c, t, g, unknown or other

<400> SEQUENCE: 81
ttttctaaga ggtatgcaca atttangtat tttatgtaat aataattgaa a 51

<210> SEQ ID NO 82
<211> LENGTH: 51
<212> TYPE: DNA
<213> ORGANISM: Homo sapiens
<220> FEATURE:
<221> NAME/KEY: modified_base
<222> LOCATION: (26)..(26)
<223> OTHER INFORMATION: a, c, t, g, unknown or other

<400> SEQUENCE: 82
ctcaatgagt ctctgtaatc catacnttcc caaatataac ctagaaagaa a 51

<210> SEQ ID NO 83
<211> LENGTH: 541
<212> TYPE: PRT
<213> ORGANISM: Homo sapiens

<400> SEQUENCE: 83

Met Asn Cys Arg Glu Leu Pro Leu Thr Leu Trp Val Leu Ile Ser Val
1 5 10 15

Ser Thr Ala Glu Ser Cys Thr Ser Arg Pro His Ile Thr Val Val Glu
20 25 30

Gly Glu Pro Phe Tyr Leu Lys His Cys Ser Cys Ser Leu Ala His Glu
35 40 45

Ile Glu Thr Thr Thr Lys Ser Trp Tyr Lys Ser Ser Gly Ser Gln Glu
50 55 60

His Val Glu Leu Asn Pro Arg Ser Ser Ser Arg Ile Ala Leu His Asp
65 70 75 80

Cys Val Leu Glu Phe Trp Pro Val Glu Leu Asn Asp Thr Gly Ser Tyr
85 90 95

Phe Phe Gln Met Lys Asn Tyr Thr Gln Lys Trp Lys Leu Asn Val Ile
100 105 110

Arg Arg Asn Lys His Ser Cys Phe Thr Glu Arg Gln Val Thr Ser Lys
115 120 125

Ile Val Glu Val Lys Lys Phe Phe Gln Ile Thr Cys Glu Asn Ser Tyr
130 135 140

Tyr Gln Thr Leu Val Asn Ser Thr Ser Leu Tyr Lys Asn Cys Lys Lys
145 150 155 160

Leu Leu Leu Glu Asn Asn Lys Asn Pro Thr Ile Lys Lys Asn Ala Glu
165 170 175

Phe Glu Asp Gln Gly Tyr Tyr Ser Cys Val His Phe Leu His His Asn
180 185 190

Gly Lys Leu Phe Asn Ile Thr Lys Thr Phe Asn Ile Thr Ile Val Glu
195 200 205

Asp Arg Ser Asn Ile Val Pro Val Leu Leu Gly Pro Lys Leu Asn His
210 215 220

Val Ala Val Glu Leu Gly Lys Asn Val Arg Leu Asn Cys Ser Ala Leu
225 230 235 240

Leu Asn Glu Glu Asp Val Ile Tyr Trp Met Phe Gly Glu Glu Asn Gly
245 250 255

Ser Asp Pro Asn Ile His Glu Glu Lys Glu Met Arg Ile Met Thr Pro
260 265 270

Glu Gly Lys Trp His Ala Ser Lys Val Leu Arg Ile Glu Asn Ile Gly
275 280 285

Glu Ser Asn Leu Asn Val Leu Tyr Asn Cys Thr Val Ala Ser Thr Gly
290 295 300

Gly Thr Asp Thr Lys Ser Phe Ile Leu Val Arg Lys Ala Asp Met Ala
305 310 315 320

Asp Ile Pro Gly His Val Phe Thr Arg Gly Met Ile Ile Ala Val Leu
325 330 335

Ile Leu Val Ala Val Val Cys Leu Val Thr Val Cys Val Ile Tyr Arg
340 345 350

Val Asp Leu Val Leu Phe Tyr Arg His Leu Thr Arg Arg Asp Glu Thr
355 360 365

Leu Thr Asp Gly Lys Thr Tyr Asp Ala Phe Val Ser Tyr Leu Lys Glu
370 375 380

Cys Arg Pro Glu Asn Gly Glu Glu His Thr Phe Ala Val Glu Ile Leu
385 390 395 400

Pro Arg Val Leu Glu Lys His Phe Gly Tyr Lys Leu Cys Ile Phe Glu
405 410 415

Arg Asp Val Val Pro Gly Gly Ala Val Val Asp Glu Ile His Ser Leu
420 425 430

Ile Glu Lys Ser Arg Arg Leu Ile Ile Val Leu Ser Lys Ser Tyr Met
435 440 445

Ser Asn Glu Val Arg Tyr Glu Leu Glu Ser Gly Leu His Glu Ala Leu
450 455 460

Val Glu Arg Lys Ile Lys Ile Ile Leu Ile Glu Phe Thr Pro Val Thr
465 470 475 480

Asp Phe Thr Phe Leu Pro Gln Ser Leu Lys Leu Leu Lys Ser His Arg
485 490 495

Val Leu Lys Trp Lys Ala Asp Lys Ser Leu Ser Tyr Asn Ser Arg Phe
500 505 510

Trp Lys Asn Leu Leu Tyr Leu Met Pro Ala Lys Thr Val Lys Pro Gly
515 520 525

Arg Asp Glu Pro Glu Val Leu Pro Val Leu Ser Glu Ser
530 535 540

<210> SEQ ID NO 84
<211> LENGTH: 385
<212> TYPE: PRT
<213> ORGANISM: Homo sapiens

<400> SEQUENCE: 84

Met Asn Cys Lys Lys Leu Leu Leu Glu Asn Asn Lys Asn Pro Thr Ile
1 5 10 15

Lys Lys Asn Ala Glu Phe Glu Asp Gln Gly Tyr Tyr Ser Cys Val His
20 25 30

Phe Leu His His Asn Gly Lys Leu Phe Asn Ile Thr Lys Thr Phe Asn
35 40 45

Ile Thr Ile Val Glu Asp Arg Ser Asn Ile Val Pro Val Leu Leu Gly
50 55 60

Pro Lys Leu Asn His Val Ala Val Glu Leu Gly Lys Asn Val Arg Leu
65 70 75 80

Asn Cys Ser Ala Leu Leu Asn Glu Glu Asp Val Ile Tyr Trp Met Phe
85 90 95

Gly Glu Glu Asn Gly Ser Asp Pro Asn Ile His Glu Glu Lys Glu Met
100 105 110

Arg Ile Met Thr Pro Glu Gly Lys Trp His Ala Ser Lys Val Leu Arg
115 120 125

Ile Glu Asn Ile Gly Glu Ser Asn Leu Asn Val Leu Tyr Asn Cys Thr
130 135 140

Val Ala Ser Thr Gly Gly Thr Asp Thr Lys Ser Phe Ile Leu Val Arg
145 150 155 160

Lys Asp Met Ala Asp Ile Pro Gly His Val Phe Thr Arg Gly Met Ile
165 170 175

Ile Ala Val Leu Ile Leu Val Ala Val Val Cys Leu Val Thr Val Cys
180 185 190

Val Ile Tyr Arg Val Asp Leu Val Leu Phe Tyr Arg His Leu Thr Arg
195 200 205

Arg Asp Glu Thr Leu Thr Asp Gly Lys Thr Tyr Asp Ala Phe Val Ser
210 215 220

Tyr Leu Lys Glu Cys Arg Pro Glu Asn Gly Glu Glu His Thr Phe Ala
225 230 235 240

Val Glu Ile Leu Pro Arg Val Leu Glu Lys His Phe Gly Tyr Lys Leu
245 250 255

Cys Ile Phe Glu Arg Asp Val Val Pro Gly Gly Ala Val Val Asp Glu
260 265 270

Ile His Ser Leu Ile Glu Lys Ser Arg Arg Leu Ile Ile Val Leu Ser
275 280 285

Lys Ser Tyr Met Ser Asn Glu Val Arg Tyr Glu Leu Glu Ser Gly Leu
290 295 300

His Glu Ala Leu Val Glu Arg Lys Ile Lys Ile Ile Leu Ile Glu Phe
305 310 315 320

Thr Pro Val Thr Asp Phe Thr Phe Leu Pro Gln Ser Leu Lys Leu Leu
325 330 335

Lys Ser His Arg Val Leu Lys Trp Lys Ala Asp Lys Ser Leu Ser Tyr
340 345 350

Asn Ser Arg Phe Trp Lys Asn Leu Leu Tyr Leu Met Pro Ala Lys Thr
355 360 365

Val Lys Pro Gly Arg Asp Glu Pro Glu Val Leu Pro Val Leu Ser Glu
370 375 380

Ser
385

<210> SEQ ID NO 85
<211> LENGTH: 599
<212> TYPE: PRT
<213> ORGANISM: Homo sapiens

<400> SEQUENCE: 85

Met Leu Cys Leu Gly Trp Ile Phe Leu Trp Leu Val Ala Gly Glu Arg
1 5 10 15

Ile Lys Gly Phe Asn Ile Ser Gly Cys Ser Thr Lys Lys Leu Leu Trp
20 25 30

Thr Tyr Ser Thr Arg Ser Glu Glu Glu Phe Val Leu Phe Cys Asp Leu
35 40 45

Pro Glu Pro Gln Lys Ser His Phe Cys His Arg Asn Arg Leu Ser Pro
50 55 60

Lys Gln Val Pro Glu His Leu Pro Phe Met Gly Ser Asn Asp Leu Ser
65 70 75 80

Asp Val Gln Trp Tyr Gln Gln Pro Ser Asn Gly Asp Pro Leu Glu Asp

-continued

```
                85                  90                  95

Ile Arg Lys Ser Tyr Pro His Ile Ile Gln Asp Lys Cys Thr Leu His
            100                 105                 110

Phe Leu Thr Pro Gly Val Asn Asn Ser Gly Ser Tyr Ile Cys Arg Pro
        115                 120                 125

Lys Met Ile Lys Ser Pro Tyr Asp Val Ala Cys Cys Val Lys Met Ile
    130                 135                 140

Leu Glu Val Lys Pro Gln Thr Asn Ala Ser Cys Glu Tyr Ser Ala Ser
145                 150                 155                 160

His Lys Gln Asp Leu Leu Leu Gly Ser Thr Gly Ser Ile Ser Cys Pro
                165                 170                 175

Ser Leu Ser Cys Gln Ser Asp Ala Gln Ser Pro Ala Val Thr Trp Tyr
            180                 185                 190

Lys Asn Gly Lys Leu Leu Ser Val Glu Arg Ser Asn Arg Ile Val Val
        195                 200                 205

Asp Glu Val Tyr Asp Tyr His Gln Gly Thr Tyr Val Cys Asp Tyr Thr
    210                 215                 220

Gln Ser Asp Thr Val Ser Ser Trp Thr Val Arg Ala Val Val Gln Val
225                 230                 235                 240

Arg Thr Ile Val Gly Asp Thr Lys Leu Lys Pro Asp Ile Leu Asp Pro
                245                 250                 255

Val Glu Asp Thr Leu Glu Val Glu Leu Gly Lys Pro Leu Thr Ile Ser
            260                 265                 270

Cys Lys Ala Arg Phe Gly Phe Glu Arg Val Phe Asn Pro Val Ile Lys
        275                 280                 285

Trp Tyr Ile Lys Asp Ser Asp Leu Glu Trp Glu Val Ser Val Pro Glu
    290                 295                 300

Ala Lys Ser Ile Lys Ser Thr Leu Lys Asp Glu Ile Ile Glu Arg Asn
305                 310                 315                 320

Ile Ile Leu Glu Lys Val Thr Gln Arg Asp Leu Arg Arg Lys Phe Val
                325                 330                 335

Cys Phe Val Gln Asn Ser Ile Gly Asn Thr Thr Gln Ser Val Gln Leu
            340                 345                 350

Lys Glu Lys Arg Gly Val Val Leu Leu Tyr Ile Leu Leu Gly Thr Ile
        355                 360                 365

Gly Thr Leu Val Ala Val Leu Ala Ala Ser Ala Leu Leu Tyr Arg His
    370                 375                 380

Trp Ile Glu Ile Val Leu Leu Tyr Arg Thr Tyr Gln Ser Lys Asp Gln
385                 390                 395                 400

Thr Leu Gly Asp Lys Lys Asp Phe Asp Ala Phe Val Ser Tyr Ala Lys
                405                 410                 415

Trp Ser Ser Phe Pro Ser Glu Ala Thr Ser Ser Leu Ser Glu Glu His
            420                 425                 430

Leu Ala Leu Ser Leu Phe Pro Asp Val Leu Glu Asn Lys Tyr Gly Tyr
        435                 440                 445

Ser Leu Cys Leu Leu Glu Arg Asp Val Ala Pro Gly Gly Val Tyr Ala
    450                 455                 460

Glu Asp Ile Val Ser Ile Ile Lys Arg Ser Arg Arg Gly Ile Phe Ile
465                 470                 475                 480

Leu Ser Pro Asn Tyr Val Asn Gly Pro Ser Ile Phe Glu Leu Gln Ala
                485                 490                 495

Ala Val Asn Leu Ala Leu Asp Asp Gln Thr Leu Lys Leu Ile Leu Ile
            500                 505                 510
```

```
Lys Phe Cys Tyr Phe Gln Glu Pro Glu Ser Leu Pro His Leu Val Lys
        515                 520                 525

Lys Ala Leu Arg Val Leu Pro Thr Val Thr Trp Arg Gly Leu Lys Ser
    530                 535                 540

Val Pro Pro Asn Ser Arg Phe Trp Ala Lys Met Arg Tyr His Met Pro
545                 550                 555                 560

Val Lys Asn Ser Gln Gly Phe Thr Trp Asn Gln Leu Arg Ile Thr Ser
                565                 570                 575

Arg Ile Phe Gln Trp Lys Gly Leu Ser Arg Thr Glu Thr Thr Gly Arg
            580                 585                 590

Ser Ser Gln Pro Lys Glu Trp
        595


<210> SEQ ID NO 86
<211> LENGTH: 599
<212> TYPE: PRT
<213> ORGANISM: Homo sapiens

<400> SEQUENCE: 86

Met Leu Cys Leu Gly Trp Ile Phe Leu Trp Leu Val Ala Gly Glu Arg
1               5                   10                  15

Ile Lys Gly Phe Asn Ile Ser Gly Cys Ser Thr Lys Lys Leu Leu Trp
            20                  25                  30

Thr Tyr Ser Thr Arg Ser Glu Glu Glu Phe Val Leu Phe Cys Asp Leu
        35                  40                  45

Pro Glu Pro Gln Lys Ser His Phe Cys His Arg Asn Arg Leu Ser Pro
    50                  55                  60

Lys Gln Val Pro Glu His Leu Pro Phe Met Gly Ser Asn Asp Leu Ser
65                  70                  75                  80

Asp Val Gln Trp Tyr Gln Gln Pro Ser Asn Gly Asp Pro Leu Glu Asp
                85                  90                  95

Ile Arg Lys Ser Tyr Pro His Ile Ile Gln Asp Lys Cys Thr Leu His
            100                 105                 110

Phe Leu Thr Pro Gly Val Asn Asn Ser Gly Ser Tyr Ile Cys Arg Pro
        115                 120                 125

Lys Met Ile Lys Ser Pro Tyr Asp Val Ala Cys Cys Val Lys Met Ile
    130                 135                 140

Leu Glu Val Lys Pro Gln Thr Asn Ala Ser Cys Glu Tyr Ser Ala Ser
145                 150                 155                 160

His Lys Gln Asp Leu Leu Leu Gly Ser Thr Gly Ser Ile Ser Cys Pro
                165                 170                 175

Ser Leu Ser Cys Gln Ser Asp Ala Gln Ser Pro Ala Val Thr Trp Tyr
            180                 185                 190

Lys Asn Gly Lys Leu Leu Ser Val Glu Arg Ser Asn Arg Ile Val Val
        195                 200                 205

Asp Glu Val Tyr Asp Tyr His Gln Gly Thr Tyr Val Cys Asp Tyr Thr
    210                 215                 220

Gln Ser Asp Thr Val Ser Ser Trp Thr Val Arg Ala Val Val Gln Val
225                 230                 235                 240

Arg Thr Ile Val Gly Asp Thr Lys Leu Lys Pro Asp Ile Leu Asp Pro
                245                 250                 255

Val Glu Asp Thr Leu Glu Val Glu Leu Gly Lys Pro Leu Thr Ile Ser
            260                 265                 270

Cys Lys Ala Arg Phe Gly Phe Glu Arg Val Phe Asn Pro Val Ile Lys
```

-continued

```
        275                 280                 285

Trp Tyr Ile Lys Asp Ser Asp Leu Glu Trp Glu Val Ser Val Pro Glu
    290                 295                 300

Ala Lys Ser Ile Lys Ser Thr Leu Lys Asp Glu Ile Ile Glu Arg Asn
305                 310                 315                 320

Ile Ile Leu Glu Lys Val Thr Gln Arg Asp Leu Arg Arg Lys Phe Val
                325                 330                 335

Cys Phe Val Gln Asn Ser Ile Gly Asn Thr Thr Gln Ser Val Gln Leu
            340                 345                 350

Lys Glu Lys Arg Gly Val Val Leu Leu Tyr Ile Leu Leu Gly Thr Ile
        355                 360                 365

Gly Thr Leu Val Ala Val Leu Ala Ala Ser Ala Leu Leu Tyr Arg His
    370                 375                 380

Trp Ile Glu Ile Val Leu Leu Tyr Arg Thr Tyr Gln Ser Lys Asp Gln
385                 390                 395                 400

Thr Leu Gly Asp Lys Lys Asp Phe Asp Ala Phe Val Ser Tyr Ala Lys
                405                 410                 415

Trp Ser Ser Phe Pro Ser Glu Ala Thr Ser Ser Leu Ser Glu Glu His
            420                 425                 430

Leu Ala Leu Ser Leu Phe Pro Asp Val Leu Glu Asn Lys Tyr Gly Tyr
        435                 440                 445

Ser Leu Cys Leu Leu Glu Arg Asp Val Ala Pro Gly Gly Val Tyr Ala
    450                 455                 460

Glu Asp Ile Val Ser Ile Ile Lys Arg Ser Arg Arg Gly Ile Phe Ile
465                 470                 475                 480

Leu Ser Pro Asn Tyr Val Asn Gly Pro Ser Ile Phe Glu Leu Gln Ala
                485                 490                 495

Ala Val Asn Leu Ala Leu Asp Asp Gln Thr Leu Lys Leu Ile Leu Ile
            500                 505                 510

Lys Phe Cys Tyr Phe Gln Glu Pro Glu Ser Leu Pro His Leu Val Lys
        515                 520                 525

Lys Ala Leu Arg Val Leu Pro Thr Val Thr Trp Arg Gly Leu Lys Ser
    530                 535                 540

Val Pro Pro Asn Ser Arg Phe Trp Ala Lys Met Arg Tyr His Met Pro
545                 550                 555                 560

Val Lys Asn Ser Gln Gly Phe Thr Trp Asn Gln Leu Arg Ile Thr Ser
                565                 570                 575

Arg Ile Phe Gln Trp Lys Gly Leu Ser Arg Thr Glu Thr Thr Gly Arg
            580                 585                 590

Ser Ser Gln Pro Lys Glu Trp
        595
```

<210> SEQ ID NO 87
<211> LENGTH: 457
<212> TYPE: PRT
<213> ORGANISM: Homo sapiens

<400> SEQUENCE: 87

```
Met Ile Leu Glu Val Lys Pro Gln Thr Asn Ala Ser Cys Glu Tyr Ser
1               5                   10                  15

Ala Ser His Lys Gln Asp Leu Leu Leu Gly Ser Thr Gly Ser Ile Ser
            20                  25                  30

Cys Pro Ser Leu Ser Cys Gln Ser Asp Ala Gln Ser Pro Ala Val Thr
        35                  40                  45
```

-continued

```
Trp Tyr Lys Asn Gly Lys Leu Leu Ser Val Glu Arg Ser Asn Arg Ile
    50                  55                  60

Val Val Asp Glu Val Tyr Asp Tyr His Gln Gly Thr Tyr Val Cys Asp
65                  70                  75                  80

Tyr Thr Gln Ser Asp Thr Val Ser Ser Trp Thr Val Arg Ala Val Val
                85                  90                  95

Gln Val Arg Thr Ile Val Gly Asp Thr Lys Leu Lys Pro Asp Ile Leu
            100                 105                 110

Asp Pro Val Glu Asp Thr Leu Glu Val Glu Leu Gly Lys Pro Leu Thr
        115                 120                 125

Ile Ser Cys Lys Ala Arg Phe Gly Phe Glu Arg Val Phe Asn Pro Val
    130                 135                 140

Ile Lys Trp Tyr Ile Lys Asp Ser Asp Leu Glu Trp Glu Val Ser Val
145                 150                 155                 160

Pro Glu Ala Lys Ser Ile Lys Ser Thr Leu Lys Asp Glu Ile Ile Glu
                165                 170                 175

Arg Asn Ile Ile Leu Glu Lys Val Thr Gln Arg Asp Leu Arg Arg Lys
            180                 185                 190

Phe Val Cys Phe Val Gln Asn Ser Ile Gly Asn Thr Thr Gln Ser Val
        195                 200                 205

Gln Leu Lys Glu Lys Arg Gly Val Val Leu Leu Tyr Ile Leu Leu Gly
    210                 215                 220

Thr Ile Gly Thr Leu Val Ala Val Leu Ala Ala Ser Ala Leu Leu Tyr
225                 230                 235                 240

Arg His Trp Ile Glu Ile Val Leu Leu Tyr Arg Thr Tyr Gln Ser Lys
                245                 250                 255

Asp Gln Thr Leu Gly Asp Lys Lys Asp Phe Asp Ala Phe Val Ser Tyr
            260                 265                 270

Ala Lys Trp Ser Ser Phe Pro Ser Glu Ala Thr Ser Ser Leu Ser Glu
        275                 280                 285

Glu His Leu Ala Leu Ser Leu Phe Pro Asp Val Leu Glu Asn Lys Tyr
    290                 295                 300

Gly Tyr Ser Leu Cys Leu Leu Glu Arg Asp Val Ala Pro Gly Gly Val
305                 310                 315                 320

Tyr Ala Glu Asp Ile Val Ser Ile Ile Lys Arg Ser Arg Arg Gly Ile
                325                 330                 335

Phe Ile Leu Ser Pro Asn Tyr Val Asn Gly Pro Ser Ile Phe Glu Leu
            340                 345                 350

Gln Ala Ala Val Asn Leu Ala Leu Asp Asp Gln Thr Leu Lys Leu Ile
        355                 360                 365

Leu Ile Lys Phe Cys Tyr Phe Gln Glu Pro Glu Ser Leu Pro His Leu
    370                 375                 380

Val Lys Lys Ala Leu Arg Val Leu Pro Thr Val Thr Trp Arg Gly Leu
385                 390                 395                 400

Lys Ser Val Pro Pro Asn Ser Arg Phe Trp Ala Lys Met Arg Tyr His
                405                 410                 415

Met Pro Val Lys Asn Ser Gln Gly Phe Thr Trp Asn Gln Leu Arg Ile
            420                 425                 430

Thr Ser Arg Ile Phe Gln Trp Lys Gly Leu Ser Arg Thr Glu Thr Thr
        435                 440                 445

Gly Arg Ser Ser Gln Pro Lys Glu Trp
    450                 455
```

-continued

<210> SEQ ID NO 88
<211> LENGTH: 149
<212> TYPE: PRT
<213> ORGANISM: Homo sapiens

<400> SEQUENCE: 88

Met Leu Cys Leu Gly Trp Ile Phe Leu Trp Leu Val Ala Gly Glu Arg
1               5                   10                  15

Ile Lys Gly Phe Asn Ile Ser Gly Cys Ser Thr Lys Lys Leu Leu Trp
            20                  25                  30

Thr Tyr Ser Thr Arg Ser Glu Glu Glu Phe Val Leu Phe Cys Asp Leu
        35                  40                  45

Pro Glu Pro Gln Lys Ser His Phe Cys His Arg Asn Arg Leu Ser Pro
    50                  55                  60

Lys Gln Val Pro Glu His Leu Pro Phe Met Gly Ser Asn Asp Leu Ser
65                  70                  75                  80

Asp Val Gln Trp Tyr Gln Gln Pro Ser Asn Gly Asp Pro Leu Glu Asp
                85                  90                  95

Ile Arg Lys Ser Tyr Pro His Ile Ile Gln Asp Lys Cys Thr Leu His
            100                 105                 110

Phe Leu Thr Pro Gly Val Asn Asn Ser Gly Ser Tyr Ile Cys Arg Pro
        115                 120                 125

Lys Met Ile Lys Tyr Asp Pro Asn Thr Phe Leu Ser Glu Asn Ile Ser
    130                 135                 140

Lys Ser Ser Ile Ile
145

<210> SEQ ID NO 89
<211> LENGTH: 126
<212> TYPE: PRT
<213> ORGANISM: Homo sapiens

<400> SEQUENCE: 89

Met Leu Cys Leu Gly Trp Ile Phe Leu Trp Leu Val Ala Gly Glu Arg
1               5                   10                  15

Ile Lys Gly Phe Asn Ile Ser Gly Cys Ser Thr Lys Lys Leu Leu Trp
            20                  25                  30

Thr Tyr Ser Thr Arg Ser Glu Glu Glu Phe Val Leu Phe Cys Asp Leu
        35                  40                  45

Pro Glu Pro Gln Lys Ser His Phe Cys His Arg Asn Arg Leu Ser Pro
    50                  55                  60

Lys Gln Val Pro Glu His Leu Pro Phe Met Gly Ser Asn Asp Leu Ser
65                  70                  75                  80

Asp Val Gln Trp Tyr Gln Gln Pro Ser Asn Gly Asp Pro Leu Glu Asp
                85                  90                  95

Ile Arg Lys Ser Tyr Pro His Ile Ile Gln Asp Lys Cys Thr Leu His
            100                 105                 110

Phe Leu Thr Pro Gly Leu Gly His Ile Phe Val Asp Pro Arg
        115                 120                 125

<210> SEQ ID NO 90
<211> LENGTH: 337
<212> TYPE: PRT
<213> ORGANISM: Homo sapiens

<400> SEQUENCE: 90

Met Asn Ser Thr Cys Ile Glu Glu Gln His Asp Leu Asp His Tyr Leu
1               5                   10                  15

Phe Pro Ile Val Tyr Ile Phe Val Ile Ile Val Ser Ile Pro Ala Asn
20 25 30

Ile Gly Ser Leu Cys Val Ser Phe Leu Gln Ala Lys Lys Glu Ser Glu
35 40 45

Leu Gly Ile Tyr Leu Phe Ser Leu Ser Leu Ser Asp Leu Leu Tyr Ala
50 55 60

Leu Thr Leu Pro Leu Trp Ile Asp Tyr Thr Trp Asn Lys Asp Asn Trp
65 70 75 80

Thr Phe Ser Pro Ala Leu Cys Lys Gly Ser Ala Phe Leu Met Tyr Met
85 90 95

Asn Phe Tyr Ser Ser Thr Ala Phe Leu Thr Cys Ile Ala Val Asp Arg
100 105 110

Tyr Leu Ala Val Val Tyr Pro Leu Lys Phe Phe Phe Leu Arg Thr Arg
115 120 125

Arg Phe Ala Leu Met Val Ser Leu Ser Ile Trp Ile Leu Glu Thr Ile
130 135 140

Phe Asn Ala Val Met Leu Trp Glu Asp Glu Thr Val Val Glu Tyr Cys
145 150 155 160

Asp Ala Glu Lys Ser Asn Phe Thr Leu Cys Tyr Asp Lys Tyr Pro Leu
165 170 175

Glu Lys Trp Gln Ile Asn Leu Asn Leu Phe Arg Thr Cys Thr Gly Tyr
180 185 190

Ala Ile Pro Leu Val Thr Ile Leu Ile Cys Asn Arg Lys Val Tyr Gln
195 200 205

Ala Val Arg His Asn Lys Ala Thr Glu Asn Lys Glu Lys Lys Arg Ile
210 215 220

Ile Lys Leu Leu Val Ser Ile Thr Val Thr Phe Val Leu Cys Phe Thr
225 230 235 240

Pro Phe His Val Met Leu Leu Ile Arg Cys Ile Leu Glu His Ala Val
245 250 255

Asn Phe Glu Asp His Ser Asn Ser Gly Lys Arg Thr Tyr Thr Met Tyr
260 265 270

Arg Ile Thr Val Ala Leu Thr Ser Leu Asn Cys Val Ala Asp Pro Ile
275 280 285

Leu Tyr Cys Phe Val Thr Glu Thr Gly Arg Tyr Asp Met Trp Asn Ile
290 295 300

Leu Lys Phe Cys Thr Gly Arg Cys Asn Thr Ser Gln Arg Gln Arg Lys
305 310 315 320

Arg Ile Leu Ser Val Ser Thr Lys Asp Thr Met Glu Leu Glu Val Leu
325 330 335

Glu

<210> SEQ ID NO 91
<211> LENGTH: 417
<212> TYPE: PRT
<213> ORGANISM: Homo sapiens

<400> SEQUENCE: 91

Met Thr Glu Glu Thr His Pro Asp Asp Asp Ser Tyr Ile Val Arg Val
1 5 10 15

Lys Ala Val Val Met Thr Arg Asp Asp Ser Ser Gly Gly Trp Phe Pro
20 25 30

Gln Glu Gly Gly Gly Ile Ser Arg Val Gly Val Cys Lys Val Met His
35 40 45

Pro Glu Gly Asn Gly Arg Ser Gly Phe Leu Ile His Gly Glu Arg Gln
    50                  55                  60

Lys Asp Lys Leu Val Val Leu Glu Cys Tyr Val Arg Lys Asp Leu Val
65                  70                  75                  80

Tyr Thr Lys Ala Asn Pro Thr Phe His His Trp Lys Val Asp Asn Arg
                85                  90                  95

Lys Phe Gly Leu Thr Phe Gln Ser Pro Ala Asp Ala Arg Ala Phe Asp
            100                 105                 110

Arg Gly Val Arg Lys Ala Ile Glu Asp Leu Ile Glu Gly Ser Thr Thr
        115                 120                 125

Ser Ser Ser Thr Ile His Asn Glu Ala Glu Leu Gly Asp Asp Asp Val
    130                 135                 140

Phe Thr Thr Ala Thr Asp Ser Ser Ser Asn Ser Ser Gln Lys Arg Glu
145                 150                 155                 160

Gln Pro Thr Arg Thr Ile Ser Ser Pro Thr Ser Cys Glu His Arg Arg
                165                 170                 175

Ile Tyr Thr Leu Gly His Leu His Asp Ser Tyr Pro Thr Asp His Tyr
            180                 185                 190

His Leu Asp Gln Pro Met Pro Arg Pro Tyr Arg Gln Val Ser Phe Pro
        195                 200                 205

Asp Asp Asp Glu Glu Ile Val Arg Ile Asn Pro Arg Glu Lys Ile Trp
    210                 215                 220

Met Thr Gly Tyr Glu Asp Tyr Arg His Ala Pro Val Arg Gly Lys Tyr
225                 230                 235                 240

Pro Asp Pro Ser Glu Asp Ala Asp Ser Ser Tyr Val Arg Phe Ala Lys
                245                 250                 255

Gly Glu Val Pro Lys His Asp Tyr Asn Tyr Pro Tyr Val Asp Ser Ser
            260                 265                 270

Asp Phe Gly Leu Gly Glu Asp Pro Lys Gly Arg Gly Gly Ser Val Ile
        275                 280                 285

Lys Thr Gln Pro Ser Arg Gly Lys Ser Arg Arg Arg Lys Glu Asp Gly
    290                 295                 300

Glu Arg Ser Arg Cys Val Tyr Cys Arg Asp Met Phe Asn His Glu Glu
305                 310                 315                 320

Asn Arg Arg Gly His Cys Gln Asp Ala Pro Asp Ser Val Arg Thr Cys
                325                 330                 335

Ile Arg Arg Val Ser Cys Met Trp Cys Ala Asp Ser Met Leu Tyr His
            340                 345                 350

Cys Met Ser Asp Pro Glu Gly Asp Tyr Thr Asp Pro Cys Ser Cys Asp
        355                 360                 365

Thr Ser Asp Glu Lys Phe Cys Leu Arg Trp Met Ala Leu Ile Ala Leu
    370                 375                 380

Ser Phe Leu Ala Pro Cys Met Cys Cys Tyr Leu Pro Leu Arg Ala Cys
385                 390                 395                 400

Tyr His Cys Gly Val Met Cys Arg Cys Cys Gly Gly Lys His Lys Ala
                405                 410                 415

Ala

<210> SEQ ID NO 92
<211> LENGTH: 359
<212> TYPE: PRT
<213> ORGANISM: Homo sapiens

<400> SEQUENCE: 92

```
Met Pro Asn Pro Ser Ser Thr Ser Ser Pro Tyr Pro Leu Pro Glu Glu
1               5                   10                  15

Ile Arg Asn Leu Leu Ala Asp Val Glu Thr Phe Val Ala Asp Ile Leu
            20                  25                  30

Lys Gly Glu Asn Leu Ser Lys Lys Ala Lys Glu Lys Arg Glu Ser Leu
        35                  40                  45

Ile Lys Lys Ile Lys Asp Val Lys Ser Ile Tyr Leu Gln Glu Phe Gln
    50                  55                  60

Asp Lys Gly Asp Ala Glu Asp Gly Glu Glu Tyr Asp Asp Pro Phe Ala
65                  70                  75                  80

Gly Pro Pro Asp Thr Ile Ser Leu Ala Ser Glu Arg Tyr Asp Lys Asp
                85                  90                  95

Asp Glu Ala Pro Ser Asp Gly Ala Gln Phe Pro Pro Ile Ala Ala Gln
            100                 105                 110

Asp Leu Pro Phe Val Leu Lys Ala Gly Tyr Leu Glu Lys Arg Arg Lys
        115                 120                 125

Asp His Ser Phe Leu Gly Phe Glu Trp Gln Lys Arg Trp Cys Ala Leu
    130                 135                 140

Ser Lys Thr Val Phe Tyr Tyr Tyr Gly Ser Asp Lys Asp Lys Gln Gln
145                 150                 155                 160

Lys Gly Glu Phe Ala Ile Asp Gly Tyr Ser Val Arg Met Asn Asn Thr
                165                 170                 175

Leu Arg Lys Asp Gly Lys Lys Asp Cys Cys Phe Glu Ile Ser Ala Pro
            180                 185                 190

Asp Lys Arg Ile Tyr Gln Phe Thr Ala Ala Ser Pro Lys Asp Ala Glu
        195                 200                 205

Glu Trp Val Gln Gln Leu Lys Phe Val Leu Gln Asp Met Glu Ser Asp
    210                 215                 220

Ile Ile Pro Glu Asp Tyr Asp Glu Arg Gly Glu Leu Tyr Asp Asp Val
225                 230                 235                 240

Asp His Pro Leu Pro Ile Ser Asn Pro Leu Thr Ser Ser Gln Pro Ile
                245                 250                 255

Asp Asp Glu Ile Tyr Glu Glu Leu Pro Glu Glu Glu Glu Asp Ser Ala
            260                 265                 270

Pro Val Lys Val Glu Glu Gln Arg Lys Met Ser Gln Asp Ser Val His
        275                 280                 285

His Thr Ser Gly Asp Lys Ser Thr Asp Tyr Ala Asn Phe Tyr Gln Gly
    290                 295                 300

Leu Trp Asp Cys Thr Gly Ala Phe Ser Asp Glu Leu Ser Phe Lys Arg
305                 310                 315                 320

Gly Asp Val Ile Tyr Ile Leu Ser Lys Glu Tyr Asn Arg Tyr Gly Trp
                325                 330                 335

Trp Val Gly Glu Met Lys Gly Ala Ile Gly Leu Val Pro Lys Ala Tyr
            340                 345                 350

Ile Met Glu Met Tyr Asp Ile
        355
```

<210> SEQ ID NO 93
<211> LENGTH: 187
<212> TYPE: PRT
<213> ORGANISM: Homo sapiens

<400> SEQUENCE: 93

```
Met Asn Asn Thr Leu Arg Lys Asp Gly Lys Lys Asp Cys Cys Phe Glu
```

-continued 1 5 10 15

Ile Ser Ala Pro Asp Lys Arg Ile Tyr Gln Phe Thr Ala Ala Ser Pro
20 25 30

Lys Asp Ala Glu Glu Trp Val Gln Gln Leu Lys Phe Val Leu Gln Asp
35 40 45

Met Glu Ser Asp Ile Ile Pro Glu Asp Tyr Asp Glu Arg Gly Glu Leu
50 55 60

Tyr Asp Asp Val Asp His Pro Leu Pro Ile Ser Asn Pro Leu Thr Ser
65 70 75 80

Ser Gln Pro Ile Asp Asp Glu Ile Tyr Glu Glu Leu Pro Glu Glu Glu
85 90 95

Glu Asp Ser Ala Pro Val Lys Val Glu Glu Gln Arg Lys Met Ser Gln
100 105 110

Asp Ser Val His His Thr Ser Gly Asp Lys Ser Thr Asp Tyr Ala Asn
115 120 125

Phe Tyr Gln Gly Leu Trp Asp Cys Thr Gly Ala Phe Ser Asp Glu Leu
130 135 140

Ser Phe Lys Arg Gly Asp Val Ile Tyr Ile Leu Ser Lys Glu Tyr Asn
145 150 155 160

Arg Tyr Gly Trp Trp Val Gly Glu Met Lys Gly Ala Ile Gly Leu Val
165 170 175

Pro Lys Ala Tyr Ile Met Glu Met Tyr Asp Ile
180 185

<210> SEQ ID NO 94
<211> LENGTH: 483
<212> TYPE: PRT
<213> ORGANISM: Homo sapiens

<400> SEQUENCE: 94

Met Phe Cys Ser Thr Ser Ala Val Asn Ser Cys Ala Arg Cys Phe Phe
1 5 10 15

His Ser Val Cys Pro Ala Gly Met Ile Val Lys Phe Pro Gly Thr Ala
20 25 30

Gln Lys Asn Thr Val Cys Glu Pro Ala Ser Pro Gly Val Ser Pro Ala
35 40 45

Cys Ala Ser Pro Glu Asn Cys Lys Glu Pro Ser Ser Gly Thr Ile Pro
50 55 60

Gln Ala Lys Pro Thr Pro Val Ser Pro Ala Thr Ser Ser Ala Ser Thr
65 70 75 80

Met Pro Val Arg Gly Gly Thr Arg Leu Ala Gln Glu Ala Ala Ser Lys
85 90 95

Leu Thr Arg Ala Pro Asp Ser Pro Ser Ser Val Gly Arg Pro Ser Ser
100 105 110

Asp Pro Gly Leu Ser Pro Thr Gln Pro Cys Pro Glu Gly Ser Gly Asp
115 120 125

Cys Arg Lys Gln Cys Glu Pro Asp Tyr Tyr Leu Asp Glu Ala Gly Arg
130 135 140

Cys Thr Ala Cys Val Ser Cys Ser Arg Asp Asp Leu Val Glu Lys Thr
145 150 155 160

Pro Cys Ala Trp Asn Ser Ser Arg Thr Cys Glu Cys Arg Pro Gly Met
165 170 175

Ile Cys Ala Thr Ser Ala Thr Asn Ser Cys Ala Arg Cys Val Pro Tyr
180 185 190

Pro Ile Cys Ala Ala Glu Thr Val Thr Lys Pro Gln Asp Met Ala Glu
195 200 205

Lys Asp Thr Thr Phe Glu Ala Pro Pro Leu Gly Thr Gln Pro Asp Cys
210 215 220

Asn Pro Thr Pro Glu Asn Gly Glu Ala Pro Ala Ser Thr Ser Pro Thr
225 230 235 240

Gln Ser Leu Leu Val Asp Ser Gln Ala Ser Lys Thr Leu Pro Ile Pro
245 250 255

Thr Ser Ala Pro Val Ala Leu Ser Ser Thr Gly Lys Pro Val Leu Asp
260 265 270

Ala Gly Pro Val Leu Phe Trp Val Ile Leu Val Leu Val Val Val Val
275 280 285

Gly Ser Ser Ala Phe Leu Leu Cys His Arg Arg Ala Cys Arg Lys Arg
290 295 300

Ile Arg Gln Lys Leu His Leu Cys Tyr Pro Val Gln Thr Ser Gln Pro
305 310 315 320

Lys Leu Glu Leu Val Asp Ser Arg Pro Arg Arg Ser Ser Thr Leu Arg
325 330 335

Ser Gly Ala Ser Val Thr Glu Pro Val Ala Glu Glu Arg Gly Leu Met
340 345 350

Ser Gln Pro Leu Met Glu Thr Cys His Ser Val Gly Ala Ala Tyr Leu
355 360 365

Glu Ser Leu Pro Leu Gln Asp Ala Ser Pro Ala Gly Gly Pro Ser Ser
370 375 380

Pro Arg Asp Leu Pro Glu Pro Arg Val Ser Thr Glu His Thr Asn Asn
385 390 395 400

Lys Ile Glu Lys Ile Tyr Ile Met Lys Ala Asp Thr Val Ile Val Gly
405 410 415

Thr Val Lys Ala Glu Leu Pro Glu Gly Arg Gly Leu Ala Gly Pro Ala
420 425 430

Glu Pro Glu Leu Glu Glu Glu Leu Glu Ala Asp His Thr Pro His Tyr
435 440 445

Pro Glu Gln Glu Thr Glu Pro Pro Leu Gly Ser Cys Ser Asp Val Met
450 455 460

Leu Ser Val Glu Glu Glu Gly Lys Glu Asp Pro Leu Pro Thr Ala Ala
465 470 475 480

Ser Gly Lys

<210> SEQ ID NO 95
<211> LENGTH: 595
<212> TYPE: PRT
<213> ORGANISM: Homo sapiens

<400> SEQUENCE: 95

Met Arg Val Leu Leu Ala Ala Leu Gly Leu Leu Phe Leu Gly Ala Leu
1 5 10 15

Arg Ala Phe Pro Gln Asp Arg Pro Phe Glu Asp Thr Cys His Gly Asn
20 25 30

Pro Ser His Tyr Tyr Asp Lys Ala Val Arg Arg Cys Cys Tyr Arg Cys
35 40 45

Pro Met Gly Leu Phe Pro Thr Gln Gln Cys Pro Gln Arg Pro Thr Asp
50 55 60

Cys Arg Lys Gln Cys Glu Pro Asp Tyr Tyr Leu Asp Glu Ala Asp Arg
65 70 75 80

-continued

```
Cys Thr Ala Cys Val Thr Cys Ser Arg Asp Asp Leu Val Glu Lys Thr
                85                  90                  95

Pro Cys Ala Trp Asn Ser Ser Arg Val Cys Glu Cys Arg Pro Gly Met
            100                 105                 110

Phe Cys Ser Thr Ser Ala Val Asn Ser Cys Ala Arg Cys Phe Phe His
        115                 120                 125

Ser Val Cys Pro Ala Gly Met Ile Val Lys Phe Pro Gly Thr Ala Gln
    130                 135                 140

Lys Asn Thr Val Cys Glu Pro Ala Ser Pro Gly Val Ser Pro Ala Cys
145                 150                 155                 160

Ala Ser Pro Glu Asn Cys Lys Glu Pro Ser Ser Gly Thr Ile Pro Gln
                165                 170                 175

Ala Lys Pro Thr Pro Val Ser Pro Ala Thr Ser Ser Ala Ser Thr Met
            180                 185                 190

Pro Val Arg Gly Gly Thr Arg Leu Ala Gln Glu Ala Ala Ser Lys Leu
        195                 200                 205

Thr Arg Ala Pro Asp Ser Pro Ser Ser Val Gly Arg Pro Ser Ser Asp
    210                 215                 220

Pro Gly Leu Ser Pro Thr Gln Pro Cys Pro Glu Gly Ser Gly Asp Cys
225                 230                 235                 240

Arg Lys Gln Cys Glu Pro Asp Tyr Tyr Leu Asp Glu Ala Gly Arg Cys
                245                 250                 255

Thr Ala Cys Val Ser Cys Ser Arg Asp Asp Leu Val Glu Lys Thr Pro
            260                 265                 270

Cys Ala Trp Asn Ser Ser Arg Thr Cys Glu Cys Arg Pro Gly Met Ile
        275                 280                 285

Cys Ala Thr Ser Ala Thr Asn Ser Cys Ala Arg Cys Val Pro Tyr Pro
    290                 295                 300

Ile Cys Ala Ala Glu Thr Val Thr Lys Pro Gln Asp Met Ala Glu Lys
305                 310                 315                 320

Asp Thr Thr Phe Glu Ala Pro Pro Leu Gly Thr Gln Pro Asp Cys Asn
                325                 330                 335

Pro Thr Pro Glu Asn Gly Glu Ala Pro Ala Ser Thr Ser Pro Thr Gln
            340                 345                 350

Ser Leu Leu Val Asp Ser Gln Ala Ser Lys Thr Leu Pro Ile Pro Thr
        355                 360                 365

Ser Ala Pro Val Ala Leu Ser Ser Thr Gly Lys Pro Val Leu Asp Ala
    370                 375                 380

Gly Pro Val Leu Phe Trp Val Ile Leu Val Leu Val Val Val Val Gly
385                 390                 395                 400

Ser Ser Ala Phe Leu Leu Cys His Arg Arg Ala Cys Arg Lys Arg Ile
                405                 410                 415

Arg Gln Lys Leu His Leu Cys Tyr Pro Val Gln Thr Ser Gln Pro Lys
            420                 425                 430

Leu Glu Leu Val Asp Ser Arg Pro Arg Arg Ser Ser Thr Gln Leu Arg
        435                 440                 445

Ser Gly Ala Ser Val Thr Glu Pro Val Ala Glu Glu Arg Gly Leu Met
    450                 455                 460

Ser Gln Pro Leu Met Glu Thr Cys His Ser Val Gly Ala Ala Tyr Leu
465                 470                 475                 480

Glu Ser Leu Pro Leu Gln Asp Ala Ser Pro Ala Gly Gly Pro Ser Ser
                485                 490                 495

Pro Arg Asp Leu Pro Glu Pro Arg Val Ser Thr Glu His Thr Asn Asn
```

-continued

```
            500                 505                 510

Lys Ile Glu Lys Ile Tyr Ile Met Lys Ala Asp Thr Val Ile Val Gly
        515                 520                 525

Thr Val Lys Ala Glu Leu Pro Glu Gly Arg Gly Leu Ala Gly Pro Ala
    530                 535                 540

Glu Pro Glu Leu Glu Glu Glu Leu Glu Ala Asp His Thr Pro His Tyr
545                 550                 555                 560

Pro Glu Gln Glu Thr Glu Pro Pro Leu Gly Ser Cys Ser Asp Val Met
                565                 570                 575

Leu Ser Val Glu Glu Glu Gly Lys Glu Asp Pro Leu Pro Thr Ala Ala
            580                 585                 590

Ser Gly Lys
        595


<210> SEQ ID NO 96
<211> LENGTH: 116
<212> TYPE: PRT
<213> ORGANISM: Homo sapiens

<400> SEQUENCE: 96

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Phe Thr Asp Tyr
            20                  25                  30

Tyr Ile Thr Trp Val Arg Gln Ala Pro Gly Gln Ala Leu Glu Trp Met
        35                  40                  45

Gly Trp Ile Tyr Pro Gly Ser Gly Asn Thr Lys Tyr Ser Gln Lys Phe
    50                  55                  60

Gln Gly Arg Phe Val Phe Ser Val Asp Thr Ser Ala Ser Thr Ala Tyr
65                  70                  75                  80

Leu Gln Ile Ser Ser Leu Lys Ala Glu Asp Thr Ala Val Tyr Tyr Cys
                85                  90                  95

Ala Asn Tyr Gly Asn Tyr Trp Phe Ala Tyr Trp Gly Gln Gly Thr Leu
            100                 105                 110

Val Thr Val Ser
        115


<210> SEQ ID NO 97
<211> LENGTH: 111
<212> TYPE: PRT
<213> ORGANISM: Homo sapiens

<400> SEQUENCE: 97

Glu Ile Val Leu Thr Gln Ser Pro Asp Ser Leu Ala Val Ser Leu Gly
1               5                   10                  15

Glu Arg Ala Thr Ile Asn Cys Lys Ala Ser Gln Ser Val Asp Phe Asp
            20                  25                  30

Gly Asp Ser Tyr Leu Asn Trp Tyr Gln Gln Lys Pro Gly Gln Pro Pro
        35                  40                  45

Lys Val Leu Ile Tyr Ala Ala Ser Thr Leu Gln Ser Gly Val Pro Ser
    50                  55                  60

Arg Phe Ser Gly Ser Gly Ser Gly Thr Asp Phe Thr Leu Thr Ile Asn
65                  70                  75                  80

Ser Leu Glu Ala Glu Asp Ala Ala Thr Tyr Tyr Cys Gln Gln Ser Asn
                85                  90                  95

Glu Asp Pro Trp Thr Phe Gly Gly Gly Thr Lys Val Glu Ile Lys
```

100 105 110

<210> SEQ ID NO 98

<400> SEQUENCE: 98

000

<210> SEQ ID NO 99

<400> SEQUENCE: 99

000

<210> SEQ ID NO 100
<211> LENGTH: 5
<212> TYPE: PRT
<213> ORGANISM: Homo sapiens

<400> SEQUENCE: 100

Ser Tyr Ile Trp Ser
1 5

<210> SEQ ID NO 101
<211> LENGTH: 16
<212> TYPE: PRT
<213> ORGANISM: Homo sapiens

<400> SEQUENCE: 101

Arg Ile Tyr Ala Ser Gly Asn Thr Asn Tyr Asn Pro Ser Leu Lys Ser
1 5 10 15

<210> SEQ ID NO 102
<211> LENGTH: 16
<212> TYPE: PRT
<213> ORGANISM: Homo sapiens

<400> SEQUENCE: 102

Asp Tyr Arg Val Ala Gly Thr Tyr Tyr Tyr Tyr Tyr Gly Leu Asp Val
1 5 10 15

<210> SEQ ID NO 103
<211> LENGTH: 14
<212> TYPE: PRT
<213> ORGANISM: Homo sapiens

<400> SEQUENCE: 103

Thr Gly Thr Ser Ser Asp Val Gly Val Tyr Asp Tyr Val Ser
1 5 10

<210> SEQ ID NO 104
<211> LENGTH: 7
<212> TYPE: PRT
<213> ORGANISM: Homo sapiens

<400> SEQUENCE: 104

Glu Val Ser Asn Arg Pro Ser
1 5

<210> SEQ ID NO 105
<211> LENGTH: 10
<212> TYPE: PRT
<213> ORGANISM: Homo sapiens

<400> SEQUENCE: 105

Ser Ser Tyr Thr Ser Arg Ser Thr Trp Val
1 5 10

<210> SEQ ID NO 106
<211> LENGTH: 5
<212> TYPE: PRT
<213> ORGANISM: Homo sapiens

<400> SEQUENCE: 106

Ser Tyr Tyr Trp Thr
1 5

<210> SEQ ID NO 107
<211> LENGTH: 16
<212> TYPE: PRT
<213> ORGANISM: Homo sapiens

<400> SEQUENCE: 107

Arg Ile Tyr Thr Ser Gly Ile Thr Asn Tyr Asn Pro Ser Leu Lys Ser
1 5 10 15

<210> SEQ ID NO 108
<211> LENGTH: 16
<212> TYPE: PRT
<213> ORGANISM: Homo sapiens

<400> SEQUENCE: 108

Glu Arg Val Val Gly Ala Ser Arg Tyr Tyr Tyr Tyr Gly Val Asp Val
1 5 10 15

<210> SEQ ID NO 109
<211> LENGTH: 14
<212> TYPE: PRT
<213> ORGANISM: Homo sapiens

<400> SEQUENCE: 109

Thr Gly Thr Ser Ser Asp Val Gly Leu Tyr Asn Tyr Val Ser
1 5 10

<210> SEQ ID NO 110
<211> LENGTH: 7
<212> TYPE: PRT
<213> ORGANISM: Homo sapiens

<400> SEQUENCE: 110

Glu Val Asn Asn Arg Pro Ser
1 5

<210> SEQ ID NO 111
<211> LENGTH: 10
<212> TYPE: PRT
<213> ORGANISM: Homo sapiens

<400> SEQUENCE: 111

Ser Ser Tyr Thr Ser Ser Ser Thr Trp Val
1 5 10

<210> SEQ ID NO 112
<211> LENGTH: 5
<212> TYPE: PRT
<213> ORGANISM: Homo sapiens

<400> SEQUENCE: 112

Ser Tyr Tyr Trp Thr
1 5

<210> SEQ ID NO 113
<211> LENGTH: 16
<212> TYPE: PRT
<213> ORGANISM: Homo sapiens

<400> SEQUENCE: 113

```
Arg Ile Tyr Thr Ser Gly Ile Thr Asn Tyr Asn Pro Ser Leu Lys Ser
1               5                   10                  15
```

<210> SEQ ID NO 114
<211> LENGTH: 16
<212> TYPE: PRT
<213> ORGANISM: Homo sapiens

<400> SEQUENCE: 114

```
Glu Arg Val Val Gly Ala Ser Arg Tyr Tyr Tyr Tyr Gly Val Asp Val
1               5                   10                  15
```

<210> SEQ ID NO 115
<211> LENGTH: 14
<212> TYPE: PRT
<213> ORGANISM: Homo sapiens

<400> SEQUENCE: 115

```
Thr Gly Thr Ser Ser Asp Ile Gly Leu Tyr Asp Tyr Val Ser
1               5                   10
```

<210> SEQ ID NO 116
<211> LENGTH: 7
<212> TYPE: PRT
<213> ORGANISM: Homo sapiens

<400> SEQUENCE: 116

```
Glu Val Asn Asn Arg Pro Ser
1               5
```

<210> SEQ ID NO 117
<211> LENGTH: 10
<212> TYPE: PRT
<213> ORGANISM: Homo sapiens

<400> SEQUENCE: 117

```
Ser Ser Tyr Thr Ser Ser Ser Thr Trp Val
1               5                   10
```

<210> SEQ ID NO 118
<211> LENGTH: 5
<212> TYPE: PRT
<213> ORGANISM: Homo sapiens

<400> SEQUENCE: 118

```
Ser Tyr Ser Trp Ser
1               5
```

<210> SEQ ID NO 119
<211> LENGTH: 16
<212> TYPE: PRT
<213> ORGANISM: Homo sapiens

<400> SEQUENCE: 119

```
Arg Thr Ser Thr Ser Gly Arg Asn Asn Tyr Asn Pro Ser Leu Lys Ser
1               5                   10                  15
```

<210> SEQ ID NO 120
<211> LENGTH: 16
<212> TYPE: PRT
<213> ORGANISM: Homo sapiens

<400> SEQUENCE: 120

Asp Phe Thr Ile Ala Ala Arg Arg Tyr Tyr Tyr Tyr Gly Met Asp Val
1 5 10 15

<210> SEQ ID NO 121
<211> LENGTH: 14
<212> TYPE: PRT
<213> ORGANISM: Homo sapiens

<400> SEQUENCE: 121

Thr Gly Thr Ser Ser Asp Ile Gly Leu Tyr Asn Tyr Val Ser
1 5 10

<210> SEQ ID NO 122
<211> LENGTH: 7
<212> TYPE: PRT
<213> ORGANISM: Homo sapiens

<400> SEQUENCE: 122

Glu Val Ile Asn Arg Pro Ser
1 5

<210> SEQ ID NO 123
<211> LENGTH: 10
<212> TYPE: PRT
<213> ORGANISM: Homo sapiens

<400> SEQUENCE: 123

Ser Ser Tyr Thr Ser Ser Ser Thr Trp Val
1 5 10

<210> SEQ ID NO 124
<211> LENGTH: 5
<212> TYPE: PRT
<213> ORGANISM: Homo sapiens

<400> SEQUENCE: 124

Asn Asn Tyr Trp Ser
1 5

<210> SEQ ID NO 125
<211> LENGTH: 16
<212> TYPE: PRT
<213> ORGANISM: Homo sapiens

<400> SEQUENCE: 125

Arg Val Tyr Ser Ser Gly Leu Thr Asn Tyr Lys Pro Ser Leu Lys Ser
1 5 10 15

<210> SEQ ID NO 126
<211> LENGTH: 16
<212> TYPE: PRT
<213> ORGANISM: Homo sapiens

<400> SEQUENCE: 126

Glu Arg Ala Thr Val Thr Thr Arg Tyr His Tyr Asp Gly Met Asp Val
1 5 10 15

<210> SEQ ID NO 127
<211> LENGTH: 14

<212> TYPE: PRT
<213> ORGANISM: Homo sapiens

<400> SEQUENCE: 127

Thr Gly Ser Ser Ser Asp Ile Gly Thr Tyr Asn Tyr Val Ser
1               5                   10

<210> SEQ ID NO 128
<211> LENGTH: 7
<212> TYPE: PRT
<213> ORGANISM: Homo sapiens

<400> SEQUENCE: 128

Glu Val Asn Asn Arg Pro Ser
1               5

<210> SEQ ID NO 129
<211> LENGTH: 10
<212> TYPE: PRT
<213> ORGANISM: Homo sapiens

<400> SEQUENCE: 129

Ser Ser Tyr Ser Ser Ser Ser Thr Trp Val
1               5                   10

<210> SEQ ID NO 130
<211> LENGTH: 5
<212> TYPE: PRT
<213> ORGANISM: Homo sapiens

<400> SEQUENCE: 130

Ser Tyr Tyr Trp Ser
1               5

<210> SEQ ID NO 131
<211> LENGTH: 16
<212> TYPE: PRT
<213> ORGANISM: Homo sapiens

<400> SEQUENCE: 131

Arg Ile Phe Ala Ser Gly Ser Thr Asn Tyr Asn Pro Ser Leu Arg Ser
1               5                   10                  15

<210> SEQ ID NO 132
<211> LENGTH: 16
<212> TYPE: PRT
<213> ORGANISM: Homo sapiens

<400> SEQUENCE: 132

Glu Arg Val Gly Val Gln Asp Tyr Tyr His Tyr Ser Gly Met Asp Val
1               5                   10                  15

<210> SEQ ID NO 133
<211> LENGTH: 14
<212> TYPE: PRT
<213> ORGANISM: Homo sapiens

<400> SEQUENCE: 133

Thr Gly Thr Ser Ser Asp Val Gly Leu Tyr Asn Tyr Val Ser
1               5                   10

<210> SEQ ID NO 134
<211> LENGTH: 7
<212> TYPE: PRT
<213> ORGANISM: Homo sapiens

<400> SEQUENCE: 134

Glu Val Ser Lys Arg Pro Ser
1               5

<210> SEQ ID NO 135
<211> LENGTH: 10
<212> TYPE: PRT
<213> ORGANISM: Homo sapiens

<400> SEQUENCE: 135

Ser Ser Tyr Thr Ser Ser Ser Thr Trp Val
1               5                   10

<210> SEQ ID NO 136
<211> LENGTH: 124
<212> TYPE: PRT
<213> ORGANISM: Homo sapiens

<400> SEQUENCE: 136

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Thr Trp Ile Arg Gln Pro Ala Gly Lys Gly Leu Glu Trp Ile
        35                  40                  45

Gly Arg Ile Tyr Thr Ser Gly Ile Thr Asn Tyr Asn Pro Ser Leu Lys
    50                  55                  60

Ser Arg Val Thr Met Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Glu Arg Val Val Gly Ala Ser Arg Tyr Tyr Tyr Tyr Gly Val Asp
            100                 105                 110

Val Trp Gly Gln Gly Thr Thr Val Thr Val Ser Ser
        115                 120

<210> SEQ ID NO 137
<211> LENGTH: 110
<212> TYPE: PRT
<213> ORGANISM: Homo sapiens

<400> SEQUENCE: 137

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Leu Tyr
            20                  25                  30

Asn Tyr Val Ser Trp Tyr Gln Gln His Pro Asp Lys Ala Pro Lys Leu
        35                  40                  45

Met Ile Phe Glu Val Asn Asn Arg Pro Ser Gly Val Ser Asn Arg Phe
    50                  55                  60

Ser Gly Ser Asn Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Trp Val Phe Gly Gly Gly Thr Lys Leu Thr Val Leu
            100                 105                 110

<210> SEQ ID NO 138
<211> LENGTH: 124
<212> TYPE: PRT
<213> ORGANISM: Homo sapiens

<400> SEQUENCE: 138

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Thr Trp Ile Arg Gln Pro Ala Gly Lys Gly Leu Glu Trp Ile
        35                  40                  45

Gly Arg Ile Tyr Thr Ser Gly Ile Thr Asn Tyr Asn Pro Ser Leu Lys
    50                  55                  60

Ser Arg Val Thr Met Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Glu Arg Val Val Gly Ala Ser Arg Tyr Tyr Tyr Tyr Gly Val Asp
            100                 105                 110

Val Trp Gly Gln Gly Thr Thr Val Thr Val Ser Ser
        115                 120
```

<210> SEQ ID NO 139
<211> LENGTH: 110
<212> TYPE: PRT
<213> ORGANISM: Homo sapiens

<400> SEQUENCE: 139

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Ile Gly Leu Tyr
            20                  25                  30

Asp Tyr Val Ser Trp Tyr Gln Gln His Pro Asp Arg Ala Pro Lys Leu
        35                  40                  45

Ile Ile Phe Glu Val Asn Asn Arg Pro Ser Gly Val Ser Tyr Arg Phe
    50                  55                  60

Ser Gly Ser Asn Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Trp Val Phe Gly Gly Gly Thr Lys Leu Thr Val Leu
            100                 105                 110
```

<210> SEQ ID NO 140
<211> LENGTH: 124
<212> TYPE: PRT
<213> ORGANISM: Homo sapiens

<400> SEQUENCE: 140

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Ser Trp Ser Trp Ile Arg Gln Pro Ala Gly Lys Gly Leu Glu Trp Ile
        35                  40                  45

Gly Arg Thr Ser Thr Ser Gly Arg Asn Asn Tyr Asn Pro Ser Leu Lys
    50                  55                  60
```

```
Ser Arg Val Thr Met Ser Val Asp Thr Ser Lys Asn Gln Phe Ser Leu
65                  70                  75                  80

Lys Leu Asn Ser Val Thr Ala Ala Asp Thr Ala Val Tyr Tyr Cys Ala
                85                  90                  95

Arg Asp Phe Thr Ile Ala Ala Arg Arg Tyr Tyr Tyr Tyr Gly Met Asp
            100                 105                 110

Val Trp Gly Gln Gly Thr Thr Val Thr Val Ser Ser
        115                 120


<210> SEQ ID NO 141
<211> LENGTH: 110
<212> TYPE: PRT
<213> ORGANISM: Homo sapiens

<400> SEQUENCE: 141

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Ile Gly Leu Tyr
            20                  25                  30

Asn Tyr Val Ser Trp Tyr Gln Gln His Pro Gly Lys Ala Pro Lys Leu
        35                  40                  45

Ile Ile Tyr Glu Val Ile Asn Arg Pro Ser Gly Val Ser Asn Arg Phe
    50                  55                  60

Ser Gly Ser Glu Ser Gly Asn Thr Ala Ser Leu Thr Ile Ser Gly Leu
65                  70                  75                  80

Gln Ala Glu Asp Glu Ala Asn Tyr Tyr Cys Ser Ser Tyr Thr Ser Ser
                85                  90                  95

Ser Thr Trp Val Phe Gly Gly Gly Thr Lys Leu Thr Val Leu
            100                 105                 110


<210> SEQ ID NO 142
<211> LENGTH: 124
<212> TYPE: PRT
<213> ORGANISM: Homo sapiens

<400> SEQUENCE: 142

Gln Val Gln Leu Gln Glu Ser Gly Pro Arg Leu Val Lys Pro Ser Glu
1               5                   10                  15

Thr Leu Ser Leu Thr Cys Thr Val Ser Gly Gly Ser Ile Thr Asn Asn
            20                  25                  30

Tyr Trp Ser Trp Ile Arg Gln Pro Ala Gly Lys Gly Leu Glu Trp Ile
        35                  40                  45

Gly Arg Val Tyr Ser Ser Gly Leu Thr Asn Tyr Lys Pro Ser Leu Lys
    50                  55                  60

Ser Arg Val Thr Met Ser Val Asp Thr Ser Lys Asn Gln Phe Ser Leu
65                  70                  75                  80

Arg Leu Asn Ser Val Thr Ala Ala Asp Thr Ala Val Tyr Tyr Cys Ala
                85                  90                  95

Arg Glu Arg Ala Thr Val Thr Thr Arg Tyr His Tyr Asp Gly Met Asp
            100                 105                 110

Val Trp Gly Gln Gly Thr Ser Val Thr Val Ser Ser
        115                 120


<210> SEQ ID NO 143
<211> LENGTH: 110
<212> TYPE: PRT
<213> ORGANISM: Homo sapiens
```

-continued

<400> SEQUENCE: 143

```
Gln Ser Ala Leu Thr Gln Pro Ala Ser Val Ser Gly Ser Pro Gly Gln
1               5                   10                  15

Ser Ile Thr Ile Ser Cys Thr Gly Ser Ser Ser Asp Ile Gly Thr Tyr
            20                  25                  30

Asn Tyr Val Ser Trp Tyr Gln Gln Tyr Pro Gly Lys Ala Pro Glu Leu
        35                  40                  45

Met Ile Tyr Glu Val Asn Asn Arg Pro Ser Gly Val Ser Asp Arg Phe
    50                  55                  60

Ser Gly Ser Thr Ser Gly Asn Thr Ala Ser Leu Thr Ile Ser Gly Leu
65                  70                  75                  80

Gln Ala Asn Asp Glu Ala Asp Tyr Tyr Cys Ser Ser Tyr Ser Ser Ser
                85                  90                  95

Ser Thr Trp Val Phe Gly Gly Gly Thr Lys Leu Thr Val Leu
            100                 105                 110
```

<210> SEQ ID NO 144
<211> LENGTH: 124
<212> TYPE: PRT
<213> ORGANISM: Homo sapiens

<400> SEQUENCE: 144

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Ala Gly Lys Gly Leu Glu Trp Ile
        35                  40                  45

Gly Arg Ile Phe Ala Ser Gly Ser Thr Asn Tyr Asn Pro Ser Leu Arg
    50                  55                  60

Ser Arg Val Thr Met Ser Arg Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Lys Glu Arg Val Gly Val Gln Asp Tyr Tyr His Tyr Ser Gly Met Asp
            100                 105                 110

Val Trp Gly Gln Gly Thr Thr Val Thr Val Ser Ser
        115                 120
```

<210> SEQ ID NO 145
<211> LENGTH: 110
<212> TYPE: PRT
<213> ORGANISM: Homo sapiens

<400> SEQUENCE: 145

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Leu Tyr
            20                  25                  30

Asn Tyr Val Ser Trp Tyr Gln Gln Gln Pro Gly Lys Ala Pro Lys Leu
        35                  40                  45

Met Ile Tyr Glu Val Ser Lys Arg Pro Ser Gly Val Ser Asn Arg Phe
    50                  55                  60

Ser Gly Ser Thr Ser Gly Asn Thr Ala Ser Leu Thr Ile Ser Gly Leu
65                  70                  75                  80
```

```
Gln Ala Asp Asp Glu Ala Asp Tyr Ser Cys Ser Ser Tyr Thr Ser Ser
                85                  90                  95

Ser Thr Trp Val Phe Gly Gly Gly Thr Lys Leu Thr Val Leu
            100                 105                 110


<210> SEQ ID NO 146
<211> LENGTH: 124
<212> TYPE: PRT
<213> ORGANISM: Homo sapiens

<400> SEQUENCE: 146

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Ile Trp Ser Trp Ile Arg Gln Pro Ala Gly Lys Gly Leu Glu Trp Ile
        35                  40                  45

Gly Arg Ile Tyr Ala Ser Gly Asn Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Met Thr Ala Ala Asp Thr Ala Val Tyr Tyr Cys Ala
                85                  90                  95

Arg Asp Tyr Arg Val Ala Gly Thr Tyr Tyr Tyr Tyr Tyr Gly Leu Asp
            100                 105                 110

Val Trp Gly Gln Gly Thr Thr Val Thr Val Ser Ser
        115                 120


<210> SEQ ID NO 147
<211> LENGTH: 124
<212> TYPE: PRT
<213> ORGANISM: Homo sapiens

<400> SEQUENCE: 147

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Ile Trp Ser Trp Ile Arg Gln Pro Ala Gly Lys Gly Leu Glu Trp Ile
        35                  40                  45

Gly Arg Ile Tyr Ala Ser Gly Asn Thr Asn Tyr Asn Pro Ser Leu Lys
    50                  55                  60

Ser Arg Val Thr Met Ser Val Asp Thr Ser Lys Asn Gln Phe Ser Leu
65                  70                  75                  80

Lys Leu Ser Ser Met Thr Ala Ala Asp Thr Ala Val Tyr Tyr Cys Ala
                85                  90                  95

Arg Asp Tyr Arg Val Ala Gly Thr Tyr Tyr Tyr Tyr Tyr Gly Leu Asp
            100                 105                 110

Val Trp Gly Gln Gly Thr Thr Val Thr Val Ser Ser
        115                 120


<210> SEQ ID NO 148
<211> LENGTH: 124
<212> TYPE: PRT
<213> ORGANISM: Homo sapiens

<400> SEQUENCE: 148

Gln Val Gln Leu Gln Glu Ser Gly Pro Gly Leu Val Lys Pro Ser Glu
```

```
1               5                   10                  15

Thr Leu Ser Leu Thr Cys Thr Val Ser Gly Gly Ser Ile Ser Ser Tyr
            20                  25                  30

Ile Trp Ser Trp Ile Arg Gln Pro Ala Gly Lys Gly Leu Glu Trp Ile
        35                  40                  45

Gly Arg Ile Tyr Ala Ser Gly Asn Thr Asn Tyr Asn Pro Ser Leu Lys
    50                  55                  60

Ser Arg Val Thr Met Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Tyr Arg Val Ala Gly Thr Tyr Tyr Tyr Tyr Tyr Gly Leu Asp
            100                 105                 110

Val Trp Gly Gln Gly Thr Thr Val Thr Val Ser Ser
        115                 120


<210> SEQ ID NO 149
<211> LENGTH: 124
<212> TYPE: PRT
<213> ORGANISM: Homo sapiens

<400> SEQUENCE: 149

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Ile Trp Ser Trp Ile Arg Gln Pro Ala Gly Lys Gly Leu Glu Trp Ile
        35                  40                  45

Gly Arg Ile Tyr Ala Ser Gly Gln Thr Asn Tyr Asn Pro Ser Leu Lys
    50                  55                  60

Ser Arg Val Thr Met Ser Val Asp Thr Ser Lys Asn Gln Phe Ser Leu
65                  70                  75                  80

Lys Leu Ser Ser Met Thr Ala Ala Asp Thr Ala Val Tyr Tyr Cys Ala
                85                  90                  95

Arg Asp Tyr Arg Val Ala Gly Thr Tyr Tyr Tyr Tyr Tyr Gly Leu Asp
            100                 105                 110

Val Trp Gly Gln Gly Thr Thr Val Thr Val Ser Ser
        115                 120


<210> SEQ ID NO 150
<211> LENGTH: 124
<212> TYPE: PRT
<213> ORGANISM: Homo sapiens

<400> SEQUENCE: 150

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Ile Trp Ser Trp Ile Arg Gln Pro Ala Gly Lys Gly Leu Glu Trp Ile
        35                  40                  45

Gly Arg Ile Tyr Ala Ser Gly Gln Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
```

```
                85                  90                  95

Arg Asp Tyr Arg Val Ala Gly Thr Tyr Tyr Tyr Tyr Tyr Gly Leu Asp
            100                 105                 110

Val Trp Gly Gln Gly Thr Thr Val Thr Val Ser Ser
        115                 120


<210> SEQ ID NO 151
<211> LENGTH: 124
<212> TYPE: PRT
<213> ORGANISM: Homo sapiens

<400> SEQUENCE: 151

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Ile Trp Ser Trp Ile Arg Gln Pro Ala Gly Lys Gly Leu Glu Trp Ile
        35                  40                  45

Gly Arg Ile Tyr Ala Ser Gly Asn Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Tyr Arg Val Ala Gly Thr Tyr Tyr Tyr Tyr Tyr Gly Leu Asp
            100                 105                 110

Val Trp Gly Gln Gly Thr Thr Val Thr Val Ser Ser
        115                 120


<210> SEQ ID NO 152
<211> LENGTH: 124
<212> TYPE: PRT
<213> ORGANISM: Homo sapiens

<400> SEQUENCE: 152

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Ile Trp Ser Trp Ile Arg Gln Pro Ala Gly Lys Gly Leu Glu Trp Ile
        35                  40                  45

Gly Arg Ile Tyr Ala Ser Gly Gln Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Met Thr Ala Ala Asp Thr Ala Val Tyr Tyr Cys Ala
                85                  90                  95

Arg Asp Tyr Arg Val Ala Gly Thr Tyr Tyr Tyr Tyr Tyr Gly Leu Asp
            100                 105                 110

Val Trp Gly Gln Gly Thr Thr Val Thr Val Ser Ser
        115                 120


<210> SEQ ID NO 153
<211> LENGTH: 124
<212> TYPE: PRT
<213> ORGANISM: Homo sapiens

<400> SEQUENCE: 153
```

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Ile Trp Ser Trp Ile Arg Gln Pro Ala Gly Lys Gly Leu Glu Trp Ile
        35                  40                  45

Gly Arg Ile Tyr Ala Ser Gly Gln Thr Asn Tyr Asn Pro Ser Leu Lys
    50                  55                  60

Ser Arg Val Thr Met Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Tyr Arg Val Ala Gly Thr Tyr Tyr Tyr Tyr Tyr Gly Leu Asp
            100                 105                 110

Val Trp Gly Gln Gly Thr Thr Val Thr Val Ser Ser
        115                 120


<210> SEQ ID NO 154
<211> LENGTH: 110
<212> TYPE: PRT
<213> ORGANISM: Homo sapiens

<400> SEQUENCE: 154

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Val Tyr
            20                  25                  30

Asp Tyr Val Ser Trp Tyr Gln Gln His Pro Gly Lys Ala Pro Lys Leu
        35                  40                  45

Met Ile Tyr Glu Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Thr Glu Asp Glu Ala Asp Tyr Tyr Cys Ser Ser Tyr Thr Ser Arg
                85                  90                  95

Ser Thr Trp Val Phe Gly Gly Gly Thr Lys Leu Thr Val Leu
            100                 105                 110


<210> SEQ ID NO 155

<400> SEQUENCE: 155

000


<210> SEQ ID NO 156

<400> SEQUENCE: 156

000


<210> SEQ ID NO 157

<400> SEQUENCE: 157

000


<210> SEQ ID NO 158

<400> SEQUENCE: 158
```

000

<210> SEQ ID NO 159

<400> SEQUENCE: 159

000

<210> SEQ ID NO 160

<400> SEQUENCE: 160

000

<210> SEQ ID NO 161

<400> SEQUENCE: 161

000

<210> SEQ ID NO 162

<400> SEQUENCE: 162

000

<210> SEQ ID NO 163

<400> SEQUENCE: 163

000

<210> SEQ ID NO 164

<400> SEQUENCE: 164

000

<210> SEQ ID NO 165

<400> SEQUENCE: 165

000

<210> SEQ ID NO 166

<400> SEQUENCE: 166

000

<210> SEQ ID NO 167

<400> SEQUENCE: 167

000

<210> SEQ ID NO 168

<400> SEQUENCE: 168

000

<210> SEQ ID NO 169

<400> SEQUENCE: 169

000

<210> SEQ ID NO 170

<400> SEQUENCE: 170

000

<210> SEQ ID NO 171

<400> SEQUENCE: 171

000

<210> SEQ ID NO 172

<400> SEQUENCE: 172

000

<210> SEQ ID NO 173

<400> SEQUENCE: 173

000

<210> SEQ ID NO 174

<400> SEQUENCE: 174

000

<210> SEQ ID NO 175

<400> SEQUENCE: 175

000

<210> SEQ ID NO 176

<400> SEQUENCE: 176

000

<210> SEQ ID NO 177

<400> SEQUENCE: 177

000

<210> SEQ ID NO 178

<400> SEQUENCE: 178

000

<210> SEQ ID NO 179

<400> SEQUENCE: 179

000

<210> SEQ ID NO 180

<400> SEQUENCE: 180

000

-continued

<210> SEQ ID NO 181

<400> SEQUENCE: 181

000

<210> SEQ ID NO 182

<400> SEQUENCE: 182

000

<210> SEQ ID NO 183

<400> SEQUENCE: 183

000

<210> SEQ ID NO 184

<400> SEQUENCE: 184

000

<210> SEQ ID NO 185

<400> SEQUENCE: 185

000

<210> SEQ ID NO 186

<400> SEQUENCE: 186

000

<210> SEQ ID NO 187

<400> SEQUENCE: 187

000

<210> SEQ ID NO 188

<400> SEQUENCE: 188

000

<210> SEQ ID NO 189

<400> SEQUENCE: 189

000

<210> SEQ ID NO 190

<400> SEQUENCE: 190

000

<210> SEQ ID NO 191

<400> SEQUENCE: 191

000

<210> SEQ ID NO 192

<400> SEQUENCE: 192

000

<210> SEQ ID NO 193

<400> SEQUENCE: 193

000

<210> SEQ ID NO 194

<400> SEQUENCE: 194

000

<210> SEQ ID NO 195

<400> SEQUENCE: 195

000

<210> SEQ ID NO 196

<400> SEQUENCE: 196

000

<210> SEQ ID NO 197

<400> SEQUENCE: 197

000

<210> SEQ ID NO 198

<400> SEQUENCE: 198

000

<210> SEQ ID NO 199

<400> SEQUENCE: 199

000

<210> SEQ ID NO 200

<400> SEQUENCE: 200

000

<210> SEQ ID NO 201

<400> SEQUENCE: 201

000

<210> SEQ ID NO 202

<400> SEQUENCE: 202

000

<210> SEQ ID NO 203

<400> SEQUENCE: 203

000

<210> SEQ ID NO 204

<400> SEQUENCE: 204

000

<210> SEQ ID NO 205

<400> SEQUENCE: 205

000

<210> SEQ ID NO 206

<400> SEQUENCE: 206

000

<210> SEQ ID NO 207

<400> SEQUENCE: 207

000

<210> SEQ ID NO 208

<400> SEQUENCE: 208

000

<210> SEQ ID NO 209
<211> LENGTH: 8
<212> TYPE: PRT
<213> ORGANISM: Homo sapiens

<400> SEQUENCE: 209

Gly Phe Thr Phe Ser Thr Tyr Gly
1               5

<210> SEQ ID NO 210
<211> LENGTH: 8
<212> TYPE: PRT
<213> ORGANISM: Homo sapiens

<400> SEQUENCE: 210

Ile Ser Gly Thr Gly Arg Thr Thr
1               5

<210> SEQ ID NO 211
<211> LENGTH: 14
<212> TYPE: PRT
<213> ORGANISM: Homo sapiens

<400> SEQUENCE: 211

Thr Lys Glu Arg Gly Asp Tyr Tyr Tyr Gly Val Phe Asp Tyr
1               5                   10

<210> SEQ ID NO 212
<211> LENGTH: 6
<212> TYPE: PRT
<213> ORGANISM: Homo sapiens

<400> SEQUENCE: 212

Gln Thr Ile Ser Ser Trp 1 5

<210> SEQ ID NO 213
<211> LENGTH: 3
<212> TYPE: PRT
<213> ORGANISM: Homo sapiens

<400> SEQUENCE: 213

Ala Ala Ser
1

<210> SEQ ID NO 214
<211> LENGTH: 8
<212> TYPE: PRT
<213> ORGANISM: Homo sapiens

<400> SEQUENCE: 214

Gln Gln Tyr His Arg Ser Trp Thr
1 5

<210> SEQ ID NO 215
<211> LENGTH: 121
<212> TYPE: PRT
<213> ORGANISM: Homo sapiens

<400> SEQUENCE: 215

Glu Val Gln Leu Leu Glu Ser Gly Gly Gly Leu Val Gln Pro Gly Lys
1 5 10 15

Ser Leu Arg Leu Ser Cys Ala Val Ser Gly Phe Thr Phe Ser Thr Tyr
20 25 30

Gly Met Asn Trp Val Arg Gln Ala Pro Gly Lys Gly Leu Glu Trp Val
35 40 45

Ser Ser Ile Ser Gly Thr Gly Arg Thr Thr Tyr His Ala Asp Ser Val
50 55 60

Gln Gly Arg Phe Thr Val Ser Arg Asp Asn Ser Lys Asn Ile Leu Tyr
65 70 75 80

Leu Gln Met Asn Ser Leu Arg Ala Asp Asp Thr Ala Val Tyr Phe Cys
85 90 95

Thr Lys Glu Arg Gly Asp Tyr Tyr Tyr Gly Val Phe Asp Tyr Trp Gly
100 105 110

Gln Gly Thr Leu Val Thr Val Ser Ser
115 120

<210> SEQ ID NO 216
<211> LENGTH: 106
<212> TYPE: PRT
<213> ORGANISM: Homo sapiens

<400> SEQUENCE: 216

Asp Ile Gln Met Thr Gln Ser Pro Ser Thr Leu Ser Ala Ser Val Gly
1 5 10 15

Asp Arg Val Thr Ile Thr Cys Arg Ala Ser Gln Thr Ile Ser Ser Trp
20 25 30

Leu Ala Trp Tyr Gln Gln Thr Pro Glu Lys Ala Pro Lys Leu Leu Ile
35 40 45

Tyr Ala Ala Ser Asn Leu Gln Ser Gly Val Pro Ser Arg Phe Ser Gly
50 55 60

Ser Gly Ser Gly Thr Glu Phe Thr Leu Thr Ile Ser Ser Leu Gln Pro
65 70 75 80

Asp Asp Phe Ala Thr Tyr Tyr Cys Gln Gln Tyr His Arg Ser Trp Thr
                85                  90                  95

Phe Gly Gln Gly Thr Lys Val Glu Ile Thr
            100                 105

<210> SEQ ID NO 217
<211> LENGTH: 8
<212> TYPE: PRT
<213> ORGANISM: Homo sapiens

<400> SEQUENCE: 217

Gly Phe Thr Phe Ser Ser Tyr Trp
1               5

<210> SEQ ID NO 218
<211> LENGTH: 8
<212> TYPE: PRT
<213> ORGANISM: Homo sapiens

<400> SEQUENCE: 218

Ile Lys Glu Asp Gly Ser Glu Lys
1               5

<210> SEQ ID NO 219
<211> LENGTH: 15
<212> TYPE: PRT
<213> ORGANISM: Homo sapiens

<400> SEQUENCE: 219

Ala Arg Glu Asp Tyr Asp Ser Tyr Tyr Lys Tyr Gly Met Asp Val
1               5                   10                  15

<210> SEQ ID NO 220
<211> LENGTH: 12
<212> TYPE: PRT
<213> ORGANISM: Homo sapiens

<400> SEQUENCE: 220

Gln Ser Ile Leu Tyr Ser Ser Asn Asn Lys Asn Tyr
1               5                   10

<210> SEQ ID NO 221
<211> LENGTH: 3
<212> TYPE: PRT
<213> ORGANISM: Homo sapiens

<400> SEQUENCE: 221

Trp Ala Ser
1

<210> SEQ ID NO 222
<211> LENGTH: 9
<212> TYPE: PRT
<213> ORGANISM: Homo sapiens

<400> SEQUENCE: 222

Gln Gln Tyr Tyr Ser Thr Pro Phe Thr
1               5

<210> SEQ ID NO 223
<211> LENGTH: 122
<212> TYPE: PRT
<213> ORGANISM: Homo sapiens

<400> SEQUENCE: 223

Glu Val Gln Leu Val Glu Ser Gly Gly Gly Leu Val Gln Pro Gly Gly
1 5 10 15

Ser Leu Arg Leu Ser Cys Ala Val Ser Gly Phe Thr Phe Ser Ser Tyr
20 25 30

Trp Met Ser Trp Val Arg Gln Ala Pro Gly Lys Gly Leu Glu Trp Val
35 40 45

Ala Asn Ile Lys Glu Asp Gly Ser Glu Lys Asn Tyr Val Asp Ser Val
50 55 60

Lys Gly Arg Phe Thr Leu Ser Ser Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Ala Arg Glu Asp Tyr Asp Ser Tyr Tyr Lys Tyr Gly Met Asp Val Trp
100 105 110

Gly Gln Gly Thr Ala Val Ile Val Ser Ser
115 120

<210> SEQ ID NO 224
<211> LENGTH: 113
<212> TYPE: PRT
<213> ORGANISM: Homo sapiens

<400> SEQUENCE: 224

Asp Ile Val Met Thr Gln Ser Pro Asp Ser Leu Ala Val Ser Leu Gly
1 5 10 15

Glu Arg Ala Thr Ile Asn Cys Lys Ser Ser Gln Ser Ile Leu Tyr Ser
20 25 30

Ser Asn Asn Lys Asn Tyr Leu Ala Trp Tyr Gln Gln Lys Pro Gly Gln
35 40 45

Pro Pro Lys Leu Leu Ile Tyr Trp Ala Ser Thr Arg Glu Ser Gly Val
50 55 60

Pro Asp Arg Phe Ser Gly Ser Gly Ser Gly Thr Asp Phe Thr Leu Thr
65 70 75 80

Ile Ser Ser Leu Gln Ala Glu Asp Val Ser Val Tyr Tyr Cys Gln Gln
85 90 95

Tyr Tyr Ser Thr Pro Phe Thr Phe Gly Pro Gly Thr Lys Val Asp Ile
100 105 110

Lys

<210> SEQ ID NO 225
<211> LENGTH: 8
<212> TYPE: PRT
<213> ORGANISM: Homo sapiens

<400> SEQUENCE: 225

Gly Gly Ser Phe Thr Gly Phe Tyr
1 5

<210> SEQ ID NO 226
<211> LENGTH: 7
<212> TYPE: PRT
<213> ORGANISM: Homo sapiens

<400> SEQUENCE: 226

Ile Asn His Arg Gly Asn Thr
1 5

<210> SEQ ID NO 227
<211> LENGTH: 13
<212> TYPE: PRT
<213> ORGANISM: Homo sapiens

<400> SEQUENCE: 227

Ala Ser Pro Phe Tyr Asp Phe Trp Ser Gly Ser Asp Tyr
1 5 10

<210> SEQ ID NO 228
<211> LENGTH: 11
<212> TYPE: PRT
<213> ORGANISM: Homo sapiens

<400> SEQUENCE: 228

Gln Ser Leu Val His Ser Asp Gly Asn Thr Tyr
1 5 10

<210> SEQ ID NO 229
<211> LENGTH: 3
<212> TYPE: PRT
<213> ORGANISM: Homo sapiens

<400> SEQUENCE: 229

Lys Ile Ser
1

<210> SEQ ID NO 230
<211> LENGTH: 9
<212> TYPE: PRT
<213> ORGANISM: Homo sapiens

<400> SEQUENCE: 230

Met Gln Ala Thr Gln Phe Pro Leu Thr
1 5

<210> SEQ ID NO 231
<211> LENGTH: 119
<212> TYPE: PRT
<213> ORGANISM: Homo sapiens

<400> SEQUENCE: 231

Gln Val Gln Leu Gln Gln Trp Gly Ala Gly Leu Leu Lys Pro Ser Glu
1 5 10 15

Thr Leu Ser Leu Thr Cys Ala Val Tyr Gly Gly Ser Phe Thr Gly Phe
20 25 30

Tyr Trp Ser Trp Ile Arg Gln Pro Pro Gly Lys Gly Leu Glu Trp Ile
35 40 45

Gly Glu Ile Asn His Arg Gly Asn Thr Asn Tyr Asn Pro Ser Leu Lys
50 55 60

Ser Arg Val Thr Met Ser Val Asp Thr Ser Lys Asn Gln Phe Ser Leu
65 70 75 80

Asn Met Ile Ser Val Thr Ala Ala Asp Thr Ala Met Tyr Phe Cys Ala
85 90 95

Ser Pro Phe Tyr Asp Phe Trp Ser Gly Ser Asp Tyr Trp Gly Gln Gly
100 105 110

Thr Leu Val Thr Val Ser Ser
115

<210> SEQ ID NO 232
<211> LENGTH: 112
<212> TYPE: PRT

<213> ORGANISM: Homo sapiens

<400> SEQUENCE: 232

Asp Ile Met Leu Thr Gln Thr Pro Leu Thr Ser Pro Val Thr Leu Gly
1 5 10 15

Gln Pro Ala Ser Ile Ser Cys Lys Ser Ser Gln Ser Leu Val His Ser
20 25 30

Asp Gly Asn Thr Tyr Leu Ser Trp Leu Gln Gln Arg Pro Gly Gln Pro
35 40 45

Pro Arg Leu Leu Phe Tyr Lys Ile Ser Asn Arg Phe Ser Gly Val Pro
50 55 60

Asp Arg Phe Ser Gly Ser Gly Ala Gly Thr Asp Phe Thr Leu Lys Ile
65 70 75 80

Ser Arg Val Glu Ala Glu Asp Val Gly Val Tyr Tyr Cys Met Gln Ala
85 90 95

Thr Gln Phe Pro Leu Thr Phe Gly Gly Gly Thr Lys Val Glu Ile Lys
100 105 110

<210> SEQ ID NO 233
<211> LENGTH: 10
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Pro, Ser, Asp, Gln or Asn
<220> FEATURE:
<221> NAME/KEY: MOD_RES
<222> LOCATION: (5)..(5)
<223> OTHER INFORMATION: Thr or Arg
<220> FEATURE:
<221> NAME/KEY: MOD_RES
<222> LOCATION: (6)..(6)
<223> OTHER INFORMATION: Asn, Thr, Tyr or His

<400> SEQUENCE: 233

Gly Tyr Xaa Phe Xaa Xaa Tyr Gly Ile Ser
1 5 10

<210> SEQ ID NO 234
<211> LENGTH: 17
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Thr, Pro, Ser or Ala
<220> FEATURE:
<221> NAME/KEY: MOD_RES
<222> LOCATION: (8)..(8)
<223> OTHER INFORMATION: Asn, Gly, Val, Lys or Ala
<220> FEATURE:
<221> NAME/KEY: MOD_RES
<222> LOCATION: (9)..(9)
<223> OTHER INFORMATION: Thr or Lys
<220> FEATURE:
<221> NAME/KEY: MOD_RES
<222> LOCATION: (10)..(10)
<223> OTHER INFORMATION: His or Asn
<220> FEATURE:
<221> NAME/KEY: MOD_RES
<222> LOCATION: (13)..(13)
<223> OTHER INFORMATION: Gln or Arg
<220> FEATURE:
<221> NAME/KEY: MOD_RES
<222> LOCATION: (14)..(14)
<223> OTHER INFORMATION: Lys or Met
<220> FEATURE:
<221> NAME/KEY: MOD_RES
<222> LOCATION: (15)..(15)
<223> OTHER INFORMATION: Leu or His

<400> SEQUENCE: 234

Trp Ile Ser Xaa Tyr Asn Gly Xaa Xaa Xaa Tyr Ala Xaa Xaa Xaa Gln
1 5 10 15

Gly

<210> SEQ ID NO 235
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Ser or Ala
<220> FEATURE:
<221> NAME/KEY: MOD_RES
<222> LOCATION: (9)..(9)
<223> OTHER INFORMATION: Tyr or Pro
<220> FEATURE:
<221> NAME/KEY: MOD_RES
<222> LOCATION: (15)..(15)
<223> OTHER INFORMATION: Val, Ala or Gly

<400> SEQUENCE: 235

Glu Asn Tyr Tyr Gly Ser Gly Xaa Xaa Arg Gly Gly Met Asp Xaa
1 5 10 15

<210> SEQ ID NO 236
<211> LENGTH: 10
<212> TYPE: PRT
<213> ORGANISM: Homo sapiens

<400> SEQUENCE: 236

Gly Tyr Asp Phe Thr Tyr Tyr Gly Ile Ser
1 5 10

<210> SEQ ID NO 237
<211> LENGTH: 17
<212> TYPE: PRT
<213> ORGANISM: Homo sapiens

<400> SEQUENCE: 237

Trp Ile Ser Thr Tyr Asn Gly Asn Thr His Tyr Ala Arg Met Leu Gln
1 5 10 15

Gly

<210> SEQ ID NO 238
<211> LENGTH: 15
<212> TYPE: PRT
<213> ORGANISM: Homo sapiens

<400> SEQUENCE: 238

Glu Asn Tyr Tyr Gly Ser Gly Ala Tyr Arg Gly Gly Met Asp Val
1 5 10 15

<210> SEQ ID NO 239
<211> LENGTH: 11
<212> TYPE: PRT
<213> ORGANISM: Homo sapiens

<400> SEQUENCE: 239

Arg Ala Ser Gln Ser Val Ser Ser Tyr Leu Ala
1 5 10

<210> SEQ ID NO 240
<211> LENGTH: 7
<212> TYPE: PRT
<213> ORGANISM: Homo sapiens

<400> SEQUENCE: 240

```
Asp Ala Ser Asn Arg Ala Thr
1               5
```

<210> SEQ ID NO 241
<211> LENGTH: 9
<212> TYPE: PRT
<213> ORGANISM: Homo sapiens

<400> SEQUENCE: 241

```
Gln Gln Arg Ser Asn Trp Pro Trp Thr
1               5
```

<210> SEQ ID NO 242
<211> LENGTH: 124
<212> TYPE: PRT
<213> ORGANISM: Homo sapiens

<400> SEQUENCE: 242

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Asp Phe Thr Tyr Tyr
            20                  25                  30

Gly Ile Ser Trp Val Arg Gln Ala Pro Gly Gln Gly Leu Glu Trp Met
        35                  40                  45

Gly Trp Ile Ser Thr Tyr Asn Gly Asn Thr His Tyr Ala Arg Met Leu
    50                  55                  60

Gln Gly Arg Val Thr Met Thr Thr Asp Thr Ser Thr Arg Thr Ala Tyr
65                  70                  75                  80

Met Glu Leu Arg Ser Leu Arg Ser Asp Asp Thr Ala Val Tyr Tyr Cys
                85                  90                  95

Ala Arg Glu Asn Tyr Tyr Gly Ser Gly Ala Tyr Arg Gly Gly Met Asp
            100                 105                 110

Val Trp Gly Gln Gly Thr Thr Val Thr Val Ser Ser
        115                 120
```

<210> SEQ ID NO 243
<211> LENGTH: 107
<212> TYPE: PRT
<213> ORGANISM: Homo sapiens

<400> SEQUENCE: 243

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Trp
                85                  90                  95
```

Thr Phe Gly Gln Gly Thr Lys Val Glu Ile Lys
100 105

<210> SEQ ID NO 244
<211> LENGTH: 453
<212> TYPE: PRT
<213> ORGANISM: Homo sapiens

<400> SEQUENCE: 244

Gln Val Gln Leu Val Gln Ser Gly Ala Glu Val Lys Lys Pro Gly Ala
1 5 10 15

Ser Val Lys Val Ser Cys Lys Ala Ser Gly Tyr Asp Phe Thr Tyr Tyr
20 25 30

Gly Ile Ser Trp Val Arg Gln Ala Pro Gly Gln Gly Leu Glu Trp Met
35 40 45

Gly Trp Ile Ser Thr Tyr Asn Gly Asn Thr His Tyr Ala Arg Met Leu
50 55 60

Gln Gly Arg Val Thr Met Thr Thr Asp Thr Ser Thr Arg Thr Ala Tyr
65 70 75 80

Met Glu Leu Arg Ser Leu Arg Ser Asp Asp Thr Ala Val Tyr Tyr Cys
85 90 95

Ala Arg Glu Asn Tyr Tyr Gly Ser Gly Ala Tyr Arg Gly Gly Met Asp
100 105 110

Val Trp Gly Gln Gly Thr Thr Val Thr Val Ser Ser Ala Ser Thr Lys
115 120 125

Gly Pro Ser Val Phe Pro Leu Ala Pro Ser Ser Lys Ser Thr Ser Gly
130 135 140

Gly Thr Ala Ala Leu Gly Cys Leu Val Lys Asp Tyr Phe Pro Glu Pro
145 150 155 160

Val Thr Val Ser Trp Asn Ser Gly Ala Leu Thr Ser Gly Val His Thr
165 170 175

Phe Pro Ala Val Leu Gln Ser Ser Gly Leu Tyr Ser Leu Ser Ser Val
180 185 190

Val Thr Val Pro Ser Ser Ser Leu Gly Thr Gln Thr Tyr Ile Cys Asn
195 200 205

Val Asn His Lys Pro Ser Asn Thr Lys Val Asp Lys Lys Val Glu Pro
210 215 220

Lys Ser Cys Asp Lys Thr His Thr Cys Pro Pro Cys Pro Ala Pro Glu
225 230 235 240

Ala Ala Gly Ala Pro Ser Val Phe Leu Phe Pro Pro Lys Pro Lys Asp
245 250 255

Thr Leu Met Ile Ser Arg Thr Pro Glu Val Thr Cys Val Val Val Asp
260 265 270

Val Ser His Glu Asp Pro Glu Val Lys Phe Asn Trp Tyr Val Asp Gly
275 280 285

Val Glu Val His Asn Ala Lys Thr Lys Pro Arg Glu Glu Gln Tyr Asn
290 295 300

Ser Thr Tyr Arg Val Val Ser Val Leu Thr Val Leu His Gln Asp Trp
305 310 315 320

Leu Asn Gly Lys Glu Tyr Lys Cys Lys Val Ser Asn Lys Ala Leu Pro
325 330 335

Ala Pro Ile Glu Lys Thr Ile Ser Lys Ala Lys Gly Gln Pro Arg Glu
340 345 350

Pro Gln Val Tyr Thr Leu Pro Pro Ser Arg Glu Glu Met Thr Lys Asn

```
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly
    450


<210> SEQ ID NO 245
<211> LENGTH: 214
<212> TYPE: PRT
<213> ORGANISM: Homo sapiens

<400> SEQUENCE: 245

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 246
<211> LENGTH: 7
<212> TYPE: PRT
<213> ORGANISM: Homo sapiens

<400> SEQUENCE: 246

Ser Arg Ser Tyr Tyr Trp Gly
```

1 5

<210> SEQ ID NO 247
<211> LENGTH: 16
<212> TYPE: PRT
<213> ORGANISM: Homo sapiens

<400> SEQUENCE: 247

Ser Ile Tyr Tyr Asn Gly Arg Thr Tyr Tyr Asn Pro Ser Leu Lys Ser
1 5 10 15

<210> SEQ ID NO 248
<211> LENGTH: 11
<212> TYPE: PRT
<213> ORGANISM: Homo sapiens

<400> SEQUENCE: 248

Glu Asp Tyr Gly Asp Tyr Gly Ala Phe Asp Ile
1 5 10

<210> SEQ ID NO 249
<211> LENGTH: 11
<212> TYPE: PRT
<213> ORGANISM: Homo sapiens

<400> SEQUENCE: 249

Arg Ala Ser Gln Gly Ile Ser Ser Ala Leu Ala
1 5 10

<210> SEQ ID NO 250
<211> LENGTH: 7
<212> TYPE: PRT
<213> ORGANISM: Homo sapiens

<400> SEQUENCE: 250

Asp Ala Ser Ser Leu Glu Ser
1 5

<210> SEQ ID NO 251
<211> LENGTH: 9
<212> TYPE: PRT
<213> ORGANISM: Homo sapiens

<400> SEQUENCE: 251

Gln Gln Phe Asn Ser Tyr Pro Leu Thr
1 5

<210> SEQ ID NO 252
<211> LENGTH: 121
<212> TYPE: PRT
<213> ORGANISM: Homo sapiens

<400> SEQUENCE: 252

Gln Leu Gln Leu Gln Glu Ser Gly Pro Gly Leu Val Lys Pro Ser Glu
1 5 10 15

Thr Leu Ser Leu Thr Cys Thr Val Ser Gly Gly Ser Ile Ser Ser Arg
20 25 30

Ser Tyr Tyr Trp Gly Trp Ile Arg Gln Pro Pro Gly Lys Gly Leu Glu
35 40 45

Trp Ile Gly Ser Ile Tyr Tyr Asn Gly Arg Thr Tyr Tyr Asn Pro Ser
50 55 60

Leu Lys Ser Arg Val Thr Ile Ser Val Asp Thr Ser Lys Asn Gln Phe
65 70 75 80

Ser Leu Lys Leu Ser Ser Val Thr Ala Ala Asp Thr Ala Val Tyr Tyr
85 90 95

Cys Ala Arg Glu Asp Tyr Gly Asp Tyr Gly Ala Phe Asp Ile Trp Gly
100 105 110

Gln Gly Thr Met Val Thr Val Ser Ser
115 120

<210> SEQ ID NO 253
<211> LENGTH: 107
<212> TYPE: PRT
<213> ORGANISM: Homo sapiens

<400> SEQUENCE: 253

Ala Ile Gln Leu Thr Gln Ser Pro Ser Ser Leu Ser Ala Ser Val Gly
1 5 10 15

Asp Arg Val Thr Ile Thr Cys Arg Ala Ser Gln Gly Ile Ser Ser Ala
20 25 30

Leu Ala Trp Tyr Gln Gln Lys Pro Gly Lys Ala Pro Lys Leu Leu Ile
35 40 45

Tyr Asp Ala Ser Ser Leu Glu Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Phe Asn Ser Tyr Pro Leu
85 90 95

Thr Phe Gly Gly Gly Thr Lys Val Glu Ile Lys
100 105

<210> SEQ ID NO 254
<211> LENGTH: 7
<212> TYPE: PRT
<213> ORGANISM: Homo sapiens

<400> SEQUENCE: 254

Thr Ser Asn Met Gly Val Val
1 5

<210> SEQ ID NO 255
<211> LENGTH: 16
<212> TYPE: PRT
<213> ORGANISM: Homo sapiens

<400> SEQUENCE: 255

His Ile Leu Trp Asp Asp Arg Glu Tyr Ser Asn Pro Ala Leu Lys Ser
1 5 10 15

<210> SEQ ID NO 256
<211> LENGTH: 14
<212> TYPE: PRT
<213> ORGANISM: Homo sapiens

<400> SEQUENCE: 256

Met Ser Arg Asn Tyr Tyr Gly Ser Ser Tyr Val Met Asp Tyr
1 5 10

<210> SEQ ID NO 257
<211> LENGTH: 10
<212> TYPE: PRT
<213> ORGANISM: Homo sapiens

<400> SEQUENCE: 257

```
Ser Ala Ser Ser Ser Val Asn Tyr Met His
1               5                   10


<210> SEQ ID NO 258
<211> LENGTH: 7
<212> TYPE: PRT
<213> ORGANISM: Homo sapiens

<400> SEQUENCE: 258

Ser Thr Ser Asn Leu Ala Ser
1               5


<210> SEQ ID NO 259
<211> LENGTH: 8
<212> TYPE: PRT
<213> ORGANISM: Homo sapiens

<400> SEQUENCE: 259

His Gln Trp Asn Asn Tyr Gly Thr
1               5


<210> SEQ ID NO 260
<211> LENGTH: 124
<212> TYPE: PRT
<213> ORGANISM: Homo sapiens

<400> SEQUENCE: 260

Gln Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Asn Met Gly Val Val Trp Ile Arg Gln Pro Pro Gly Lys Ala Leu Glu
        35                  40                  45

Trp Leu Ala His Ile Leu Trp Asp Asp Arg Glu Tyr Ser Asn Pro Ala
    50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Met Ser Arg Asn Tyr Tyr Gly Ser Ser Tyr Val Met Asp
            100                 105                 110

Tyr Trp Gly Gln Gly Thr Leu Val Thr Val Ser Ser
        115                 120


<210> SEQ ID NO 261
<211> LENGTH: 106
<212> TYPE: PRT
<213> ORGANISM: Homo sapiens

<400> SEQUENCE: 261

Asp Ile Gln Leu Thr Gln Ser Pro Ser Phe Leu Ser Ala Ser Val Gly
1               5                   10                  15

Asp Arg Val Thr Ile Thr Cys Ser Ala Ser Ser Ser Val Asn Tyr Met
            20                  25                  30

His Trp Tyr Gln Gln Lys Pro Gly Lys Ala Pro Lys Leu Leu Ile Tyr
        35                  40                  45

Ser Thr Ser Asn Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Glu
```

65 70 75 80

Asp Phe Ala Thr Tyr Tyr Cys His Gln Trp Asn Asn Tyr Gly Thr Phe
85 90 95

Gly Gln Gly Thr Lys Val Glu Ile Lys Arg
100 105

<210> SEQ ID NO 262
<211> LENGTH: 5
<212> TYPE: PRT
<213> ORGANISM: Homo sapiens

<400> SEQUENCE: 262

Leu Tyr Gly Met Asn
1 5

<210> SEQ ID NO 263
<211> LENGTH: 5
<212> TYPE: PRT
<213> ORGANISM: Homo sapiens

<400> SEQUENCE: 263

Asn Tyr Gly Met Asn
1 5

<210> SEQ ID NO 264
<211> LENGTH: 17
<212> TYPE: PRT
<213> ORGANISM: Homo sapiens

<400> SEQUENCE: 264

Trp Ile Asn Thr Tyr Thr Gly Glu Pro Thr Tyr Ala Asp Asp Phe Lys
1 5 10 15

Gly

<210> SEQ ID NO 265
<211> LENGTH: 10
<212> TYPE: PRT
<213> ORGANISM: Homo sapiens

<400> SEQUENCE: 265

Asp Thr Ala Met Asp Tyr Ala Met Ala Tyr
1 5 10

<210> SEQ ID NO 266
<211> LENGTH: 13
<212> TYPE: PRT
<213> ORGANISM: Homo sapiens

<400> SEQUENCE: 266

Asp Tyr Gly Lys Tyr Gly Asp Tyr Tyr Ala Met Asp Tyr
1 5 10

<210> SEQ ID NO 267
<211> LENGTH: 16
<212> TYPE: PRT
<213> ORGANISM: Homo sapiens

<400> SEQUENCE: 267

Lys Ser Ser Gln Asn Ile Val His Ser Asp Gly Asn Thr Tyr Leu Glu
1 5 10 15

<210> SEQ ID NO 268
<211> LENGTH: 16

<212> TYPE: PRT
<213> ORGANISM: Homo sapiens

<400> SEQUENCE: 268

```
Arg Ser Ser Gln Ser Ile Val His Ser Asn Gly Asn Thr Tyr Leu Asp
1               5                   10                  15
```

<210> SEQ ID NO 269
<211> LENGTH: 7
<212> TYPE: PRT
<213> ORGANISM: Homo sapiens

<400> SEQUENCE: 269

```
Lys Val Ser Asn Arg Phe Ser
1               5
```

<210> SEQ ID NO 270
<211> LENGTH: 9
<212> TYPE: PRT
<213> ORGANISM: Homo sapiens

<400> SEQUENCE: 270

```
Phe Gln Gly Ser His Val Pro Leu Thr
1               5
```

<210> SEQ ID NO 271
<211> LENGTH: 119
<212> TYPE: PRT
<213> ORGANISM: Homo sapiens

<400> SEQUENCE: 271

```
Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Leu Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Pro Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Asp Thr Ala Met Asp Tyr Ala Met Ala Tyr Trp Gly Gln Gly
            100                 105                 110

Thr Leu Val Thr Val Ser Ser
        115
```

<210> SEQ ID NO 272
<211> LENGTH: 119
<212> TYPE: PRT
<213> ORGANISM: Homo sapiens

<400> SEQUENCE: 272

```
Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Leu Tyr
            20                  25                  30

Gly Met Asn Trp Val Lys Gln Ala Pro Gly Lys Gly Leu Lys Trp Met
        35                  40                  45
```

```
Gly Trp Ile Asn Thr Tyr Thr Gly Glu Pro Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Phe Cys
                85                  90                  95

Ala Arg Asp Thr Ala Met Asp Tyr Ala Met Ala Tyr Trp Gly Gln Gly
            100                 105                 110

Thr Leu Val Thr Val Ser Ser
        115


<210> SEQ ID NO 273
<211> LENGTH: 122
<212> TYPE: PRT
<213> ORGANISM: Homo sapiens

<400> SEQUENCE: 273

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Pro Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Asp Tyr Gly Lys Tyr Gly Asp Tyr Tyr Ala Met Asp Tyr Trp
            100                 105                 110

Gly Gln Gly Thr Leu Val Thr Val Ser Ser
        115                 120


<210> SEQ ID NO 274
<211> LENGTH: 122
<212> TYPE: PRT
<213> ORGANISM: Homo sapiens

<400> SEQUENCE: 274

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Lys Gly Leu Lys Trp Met
        35                  40                  45

Gly Trp Ile Asn Thr Tyr Thr Gly Glu Pro Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Phe Cys
                85                  90                  95

Ala Arg Asp Tyr Gly Lys Tyr Gly Asp Tyr Tyr Ala Met Asp Tyr Trp
            100                 105                 110

Gly Gln Gly Thr Leu Val Thr Val Ser Ser
        115                 120
```

<210> SEQ ID NO 275
<211> LENGTH: 113
<212> TYPE: PRT
<213> ORGANISM: Homo sapiens

<400> SEQUENCE: 275

Asp Val Val Met Thr Gln Ser Pro Leu Ser Leu Pro Val Thr Leu Gly
1 5 10 15

Gln Pro Ala Ser Ile Ser Cys Lys Ser Ser Gln Asn Ile Val His Ser
20 25 30

Asp Gly Asn Thr Tyr Leu Glu Trp Phe Gln Gln Arg Pro Gly Gln Ser
35 40 45

Pro Arg Arg Leu Ile Tyr Lys Val Ser Asn Arg Phe Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Phe Gln Gly
85 90 95

Ser His Val Pro Leu Thr Phe Gly Gly Gly Thr Lys Val Glu Ile Lys
100 105 110

Arg

<210> SEQ ID NO 276
<211> LENGTH: 113
<212> TYPE: PRT
<213> ORGANISM: Homo sapiens

<400> SEQUENCE: 276

Asp Val Val Met Thr Gln Ser Pro Leu Ser Leu Pro Val Thr Leu Gly
1 5 10 15

Gln Pro Ala Ser Ile Ser Cys Lys Ser Ser Gln Asn Ile Val His Ser
20 25 30

Asp Gly Asn Thr Tyr Leu Glu Trp Phe Gln Gln Arg Pro Gly Gln Ser
35 40 45

Pro Arg Arg Leu Ile Tyr Lys Val Ser Asn Arg Phe Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Phe Gln Gly
85 90 95

Ser His Val Pro Leu Thr Phe Gly Gln Gly Thr Lys Val Glu Ile Lys
100 105 110

Arg

<210> SEQ ID NO 277
<211> LENGTH: 113
<212> TYPE: PRT
<213> ORGANISM: Homo sapiens

<400> SEQUENCE: 277

Asp Val Val Met Thr Gln Thr Pro Leu Ser Leu Pro Val Thr Pro Gly
1 5 10 15

Glu Pro Ala Ser Ile Ser Cys Lys Ser Ser Gln Asn Ile Val His Ser
20 25 30

Asp Gly Asn Thr Tyr Leu Glu Trp Tyr Leu Gln Lys Pro Gly Gln Ser
35 40 45

Pro Gln Leu Leu Ile Tyr Lys Val Ser Asn Arg Phe Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Leu Gly Val Tyr Tyr Cys Phe Gln Gly
85 90 95

Ser His Val Pro Leu Thr Phe Gly Gly Gly Thr Lys Val Glu Ile Lys
100 105 110

Arg

<210> SEQ ID NO 278
<211> LENGTH: 113
<212> TYPE: PRT
<213> ORGANISM: Homo sapiens

<400> SEQUENCE: 278

Asp Val Val Met Thr Gln Thr Pro Leu Ser Leu Pro Val Ser Leu Gly
1 5 10 15

Asp Gln Ala Ser Ile Ser Cys Lys Ser Ser Gln Asn Ile Val His Ser
20 25 30

Asp Gly Asn Thr Tyr Leu Glu Trp Tyr Leu Gln Lys Pro Gly Gln Ser
35 40 45

Pro Lys Val Leu Ile Tyr Lys Val Ser Asn Arg Phe Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Leu Gly Val Tyr Tyr Cys Phe Gln Gly
85 90 95

Ser His Val Pro Leu Thr Phe Gly Gly Gly Thr Lys Val Glu Ile Lys
100 105 110

Arg

<210> SEQ ID NO 279
<211> LENGTH: 113
<212> TYPE: PRT
<213> ORGANISM: Homo sapiens

<400> SEQUENCE: 279

Asp Val Val Met Thr Gln Ser Pro Leu Ser Leu Pro Val Thr Leu Gly
1 5 10 15

Gln Pro Ala Ser Ile Ser Cys Arg Ser Ser Gln Ser Ile Val His Ser
20 25 30

Asn Gly Asn Thr Tyr Leu Asp Trp Phe Gln Gln Arg Pro Gly Gln Ser
35 40 45

Pro Arg Arg Leu Ile Tyr Lys Val Ser Asn Arg Phe Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Phe Gln Gly
85 90 95

Ser His Val Pro Leu Thr Phe Gly Gly Gly Thr Lys Val Glu Ile Lys
100 105 110

Arg

<210> SEQ ID NO 280
<211> LENGTH: 113

<212> TYPE: PRT
<213> ORGANISM: Homo sapiens

<400> SEQUENCE: 280

Asp Val Val Met Thr Gln Ser Pro Leu Ser Leu Pro Val Thr Leu Gly
1 5 10 15

Gln Pro Ala Ser Ile Ser Cys Arg Ser Ser Gln Ser Ile Val His Ser
20 25 30

Asn Gly Asn Thr Tyr Leu Asp Trp Phe Gln Gln Arg Pro Gly Gln Ser
35 40 45

Pro Arg Arg Leu Ile Tyr Lys Val Ser Asn Arg Phe Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Phe Gln Gly
85 90 95

Ser His Val Pro Leu Thr Phe Gly Gln Gly Thr Lys Val Glu Ile Lys
100 105 110

Arg

<210> SEQ ID NO 281
<211> LENGTH: 113
<212> TYPE: PRT
<213> ORGANISM: Homo sapiens

<400> SEQUENCE: 281

Asp Val Val Met Thr Gln Thr Pro Leu Ser Leu Pro Val Thr Pro Gly
1 5 10 15

Glu Pro Ala Ser Ile Ser Cys Arg Ser Ser Gln Ser Ile Val His Ser
20 25 30

Asn Gly Asn Thr Tyr Leu Asp Trp Tyr Leu Gln Lys Pro Gly Gln Ser
35 40 45

Pro Gln Leu Leu Ile Tyr Lys Val Ser Asn Arg Phe Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Leu Gly Val Tyr Tyr Cys Phe Gln Gly
85 90 95

Ser His Val Pro Leu Thr Phe Gly Gly Gly Thr Lys Val Glu Ile Lys
100 105 110

Arg

<210> SEQ ID NO 282
<211> LENGTH: 113
<212> TYPE: PRT
<213> ORGANISM: Homo sapiens

<400> SEQUENCE: 282

Asp Val Val Met Thr Gln Thr Pro Leu Ser Leu Pro Val Ser Leu Gly
1 5 10 15

Asp Gln Ala Ser Ile Ser Cys Arg Ser Ser Gln Ser Ile Val His Ser
20 25 30

Asn Gly Asn Thr Tyr Leu Asp Trp Tyr Leu Gln Lys Pro Gly Gln Ser
35 40 45

Pro Lys Val Leu Ile Tyr Lys Val Ser Asn Arg Phe Ser Gly Val Pro
50 55 60

```
Asp Arg Phe Ser Gly Ser Gly Ser Gly Thr Asp Phe Thr Leu Lys Ile
65                  70                  75                  80

Asn Arg Val Glu Ala Glu Asp Leu Gly Val Tyr Phe Cys Phe Gln Gly
                85                  90                  95

Ser His Val Pro Leu Thr Phe Gly Gly Gly Thr Lys Leu Glu Ile Lys
            100                 105                 110

Arg


<210> SEQ ID NO 283
<211> LENGTH: 10
<212> TYPE: PRT
<213> ORGANISM: Homo sapiens

<400> SEQUENCE: 283

Gly Tyr Thr Phe Thr Ser Ser Trp Met His
1               5                   10


<210> SEQ ID NO 284
<211> LENGTH: 8
<212> TYPE: PRT
<213> ORGANISM: Homo sapiens

<400> SEQUENCE: 284

Ile His Pro Asn Ser Gly Gly Thr
1               5


<210> SEQ ID NO 285
<211> LENGTH: 14
<212> TYPE: PRT
<213> ORGANISM: Homo sapiens

<400> SEQUENCE: 285

Ala Arg Gly Asp Tyr Tyr Gly Tyr Val Ser Trp Phe Ala Tyr
1               5                   10


<210> SEQ ID NO 286
<211> LENGTH: 6
<212> TYPE: PRT
<213> ORGANISM: Homo sapiens

<400> SEQUENCE: 286

Gln Asn Ile Asn Val Leu
1               5


<210> SEQ ID NO 287
<211> LENGTH: 3
<212> TYPE: PRT
<213> ORGANISM: Homo sapiens

<400> SEQUENCE: 287

Lys Ala Ser
1


<210> SEQ ID NO 288
<211> LENGTH: 9
<212> TYPE: PRT
<213> ORGANISM: Homo sapiens

<400> SEQUENCE: 288

Gln Gln Gly Gln Ser Tyr Pro Tyr Thr
1               5


<210> SEQ ID NO 289
```

```
<211> LENGTH: 119
<212> TYPE: PRT
<213> ORGANISM: Homo sapiens

<400> SEQUENCE: 289

Gln Val Gln Leu Gln Gln Pro Gly Ser Val Leu Val Arg Pro Gly Ala
1               5                   10                  15

Ser Val Lys Val Ser Cys Lys Ala Ser Gly Tyr Thr Phe Thr Ser Ser
            20                  25                  30

Trp Met His Trp Ala Lys Gln Arg Pro Gly Gln Gly Leu Glu Trp Ile
        35                  40                  45

Gly Glu Ile His Pro Asn Ser Gly Gly Thr Asn Tyr Asn Glu Lys Phe
    50                  55                  60

Lys Gly Lys Ala Thr Val Asp Thr Ser Ser Ser Thr Ala Tyr Val Asp
65                  70                  75                  80

Leu Ser Ser Leu Thr Ser Glu Asp Ser Ala Val Tyr Tyr Cys Ala Arg
                85                  90                  95

Gly Asp Tyr Tyr Gly Tyr Val Ser Trp Phe Ala Tyr Trp Gly Gln Gly
            100                 105                 110

Thr Leu Val Thr Val Ser Ser
        115


<210> SEQ ID NO 290
<211> LENGTH: 121
<212> TYPE: PRT
<213> ORGANISM: Homo sapiens

<400> SEQUENCE: 290

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Ser
            20                  25                  30

Trp Met His Trp Ala Arg Gln Ala Pro Gly Gln Gly Leu Glu Trp Ile
        35                  40                  45

Gly Glu Ile His Pro Asn Ser Gly Gly Thr Asn Tyr Ala Gln Lys Phe
    50                  55                  60

Gln Gly Arg Ala Thr Leu Thr Val Asp Thr Ser Ser Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Asp Tyr Tyr Gly Tyr Val Ser Trp Phe Ala Tyr Trp Gly
            100                 105                 110

Gln Gly Thr Leu Val Thr Val Ser Ser
        115                 120


<210> SEQ ID NO 291
<211> LENGTH: 121
<212> TYPE: PRT
<213> ORGANISM: Homo sapiens

<400> SEQUENCE: 291

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Ser
            20                  25                  30

Trp Met His Trp Ala Arg Gln Ala Pro Gly Gln Gly Leu Glu Trp Ile
        35                  40                  45
```

```
Gly Glu Ile His Pro Asn Ser Gly Gly Thr Asn Tyr Ala Gln Lys Phe
    50                  55                  60

Gln Gly Arg Ala Thr Met Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Asp Tyr Tyr Gly Tyr Val Ser Trp Phe Ala Tyr Trp Gly
            100                 105                 110

Gln Gly Thr Leu Val Thr Val Ser Ser
        115                 120
```

<210> SEQ ID NO 292
<211> LENGTH: 121
<212> TYPE: PRT
<213> ORGANISM: Homo sapiens

<400> SEQUENCE: 292

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Ser
            20                  25                  30

Trp Met His Trp Ala Arg Gln Ala Pro Gly Gln Gly Leu Glu Trp Ile
        35                  40                  45

Gly Glu Ile His Pro Asn Ser Gly Gly Thr Asn Tyr Ala Gln Lys Phe
    50                  55                  60

Gln Gly Arg Val Thr Met Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Asp Tyr Tyr Gly Tyr Val Ser Trp Phe Ala Tyr Trp Gly
            100                 105                 110

Gln Gly Thr Leu Val Thr Val Ser Ser
        115                 120
```

<210> SEQ ID NO 293
<211> LENGTH: 121
<212> TYPE: PRT
<213> ORGANISM: Homo sapiens

<400> SEQUENCE: 293

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Ser
            20                  25                  30

Trp Met His Trp Ala Arg Gln Ala Pro Gly Gln Gly Leu Glu Trp Met
        35                  40                  45

Gly Glu Ile His Pro Asn Ser Gly Gly Thr Asn Tyr Ala Gln Lys Phe
    50                  55                  60

Gln Gly Arg Val Thr Met Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Asp Tyr Tyr Gly Tyr Val Ser Trp Phe Ala Tyr Trp Gly
            100                 105                 110

Gln Gly Thr Leu Val Thr Val Ser Ser
        115                 120
```

<210> SEQ ID NO 294
<211> LENGTH: 107
<212> TYPE: PRT
<213> ORGANISM: Homo sapiens

<400> SEQUENCE: 294

Asp Ile Gln Met Asn Gln Ser Pro Ser Ser Leu Ser Ala Ser Leu Gly
1 5 10 15

Asp Thr Ile Thr Ile Thr Cys His Ala Ser Gln Asn Ile Asn Val Leu
20 25 30

Leu Ser Trp Tyr Gln Gln Lys Pro Gly Asn Ile Pro Lys Leu Leu Ile
35 40 45

Tyr Lys Ala Ser Asn Leu His Thr Gly Val Pro Ser Arg Phe Ser Gly
50 55 60

Ser Gly Ser Gly Thr Gly Phe Thr Phe Thr Ile Ser Ser Leu Gln Pro
65 70 75 80

Glu Asp Ile Ala Thr Tyr Tyr Cys Gln Gln Gly Gln Ser Tyr Pro Tyr
85 90 95

Thr Phe Gly Gly Gly Thr Lys Leu Glu Ile Lys
100 105

<210> SEQ ID NO 295
<211> LENGTH: 107
<212> TYPE: PRT
<213> ORGANISM: Homo sapiens

<400> SEQUENCE: 295

Asp Ile Gln Met Thr Gln Ser Pro Ser Ser Leu Ser Ala Ser Val Gly
1 5 10 15

Asp Arg Val Thr Ile Thr Cys Gln Ala Ser Gln Asp Ile Ser Asn Tyr
20 25 30

Leu Asn Trp Tyr Gln Gln Lys Pro Gly Lys Ala Pro Lys Leu Leu Ile
35 40 45

Tyr Asp Ala Ser Asn Leu Glu Thr Gly Val Pro Ser Arg Phe Ser Gly
50 55 60

Ser Gly Ser Gly Thr Asp Phe Thr Phe Thr Ile Ser Ser Leu Gln Pro
65 70 75 80

Glu Asp Ile Ala Thr Tyr Tyr Cys Gln Gln Tyr Asp Asn Leu Pro Tyr
85 90 95

Thr Phe Gly Gln Gly Thr Lys Leu Glu Ile Lys
100 105

<210> SEQ ID NO 296
<211> LENGTH: 107
<212> TYPE: PRT
<213> ORGANISM: Homo sapiens

<400> SEQUENCE: 296

Asp Ile Gln Met Thr Gln Ser Pro Ser Ser Leu Ser Ala Ser Val Gly
1 5 10 15

Asp Arg Val Thr Ile Thr Cys Gln Ala Ser Gln Asn Ile Asn Val Leu
20 25 30

Leu Asn Trp Tyr Gln Gln Lys Pro Gly Lys Ala Pro Lys Leu Leu Ile
35 40 45

Tyr Lys Ala Ser Asn Leu His Thr Gly Val Pro Ser Arg Phe Ser Gly
50 55 60

Ser Gly Ser Gly Thr Asp Phe Thr Phe Thr Ile Ser Ser Leu Gln Pro

```
65                  70                  75                  80

Glu Asp Ile Ala Thr Tyr Tyr Cys Gln Gln Gly Gln Ser Tyr Pro Tyr
                85                  90                  95

Thr Phe Gly Gln Gly Thr Lys Leu Glu Ile Lys
            100                 105


<210> SEQ ID NO 297
<211> LENGTH: 107
<212> TYPE: PRT
<213> ORGANISM: Homo sapiens

<400> SEQUENCE: 297

Asp Ile Gln Met Asn Gln Ser Pro Ser Ser Leu Ser Ala Ser Val Gly
1               5                   10                  15

Asp Arg Val Thr Ile Thr Cys Gln Ala Ser Gln Asn Ile Asn Val Leu
            20                  25                  30

Leu Ser Trp Tyr Gln Gln Lys Pro Gly Lys Ala Pro Lys Leu Leu Ile
        35                  40                  45

Tyr Lys Ala Ser Asn Leu His Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Gln Ser Tyr Pro Tyr
                85                  90                  95

Thr Phe Gly Gln Gly Thr Lys Leu Glu Ile Lys
            100                 105


<210> SEQ ID NO 298
<211> LENGTH: 10
<212> TYPE: PRT
<213> ORGANISM: Homo sapiens

<400> SEQUENCE: 298

Gly Tyr Thr Phe Thr Ser Tyr Asp Ile Asn
1               5                   10


<210> SEQ ID NO 299
<211> LENGTH: 10
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Asn or Tyr

<400> SEQUENCE: 299

Trp Leu Asn Pro Asn Ser Gly Xaa Thr Gly
1               5                   10


<210> SEQ ID NO 300
<211> LENGTH: 10
<212> TYPE: PRT
<213> ORGANISM: Homo sapiens

<400> SEQUENCE: 300

Glu Val Pro Glu Thr Ala Ala Phe Glu Tyr
1               5                   10


<210> SEQ ID NO 301
<211> LENGTH: 14
<212> TYPE: PRT
<213> ORGANISM: Homo sapiens
```

-continued

<220> FEATURE:
<221> NAME/KEY: MOD_RES
<222> LOCATION: (10)..(10)
<223> OTHER INFORMATION: Gly or Ala
<220> FEATURE:
<221> NAME/KEY: MOD_RES
<222> LOCATION: (11)..(11)
<223> OTHER INFORMATION: Leu, Ser or Gln
<220> FEATURE:
<221> NAME/KEY: MOD_RES
<222> LOCATION: (14)..(14)
<223> OTHER INFORMATION: His or Leu

<400> SEQUENCE: 301

```
Thr Ser Ser Ser Ser Asp Ile Gly Ala Xaa Xaa Gly Val Xaa
1               5                   10
```

<210> SEQ ID NO 302
<211> LENGTH: 7
<212> TYPE: PRT
<213> ORGANISM: Homo sapiens

<400> SEQUENCE: 302

```
Gly Tyr Tyr Asn Arg Pro Ser
1               5
```

<210> SEQ ID NO 303
<211> LENGTH: 10
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Tyr, Trp or Phe

<400> SEQUENCE: 303

```
Gln Ser Xaa Asp Gly Thr Leu Ser Ala Leu
1               5                   10
```

<210> SEQ ID NO 304
<211> LENGTH: 119
<212> TYPE: PRT
<213> ORGANISM: Homo sapiens

<400> SEQUENCE: 304

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Pro Gly Gln Gly Leu Glu Trp Met
        35                  40                  45

Gly Trp Leu Asn Pro Asn Ser Gly Asn Thr Gly Tyr Ala Gln Lys Phe
    50                  55                  60

Gln Gly Arg Val Thr Met Thr Ala Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Val Pro Glu Thr Ala Ala Phe Glu Tyr Trp Gly Gln Gly
            100                 105                 110

Thr Leu Val Thr Val Ser Ser
        115
```

<210> SEQ ID NO 305
<211> LENGTH: 111

-continued

<212> TYPE: PRT
<213> ORGANISM: Homo sapiens
<220> FEATURE:
<221> NAME/KEY: MOD_RES
<222> LOCATION: (32)..(32)
<223> OTHER INFORMATION: Any amino acid
<220> FEATURE:
<221> NAME/KEY: MOD_RES
<222> LOCATION: (33)..(33)
<223> OTHER INFORMATION: Any amino acid
<220> FEATURE:
<221> NAME/KEY: MOD_RES
<222> LOCATION: (36)..(36)
<223> OTHER INFORMATION: Any amino acid
<220> FEATURE:
<221> NAME/KEY: MOD_RES
<222> LOCATION: (93)..(93)
<223> OTHER INFORMATION: Any amino acid

<400> SEQUENCE: 305

```
Gln Ser Val Leu Thr Gln Pro Pro Ser Val Ser Gly Ala Pro Gly Gln
1               5                   10                  15

Arg Val Thr Ile Ser Cys Thr Ser Ser Ser Ser Asp Ile Gly Ala Xaa
            20                  25                  30

Xaa Gly Val Xaa Trp Tyr Gln Gln Leu Pro Gly Thr Ala Pro Lys Leu
        35                  40                  45

Leu Ile Glu Gly Tyr Tyr Asn Arg Pro Ser Gly Val Pro Asp Arg Phe
    50                  55                  60

Ser Gly Ser Lys Ser Gly Thr Ser Ala Ser Leu Thr Ile Thr Gly Leu
65                  70                  75                  80

Leu Pro Glu Asp Glu Gly Asp Tyr Tyr Cys Gln Ser Xaa Asp Gly Thr
                85                  90                  95

Leu Ser Ala Leu Phe Gly Gly Gly Thr Lys Leu Thr Val Leu Gly
            100                 105                 110
```

<210> SEQ ID NO 306
<211> LENGTH: 119
<212> TYPE: PRT
<213> ORGANISM: Homo sapiens

<400> SEQUENCE: 306

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Pro Gly Gln Gly Leu Glu Trp Met
        35                  40                  45

Gly Trp Leu Asn Pro Asn Ser Gly Asn Thr Gly Tyr Ala Gln Lys Phe
    50                  55                  60

Gln Gly Arg Val Thr Met Thr Ala Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Val Pro Glu Thr Ala Ala Phe Glu Tyr Trp Gly Gln Gly
            100                 105                 110

Thr Leu Val Thr Val Ser Ser
        115
```

<210> SEQ ID NO 307
<211> LENGTH: 111
<212> TYPE: PRT
<213> ORGANISM: Homo sapiens

<400> SEQUENCE: 307

Gln Ser Val Leu Thr Gln Pro Pro Ser Val Ser Gly Ala Pro Gly Gln
1               5                   10                  15

Arg Val Thr Ile Ser Cys Thr Ser Ser Ser Ser Asp Ile Gly Ala Gly
            20                  25                  30

Leu Gly Val His Trp Tyr Gln Gln Leu Pro Gly Thr Ala Pro Lys Leu
        35                  40                  45

Leu Ile Glu Gly Tyr Tyr Asn Arg Pro Ser Gly Val Pro Asp Arg Phe
    50                  55                  60

Ser Gly Ser Lys Ser Gly Thr Ser Ala Ser Leu Thr Ile Thr Gly Leu
65                  70                  75                  80

Leu Pro Glu Asp Glu Gly Asp Tyr Tyr Cys Gln Ser Trp Asp Gly Thr
                85                  90                  95

Leu Ser Ala Leu Phe Gly Gly Gly Thr Lys Leu Thr Val Leu Gly
            100                 105                 110

<210> SEQ ID NO 308
<211> LENGTH: 119
<212> TYPE: PRT
<213> ORGANISM: Homo sapiens

<400> SEQUENCE: 308

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Pro Gly Gln Gly Leu Glu Trp Met
        35                  40                  45

Gly Trp Leu Asn Pro Asn Ser Gly Tyr Thr Gly Tyr Ala Gln Lys Phe
    50                  55                  60

Gln Gly Arg Val Thr Met Thr Ala Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Val Pro Glu Thr Ala Ala Phe Glu Tyr Trp Gly Gln Gly
            100                 105                 110

Thr Leu Val Thr Val Ser Ser
        115

<210> SEQ ID NO 309
<211> LENGTH: 111
<212> TYPE: PRT
<213> ORGANISM: Homo sapiens

<400> SEQUENCE: 309

Gln Ser Val Leu Thr Gln Pro Pro Ser Val Ser Gly Ala Pro Gly Gln
1               5                   10                  15

Arg Val Thr Ile Ser Cys Thr Ser Ser Ser Ser Asp Ile Gly Ala Gly
            20                  25                  30

Leu Gly Val His Trp Tyr Gln Gln Leu Pro Gly Thr Ala Pro Lys Leu
        35                  40                  45

Leu Ile Glu Gly Tyr Tyr Asn Arg Pro Ser Gly Val Pro Asp Arg Phe
    50                  55                  60

Ser Gly Ser Lys Ser Gly Thr Ser Ala Ser Leu Thr Ile Thr Gly Leu
65                  70                  75                  80

```
Leu Pro Glu Asp Glu Gly Asp Tyr Tyr Cys Gln Ser Tyr Asp Gly Thr
                85                  90                  95

Leu Ser Ala Leu Phe Gly Gly Gly Thr Lys Leu Thr Val Leu Gly
            100                 105                 110


<210> SEQ ID NO 310
<211> LENGTH: 119
<212> TYPE: PRT
<213> ORGANISM: Homo sapiens

<400> SEQUENCE: 310

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Pro Gly Gln Gly Leu Glu Trp Met
        35                  40                  45

Gly Trp Leu Asn Pro Asn Ser Gly Asn Thr Gly Tyr Ala Gln Lys Phe
    50                  55                  60

Gln Gly Arg Val Thr Met Thr Ala Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Val Pro Glu Thr Ala Ala Phe Glu Tyr Trp Gly Gln Gly
            100                 105                 110

Thr Leu Val Thr Val Ser Ser
        115


<210> SEQ ID NO 311
<211> LENGTH: 111
<212> TYPE: PRT
<213> ORGANISM: Homo sapiens

<400> SEQUENCE: 311

Gln Ser Val Leu Thr Gln Pro Pro Ser Val Ser Gly Ala Pro Gly Gln
1               5                   10                  15

Arg Val Thr Ile Ser Cys Thr Ser Ser Ser Ser Asp Ile Gly Ala Ala
            20                  25                  30

Leu Gly Val His Trp Tyr Gln Gln Leu Pro Gly Thr Ala Pro Lys Leu
        35                  40                  45

Leu Ile Glu Gly Tyr Tyr Asn Arg Pro Ser Gly Val Pro Asp Arg Phe
    50                  55                  60

Ser Gly Ser Lys Ser Gly Thr Ser Ala Ser Leu Thr Ile Thr Gly Leu
65                  70                  75                  80

Leu Pro Glu Asp Glu Gly Asp Tyr Tyr Cys Gln Ser Trp Asp Gly Thr
                85                  90                  95

Leu Ser Ala Leu Phe Gly Gly Gly Thr Lys Leu Thr Val Leu Gly
            100                 105                 110


<210> SEQ ID NO 312
<211> LENGTH: 119
<212> TYPE: PRT
<213> ORGANISM: Homo sapiens

<400> SEQUENCE: 312

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
```

```
            20                  25                  30

Asp Ile Asn Trp Val Arg Gln Ala Pro Gly Gln Gly Leu Glu Trp Met
        35                  40                  45

Gly Trp Leu Asn Pro Asn Ser Gly Asn Thr Gly Tyr Ala Gln Lys Phe
    50                  55                  60

Gln Gly Arg Val Thr Met Thr Ala Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Val Pro Glu Thr Ala Ala Phe Glu Tyr Trp Gly Gln Gly
            100                 105                 110

Thr Leu Val Thr Val Ser Ser
        115


<210> SEQ ID NO 313
<211> LENGTH: 111
<212> TYPE: PRT
<213> ORGANISM: Homo sapiens

<400> SEQUENCE: 313

Gln Ser Val Leu Thr Gln Pro Pro Ser Val Ser Gly Ala Pro Gly Gln
1               5                   10                  15

Arg Val Thr Ile Ser Cys Thr Ser Ser Ser Ser Asp Ile Gly Ala Gly
            20                  25                  30

Ser Gly Val His Trp Tyr Gln Gln Leu Pro Gly Thr Ala Pro Lys Leu
        35                  40                  45

Leu Ile Glu Gly Tyr Tyr Asn Arg Pro Ser Gly Val Pro Asp Arg Phe
    50                  55                  60

Ser Gly Ser Lys Ser Gly Thr Ser Ala Ser Leu Thr Ile Thr Gly Leu
65                  70                  75                  80

Leu Pro Glu Asp Glu Gly Asp Tyr Tyr Cys Gln Ser Trp Asp Gly Thr
                85                  90                  95

Leu Ser Ala Leu Phe Gly Gly Gly Thr Lys Leu Thr Val Leu Gly
            100                 105                 110


<210> SEQ ID NO 314
<211> LENGTH: 119
<212> TYPE: PRT
<213> ORGANISM: Homo sapiens

<400> SEQUENCE: 314

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Pro Gly Gln Gly Leu Glu Trp Met
        35                  40                  45

Gly Trp Leu Asn Pro Asn Ser Gly Asn Thr Gly Tyr Ala Gln Lys Phe
    50                  55                  60

Gln Gly Arg Val Thr Met Thr Ala Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Val Pro Glu Thr Ala Ala Phe Glu Tyr Trp Gly Gln Gly
            100                 105                 110

Thr Leu Val Thr Val Ser Ser
```

115

<210> SEQ ID NO 315
<211> LENGTH: 111
<212> TYPE: PRT
<213> ORGANISM: Homo sapiens

<400> SEQUENCE: 315

Gln Ser Val Leu Thr Gln Pro Pro Ser Val Ser Gly Ala Pro Gly Gln
1 5 10 15

Arg Val Thr Ile Ser Cys Thr Ser Ser Ser Ser Asp Ile Gly Ala Gly
20 25 30

Gln Gly Val His Trp Tyr Gln Gln Leu Pro Gly Thr Ala Pro Lys Leu
35 40 45

Leu Ile Glu Gly Tyr Tyr Asn Arg Pro Ser Gly Val Pro Asp Arg Phe
50 55 60

Ser Gly Ser Lys Ser Gly Thr Ser Ala Ser Leu Thr Ile Thr Gly Leu
65 70 75 80

Leu Pro Glu Asp Glu Gly Asp Tyr Tyr Cys Gln Ser Trp Asp Gly Thr
85 90 95

Leu Ser Ala Leu Phe Gly Gly Gly Thr Lys Leu Thr Val Leu Gly
100 105 110

<210> SEQ ID NO 316
<211> LENGTH: 119
<212> TYPE: PRT
<213> ORGANISM: Homo sapiens

<400> SEQUENCE: 316

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Ser Tyr
20 25 30

Asp Ile Asn Trp Val Arg Gln Ala Pro Gly Gln Gly Leu Glu Trp Met
35 40 45

Gly Trp Leu Asn Pro Asn Ser Gly Asn Thr Gly Tyr Ala Gln Lys Phe
50 55 60

Gln Gly Arg Val Thr Met Thr Ala Asp Arg Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Glu Val Pro Glu Thr Ala Ala Phe Glu Tyr Trp Gly Gln Gly
100 105 110

Thr Leu Val Thr Val Ser Ser
115

<210> SEQ ID NO 317
<211> LENGTH: 111
<212> TYPE: PRT
<213> ORGANISM: Homo sapiens

<400> SEQUENCE: 317

Gln Ser Val Leu Thr Gln Pro Pro Ser Val Ser Gly Ala Pro Gly Gln
1 5 10 15

Arg Val Thr Ile Ser Cys Thr Ser Ser Ser Ser Asp Ile Gly Ala Gly
20 25 30

Leu Gly Val Leu Trp Tyr Gln Gln Leu Pro Gly Thr Ala Pro Lys Leu
35 40 45

-continued

Leu Ile Glu Gly Tyr Tyr Asn Arg Pro Ser Gly Val Pro Asp Arg Phe
50 55 60

Ser Gly Ser Lys Ser Gly Thr Ser Ala Ser Leu Thr Ile Thr Gly Leu
65 70 75 80

Leu Pro Glu Asp Glu Gly Asp Tyr Tyr Cys Gln Ser Trp Asp Gly Thr
85 90 95

Leu Ser Ala Leu Phe Gly Gly Gly Thr Lys Leu Thr Val Leu Gly
100 105 110

<210> SEQ ID NO 318
<211> LENGTH: 119
<212> TYPE: PRT
<213> ORGANISM: Homo sapiens

<400> SEQUENCE: 318

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Ser Tyr
20 25 30

Asp Ile Asn Trp Val Arg Gln Ala Pro Gly Gln Gly Leu Glu Trp Met
35 40 45

Gly Trp Leu Asn Pro Asn Ser Gly Tyr Thr Gly Tyr Ala Gln Lys Phe
50 55 60

Gln Gly Arg Val Thr Met Thr Ala Asp Arg Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Glu Val Pro Glu Thr Ala Ala Phe Glu Tyr Trp Gly Gln Gly
100 105 110

Thr Leu Val Thr Val Ser Ser
115

<210> SEQ ID NO 319
<211> LENGTH: 111
<212> TYPE: PRT
<213> ORGANISM: Homo sapiens

<400> SEQUENCE: 319

Gln Ser Val Leu Thr Gln Pro Pro Ser Val Ser Gly Ala Pro Gly Gln
1 5 10 15

Arg Val Thr Ile Ser Cys Thr Ser Ser Ser Ser Asp Ile Gly Ala Gly
20 25 30

Leu Gly Val His Trp Tyr Gln Gln Leu Pro Gly Thr Ala Pro Lys Leu
35 40 45

Leu Ile Glu Gly Tyr Tyr Asn Arg Pro Ser Gly Val Pro Asp Arg Phe
50 55 60

Ser Gly Ser Lys Ser Gly Thr Ser Ala Ser Leu Thr Ile Thr Gly Leu
65 70 75 80

Leu Pro Glu Asp Glu Gly Asp Tyr Tyr Cys Gln Ser Trp Asp Gly Thr
85 90 95

Leu Ser Ala Leu Phe Gly Gly Gly Thr Lys Leu Thr Val Leu Gly
100 105 110

<210> SEQ ID NO 320
<211> LENGTH: 119
<212> TYPE: PRT
<213> ORGANISM: Homo sapiens

<400> SEQUENCE: 320

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Pro Gly Gln Gly Leu Glu Trp Met
        35                  40                  45

Gly Trp Leu Asn Pro Asn Ser Gly Tyr Thr Gly Tyr Ala Gln Lys Phe
    50                  55                  60

Gln Gly Arg Val Thr Met Thr Ala Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Val Pro Glu Thr Ala Ala Phe Glu Tyr Trp Gly Gln Gly
            100                 105                 110

Thr Leu Val Thr Val Ser Ser
        115

<210> SEQ ID NO 321
<211> LENGTH: 111
<212> TYPE: PRT
<213> ORGANISM: Homo sapiens

<400> SEQUENCE: 321

Gln Ser Val Leu Thr Gln Pro Pro Ser Val Ser Gly Ala Pro Gly Gln
1               5                   10                  15

Arg Val Thr Ile Ser Cys Thr Ser Ser Ser Ser Asp Ile Gly Ala Gly
            20                  25                  30

Ser Gly Val His Trp Tyr Gln Gln Leu Pro Gly Thr Ala Pro Lys Leu
        35                  40                  45

Leu Ile Glu Gly Tyr Tyr Asn Arg Pro Ser Gly Val Pro Asp Arg Phe
    50                  55                  60

Ser Gly Ser Lys Ser Gly Thr Ser Ala Ser Leu Thr Ile Thr Gly Leu
65                  70                  75                  80

Leu Pro Glu Asp Glu Gly Asp Tyr Tyr Cys Gln Ser Trp Asp Gly Thr
                85                  90                  95

Leu Ser Ala Leu Phe Gly Gly Gly Thr Lys Leu Thr Val Leu Gly
            100                 105                 110

<210> SEQ ID NO 322
<211> LENGTH: 119
<212> TYPE: PRT
<213> ORGANISM: Homo sapiens

<400> SEQUENCE: 322

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Pro Gly Gln Gly Leu Glu Trp Met
        35                  40                  45

Gly Trp Leu Asn Pro Asn Ser Gly Tyr Thr Gly Tyr Ala Gln Lys Phe
    50                  55                  60

Gln Gly Arg Val Thr Met Thr Ala Asp Arg Ser Thr Ser Thr Ala Tyr
65                  70                  75                  80

Met Glu Leu Ser Ser Leu Arg Ser Glu Asp Thr Ala Val Tyr Tyr Cys
85 90 95

Ala Arg Glu Val Pro Glu Thr Ala Ala Phe Glu Tyr Trp Gly Gln Gly
100 105 110

Thr Leu Val Thr Val Ser Ser
115

<210> SEQ ID NO 323
<211> LENGTH: 111
<212> TYPE: PRT
<213> ORGANISM: Homo sapiens

<400> SEQUENCE: 323

Gln Ser Val Leu Thr Gln Pro Pro Ser Val Ser Gly Ala Pro Gly Gln
1 5 10 15

Arg Val Thr Ile Ser Cys Thr Ser Ser Ser Ser Asp Ile Gly Ala Gly
20 25 30

Gln Gly Val His Trp Tyr Gln Gln Leu Pro Gly Thr Ala Pro Lys Leu
35 40 45

Leu Ile Glu Gly Tyr Tyr Asn Arg Pro Ser Gly Val Pro Asp Arg Phe
50 55 60

Ser Gly Ser Lys Ser Gly Thr Ser Ala Ser Leu Thr Ile Thr Gly Leu
65 70 75 80

Leu Pro Glu Asp Glu Gly Asp Tyr Tyr Cys Gln Ser Trp Asp Gly Thr
85 90 95

Leu Ser Ala Leu Phe Gly Gly Gly Thr Lys Leu Thr Val Leu Gly
100 105 110

<210> SEQ ID NO 324
<211> LENGTH: 119
<212> TYPE: PRT
<213> ORGANISM: Homo sapiens

<400> SEQUENCE: 324

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Ser Tyr
20 25 30

Asp Ile Asn Trp Val Arg Gln Ala Pro Gly Gln Gly Leu Glu Trp Met
35 40 45

Gly Trp Leu Asn Pro Asn Ser Gly Tyr Thr Gly Tyr Ala Gln Lys Phe
50 55 60

Gln Gly Arg Val Thr Met Thr Ala Asp Arg Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Glu Val Pro Glu Thr Ala Ala Phe Glu Tyr Trp Gly Gln Gly
100 105 110

Thr Leu Val Thr Val Ser Ser
115

<210> SEQ ID NO 325
<211> LENGTH: 111
<212> TYPE: PRT
<213> ORGANISM: Homo sapiens

<400> SEQUENCE: 325

Gln Ser Val Leu Thr Gln Pro Pro Ser Val Ser Gly Ala Pro Gly Gln

```
1               5                   10                  15

Arg Val Thr Ile Ser Cys Thr Ser Ser Ser Ser Asp Ile Gly Ala Gly
            20                  25                  30

Leu Gly Val Leu Trp Tyr Gln Gln Leu Pro Gly Thr Ala Pro Lys Leu
        35                  40                  45

Leu Ile Glu Gly Tyr Tyr Asn Arg Pro Ser Gly Val Pro Asp Arg Phe
    50                  55                  60

Ser Gly Ser Lys Ser Gly Thr Ser Ala Ser Leu Thr Ile Thr Gly Leu
65                  70                  75                  80

Leu Pro Glu Asp Glu Gly Asp Tyr Tyr Cys Gln Ser Trp Asp Gly Thr
                85                  90                  95

Leu Ser Ala Leu Phe Gly Gly Gly Thr Lys Leu Thr Val Leu Gly
            100                 105                 110


<210> SEQ ID NO 326
<211> LENGTH: 119
<212> TYPE: PRT
<213> ORGANISM: Homo sapiens

<400> SEQUENCE: 326

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Pro Gly Gln Gly Leu Glu Trp Met
        35                  40                  45

Gly Trp Leu Asn Pro Asn Ser Gly Tyr Thr Gly Tyr Ala Gln Lys Phe
    50                  55                  60

Gln Gly Arg Val Thr Met Thr Ala Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Val Pro Glu Thr Ala Ala Phe Glu Tyr Trp Gly Gln Gly
            100                 105                 110

Thr Leu Val Thr Val Ser Ser
        115


<210> SEQ ID NO 327
<211> LENGTH: 111
<212> TYPE: PRT
<213> ORGANISM: Homo sapiens

<400> SEQUENCE: 327

Gln Ser Val Leu Thr Gln Pro Pro Ser Val Ser Gly Ala Pro Gly Gln
1               5                   10                  15

Arg Val Thr Ile Ser Cys Thr Ser Ser Ser Ser Asp Ile Gly Ala Gly
            20                  25                  30

Leu Gly Val His Trp Tyr Gln Gln Leu Pro Gly Thr Ala Pro Lys Leu
        35                  40                  45

Leu Ile Glu Gly Tyr Tyr Asn Arg Pro Ser Gly Val Pro Asp Arg Phe
    50                  55                  60

Ser Gly Ser Lys Ser Gly Thr Ser Ala Ser Leu Thr Ile Thr Gly Leu
65                  70                  75                  80

Leu Pro Glu Asp Glu Gly Asp Tyr Tyr Cys Gln Ser Phe Asp Gly Thr
                85                  90                  95

Leu Ser Ala Leu Phe Gly Gly Gly Thr Lys Leu Thr Val Leu Gly
```

100 105 110

<210> SEQ ID NO 328
<211> LENGTH: 5
<212> TYPE: PRT
<213> ORGANISM: Homo sapiens

<400> SEQUENCE: 328

Ser Tyr Phe Trp Ser
1 5

<210> SEQ ID NO 329
<211> LENGTH: 16
<212> TYPE: PRT
<213> ORGANISM: Homo sapiens

<400> SEQUENCE: 329

Tyr Ile Tyr Tyr Ser Gly Asn Thr Lys Tyr Asn Pro Ser Leu Lys Ser
1 5 10 15

<210> SEQ ID NO 330
<211> LENGTH: 10
<212> TYPE: PRT
<213> ORGANISM: Homo sapiens

<400> SEQUENCE: 330

Glu Thr Gly Ser Tyr Tyr Gly Phe Asp Tyr
1 5 10

<210> SEQ ID NO 331
<211> LENGTH: 11
<212> TYPE: PRT
<213> ORGANISM: Homo sapiens

<400> SEQUENCE: 331

Arg Ala Ser Gln Ser Ile Asn Asn Tyr Leu Asn
1 5 10

<210> SEQ ID NO 332
<211> LENGTH: 7
<212> TYPE: PRT
<213> ORGANISM: Homo sapiens

<400> SEQUENCE: 332

Ala Ala Ser Ser Leu Gln Ser
1 5

<210> SEQ ID NO 333
<211> LENGTH: 9
<212> TYPE: PRT
<213> ORGANISM: Homo sapiens

<400> SEQUENCE: 333

Gln Gln Ser Tyr Ser Thr Pro Arg Thr
1 5

<210> SEQ ID NO 334
<211> LENGTH: 118
<212> TYPE: PRT
<213> ORGANISM: Homo sapiens

<400> SEQUENCE: 334

Gln Val Gln Leu Gln Glu Ser Gly Pro Gly Leu Val Lys Pro Ser Glu
1 5 10 15

```
Thr Leu Ser Leu Thr Cys Thr Val Ser Gly Gly Ser Ile Ser Ser Tyr
            20                  25                  30

Phe Trp Ser Trp Ile Arg Gln Pro Pro Gly Lys Gly Leu Glu Trp Ile
        35                  40                  45

Gly Tyr Ile Tyr Tyr Ser Gly Asn Thr Lys Tyr Asn Pro Ser Leu Lys
    50                  55                  60

Ser Arg Val Thr Ile Ser Ile Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Glu Thr Gly Ser Tyr Tyr Gly Phe Asp Tyr Trp Gly Gln Gly Thr
            100                 105                 110

Leu Val Thr Val Ser Ser
        115


<210> SEQ ID NO 335
<211> LENGTH: 107
<212> TYPE: PRT
<213> ORGANISM: Homo sapiens

<400> SEQUENCE: 335

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asn Asn Tyr
            20                  25                  30

Leu Asn Trp Tyr Gln Gln Arg Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Gly Asp Phe Ala Thr Tyr Tyr Cys Gln Gln Ser Tyr Ser Thr Pro Arg
                85                  90                  95

Thr Phe Gly Gln Gly Thr Lys Leu Glu Ile Lys
            100                 105


<210> SEQ ID NO 336
<211> LENGTH: 5
<212> TYPE: PRT
<213> ORGANISM: Homo sapiens

<400> SEQUENCE: 336

Gly Tyr Tyr Trp Asn
1               5


<210> SEQ ID NO 337
<211> LENGTH: 16
<212> TYPE: PRT
<213> ORGANISM: Homo sapiens

<400> SEQUENCE: 337

Glu Ile Asn His Ala Gly Asn Thr Asn Tyr Asn Pro Ser Leu Lys Ser
1               5                   10                  15


<210> SEQ ID NO 338
<211> LENGTH: 12
<212> TYPE: PRT
<213> ORGANISM: Homo sapiens

<400> SEQUENCE: 338
```

```
Gly Tyr Cys Arg Ser Thr Thr Cys Tyr Phe Asp Tyr
1               5                   10


<210> SEQ ID NO 339
<211> LENGTH: 12
<212> TYPE: PRT
<213> ORGANISM: Homo sapiens

<400> SEQUENCE: 339

Arg Ala Ser Gln Ser Val Arg Ser Ser Tyr Leu Ala
1               5                   10


<210> SEQ ID NO 340
<211> LENGTH: 7
<212> TYPE: PRT
<213> ORGANISM: Homo sapiens

<400> SEQUENCE: 340

Gly Ala Ser Ser Arg Ala Thr
1               5


<210> SEQ ID NO 341
<211> LENGTH: 8
<212> TYPE: PRT
<213> ORGANISM: Homo sapiens

<400> SEQUENCE: 341

Gln Gln Tyr Gly Ser Ser Pro Thr
1               5


<210> SEQ ID NO 342
<211> LENGTH: 120
<212> TYPE: PRT
<213> ORGANISM: Homo sapiens

<400> SEQUENCE: 342

Gln Val Gln Leu Gln Gln Trp Gly Ala Gly Leu Leu Lys Pro Ser Glu
1               5                   10                  15

Thr Leu Ser Leu Thr Cys Ala Val His Gly Gly Ser Phe Ser Gly Tyr
            20                  25                  30

Tyr Trp Asn Trp Ile Arg Gln Pro Pro Gly Lys Gly Leu Glu Trp Ile
        35                  40                  45

Gly Glu Ile Asn His Ala Gly Asn Thr Asn Tyr Asn Pro Ser Leu Lys
    50                  55                  60

Ser Arg Val Thr Ile Ser Leu Asp Thr Ser Lys Asn Gln Phe Ser Leu
65                  70                  75                  80

Thr Leu Thr Ser Val Thr Ala Ala Asp Thr Ala Val Tyr Tyr Cys Ala
                85                  90                  95

Arg Gly Tyr Cys Arg Ser Thr Thr Cys Tyr Phe Asp Tyr Trp Gly Gln
            100                 105                 110

Gly Thr Leu Val Thr Val Ser Ser
        115                 120


<210> SEQ ID NO 343
<211> LENGTH: 107
<212> TYPE: PRT
<213> ORGANISM: Homo sapiens

<400> SEQUENCE: 343

Glu Ile Val Leu Thr Gln Ser Pro Gly Thr Leu Ser Leu Ser Pro Gly
1               5                   10                  15
```

```
Glu Arg Ala Thr Leu Ser Cys Arg Ala Ser Gln Ser Val Arg Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Thr Phe Gly Gln Gly Thr Arg Leu Glu Ile Lys
            100                 105


<210> SEQ ID NO 344
<211> LENGTH: 116
<212> TYPE: PRT
<213> ORGANISM: Homo sapiens

<400> SEQUENCE: 344

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asp Ile Gln Asp Thr
            20                  25                  30

Tyr Met His Trp Val Lys Gln Arg Pro Glu Gln Gly Leu Glu Trp Ile
        35                  40                  45

Gly Arg Ile Asp Pro Ala Ser Gly His Thr Lys Tyr Asp Pro Lys Phe
    50                  55                  60

Gln Val Lys Ala Thr Ile Thr Thr Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ser Arg Ser Gly Gly Leu Pro Asp Val Trp Gly Ala Gly Thr Thr Val
            100                 105                 110

Thr Val Ser Ser
        115


<210> SEQ ID NO 345
<211> LENGTH: 106
<212> TYPE: PRT
<213> ORGANISM: Homo sapiens

<400> SEQUENCE: 345

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Met
            20                  25                  30

Tyr Trp Tyr Gln Gln Lys Pro Gly Ser Ser Pro Lys Pro Trp Ile Tyr
        35                  40                  45

Ala Thr Ser Asn Leu Ala Ser Gly Val Pro Asp Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Ser Gly Asn Pro Arg Thr
                85                  90                  95

Phe Gly Gly Gly Thr Lys Leu Glu Ile Lys
            100                 105
```

<210> SEQ ID NO 346
<211> LENGTH: 10
<212> TYPE: PRT
<213> ORGANISM: Homo sapiens

<400> SEQUENCE: 346

Gly Phe Asp Ile Gln Asp Thr Tyr Met His
1               5                   10

<210> SEQ ID NO 347
<211> LENGTH: 17
<212> TYPE: PRT
<213> ORGANISM: Homo sapiens

<400> SEQUENCE: 347

Arg Ile Asp Pro Ala Ser Gly His Thr Lys Tyr Asp Pro Lys Phe Gln
1               5                   10                  15

Val

<210> SEQ ID NO 348
<211> LENGTH: 7
<212> TYPE: PRT
<213> ORGANISM: Homo sapiens

<400> SEQUENCE: 348

Ser Gly Gly Leu Pro Asp Val
1               5

<210> SEQ ID NO 349
<211> LENGTH: 10
<212> TYPE: PRT
<213> ORGANISM: Homo sapiens

<400> SEQUENCE: 349

Arg Ala Ser Ser Ser Val Ser Tyr Met Tyr
1               5                   10

<210> SEQ ID NO 350
<211> LENGTH: 7
<212> TYPE: PRT
<213> ORGANISM: Homo sapiens

<400> SEQUENCE: 350

Ala Thr Ser Asn Leu Ala Ser
1               5

<210> SEQ ID NO 351
<211> LENGTH: 9
<212> TYPE: PRT
<213> ORGANISM: Homo sapiens

<400> SEQUENCE: 351

Gln Gln Trp Ser Gly Asn Pro Arg Thr
1               5

<210> SEQ ID NO 352
<211> LENGTH: 116
<212> TYPE: PRT
<213> ORGANISM: Homo sapiens

<400> SEQUENCE: 352

Gln Val Gln Leu Val Gln Ser Gly Ala Glu Val Lys Lys Pro Gly Ala
1               5                   10                  15

```
Ser Val Lys Leu Ser Cys Lys Ala Ser Gly Phe Asp Ile Gln Asp Thr
            20                  25                  30

Tyr Met His Trp Val Arg Gln Ala Pro Gly Gln Gly Leu Glu Trp Met
        35                  40                  45

Gly Arg Ile Asp Pro Ala Ser Gly His Thr Lys Tyr Asp Pro Lys Phe
    50                  55                  60

Gln Val Arg Val Thr Met Thr Thr Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ser Arg Ser Gly Gly Leu Pro Asp Val Trp Gly Gln Gly Thr Thr Val
            100                 105                 110

Thr Val Ser Ser
        115


<210> SEQ ID NO 353
<211> LENGTH: 106
<212> TYPE: PRT
<213> ORGANISM: Homo sapiens

<400> SEQUENCE: 353

Glu Ile Val Leu Thr Gln Ser Pro Gly Thr Leu Ser Leu Ser Pro Gly
1               5                   10                  15

Glu Arg Val Thr Met Ser Cys Arg Ala Ser Ser Ser Val Ser Tyr Met
            20                  25                  30

Tyr Trp Tyr Gln Gln Lys Pro Gly Gln Ala Pro Arg Pro Trp Ile Tyr
        35                  40                  45

Ala Thr Ser Asn Leu Ala Ser Gly Val Pro Asp Arg Phe Ser Gly Ser
    50                  55                  60

Gly Ser Gly Thr Asp Tyr Thr Leu Thr Ile Ser Arg Leu Glu Pro Glu
65                  70                  75                  80

Asp Phe Ala Val Tyr Tyr Cys Gln Gln Trp Ser Gly Asn Pro Arg Thr
                85                  90                  95

Phe Gly Gly Gly Thr Lys Leu Glu Ile Lys
            100                 105


<210> SEQ ID NO 354
<211> LENGTH: 116
<212> TYPE: PRT
<213> ORGANISM: Homo sapiens

<400> SEQUENCE: 354

Gln Val Gln Leu Val Gln Ser Gly Ala Glu Val Lys Lys Pro Gly Ala
1               5                   10                  15

Ser Val Lys Leu Ser Cys Lys Ala Ser Gly Phe Asp Ile Gln Asp Thr
            20                  25                  30

Tyr Met His Trp Val Arg Gln Ala Pro Gly Gln Gly Leu Glu Trp Met
        35                  40                  45

Gly Arg Ile Asp Pro Ala Ser Gly His Thr Lys Tyr Asp Pro Lys Phe
    50                  55                  60

Gln Val Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ser Arg Ser Gly Gly Leu Pro Asp Val Trp Gly Gln Gly Thr Thr Val
            100                 105                 110
```

```
Thr Val Ser Ser
        115


<210> SEQ ID NO 355
<211> LENGTH: 106
<212> TYPE: PRT
<213> ORGANISM: Homo sapiens

<400> SEQUENCE: 355

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Ser Ser Val Ser Tyr Met
            20                  25                  30

Tyr Trp Tyr Gln Gln Lys Pro Gly Gln Ala Pro Arg Leu Leu Ile Tyr
        35                  40                  45

Ala Thr Ser Asn Leu Ala Ser Gly Ile Pro Asp Arg Phe Ser Gly Ser
    50                  55                  60

Gly Ser Gly Thr Asp Phe Thr Leu Thr Ile Ser Arg Leu Glu Pro Glu
65                  70                  75                  80

Asp Phe Ala Val Tyr Tyr Cys Gln Gln Trp Ser Gly Asn Pro Arg Thr
                85                  90                  95

Phe Gly Gly Gly Thr Lys Leu Glu Ile Lys
            100                 105


<210> SEQ ID NO 356
<211> LENGTH: 116
<212> TYPE: PRT
<213> ORGANISM: Homo sapiens

<400> SEQUENCE: 356

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asp Ile Gln Asp Thr
            20                  25                  30

Tyr Met His Trp Val Arg Gln Ala Pro Gly Gln Gly Leu Glu Trp Met
        35                  40                  45

Gly Arg Ile Asp Pro Ala Ser Gly His Thr Lys Tyr Asp Pro Lys Phe
    50                  55                  60

Gln Val Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Gly Gly Leu Pro Asp Val Trp Gly Gln Gly Thr Thr Val
            100                 105                 110

Thr Val Ser Ser
        115


<210> SEQ ID NO 357
<211> LENGTH: 106
<212> TYPE: PRT
<213> ORGANISM: Homo sapiens

<400> SEQUENCE: 357

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Ser Ser Val Ser Tyr Met
            20                  25                  30
```

```
Tyr Trp Tyr Gln Gln Lys Pro Gly Gln Ala Pro Arg Leu Leu Ile Tyr
        35                  40                  45

Ala Thr Ser Asn Leu Ala Ser Gly Val Pro Asp Arg Phe Ser Gly Ser
    50                  55                  60

Gly Ser Gly Thr Asp Tyr Thr Leu Thr Ile Ser Arg Leu Glu Pro Glu
65                  70                  75                  80

Asp Phe Ala Val Tyr Tyr Cys Gln Gln Trp Ser Gly Asn Pro Arg Thr
                85                  90                  95

Phe Gly Gly Gly Thr Lys Leu Glu Ile Lys
            100                 105


<210> SEQ ID NO 358
<211> LENGTH: 121
<212> TYPE: PRT
<213> ORGANISM: Homo sapiens

<400> SEQUENCE: 358

Glu Val Met Leu Val Glu Ser Gly Gly Gly Leu Val Lys Pro Gly Gly
1               5                   10                  15

Ser Leu Lys Leu Ser Cys Ala Ala Ser Gly Phe Thr Phe Thr Asn Tyr
            20                  25                  30

Ala Met Ser Trp Val Arg Gln Thr Pro Glu Lys Arg Leu Glu Trp Val
        35                  40                  45

Ala Thr Ile Thr Ser Gly Gly Ser Tyr Ile Tyr Tyr Leu Asp Ser Val
    50                  55                  60

Lys Gly Arg Phe Thr Ile Ser Arg Asp Asn Ala Lys Ser Thr Leu Tyr
65                  70                  75                  80

Leu Gln Met Ser Ser Leu Arg Ser Glu Asp Thr Ala Ile Tyr Asn Cys
                85                  90                  95

Ala Arg Arg Lys Asp Gly Asn Tyr Tyr Tyr Ala Met Asp Tyr Trp Gly
            100                 105                 110

Gln Gly Thr Ser Val Thr Val Ser Ser
        115                 120


<210> SEQ ID NO 359
<211> LENGTH: 121
<212> TYPE: PRT
<213> ORGANISM: Homo sapiens

<400> SEQUENCE: 359

Glu Val Met Leu Val Glu Ser Gly Gly Gly Leu Val Lys Pro Gly Gly
1               5                   10                  15

Ser Leu Lys Leu Ser Cys Ala Ala Ser Gly Phe Thr Phe Thr Asn Tyr
            20                  25                  30

Ala Met Ser Trp Val Arg Gln Thr Pro Glu Lys Arg Leu Glu Trp Val
        35                  40                  45

Ala Thr Ile Thr Ser Gly Gly Ser Tyr Ile Tyr Tyr Leu Asp Ser Val
    50                  55                  60

Lys Gly Arg Phe Thr Ile Ser Arg Asp Asn Ala Lys Ser Thr Leu Tyr
65                  70                  75                  80

Leu Gln Met Ser Ser Leu Arg Ser Glu Asp Thr Ala Ile Tyr Tyr Cys
                85                  90                  95

Ala Arg Arg Lys Asp Gly Asn Tyr Tyr Tyr Ala Met Asp Tyr Trp Gly
            100                 105                 110

Gln Gly Thr Ser Val Thr Val Ser Ser
        115                 120
```

<210> SEQ ID NO 360
<211> LENGTH: 121
<212> TYPE: PRT
<213> ORGANISM: Homo sapiens

<400> SEQUENCE: 360

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Thr Asn Tyr
            20                  25                  30

Ala Met Ser Trp Val Arg Gln Ala Pro Gly Gln Arg Leu Glu Trp Val
        35                  40                  45

Ser Thr Ile Thr Ser Gly Gly Ser Tyr Ile Tyr Tyr Leu Asp Ser Val
    50                  55                  60

Lys Gly Arg Phe Thr Ile Ser Arg Asp Asn Ala Lys Ser Thr Leu Tyr
65                  70                  75                  80

Leu Gln Met Asn Ser Leu Arg Ala Glu Asp Thr Ala Val Tyr Asn Cys
                85                  90                  95

Ala Arg Arg Lys Asp Gly Asn Tyr Tyr Tyr Ala Met Asp Tyr Trp Gly
            100                 105                 110

Gln Gly Thr Thr Val Thr Val Ser Ser
        115                 120
```

<210> SEQ ID NO 361
<211> LENGTH: 121
<212> TYPE: PRT
<213> ORGANISM: Homo sapiens

<400> SEQUENCE: 361

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Thr Asn Tyr
            20                  25                  30

Ala Met Ser Trp Val Arg Gln Ala Pro Gly Gln Arg Leu Glu Trp Val
        35                  40                  45

Ser Thr Ile Thr Ser Gly Gly Ser Tyr Ile Tyr Tyr Leu Asp Ser Val
    50                  55                  60

Lys Gly Arg Phe Thr Ile Ser Arg Asp Asn Ala Lys Ser Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Lys Asp Gly Asn Tyr Tyr Tyr Ala Met Asp Tyr Trp Gly
            100                 105                 110

Gln Gly Thr Thr Val Thr Val Ser Ser
        115                 120
```

<210> SEQ ID NO 362
<211> LENGTH: 121
<212> TYPE: PRT
<213> ORGANISM: Homo sapiens

<400> SEQUENCE: 362

```
Glu Val Gln Leu Leu Glu Ser Gly Gly Gly Leu Val Gln Pro Gly Arg
1               5                   10                  15

Ser Leu Arg Leu Ser Cys Ala Ala Ser Gly Phe Thr Phe Thr Asn Tyr
            20                  25                  30

Ala Met Ser Trp Val Arg Gln Ala Pro Gly Gln Arg Leu Glu Trp Leu
```

```
        35                  40                  45

Ala Thr Ile Thr Ser Gly Gly Ser Tyr Ile Tyr Tyr Leu Asp Ser Val
    50                  55                  60

Lys Gly Arg Phe Thr Ile Ser Arg Asp Asn Ser Lys Ser Thr Leu Tyr
65                  70                  75                  80

Leu Gln Met Gly Ser Leu Arg Ala Glu Asp Met Ala Val Tyr Asn Cys
                85                  90                  95

Ala Arg Arg Lys Asp Gly Asn Tyr Tyr Tyr Ala Met Asp Tyr Trp Gly
            100                 105                 110

Gln Gly Thr Thr Val Thr Val Ser Ser
        115                 120
```

<210> SEQ ID NO 363
<211> LENGTH: 121
<212> TYPE: PRT
<213> ORGANISM: Homo sapiens

<400> SEQUENCE: 363

```
Glu Val Gln Leu Leu Glu Ser Gly Gly Gly Leu Val Gln Pro Gly Arg
1               5                   10                  15

Ser Leu Arg Leu Ser Cys Ala Ala Ser Gly Phe Thr Phe Thr Asn Tyr
            20                  25                  30

Ala Met Ser Trp Val Arg Gln Ala Pro Gly Gln Arg Leu Glu Trp Leu
        35                  40                  45

Ala Thr Ile Thr Ser Gly Gly Ser Tyr Ile Tyr Tyr Leu Asp Ser Val
    50                  55                  60

Lys Gly Arg Phe Thr Ile Ser Arg Asp Asn Ser Lys Ser Thr Leu Tyr
65                  70                  75                  80

Leu Gln Met Gly Ser Leu Arg Ala Glu Asp Met Ala Val Tyr Tyr Cys
                85                  90                  95

Ala Arg Arg Lys Asp Gly Asn Tyr Tyr Tyr Ala Met Asp Tyr Trp Gly
            100                 105                 110

Gln Gly Thr Thr Val Thr Val Ser Ser
        115                 120
```

<210> SEQ ID NO 364
<211> LENGTH: 121
<212> TYPE: PRT
<213> ORGANISM: Homo sapiens

<400> SEQUENCE: 364

```
Gln Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Phe Thr Asn Tyr
            20                  25                  30

Ala Met Ser Trp Val Arg Gln Ala Arg Gly Gln Arg Leu Glu Trp Val
        35                  40                  45

Ser Thr Ile Thr Ser Gly Gly Ser Tyr Ile Tyr Tyr Leu Asp Ser Val
    50                  55                  60

Lys Gly Arg Phe Thr Ile Ser Arg Asp Asn Ser Lys Ser Thr Leu Tyr
65                  70                  75                  80

Met Glu Leu Ser Ser Leu Arg Ser Glu Asp Thr Ala Val Tyr Asn Cys
                85                  90                  95

Ala Arg Arg Lys Asp Gly Asn Tyr Tyr Tyr Ala Met Asp Tyr Trp Gly
            100                 105                 110

Gln Gly Thr Thr Val Thr Val Ser Ser
```

115 120

<210> SEQ ID NO 365
<211> LENGTH: 121
<212> TYPE: PRT
<213> ORGANISM: Homo sapiens

<400> SEQUENCE: 365

Gln Val Gln Leu Val Glu Ser Gly Gly Gly Leu Ile Gln Pro Gly Gly
1 5 10 15

Ser Leu Arg Leu Ser Cys Ala Ala Ser Gly Phe Thr Phe Thr Asn Tyr
20 25 30

Ala Met Ser Trp Val Arg Gln Ala Arg Gly Gln Arg Leu Glu Trp Val
35 40 45

Ser Thr Ile Thr Ser Gly Gly Ser Tyr Ile Tyr Tyr Leu Asp Ser Val
50 55 60

Lys Gly Arg Phe Thr Ile Ser Arg Asp Asn Ser Lys Ser Thr Leu Tyr
65 70 75 80

Met Glu Leu Ser Ser Leu Arg Ser Glu Asp Thr Ala Val Tyr Tyr Cys
85 90 95

Ala Arg Arg Lys Asp Gly Asn Tyr Tyr Tyr Ala Met Asp Tyr Trp Gly
100 105 110

Gln Gly Thr Thr Val Thr Val Ser Ser
115 120

<210> SEQ ID NO 366
<211> LENGTH: 121
<212> TYPE: PRT
<213> ORGANISM: Homo sapiens

<400> SEQUENCE: 366

Gln Val Gln Leu Val Gln Ser Gly Ser Glu Leu Lys Lys Pro Gly Ala
1 5 10 15

Ser Val Lys Val Ser Cys Lys Ala Ser Gly Phe Thr Phe Thr Asn Tyr
20 25 30

Ala Met Ser Trp Val Arg Gln Ala Pro Gly Lys Arg Leu Glu Trp Val
35 40 45

Ser Thr Ile Thr Ser Gly Gly Ser Tyr Ile Tyr Tyr Leu Asp Ser Val
50 55 60

Lys Gly Arg Phe Thr Ile Ser Arg Glu Asn Ala Lys Ser Thr Leu Tyr
65 70 75 80

Leu Gln Met Asn Ser Leu Arg Thr Glu Asp Thr Ala Leu Tyr Asn Cys
85 90 95

Ala Arg Arg Lys Asp Gly Asn Tyr Tyr Tyr Ala Met Asp Tyr Trp Gly
100 105 110

Gln Gly Thr Thr Val Thr Val Ser Ser
115 120

<210> SEQ ID NO 367
<211> LENGTH: 121
<212> TYPE: PRT
<213> ORGANISM: Homo sapiens

<400> SEQUENCE: 367

Gln Val Gln Leu Val Gln Ser Gly Ser Glu Leu Lys Lys Pro Gly Ala
1 5 10 15

Ser Val Lys Val Ser Cys Lys Ala Ser Gly Phe Thr Phe Thr Asn Tyr
20 25 30

Ala Met Ser Trp Val Arg Gln Ala Pro Gly Lys Arg Leu Glu Trp Val
35 40 45

Ala Thr Ile Thr Ser Gly Gly Ser Tyr Ile Tyr Tyr Leu Asp Ser Val
50 55 60

Lys Gly Arg Phe Thr Ile Ser Arg Glu Asn Ala Lys Ser Thr Leu Tyr
65 70 75 80

Leu Gln Met Asn Ser Leu Arg Thr Glu Asp Thr Ala Leu Tyr Tyr Cys
85 90 95

Ala Arg Arg Lys Asp Gly Asn Tyr Tyr Tyr Ala Met Asp Tyr Trp Gly
100 105 110

Gln Gly Thr Thr Val Thr Val Ser Ser
115 120

<210> SEQ ID NO 368
<211> LENGTH: 121
<212> TYPE: PRT
<213> ORGANISM: Homo sapiens

<400> SEQUENCE: 368

Glu Val Gln Leu Leu Gln Ser Gly Ala Glu Val Lys Lys Pro Gly Ala
1 5 10 15

Ser Val Lys Val Ser Cys Lys Ala Ser Gly Phe Thr Phe Thr Asn Tyr
20 25 30

Ala Met Ser Trp Val Arg Gln Ala Pro Gly Gln Arg Leu Glu Trp Val
35 40 45

Ala Thr Ile Thr Ser Gly Gly Ser Tyr Ile Tyr Tyr Leu Asp Ser Val
50 55 60

Lys Gly Arg Phe Thr Ile Ser Arg Asp Asn Ala Lys Ser Thr Leu His
65 70 75 80

Leu Gln Met Asn Ser Leu Arg Ala Glu Asp Thr Ala Val Tyr Asn Cys
85 90 95

Ala Arg Arg Lys Asp Gly Asn Tyr Tyr Tyr Ala Met Asp Tyr Trp Gly
100 105 110

Gln Gly Thr Thr Val Thr Val Ser Ser
115 120

<210> SEQ ID NO 369
<211> LENGTH: 121
<212> TYPE: PRT
<213> ORGANISM: Homo sapiens

<400> SEQUENCE: 369

Glu Val Gln Leu Leu Gln Ser Gly Ala Glu Val Lys Lys Pro Gly Ala
1 5 10 15

Ser Val Lys Val Ser Cys Lys Ala Ser Gly Phe Thr Phe Thr Asn Tyr
20 25 30

Ala Met Ser Trp Val Arg Gln Ala Pro Gly Gln Arg Leu Glu Trp Val
35 40 45

Ala Thr Ile Thr Ser Gly Gly Ser Tyr Ile Tyr Tyr Leu Asp Ser Val
50 55 60

Lys Gly Arg Phe Thr Ile Ser Arg Asp Asn Ala Lys Ser Thr Leu His
65 70 75 80

Leu Gln Met Asn Ser Leu Arg Ala Glu Asp Thr Ala Ile Tyr Tyr Cys
85 90 95

Ala Arg Arg Lys Asp Gly Asn Tyr Tyr Tyr Ala Met Asp Tyr Trp Gly
100 105 110

Gln Gly Thr Thr Val Thr Val Ser Ser
115 120

<210> SEQ ID NO 370
<211> LENGTH: 121
<212> TYPE: PRT
<213> ORGANISM: Homo sapiens

<400> SEQUENCE: 370

Glu Val Met Leu Leu Gln Ser Gly Ala Glu Val Lys Lys Pro Gly Ala
1 5 10 15

Ser Val Lys Val Ser Cys Lys Ala Ser Gly Phe Thr Phe Thr Asn Tyr
20 25 30

Ala Met Ser Trp Val Arg Gln Ala Pro Gly Gln Arg Leu Glu Trp Val
35 40 45

Ala Thr Ile Thr Ser Gly Gly Ser Tyr Ile Tyr Tyr Leu Asp Ser Val
50 55 60

Lys Gly Arg Phe Thr Ile Ser Arg Asp Asn Ala Lys Ser Thr Leu His
65 70 75 80

Leu Gln Met Asn Ser Leu Arg Ala Glu Asp Thr Ala Val Tyr Tyr Cys
85 90 95

Ala Arg Arg Lys Asp Gly Asn Tyr Tyr Tyr Ala Met Asp Tyr Trp Gly
100 105 110

Gln Gly Thr Thr Val Thr Val Ser Ser
115 120

<210> SEQ ID NO 371
<211> LENGTH: 111
<212> TYPE: PRT
<213> ORGANISM: Homo sapiens

<400> SEQUENCE: 371

Asp Ile Val Leu Thr Gln Ser Pro Ala Ser Leu Ala Val Ser Leu Gly
1 5 10 15

Gln Arg Ala Thr Ile Ser Cys Arg Ala Ser Glu Ser Val Asp Ser Tyr
20 25 30

Gly Asn Ser Phe Ile His Trp Tyr Gln Gln Lys Ala Gly Gln Pro Pro
35 40 45

Lys Leu Leu Ile Tyr Arg Ala Ser Asn Leu Glu Ser Gly Ile Pro Ala
50 55 60

Arg Phe Ser Gly Ser Gly Ser Arg Thr Asp Phe Thr Leu Thr Ile Asn
65 70 75 80

Pro Val Glu Ala Asp Asp Val Ala Thr Tyr Tyr Cys Gln Gln Ser Tyr
85 90 95

Glu Asp Pro Trp Thr Phe Gly Gly Gly Thr Lys Leu Glu Ile Lys
100 105 110

<210> SEQ ID NO 372
<211> LENGTH: 111
<212> TYPE: PRT
<213> ORGANISM: Homo sapiens
<220> FEATURE:
<221> NAME/KEY: MOD_RES
<222> LOCATION: (108)..(108)
<223> OTHER INFORMATION: Any amino acid

<400> SEQUENCE: 372

Asp Ile Val Leu Thr Gln Ser Pro Ala Thr Leu Ser Leu Ser Pro Gly
1 5 10 15

```
Glu Arg Ala Thr Leu Ser Cys Arg Ala Ser Glu Ser Val Asp Ser Tyr
            20                  25                  30

Gly Asn Ser Phe Ile His Trp Tyr Gln Gln Lys Pro Gly Gln Pro Pro
        35                  40                  45

Lys Leu Leu Ile Tyr Arg Ala Ser Asn Leu Glu Ser Gly Ile Pro Ala
    50                  55                  60

Arg Phe Ser Gly Ser Gly Ser Arg Thr Asp Phe Thr Leu Thr Ile Ser
65                  70                  75                  80

Ser Leu Glu Pro Glu Asp Phe Ala Val Tyr Tyr Cys Gln Gln Ser Tyr
                85                  90                  95

Glu Asp Pro Trp Thr Phe Gly Gly Gly Thr Lys Xaa Glu Ile Lys
            100                 105                 110


<210> SEQ ID NO 373
<211> LENGTH: 111
<212> TYPE: PRT
<213> ORGANISM: Homo sapiens
<220> FEATURE:
<221> NAME/KEY: MOD_RES
<222> LOCATION: (108)..(108)
<223> OTHER INFORMATION: Any amino acid

<400> SEQUENCE: 373

Asp Ile Val Leu Thr Gln Ser Pro Ser Ser Leu Ser Ala Ser Val Gly
1               5                   10                  15

Asp Arg Val Thr Ile Thr Cys Arg Ala Ser Glu Ser Val Asp Ser Tyr
            20                  25                  30

Gly Asn Ser Phe Ile His Trp Tyr Gln Gln Lys Pro Gly Gln Pro Pro
        35                  40                  45

Lys Leu Leu Ile Tyr Arg Ala Ser Asn Leu Glu Ser Gly Ile Pro Ala
    50                  55                  60

Arg Phe Ser Gly Ser Gly Ser Arg Thr Asp Phe Thr Leu Thr Ile Ser
65                  70                  75                  80

Ser Leu Gln Pro Glu Asp Phe Ala Thr Tyr Tyr Cys Gln Gln Ser Tyr
                85                  90                  95

Glu Asp Pro Trp Thr Phe Gly Gly Gly Thr Lys Xaa Glu Ile Lys
            100                 105                 110


<210> SEQ ID NO 374
<211> LENGTH: 111
<212> TYPE: PRT
<213> ORGANISM: Homo sapiens
<220> FEATURE:
<221> NAME/KEY: MOD_RES
<222> LOCATION: (108)..(108)
<223> OTHER INFORMATION: Any amino acid

<400> SEQUENCE: 374

Asp Ile Val Leu Thr Gln Ser Pro Asp Phe Gln Ser Val Thr Pro Lys
1               5                   10                  15

Glu Lys Val Thr Ile Thr Cys Arg Ala Ser Glu Ser Val Asp Ser Tyr
            20                  25                  30

Gly Asn Ser Phe Ile His Trp Tyr Gln Gln Lys Pro Gly Gln Pro Pro
        35                  40                  45

Lys Leu Leu Ile Tyr Arg Ala Ser Asn Leu Glu Ser Gly Ile Pro Ala
    50                  55                  60

Arg Phe Ser Gly Ser Gly Ser Arg Thr Asp Phe Thr Leu Thr Ile Ser
65                  70                  75                  80
```

-continued

```
Ser Leu Glu Ala Glu Asp Ala Ala Thr Tyr Tyr Cys Gln Gln Ser Tyr
                85                  90                  95

Glu Asp Pro Trp Thr Phe Gly Gly Gly Thr Lys Xaa Glu Ile Lys
            100                 105                 110


<210> SEQ ID NO 375
<211> LENGTH: 111
<212> TYPE: PRT
<213> ORGANISM: Homo sapiens
<220> FEATURE:
<221> NAME/KEY: MOD_RES
<222> LOCATION: (108)..(108)
<223> OTHER INFORMATION: Any amino acid

<400> SEQUENCE: 375

Asp Ile Val Leu Thr Gln Thr Pro Leu Ser Leu Ser Val Thr Pro Gly
1               5                   10                  15

Gln Pro Ala Ser Ile Ser Cys Arg Ala Ser Glu Ser Val Asp Ser Tyr
            20                  25                  30

Gly Asn Ser Phe Ile His Trp Tyr Gln Gln Lys Pro Gly Gln Pro Pro
        35                  40                  45

Lys Leu Leu Ile Tyr Arg Ala Ser Asn Leu Glu Ser Gly Ile Pro Ala
    50                  55                  60

Arg Phe Ser Gly Ser Gly Ser Arg Thr Asp Phe Thr Leu Lys Ile Ser
65                  70                  75                  80

Arg Val Glu Ala Glu Asp Val Gly Val Tyr Tyr Cys Gln Gln Ser Tyr
                85                  90                  95

Glu Asp Pro Trp Thr Phe Gly Gly Gly Thr Lys Xaa Glu Ile Lys
            100                 105                 110


<210> SEQ ID NO 376
<211> LENGTH: 5
<212> TYPE: PRT
<213> ORGANISM: Homo sapiens

<400> SEQUENCE: 376

Thr Tyr Gly Met Ser
1               5


<210> SEQ ID NO 377
<211> LENGTH: 17
<212> TYPE: PRT
<213> ORGANISM: Homo sapiens

<400> SEQUENCE: 377

Trp Met Asn Thr Tyr Ser Gly Val Thr Thr Tyr Ala Asp Asp Phe Lys
1               5                   10                  15

Gly


<210> SEQ ID NO 378
<211> LENGTH: 13
<212> TYPE: PRT
<213> ORGANISM: Homo sapiens

<400> SEQUENCE: 378

Glu Gly Tyr Val Phe Asp Asp Tyr Tyr Ala Thr Asp Tyr
1               5                   10


<210> SEQ ID NO 379
<211> LENGTH: 16
<212> TYPE: PRT
<213> ORGANISM: Homo sapiens
```

<400> SEQUENCE: 379

Arg Ser Ser Gln Asn Ile Val His Ser Asp Gly Asn Thr Tyr Leu Glu
1 5 10 15

<210> SEQ ID NO 380
<211> LENGTH: 7
<212> TYPE: PRT
<213> ORGANISM: Homo sapiens

<400> SEQUENCE: 380

Lys Val Ser Asn Arg Phe Ser
1 5

<210> SEQ ID NO 381
<211> LENGTH: 9
<212> TYPE: PRT
<213> ORGANISM: Homo sapiens

<400> SEQUENCE: 381

Phe Gln Gly Ser His Val Pro Leu Thr
1 5

<210> SEQ ID NO 382
<211> LENGTH: 122
<212> TYPE: PRT
<213> ORGANISM: Homo sapiens

<400> SEQUENCE: 382

Gln Ile Gln Leu Val Gln Ser Gly Pro Glu Leu Lys Lys Pro Gly Glu
1 5 10 15

Thr Val Lys Ile Ser Cys Lys Ala Ser Gly Tyr Thr Phe Thr Thr Tyr
20 25 30

Gly Met Ser Trp Val Lys Gln Ala Pro Gly Lys Gly Leu Lys Trp Met
35 40 45

Gly Trp Met Asn Thr Tyr Ser Gly Val Thr Thr Tyr Ala Asp Asp Phe
50 55 60

Lys Gly Arg Phe Ala Phe Ser Leu Glu Thr Ser Ala Ser Thr Ala Tyr
65 70 75 80

Met Gln Ile Asp Asn Leu Lys Asn Glu Asp Thr Ala Thr Tyr Phe Cys
85 90 95

Ala Arg Glu Gly Tyr Val Phe Asp Asp Tyr Tyr Ala Thr Asp Tyr Trp
100 105 110

Gly Gln Gly Thr Ser Val Thr Val Ser Ser
115 120

<210> SEQ ID NO 383
<211> LENGTH: 112
<212> TYPE: PRT
<213> ORGANISM: Homo sapiens

<400> SEQUENCE: 383

Asp Val Leu Met Thr Gln Thr Pro Leu Ser Leu Pro Val Ser Leu Gly
1 5 10 15

Asp Gln Ala Ser Ile Ser Cys Arg Ser Ser Gln Asn Ile Val His Ser
20 25 30

Asp Gly Asn Thr Tyr Leu Glu Trp Tyr Leu Gln Lys Pro Gly Gln Ser
35 40 45

Pro Lys Leu Leu Ile Tyr Lys Val Ser Asn Arg Phe Ser Gly Val Pro
50 55 60

```
Asp Arg Phe Ser Gly Ser Gly Ser Gly Thr Asp Phe Thr Leu Lys Ile
65                  70                  75                  80

Ser Arg Val Glu Ala Glu Asp Leu Gly Ile Tyr Tyr Cys Phe Gln Gly
                85                  90                  95

Ser His Val Pro Leu Thr Phe Gly Ala Gly Thr Lys Leu Glu Leu Lys
            100                 105                 110


<210> SEQ ID NO 384
<211> LENGTH: 5
<212> TYPE: PRT
<213> ORGANISM: Homo sapiens

<400> SEQUENCE: 384

Lys Tyr Asp Ile Asn
1               5


<210> SEQ ID NO 385
<211> LENGTH: 17
<212> TYPE: PRT
<213> ORGANISM: Homo sapiens

<400> SEQUENCE: 385

Trp Ile Phe Pro Gly Asp Gly Arg Thr Asp Tyr Asn Glu Lys Phe Lys
1               5                   10                  15

Gly


<210> SEQ ID NO 386
<211> LENGTH: 7
<212> TYPE: PRT
<213> ORGANISM: Homo sapiens

<400> SEQUENCE: 386

Tyr Gly Pro Ala Met Asp Tyr
1               5


<210> SEQ ID NO 387
<211> LENGTH: 16
<212> TYPE: PRT
<213> ORGANISM: Homo sapiens

<400> SEQUENCE: 387

Arg Ser Ser Gln Thr Ile Val His Ser Asn Gly Asp Thr Tyr Leu Asp
1               5                   10                  15


<210> SEQ ID NO 388
<211> LENGTH: 7
<212> TYPE: PRT
<213> ORGANISM: Homo sapiens

<400> SEQUENCE: 388

Lys Val Ser Asn Arg Phe Ser
1               5


<210> SEQ ID NO 389
<211> LENGTH: 9
<212> TYPE: PRT
<213> ORGANISM: Homo sapiens

<400> SEQUENCE: 389

Phe Gln Gly Ser His Val Pro Tyr Thr
1               5
```

<210> SEQ ID NO 390
<211> LENGTH: 135
<212> TYPE: PRT
<213> ORGANISM: Homo sapiens

<400> SEQUENCE: 390

Met Gly Trp Ser Trp Val Phe Leu Phe Leu Leu Ser Val Thr Ala Gly
1 5 10 15

Val His Ser Gln Val His Leu Gln Gln Ser Gly Pro Glu Leu Val Lys
20 25 30

Pro Gly Ala Ser Val Lys Leu Ser Cys Lys Ala Ser Gly Tyr Thr Phe
35 40 45

Thr Lys Tyr Asp Ile Asn Trp Val Arg Gln Arg Pro Glu Gln Gly Leu
50 55 60

Glu Trp Ile Gly Trp Ile Phe Pro Gly Asp Gly Arg Thr Asp Tyr Asn
65 70 75 80

Glu Lys Phe Lys Gly Lys Ala Thr Leu Thr Thr Asp Lys Ser Ser Ser
85 90 95

Thr Ala Tyr Met Glu Val Ser Arg Leu Thr Ser Glu Asp Ser Ala Val
100 105 110

Tyr Phe Cys Ala Arg Tyr Gly Pro Ala Met Asp Tyr Trp Gly Gln Gly
115 120 125

Thr Ser Val Thr Val Ala Ser
130 135

<210> SEQ ID NO 391
<211> LENGTH: 131
<212> TYPE: PRT
<213> ORGANISM: Homo sapiens

<400> SEQUENCE: 391

Met Lys Leu Pro Val Arg Leu Leu Val Leu Met Phe Trp Ile Pro Ala
1 5 10 15

Ser Ser Ser Asp Val Leu Met Thr Gln Thr Pro Leu Ser Leu Pro Val
20 25 30

Ser Leu Gly Asp Gln Ala Ser Ile Ser Cys Arg Ser Ser Gln Thr Ile
35 40 45

Val His Ser Asn Gly Asp Thr Tyr Leu Asp Trp Phe Leu Gln Lys Pro
50 55 60

Gly Gln Ser Pro Lys Leu Leu Ile Tyr Lys Val Ser Asn Arg Phe Ser
65 70 75 80

Gly Val Pro Asp Arg Phe Ser Gly Ser Gly Ser Gly Thr Asp Phe Thr
85 90 95

Leu Lys Ile Ser Arg Val Glu Ala Glu Asp Leu Gly Val Tyr Tyr Cys
100 105 110

Phe Gln Gly Ser His Val Pro Tyr Thr Phe Gly Gly Gly Thr Lys Leu
115 120 125

Glu Ile Lys
130

<210> SEQ ID NO 392
<211> LENGTH: 25
<212> TYPE: DNA
<213> ORGANISM: Homo sapiens

<400> SEQUENCE: 392
tctagttggt catcttcgcc ccaca 25

<210> SEQ ID NO 393
<211> LENGTH: 25
<212> TYPE: DNA
<213> ORGANISM: Homo sapiens

<400> SEQUENCE: 393
tataaaatta ctgaatatcc cataa 25

<210> SEQ ID NO 394
<211> LENGTH: 25
<212> TYPE: DNA
<213> ORGANISM: Homo sapiens

<400> SEQUENCE: 394
gctcaagcaa tcttcctgcc tcggc 25

<210> SEQ ID NO 395
<211> LENGTH: 25
<212> TYPE: DNA
<213> ORGANISM: Homo sapiens

<400> SEQUENCE: 395
gtggtctcta ccaccctcca gcaga 25

<210> SEQ ID NO 396
<211> LENGTH: 25
<212> TYPE: DNA
<213> ORGANISM: Homo sapiens

<400> SEQUENCE: 396
tataaaatta ctgaatatcc cataa 25

<210> SEQ ID NO 397
<211> LENGTH: 25
<212> TYPE: DNA
<213> ORGANISM: Homo sapiens

<400> SEQUENCE: 397
ggagtggaaa taacttgatt ggggt 25

<210> SEQ ID NO 398
<211> LENGTH: 25
<212> TYPE: DNA
<213> ORGANISM: Homo sapiens

<400> SEQUENCE: 398
aagaatgagt atagaatatg tgatc 25

<210> SEQ ID NO 399
<211> LENGTH: 25
<212> TYPE: DNA
<213> ORGANISM: Homo sapiens

<400> SEQUENCE: 399
aagaatgagt atagaatatg tgatc 25

<210> SEQ ID NO 400
<211> LENGTH: 25
<212> TYPE: DNA
<213> ORGANISM: Homo sapiens

<400> SEQUENCE: 400
tgtgtttcaa tatttccatg tcttt 25

<210> SEQ ID NO 401
<211> LENGTH: 25
<212> TYPE: DNA
<213> ORGANISM: Homo sapiens

<400> SEQUENCE: 401
acaaaattat gtatatagtg tgacc 25

<210> SEQ ID NO 402
<211> LENGTH: 25
<212> TYPE: DNA
<213> ORGANISM: Homo sapiens

<400> SEQUENCE: 402
gataactctt cttggctcaa tttca 25

<210> SEQ ID NO 403
<211> LENGTH: 25
<212> TYPE: DNA
<213> ORGANISM: Homo sapiens

<400> SEQUENCE: 403
atttatgtta gagaaatctc tgttc 25

<210> SEQ ID NO 404
<211> LENGTH: 25
<212> TYPE: DNA
<213> ORGANISM: Homo sapiens

<400> SEQUENCE: 404
tgtttgtcta acaggagcct gaaaa 25

<210> SEQ ID NO 405
<211> LENGTH: 25
<212> TYPE: DNA
<213> ORGANISM: Homo sapiens

<400> SEQUENCE: 405
tctagttggt catcttcgcc ccaca 25

<210> SEQ ID NO 406
<211> LENGTH: 25
<212> TYPE: DNA
<213> ORGANISM: Homo sapiens

<400> SEQUENCE: 406
gatttggaga cgaggagcaa caaat 25

<210> SEQ ID NO 407
<211> LENGTH: 30
<212> TYPE: DNA
<213> ORGANISM: Homo sapiens

<400> SEQUENCE: 407
catttccttt taatgtcgta actatgttac 30

<210> SEQ ID NO 408
<211> LENGTH: 25
<212> TYPE: DNA
<213> ORGANISM: Homo sapiens

<400> SEQUENCE: 408

-continued ggagtggaaa taacttgatt ggggt 25

<210> SEQ ID NO 409
<211> LENGTH: 25
<212> TYPE: DNA
<213> ORGANISM: Homo sapiens

<400> SEQUENCE: 409
aaaagacatg ataaagtagt gatac 25

<210> SEQ ID NO 410
<211> LENGTH: 25
<212> TYPE: DNA
<213> ORGANISM: Homo sapiens

<400> SEQUENCE: 410
tgtttgtcta acaggagcct gaaaa 25

<210> SEQ ID NO 411
<211> LENGTH: 25
<212> TYPE: DNA
<213> ORGANISM: Homo sapiens

<400> SEQUENCE: 411
gatttggaga cgaggagcaa caaat 25

<210> SEQ ID NO 412
<211> LENGTH: 25
<212> TYPE: DNA
<213> ORGANISM: Homo sapiens

<400> SEQUENCE: 412
tctggttatt tttcacactt cttcc 25

<210> SEQ ID NO 413
<211> LENGTH: 25
<212> TYPE: DNA
<213> ORGANISM: Homo sapiens

<400> SEQUENCE: 413
ggtttagtag agtcttttca acaat 25

<210> SEQ ID NO 414
<211> LENGTH: 25
<212> TYPE: DNA
<213> ORGANISM: Homo sapiens

<400> SEQUENCE: 414 tttattttt ttttcttttt ggcct 25

<210> SEQ ID NO 415
<211> LENGTH: 25
<212> TYPE: DNA
<213> ORGANISM: Homo sapiens

<400> SEQUENCE: 415
tttacaattt tcaccaagga atctt 25

<210> SEQ ID NO 416
<211> LENGTH: 25
<212> TYPE: DNA
<213> ORGANISM: Homo sapiens

<400> SEQUENCE: 416
tttatttttt ttttcttttt ggcct 25

<210> SEQ ID NO 417
<211> LENGTH: 25
<212> TYPE: DNA
<213> ORGANISM: Homo sapiens

<400> SEQUENCE: 417
ggagtggaaa taacttgatt ggggt 25

<210> SEQ ID NO 418
<211> LENGTH: 25
<212> TYPE: DNA
<213> ORGANISM: Homo sapiens

<400> SEQUENCE: 418
gaaccctgac ttggataata cagat 25

<210> SEQ ID NO 419
<211> LENGTH: 25
<212> TYPE: DNA
<213> ORGANISM: Homo sapiens

<400> SEQUENCE: 419
atgaagagag ttcagaaagc aagga 25

<210> SEQ ID NO 420
<211> LENGTH: 25
<212> TYPE: DNA
<213> ORGANISM: Homo sapiens

<400> SEQUENCE: 420
aacaaaaacc caatctatat attca 25

<210> SEQ ID NO 421
<211> LENGTH: 25
<212> TYPE: DNA
<213> ORGANISM: Homo sapiens

<400> SEQUENCE: 421
tggagaaaca ccagagactg cataa 25

<210> SEQ ID NO 422
<211> LENGTH: 25
<212> TYPE: DNA
<213> ORGANISM: Homo sapiens

<400> SEQUENCE: 422
gaatgcagct cccagaccgc acccc 25

<210> SEQ ID NO 423
<211> LENGTH: 25
<212> TYPE: DNA
<213> ORGANISM: Homo sapiens

<400> SEQUENCE: 423
tgtcttgtct agcttgtttg atacc 25

<210> SEQ ID NO 424
<211> LENGTH: 25
<212> TYPE: DNA
<213> ORGANISM: Homo sapiens

<400> SEQUENCE: 424
gctcaagcaa tcttcctgcc tcggc 25

<210> SEQ ID NO 425
<211> LENGTH: 25
<212> TYPE: DNA
<213> ORGANISM: Homo sapiens

<400> SEQUENCE: 425
tttacaattt tcaccaagga atctt 25

<210> SEQ ID NO 426
<211> LENGTH: 25
<212> TYPE: DNA
<213> ORGANISM: Homo sapiens

<400> SEQUENCE: 426
ggagcatgag atcactttta aaatt 25

<210> SEQ ID NO 427
<211> LENGTH: 25
<212> TYPE: DNA
<213> ORGANISM: Homo sapiens

<400> SEQUENCE: 427
tgtccttgac ctaacacttt gtatc 25

<210> SEQ ID NO 428
<211> LENGTH: 25
<212> TYPE: DNA
<213> ORGANISM: Homo sapiens

<400> SEQUENCE: 428
cagaagaagg agaaacaggt agatc 25

<210> SEQ ID NO 429
<211> LENGTH: 25
<212> TYPE: DNA
<213> ORGANISM: Homo sapiens

<400> SEQUENCE: 429
gaaagaagct cttgagccat tcact 25

<210> SEQ ID NO 430
<211> LENGTH: 25
<212> TYPE: DNA
<213> ORGANISM: Homo sapiens

<400> SEQUENCE: 430
tataaaatta ctgaatatcc cataa 25

<210> SEQ ID NO 431
<211> LENGTH: 30
<212> TYPE: DNA
<213> ORGANISM: Homo sapiens

<400> SEQUENCE: 431
cacaaaatat tggcagaata tatatacata 30

<210> SEQ ID NO 432
<211> LENGTH: 25
<212> TYPE: DNA
<213> ORGANISM: Homo sapiens

<400> SEQUENCE: 432
atacagcatt tagtccataa cacaa 25

<210> SEQ ID NO 433
<211> LENGTH: 25
<212> TYPE: DNA
<213> ORGANISM: Homo sapiens

<400> SEQUENCE: 433
atgaagagag ttcagaaagc aagga 25

<210> SEQ ID NO 434
<211> LENGTH: 25
<212> TYPE: DNA
<213> ORGANISM: Homo sapiens

<400> SEQUENCE: 434
tcccattctt tgctgagaga ctttg 25

<210> SEQ ID NO 435
<211> LENGTH: 25
<212> TYPE: DNA
<213> ORGANISM: Homo sapiens

<400> SEQUENCE: 435
tctgcttcag catcacaagt acatc 25

<210> SEQ ID NO 436
<211> LENGTH: 25
<212> TYPE: DNA
<213> ORGANISM: Homo sapiens

<400> SEQUENCE: 436
aaggttggtg ccatctctcc agacc 25

<210> SEQ ID NO 437
<211> LENGTH: 25
<212> TYPE: DNA
<213> ORGANISM: Homo sapiens

<400> SEQUENCE: 437
gctcaagcaa tcttcctgcc tcggc 25

<210> SEQ ID NO 438
<211> LENGTH: 25
<212> TYPE: DNA
<213> ORGANISM: Homo sapiens

<400> SEQUENCE: 438
ctgtcagtag cagtccctca aaatc 25

<210> SEQ ID NO 439
<211> LENGTH: 25
<212> TYPE: DNA
<213> ORGANISM: Homo sapiens

<400> SEQUENCE: 439
aacagacaaa tttatagaga cagaa 25

<210> SEQ ID NO 440
<211> LENGTH: 30
<212> TYPE: DNA

<213> ORGANISM: Homo sapiens

<400> SEQUENCE: 440
atctaaagaa ttatgtattt caaggggttg 30

<210> SEQ ID NO 441
<211> LENGTH: 25
<212> TYPE: DNA
<213> ORGANISM: Homo sapiens

<400> SEQUENCE: 441
aacaaaaacc caatctatat attca 25

<210> SEQ ID NO 442
<211> LENGTH: 25
<212> TYPE: DNA
<213> ORGANISM: Homo sapiens

<400> SEQUENCE: 442
tagcactctg aagcattgcc tctgg 25

<210> SEQ ID NO 443
<211> LENGTH: 25
<212> TYPE: DNA
<213> ORGANISM: Homo sapiens

<400> SEQUENCE: 443
ttgctccctg caggagcttt ttatg 25

<210> SEQ ID NO 444
<211> LENGTH: 25
<212> TYPE: DNA
<213> ORGANISM: Homo sapiens

<400> SEQUENCE: 444
agcactgaag tgcaaacagt ccttg 25

<210> SEQ ID NO 445
<211> LENGTH: 25
<212> TYPE: DNA
<213> ORGANISM: Homo sapiens

<400> SEQUENCE: 445
tgtttgtcta acaggagcct gaaaa 25

<210> SEQ ID NO 446
<211> LENGTH: 25
<212> TYPE: DNA
<213> ORGANISM: Homo sapiens

<400> SEQUENCE: 446
acaagtaaag tcttttggtt attac 25

<210> SEQ ID NO 447
<211> LENGTH: 25
<212> TYPE: DNA
<213> ORGANISM: Homo sapiens

<400> SEQUENCE: 447
tctggttatt tttcacactt cttcc 25

<210> SEQ ID NO 448
<211> LENGTH: 25

<212> TYPE: DNA
<213> ORGANISM: Homo sapiens

<400> SEQUENCE: 448
acaagtaaag tcttttggtt attac 25

<210> SEQ ID NO 449
<211> LENGTH: 25
<212> TYPE: DNA
<213> ORGANISM: Homo sapiens

<400> SEQUENCE: 449
acaagtaaag tcttttggtt attac 25

<210> SEQ ID NO 450
<211> LENGTH: 25
<212> TYPE: DNA
<213> ORGANISM: Homo sapiens

<400> SEQUENCE: 450
gcaatttcgt aacagaggta taatc 25

<210> SEQ ID NO 451
<211> LENGTH: 25
<212> TYPE: DNA
<213> ORGANISM: Homo sapiens

<400> SEQUENCE: 451
agcaggtaac ctagaaggtg aaatt 25

<210> SEQ ID NO 452
<211> LENGTH: 25
<212> TYPE: DNA
<213> ORGANISM: Homo sapiens

<400> SEQUENCE: 452
acagatgcac tacatctttg ctacc 25

<210> SEQ ID NO 453
<211> LENGTH: 25
<212> TYPE: DNA
<213> ORGANISM: Homo sapiens

<400> SEQUENCE: 453
tttcccatct taaccaaggt cctgc 25

<210> SEQ ID NO 454
<211> LENGTH: 30
<212> TYPE: DNA
<213> ORGANISM: Homo sapiens

<400> SEQUENCE: 454
agataaatcc ctttgatatt aaaaaaaaaa 30

<210> SEQ ID NO 455
<211> LENGTH: 25
<212> TYPE: DNA
<213> ORGANISM: Homo sapiens

<400> SEQUENCE: 455
atggagcaaa atccagtggc aataa 25

<210> SEQ ID NO 456

<211> LENGTH: 25
<212> TYPE: DNA
<213> ORGANISM: Homo sapiens

<400> SEQUENCE: 456
cagcaggcag gtattaggag gatta 25

<210> SEQ ID NO 457
<211> LENGTH: 25
<212> TYPE: DNA
<213> ORGANISM: Homo sapiens

<400> SEQUENCE: 457
tatgtctgag gattttgaga tgtgc 25

<210> SEQ ID NO 458
<211> LENGTH: 25
<212> TYPE: DNA
<213> ORGANISM: Homo sapiens

<400> SEQUENCE: 458
ctccctggca cttgctcctg tctcc 25

<210> SEQ ID NO 459
<211> LENGTH: 30
<212> TYPE: DNA
<213> ORGANISM: Homo sapiens

<400> SEQUENCE: 459
tccccatatc ttttggttcc aagtgcctca 30

<210> SEQ ID NO 460
<211> LENGTH: 25
<212> TYPE: DNA
<213> ORGANISM: Homo sapiens

<400> SEQUENCE: 460
tgagccagac aacttgagtt gcctt 25

<210> SEQ ID NO 461
<211> LENGTH: 25
<212> TYPE: DNA
<213> ORGANISM: Homo sapiens

<400> SEQUENCE: 461
aggcatttcc cagagccttt tgctg 25

<210> SEQ ID NO 462
<211> LENGTH: 25
<212> TYPE: DNA
<213> ORGANISM: Homo sapiens

<400> SEQUENCE: 462
gtcatgggat ttttacagag ttaag 25

<210> SEQ ID NO 463
<211> LENGTH: 25
<212> TYPE: DNA
<213> ORGANISM: Homo sapiens

<400> SEQUENCE: 463
aggcagacag agctcaggcg gtaac 25

<210> SEQ ID NO 464
<211> LENGTH: 25
<212> TYPE: DNA
<213> ORGANISM: Homo sapiens

<400> SEQUENCE: 464
atggagcaaa atccagtggc aataa 25

<210> SEQ ID NO 465
<211> LENGTH: 25
<212> TYPE: DNA
<213> ORGANISM: Homo sapiens

<400> SEQUENCE: 465
gaaaagatag cacatagtga attct 25

<210> SEQ ID NO 466
<211> LENGTH: 25
<212> TYPE: DNA
<213> ORGANISM: Homo sapiens

<400> SEQUENCE: 466
gaaaggacct catcactctt cccat 25

<210> SEQ ID NO 467
<211> LENGTH: 25
<212> TYPE: DNA
<213> ORGANISM: Homo sapiens

<400> SEQUENCE: 467
gatgagctga gctcttagaa gtaac 25

<210> SEQ ID NO 468
<211> LENGTH: 25
<212> TYPE: DNA
<213> ORGANISM: Homo sapiens

<400> SEQUENCE: 468
aggaaagggc agacatcaag ggacc 25

<210> SEQ ID NO 469
<211> LENGTH: 25
<212> TYPE: DNA
<213> ORGANISM: Homo sapiens

<400> SEQUENCE: 469
ttagaccttg ggaaagctac ttctc 25

<210> SEQ ID NO 470
<211> LENGTH: 25
<212> TYPE: DNA
<213> ORGANISM: Homo sapiens

<400> SEQUENCE: 470
ttttctaaga ggtatgcaca attta 25

<210> SEQ ID NO 471
<211> LENGTH: 25
<212> TYPE: DNA
<213> ORGANISM: Homo sapiens

<400> SEQUENCE: 471
ctccctggca cttgctcctg tctcc 25

<210> SEQ ID NO 472
<211> LENGTH: 25
<212> TYPE: DNA
<213> ORGANISM: Homo sapiens

<400> SEQUENCE: 472
tggtggccct gttggcatta ctggg 25

<210> SEQ ID NO 473
<211> LENGTH: 25
<212> TYPE: DNA
<213> ORGANISM: Homo sapiens

<400> SEQUENCE: 473
tttacttcat atttattttt gaatc 25

<210> SEQ ID NO 474
<211> LENGTH: 25
<212> TYPE: DNA
<213> ORGANISM: Homo sapiens

<400> SEQUENCE: 474
atggagcaaa atccagtggc aataa 25

<210> SEQ ID NO 475
<211> LENGTH: 25
<212> TYPE: DNA
<213> ORGANISM: Homo sapiens

<400> SEQUENCE: 475
tagctagaaa ttaacacatg cccgg 25

<210> SEQ ID NO 476
<211> LENGTH: 25
<212> TYPE: DNA
<213> ORGANISM: Homo sapiens

<400> SEQUENCE: 476
atggagcaaa atccagtggc aataa 25

<210> SEQ ID NO 477
<211> LENGTH: 25
<212> TYPE: DNA
<213> ORGANISM: Homo sapiens

<400> SEQUENCE: 477
tggattctac aaacaatact ttaac 25

<210> SEQ ID NO 478
<211> LENGTH: 25
<212> TYPE: DNA
<213> ORGANISM: Homo sapiens

<400> SEQUENCE: 478
cagcaggcag gtattaggag gatta 25

<210> SEQ ID NO 479
<211> LENGTH: 30
<212> TYPE: DNA
<213> ORGANISM: Homo sapiens

<400> SEQUENCE: 479
cccacagtcg agtgcagagg tctccgaagc 30

<210> SEQ ID NO 480
<211> LENGTH: 25
<212> TYPE: DNA
<213> ORGANISM: Homo sapiens

<400> SEQUENCE: 480
tcctgcattc tggattttgc tgatc 25

<210> SEQ ID NO 481
<211> LENGTH: 25
<212> TYPE: DNA
<213> ORGANISM: Homo sapiens

<400> SEQUENCE: 481
ttatttgtaa tcaacatgta gttgg 25

<210> SEQ ID NO 482
<211> LENGTH: 25
<212> TYPE: DNA
<213> ORGANISM: Homo sapiens

<400> SEQUENCE: 482
aagatgtcaa atattctcta cataa 25

<210> SEQ ID NO 483
<211> LENGTH: 30
<212> TYPE: DNA
<213> ORGANISM: Homo sapiens

<400> SEQUENCE: 483
gttggttgct attagagact ggtggtcagg 30

<210> SEQ ID NO 484
<211> LENGTH: 25
<212> TYPE: DNA
<213> ORGANISM: Homo sapiens

<400> SEQUENCE: 484
ttttctaaga ggtatgcaca attta 25

<210> SEQ ID NO 485
<211> LENGTH: 25
<212> TYPE: DNA
<213> ORGANISM: Homo sapiens

<400> SEQUENCE: 485
cactgtttga aaattgagag actgc 25

<210> SEQ ID NO 486
<211> LENGTH: 25
<212> TYPE: DNA
<213> ORGANISM: Homo sapiens

<400> SEQUENCE: 486
actggccaag taaccacaga catgg 25

<210> SEQ ID NO 487
<211> LENGTH: 25
<212> TYPE: DNA
<213> ORGANISM: Homo sapiens

<400> SEQUENCE: 487
gctcataggc cttacaacca cagac 25

<210> SEQ ID NO 488
<211> LENGTH: 25
<212> TYPE: DNA
<213> ORGANISM: Homo sapiens

<400> SEQUENCE: 488
attctgacct gtcactgtgc caggc 25

<210> SEQ ID NO 489
<211> LENGTH: 25
<212> TYPE: DNA
<213> ORGANISM: Homo sapiens

<400> SEQUENCE: 489
tagctagaaa ttaacacatg cccgg 25

<210> SEQ ID NO 490
<211> LENGTH: 25
<212> TYPE: DNA
<213> ORGANISM: Homo sapiens

<400> SEQUENCE: 490
tttccctcca gtggctcatg ggact 25

<210> SEQ ID NO 491
<211> LENGTH: 25
<212> TYPE: DNA
<213> ORGANISM: Homo sapiens

<400> SEQUENCE: 491
ttcagcacta ttcagcgcct atcac 25

<210> SEQ ID NO 492
<211> LENGTH: 30
<212> TYPE: DNA
<213> ORGANISM: Homo sapiens

<400> SEQUENCE: 492
gtgattgtca ggcattatgg aaaggtcaaa 30

<210> SEQ ID NO 493
<211> LENGTH: 25
<212> TYPE: DNA
<213> ORGANISM: Homo sapiens

<400> SEQUENCE: 493
taaggtgtgt aaggaaagtg aaatg 25

<210> SEQ ID NO 494
<211> LENGTH: 25
<212> TYPE: DNA
<213> ORGANISM: Homo sapiens

<400> SEQUENCE: 494
ctcaatgagt ctctgtaatc catac 25

<210> SEQ ID NO 495
<211> LENGTH: 30
<212> TYPE: DNA
<213> ORGANISM: Homo sapiens

<400> SEQUENCE: 495
tgtggaggat gaactggatc cctctccgac 30

<210> SEQ ID NO 496
<211> LENGTH: 25
<212> TYPE: DNA
<213> ORGANISM: Homo sapiens

<400> SEQUENCE: 496
ggtggatgta gacattcact ccctc 25

<210> SEQ ID NO 497
<211> LENGTH: 25
<212> TYPE: DNA
<213> ORGANISM: Homo sapiens

<400> SEQUENCE: 497
tatcatttct caactattga tttca 25

<210> SEQ ID NO 498
<211> LENGTH: 25
<212> TYPE: DNA
<213> ORGANISM: Homo sapiens

<400> SEQUENCE: 498
attcagcttt gtgtaactgg gtaac 25

<210> SEQ ID NO 499
<211> LENGTH: 30
<212> TYPE: DNA
<213> ORGANISM: Homo sapiens

<400> SEQUENCE: 499
attctccaaa cccagccctg ctgagttcct 30

<210> SEQ ID NO 500
<211> LENGTH: 30
<212> TYPE: DNA
<213> ORGANISM: Homo sapiens

<400> SEQUENCE: 500
tccccatatc ttttggttcc aagtgcctca 30

<210> SEQ ID NO 501
<211> LENGTH: 25
<212> TYPE: DNA
<213> ORGANISM: Homo sapiens

<400> SEQUENCE: 501
gcattgcact tcccttgttt tccac 25

<210> SEQ ID NO 502
<211> LENGTH: 30
<212> TYPE: DNA
<213> ORGANISM: Homo sapiens

<400> SEQUENCE: 502
gttggttgct attagagact ggtggtcagg 30

<210> SEQ ID NO 503
<211> LENGTH: 25
<212> TYPE: DNA
<213> ORGANISM: Homo sapiens

<400> SEQUENCE: 503
atactttgca gagtgttggg aagaa 25

<210> SEQ ID NO 504
<211> LENGTH: 25
<212> TYPE: DNA
<213> ORGANISM: Homo sapiens

<400> SEQUENCE: 504
caatgtaaat tatagtaaga aaaga 25

<210> SEQ ID NO 505
<211> LENGTH: 25
<212> TYPE: DNA
<213> ORGANISM: Homo sapiens

<400> SEQUENCE: 505
tcgatcagta ctctgtggaa caccc 25

<210> SEQ ID NO 506
<211> LENGTH: 25
<212> TYPE: DNA
<213> ORGANISM: Homo sapiens

<400> SEQUENCE: 506
caggaaaaac agcagattct gtgtt 25

<210> SEQ ID NO 507
<211> LENGTH: 25
<212> TYPE: DNA
<213> ORGANISM: Homo sapiens

<400> SEQUENCE: 507
gaggcagggg catggacgag atgac 25

<210> SEQ ID NO 508
<211> LENGTH: 25
<212> TYPE: DNA
<213> ORGANISM: Homo sapiens

<400> SEQUENCE: 508
tggcttgttt acagcatcct cctat 25

<210> SEQ ID NO 509
<211> LENGTH: 25
<212> TYPE: DNA
<213> ORGANISM: Homo sapiens

<400> SEQUENCE: 509
ggactgagta tacatatatt aagac 25

<210> SEQ ID NO 510
<211> LENGTH: 25
<212> TYPE: DNA
<213> ORGANISM: Homo sapiens

<400> SEQUENCE: 510
tttcccatct taaccaaggt cctgc 25

<210> SEQ ID NO 511
<211> LENGTH: 25
<212> TYPE: DNA
<213> ORGANISM: Homo sapiens

<400> SEQUENCE: 511
gcactcaaca atggtagctg ctgtt 25

<210> SEQ ID NO 512
<211> LENGTH: 25
<212> TYPE: DNA
<213> ORGANISM: Homo sapiens

<400> SEQUENCE: 512
aatttggaaa atacagaaac tacct 25

<210> SEQ ID NO 513
<211> LENGTH: 25
<212> TYPE: DNA
<213> ORGANISM: Homo sapiens

<400> SEQUENCE: 513
tataacagga agtctcagaa gctgg 25

<210> SEQ ID NO 514
<211> LENGTH: 25
<212> TYPE: DNA
<213> ORGANISM: Homo sapiens

<400> SEQUENCE: 514
cttctcccac caagctaaca catgg 25

<210> SEQ ID NO 515
<211> LENGTH: 25
<212> TYPE: DNA
<213> ORGANISM: Homo sapiens

<400> SEQUENCE: 515
cttctcccac caagctaaca catgg 25

<210> SEQ ID NO 516
<211> LENGTH: 25
<212> TYPE: DNA
<213> ORGANISM: Homo sapiens

<400> SEQUENCE: 516
ctaacagctg tcctctgtat taagg 25

<210> SEQ ID NO 517
<211> LENGTH: 30
<212> TYPE: DNA
<213> ORGANISM: Homo sapiens

<400> SEQUENCE: 517
taaaccaact gcacccacag gcaaaacacc 30

<210> SEQ ID NO 518
<211> LENGTH: 30
<212> TYPE: DNA
<213> ORGANISM: Homo sapiens

<400> SEQUENCE: 518
aaacaaattt aatgtatttt attttaaagt 30

<210> SEQ ID NO 519
<211> LENGTH: 25
<212> TYPE: DNA

<213> ORGANISM: Homo sapiens

<400> SEQUENCE: 519
gtagcattcc caaatgtaag tccgc 25

<210> SEQ ID NO 520
<211> LENGTH: 25
<212> TYPE: DNA
<213> ORGANISM: Homo sapiens

<400> SEQUENCE: 520
tcctcttctc cgcctcctct ttcag 25

<210> SEQ ID NO 521
<211> LENGTH: 25
<212> TYPE: DNA
<213> ORGANISM: Homo sapiens

<400> SEQUENCE: 521
tacaaacctg gcttagaata aagta 25

<210> SEQ ID NO 522
<211> LENGTH: 30
<212> TYPE: DNA
<213> ORGANISM: Homo sapiens

<400> SEQUENCE: 522
taatgattat agcaaatttg taggatacag 30

<210> SEQ ID NO 523
<211> LENGTH: 25
<212> TYPE: DNA
<213> ORGANISM: Homo sapiens

<400> SEQUENCE: 523
gaaggaaggt gagtatgaga tatat 25

<210> SEQ ID NO 524
<211> LENGTH: 30
<212> TYPE: DNA
<213> ORGANISM: Homo sapiens

<400> SEQUENCE: 524
ggacaaagca agtgctaact cggggtggag 30

<210> SEQ ID NO 525
<211> LENGTH: 25
<212> TYPE: DNA
<213> ORGANISM: Homo sapiens

<400> SEQUENCE: 525
gaaagtccaa aatctgtagt tttgc 25

<210> SEQ ID NO 526
<211> LENGTH: 25
<212> TYPE: DNA
<213> ORGANISM: Homo sapiens

<400> SEQUENCE: 526
tgctgaatat ataaagacaa ctata 25

<210> SEQ ID NO 527
<211> LENGTH: 25

<212> TYPE: DNA
<213> ORGANISM: Homo sapiens

<400> SEQUENCE: 527
catataccct tgtactaaca tgctt 25

<210> SEQ ID NO 528
<211> LENGTH: 25
<212> TYPE: DNA
<213> ORGANISM: Homo sapiens

<400> SEQUENCE: 528
cgccatcccc tcctttcctt tctgc 25

<210> SEQ ID NO 529
<211> LENGTH: 25
<212> TYPE: DNA
<213> ORGANISM: Homo sapiens

<400> SEQUENCE: 529
cttctcccac caagctaaca catgg 25

<210> SEQ ID NO 530
<211> LENGTH: 25
<212> TYPE: DNA
<213> ORGANISM: Homo sapiens

<400> SEQUENCE: 530
cttctcccac caagctaaca catgg 25

<210> SEQ ID NO 531
<211> LENGTH: 25
<212> TYPE: DNA
<213> ORGANISM: Homo sapiens

<400> SEQUENCE: 531
atataatata cctcggagat atggc 25

<210> SEQ ID NO 532
<211> LENGTH: 25
<212> TYPE: DNA
<213> ORGANISM: Homo sapiens

<400> SEQUENCE: 532
tttgaatcct gcaggtacat ttatg 25

<210> SEQ ID NO 533
<211> LENGTH: 25
<212> TYPE: DNA
<213> ORGANISM: Homo sapiens

<400> SEQUENCE: 533
cccagccttc tcccagctgc cctga 25

<210> SEQ ID NO 534
<211> LENGTH: 25
<212> TYPE: DNA
<213> ORGANISM: Homo sapiens

<400> SEQUENCE: 534
agactggtgg caacagagta gccct 25

<210> SEQ ID NO 535

<211> LENGTH: 25
<212> TYPE: DNA
<213> ORGANISM: Homo sapiens

<400> SEQUENCE: 535
gcactcaaca atggtagctg ctgtt 25

<210> SEQ ID NO 536
<211> LENGTH: 25
<212> TYPE: DNA
<213> ORGANISM: Homo sapiens

<400> SEQUENCE: 536
aaatgtggtc atggaaagta agaat 25

<210> SEQ ID NO 537
<211> LENGTH: 25
<212> TYPE: DNA
<213> ORGANISM: Homo sapiens

<400> SEQUENCE: 537
gaggacattc caaataggaa ctacg 25

<210> SEQ ID NO 538
<211> LENGTH: 25
<212> TYPE: DNA
<213> ORGANISM: Homo sapiens

<400> SEQUENCE: 538
aaaacttcaa agtgattttt aaaaa 25

<210> SEQ ID NO 539
<211> LENGTH: 25
<212> TYPE: DNA
<213> ORGANISM: Homo sapiens

<400> SEQUENCE: 539
attattgagc tctatttcct cttcc 25

<210> SEQ ID NO 540
<211> LENGTH: 25
<212> TYPE: DNA
<213> ORGANISM: Homo sapiens

<400> SEQUENCE: 540
aaaggaggag cagagagcaa tactg 25

<210> SEQ ID NO 541
<211> LENGTH: 25
<212> TYPE: DNA
<213> ORGANISM: Homo sapiens

<400> SEQUENCE: 541
aaccgctagt ttctaagcaa tcccc 25

<210> SEQ ID NO 542
<211> LENGTH: 25
<212> TYPE: DNA
<213> ORGANISM: Homo sapiens

<400> SEQUENCE: 542
ggaatagaat tttgttacct tttct 25

<210> SEQ ID NO 543
<211> LENGTH: 25
<212> TYPE: DNA
<213> ORGANISM: Homo sapiens

<400> SEQUENCE: 543
ggcaaaataa aggctggaag caatt 25

<210> SEQ ID NO 544
<211> LENGTH: 25
<212> TYPE: DNA
<213> ORGANISM: Homo sapiens

<400> SEQUENCE: 544
ctatactgtt tcacttcaag ccttt 25

<210> SEQ ID NO 545
<211> LENGTH: 25
<212> TYPE: DNA
<213> ORGANISM: Homo sapiens

<400> SEQUENCE: 545
gtcatgggat ttttacagag ttaag 25

<210> SEQ ID NO 546
<211> LENGTH: 25
<212> TYPE: DNA
<213> ORGANISM: Homo sapiens

<400> SEQUENCE: 546
tggattctac aaacaatact ttaac 25

<210> SEQ ID NO 547
<211> LENGTH: 25
<212> TYPE: DNA
<213> ORGANISM: Homo sapiens

<400> SEQUENCE: 547
gtggtctcta ccaccctcca gcaga 25

<210> SEQ ID NO 548
<211> LENGTH: 25
<212> TYPE: DNA
<213> ORGANISM: Homo sapiens

<400> SEQUENCE: 548
tgctgggatt acaggcgtga gccac 25

<210> SEQ ID NO 549
<211> LENGTH: 25
<212> TYPE: DNA
<213> ORGANISM: Homo sapiens

<400> SEQUENCE: 549
aaagtgaaca gctctaaaga gcttt 25

<210> SEQ ID NO 550
<211> LENGTH: 25
<212> TYPE: DNA
<213> ORGANISM: Homo sapiens

<400> SEQUENCE: 550
ggtggatgta gacattcact ccctc 25

<210> SEQ ID NO 551
<211> LENGTH: 30
<212> TYPE: DNA
<213> ORGANISM: Homo sapiens

<400> SEQUENCE: 551
ttcttacccc cattccacag gggagaaact 30

<210> SEQ ID NO 552
<211> LENGTH: 25
<212> TYPE: DNA
<213> ORGANISM: Homo sapiens

<400> SEQUENCE: 552
tgttgaagat cattgaccat aaatg 25

<210> SEQ ID NO 553
<211> LENGTH: 25
<212> TYPE: DNA
<213> ORGANISM: Homo sapiens

<400> SEQUENCE: 553
taatactttt gtcttttaac tttta 25

<210> SEQ ID NO 554
<211> LENGTH: 25
<212> TYPE: DNA
<213> ORGANISM: Homo sapiens

<400> SEQUENCE: 554
attcagcttt gtgtaactgg gtaac 25

<210> SEQ ID NO 555
<211> LENGTH: 25
<212> TYPE: DNA
<213> ORGANISM: Homo sapiens

<400> SEQUENCE: 555
cgaacctata tgcctgtttt tgtgc 25

<210> SEQ ID NO 556
<211> LENGTH: 25
<212> TYPE: DNA
<213> ORGANISM: Homo sapiens

<400> SEQUENCE: 556
ttgaacaaaa taagacggct ctcac 25

<210> SEQ ID NO 557
<211> LENGTH: 25
<212> TYPE: DNA
<213> ORGANISM: Homo sapiens

<400> SEQUENCE: 557
aagtctgggc agcctccacc ttccc 25

<210> SEQ ID NO 558
<211> LENGTH: 25
<212> TYPE: DNA
<213> ORGANISM: Homo sapiens

<400> SEQUENCE: 558
ccacagcaga tttctgatgc tttta 25

<210> SEQ ID NO 559
<211> LENGTH: 25
<212> TYPE: DNA
<213> ORGANISM: Homo sapiens

<400> SEQUENCE: 559
gacactactc atctgatttg ccccc 25

<210> SEQ ID NO 560
<211> LENGTH: 25
<212> TYPE: DNA
<213> ORGANISM: Homo sapiens

<400> SEQUENCE: 560
actcaaggct tgtttactat acttg 25

<210> SEQ ID NO 561
<211> LENGTH: 25
<212> TYPE: DNA
<213> ORGANISM: Homo sapiens

<400> SEQUENCE: 561
cactgtttga aaattgagag actgc 25

<210> SEQ ID NO 562
<211> LENGTH: 25
<212> TYPE: DNA
<213> ORGANISM: Homo sapiens

<400> SEQUENCE: 562
agaccagctt cagggccgag tacaa 25

<210> SEQ ID NO 563
<211> LENGTH: 25
<212> TYPE: DNA
<213> ORGANISM: Homo sapiens

<400> SEQUENCE: 563
cgccgactca tcttatggtg tgagg 25

<210> SEQ ID NO 564
<211> LENGTH: 25
<212> TYPE: DNA
<213> ORGANISM: Homo sapiens

<400> SEQUENCE: 564
tttacttcat atttattttt gaatc 25

<210> SEQ ID NO 565
<211> LENGTH: 25
<212> TYPE: DNA
<213> ORGANISM: Homo sapiens

<400> SEQUENCE: 565
tgctgggatt acaggcgtga gccac 25

<210> SEQ ID NO 566
<211> LENGTH: 25
<212> TYPE: DNA
<213> ORGANISM: Homo sapiens

<400> SEQUENCE: 566

-continued tgctgggatt acaggcgtga gccac 25

<210> SEQ ID NO 567
<211> LENGTH: 25
<212> TYPE: DNA
<213> ORGANISM: Homo sapiens

<400> SEQUENCE: 567
attacaggca tgagccactg cgccc 25

<210> SEQ ID NO 568
<211> LENGTH: 25
<212> TYPE: DNA
<213> ORGANISM: Homo sapiens

<400> SEQUENCE: 568
tatgtctgag gattttgaga tgtgc 25

<210> SEQ ID NO 569
<211> LENGTH: 25
<212> TYPE: DNA
<213> ORGANISM: Homo sapiens

<400> SEQUENCE: 569
agctgggcat ttaattatgt ataca 25

<210> SEQ ID NO 570
<211> LENGTH: 25
<212> TYPE: DNA
<213> ORGANISM: Homo sapiens

<400> SEQUENCE: 570
gagagacgtg gaatgagctg gaggc 25

<210> SEQ ID NO 571
<211> LENGTH: 25
<212> TYPE: DNA
<213> ORGANISM: Homo sapiens

<400> SEQUENCE: 571
aaaagacatg ataaagtagt gatac 25

<210> SEQ ID NO 572
<211> LENGTH: 25
<212> TYPE: DNA
<213> ORGANISM: Homo sapiens

<400> SEQUENCE: 572
attttgtctg ctcaattata cagtt 25

<210> SEQ ID NO 573
<211> LENGTH: 25
<212> TYPE: DNA
<213> ORGANISM: Homo sapiens

<400> SEQUENCE: 573
ggagcatgag atcactttta aaatt 25

<210> SEQ ID NO 574
<211> LENGTH: 25
<212> TYPE: DNA
<213> ORGANISM: Homo sapiens

<400> SEQUENCE: 574
tgtccttgac ctaacacttt gtatc 25

<210> SEQ ID NO 575
<211> LENGTH: 25
<212> TYPE: DNA
<213> ORGANISM: Homo sapiens

<400> SEQUENCE: 575
cagaagaagg agaaacaggt agatc 25

<210> SEQ ID NO 576
<211> LENGTH: 25
<212> TYPE: DNA
<213> ORGANISM: Homo sapiens

<400> SEQUENCE: 576
gaaagaagct cttgagccat tcact 25

<210> SEQ ID NO 577
<211> LENGTH: 25
<212> TYPE: DNA
<213> ORGANISM: Homo sapiens

<400> SEQUENCE: 577
gtcgagtgca gaggtctccg aagca 25

<210> SEQ ID NO 578
<211> LENGTH: 25
<212> TYPE: DNA
<213> ORGANISM: Homo sapiens

<400> SEQUENCE: 578
ataatttgtc tttgatacct gaaaa 25

<210> SEQ ID NO 579
<211> LENGTH: 25
<212> TYPE: DNA
<213> ORGANISM: Homo sapiens

<400> SEQUENCE: 579
acctcttagc taagcacagc tgaag 25

<210> SEQ ID NO 580
<211> LENGTH: 25
<212> TYPE: DNA
<213> ORGANISM: Homo sapiens

<400> SEQUENCE: 580
gagagacgtg gaatgagctg gaggc 25

<210> SEQ ID NO 581
<211> LENGTH: 25
<212> TYPE: DNA
<213> ORGANISM: Homo sapiens

<400> SEQUENCE: 581
cctagtgtga ctatctttgg agata 25

<210> SEQ ID NO 582
<211> LENGTH: 25
<212> TYPE: DNA
<213> ORGANISM: Homo sapiens

<400> SEQUENCE: 582
gattttctct cggtttttct tcttt 25

<210> SEQ ID NO 583
<211> LENGTH: 25
<212> TYPE: DNA
<213> ORGANISM: Homo sapiens

<400> SEQUENCE: 583
caactgcata tcatcctccc agaaa 25

<210> SEQ ID NO 584
<211> LENGTH: 25
<212> TYPE: DNA
<213> ORGANISM: Homo sapiens

<400> SEQUENCE: 584
tctaccccac ttttgtccaa acctc 25

<210> SEQ ID NO 585
<211> LENGTH: 25
<212> TYPE: DNA
<213> ORGANISM: Homo sapiens

<400> SEQUENCE: 585
aaatgagaca tgggagggat aggat 25

<210> SEQ ID NO 586
<211> LENGTH: 25
<212> TYPE: DNA
<213> ORGANISM: Homo sapiens

<400> SEQUENCE: 586
ttttgaaaaa caccaaaggg caatt 25

<210> SEQ ID NO 587
<211> LENGTH: 25
<212> TYPE: DNA
<213> ORGANISM: Homo sapiens

<400> SEQUENCE: 587
gacaagggtg actccagtat ctccc 25

<210> SEQ ID NO 588
<211> LENGTH: 25
<212> TYPE: DNA
<213> ORGANISM: Homo sapiens

<400> SEQUENCE: 588
cttcgccctt ttggaggctc tgttc 25

<210> SEQ ID NO 589
<211> LENGTH: 25
<212> TYPE: DNA
<213> ORGANISM: Homo sapiens

<400> SEQUENCE: 589
aagtgattgt gatgcaactg gtctg 25

<210> SEQ ID NO 590
<211> LENGTH: 25
<212> TYPE: DNA
<213> ORGANISM: Homo sapiens

<400> SEQUENCE: 590
ttccggatca ggcgccctgg ctcac 25

<210> SEQ ID NO 591
<211> LENGTH: 25
<212> TYPE: DNA
<213> ORGANISM: Homo sapiens

<400> SEQUENCE: 591
ttattttggg atgacaaaaa tgttt 25

<210> SEQ ID NO 592
<211> LENGTH: 25
<212> TYPE: DNA
<213> ORGANISM: Homo sapiens

<400> SEQUENCE: 592
agatcaaaac aatcttgatc ataaa 25

<210> SEQ ID NO 593
<211> LENGTH: 25
<212> TYPE: DNA
<213> ORGANISM: Homo sapiens

<400> SEQUENCE: 593
ctcaatagat gcaggcaatt atcat 25

<210> SEQ ID NO 594
<211> LENGTH: 25
<212> TYPE: DNA
<213> ORGANISM: Homo sapiens

<400> SEQUENCE: 594
tatttctttc tgttcctcgg gttgg 25

<210> SEQ ID NO 595
<211> LENGTH: 25
<212> TYPE: DNA
<213> ORGANISM: Homo sapiens

<400> SEQUENCE: 595
acatagaagg tgctttcccc caagc 25

<210> SEQ ID NO 596
<211> LENGTH: 25
<212> TYPE: DNA
<213> ORGANISM: Homo sapiens

<400> SEQUENCE: 596
aaagtgaaca gctctaaaga gcttt 25

<210> SEQ ID NO 597
<211> LENGTH: 25
<212> TYPE: DNA
<213> ORGANISM: Homo sapiens

<400> SEQUENCE: 597
cagaaatcaa aacaatatta agtag 25

<210> SEQ ID NO 598
<211> LENGTH: 25
<212> TYPE: DNA

<213> ORGANISM: Homo sapiens

<400> SEQUENCE: 598
aggaaagggc agacatcaag ggacc 25

<210> SEQ ID NO 599
<211> LENGTH: 25
<212> TYPE: DNA
<213> ORGANISM: Homo sapiens

<400> SEQUENCE: 599
tagctagaaa ttaacacatg cccgg 25

<210> SEQ ID NO 600
<211> LENGTH: 25
<212> TYPE: DNA
<213> ORGANISM: Homo sapiens

<400> SEQUENCE: 600
atctgttctt ttggctgtgc gtcct 25

<210> SEQ ID NO 601
<211> LENGTH: 25
<212> TYPE: DNA
<213> ORGANISM: Homo sapiens

<400> SEQUENCE: 601
gctatggaac agctggctga tctga 25

<210> SEQ ID NO 602
<211> LENGTH: 25
<212> TYPE: DNA
<213> ORGANISM: Homo sapiens

<400> SEQUENCE: 602
agacatattt gggacatctc agaag 25

<210> SEQ ID NO 603
<211> LENGTH: 25
<212> TYPE: DNA
<213> ORGANISM: Homo sapiens

<400> SEQUENCE: 603
tagcactctg aagcattgcc tctgg 25

<210> SEQ ID NO 604
<211> LENGTH: 25
<212> TYPE: DNA
<213> ORGANISM: Homo sapiens

<400> SEQUENCE: 604
ttgctccctg caggagcttt ttatg 25

<210> SEQ ID NO 605
<211> LENGTH: 25
<212> TYPE: DNA
<213> ORGANISM: Homo sapiens

<400> SEQUENCE: 605
gagataaagc aaggatgttc tcagg 25

<210> SEQ ID NO 606
<211> LENGTH: 25

<212> TYPE: DNA
<213> ORGANISM: Homo sapiens

<400> SEQUENCE: 606
acaactaagt gaactaagtt gcttc 25

<210> SEQ ID NO 607
<211> LENGTH: 30
<212> TYPE: DNA
<213> ORGANISM: Homo sapiens

<400> SEQUENCE: 607
gcgcggggca agggggatgg ggtgccacag 30

<210> SEQ ID NO 608
<211> LENGTH: 25
<212> TYPE: DNA
<213> ORGANISM: Homo sapiens

<400> SEQUENCE: 608
agcactgaag tgcaaacagt ccttg 25

<210> SEQ ID NO 609
<211> LENGTH: 25
<212> TYPE: DNA
<213> ORGANISM: Homo sapiens

<400> SEQUENCE: 609
ccagcactcc actctgtgct cacat 25

<210> SEQ ID NO 610
<211> LENGTH: 30
<212> TYPE: DNA
<213> ORGANISM: Homo sapiens

<400> SEQUENCE: 610
gcagtttttc aaggacaaaa ttagttatta 30

<210> SEQ ID NO 611
<211> LENGTH: 25
<212> TYPE: DNA
<213> ORGANISM: Homo sapiens

<400> SEQUENCE: 611
ttaaaatttg tcttcaaatg tgtac 25

<210> SEQ ID NO 612
<211> LENGTH: 25
<212> TYPE: DNA
<213> ORGANISM: Homo sapiens

<400> SEQUENCE: 612
ggaaggcttg tcccaggtct agccc 25

<210> SEQ ID NO 613
<211> LENGTH: 25
<212> TYPE: DNA
<213> ORGANISM: Homo sapiens

<400> SEQUENCE: 613
aacctgaaaa ctacatgaag cacaa 25

<210> SEQ ID NO 614

<211> LENGTH: 25
<212> TYPE: DNA
<213> ORGANISM: Homo sapiens

<400> SEQUENCE: 614
ggcaaaagga gaaagggacc aagga 25

<210> SEQ ID NO 615
<211> LENGTH: 25
<212> TYPE: DNA
<213> ORGANISM: Homo sapiens

<400> SEQUENCE: 615
aacctgaaaa ctacatgaag cacaa 25

<210> SEQ ID NO 616
<211> LENGTH: 25
<212> TYPE: DNA
<213> ORGANISM: Homo sapiens

<400> SEQUENCE: 616
ctgtgggtaa aagccagtct tgcat 25

<210> SEQ ID NO 617
<211> LENGTH: 25
<212> TYPE: DNA
<213> ORGANISM: Homo sapiens

<400> SEQUENCE: 617
tgaagtgttt ttctaattat tcgac 25

<210> SEQ ID NO 618
<211> LENGTH: 25
<212> TYPE: DNA
<213> ORGANISM: Homo sapiens

<400> SEQUENCE: 618
ctccctggca cttgctcctg tctcc 25

<210> SEQ ID NO 619
<211> LENGTH: 25
<212> TYPE: DNA
<213> ORGANISM: Homo sapiens

<400> SEQUENCE: 619
atagattaag cttcttggtg aacca 25

<210> SEQ ID NO 620
<211> LENGTH: 25
<212> TYPE: DNA
<213> ORGANISM: Homo sapiens

<400> SEQUENCE: 620
cagagagaag ccgctcacca ggcct 25

<210> SEQ ID NO 621
<211> LENGTH: 25
<212> TYPE: DNA
<213> ORGANISM: Homo sapiens

<400> SEQUENCE: 621
gtctatttgg gtctgttgcc cattt 25

<210> SEQ ID NO 622
<211> LENGTH: 25
<212> TYPE: DNA
<213> ORGANISM: Homo sapiens

<400> SEQUENCE: 622
cagagagaag ccgctcacca ggcct 25

<210> SEQ ID NO 623
<211> LENGTH: 25
<212> TYPE: DNA
<213> ORGANISM: Homo sapiens

<400> SEQUENCE: 623
atagattaag cttcttggtg aacca 25

<210> SEQ ID NO 624
<211> LENGTH: 30
<212> TYPE: DNA
<213> ORGANISM: Homo sapiens

<400> SEQUENCE: 624
gcaccactgt actccagcct gggtaacaga 30

<210> SEQ ID NO 625
<211> LENGTH: 25
<212> TYPE: DNA
<213> ORGANISM: Homo sapiens

<400> SEQUENCE: 625
ccccggaaga ttctctttga atagt 25

<210> SEQ ID NO 626
<211> LENGTH: 25
<212> TYPE: DNA
<213> ORGANISM: Homo sapiens

<400> SEQUENCE: 626
tatatatgat tataattggt caaag 25

<210> SEQ ID NO 627
<211> LENGTH: 25
<212> TYPE: DNA
<213> ORGANISM: Homo sapiens

<400> SEQUENCE: 627
tctcaaagca cagaaattac agaca 25

<210> SEQ ID NO 628
<211> LENGTH: 25
<212> TYPE: DNA
<213> ORGANISM: Homo sapiens

<400> SEQUENCE: 628
gcaggttgct ctgcgggttg tgggc 25

<210> SEQ ID NO 629
<211> LENGTH: 25
<212> TYPE: DNA
<213> ORGANISM: Homo sapiens

<400> SEQUENCE: 629
tatatatgat tataattggt caaag 25

<210> SEQ ID NO 630
<211> LENGTH: 25
<212> TYPE: DNA
<213> ORGANISM: Homo sapiens

<400> SEQUENCE: 630
tatgttatat atcatataat tcact 25

<210> SEQ ID NO 631
<211> LENGTH: 25
<212> TYPE: DNA
<213> ORGANISM: Homo sapiens

<400> SEQUENCE: 631
gaagtaactg caaaactgag tcact 25

<210> SEQ ID NO 632
<211> LENGTH: 25
<212> TYPE: DNA
<213> ORGANISM: Homo sapiens

<400> SEQUENCE: 632
gaagtaactg caaaactgag tcact 25

<210> SEQ ID NO 633
<211> LENGTH: 25
<212> TYPE: DNA
<213> ORGANISM: Homo sapiens

<400> SEQUENCE: 633
tgcttcaaat atgcttctta taaat 25

<210> SEQ ID NO 634
<211> LENGTH: 25
<212> TYPE: DNA
<213> ORGANISM: Homo sapiens

<400> SEQUENCE: 634
catttgctta aaaaatatat atgta 25

<210> SEQ ID NO 635
<211> LENGTH: 25
<212> TYPE: DNA
<213> ORGANISM: Homo sapiens

<400> SEQUENCE: 635
catctcactc atccatctat ccatt 25

<210> SEQ ID NO 636
<211> LENGTH: 25
<212> TYPE: DNA
<213> ORGANISM: Homo sapiens

<400> SEQUENCE: 636
ctagtgataa gcccaagggc tatgt 25

<210> SEQ ID NO 637
<211> LENGTH: 25
<212> TYPE: DNA
<213> ORGANISM: Homo sapiens

<400> SEQUENCE: 637
tgtctagtat ttattataaa tcaga 25

<210> SEQ ID NO 638
<211> LENGTH: 25
<212> TYPE: DNA
<213> ORGANISM: Homo sapiens

<400> SEQUENCE: 638
ccccggaaga ttctctttga atagt 25

<210> SEQ ID NO 639
<211> LENGTH: 25
<212> TYPE: DNA
<213> ORGANISM: Homo sapiens

<400> SEQUENCE: 639
ggtaatggac acatcctctg atagc 25

<210> SEQ ID NO 640
<211> LENGTH: 30
<212> TYPE: DNA
<213> ORGANISM: Homo sapiens

<400> SEQUENCE: 640
ggaaaagagt ctaatcatag attattttag 30

<210> SEQ ID NO 641
<211> LENGTH: 25
<212> TYPE: DNA
<213> ORGANISM: Homo sapiens

<400> SEQUENCE: 641
tatgttatat atcatataat tcact 25

<210> SEQ ID NO 642
<211> LENGTH: 25
<212> TYPE: DNA
<213> ORGANISM: Homo sapiens

<400> SEQUENCE: 642
gaaacaaaaa ttagctgctt aaatc 25

<210> SEQ ID NO 643
<211> LENGTH: 25
<212> TYPE: DNA
<213> ORGANISM: Homo sapiens

<400> SEQUENCE: 643
tgtctagtat ttattataaa tcaga 25

<210> SEQ ID NO 644
<211> LENGTH: 25
<212> TYPE: DNA
<213> ORGANISM: Homo sapiens

<400> SEQUENCE: 644
ggtaatggac acatcctctg atagc 25

<210> SEQ ID NO 645
<211> LENGTH: 25
<212> TYPE: DNA
<213> ORGANISM: Homo sapiens

<400> SEQUENCE: 645
aatggtatca taggatgcta tgcct 25

<210> SEQ ID NO 646
<211> LENGTH: 25
<212> TYPE: DNA
<213> ORGANISM: Homo sapiens

<400> SEQUENCE: 646
gagtttccag ccttatgccc aagct 25

<210> SEQ ID NO 647
<211> LENGTH: 25
<212> TYPE: DNA
<213> ORGANISM: Homo sapiens

<400> SEQUENCE: 647
agtttcaatg acattctgga agatg 25

<210> SEQ ID NO 648
<211> LENGTH: 25
<212> TYPE: DNA
<213> ORGANISM: Homo sapiens

<400> SEQUENCE: 648
gtaagtatgg taaccttcta ttctg 25

<210> SEQ ID NO 649
<211> LENGTH: 25
<212> TYPE: DNA
<213> ORGANISM: Homo sapiens

<400> SEQUENCE: 649
agtttcaatg acattctgga agatg 25

<210> SEQ ID NO 650
<211> LENGTH: 25
<212> TYPE: DNA
<213> ORGANISM: Homo sapiens

<400> SEQUENCE: 650
tatgttatat atcatataat tcact 25

<210> SEQ ID NO 651
<211> LENGTH: 25
<212> TYPE: DNA
<213> ORGANISM: Homo sapiens

<400> SEQUENCE: 651
gcgagattgg agcaatgact aaagc 25

<210> SEQ ID NO 652
<211> LENGTH: 25
<212> TYPE: DNA
<213> ORGANISM: Homo sapiens

<400> SEQUENCE: 652
atgacaagtc ctaacaagtt gttag 25

<210> SEQ ID NO 653
<211> LENGTH: 25
<212> TYPE: DNA
<213> ORGANISM: Homo sapiens

<400> SEQUENCE: 653
ggaaatgtaa acattcaatt aatca 25

<210> SEQ ID NO 654
<211> LENGTH: 25
<212> TYPE: DNA
<213> ORGANISM: Homo sapiens

<400> SEQUENCE: 654
ttattttgtt aaaaaagagt tttaa 25

<210> SEQ ID NO 655
<211> LENGTH: 25
<212> TYPE: DNA
<213> ORGANISM: Homo sapiens

<400> SEQUENCE: 655
catctcccac cagcggaccc ttgaa 25

<210> SEQ ID NO 656
<211> LENGTH: 25
<212> TYPE: DNA
<213> ORGANISM: Homo sapiens

<400> SEQUENCE: 656
tttgtcttct gtgtctctca aagga 25

<210> SEQ ID NO 657
<211> LENGTH: 25
<212> TYPE: DNA
<213> ORGANISM: Homo sapiens

<400> SEQUENCE: 657
tctcaaagca cagaaattac agaca 25

<210> SEQ ID NO 658
<211> LENGTH: 25
<212> TYPE: DNA
<213> ORGANISM: Homo sapiens

<400> SEQUENCE: 658
gtaagtatgg taaccttcta ttctg 25

<210> SEQ ID NO 659
<211> LENGTH: 25
<212> TYPE: DNA
<213> ORGANISM: Homo sapiens

<400> SEQUENCE: 659
attaagtgtt tattttccag tttat 25

<210> SEQ ID NO 660
<211> LENGTH: 25
<212> TYPE: DNA
<213> ORGANISM: Homo sapiens

<400> SEQUENCE: 660
atggatattt cagcttctcc ttgat 25

<210> SEQ ID NO 661
<211> LENGTH: 25
<212> TYPE: DNA
<213> ORGANISM: Homo sapiens

<400> SEQUENCE: 661
gagaataatc aatgcctagg aggaa 25

<210> SEQ ID NO 662
<211> LENGTH: 25
<212> TYPE: DNA
<213> ORGANISM: Homo sapiens

<400> SEQUENCE: 662
tagcccttcc agaaggtcta ttcac 25

<210> SEQ ID NO 663
<211> LENGTH: 25
<212> TYPE: DNA
<213> ORGANISM: Homo sapiens

<400> SEQUENCE: 663
tatatatgat tataattggt caaag 25

<210> SEQ ID NO 664
<211> LENGTH: 30
<212> TYPE: DNA
<213> ORGANISM: Homo sapiens

<400> SEQUENCE: 664
acacacacac acacacacac acacagagag 30

<210> SEQ ID NO 665
<211> LENGTH: 25
<212> TYPE: DNA
<213> ORGANISM: Homo sapiens

<400> SEQUENCE: 665
catgtgccat aaaataacca gtcac 25

<210> SEQ ID NO 666
<211> LENGTH: 25
<212> TYPE: DNA
<213> ORGANISM: Homo sapiens

<400> SEQUENCE: 666
atgacaagtc ctaacaagtt gttag 25

<210> SEQ ID NO 667
<211> LENGTH: 25
<212> TYPE: DNA
<213> ORGANISM: Homo sapiens

<400> SEQUENCE: 667
gtgcacttgg gggcacaccc tggac 25

<210> SEQ ID NO 668
<211> LENGTH: 25
<212> TYPE: DNA
<213> ORGANISM: Homo sapiens

<400> SEQUENCE: 668
ccacgctgca aggtacaata ccact 25

<210> SEQ ID NO 669
<211> LENGTH: 25
<212> TYPE: DNA
<213> ORGANISM: Homo sapiens

<400> SEQUENCE: 669
gggccccaag gaaagtctgt tttcc 25

<210> SEQ ID NO 670
<211> LENGTH: 25
<212> TYPE: DNA
<213> ORGANISM: Homo sapiens

<400> SEQUENCE: 670
tctcaaagca cagaaattac agaca 25

<210> SEQ ID NO 671
<211> LENGTH: 25
<212> TYPE: DNA
<213> ORGANISM: Homo sapiens

<400> SEQUENCE: 671
tgtccatcac ctaaaatcct ccagt 25

<210> SEQ ID NO 672
<211> LENGTH: 25
<212> TYPE: DNA
<213> ORGANISM: Homo sapiens

<400> SEQUENCE: 672
gtggagtagt ggttaccagg ggctg 25

<210> SEQ ID NO 673
<211> LENGTH: 30
<212> TYPE: DNA
<213> ORGANISM: Homo sapiens

<400> SEQUENCE: 673
atatttgact ctgaatcatc ttttcttttc 30

<210> SEQ ID NO 674
<211> LENGTH: 25
<212> TYPE: DNA
<213> ORGANISM: Homo sapiens

<400> SEQUENCE: 674
ggaaatgtaa acattcaatt aatca 25

<210> SEQ ID NO 675
<211> LENGTH: 25
<212> TYPE: DNA
<213> ORGANISM: Homo sapiens

<400> SEQUENCE: 675
tctcttcaga gaaagcgtgg tcagg 25

<210> SEQ ID NO 676
<211> LENGTH: 25
<212> TYPE: DNA
<213> ORGANISM: Homo sapiens

<400> SEQUENCE: 676
actcagccct aattatttct tgcag 25

<210> SEQ ID NO 677
<211> LENGTH: 25
<212> TYPE: DNA

<213> ORGANISM: Homo sapiens

<400> SEQUENCE: 677
caaaacagat tttatggaaa aatct 25

<210> SEQ ID NO 678
<211> LENGTH: 25
<212> TYPE: DNA
<213> ORGANISM: Homo sapiens

<400> SEQUENCE: 678
tgtctagtat ttattataaa tcaga 25

<210> SEQ ID NO 679
<211> LENGTH: 25
<212> TYPE: DNA
<213> ORGANISM: Homo sapiens

<400> SEQUENCE: 679
aagttgtttt tggtgaccag aggac 25

<210> SEQ ID NO 680
<211> LENGTH: 25
<212> TYPE: DNA
<213> ORGANISM: Homo sapiens

<400> SEQUENCE: 680
aatggtatca taggatgcta tgcct 25

<210> SEQ ID NO 681
<211> LENGTH: 25
<212> TYPE: DNA
<213> ORGANISM: Homo sapiens

<400> SEQUENCE: 681
aagttgtttt tggtgaccag aggac 25

<210> SEQ ID NO 682
<211> LENGTH: 25
<212> TYPE: DNA
<213> ORGANISM: Homo sapiens

<400> SEQUENCE: 682
aagttgtttt tggtgaccag aggac 25

<210> SEQ ID NO 683
<211> LENGTH: 25
<212> TYPE: DNA
<213> ORGANISM: Homo sapiens

<400> SEQUENCE: 683
cttgctctca accgtataga ctggg 25

<210> SEQ ID NO 684
<211> LENGTH: 25
<212> TYPE: DNA
<213> ORGANISM: Homo sapiens

<400> SEQUENCE: 684
aggtcagaaa tttcaactgg ctttg 25

<210> SEQ ID NO 685
<211> LENGTH: 25

<212> TYPE: DNA
<213> ORGANISM: Homo sapiens

<400> SEQUENCE: 685
tagtagagaa aatatctcag atatg 25

<210> SEQ ID NO 686
<211> LENGTH: 25
<212> TYPE: DNA
<213> ORGANISM: Homo sapiens

<400> SEQUENCE: 686
gtccggcagg tctatgctgg gggtt 25

<210> SEQ ID NO 687
<211> LENGTH: 30
<212> TYPE: DNA
<213> ORGANISM: Homo sapiens

<400> SEQUENCE: 687
taatgcattt acgagattag gaaattagag 30

<210> SEQ ID NO 688
<211> LENGTH: 25
<212> TYPE: DNA
<213> ORGANISM: Homo sapiens

<400> SEQUENCE: 688
gaacttaagg tttagaatgt acttc 25

<210> SEQ ID NO 689
<211> LENGTH: 25
<212> TYPE: DNA
<213> ORGANISM: Homo sapiens

<400> SEQUENCE: 689
agcattgaca ctaaggttta aatgc 25

<210> SEQ ID NO 690
<211> LENGTH: 25
<212> TYPE: DNA
<213> ORGANISM: Homo sapiens

<400> SEQUENCE: 690
tatatgcaat tatgtatgaa ttttg 25

<210> SEQ ID NO 691
<211> LENGTH: 25
<212> TYPE: DNA
<213> ORGANISM: Homo sapiens

<400> SEQUENCE: 691
ccatggagag aactatgatg ataac 25

<210> SEQ ID NO 692
<211> LENGTH: 30
<212> TYPE: DNA
<213> ORGANISM: Homo sapiens

<400> SEQUENCE: 692
cctctctgtc tatgtagaac ggaaacttgc 30

<210> SEQ ID NO 693

<211> LENGTH: 25
<212> TYPE: DNA
<213> ORGANISM: Homo sapiens

<400> SEQUENCE: 693
ggccttcctg gattcagcac tcaac 25

<210> SEQ ID NO 694
<211> LENGTH: 25
<212> TYPE: DNA
<213> ORGANISM: Homo sapiens

<400> SEQUENCE: 694
aatgttctaa aatgcagcat cgaca 25

<210> SEQ ID NO 695
<211> LENGTH: 25
<212> TYPE: DNA
<213> ORGANISM: Homo sapiens

<400> SEQUENCE: 695
agtaaaagaa agcccatgaa aatga 25

<210> SEQ ID NO 696
<211> LENGTH: 25
<212> TYPE: DNA
<213> ORGANISM: Homo sapiens

<400> SEQUENCE: 696
ctccctcatc ctccactcac ctcct 25

<210> SEQ ID NO 697
<211> LENGTH: 25
<212> TYPE: DNA
<213> ORGANISM: Homo sapiens

<400> SEQUENCE: 697
gaacttaagg tttagaatgt acttc 25

<210> SEQ ID NO 698
<211> LENGTH: 25
<212> TYPE: DNA
<213> ORGANISM: Homo sapiens

<400> SEQUENCE: 698
aatatatgta tctcttatta gattt 25

<210> SEQ ID NO 699
<211> LENGTH: 25
<212> TYPE: DNA
<213> ORGANISM: Homo sapiens

<400> SEQUENCE: 699
tagatgcctt gctagtgaat cagag 25

<210> SEQ ID NO 700
<211> LENGTH: 25
<212> TYPE: DNA
<213> ORGANISM: Homo sapiens

<400> SEQUENCE: 700
gctggcattc acactctgtg ctcta 25

<210> SEQ ID NO 701
<211> LENGTH: 25
<212> TYPE: DNA
<213> ORGANISM: Homo sapiens

<400> SEQUENCE: 701
gaagacccca gaagcttcag ttctg 25

<210> SEQ ID NO 702
<211> LENGTH: 25
<212> TYPE: DNA
<213> ORGANISM: Homo sapiens

<400> SEQUENCE: 702
gagccttagt ttccgtatct actaa 25

<210> SEQ ID NO 703
<211> LENGTH: 25
<212> TYPE: DNA
<213> ORGANISM: Homo sapiens

<400> SEQUENCE: 703
gtattttatg taataataat tgaaa 25

<210> SEQ ID NO 704
<211> LENGTH: 25
<212> TYPE: DNA
<213> ORGANISM: Homo sapiens

<400> SEQUENCE: 704
ccatggagag aactatgatg ataac 25

<210> SEQ ID NO 705
<211> LENGTH: 25
<212> TYPE: DNA
<213> ORGANISM: Homo sapiens

<400> SEQUENCE: 705
agagcttgcc tgagaataaa atcac 25

<210> SEQ ID NO 706
<211> LENGTH: 25
<212> TYPE: DNA
<213> ORGANISM: Homo sapiens

<400> SEQUENCE: 706
gtccactttt tcctttcaca attac 25

<210> SEQ ID NO 707
<211> LENGTH: 25
<212> TYPE: DNA
<213> ORGANISM: Homo sapiens

<400> SEQUENCE: 707
gaacttaagg tttagaatgt acttc 25

<210> SEQ ID NO 708
<211> LENGTH: 25
<212> TYPE: DNA
<213> ORGANISM: Homo sapiens

<400> SEQUENCE: 708
acatagtagc tgtttgttca gtaaa 25

<210> SEQ ID NO 709
<211> LENGTH: 25
<212> TYPE: DNA
<213> ORGANISM: Homo sapiens

<400> SEQUENCE: 709
gaacttaagg tttagaatgt acttc 25

<210> SEQ ID NO 710
<211> LENGTH: 25
<212> TYPE: DNA
<213> ORGANISM: Homo sapiens

<400> SEQUENCE: 710
tggaaatgtg tacttggatg aagaa 25

<210> SEQ ID NO 711
<211> LENGTH: 25
<212> TYPE: DNA
<213> ORGANISM: Homo sapiens

<400> SEQUENCE: 711
agcattgaca ctaaggttta aatgc 25

<210> SEQ ID NO 712
<211> LENGTH: 30
<212> TYPE: DNA
<213> ORGANISM: Homo sapiens

<400> SEQUENCE: 712
ctcagtcccg cctacaatct agccatgggg 30

<210> SEQ ID NO 713
<211> LENGTH: 25
<212> TYPE: DNA
<213> ORGANISM: Homo sapiens

<400> SEQUENCE: 713
tgtggcatct ttcctctgtc ctatg 25

<210> SEQ ID NO 714
<211> LENGTH: 25
<212> TYPE: DNA
<213> ORGANISM: Homo sapiens

<400> SEQUENCE: 714
tcttgctttt tatcaaatct gtcac 25

<210> SEQ ID NO 715
<211> LENGTH: 25
<212> TYPE: DNA
<213> ORGANISM: Homo sapiens

<400> SEQUENCE: 715
gattttaatt ttaaaaataa gactt 25

<210> SEQ ID NO 716
<211> LENGTH: 30
<212> TYPE: DNA
<213> ORGANISM: Homo sapiens

<400> SEQUENCE: 716
tatggcatgg tagagagaga gccctactca 30

<210> SEQ ID NO 717
<211> LENGTH: 25
<212> TYPE: DNA
<213> ORGANISM: Homo sapiens

<400> SEQUENCE: 717
gtattttatg taataataat tgaaa 25

<210> SEQ ID NO 718
<211> LENGTH: 25
<212> TYPE: DNA
<213> ORGANISM: Homo sapiens

<400> SEQUENCE: 718
catcaaaatc tagagttcca gttac 25

<210> SEQ ID NO 719
<211> LENGTH: 25
<212> TYPE: DNA
<213> ORGANISM: Homo sapiens

<400> SEQUENCE: 719
ccttcttcac actgagtcca cctgc 25

<210> SEQ ID NO 720
<211> LENGTH: 25
<212> TYPE: DNA
<213> ORGANISM: Homo sapiens

<400> SEQUENCE: 720
tgctgggtcg cggcagtgat caacc 25

<210> SEQ ID NO 721
<211> LENGTH: 25
<212> TYPE: DNA
<213> ORGANISM: Homo sapiens

<400> SEQUENCE: 721
gtctacctgc tgtatctcct gccat 25

<210> SEQ ID NO 722
<211> LENGTH: 25
<212> TYPE: DNA
<213> ORGANISM: Homo sapiens

<400> SEQUENCE: 722
acatagtagc tgtttgttca gtaaa 25

<210> SEQ ID NO 723
<211> LENGTH: 25
<212> TYPE: DNA
<213> ORGANISM: Homo sapiens

<400> SEQUENCE: 723
gtagttcctt ggccagagct ggtcg 25

<210> SEQ ID NO 724
<211> LENGTH: 25
<212> TYPE: DNA
<213> ORGANISM: Homo sapiens

<400> SEQUENCE: 724
gccagctgaa aactgtatag ccatt 25

<210> SEQ ID NO 725
<211> LENGTH: 30
<212> TYPE: DNA
<213> ORGANISM: Homo sapiens

<400> SEQUENCE: 725
aaaatatgct cactggctat ctatggccca 30

<210> SEQ ID NO 726
<211> LENGTH: 25
<212> TYPE: DNA
<213> ORGANISM: Homo sapiens

<400> SEQUENCE: 726
gttttttttg ttttgttttg ttttg 25

<210> SEQ ID NO 727
<211> LENGTH: 25
<212> TYPE: DNA
<213> ORGANISM: Homo sapiens

<400> SEQUENCE: 727
ttcccaaata taacctagaa agaaa 25

<210> SEQ ID NO 728
<211> LENGTH: 30
<212> TYPE: DNA
<213> ORGANISM: Homo sapiens

<400> SEQUENCE: 728
gagacagaaa gaaggcaaat ctttgggatg 30

<210> SEQ ID NO 729
<211> LENGTH: 25
<212> TYPE: DNA
<213> ORGANISM: Homo sapiens

<400> SEQUENCE: 729
aagttttcct gtaagttagc tccca 25

<210> SEQ ID NO 730
<211> LENGTH: 25
<212> TYPE: DNA
<213> ORGANISM: Homo sapiens

<400> SEQUENCE: 730
ttaccttatc taggtcctta ggaca 25

<210> SEQ ID NO 731
<211> LENGTH: 25
<212> TYPE: DNA
<213> ORGANISM: Homo sapiens

<400> SEQUENCE: 731
acacacttgt gaaagttttt ttttc 25

<210> SEQ ID NO 732
<211> LENGTH: 30
<212> TYPE: DNA
<213> ORGANISM: Homo sapiens

<400> SEQUENCE: 732
ttctccacag gcgaaaagca gatgcgcttc 30

<210> SEQ ID NO 733
<211> LENGTH: 30
<212> TYPE: DNA
<213> ORGANISM: Homo sapiens

<400> SEQUENCE: 733
cctctctgtc tatgtagaac ggaaacttgc 30

<210> SEQ ID NO 734
<211> LENGTH: 25
<212> TYPE: DNA
<213> ORGANISM: Homo sapiens

<400> SEQUENCE: 734
taggatgtaa tttccagcac cactg 25

<210> SEQ ID NO 735
<211> LENGTH: 30
<212> TYPE: DNA
<213> ORGANISM: Homo sapiens

<400> SEQUENCE: 735
tatggcatgg tagagagaga gccctactca 30

<210> SEQ ID NO 736
<211> LENGTH: 25
<212> TYPE: DNA
<213> ORGANISM: Homo sapiens

<400> SEQUENCE: 736
caaataacca agtaatccaa cttgc 25

<210> SEQ ID NO 737
<211> LENGTH: 25
<212> TYPE: DNA
<213> ORGANISM: Homo sapiens

<400> SEQUENCE: 737
atgatgtaag ttttagatac ccaaa 25

<210> SEQ ID NO 738
<211> LENGTH: 25
<212> TYPE: DNA
<213> ORGANISM: Homo sapiens

<400> SEQUENCE: 738
agagggaccc ttggcagatc ctcag 25

<210> SEQ ID NO 739
<211> LENGTH: 25
<212> TYPE: DNA
<213> ORGANISM: Homo sapiens

<400> SEQUENCE: 739
agctcaagaa agactgcttc aggca 25

<210> SEQ ID NO 740
<211> LENGTH: 25
<212> TYPE: DNA
<213> ORGANISM: Homo sapiens

<400> SEQUENCE: 740
tcctaaggac tctacaggct tttag 25

<210> SEQ ID NO 741
<211> LENGTH: 25
<212> TYPE: DNA
<213> ORGANISM: Homo sapiens

<400> SEQUENCE: 741
ctacatttgt tgaagactta ctgcc 25

<210> SEQ ID NO 742
<211> LENGTH: 25
<212> TYPE: DNA
<213> ORGANISM: Homo sapiens

<400> SEQUENCE: 742
ttgataatga agatggttaa aagac 25

<210> SEQ ID NO 743
<211> LENGTH: 25
<212> TYPE: DNA
<213> ORGANISM: Homo sapiens

<400> SEQUENCE: 743
gtccggcagg tctatgctgg gggtt 25

<210> SEQ ID NO 744
<211> LENGTH: 25
<212> TYPE: DNA
<213> ORGANISM: Homo sapiens

<400> SEQUENCE: 744
ttactattct agcctttatt tgggt 25

<210> SEQ ID NO 745
<211> LENGTH: 25
<212> TYPE: DNA
<213> ORGANISM: Homo sapiens

<400> SEQUENCE: 745
taatttttcc attgttaaca tttga 25

<210> SEQ ID NO 746
<211> LENGTH: 25
<212> TYPE: DNA
<213> ORGANISM: Homo sapiens

<400> SEQUENCE: 746
taaatatcca acctctggaa atggt 25

<210> SEQ ID NO 747
<211> LENGTH: 25
<212> TYPE: DNA
<213> ORGANISM: Homo sapiens

<400> SEQUENCE: 747
gctcaacctg aaacagacag cactc 25

<210> SEQ ID NO 748
<211> LENGTH: 25
<212> TYPE: DNA
<213> ORGANISM: Homo sapiens

<400> SEQUENCE: 748
gctcaacctg aaacagacag cactc 25

<210> SEQ ID NO 749
<211> LENGTH: 25
<212> TYPE: DNA
<213> ORGANISM: Homo sapiens

<400> SEQUENCE: 749
catctttagc ttgtcttgca aatac 25

<210> SEQ ID NO 750
<211> LENGTH: 30
<212> TYPE: DNA
<213> ORGANISM: Homo sapiens

<400> SEQUENCE: 750
gtagaggaac acgtccctaa ggatttcact 30

<210> SEQ ID NO 751
<211> LENGTH: 30
<212> TYPE: DNA
<213> ORGANISM: Homo sapiens

<400> SEQUENCE: 751
cttgaatgct tgatgaaacc ttcccaatcc 30

<210> SEQ ID NO 752
<211> LENGTH: 25
<212> TYPE: DNA
<213> ORGANISM: Homo sapiens

<400> SEQUENCE: 752
tggctaagac cacgggcagg gctcc 25

<210> SEQ ID NO 753
<211> LENGTH: 25
<212> TYPE: DNA
<213> ORGANISM: Homo sapiens

<400> SEQUENCE: 753
gcctctgact gctggagctc actga 25

<210> SEQ ID NO 754
<211> LENGTH: 25
<212> TYPE: DNA
<213> ORGANISM: Homo sapiens

<400> SEQUENCE: 754
tccaatttac gtaccaagaa accaa 25

<210> SEQ ID NO 755
<211> LENGTH: 30
<212> TYPE: DNA
<213> ORGANISM: Homo sapiens

<400> SEQUENCE: 755
ttaatataaa aaagtacatt gcttttcttt 30

<210> SEQ ID NO 756
<211> LENGTH: 25
<212> TYPE: DNA

<213> ORGANISM: Homo sapiens

<400> SEQUENCE: 756
atccaggcag tgtgttcttt taaaa 25

<210> SEQ ID NO 757
<211> LENGTH: 30
<212> TYPE: DNA
<213> ORGANISM: Homo sapiens

<400> SEQUENCE: 757
cttctgtaat gatgctccct ttgcctcatc 30

<210> SEQ ID NO 758
<211> LENGTH: 25
<212> TYPE: DNA
<213> ORGANISM: Homo sapiens

<400> SEQUENCE: 758
tctgaaggcc aggagctgct gtaga 25

<210> SEQ ID NO 759
<211> LENGTH: 25
<212> TYPE: DNA
<213> ORGANISM: Homo sapiens

<400> SEQUENCE: 759
aaagtttggt ttcataaaga gattt 25

<210> SEQ ID NO 760
<211> LENGTH: 25
<212> TYPE: DNA
<213> ORGANISM: Homo sapiens

<400> SEQUENCE: 760
gctatacttc actttatttt cagcc 25

<210> SEQ ID NO 761
<211> LENGTH: 25
<212> TYPE: DNA
<213> ORGANISM: Homo sapiens

<400> SEQUENCE: 761
tgggacactc ctgcctatgt gcatg 25

<210> SEQ ID NO 762
<211> LENGTH: 25
<212> TYPE: DNA
<213> ORGANISM: Homo sapiens

<400> SEQUENCE: 762
gctcaacctg aaacagacag cactc 25

<210> SEQ ID NO 763
<211> LENGTH: 25
<212> TYPE: DNA
<213> ORGANISM: Homo sapiens

<400> SEQUENCE: 763
gctcaacctg aaacagacag cactc 25

<210> SEQ ID NO 764
<211> LENGTH: 25

-continued

<212> TYPE: DNA
<213> ORGANISM: Homo sapiens

<400> SEQUENCE: 764
ggtttggttc cagaccacca caata 25

<210> SEQ ID NO 765
<211> LENGTH: 25
<212> TYPE: DNA
<213> ORGANISM: Homo sapiens

<400> SEQUENCE: 765
gcaaattctt gtcaataaat atgct 25

<210> SEQ ID NO 766
<211> LENGTH: 25
<212> TYPE: DNA
<213> ORGANISM: Homo sapiens

<400> SEQUENCE: 766
aaagagtcct tggaggtcca gaagg 25

<210> SEQ ID NO 767
<211> LENGTH: 25
<212> TYPE: DNA
<213> ORGANISM: Homo sapiens

<400> SEQUENCE: 767
ttctacttag aactaaacat cccca 25

<210> SEQ ID NO 768
<211> LENGTH: 25
<212> TYPE: DNA
<213> ORGANISM: Homo sapiens

<400> SEQUENCE: 768
ttactattct agcctttatt tgggt 25

<210> SEQ ID NO 769
<211> LENGTH: 25
<212> TYPE: DNA
<213> ORGANISM: Homo sapiens

<400> SEQUENCE: 769
catcacactt actttctata tatag 25

<210> SEQ ID NO 770
<211> LENGTH: 25
<212> TYPE: DNA
<213> ORGANISM: Homo sapiens

<400> SEQUENCE: 770
aagtttttcc ccatggaaac atact 25

<210> SEQ ID NO 771
<211> LENGTH: 25
<212> TYPE: DNA
<213> ORGANISM: Homo sapiens

<400> SEQUENCE: 771
catttgtaag tacaagctaa catgt 25

<210> SEQ ID NO 772

<211> LENGTH: 25
<212> TYPE: DNA
<213> ORGANISM: Homo sapiens

<400> SEQUENCE: 772
accttcaatc tgtacatgtc cattt 25

<210> SEQ ID NO 773
<211> LENGTH: 25
<212> TYPE: DNA
<213> ORGANISM: Homo sapiens

<400> SEQUENCE: 773
tacatgacag gcatttaatt aatac 25

<210> SEQ ID NO 774
<211> LENGTH: 25
<212> TYPE: DNA
<213> ORGANISM: Homo sapiens

<400> SEQUENCE: 774
gtcctgccag ctcccgggtc tggct 25

<210> SEQ ID NO 775
<211> LENGTH: 25
<212> TYPE: DNA
<213> ORGANISM: Homo sapiens

<400> SEQUENCE: 775
ttacgtatat tcttcttaga aacaa 25

<210> SEQ ID NO 776
<211> LENGTH: 25
<212> TYPE: DNA
<213> ORGANISM: Homo sapiens

<400> SEQUENCE: 776
agatttaagg agaaaatgga acctg 25

<210> SEQ ID NO 777
<211> LENGTH: 25
<212> TYPE: DNA
<213> ORGANISM: Homo sapiens

<400> SEQUENCE: 777
agccttgcca ttcttctagc ccaca 25

<210> SEQ ID NO 778
<211> LENGTH: 25
<212> TYPE: DNA
<213> ORGANISM: Homo sapiens

<400> SEQUENCE: 778
agtaaaagaa agcccatgaa aatga 25

<210> SEQ ID NO 779
<211> LENGTH: 25
<212> TYPE: DNA
<213> ORGANISM: Homo sapiens

<400> SEQUENCE: 779
tggaaatgtg tacttggatg aagaa 25

<210> SEQ ID NO 780
<211> LENGTH: 25
<212> TYPE: DNA
<213> ORGANISM: Homo sapiens

<400> SEQUENCE: 780
gcaggttgct ctgcgggttg tgggc 25

<210> SEQ ID NO 781
<211> LENGTH: 25
<212> TYPE: DNA
<213> ORGANISM: Homo sapiens

<400> SEQUENCE: 781
gcgcccagcc atgggctgca gatat 25

<210> SEQ ID NO 782
<211> LENGTH: 25
<212> TYPE: DNA
<213> ORGANISM: Homo sapiens

<400> SEQUENCE: 782
ctctcagccg ggcgcagtgg ctcaa 25

<210> SEQ ID NO 783
<211> LENGTH: 25
<212> TYPE: DNA
<213> ORGANISM: Homo sapiens

<400> SEQUENCE: 783
aagttttcct gtaagttagc tccca 25

<210> SEQ ID NO 784
<211> LENGTH: 30
<212> TYPE: DNA
<213> ORGANISM: Homo sapiens

<400> SEQUENCE: 784
aggcttaggg agatttaagg atcatgctga 30

<210> SEQ ID NO 785
<211> LENGTH: 25
<212> TYPE: DNA
<213> ORGANISM: Homo sapiens

<400> SEQUENCE: 785
gtggatttgt ttctgggctc tattc 25

<210> SEQ ID NO 786
<211> LENGTH: 25
<212> TYPE: DNA
<213> ORGANISM: Homo sapiens

<400> SEQUENCE: 786
attggagtta aaagttattt atgca 25

<210> SEQ ID NO 787
<211> LENGTH: 25
<212> TYPE: DNA
<213> ORGANISM: Homo sapiens

<400> SEQUENCE: 787
acacacttgt gaaagttttt ttttc 25

<210> SEQ ID NO 788
<211> LENGTH: 25
<212> TYPE: DNA
<213> ORGANISM: Homo sapiens

<400> SEQUENCE: 788
aatactatac tcttttgatt acaat 25

<210> SEQ ID NO 789
<211> LENGTH: 25
<212> TYPE: DNA
<213> ORGANISM: Homo sapiens

<400> SEQUENCE: 789
tgaccacaaa atgctggcag ctcgg 25

<210> SEQ ID NO 790
<211> LENGTH: 25
<212> TYPE: DNA
<213> ORGANISM: Homo sapiens

<400> SEQUENCE: 790
agcctgtgtg tggctggcat tcccg 25

<210> SEQ ID NO 791
<211> LENGTH: 25
<212> TYPE: DNA
<213> ORGANISM: Homo sapiens

<400> SEQUENCE: 791
tggataacac aatgttaaag aagat 25

<210> SEQ ID NO 792
<211> LENGTH: 25
<212> TYPE: DNA
<213> ORGANISM: Homo sapiens

<400> SEQUENCE: 792
tgcctgaaga tgttaccgag agggc 25

<210> SEQ ID NO 793
<211> LENGTH: 25
<212> TYPE: DNA
<213> ORGANISM: Homo sapiens

<400> SEQUENCE: 793
acagggatct agattgctta acttt 25

<210> SEQ ID NO 794
<211> LENGTH: 25
<212> TYPE: DNA
<213> ORGANISM: Homo sapiens

<400> SEQUENCE: 794
catcaaaatc tagagttcca gttac 25

<210> SEQ ID NO 795
<211> LENGTH: 25
<212> TYPE: DNA
<213> ORGANISM: Homo sapiens

<400> SEQUENCE: 795
gccagtggcg gcccctccgt cttcc 25

<210> SEQ ID NO 796
<211> LENGTH: 25
<212> TYPE: DNA
<213> ORGANISM: Homo sapiens

<400> SEQUENCE: 796
agtggccagg cctacaaagc ttcgc 25

<210> SEQ ID NO 797
<211> LENGTH: 25
<212> TYPE: DNA
<213> ORGANISM: Homo sapiens

<400> SEQUENCE: 797
gtccactttt tcctttcaca attac 25

<210> SEQ ID NO 798
<211> LENGTH: 25
<212> TYPE: DNA
<213> ORGANISM: Homo sapiens

<400> SEQUENCE: 798
gcgcccagcc atgggctgca gatat 25

<210> SEQ ID NO 799
<211> LENGTH: 25
<212> TYPE: DNA
<213> ORGANISM: Homo sapiens

<400> SEQUENCE: 799
gcgcccagcc atgggctgca gatat 25

<210> SEQ ID NO 800
<211> LENGTH: 25
<212> TYPE: DNA
<213> ORGANISM: Homo sapiens

<400> SEQUENCE: 800
gccttcacaa gacttttcta acagc 25

<210> SEQ ID NO 801
<211> LENGTH: 25
<212> TYPE: DNA
<213> ORGANISM: Homo sapiens

<400> SEQUENCE: 801
tatatgcaat tatgtatgaa ttttg 25

<210> SEQ ID NO 802
<211> LENGTH: 25
<212> TYPE: DNA
<213> ORGANISM: Homo sapiens

<400> SEQUENCE: 802
ctacacattc ttgtcaggta cctca 25

<210> SEQ ID NO 803
<211> LENGTH: 25
<212> TYPE: DNA
<213> ORGANISM: Homo sapiens

<400> SEQUENCE: 803

-continued tgggcttctg gtggtgactg cacga 25

<210> SEQ ID NO 804
<211> LENGTH: 25
<212> TYPE: DNA
<213> ORGANISM: Homo sapiens

<400> SEQUENCE: 804
gaaacaaaaa ttagctgctt aaatc 25

<210> SEQ ID NO 805
<211> LENGTH: 25
<212> TYPE: DNA
<213> ORGANISM: Homo sapiens

<400> SEQUENCE: 805
atgtaggaaa ggcaagacaa atgct 25

<210> SEQ ID NO 806
<211> LENGTH: 25
<212> TYPE: DNA
<213> ORGANISM: Homo sapiens

<400> SEQUENCE: 806
attaagtgtt tattttccag tttat 25

<210> SEQ ID NO 807
<211> LENGTH: 25
<212> TYPE: DNA
<213> ORGANISM: Homo sapiens

<400> SEQUENCE: 807
atggatattt cagcttctcc ttgat 25

<210> SEQ ID NO 808
<211> LENGTH: 25
<212> TYPE: DNA
<213> ORGANISM: Homo sapiens

<400> SEQUENCE: 808
gagaataatc aatgcctagg aggaa 25

<210> SEQ ID NO 809
<211> LENGTH: 25
<212> TYPE: DNA
<213> ORGANISM: Homo sapiens

<400> SEQUENCE: 809
tagcccttcc agaaggtcta ttcac 25

<210> SEQ ID NO 810
<211> LENGTH: 25
<212> TYPE: DNA
<213> ORGANISM: Homo sapiens

<400> SEQUENCE: 810
ctcagtcccg cctacaatct agcca 25

<210> SEQ ID NO 811
<211> LENGTH: 25
<212> TYPE: DNA
<213> ORGANISM: Homo sapiens

<400> SEQUENCE: 811
gcccatctca taagaggcct ctcta 25

<210> SEQ ID NO 812
<211> LENGTH: 25
<212> TYPE: DNA
<213> ORGANISM: Homo sapiens

<400> SEQUENCE: 812
gacctacttc ccctaaggtc ccagc 25

<210> SEQ ID NO 813
<211> LENGTH: 25
<212> TYPE: DNA
<213> ORGANISM: Homo sapiens

<400> SEQUENCE: 813
tgggcttctg gtggtgactg cacga 25

<210> SEQ ID NO 814
<211> LENGTH: 25
<212> TYPE: DNA
<213> ORGANISM: Homo sapiens

<400> SEQUENCE: 814
ggcctttaag tgattaatta aggtt 25

<210> SEQ ID NO 815
<211> LENGTH: 25
<212> TYPE: DNA
<213> ORGANISM: Homo sapiens

<400> SEQUENCE: 815
ttgagaggag catactcctt tcgat 25

<210> SEQ ID NO 816
<211> LENGTH: 25
<212> TYPE: DNA
<213> ORGANISM: Homo sapiens

<400> SEQUENCE: 816
aggaacggag cacgatacat gccac 25

<210> SEQ ID NO 817
<211> LENGTH: 25
<212> TYPE: DNA
<213> ORGANISM: Homo sapiens

<400> SEQUENCE: 817
ctttctttgt ctttattgtc catgt 25

<210> SEQ ID NO 818
<211> LENGTH: 25
<212> TYPE: DNA
<213> ORGANISM: Homo sapiens

<400> SEQUENCE: 818
gtttcttctc ccactcataa acctt 25

<210> SEQ ID NO 819
<211> LENGTH: 25
<212> TYPE: DNA
<213> ORGANISM: Homo sapiens

<400> SEQUENCE: 819
tgaatctaat gatttggaaa tgaaa 25

<210> SEQ ID NO 820
<211> LENGTH: 25
<212> TYPE: DNA
<213> ORGANISM: Homo sapiens

<400> SEQUENCE: 820
cactgaggga tgaagtctgt ggaac 25

<210> SEQ ID NO 821
<211> LENGTH: 25
<212> TYPE: DNA
<213> ORGANISM: Homo sapiens

<400> SEQUENCE: 821
ttggagcctc tcaggcaatt tccac 25

<210> SEQ ID NO 822
<211> LENGTH: 25
<212> TYPE: DNA
<213> ORGANISM: Homo sapiens

<400> SEQUENCE: 822
ggactatact gcagagcaga tggtg 25

<210> SEQ ID NO 823
<211> LENGTH: 25
<212> TYPE: DNA
<213> ORGANISM: Homo sapiens

<400> SEQUENCE: 823
gctgtaatcc caacactttg ggagg 25

<210> SEQ ID NO 824
<211> LENGTH: 25
<212> TYPE: DNA
<213> ORGANISM: Homo sapiens

<400> SEQUENCE: 824
gggctgtgca gtggctcatg cctgt 25

<210> SEQ ID NO 825
<211> LENGTH: 25
<212> TYPE: DNA
<213> ORGANISM: Homo sapiens

<400> SEQUENCE: 825
cctggcttac tgagtattct tgcct 25

<210> SEQ ID NO 826
<211> LENGTH: 25
<212> TYPE: DNA
<213> ORGANISM: Homo sapiens

<400> SEQUENCE: 826
atttactatt ttttttttc tgaga 25

<210> SEQ ID NO 827
<211> LENGTH: 25
<212> TYPE: DNA
<213> ORGANISM: Homo sapiens

<400> SEQUENCE: 827
taatcacaat tgacctatct tcaag 25

<210> SEQ ID NO 828
<211> LENGTH: 25
<212> TYPE: DNA
<213> ORGANISM: Homo sapiens

<400> SEQUENCE: 828
tttgcttatg tgctctcctc cactt 25

<210> SEQ ID NO 829
<211> LENGTH: 25
<212> TYPE: DNA
<213> ORGANISM: Homo sapiens

<400> SEQUENCE: 829
ctctcagccg ggcgcagtgg ctcaa 25

<210> SEQ ID NO 830
<211> LENGTH: 25
<212> TYPE: DNA
<213> ORGANISM: Homo sapiens

<400> SEQUENCE: 830
ttgaaaaatg ttgcccctta gggta 25

<210> SEQ ID NO 831
<211> LENGTH: 25
<212> TYPE: DNA
<213> ORGANISM: Homo sapiens

<400> SEQUENCE: 831
gaagacccca gaagcttcag ttctg 25

<210> SEQ ID NO 832
<211> LENGTH: 25
<212> TYPE: DNA
<213> ORGANISM: Homo sapiens

<400> SEQUENCE: 832
acatagtagc tgtttgttca gtaaa 25

<210> SEQ ID NO 833
<211> LENGTH: 25
<212> TYPE: DNA
<213> ORGANISM: Homo sapiens

<400> SEQUENCE: 833
taacgcagtg atcctcaaac tttgg 25

<210> SEQ ID NO 834
<211> LENGTH: 25
<212> TYPE: DNA
<213> ORGANISM: Homo sapiens

<400> SEQUENCE: 834
gaactaagag gctgtatgtg tgacc 25

<210> SEQ ID NO 835
<211> LENGTH: 25
<212> TYPE: DNA

<213> ORGANISM: Homo sapiens

<400> SEQUENCE: 835
agaaggatca ggctatggaa atagg 25

<210> SEQ ID NO 836
<211> LENGTH: 25
<212> TYPE: DNA
<213> ORGANISM: Homo sapiens

<400> SEQUENCE: 836
tctcttcaga gaaagcgtgg tcagg 25

<210> SEQ ID NO 837
<211> LENGTH: 25
<212> TYPE: DNA
<213> ORGANISM: Homo sapiens

<400> SEQUENCE: 837
actcagccct aattatttct tgcag 25

<210> SEQ ID NO 838
<211> LENGTH: 25
<212> TYPE: DNA
<213> ORGANISM: Homo sapiens

<400> SEQUENCE: 838
atatgctgga tttcttttaa tatta 25

<210> SEQ ID NO 839
<211> LENGTH: 25
<212> TYPE: DNA
<213> ORGANISM: Homo sapiens

<400> SEQUENCE: 839
tcttcactct cactaatata agttt 25

<210> SEQ ID NO 840
<211> LENGTH: 30
<212> TYPE: DNA
<213> ORGANISM: Homo sapiens

<400> SEQUENCE: 840
gggctagttg caagaggacg cgtgacggct 30

<210> SEQ ID NO 841
<211> LENGTH: 25
<212> TYPE: DNA
<213> ORGANISM: Homo sapiens

<400> SEQUENCE: 841
caaaacagat tttatggaaa aatct 25

<210> SEQ ID NO 842
<211> LENGTH: 25
<212> TYPE: DNA
<213> ORGANISM: Homo sapiens

<400> SEQUENCE: 842
acagtcctgg cttcctctcc ttatc 25

<210> SEQ ID NO 843
<211> LENGTH: 30

<212> TYPE: DNA
<213> ORGANISM: Homo sapiens

<400> SEQUENCE: 843
tttgggtttt aaacatgaga aattggcaat 30

<210> SEQ ID NO 844
<211> LENGTH: 25
<212> TYPE: DNA
<213> ORGANISM: Homo sapiens

<400> SEQUENCE: 844
tagagataga tgtaaagaga tatag 25

<210> SEQ ID NO 845
<211> LENGTH: 25
<212> TYPE: DNA
<213> ORGANISM: Homo sapiens

<400> SEQUENCE: 845
atagtgcgga agtagctggt gctgt 25

<210> SEQ ID NO 846
<211> LENGTH: 25
<212> TYPE: DNA
<213> ORGANISM: Homo sapiens

<400> SEQUENCE: 846
ggagatgcat gtgtggtggg tgaaa 25

<210> SEQ ID NO 847
<211> LENGTH: 25
<212> TYPE: DNA
<213> ORGANISM: Homo sapiens

<400> SEQUENCE: 847
aagttttgct gacacaagca gggaa 25

<210> SEQ ID NO 848
<211> LENGTH: 25
<212> TYPE: DNA
<213> ORGANISM: Homo sapiens

<400> SEQUENCE: 848
ggagatgcat gtgtggtggg tgaaa 25

<210> SEQ ID NO 849
<211> LENGTH: 25
<212> TYPE: DNA
<213> ORGANISM: Homo sapiens

<400> SEQUENCE: 849
acagatgaca aagccagggt cttag 25

<210> SEQ ID NO 850
<211> LENGTH: 25
<212> TYPE: DNA
<213> ORGANISM: Homo sapiens

<400> SEQUENCE: 850
acccaactga tggaagagat gactc 25

<210> SEQ ID NO 851

<211> LENGTH: 25
<212> TYPE: DNA
<213> ORGANISM: Homo sapiens

<400> SEQUENCE: 851
ccatggagag aactatgatg ataac 25

<210> SEQ ID NO 852
<211> LENGTH: 25
<212> TYPE: DNA
<213> ORGANISM: Homo sapiens

<400> SEQUENCE: 852
ttcctggaag gactgaggta aaggg 25

<210> SEQ ID NO 853
<211> LENGTH: 25
<212> TYPE: DNA
<213> ORGANISM: Homo sapiens

<400> SEQUENCE: 853
gagtggaagg ggcgcgcctg cacat 25

<210> SEQ ID NO 854
<211> LENGTH: 25
<212> TYPE: DNA
<213> ORGANISM: Homo sapiens

<400> SEQUENCE: 854
ttaactggat tgtttgtctt tttgt 25

<210> SEQ ID NO 855
<211> LENGTH: 25
<212> TYPE: DNA
<213> ORGANISM: Homo sapiens

<400> SEQUENCE: 855
gagtggaagg ggcgcgcctg cacat 25

<210> SEQ ID NO 856
<211> LENGTH: 25
<212> TYPE: DNA
<213> ORGANISM: Homo sapiens

<400> SEQUENCE: 856
ttcctggaag gactgaggta aaggg 25

<210> SEQ ID NO 857
<211> LENGTH: 30
<212> TYPE: DNA
<213> ORGANISM: Homo sapiens

<400> SEQUENCE: 857
caagacgctg tctctggaaa aaaaaatgaa 30

<210> SEQ ID NO 858
<211> LENGTH: 114
<212> TYPE: PRT
<213> ORGANISM: Homo sapiens

<400> SEQUENCE: 858

Met Arg Leu Leu Ile Leu Ala Leu Leu Gly Ile Cys Ser Leu Thr Ala
1 5 10 15

```
Tyr Ile Val Glu Gly Val Gly Ser Glu Val Ser Asp Lys Arg Thr Cys
            20                  25                  30

Val Ser Leu Thr Thr Gln Arg Leu Pro Val Ser Arg Ile Lys Thr Tyr
        35                  40                  45

Thr Ile Thr Glu Gly Ser Leu Arg Ala Val Ile Phe Ile Thr Lys Arg
    50                  55                  60

Gly Leu Lys Val Cys Ala Asp Pro Gln Ala Thr Trp Val Arg Asp Val
65                  70                  75                  80

Val Arg Ser Met Asp Arg Lys Ser Asn Thr Arg Asn Asn Met Ile Gln
                85                  90                  95

Thr Lys Pro Thr Gly Thr Gln Gln Ser Thr Asn Thr Ala Val Thr Leu
            100                 105                 110

Thr Gly


<210> SEQ ID NO 859
<211> LENGTH: 201
<212> TYPE: PRT
<213> ORGANISM: Homo sapiens

<400> SEQUENCE: 859

Met Asp Leu Ser Leu Leu Trp Val Leu Leu Pro Leu Val Thr Met Ala
1               5                   10                  15

Trp Gly Gln Tyr Gly Asp Tyr Gly Tyr Pro Tyr Gln Gln Tyr His Asp
            20                  25                  30

Tyr Ser Asp Asp Gly Trp Val Asn Leu Asn Arg Gln Gly Phe Ser Tyr
        35                  40                  45

Gln Cys Pro Gln Gly Gln Val Ile Val Ala Val Arg Ser Ile Phe Ser
    50                  55                  60

Lys Lys Glu Gly Ser Asp Arg Gln Trp Asn Tyr Ala Cys Met Pro Thr
65                  70                  75                  80

Pro Gln Ser Leu Gly Glu Pro Thr Glu Cys Trp Trp Glu Glu Ile Asn
                85                  90                  95

Arg Ala Gly Met Glu Trp Tyr Gln Thr Cys Ser Asn Asn Gly Leu Val
            100                 105                 110

Ala Gly Phe Gln Ser Arg Tyr Phe Glu Ser Val Leu Asp Arg Glu Trp
        115                 120                 125

Gln Phe Tyr Cys Cys Arg Tyr Ser Lys Arg Cys Pro Tyr Ser Cys Trp
    130                 135                 140

Leu Thr Thr Glu Tyr Pro Gly His Tyr Gly Glu Glu Met Asp Met Ile
145                 150                 155                 160

Ser Tyr Asn Tyr Asp Tyr Tyr Ile Arg Gly Ala Thr Thr Thr Phe Ser
                165                 170                 175

Ala Val Glu Arg Asp Arg Gln Trp Lys Phe Ile Met Cys Arg Met Thr
            180                 185                 190

Glu Tyr Asp Cys Glu Phe Ala Asn Val
        195                 200


<210> SEQ ID NO 860
<211> LENGTH: 120
<212> TYPE: PRT
<213> ORGANISM: Homo sapiens

<400> SEQUENCE: 860

Met Glu Arg Val Gln Pro Leu Glu Glu Asn Val Gly Asn Ala Ala Arg
1               5                   10                  15

Pro Arg Phe Glu Arg Asn Lys Leu Leu Leu Val Ala Ser Val Ile Gln
```

```
            20                  25                  30

Gly Leu Gly Leu Leu Leu Cys Phe Thr Tyr Ile Cys Leu His Phe Ser
        35                  40                  45

Ala Leu Gln Val Ser His Arg Tyr Pro Arg Ile Gln Ser Ile Lys Val
    50                  55                  60

Gln Phe Thr Glu Tyr Lys Lys Glu Lys Gly Phe Ile Leu Thr Ser Gln
65                  70                  75                  80

Lys Glu Asp Glu Ile Met Lys Val Gln Asn Asn Ser Val Ile Ile Asn
                85                  90                  95

Cys Asp Gly Phe Tyr Leu Ile Ser Leu Lys Gly Tyr Phe Ser Gln Glu
            100                 105                 110

Val Asn Ile Ser Leu His Tyr Gln
        115                 120


<210> SEQ ID NO 861
<211> LENGTH: 196
<212> TYPE: PRT
<213> ORGANISM: Homo sapiens

<400> SEQUENCE: 861

Met Val Ser His Arg Tyr Pro Arg Ile Gln Ser Ile Lys Val Gln Phe
1               5                   10                  15

Thr Glu Tyr Lys Lys Glu Lys Gly Phe Ile Leu Thr Ser Gln Lys Glu
            20                  25                  30

Asp Glu Ile Met Lys Val Gln Asn Asn Ser Val Ile Ile Asn Cys Asp
        35                  40                  45

Gly Phe Tyr Leu Ile Ser Leu Lys Gly Tyr Phe Ser Gln Glu Val Asn
    50                  55                  60

Ile Ser Leu His Tyr Gln Lys Asp Glu Glu Pro Leu Phe Gln Leu Lys
65                  70                  75                  80

Lys Val Arg Ser Val Asn Ser Leu Met Val Ala Ser Leu Thr Tyr Lys
                85                  90                  95

Asp Lys Val Tyr Leu Asn Val Thr Thr Asp Asn Thr Ser Leu Asp Asp
            100                 105                 110

Phe His Val Asn Gly Gly Glu Leu Ile Leu Ile His Gln Asn Pro Gly
        115                 120                 125

Glu Phe Cys Val Leu Lys Asp Glu Glu Pro Leu Phe Gln Leu Lys Lys
    130                 135                 140

Val Arg Ser Val Asn Ser Leu Met Val Ala Ser Leu Thr Tyr Lys Asp
145                 150                 155                 160

Lys Val Tyr Leu Asn Val Thr Thr Asp Asn Thr Ser Leu Asp Asp Phe
                165                 170                 175

His Val Asn Gly Gly Glu Leu Ile Leu Ile His Gln Asn Pro Gly Glu
            180                 185                 190

Phe Cys Val Leu
        195


<210> SEQ ID NO 862
<211> LENGTH: 167
<212> TYPE: PRT
<213> ORGANISM: Homo sapiens

<400> SEQUENCE: 862

Met Val Ser Asn Phe Phe His Val Ile Gln Val Phe Glu Lys Ser Ala
1               5                   10                  15

Thr Leu Ile Ser Lys Thr Glu His Ile Gly Phe Val Ile Tyr Ser Trp
```

```
            20                  25                  30

Arg Lys Ser Thr Thr His Leu Gly Ser Arg Arg Lys Phe Ala Ile Ser
        35                  40                  45

Ile Tyr Leu Ser Glu Val Ser Leu Gln Lys Tyr Asp Cys Pro Phe Ser
    50                  55                  60

Gly Thr Ser Phe Val Val Phe Ser Leu Phe Leu Ile Cys Ala Met Ala
65                  70                  75                  80

Gly Asp Val Val Tyr Ala Asp Ile Lys Thr Val Arg Thr Ser Pro Leu
                85                  90                  95

Glu Leu Ala Phe Pro Leu Gln Arg Ser Val Ser Phe Asn Phe Ser Thr
            100                 105                 110

Val His Lys Ser Cys Pro Ala Lys Asp Trp Lys Val His Lys Gly Lys
        115                 120                 125

Cys Tyr Trp Ile Ala Glu Thr Lys Lys Ser Trp Asn Lys Ser Gln Asn
    130                 135                 140

Asp Cys Ala Ile Asn Asn Ser Tyr Leu Met Val Ile Gln Asp Ile Thr
145                 150                 155                 160

Ala Met Val Arg Phe Asn Ile
                165
```

<210> SEQ ID NO 863
<211> LENGTH: 191
<212> TYPE: PRT
<213> ORGANISM: Homo sapiens

<400> SEQUENCE: 863

```
Met Val Ser Asn Phe Phe His Val Ile Gln Val Phe Glu Lys Ser Ala
1               5                   10                  15

Thr Leu Ile Ser Lys Thr Glu His Ile Gly Phe Val Ile Tyr Ser Trp
            20                  25                  30

Arg Lys Ser Thr Thr His Leu Gly Ser Arg Arg Lys Phe Ala Ile Ser
        35                  40                  45

Ile Tyr Leu Ser Glu Val Ser Leu Gln Lys Tyr Asp Cys Pro Phe Ser
    50                  55                  60

Gly Thr Ser Phe Val Val Phe Ser Leu Phe Leu Ile Cys Ala Met Ala
65                  70                  75                  80

Gly Asp Val Val Tyr Ala Asp Ile Lys Thr Val Arg Thr Ser Pro Leu
                85                  90                  95

Glu Leu Ala Phe Pro Leu Gln Arg Ser Val Ser Phe Asn Phe Ser Thr
            100                 105                 110

Val His Lys Ser Cys Pro Ala Lys Asp Trp Lys Val His Lys Gly Lys
        115                 120                 125

Cys Tyr Trp Ile Ala Glu Thr Lys Lys Ser Trp Asn Lys Ser Gln Asn
    130                 135                 140

Asp Cys Ala Ile Asn Asn Ser Tyr Leu Met Val Ile Gln Asp Ile Thr
145                 150                 155                 160

Ala Met Leu Ile Thr Phe Leu Leu Tyr Leu Gln Met Ala Phe Leu Gln
                165                 170                 175

Cys Val Tyr Ile Ser Asp Val Ser Val Tyr Pro Asn Phe Phe Leu
            180                 185                 190
```

<210> SEQ ID NO 864
<211> LENGTH: 35
<212> TYPE: PRT
<213> ORGANISM: Homo sapiens

<400> SEQUENCE: 864

Gln Asp Ile Thr Ala Met Leu Ile Thr Phe Leu Leu Tyr Leu Gln Met
1 5 10 15

Ala Phe Leu Gln Cys Val Tyr Ile Ser Asp Val Ser Val Tyr Pro Asn
20 25 30

Phe Phe Leu
35

<210> SEQ ID NO 865
<211> LENGTH: 167
<212> TYPE: PRT
<213> ORGANISM: Homo sapiens

<400> SEQUENCE: 865

Met Val Ser Asn Phe Phe His Val Ile Gln Val Phe Glu Lys Ser Ala
1 5 10 15

Thr Leu Ile Ser Lys Thr Glu His Ile Gly Phe Val Ile Tyr Ser Trp
20 25 30

Arg Lys Ser Thr Thr His Leu Gly Ser Arg Arg Lys Phe Ala Ile Ser
35 40 45

Ile Tyr Leu Ser Glu Val Ser Leu Gln Lys Tyr Asp Cys Pro Phe Ser
50 55 60

Gly Thr Ser Phe Val Val Phe Ser Leu Phe Leu Ile Cys Ala Met Ala
65 70 75 80

Gly Asp Val Val Tyr Ala Asp Ile Lys Thr Val Arg Thr Ser Pro Leu
85 90 95

Glu Leu Ala Phe Pro Leu Gln Arg Ser Val Ser Phe Asn Phe Ser Thr
100 105 110

Val His Lys Ser Cys Pro Ala Lys Asp Trp Lys Val His Lys Gly Lys
115 120 125

Cys Tyr Trp Ile Ala Glu Thr Lys Lys Ser Trp Asn Lys Ser Gln Asn
130 135 140

Asp Cys Ala Ile Asn Asn Ser Tyr Leu Met Val Ile Gln Asp Ile Thr
145 150 155 160

Ala Met Lys Ser Asn Leu Phe
165

<210> SEQ ID NO 866
<211> LENGTH: 199
<212> TYPE: PRT
<213> ORGANISM: Homo sapiens

<400> SEQUENCE: 866

Met Ser Ser Glu Asn Cys Phe Val Ala Glu Asn Ser Ser Leu His Pro
1 5 10 15

Glu Ser Gly Gln Glu Asn Asp Ala Thr Ser Pro His Phe Ser Thr Arg
20 25 30

His Glu Gly Ser Phe Gln Val Pro Val Leu Cys Ala Val Met Asn Val
35 40 45

Val Phe Ile Thr Ile Leu Ile Ile Ala Leu Ile Ala Leu Ser Val Gly
50 55 60

Gln Tyr Asn Cys Pro Gly Gln Tyr Thr Phe Ser Met Pro Ser Asp Ser
65 70 75 80

His Val Ser Ser Cys Ser Glu Asp Trp Val Gly Tyr Gln Arg Lys Cys
85 90 95

Tyr Phe Ile Ser Thr Val Lys Arg Ser Trp Thr Ser Ala Gln Asn Ala

```
            100                 105                 110

Cys Ser Glu His Gly Ala Thr Leu Ala Val Ile Asp Ser Glu Lys Asp
        115                 120                 125

Met Asn Phe Leu Lys Arg Tyr Ala Gly Arg Glu Glu His Trp Val Gly
    130                 135                 140

Leu Lys Lys Glu Pro Gly His Pro Trp Lys Trp Ser Asn Gly Lys Glu
145                 150                 155                 160

Phe Asn Asn Trp Phe Asn Val Thr Gly Ser Asp Lys Cys Val Phe Leu
                165                 170                 175

Lys Asn Thr Glu Val Ser Ser Met Glu Cys Glu Lys Asn Leu Tyr Trp
            180                 185                 190

Ile Cys Asn Lys Pro Tyr Lys
        195


<210> SEQ ID NO 867
<211> LENGTH: 1318
<212> TYPE: PRT
<213> ORGANISM: Homo sapiens

<400> SEQUENCE: 867

Met Val Ser Tyr Trp Asp Thr Gly Val Leu Leu Cys Ala Leu Leu Ser
1               5                   10                  15

Cys Leu Leu Leu Thr Gly Ser Ser Ser Gly Ser Lys Leu Lys Asp Pro
            20                  25                  30

Glu Leu Ser Leu Lys Gly Thr Gln His Ile Met Gln Ala Gly Gln Thr
        35                  40                  45

Leu His Leu Gln Cys Arg Gly Glu Ala Ala His Lys Trp Ser Leu Pro
    50                  55                  60

Glu Met Val Ser Lys Glu Ser Glu Arg Leu Ser Ile Thr Lys Ser Ala
65                  70                  75                  80

Cys Gly Arg Asn Gly Lys Gln Phe Cys Ser Thr Leu Thr Leu Asn Thr
                85                  90                  95

Ala Gln Ala Asn His Thr Gly Phe Tyr Ser Cys Lys Tyr Leu Ala Val
            100                 105                 110

Pro Thr Ser Lys Lys Lys Glu Thr Glu Ser Ala Ile Tyr Ile Phe Ile
        115                 120                 125

Ser Asp Thr Gly Arg Pro Phe Val Glu Met Tyr Ser Glu Ile Pro Glu
    130                 135                 140

Ile Ile His Met Thr Glu Gly Arg Glu Leu Val Ile Pro Cys Arg Val
145                 150                 155                 160

Thr Ser Pro Asn Asp Trp Asp Ser Arg Lys Gly Phe Ile Ile Ser Asn
                165                 170                 175

Ala Thr Tyr Lys Glu Ile Gly Leu Leu Thr Cys Glu Ala Thr Val Asn
            180                 185                 190

Gly His Leu Tyr Lys Thr Asn Tyr Leu Thr His Arg Gln Thr Asn Thr
        195                 200                 205

Ile Ile Asp Val Gln Ile Ser Thr Pro Arg Pro Val Lys Leu Leu Arg
    210                 215                 220

Gly His Thr Leu Val Leu Asn Cys Thr Ala Thr Thr Pro Leu Asn Thr
225                 230                 235                 240

Arg Val Gln Met Thr Trp Ser Tyr Pro Asp Glu Lys Asn Lys Arg Ala
                245                 250                 255

Ser Val Arg Arg Arg Ile Asp Gln Ser Asn Ser His Ala Asn Ile Phe
            260                 265                 270
```

-continued

Tyr Ser Val Leu Thr Ile Asp Lys Met Gln Asn Lys Asp Lys Gly Leu
275 280 285

Tyr Thr Cys Arg Val Arg Ser Gly Pro Ser Phe Lys Ser Val Asn Thr
290 295 300

Ser Val His Ile Tyr Asp Lys Ala Phe Ile Thr Val Lys His Arg Lys
305 310 315 320

Gln Gln Val Leu Glu Thr Val Ala Gly Lys Arg Ser Tyr Arg Leu Ser
325 330 335

Met Lys Val Lys Ala Phe Pro Ser Pro Glu Val Val Trp Leu Lys Asp
340 345 350

Gly Leu Pro Ala Thr Glu Lys Ser Ala Arg Tyr Leu Thr Arg Gly Tyr
355 360 365

Ser Leu Ile Ile Lys Asp Val Thr Glu Glu Asp Ala Gly Asn Tyr Thr
370 375 380

Ile Leu Leu Ser Ile Lys Gln Ser Asn Val Phe Lys Asn Leu Thr Ala
385 390 395 400

Thr Leu Ile Val Asn Val Lys Pro Gln Ile Tyr Glu Lys Ala Val Ser
405 410 415

Ser Phe Pro Asp Pro Ala Leu Tyr Pro Leu Gly Ser Arg Gln Ile Leu
420 425 430

Thr Cys Thr Ala Tyr Gly Ile Pro Gln Pro Thr Ile Lys Trp Phe Trp
435 440 445

His Pro Cys Asn His Asn His Ser Glu Ala Arg Cys Asp Phe Cys Ser
450 455 460

Asn Asn Glu Glu Ser Phe Ile Leu Asp Ala Asp Ser Asn Met Gly Asn
465 470 475 480

Arg Ile Glu Ser Ile Thr Gln Arg Met Ala Ile Ile Glu Gly Lys Asn
485 490 495

Lys Met Ala Ser Thr Leu Val Val Ala Asp Ser Arg Ile Ser Gly Ile
500 505 510

Tyr Ile Cys Ile Ala Ser Asn Lys Val Gly Thr Val Gly Arg Asn Ile
515 520 525

Ser Phe Tyr Ile Thr Asp Val Pro Asn Gly Phe His Val Asn Leu Glu
530 535 540

Lys Met Pro Thr Glu Gly Glu Asp Leu Lys Leu Ser Cys Thr Val Asn
545 550 555 560

Lys Phe Leu Tyr Arg Asp Val Thr Trp Ile Leu Leu Arg Thr Val Asn
565 570 575

Asn Arg Thr Met His Tyr Ser Ile Ser Lys Gln Lys Met Ala Ile Thr
580 585 590

Lys Glu His Ser Ile Thr Leu Asn Leu Thr Ile Met Asn Val Ser Leu
595 600 605

Gln Asp Ser Gly Thr Tyr Ala Cys Arg Ala Arg Asn Val Tyr Thr Gly
610 615 620

Glu Glu Ile Leu Gln Lys Lys Glu Ile Thr Ile Arg Asp Gln Glu Ala
625 630 635 640

Pro Tyr Leu Leu Arg Asn Leu Ser Asp His Thr Val Ala Ile Ser Ser
645 650 655

Ser Thr Thr Leu Asp Cys His Ala Asn Gly Val Pro Glu Pro Gln Ile
660 665 670

Thr Trp Phe Lys Asn Asn His Lys Ile Gln Gln Glu Pro Gly Ile Ile
675 680 685

Leu Gly Pro Gly Ser Ser Thr Leu Phe Ile Glu Arg Val Thr Glu Glu 690 695 700

Asp Glu Gly Val Tyr His Cys Lys Ala Thr Asn Gln Lys Gly Ser Val
705 710 715 720

Glu Ser Ser Ala Tyr Leu Thr Val Gln Gly Thr Ser Asp Lys Ser Asn
725 730 735

Leu Glu Leu Ile Thr Leu Thr Cys Thr Cys Val Ala Ala Thr Leu Phe
740 745 750

Trp Leu Leu Leu Thr Leu Phe Ile Arg Lys Met Lys Arg Ser Ser Ser
755 760 765

Glu Ile Lys Thr Asp Tyr Leu Ser Ile Ile Met Asp Pro Asp Glu Val
770 775 780

Pro Leu Asp Glu Gln Cys Glu Arg Leu Pro Tyr Asp Ala Ser Lys Trp
785 790 795 800

Glu Phe Ala Arg Glu Arg Leu Lys Leu Gly Lys Ser Leu Gly Arg Gly
805 810 815

Ala Phe Gly Lys Val Val Gln Ala Ser Ala Phe Gly Ile Lys Lys Ser
820 825 830

Pro Thr Cys Arg Thr Val Ala Val Lys Met Leu Lys Glu Gly Ala Thr
835 840 845

Ala Ser Glu Tyr Lys Ala Leu Met Thr Glu Leu Lys Ile Leu Thr His
850 855 860

Ile Gly His His Leu Asn Val Val Asn Leu Leu Gly Ala Cys Thr Lys
865 870 875 880

Gln Gly Gly Pro Leu Met Val Ile Val Glu Tyr Cys Lys Tyr Gly Asn
885 890 895

Leu Ser Asn Tyr Leu Lys Ser Lys Arg Asp Leu Phe Phe Leu Asn Lys
900 905 910

Asp Ala Ala Leu His Met Glu Pro Lys Lys Glu Lys Met Glu Pro Gly
915 920 925

Leu Glu Gln Gly Lys Lys Pro Arg Leu Asp Ser Val Thr Ser Ser Glu
930 935 940

Ser Phe Ala Ser Ser Gly Phe Gln Glu Asp Lys Ser Leu Ser Asp Val
945 950 955 960

Glu Glu Glu Glu Asp Ser Asp Gly Phe Tyr Lys Glu Pro Ile Thr Met
965 970 975

Glu Asp Leu Ile Ser Tyr Ser Phe Gln Val Ala Arg Gly Met Glu Phe
980 985 990

Leu Ser Ser Arg Lys Cys Ile His Arg Asp Leu Ala Ala Arg Asn Ile
995 1000 1005

Leu Leu Ser Glu Asn Asn Val Val Lys Ile Cys Asp Phe Gly Leu
1010 1015 1020

Ala Arg Asp Ile Tyr Lys Asn Pro Asp Tyr Val Arg Lys Gly Asp
1025 1030 1035

Thr Arg Leu Pro Leu Lys Trp Met Ala Pro Glu Ser Ile Phe Asp
1040 1045 1050

Lys Ile Tyr Ser Thr Lys Ser Asp Val Trp Ser Tyr Gly Val Leu
1055 1060 1065

Leu Trp Glu Ile Phe Ser Leu Gly Gly Ser Pro Tyr Pro Gly Val
1070 1075 1080

Gln Met Asp Glu Asp Phe Cys Ser Arg Leu Arg Glu Gly Met Arg
1085 1090 1095

Met Arg Ala Pro Glu Tyr Ser Thr Pro Glu Ile Tyr Gln Ile Met
1100 1105 1110

Leu Asp Cys Trp His Arg Asp Pro Lys Glu Arg Pro Arg Phe Ala
1115 1120 1125

Glu Leu Val Glu Lys Leu Gly Asp Leu Leu Gln Ala Asn Val Gln
1130 1135 1140

Gln Asp Gly Lys Asp Tyr Ile Pro Ile Asn Ala Ile Leu Thr Gly
1145 1150 1155

Asn Ser Gly Phe Thr Tyr Ser Thr Pro Ala Phe Ser Glu Asp Phe
1160 1165 1170

Phe Lys Glu Ser Ile Ser Ala Pro Lys Phe Asn Ser Gly Ser Ser
1175 1180 1185

Asp Asp Val Arg Tyr Val Asn Ala Phe Lys Phe Met Ser Leu Glu
1190 1195 1200

Arg Ile Lys Thr Phe Glu Glu Leu Leu Pro Asn Ala Thr Ser Met
1205 1210 1215

Phe Asp Asp Tyr Gln Gly Asp Ser Ser Thr Leu Leu Ala Ser Pro
1220 1225 1230

Met Leu Lys Arg Phe Thr Trp Thr Asp Ser Lys Pro Lys Ala Ser
1235 1240 1245

Leu Lys Ile Asp Leu Arg Val Thr Ser Lys Ser Lys Glu Ser Gly
1250 1255 1260

Leu Ser Asp Val Ser Arg Pro Ser Phe Cys His Ser Ser Cys Gly
1265 1270 1275

His Val Ser Glu Gly Lys Arg Arg Phe Thr Tyr Asp His Ala Glu
1280 1285 1290

Leu Glu Arg Lys Ile Ala Cys Cys Ser Pro Pro Pro Asp Tyr Asn
1295 1300 1305

Ser Val Val Leu Tyr Ser Thr Pro Pro Ile
1310 1315

<210> SEQ ID NO 868
<211> LENGTH: 687
<212> TYPE: PRT
<213> ORGANISM: Homo sapiens

<400> SEQUENCE: 868

Met Val Ser Tyr Trp Asp Thr Gly Val Leu Leu Cys Ala Leu Leu Ser
1 5 10 15

Cys Leu Leu Leu Thr Gly Ser Ser Ser Gly Ser Lys Leu Lys Asp Pro
20 25 30

Glu Leu Ser Leu Lys Gly Thr Gln His Ile Met Gln Ala Gly Gln Thr
35 40 45

Leu His Leu Gln Cys Arg Gly Glu Ala Ala His Lys Trp Ser Leu Pro
50 55 60

Glu Met Val Ser Lys Glu Ser Glu Arg Leu Ser Ile Thr Lys Ser Ala
65 70 75 80

Cys Gly Arg Asn Gly Lys Gln Phe Cys Ser Thr Leu Thr Leu Asn Thr
85 90 95

Ala Gln Ala Asn His Thr Gly Phe Tyr Ser Cys Lys Tyr Leu Ala Val
100 105 110

Pro Thr Ser Lys Lys Lys Glu Thr Glu Ser Ala Ile Tyr Ile Phe Ile
115 120 125

Ser Asp Thr Gly Arg Pro Phe Val Glu Met Tyr Ser Glu Ile Pro Glu
130 135 140

Ile Ile His Met Thr Glu Gly Arg Glu Leu Val Ile Pro Cys Arg Val

```
145                 150                 155                 160

Thr Ser Pro Asn Ile Thr Val Thr Leu Lys Lys Phe Pro Leu Asp Thr
                165                 170                 175

Leu Ile Pro Asp Gly Lys Arg Ile Ile Trp Asp Ser Arg Lys Gly Phe
            180                 185                 190

Ile Ile Ser Asn Ala Thr Tyr Lys Glu Ile Gly Leu Leu Thr Cys Glu
        195                 200                 205

Ala Thr Val Asn Gly His Leu Tyr Lys Thr Asn Tyr Leu Thr His Arg
    210                 215                 220

Gln Thr Asn Thr Ile Ile Asp Val Gln Ile Ser Thr Pro Arg Pro Val
225                 230                 235                 240

Lys Leu Leu Arg Gly His Thr Leu Val Leu Asn Cys Thr Ala Thr Thr
                245                 250                 255

Pro Leu Asn Thr Arg Val Gln Met Thr Trp Ser Tyr Pro Asp Glu Lys
            260                 265                 270

Asn Lys Arg Ala Ser Val Arg Arg Arg Ile Asp Gln Ser Asn Ser His
        275                 280                 285

Ala Asn Ile Phe Tyr Ser Val Leu Thr Ile Asp Lys Met Gln Asn Lys
    290                 295                 300

Asp Lys Gly Leu Tyr Thr Cys Arg Val Arg Ser Gly Pro Ser Phe Lys
305                 310                 315                 320

Ser Val Asn Thr Ser Val His Ile Tyr Asp Lys Ala Phe Ile Thr Val
                325                 330                 335

Lys His Arg Lys Gln Gln Val Leu Glu Thr Val Ala Gly Lys Arg Ser
            340                 345                 350

Tyr Arg Leu Ser Met Lys Val Lys Ala Phe Pro Ser Pro Glu Val Val
        355                 360                 365

Trp Leu Lys Asp Gly Leu Pro Ala Thr Glu Lys Ser Ala Arg Tyr Leu
    370                 375                 380

Thr Arg Gly Tyr Ser Leu Ile Ile Lys Asp Val Thr Glu Glu Asp Ala
385                 390                 395                 400

Gly Asn Tyr Thr Ile Leu Leu Ser Ile Lys Gln Ser Asn Val Phe Lys
                405                 410                 415

Asn Leu Thr Ala Thr Leu Ile Val Asn Val Lys Pro Gln Ile Tyr Glu
            420                 425                 430

Lys Ala Val Ser Ser Phe Pro Asp Pro Ala Leu Tyr Pro Leu Gly Ser
        435                 440                 445

Arg Gln Ile Leu Thr Cys Thr Ala Tyr Gly Ile Pro Gln Pro Thr Ile
    450                 455                 460

Lys Trp Phe Trp His Pro Cys Asn His Asn His Ser Glu Ala Arg Cys
465                 470                 475                 480

Asp Phe Cys Ser Asn Asn Glu Glu Ser Phe Ile Leu Asp Ala Asp Ser
                485                 490                 495

Asn Met Gly Asn Arg Ile Glu Ser Ile Thr Gln Arg Met Ala Ile Ile
            500                 505                 510

Glu Gly Lys Asn Lys Met Ala Ser Thr Leu Val Val Ala Asp Ser Arg
        515                 520                 525

Ile Ser Gly Ile Tyr Ile Cys Ile Ala Ser Asn Lys Val Gly Thr Val
    530                 535                 540

Gly Arg Asn Ile Ser Phe Tyr Ile Thr Asp Val Pro Asn Gly Phe His
545                 550                 555                 560

Val Asn Leu Glu Lys Met Pro Thr Glu Gly Glu Asp Leu Lys Leu Ser
                565                 570                 575
```

```
Cys Thr Val Asn Lys Phe Leu Tyr Arg Asp Val Thr Trp Ile Leu Leu
            580                 585                 590

Arg Thr Val Asn Asn Arg Thr Met His Tyr Ser Ile Ser Lys Gln Lys
        595                 600                 605

Met Ala Ile Thr Lys Glu His Ser Ile Thr Leu Asn Leu Thr Ile Met
    610                 615                 620

Asn Val Ser Leu Gln Asp Ser Gly Thr Tyr Ala Cys Arg Ala Arg Asn
625                 630                 635                 640

Val Tyr Thr Gly Glu Glu Ile Leu Gln Lys Lys Glu Ile Thr Ile Arg
                645                 650                 655

Gly Glu His Cys Asn Lys Lys Ala Val Phe Ser Arg Ile Ser Lys Phe
            660                 665                 670

Lys Ser Thr Arg Asn Asp Cys Thr Thr Gln Ser Asn Val Lys His
        675                 680                 685


<210> SEQ ID NO 869
<211> LENGTH: 733
<212> TYPE: PRT
<213> ORGANISM: Homo sapiens

<400> SEQUENCE: 869

Met Val Ser Tyr Trp Asp Thr Gly Val Leu Leu Cys Ala Leu Leu Ser
1               5                   10                  15

Cys Leu Leu Leu Thr Gly Ser Ser Ser Gly Ser Lys Leu Lys Asp Pro
            20                  25                  30

Glu Leu Ser Leu Lys Gly Thr Gln His Ile Met Gln Ala Gly Gln Thr
        35                  40                  45

Leu His Leu Gln Cys Arg Gly Glu Ala Ala His Lys Trp Ser Leu Pro
    50                  55                  60

Glu Met Val Ser Lys Glu Ser Glu Arg Leu Ser Ile Thr Lys Ser Ala
65                  70                  75                  80

Cys Gly Arg Asn Gly Lys Gln Phe Cys Ser Thr Leu Thr Leu Asn Thr
                85                  90                  95

Ala Gln Ala Asn His Thr Gly Phe Tyr Ser Cys Lys Tyr Leu Ala Val
            100                 105                 110

Pro Thr Ser Lys Lys Lys Glu Thr Glu Ser Ala Ile Tyr Ile Phe Ile
        115                 120                 125

Ser Asp Thr Gly Arg Pro Phe Val Glu Met Tyr Ser Glu Ile Pro Glu
    130                 135                 140

Ile Ile His Met Thr Glu Gly Arg Glu Leu Val Ile Pro Cys Arg Val
145                 150                 155                 160

Thr Ser Pro Asn Ile Thr Val Thr Leu Lys Lys Phe Pro Leu Asp Thr
                165                 170                 175

Leu Ile Pro Asp Gly Lys Arg Ile Ile Trp Asp Ser Arg Lys Gly Phe
            180                 185                 190

Ile Ile Ser Asn Ala Thr Tyr Lys Glu Ile Gly Leu Leu Thr Cys Glu
        195                 200                 205

Ala Thr Val Asn Gly His Leu Tyr Lys Thr Asn Tyr Leu Thr His Arg
    210                 215                 220

Gln Thr Asn Thr Ile Ile Asp Val Gln Ile Ser Thr Pro Arg Pro Val
225                 230                 235                 240

Lys Leu Leu Arg Gly His Thr Leu Val Leu Asn Cys Thr Ala Thr Thr
                245                 250                 255

Pro Leu Asn Thr Arg Val Gln Met Thr Trp Ser Tyr Pro Asp Glu Lys
```

-continued

```
            260                 265                 270

Asn Lys Arg Ala Ser Val Arg Arg Arg Ile Asp Gln Ser Asn Ser His
        275                 280                 285

Ala Asn Ile Phe Tyr Ser Val Leu Thr Ile Asp Lys Met Gln Asn Lys
    290                 295                 300

Asp Lys Gly Leu Tyr Thr Cys Arg Val Arg Ser Gly Pro Ser Phe Lys
305                 310                 315                 320

Ser Val Asn Thr Ser Val His Ile Tyr Asp Lys Ala Phe Ile Thr Val
                325                 330                 335

Lys His Arg Lys Gln Gln Val Leu Glu Thr Val Ala Gly Lys Arg Ser
            340                 345                 350

Tyr Arg Leu Ser Met Lys Val Lys Ala Phe Pro Ser Pro Glu Val Val
        355                 360                 365

Trp Leu Lys Asp Gly Leu Pro Ala Thr Glu Lys Ser Ala Arg Tyr Leu
    370                 375                 380

Thr Arg Gly Tyr Ser Leu Ile Ile Lys Asp Val Thr Glu Glu Asp Ala
385                 390                 395                 400

Gly Asn Tyr Thr Ile Leu Leu Ser Ile Lys Gln Ser Asn Val Phe Lys
                405                 410                 415

Asn Leu Thr Ala Thr Leu Ile Val Asn Val Lys Pro Gln Ile Tyr Glu
            420                 425                 430

Lys Ala Val Ser Ser Phe Pro Asp Pro Ala Leu Tyr Pro Leu Gly Ser
        435                 440                 445

Arg Gln Ile Leu Thr Cys Thr Ala Tyr Gly Ile Pro Gln Pro Thr Ile
    450                 455                 460

Lys Trp Phe Trp His Pro Cys Asn His Asn His Ser Glu Ala Arg Cys
465                 470                 475                 480

Asp Phe Cys Ser Asn Asn Glu Glu Ser Phe Ile Leu Asp Ala Asp Ser
                485                 490                 495

Asn Met Gly Asn Arg Ile Glu Ser Ile Thr Gln Arg Met Ala Ile Ile
            500                 505                 510

Glu Gly Lys Asn Lys Met Ala Ser Thr Leu Val Val Ala Asp Ser Arg
        515                 520                 525

Ile Ser Gly Ile Tyr Ile Cys Ile Ala Ser Asn Lys Val Gly Thr Val
    530                 535                 540

Gly Arg Asn Ile Ser Phe Tyr Ile Thr Asp Val Pro Asn Gly Phe His
545                 550                 555                 560

Val Asn Leu Glu Lys Met Pro Thr Glu Gly Glu Asp Leu Lys Leu Ser
                565                 570                 575

Cys Thr Val Asn Lys Phe Leu Tyr Arg Asp Val Thr Trp Ile Leu Leu
            580                 585                 590

Arg Thr Val Asn Asn Arg Thr Met His Tyr Ser Ile Ser Lys Gln Lys
        595                 600                 605

Met Ala Ile Thr Lys Glu His Ser Ile Thr Leu Asn Leu Thr Ile Met
    610                 615                 620

Asn Val Ser Leu Gln Asp Ser Gly Thr Tyr Ala Cys Arg Ala Arg Asn
625                 630                 635                 640

Val Tyr Thr Gly Glu Glu Ile Leu Gln Lys Lys Glu Ile Thr Ile Arg
                645                 650                 655

Asp Gln Glu Ala Pro Tyr Leu Leu Arg Asn Leu Ser Asp His Thr Val
            660                 665                 670

Ala Ile Ser Ser Ser Thr Thr Leu Asp Cys His Ala Asn Gly Val Pro
        675                 680                 685
```

Glu Pro Gln Ile Thr Trp Phe Lys Asn Asn His Lys Ile Gln Gln Glu
690 695 700

Pro Glu Leu Tyr Thr Ser Thr Ser Pro Ser Ser Ser Ser Ser Ser Pro
705 710 715 720

Leu Ser Ser Ser Ser Ser Ser Ser Ser Ser Ser Ser Ser
725 730

<210> SEQ ID NO 870
<211> LENGTH: 541
<212> TYPE: PRT
<213> ORGANISM: Homo sapiens

<400> SEQUENCE: 870

Met Val Ser Tyr Trp Asp Thr Gly Val Leu Leu Cys Ala Leu Leu Ser
1 5 10 15

Cys Leu Leu Leu Thr Gly Ser Ser Ser Gly Ser Lys Leu Lys Asp Pro
20 25 30

Glu Leu Ser Leu Lys Gly Thr Gln His Ile Met Gln Ala Gly Gln Thr
35 40 45

Leu His Leu Gln Cys Arg Gly Glu Ala Ala His Lys Trp Ser Leu Pro
50 55 60

Glu Met Val Ser Lys Glu Ser Glu Arg Leu Ser Ile Thr Lys Ser Ala
65 70 75 80

Cys Gly Arg Asn Gly Lys Gln Phe Cys Ser Thr Leu Thr Leu Asn Thr
85 90 95

Ala Gln Ala Asn His Thr Gly Phe Tyr Ser Cys Lys Tyr Leu Ala Val
100 105 110

Pro Thr Ser Lys Lys Lys Glu Thr Glu Ser Ala Ile Tyr Ile Phe Ile
115 120 125

Ser Asp Thr Gly Arg Pro Phe Val Glu Met Tyr Ser Glu Ile Pro Glu
130 135 140

Ile Ile His Met Thr Glu Gly Arg Glu Leu Val Ile Pro Cys Arg Val
145 150 155 160

Thr Ser Pro Asn Ile Thr Val Thr Leu Lys Lys Phe Pro Leu Asp Thr
165 170 175

Leu Ile Pro Asp Gly Lys Arg Ile Ile Trp Asp Ser Arg Lys Gly Phe
180 185 190

Ile Ile Ser Asn Ala Thr Tyr Lys Glu Ile Gly Leu Leu Thr Cys Glu
195 200 205

Ala Thr Val Asn Gly His Leu Tyr Lys Thr Asn Tyr Leu Thr His Arg
210 215 220

Gln Thr Asn Thr Ile Ile Asp Val Gln Ile Ser Thr Pro Arg Pro Val
225 230 235 240

Lys Leu Leu Arg Gly His Thr Leu Val Leu Asn Cys Thr Ala Thr Thr
245 250 255

Pro Leu Asn Thr Arg Val Gln Met Thr Trp Ser Tyr Pro Asp Glu Lys
260 265 270

Asn Lys Arg Ala Ser Val Arg Arg Arg Ile Asp Gln Ser Asn Ser His
275 280 285

Ala Asn Ile Phe Tyr Ser Val Leu Thr Ile Asp Lys Met Gln Asn Lys
290 295 300

Asp Lys Gly Leu Tyr Thr Cys Arg Val Arg Ser Gly Pro Ser Phe Lys
305 310 315 320

Ser Val Asn Thr Ser Val His Ile Tyr Asp Lys Ala Phe Ile Thr Val

-continued

```
                325                 330                 335

Lys His Arg Lys Gln Gln Val Leu Glu Thr Val Ala Gly Lys Arg Ser
            340                 345                 350

Tyr Arg Leu Ser Met Lys Val Lys Ala Phe Pro Ser Pro Glu Val Val
        355                 360                 365

Trp Leu Lys Asp Gly Leu Pro Ala Thr Glu Lys Ser Ala Arg Tyr Leu
    370                 375                 380

Thr Arg Gly Tyr Ser Leu Ile Ile Lys Asp Val Thr Glu Glu Asp Ala
385                 390                 395                 400

Gly Asn Tyr Thr Ile Leu Leu Ser Ile Lys Gln Ser Asn Val Phe Lys
                405                 410                 415

Asn Leu Thr Ala Thr Leu Ile Val Asn Val Lys Pro Gln Ile Tyr Glu
            420                 425                 430

Lys Ala Val Ser Ser Phe Pro Asp Pro Ala Leu Tyr Pro Leu Gly Ser
        435                 440                 445

Arg Gln Ile Leu Thr Cys Thr Ala Tyr Gly Ile Pro Gln Pro Thr Ile
    450                 455                 460

Lys Trp Phe Trp His Pro Cys Asn His Asn His Ser Glu Ala Arg Cys
465                 470                 475                 480

Asp Phe Cys Ser Asn Asn Glu Glu Ser Phe Ile Leu Asp Ala Asp Ser
                485                 490                 495

Asn Met Gly Asn Arg Ile Glu Ser Ile Thr Gln Arg Met Ala Ile Ile
            500                 505                 510

Glu Gly Lys Asn Lys Leu Pro Pro Ala Asn Ser Ser Phe Met Leu Pro
        515                 520                 525

Pro Thr Ser Phe Ser Ser Asn Tyr Phe His Phe Leu Pro
    530                 535                 540
```

<210> SEQ ID NO 871
<211> LENGTH: 1124
<212> TYPE: PRT
<213> ORGANISM: Homo sapiens

<400> SEQUENCE: 871

```
Met Asp Ser Leu Ala Ser Leu Val Leu Cys Gly Val Ser Leu Leu Leu
1               5                   10                  15

Ser Gly Thr Val Glu Gly Ala Met Asp Leu Ile Leu Ile Asn Ser Leu
            20                  25                  30

Pro Leu Val Ser Asp Ala Glu Thr Ser Leu Thr Cys Ile Ala Ser Gly
        35                  40                  45

Trp Arg Pro His Glu Pro Ile Thr Ile Gly Arg Asp Phe Glu Ala Leu
    50                  55                  60

Met Asn Gln His Gln Asp Pro Leu Glu Val Thr Gln Asp Val Thr Arg
65                  70                  75                  80

Glu Trp Ala Lys Lys Val Val Trp Lys Arg Glu Lys Ala Ser Lys Ile
                85                  90                  95

Asn Gly Ala Tyr Phe Cys Glu Gly Arg Val Arg Gly Glu Ala Ile Arg
            100                 105                 110

Ile Arg Thr Met Lys Met Arg Gln Gln Ala Ser Phe Leu Pro Ala Thr
        115                 120                 125

Leu Thr Met Thr Val Asp Lys Gly Asp Asn Val Asn Ile Ser Phe Lys
    130                 135                 140

Lys Val Leu Ile Lys Glu Glu Asp Ala Val Ile Tyr Lys Asn Gly Ser
145                 150                 155                 160
```

-continued

```
Phe Ile His Ser Val Pro Arg His Glu Val Pro Asp Ile Leu Glu Val
                165                 170                 175

His Leu Pro His Ala Gln Pro Gln Asp Ala Gly Val Tyr Ser Ala Arg
            180                 185                 190

Tyr Ile Gly Gly Asn Leu Phe Thr Ser Ala Phe Thr Arg Leu Ile Val
        195                 200                 205

Arg Arg Cys Glu Ala Gln Lys Trp Gly Pro Glu Cys Asn His Leu Cys
    210                 215                 220

Thr Ala Cys Met Asn Asn Gly Val Cys His Glu Asp Thr Gly Glu Cys
225                 230                 235                 240

Ile Cys Pro Pro Gly Phe Met Gly Arg Thr Cys Glu Lys Ala Cys Glu
                245                 250                 255

Leu His Thr Phe Gly Arg Thr Cys Lys Glu Arg Cys Ser Gly Gln Glu
            260                 265                 270

Gly Cys Lys Ser Tyr Val Phe Cys Leu Pro Asp Pro Tyr Gly Cys Ser
        275                 280                 285

Cys Ala Thr Gly Trp Lys Gly Leu Gln Cys Asn Glu Ala Cys His Pro
    290                 295                 300

Gly Phe Tyr Gly Pro Asp Cys Lys Leu Arg Cys Ser Cys Asn Asn Gly
305                 310                 315                 320

Glu Met Cys Asp Arg Phe Gln Gly Cys Leu Cys Ser Pro Gly Trp Gln
                325                 330                 335

Gly Leu Gln Cys Glu Arg Glu Gly Ile Gln Arg Met Thr Pro Lys Ile
            340                 345                 350

Val Asp Leu Pro Asp His Ile Glu Val Asn Ser Gly Lys Phe Asn Pro
        355                 360                 365

Ile Cys Lys Ala Ser Gly Trp Pro Leu Pro Thr Asn Glu Glu Met Thr
    370                 375                 380

Leu Val Lys Pro Asp Gly Thr Val Leu His Pro Lys Asp Phe Asn His
385                 390                 395                 400

Thr Asp His Phe Ser Val Ala Ile Phe Thr Ile His Arg Ile Leu Pro
                405                 410                 415

Pro Asp Ser Gly Val Trp Val Cys Ser Val Asn Thr Val Ala Gly Met
            420                 425                 430

Val Glu Lys Pro Phe Asn Ile Ser Val Lys Val Leu Pro Lys Pro Leu
        435                 440                 445

Asn Ala Pro Asn Val Ile Asp Thr Gly His Asn Phe Ala Val Ile Asn
    450                 455                 460

Ile Ser Ser Glu Pro Tyr Phe Gly Asp Gly Pro Ile Lys Ser Lys Lys
465                 470                 475                 480

Leu Leu Tyr Lys Pro Val Asn His Tyr Glu Ala Trp Gln His Ile Gln
                485                 490                 495

Val Thr Asn Glu Ile Val Thr Leu Asn Tyr Leu Glu Pro Arg Thr Glu
            500                 505                 510

Tyr Glu Leu Cys Val Gln Leu Val Arg Arg Gly Glu Gly Gly Glu Gly
        515                 520                 525

His Pro Gly Pro Val Arg Arg Phe Thr Thr Ala Ser Ile Gly Leu Pro
    530                 535                 540

Pro Pro Arg Gly Leu Asn Leu Leu Pro Lys Ser Gln Thr Thr Leu Asn
545                 550                 555                 560

Leu Thr Trp Gln Pro Ile Phe Pro Ser Ser Glu Asp Asp Phe Tyr Val
                565                 570                 575

Glu Val Glu Arg Arg Ser Val Gln Lys Ser Asp Gln Gln Asn Ile Lys
```

-continued

```
            580                 585                 590

Val Pro Gly Asn Leu Thr Ser Val Leu Leu Asn Asn Leu His Pro Arg
        595                 600                 605

Glu Gln Tyr Val Val Arg Ala Arg Val Asn Thr Lys Ala Gln Gly Glu
    610                 615                 620

Trp Ser Glu Asp Leu Thr Ala Trp Thr Leu Ser Asp Ile Leu Pro Pro
625                 630                 635                 640

Gln Pro Glu Asn Ile Lys Ile Ser Asn Ile Thr His Ser Ser Ala Val
                645                 650                 655

Ile Ser Trp Thr Ile Leu Asp Gly Tyr Ser Ile Ser Ser Ile Thr Ile
            660                 665                 670

Arg Tyr Lys Val Gln Gly Lys Asn Glu Asp Gln His Val Asp Val Lys
        675                 680                 685

Ile Lys Asn Ala Thr Ile Thr Gln Tyr Gln Leu Lys Gly Leu Glu Pro
    690                 695                 700

Glu Thr Ala Tyr Gln Val Asp Ile Phe Ala Glu Asn Asn Ile Gly Ser
705                 710                 715                 720

Ser Asn Pro Ala Phe Ser His Glu Leu Val Thr Leu Pro Glu Ser Gln
                725                 730                 735

Ala Pro Ala Asp Leu Gly Gly Gly Lys Met Leu Leu Ile Ala Ile Leu
            740                 745                 750

Gly Ser Ala Gly Met Thr Cys Leu Thr Val Leu Leu Ala Phe Leu Ile
        755                 760                 765

Ile Leu Gln Leu Lys Arg Ala Asn Val Gln Arg Arg Met Ala Gln Ala
    770                 775                 780

Phe Gln Asn Val Arg Glu Glu Pro Ala Val Gln Phe Asn Ser Gly Thr
785                 790                 795                 800

Leu Ala Leu Asn Arg Lys Val Lys Asn Asn Pro Asp Pro Thr Ile Tyr
                805                 810                 815

Pro Val Leu Asp Trp Asn Asp Ile Lys Phe Gln Asp Val Ile Gly Glu
            820                 825                 830

Gly Asn Phe Gly Gln Val Leu Lys Ala Arg Ile Lys Lys Asp Gly Leu
        835                 840                 845

Arg Met Asp Ala Ala Ile Lys Arg Met Lys Glu Tyr Ala Ser Lys Asp
    850                 855                 860

Asp His Arg Asp Phe Ala Gly Glu Leu Glu Val Leu Cys Lys Leu Gly
865                 870                 875                 880

His His Pro Asn Ile Ile Asn Leu Leu Gly Ala Cys Glu His Arg Gly
                885                 890                 895

Tyr Leu Tyr Leu Ala Ile Glu Tyr Ala Pro His Gly Asn Leu Leu Asp
            900                 905                 910

Phe Leu Arg Lys Ser Arg Val Leu Glu Thr Asp Pro Ala Phe Ala Ile
        915                 920                 925

Ala Asn Ser Thr Ala Ser Thr Leu Ser Ser Gln Gln Leu Leu His Phe
    930                 935                 940

Ala Ala Asp Val Ala Arg Gly Met Asp Tyr Leu Ser Gln Lys Gln Phe
945                 950                 955                 960

Ile His Arg Asp Leu Ala Ala Arg Asn Ile Leu Val Gly Glu Asn Tyr
                965                 970                 975

Val Ala Lys Ile Ala Asp Phe Gly Leu Ser Arg Gly Gln Glu Val Tyr
            980                 985                 990

Val Lys Lys Thr Met Gly Arg Leu  Pro Val Arg Trp Met  Ala Ile Glu
        995                 1000                1005
```

```
Ser Leu  Asn Tyr Ser Val Tyr  Thr Thr Asn Ser Asp  Val Trp Ser
    1010                 1015                 1020

Tyr Gly  Val Leu Leu Trp Glu  Ile Val Ser Leu Gly  Gly Thr Pro
    1025                 1030                 1035

Tyr Cys  Gly Met Thr Cys Ala  Glu Leu Tyr Glu Lys  Leu Pro Gln
    1040                 1045                 1050

Gly Tyr  Arg Leu Glu Lys Pro  Leu Asn Cys Asp Asp  Glu Val Tyr
    1055                 1060                 1065

Asp Leu  Met Arg Gln Cys Trp  Arg Glu Lys Pro Tyr  Glu Arg Pro
    1070                 1075                 1080

Ser Phe  Ala Gln Ile Leu Val  Ser Leu Asn Arg Met  Leu Glu Glu
    1085                 1090                 1095

Arg Lys  Thr Tyr Val Asn Thr  Thr Leu Tyr Glu Lys  Phe Thr Tyr
    1100                 1105                 1110

Ala Gly  Ile Asp Cys Ser Ala  Glu Glu Ala Ala
    1115                 1120


<210> SEQ ID NO 872
<211> LENGTH: 1080
<212> TYPE: PRT
<213> ORGANISM: Homo sapiens

<400> SEQUENCE: 872

Met Asp Ser Leu Ala Ser Leu Val Leu Cys Gly Val Ser Leu Leu Leu
1               5                   10                  15

Ser Gly Thr Val Glu Gly Ala Met Asp Leu Ile Leu Ile Asn Ser Leu
            20                  25                  30

Pro Leu Val Ser Asp Ala Glu Thr Ser Leu Thr Cys Ile Ala Ser Gly
        35                  40                  45

Trp Arg Pro His Glu Pro Ile Thr Ile Gly Arg Asp Phe Glu Ala Leu
    50                  55                  60

Met Asn Gln His Gln Asp Pro Leu Glu Val Thr Gln Asp Val Thr Arg
65                  70                  75                  80

Glu Trp Ala Lys Lys Val Val Trp Lys Arg Glu Lys Ala Ser Lys Ile
                85                  90                  95

Asn Gly Ala Tyr Phe Cys Glu Gly Arg Val Arg Gly Glu Ala Ile Arg
            100                 105                 110

Ile Arg Thr Met Lys Met Arg Gln Gln Ala Ser Phe Leu Pro Ala Thr
        115                 120                 125

Leu Thr Met Thr Val Asp Lys Gly Asp Asn Val Asn Ile Ser Phe Lys
    130                 135                 140

Lys Val Leu Ile Lys Glu Glu Asp Ala Val Ile Tyr Lys Asn Gly Ser
145                 150                 155                 160

Phe Ile His Ser Val Pro Arg His Glu Val Pro Asp Ile Leu Glu Val
                165                 170                 175

His Leu Pro His Ala Gln Pro Gln Asp Ala Gly Val Tyr Ser Ala Arg
            180                 185                 190

Tyr Ile Gly Gly Asn Leu Phe Thr Ser Ala Phe Thr Arg Leu Ile Val
        195                 200                 205

Arg Arg Cys Glu Ala Gln Lys Trp Gly Pro Glu Cys Asn His Leu Cys
    210                 215                 220

Thr Ala Cys Met Asn Asn Gly Val Cys His Glu Asp Thr Gly Glu Cys
225                 230                 235                 240

Ile Cys Pro Pro Gly Phe Met Gly Arg Thr Cys Glu Lys Ala Cys Glu
```

-continued

```
                245                 250                 255

Leu His Thr Phe Gly Arg Thr Cys Lys Glu Arg Cys Ser Gly Gln Glu
            260                 265                 270

Gly Cys Lys Ser Tyr Val Phe Cys Leu Pro Asp Pro Tyr Gly Cys Ser
        275                 280                 285

Cys Ala Thr Gly Trp Lys Gly Leu Gln Cys Asn Glu Gly Ile Gln Arg
    290                 295                 300

Met Thr Pro Lys Ile Val Asp Leu Pro Asp His Ile Glu Val Asn Ser
305                 310                 315                 320

Gly Lys Phe Asn Pro Ile Cys Lys Ala Ser Gly Trp Pro Leu Pro Thr
                325                 330                 335

Asn Glu Glu Met Thr Leu Val Lys Pro Asp Gly Thr Val Leu His Pro
            340                 345                 350

Lys Asp Phe Asn His Thr Asp His Phe Ser Val Ala Ile Phe Thr Ile
        355                 360                 365

His Arg Ile Leu Pro Pro Asp Ser Gly Val Trp Val Cys Ser Val Asn
    370                 375                 380

Thr Val Ala Gly Met Val Glu Lys Pro Phe Asn Ile Ser Val Lys Val
385                 390                 395                 400

Leu Pro Lys Pro Leu Asn Ala Pro Asn Val Ile Asp Thr Gly His Asn
                405                 410                 415

Phe Ala Val Ile Asn Ile Ser Ser Glu Pro Tyr Phe Gly Asp Gly Pro
            420                 425                 430

Ile Lys Ser Lys Lys Leu Leu Tyr Lys Pro Val Asn His Tyr Glu Ala
        435                 440                 445

Trp Gln His Ile Gln Val Thr Asn Glu Ile Val Thr Leu Asn Tyr Leu
    450                 455                 460

Glu Pro Arg Thr Glu Tyr Glu Leu Cys Val Gln Leu Val Arg Arg Gly
465                 470                 475                 480

Glu Gly Gly Glu Gly His Pro Gly Pro Val Arg Arg Phe Thr Thr Ala
                485                 490                 495

Ser Ile Gly Leu Pro Pro Pro Arg Gly Leu Asn Leu Leu Pro Lys Ser
            500                 505                 510

Gln Thr Thr Leu Asn Leu Thr Trp Gln Pro Ile Phe Pro Ser Ser Glu
        515                 520                 525

Asp Asp Phe Tyr Val Glu Val Glu Arg Arg Ser Val Gln Lys Ser Asp
    530                 535                 540

Gln Gln Asn Ile Lys Val Pro Gly Asn Leu Thr Ser Val Leu Leu Asn
545                 550                 555                 560

Asn Leu His Pro Arg Glu Gln Tyr Val Val Arg Ala Arg Val Asn Thr
                565                 570                 575

Lys Ala Gln Gly Glu Trp Ser Glu Asp Leu Thr Ala Trp Thr Leu Ser
            580                 585                 590

Asp Ile Leu Pro Pro Gln Pro Glu Asn Ile Lys Ile Ser Asn Ile Thr
        595                 600                 605

His Ser Ser Ala Val Ile Ser Trp Thr Ile Leu Asp Gly Tyr Ser Ile
    610                 615                 620

Ser Ser Ile Thr Ile Arg Tyr Lys Val Gln Gly Lys Asn Glu Asp Gln
625                 630                 635                 640

His Val Asp Val Lys Ile Lys Asn Ala Thr Ile Thr Gln Tyr Gln Leu
                645                 650                 655

Lys Gly Leu Glu Pro Glu Thr Ala Tyr Gln Val Asp Ile Phe Ala Glu
            660                 665                 670
```

-continued

```
Asn Asn Ile Gly Ser Ser Asn Pro Ala Phe Ser His Glu Leu Val Thr
        675                 680                 685

Leu Pro Glu Ser Gln Ala Pro Ala Asp Leu Gly Gly Gly Lys Met Leu
    690                 695                 700

Leu Ile Ala Ile Leu Gly Ser Ala Gly Met Thr Cys Leu Thr Val Leu
705                 710                 715                 720

Leu Ala Phe Leu Ile Ile Leu Gln Leu Lys Arg Ala Asn Val Gln Arg
                725                 730                 735

Arg Met Ala Gln Ala Phe Gln Asn Val Arg Glu Glu Pro Ala Val Gln
            740                 745                 750

Phe Asn Ser Gly Thr Leu Ala Leu Asn Arg Lys Val Lys Asn Asn Pro
        755                 760                 765

Asp Pro Thr Ile Tyr Pro Val Leu Asp Trp Asn Asp Ile Lys Phe Gln
    770                 775                 780

Asp Val Ile Gly Glu Gly Asn Phe Gly Gln Val Leu Lys Ala Arg Ile
785                 790                 795                 800

Lys Lys Asp Gly Leu Arg Met Asp Ala Ala Ile Lys Arg Met Lys Glu
                805                 810                 815

Tyr Ala Ser Lys Asp Asp His Arg Asp Phe Ala Gly Glu Leu Glu Val
            820                 825                 830

Leu Cys Lys Leu Gly His His Pro Asn Ile Ile Asn Leu Leu Gly Ala
        835                 840                 845

Cys Glu His Arg Gly Tyr Leu Tyr Leu Ala Ile Glu Tyr Ala Pro His
    850                 855                 860

Gly Asn Leu Leu Asp Phe Leu Arg Lys Ser Arg Val Leu Glu Thr Asp
865                 870                 875                 880

Pro Ala Phe Ala Ile Ala Asn Ser Thr Ala Ser Thr Leu Ser Ser Gln
                885                 890                 895

Gln Leu Leu His Phe Ala Ala Asp Val Ala Arg Gly Met Asp Tyr Leu
            900                 905                 910

Ser Gln Lys Gln Phe Ile His Arg Asp Leu Ala Ala Arg Asn Ile Leu
        915                 920                 925

Val Gly Glu Asn Tyr Val Ala Lys Ile Asp Phe Gly Leu Ser Arg Gly
    930                 935                 940

Gln Glu Val Tyr Val Lys Lys Thr Met Gly Arg Leu Pro Val Arg Trp
945                 950                 955                 960

Met Ala Ile Glu Ser Leu Asn Tyr Ser Val Tyr Thr Thr Asn Ser Asp
                965                 970                 975

Val Trp Ser Tyr Gly Val Leu Leu Trp Glu Ile Val Ser Leu Gly Gly
            980                 985                 990

Thr Pro Tyr Cys Gly Met Thr Cys  Ala Glu Leu Tyr Glu  Lys Leu Pro
        995                 1000                1005

Gln Gly  Tyr Arg Leu Glu Lys  Pro Leu Asn Cys Asp  Asp Glu Val
    1010                 1015                1020

Tyr Asp  Leu Met Arg Gln Cys  Trp Arg Glu Lys Pro  Tyr Glu Arg
    1025                 1030                1035

Pro Ser  Phe Ala Gln Ile Leu  Val Ser Leu Asn Arg  Met Leu Glu
    1040                 1045                1050

Glu Arg  Lys Thr Tyr Val Asn  Thr Thr Leu Tyr Glu  Lys Phe Thr
    1055                 1060                1065

Tyr Ala  Gly Ile Asp Cys Ser  Ala Glu Glu Ala Ala
    1070                 1075                1080
```

<210> SEQ ID NO 873
<211> LENGTH: 976
<212> TYPE: PRT
<213> ORGANISM: Homo sapiens

<400> SEQUENCE: 873

Met Asp Ser Leu Ala Ser Leu Val Leu Cys Gly Val Ser Leu Leu Leu
1 5 10 15

Ser Ala Ser Phe Leu Pro Ala Thr Leu Thr Met Thr Val Asp Lys Gly
20 25 30

Asp Asn Val Asn Ile Ser Phe Lys Lys Val Leu Ile Lys Glu Glu Asp
35 40 45

Ala Val Ile Tyr Lys Asn Gly Ser Phe Ile His Ser Val Pro Arg His
50 55 60

Glu Val Pro Asp Ile Leu Glu Val His Leu Pro His Ala Gln Pro Gln
65 70 75 80

Asp Ala Gly Val Tyr Ser Ala Arg Tyr Ile Gly Gly Asn Leu Phe Thr
85 90 95

Ser Ala Phe Thr Arg Leu Ile Val Arg Arg Cys Glu Ala Gln Lys Trp
100 105 110

Gly Pro Glu Cys Asn His Leu Cys Thr Ala Cys Met Asn Asn Gly Val
115 120 125

Cys His Glu Asp Thr Gly Glu Cys Ile Cys Pro Pro Gly Phe Met Gly
130 135 140

Arg Thr Cys Glu Lys Ala Cys Glu Leu His Thr Phe Gly Arg Thr Cys
145 150 155 160

Lys Glu Arg Cys Ser Gly Gln Glu Gly Cys Lys Ser Tyr Val Phe Cys
165 170 175

Leu Pro Asp Pro Tyr Gly Cys Ser Cys Ala Thr Gly Trp Lys Gly Leu
180 185 190

Gln Cys Asn Glu Gly Ile Gln Arg Met Thr Pro Lys Ile Val Asp Leu
195 200 205

Pro Asp His Ile Glu Val Asn Ser Gly Lys Phe Asn Pro Ile Cys Lys
210 215 220

Ala Ser Gly Trp Pro Leu Pro Thr Asn Glu Glu Met Thr Leu Val Lys
225 230 235 240

Pro Asp Gly Thr Val Leu His Pro Lys Asp Phe Asn His Thr Asp His
245 250 255

Phe Ser Val Ala Ile Phe Thr Ile His Arg Ile Leu Pro Pro Asp Ser
260 265 270

Gly Val Trp Val Cys Ser Val Asn Thr Val Ala Gly Met Val Glu Lys
275 280 285

Pro Phe Asn Ile Ser Val Lys Val Leu Pro Lys Pro Leu Asn Ala Pro
290 295 300

Asn Val Ile Asp Thr Gly His Asn Phe Ala Val Ile Asn Ile Ser Ser
305 310 315 320

Glu Pro Tyr Phe Gly Asp Gly Pro Ile Lys Ser Lys Lys Leu Leu Tyr
325 330 335

Lys Pro Val Asn His Tyr Glu Ala Trp Gln His Ile Gln Val Thr Asn
340 345 350

Glu Ile Val Thr Leu Asn Tyr Leu Glu Pro Arg Thr Glu Tyr Glu Leu
355 360 365

Cys Val Gln Leu Val Arg Arg Gly Glu Gly Gly Glu Gly His Pro Gly
370 375 380

-continued

```
Pro Val Arg Arg Phe Thr Thr Ala Ser Ile Gly Leu Pro Pro Pro Arg
385                 390                 395                 400

Gly Leu Asn Leu Leu Pro Lys Ser Gln Thr Thr Leu Asn Leu Thr Trp
                405                 410                 415

Gln Pro Ile Phe Pro Ser Ser Glu Asp Asp Phe Tyr Val Glu Val Glu
            420                 425                 430

Arg Arg Ser Val Gln Lys Ser Asp Gln Gln Asn Ile Lys Val Pro Gly
        435                 440                 445

Asn Leu Thr Ser Val Leu Leu Asn Asn Leu His Pro Arg Glu Gln Tyr
    450                 455                 460

Val Val Arg Ala Arg Val Asn Thr Lys Ala Gln Gly Glu Trp Ser Glu
465                 470                 475                 480

Asp Leu Thr Ala Trp Thr Leu Ser Asp Ile Leu Pro Pro Gln Pro Glu
                485                 490                 495

Asn Ile Lys Ile Ser Asn Ile Thr His Ser Ser Ala Val Ile Ser Trp
            500                 505                 510

Thr Ile Leu Asp Gly Tyr Ser Ile Ser Ser Ile Thr Ile Arg Tyr Lys
        515                 520                 525

Val Gln Gly Lys Asn Glu Asp Gln His Val Asp Val Lys Ile Lys Asn
    530                 535                 540

Ala Thr Ile Thr Gln Tyr Gln Leu Lys Gly Leu Glu Pro Glu Thr Ala
545                 550                 555                 560

Tyr Gln Val Asp Ile Phe Ala Glu Asn Asn Ile Gly Ser Ser Asn Pro
                565                 570                 575

Ala Phe Ser His Glu Leu Val Thr Leu Pro Glu Ser Gln Ala Pro Ala
            580                 585                 590

Asp Leu Gly Gly Gly Lys Met Leu Leu Ile Ala Ile Leu Gly Ser Ala
        595                 600                 605

Gly Met Thr Cys Leu Thr Val Leu Leu Ala Phe Leu Ile Ile Leu Gln
    610                 615                 620

Leu Lys Arg Ala Asn Val Gln Arg Arg Met Ala Gln Ala Phe Gln Asn
625                 630                 635                 640

Arg Glu Glu Pro Ala Val Gln Phe Asn Ser Gly Thr Leu Ala Leu Asn
                645                 650                 655

Arg Lys Val Lys Asn Asn Pro Asp Pro Thr Ile Tyr Pro Val Leu Asp
            660                 665                 670

Trp Asn Asp Ile Lys Phe Gln Asp Val Ile Gly Glu Gly Asn Phe Gly
        675                 680                 685

Gln Val Leu Lys Ala Arg Ile Lys Lys Asp Gly Leu Arg Met Asp Ala
    690                 695                 700

Ala Ile Lys Arg Met Lys Glu Tyr Ala Ser Lys Asp Asp His Arg Asp
705                 710                 715                 720

Phe Ala Gly Glu Leu Glu Val Leu Cys Lys Leu Gly His His Pro Asn
                725                 730                 735

Ile Ile Asn Leu Leu Gly Ala Cys Glu His Arg Gly Tyr Leu Tyr Leu
            740                 745                 750

Ala Ile Glu Tyr Ala Pro His Gly Asn Leu Leu Asp Phe Leu Arg Lys
        755                 760                 765

Ser Arg Val Leu Glu Thr Asp Pro Ala Phe Ala Ile Ala Asn Ser Thr
    770                 775                 780

Ala Ser Thr Leu Ser Ser Gln Gln Leu Leu His Phe Ala Ala Asp Val
785                 790                 795                 800
```

-continued

```
Ala Arg Gly Met Asp Tyr Leu Ser Gln Lys Gln Phe Ile His Arg Asp
                805                 810                 815

Leu Ala Ala Arg Asn Ile Leu Val Gly Glu Asn Tyr Val Ala Lys Ile
            820                 825                 830

Ala Asp Phe Gly Leu Ser Arg Gly Gln Glu Val Tyr Val Lys Lys Thr
        835                 840                 845

Met Gly Arg Leu Pro Val Arg Trp Met Ala Ile Glu Ser Leu Asn Tyr
    850                 855                 860

Ser Val Tyr Thr Thr Asn Ser Asp Val Trp Ser Tyr Gly Val Leu Leu
865                 870                 875                 880

Trp Glu Ile Val Ser Leu Gly Gly Thr Pro Tyr Cys Gly Met Thr Cys
                885                 890                 895

Ala Glu Leu Tyr Glu Lys Leu Pro Gln Gly Tyr Arg Leu Glu Lys Pro
            900                 905                 910

Leu Asn Cys Asp Asp Glu Val Tyr Asp Leu Met Arg Gln Cys Trp Arg
        915                 920                 925

Glu Lys Pro Tyr Glu Arg Pro Ser Phe Ala Gln Ile Leu Val Ser Leu
    930                 935                 940

Asn Arg Met Leu Glu Glu Arg Lys Thr Tyr Val Asn Thr Thr Leu Tyr
945                 950                 955                 960

Glu Lys Phe Thr Tyr Ala Gly Ile Asp Cys Ser Ala Glu Glu Ala Ala
                965                 970                 975
```

<210> SEQ ID NO 874
<211> LENGTH: 1195
<212> TYPE: PRT
<213> ORGANISM: Homo sapiens

<400> SEQUENCE: 874

```
Met Pro Val Arg Arg Gly His Val Ala Pro Gln Asn Thr Phe Leu Gly
1               5                   10                  15

Thr Ile Ile Arg Lys Phe Glu Gly Gln Asn Lys Lys Phe Ile Ile Ala
            20                  25                  30

Asn Ala Arg Val Gln Asn Cys Ala Ile Ile Tyr Cys Asn Asp Gly Phe
        35                  40                  45

Cys Glu Met Thr Gly Phe Ser Arg Pro Asp Val Met Gln Lys Pro Cys
    50                  55                  60

Thr Cys Asp Phe Leu His Gly Pro Glu Thr Lys Arg His Asp Ile Ala
65                  70                  75                  80

Gln Ile Ala Gln Ala Leu Leu Gly Ser Glu Glu Arg Lys Val Glu Val
                85                  90                  95

Thr Tyr Tyr His Lys Asn Gly Ser Thr Phe Ile Cys Asn Thr His Ile
            100                 105                 110

Ile Pro Val Lys Asn Gln Glu Gly Val Ala Met Met Phe Ile Ile Asn
        115                 120                 125

Phe Glu Tyr Val Thr Asp Asn Glu Asn Ala Ala Thr Pro Glu Arg Val
    130                 135                 140

Asn Pro Ile Leu Pro Ile Lys Thr Val Asn Arg Lys Phe Phe Gly Phe
145                 150                 155                 160

Lys Phe Pro Gly Leu Arg Val Leu Thr Tyr Arg Lys Gln Ser Leu Pro
                165                 170                 175

Gln Glu Asp Pro Asp Val Val Val Ile Asp Ser Ser Lys His Ser Asp
            180                 185                 190

Asp Ser Val Ala Met Lys His Phe Lys Ser Pro Thr Lys Glu Ser Cys
        195                 200                 205
```

-continued

```
Ser Pro Ser Glu Ala Asp Asp Thr Lys Ala Leu Ile Gln Pro Ser Lys
    210                 215                 220

Cys Ser Pro Leu Val Asn Ile Ser Gly Pro Leu Asp His Ser Ser Pro
225                 230                 235                 240

Lys Arg Gln Trp Asp Arg Leu Tyr Pro Asp Met Leu Gln Ser Ser Ser
                245                 250                 255

Gln Leu Ser His Ser Arg Ser Arg Glu Ser Leu Cys Ser Ile Arg Arg
            260                 265                 270

Ala Ser Ser Val His Asp Ile Glu Gly Phe Gly Val His Pro Lys Asn
        275                 280                 285

Ile Phe Arg Asp Arg His Ala Ser Glu Asp Asn Gly Arg Asn Val Lys
    290                 295                 300

Gly Pro Phe Asn His Ile Lys Ser Ser Leu Leu Gly Ser Thr Ser Asp
305                 310                 315                 320

Ser Asn Leu Asn Lys Tyr Ser Thr Ile Asn Lys Ile Pro Gln Leu Thr
                325                 330                 335

Leu Asn Phe Ser Glu Val Lys Thr Glu Lys Lys Asn Ser Ser Pro Pro
            340                 345                 350

Ser Ser Asp Lys Thr Ile Ile Ala Pro Lys Val Lys Asp Arg Thr His
        355                 360                 365

Asn Val Thr Glu Lys Val Thr Gln Val Leu Ser Leu Gly Ala Asp Val
    370                 375                 380

Leu Pro Glu Tyr Lys Leu Gln Thr Pro Arg Ile Asn Lys Phe Thr Ile
385                 390                 395                 400

Leu His Tyr Ser Pro Phe Lys Ala Val Trp Asp Trp Leu Ile Leu Leu
                405                 410                 415

Leu Val Ile Tyr Thr Ala Ile Phe Thr Pro Tyr Ser Ala Ala Phe Leu
            420                 425                 430

Leu Asn Asp Arg Glu Glu Gln Lys Arg Arg Glu Cys Gly Tyr Ser Cys
        435                 440                 445

Ser Pro Leu Asn Val Val Asp Leu Ile Val Asp Ile Met Phe Ile Ile
    450                 455                 460

Asp Ile Leu Ile Asn Phe Arg Thr Thr Tyr Val Asn Gln Asn Glu Glu
465                 470                 475                 480

Val Val Ser Asp Pro Ala Lys Ile Ala Ile His Tyr Phe Lys Gly Trp
                485                 490                 495

Phe Leu Ile Asp Met Val Ala Ala Ile Pro Phe Asp Leu Leu Ile Phe
            500                 505                 510

Gly Ser Gly Ser Asp Glu Thr Thr Thr Leu Ile Gly Leu Leu Lys Thr
        515                 520                 525

Ala Arg Leu Arg Leu Val Arg Val Ala Arg Lys Leu Asp Arg Tyr Ser
    530                 535                 540

Glu Tyr Gly Ala Ala Val Leu Met Leu Leu Met Cys Ile Phe Ala Leu
545                 550                 555                 560

Ile Ala His Trp Leu Ala Cys Ile Trp Tyr Ala Ile Gly Asn Val Glu
                565                 570                 575

Arg Pro Tyr Leu Thr Asp Lys Ile Gly Trp Leu Asp Ser Leu Gly Gln
            580                 585                 590

Gln Ile Gly Lys Arg Tyr Asn Asp Ser Asp Ser Ser Ser Gly Pro Ser
        595                 600                 605

Ile Lys Asp Lys Tyr Val Thr Ala Leu Tyr Phe Thr Phe Ser Ser Leu
    610                 615                 620
```

-continued

```
Thr Ser Val Gly Phe Gly Asn Val Ser Pro Asn Thr Asn Ser Glu Lys
625                 630                 635                 640

Ile Phe Ser Ile Cys Val Met Leu Ile Gly Ser Leu Met Tyr Ala Ser
                645                 650                 655

Ile Phe Gly Asn Val Ser Ala Ile Ile Gln Arg Leu Tyr Ser Gly Thr
            660                 665                 670

Ala Arg Tyr His Met Gln Met Leu Arg Val Lys Glu Phe Ile Arg Phe
        675                 680                 685

His Gln Ile Pro Asn Pro Leu Arg Gln Arg Leu Glu Glu Tyr Phe Gln
    690                 695                 700

His Ala Trp Thr Tyr Thr Asn Gly Ile Asp Met Asn Met Val Leu Lys
705                 710                 715                 720

Gly Phe Pro Glu Cys Leu Gln Ala Asp Ile Cys Leu His Leu Asn Gln
                725                 730                 735

Thr Leu Leu Gln Asn Cys Lys Ala Phe Arg Gly Ala Ser Lys Gly Cys
            740                 745                 750

Leu Arg Ala Leu Ala Met Lys Phe Lys Thr Thr His Ala Pro Pro Gly
        755                 760                 765

Asp Thr Leu Val His Cys Gly Asp Val Leu Thr Ala Leu Tyr Phe Leu
    770                 775                 780

Ser Arg Gly Ser Ile Glu Ile Leu Lys Asp Asp Ile Val Val Ala Ile
785                 790                 795                 800

Leu Gly Lys Asn Asp Ile Phe Gly Glu Met Val His Leu Tyr Ala Lys
                805                 810                 815

Pro Gly Lys Ser Asn Ala Asp Val Arg Ala Leu Thr Tyr Cys Asp Leu
            820                 825                 830

His Lys Ile Gln Arg Glu Asp Leu Leu Glu Val Leu Asp Met Tyr Pro
        835                 840                 845

Glu Phe Ser Asp His Phe Leu Thr Asn Leu Glu Leu Thr Phe Asn Leu
    850                 855                 860

Arg His Glu Ser Ala Lys Ala Asp Leu Leu Arg Ser Gln Ser Met Asn
865                 870                 875                 880

Asp Ser Glu Gly Asp Asn Cys Lys Leu Arg Arg Arg Lys Leu Ser Phe
                885                 890                 895

Glu Ser Glu Gly Glu Lys Glu Asn Ser Thr Asn Asp Pro Glu Asp Ser
            900                 905                 910

Ala Asp Thr Ile Arg His Tyr Gln Ser Ser Lys Arg His Phe Glu Glu
        915                 920                 925

Lys Lys Ser Arg Ser Ser Ser Phe Ile Ser Ser Ile Asp Asp Glu Gln
    930                 935                 940

Lys Pro Leu Phe Ser Gly Ile Val Asp Ser Ser Pro Gly Ile Gly Lys
945                 950                 955                 960

Ala Ser Gly Leu Asp Phe Glu Glu Thr Val Pro Thr Ser Gly Arg Met
                965                 970                 975

His Ile Asp Lys Arg Ser His Ser Cys Lys Asp Ile Thr Asp Met Arg
            980                 985                 990

Ser Trp Glu Arg Glu Asn Ala His  Pro Gln Pro Glu Asp  Ser Ser Pro
        995                 1000                1005

Ser Ala  Leu Gln Arg Ala Ala  Trp Gly Ile Ser Glu  Thr Glu Ser
    1010                1015                1020

Asp Leu  Thr Tyr Gly Glu Val  Glu Gln Arg Leu Asp  Leu Leu Gln
    1025                1030                1035

Glu Gln  Leu Asn Arg Leu Glu  Ser Gln Met Thr Thr  Asp Ile Gln
```

1040 1045 1050

Thr Ile Leu Gln Leu Leu Gln Lys Gln Thr Thr Val Val Pro Pro
1055 1060 1065

Ala Tyr Ser Met Val Thr Ala Gly Ser Glu Tyr Gln Arg Pro Ile
1070 1075 1080

Ile Gln Leu Met Arg Thr Ser Gln Pro Glu Ala Ser Ile Lys Thr
1085 1090 1095

Asp Arg Ser Phe Ser Pro Ser Ser Gln Cys Pro Glu Phe Leu Asp
1100 1105 1110

Leu Glu Lys Ser Lys Leu Lys Ser Lys Glu Ser Leu Ser Ser Gly
1115 1120 1125

Val His Leu Asn Thr Ala Ser Glu Asp Asn Leu Thr Ser Leu Leu
1130 1135 1140

Lys Gln Asp Ser Asp Leu Ser Leu Glu Leu His Leu Arg Gln Arg
1145 1150 1155

Lys Thr Tyr Val His Pro Ile Arg His Pro Ser Leu Pro Asp Ser
1160 1165 1170

Ser Leu Ser Thr Val Gly Ile Val Gly Leu His Arg His Val Ser
1175 1180 1185

Asp Pro Gly Leu Pro Gly Lys
1190 1195

<210> SEQ ID NO 875
<211> LENGTH: 732
<212> TYPE: PRT
<213> ORGANISM: Homo sapiens

<400> SEQUENCE: 875

Met Pro Val Arg Arg Gly His Val Ala Pro Gln Asn Thr Phe Leu Gly
1 5 10 15

Thr Ile Ile Arg Lys Phe Glu Gly Gln Asn Lys Lys Phe Ile Ile Ala
20 25 30

Asn Ala Arg Val Gln Asn Cys Ala Ile Ile Tyr Cys Asn Asp Gly Phe
35 40 45

Cys Glu Met Thr Gly Phe Ser Arg Pro Asp Val Met Gln Lys Pro Cys
50 55 60

Thr Cys Asp Phe Leu His Gly Pro Glu Thr Lys Arg His Asp Ile Ala
65 70 75 80

Gln Ile Ala Gln Ala Leu Leu Gly Ser Glu Glu Arg Lys Val Glu Val
85 90 95

Thr Tyr Tyr His Lys Asn Gly Ser Thr Phe Ile Cys Asn Thr His Ile
100 105 110

Ile Pro Val Lys Asn Gln Glu Gly Val Ala Met Met Phe Ile Ile Asn
115 120 125

Phe Glu Tyr Val Thr Asp Asn Glu Asn Ala Ala Thr Pro Glu Arg Val
130 135 140

Asn Pro Ile Leu Pro Ile Lys Thr Val Asn Arg Lys Phe Phe Gly Phe
145 150 155 160

Lys Phe Pro Gly Leu Arg Val Leu Thr Tyr Arg Lys Gln Ser Leu Pro
165 170 175

Gln Glu Asp Pro Asp Val Val Val Ile Asp Ser Ser Lys His Ser Asp
180 185 190

Asp Ser Val Ala Met Lys His Phe Lys Ser Pro Thr Lys Glu Ser Cys
195 200 205

-continued

```
Ser Pro Ser Glu Ala Asp Asp Thr Lys Ala Leu Ile Gln Pro Ser Lys
    210                 215                 220

Cys Ser Pro Leu Val Asn Ile Ser Gly Pro Leu Asp His Ser Ser Pro
225                 230                 235                 240

Lys Arg Gln Trp Asp Arg Leu Tyr Pro Asp Met Leu Gln Ser Ser Ser
                245                 250                 255

Gln Leu Ser His Ser Arg Ser Arg Glu Ser Leu Cys Ser Ile Arg Arg
            260                 265                 270

Ala Ser Ser Val His Asp Ile Glu Gly Phe Gly Val His Pro Lys Asn
        275                 280                 285

Ile Phe Arg Asp Arg His Ala Ser Glu Gly Pro Phe Asn His Ile Lys
    290                 295                 300

Ser Ser Leu Leu Gly Ser Thr Ser Asp Ser Asn Leu Asn Lys Tyr Ser
305                 310                 315                 320

Thr Ile Asn Lys Ile Pro Gln Leu Thr Leu Asn Phe Ser Glu Val Lys
                325                 330                 335

Thr Glu Lys Lys Asn Ser Ser Pro Pro Ser Ser Asp Lys Thr Ile Ile
            340                 345                 350

Ala Pro Lys Val Lys Asp Arg Thr His Asn Val Thr Glu Lys Val Thr
        355                 360                 365

Gln Val Leu Ser Leu Gly Ala Asp Val Leu Pro Glu Tyr Lys Leu Gln
    370                 375                 380

Thr Pro Arg Ile Asn Lys Phe Thr Ile Leu His Tyr Ser Pro Phe Lys
385                 390                 395                 400

Ala Val Trp Asp Trp Leu Ile Leu Leu Leu Val Ile Tyr Thr Ala Ile
                405                 410                 415

Phe Thr Pro Tyr Ser Ala Ala Phe Leu Leu Asn Asp Arg Glu Glu Gln
            420                 425                 430

Lys Arg Arg Glu Cys Gly Tyr Ser Cys Ser Pro Leu Asn Val Val Asp
        435                 440                 445

Leu Ile Val Asp Ile Met Phe Ile Ile Asp Ile Leu Ile Asn Phe Arg
    450                 455                 460

Thr Thr Tyr Val Asn Gln Asn Glu Glu Val Val Ser Asp Pro Ala Lys
465                 470                 475                 480

Ile Ala Ile His Tyr Phe Lys Gly Trp Phe Leu Ile Asp Met Val Ala
                485                 490                 495

Ala Ile Pro Phe Asp Leu Leu Ile Phe Gly Ser Gly Ser Asp Glu Thr
            500                 505                 510

Thr Thr Leu Ile Gly Leu Leu Lys Thr Ala Arg Leu Leu Arg Leu Val
        515                 520                 525

Arg Val Ala Arg Lys Leu Asp Arg Tyr Ser Glu Tyr Gly Ala Ala Val
    530                 535                 540

Leu Met Leu Leu Met Cys Ile Phe Ala Leu Ile Ala His Trp Leu Ala
545                 550                 555                 560

Cys Ile Trp Tyr Ala Ile Gly Asn Val Glu Arg Pro Tyr Leu Thr Asp
                565                 570                 575

Lys Ile Gly Trp Leu Asp Ser Leu Gly Gln Gln Ile Gly Lys Arg Tyr
            580                 585                 590

Asn Asp Ser Asp Ser Ser Ser Gly Pro Ser Ile Lys Asp Lys Tyr Val
        595                 600                 605

Thr Ala Leu Tyr Phe Thr Phe Ser Ser Leu Thr Ser Val Gly Phe Gly
    610                 615                 620

Asn Val Ser Pro Asn Thr Asn Ser Glu Lys Ile Phe Ser Ile Cys Val
```

-continued

```
625                 630                 635                 640

Met Leu Ile Gly Ser Leu Met Tyr Ala Ser Ile Phe Gly Asn Val Ser
                645                 650                 655

Ala Ile Ile Gln Arg Leu Tyr Ser Gly Thr Ala Arg Tyr His Met Gln
            660                 665                 670

Met Leu Arg Val Lys Glu Phe Ile Arg Phe His Gln Ile Pro Asn Pro
        675                 680                 685

Leu Arg Gln Arg Leu Glu Glu Tyr Phe Gln His Ala Trp Thr Tyr Thr
    690                 695                 700

Asn Gly Ile Asp Met Asn Met Val Cys Met Ser Val Phe Gln Asn Glu
705                 710                 715                 720

Ser Ala Ala Gly Ile Ile Val Ile Ala Lys Met Glu
                725                 730
```